United States Patent
Lee et al.

(10) Patent No.: US 12,325,713 B2
(45) Date of Patent: Jun. 10, 2025

(54) COMPOUND AND ORGANIC LIGHT EMITTING DEVICE COMPRISING THE SAME

(71) Applicant: LG CHEM, LTD., Seoul (KR)

(72) Inventors: Jungha Lee, Daejeon (KR); Dong Hoon Lee, Daejeon (KR); Boon Jae Jang, Daejeon (KR); Sang Duk Suh, Daejeon (KR); Min Woo Jung, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 1098 days.

(21) Appl. No.: 17/059,170

(22) PCT Filed: Jan. 3, 2020

(86) PCT No.: PCT/KR2020/000148
§ 371 (c)(1),
(2) Date: Nov. 25, 2020

(87) PCT Pub. No.: WO2020/141949
PCT Pub. Date: Jul. 9, 2020

(65) Prior Publication Data
US 2021/0230182 A1    Jul. 29, 2021

(30) Foreign Application Priority Data

Jan. 4, 2019   (KR) .................. 10-2019-0001321

(51) Int. Cl.
| | | |
|---|---|---|
| H01L 51/54 | (2006.01) | |
| C07D 491/04 | (2006.01) | |
| C07D 495/04 | (2006.01) | |
| C07D 495/14 | (2006.01) | |
| H10K 85/60 | (2023.01) | |
| H10K 50/15 | (2023.01) | |
| H10K 50/16 | (2023.01) | |
| H10K 50/17 | (2023.01) | |
| H10K 50/18 | (2023.01) | |

(52) U.S. Cl.
CPC ......... *C07D 495/04* (2013.01); *C07D 491/04* (2013.01); *C07D 495/14* (2013.01); *H10K 85/654* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02); *H10K 50/18* (2023.02)

(58) Field of Classification Search
None
See application file for complete search history.

(56) References Cited

U.S. PATENT DOCUMENTS

| | | |
|---|---|---|
| 10,622,565 B2 | 4/2020 | Parham et al. |
| 2015/0207082 A1 | 7/2015 | Dyatkin et al. |
| 2015/0336937 A1 | 11/2015 | Lee et al. |
| 2016/0351826 A1* | 12/2016 | Kim ................ H10K 85/615 |
| 2017/0200903 A1 | 7/2017 | Park et al. |
| 2018/0205032 A1 | 7/2018 | Lee et al. |
| 2019/0198771 A1 | 6/2019 | Lui et al. |
| 2019/0198772 A1 | 6/2019 | Lui et al. |
| 2019/0341553 A1 | 11/2019 | Lui et al. |
| 2020/0010476 A1 | 1/2020 | Lee et al. |
| 2020/0111969 A1 | 4/2020 | No et al. |
| 2020/0123133 A1 | 4/2020 | No et al. |
| 2020/0127213 A1 | 4/2020 | Jang et al. |
| 2020/0161560 A1 | 5/2020 | Jang et al. |
| 2020/0190069 A1 | 6/2020 | Lee et al. |
| 2020/0259098 A1 | 8/2020 | Lee et al. |

FOREIGN PATENT DOCUMENTS

| | | |
|---|---|---|
| CN | 108250189 A | 7/2018 |
| KR | 10-2000-0051826 A | 8/2000 |
| KR | 10-2015-0088176 A | 7/2015 |
| KR | 10-2015-0136942 A | 12/2015 |
| KR | 10-2017-0007626 A | 1/2017 |
| KR | 10-2017-0113321 A | 10/2017 |
| KR | 10-2017-0139443 A | 12/2017 |
| KR | 10-2018-0010165 A | 1/2018 |
| KR | 10-1857703 B1 | 5/2018 |
| KR | 10-2018-0068869 A | 6/2018 |
| KR | 10-2018-0108426 A | 10/2018 |
| KR | 10-2019-0000185 A | 1/2019 |
| KR | 10-2019-0010474 A | 1/2019 |
| WO | 03/012890 A2 | 2/2003 |
| WO | 2019132545 A1 | 7/2019 |

* cited by examiner

*Primary Examiner* — Andrew K Bohaty
(74) *Attorney, Agent, or Firm* — Bryan Cave Leighton Paisner LLP

(57) ABSTRACT

A novel compound of the following Chemical Formula 1, and an organic light emitting device comprising the same.

Chemical Formula 1

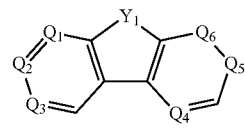

7 Claims, 1 Drawing Sheet

[FIG. 1]
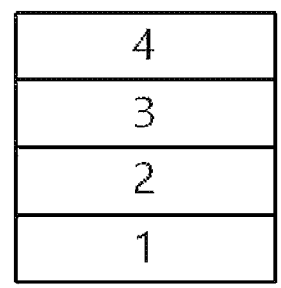
[FIG. 2]
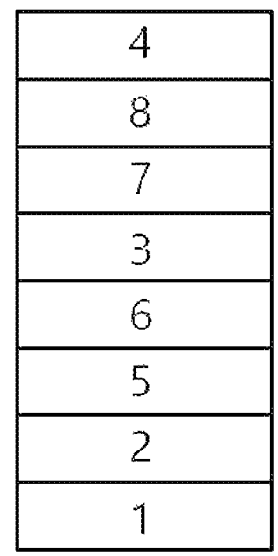

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2020/000148 filed on Jan. 3, 2020, which claims the benefit of Korean Patent Application No. 10-2019-0001321 filed on Jan. 4, 2019 with the Korean Intellectual Property Office, the disclosure of which is incorporated herein by reference in its entirety.

TECHNICAL FIELD

The present disclosure relates to a novel compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE (Patent Literature 0001) Korean Unexamined Patent Publication No. 10-2000-0051826

Technical Problem

It is an object of the present disclosure to provide a novel compound and an organic light emitting device comprising the same.

Technical Solution

According to an aspect of the present disclosure, there is provided a compound of the following Chemical Formula 1.

A compound of the Chemical Formula 1:

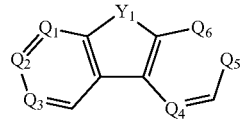

Chemical Formula 1 wherein, in the Chemical Formula 1,
$Y_1$ is O or S,
any one of $Q_1$ to $Q_3$ is the following Chemical Formula 2 and the rest are CH,
any one of $Q_4$ to $Q_6$ is the following Chemical Formula 3 and the rest are CH,
$Q_6$ is CH provided that $Q_1$ is the following Chemical Formula 2, and $Q_5$ is CH provided that $Q_2$ is the following Chemical Formula 2,

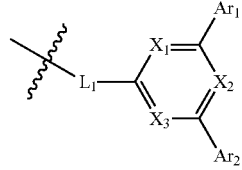

Chemical Formula 2 wherein, in the Chemical Formula 2,
$L_1$ is a single bond; a substituted or unsubstituted $C_{6-60}$ arylene; or a substituted or unsubstituted $C_{5-60}$ heteroarylene containing at least one heteroatom selected from the group consisting of N, O and S, $L_1$ is a single bond provided that $Q_3$ is Chemical Formula 2,
$X_1$ to $X_3$ are each independently N or CH, and at least one of $X_1$ to $X_3$ is N,
$Ar_1$ and $Ar_2$ are each independently a substituted or unsubstituted $C_{6-60}$ aryl; or a substituted or unsubstituted $C_{5-60}$ heteroaryl containing at least one heteroatom selected from the group consisting of N, O and S,

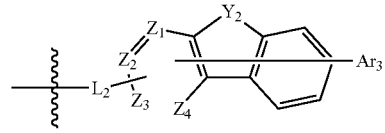

Chemical Formula 3 wherein, in the Chemical Formula 3,
$Y_2$ is O or S,
$L_2$ is a single bond; a substituted or unsubstituted $C_{6-60}$ arylene; or a substituted or unsubstituted $C_{5-60}$ heteroarylene containing at least one heteroatom selected from the group consisting of N, O and S,
$Z_1$ to $Z_4$ are each independently N or CH, and at least two of $Z_1$ to $Z_4$ are N, and
$Ar_3$ is hydrogen; a substituted or unsubstituted $C_{1-60}$ alkyl; or a substituted or unsubstituted $C_{6-60}$ aryl.

According to another aspect of the present disclosure, there is provided an organic light emitting device comprising: a first electrode; a second electrode that is provided to face the first electrode; and one or more organic material layers that are provided between the first electrode and the second electrode, wherein one or more layers of the organic material layers include the above-mentioned compound of Chemical Formula 1.

Advantageous Effects

The above-mentioned compound of Chemical Formula 1 can be used as a material of an organic material layer of an organic light emitting device, and can improve the efficiency, achieve low driving voltage and/or improve lifetime characteristics of the organic light emitting device. In particular, the compound of Chemical Formula 1 may be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 3, an electron blocking layer 7, an electron transport and injection layer 8, and a cathode 4.

DETAILED DESCRIPTION

Hereinafter, embodiments of the present disclosure will be described in more detail to facilitate understanding of the invention.

The present disclosure provides the compound of Chemical Formula 1.

As used herein, the notation

or ┊ means a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may also be interpreted as a substituent in which two phenyl groups are connected.

In the present disclosure, the carbon number of a carbonyl group is not particularly limited, but is preferably 1 to 40. Specifically, the carbonyl group may be a compound having the following structural formulas, but is not limited thereto.

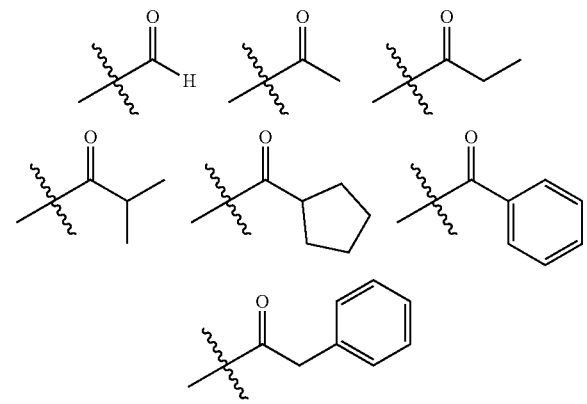

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas, but is not limited thereto.

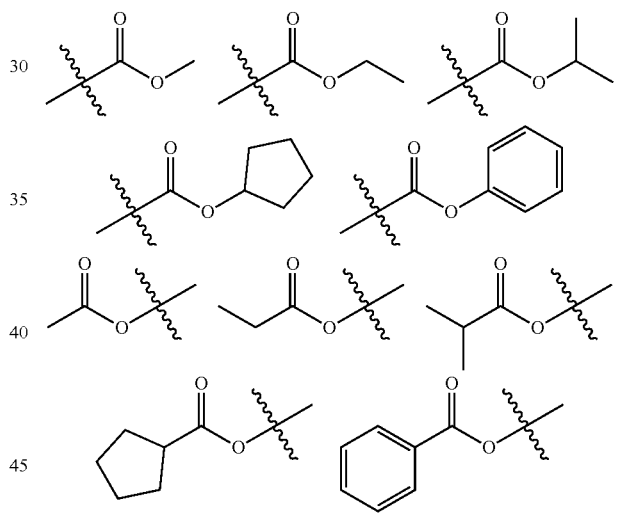

In the present disclosure, the carbon number of an imide group is not particularly limited, but is preferably 1 to 25. Specifically, the imide group may be a compound having the following structural formulas, but is not limited thereto.

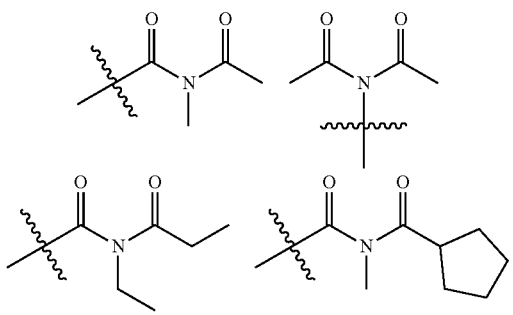

-continued

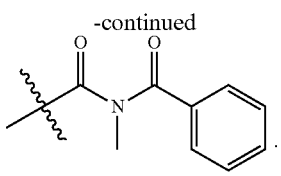

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, or the like, but is not limited thereto.

In the present disclosure, the fluorenyl group may be substituted, and two substituents may be linked with each other to form a spiro structure. In the case where the fluorenyl group is substituted,

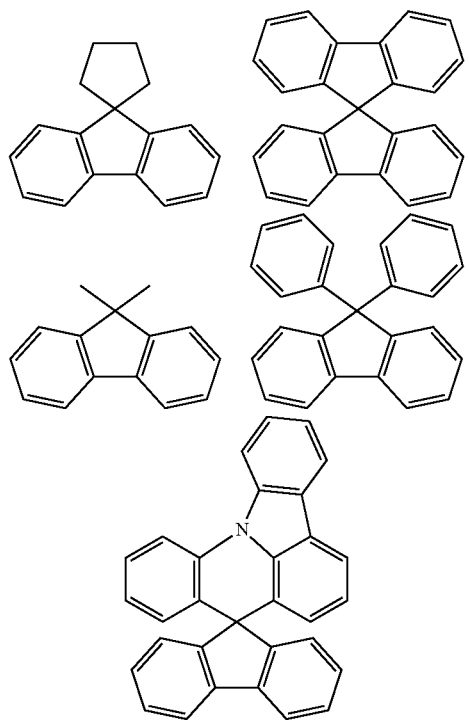

and the like can be formed. However, the structure is not limited thereto.

In the present disclosure, a heterocyclic group is a heterocyclic group containing one or more of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the aforementioned examples of the aryl group. In the present disclosure, the alkyl group in the aralkyl group, the alkylaryl group and the alkylamine group is the same as the aforementioned examples of the alkyl group. In the present disclosure, the heteroaryl in the heteroarylamine can be applied to the aforementioned description of the heterocyclic group. In the present disclosure, the alkenyl group in the aralkenyl group is the same as the aforementioned examples of the alkenyl group. In the present disclosure, the aforementioned description of the aryl group may be applied except that the arylene is a divalent group. In the present disclosure, the aforementioned description of the heteroaryl group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocyclic group is not a monovalent group but formed by combining two substituent groups.

Preferably, the Chemical Formula 1 may be any one selected from compounds of the following Chemical Formulas 1-1 to 1-7:

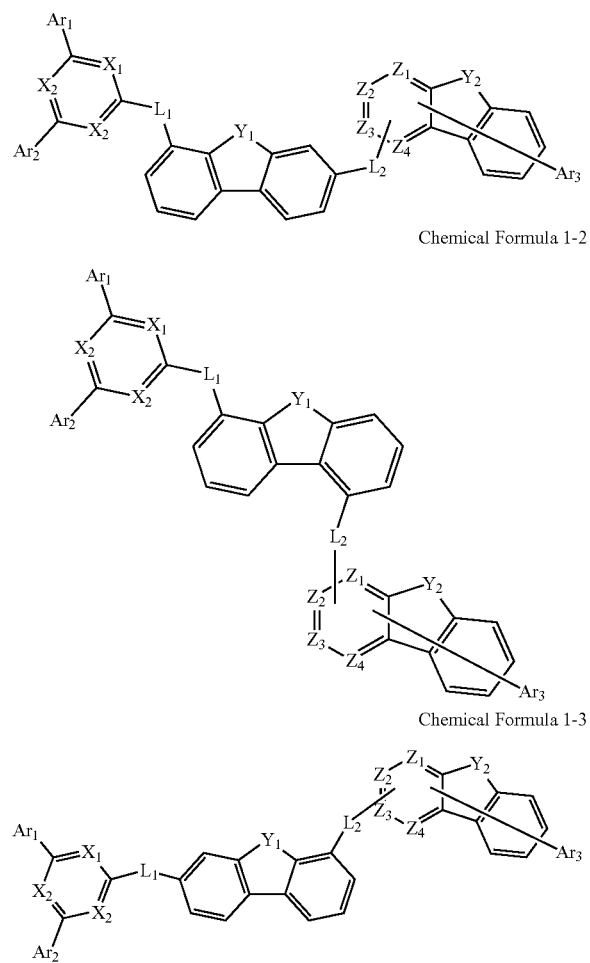

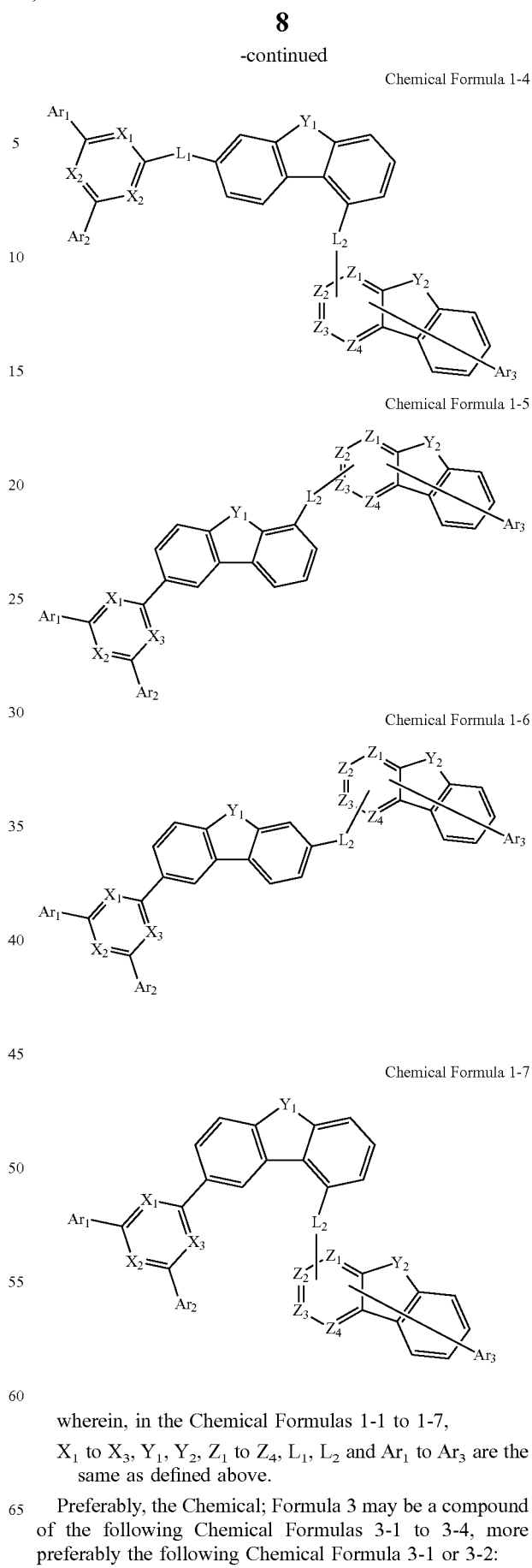

wherein, in the Chemical Formulas 1-1 to 1-7, $X_1$ to $X_3$, $Y_1$, $Y_2$, $Z_1$ to $Z_4$, $L_1$, $L_2$ and $Ar_1$ to $Ar_3$ are the same as defined above.

Preferably, the Chemical; Formula 3 may be a compound of the following Chemical Formulas 3-1 to 3-4, more preferably the following Chemical Formula 3-1 or 3-2:

Chemical Formula 3-1

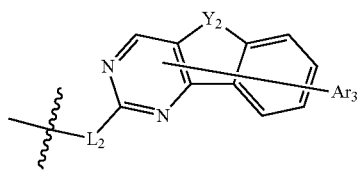

Chemical Formula 3-2

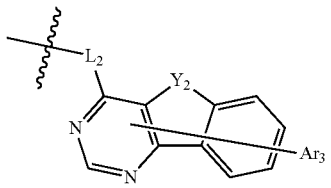

Chemical Formula 3-3

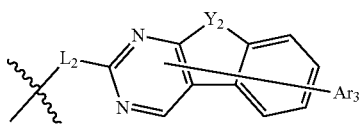

Chemical Formula 3-4

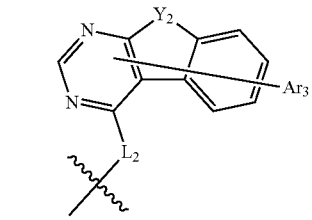

wherein, in the Chemical Formulas 3-1 to 3-4,
$Y_2$, $L_2$ and $Ar_3$ are the same as defined above.

More preferably, the Chemical Formula 3 may be any one selected from the following compounds:

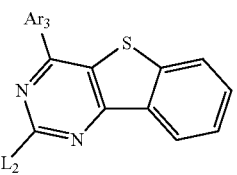

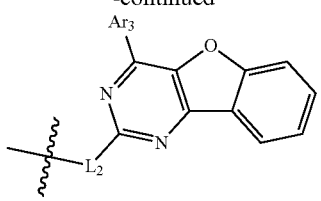

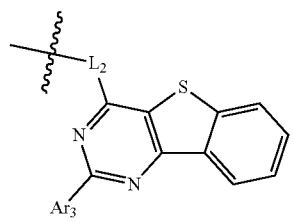

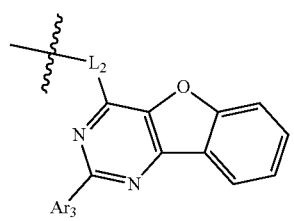

wherein, $L_2$ and $Ar_3$ are the same as defined above.

Preferably, $L_1$ and $L_2$ may each independently be a single bond or phenylene.

Preferably, $Ar_1$ and $Ar_2$ may be each independently phenyl; biphenyl; dibenzofuranyl; dibenzothiophenyl; carbazolyl; or carbazolyl substituted with phenyl.

Further, preferably $Ar_3$ may be phenyl.

For example, the compound may be selected from the group consisting of the following compounds.

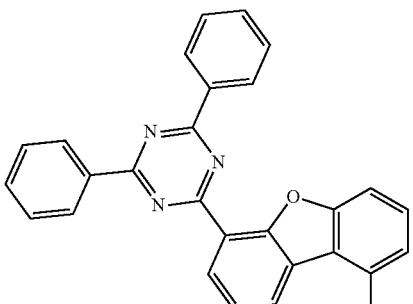

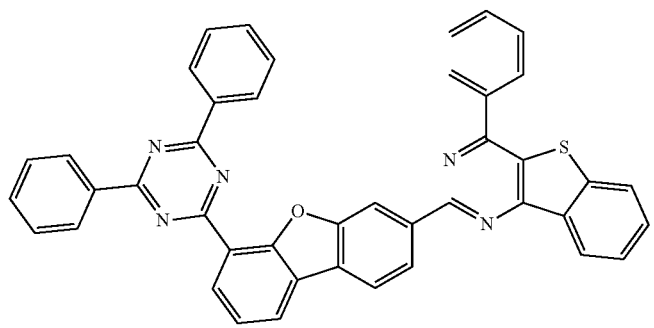

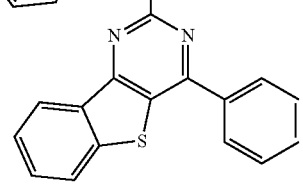

-continued
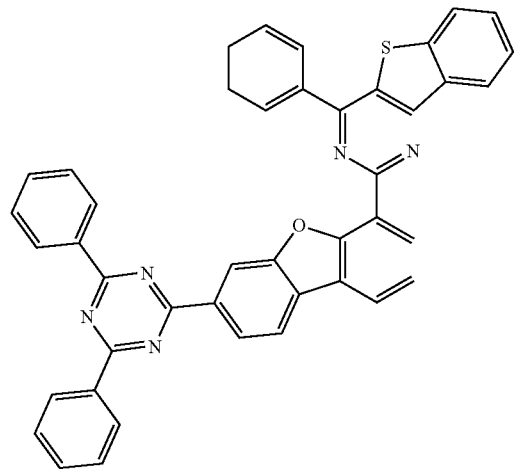
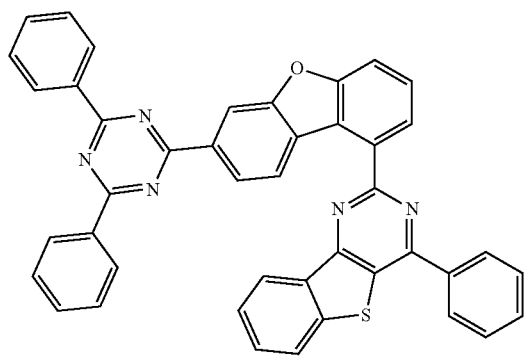
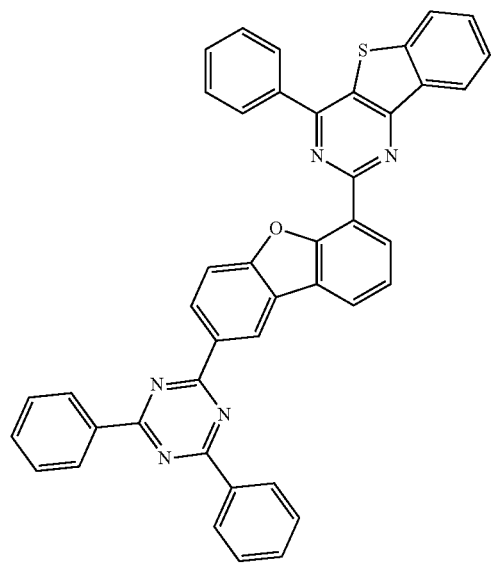
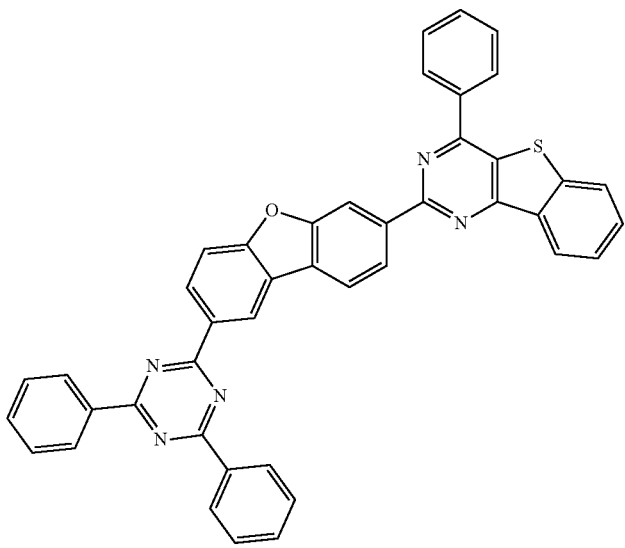
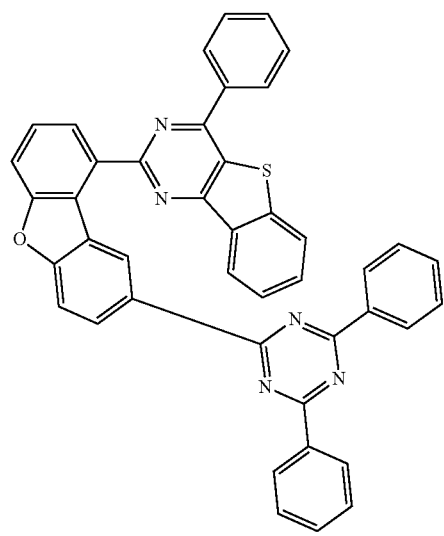
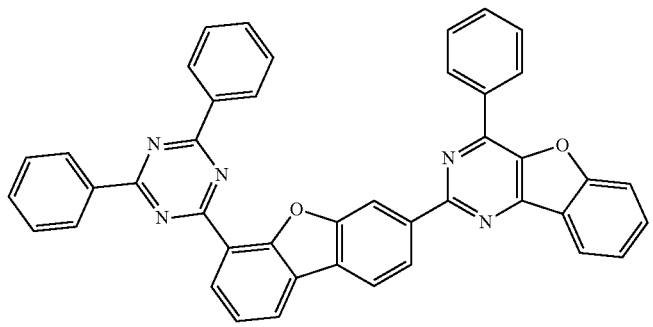

-continued
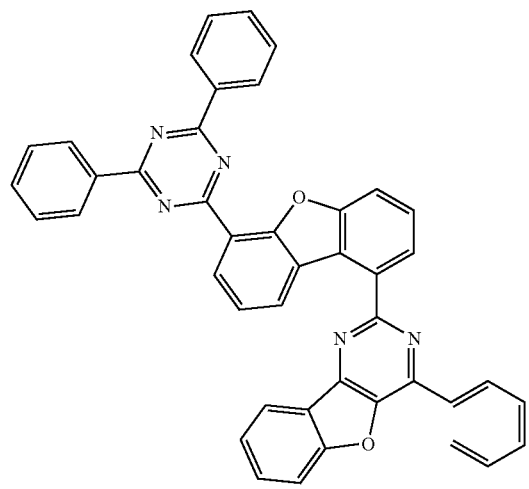
13
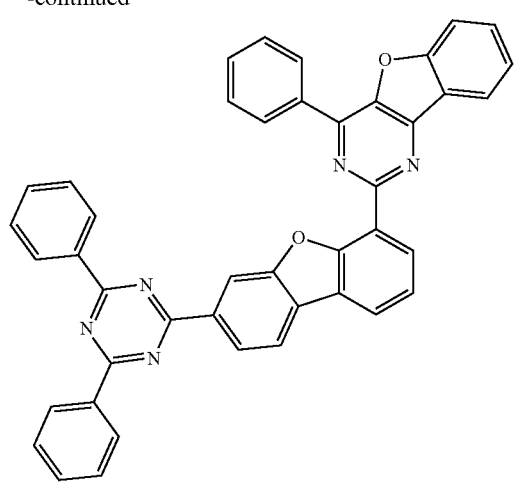
14
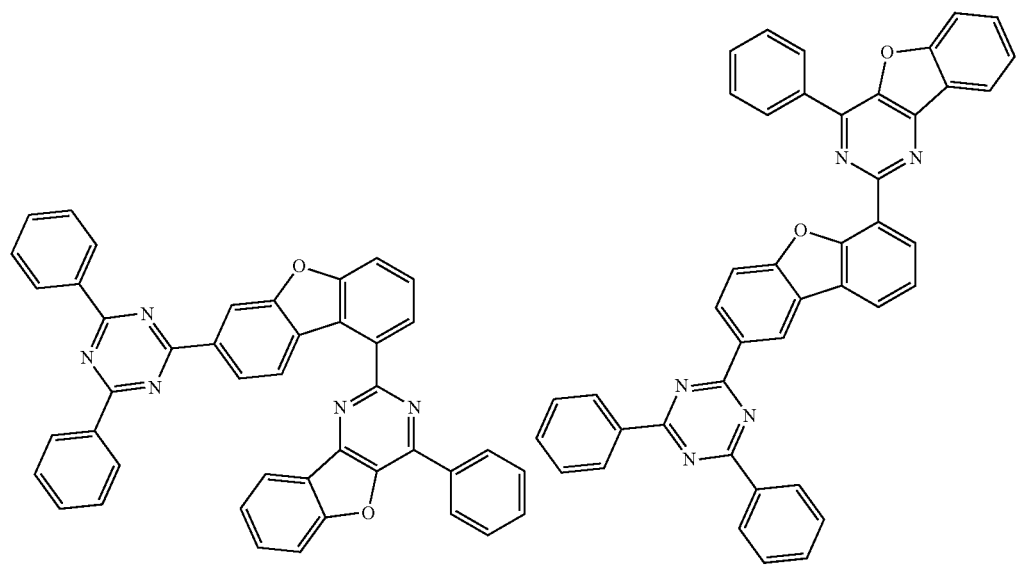
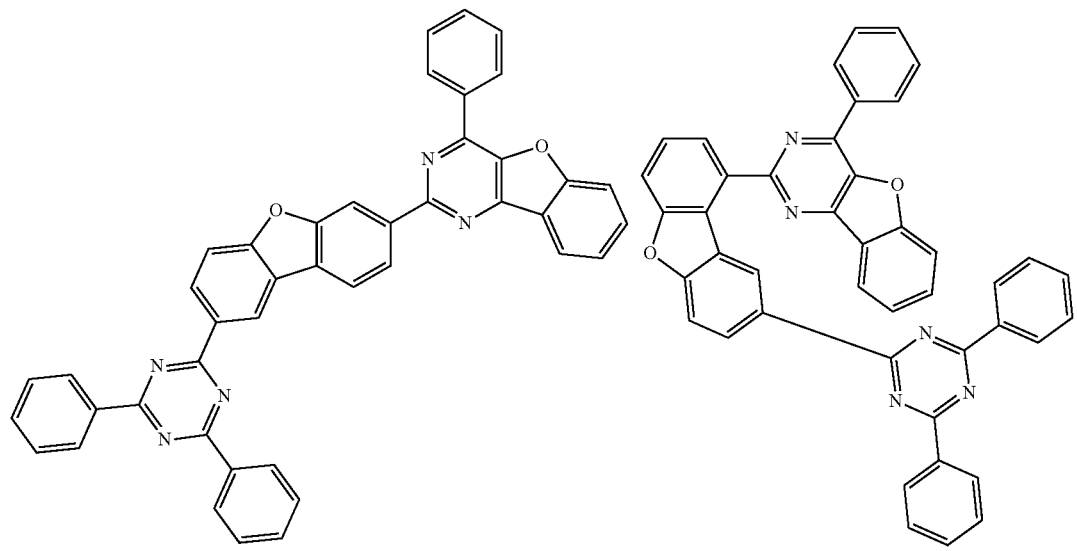

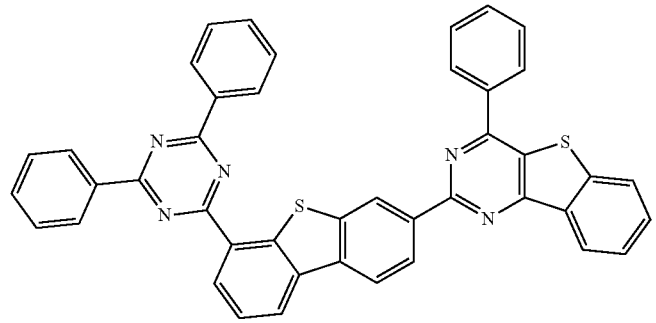
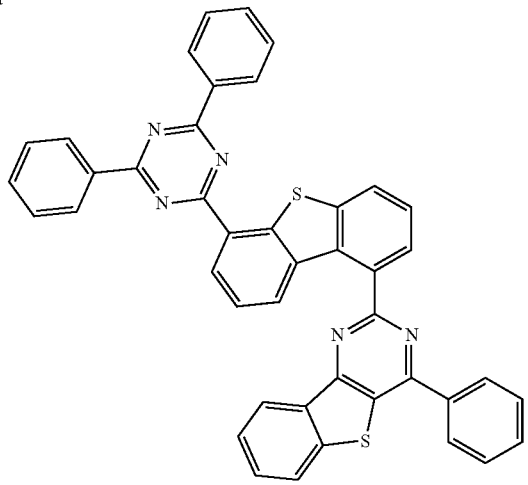
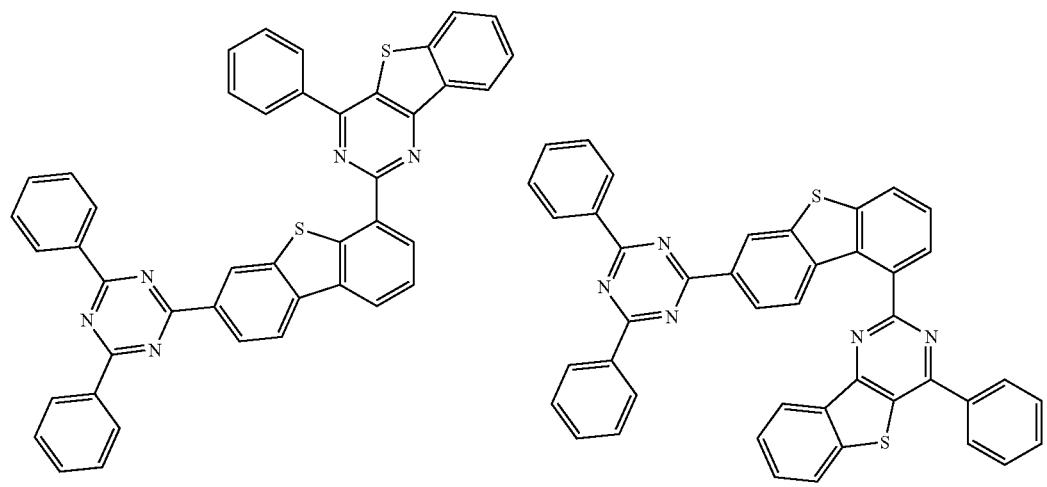
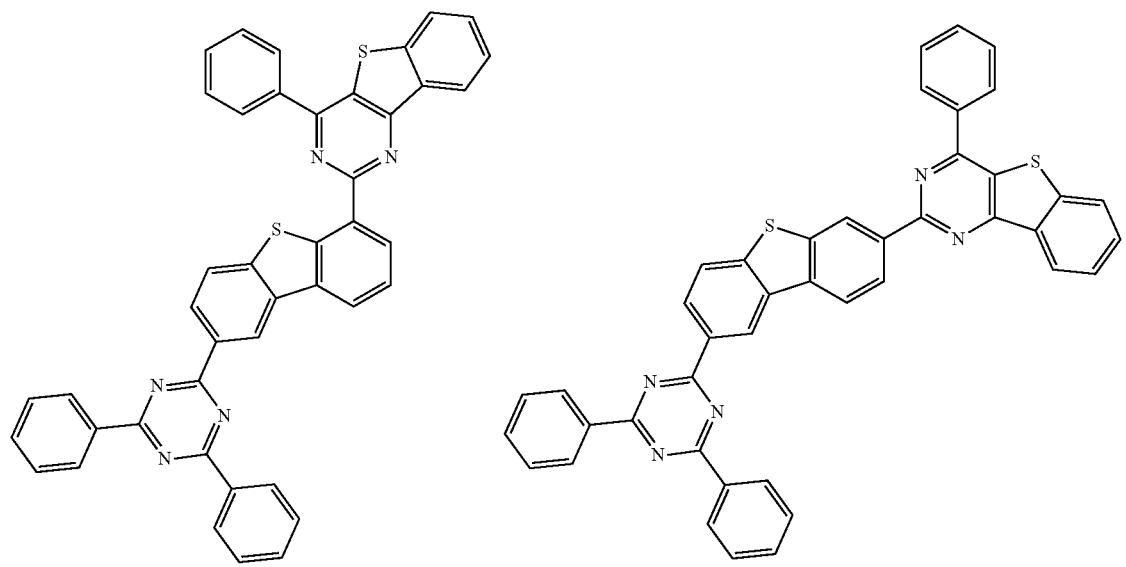

-continued
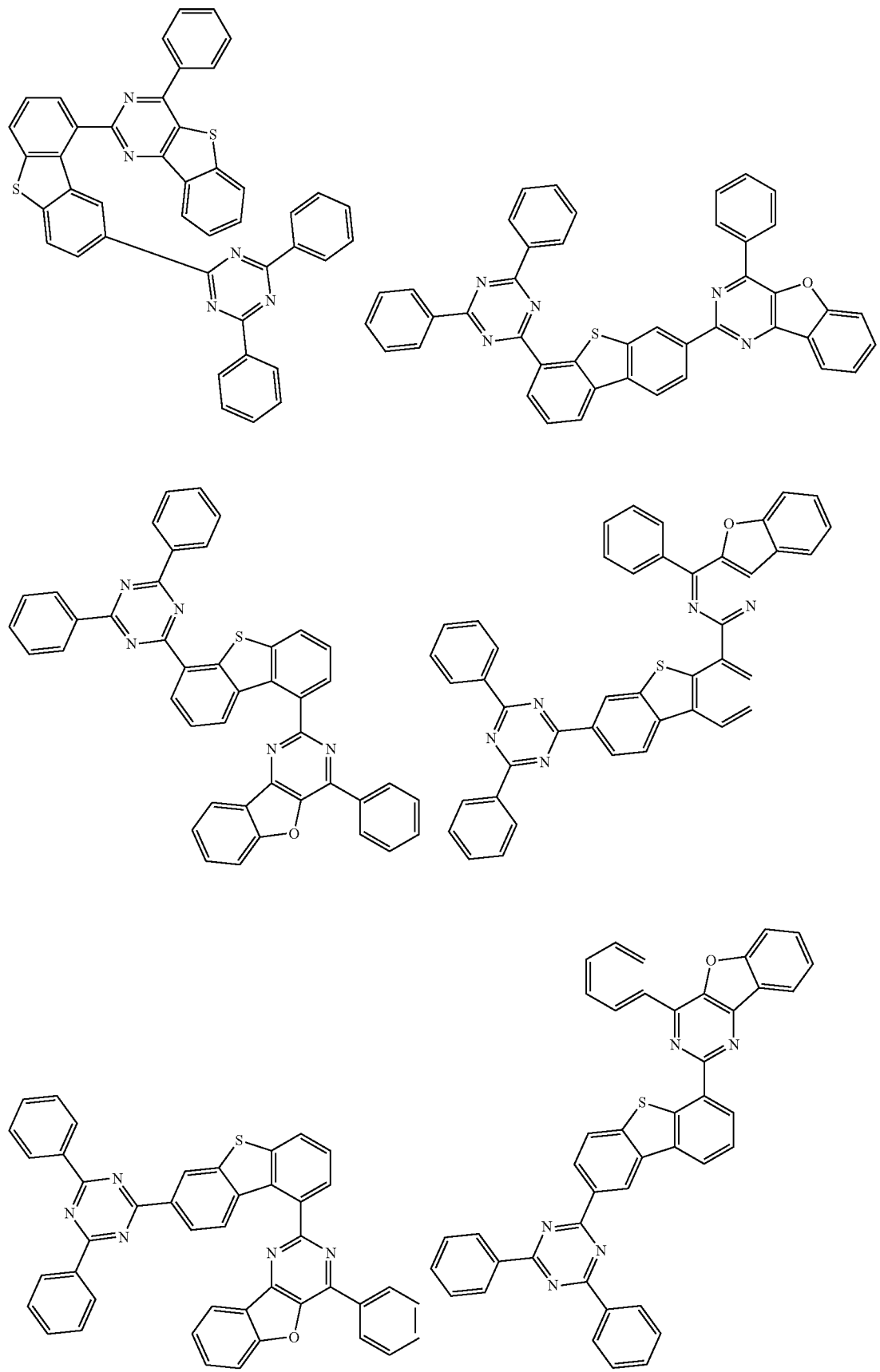

-continued
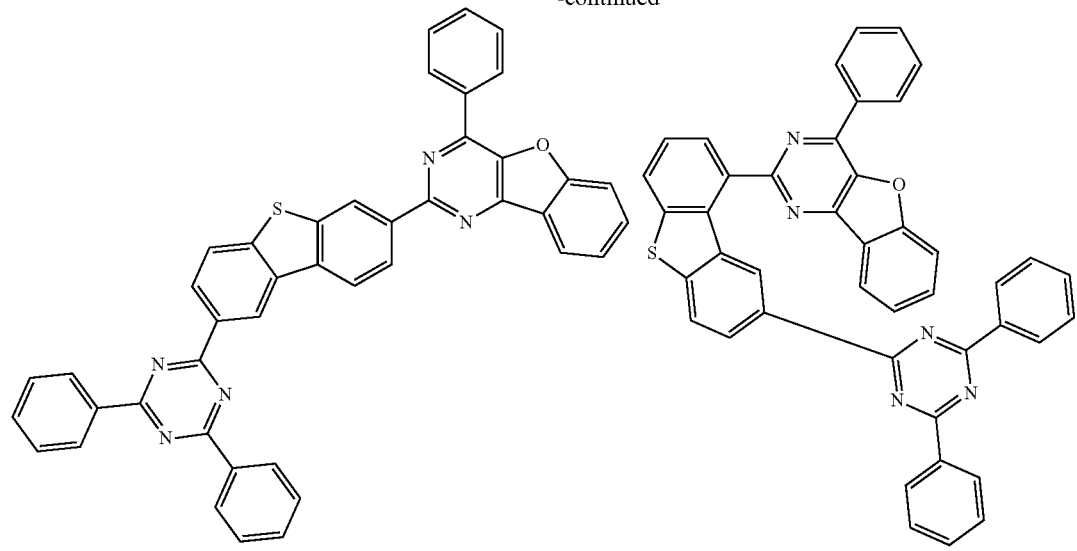

-continued
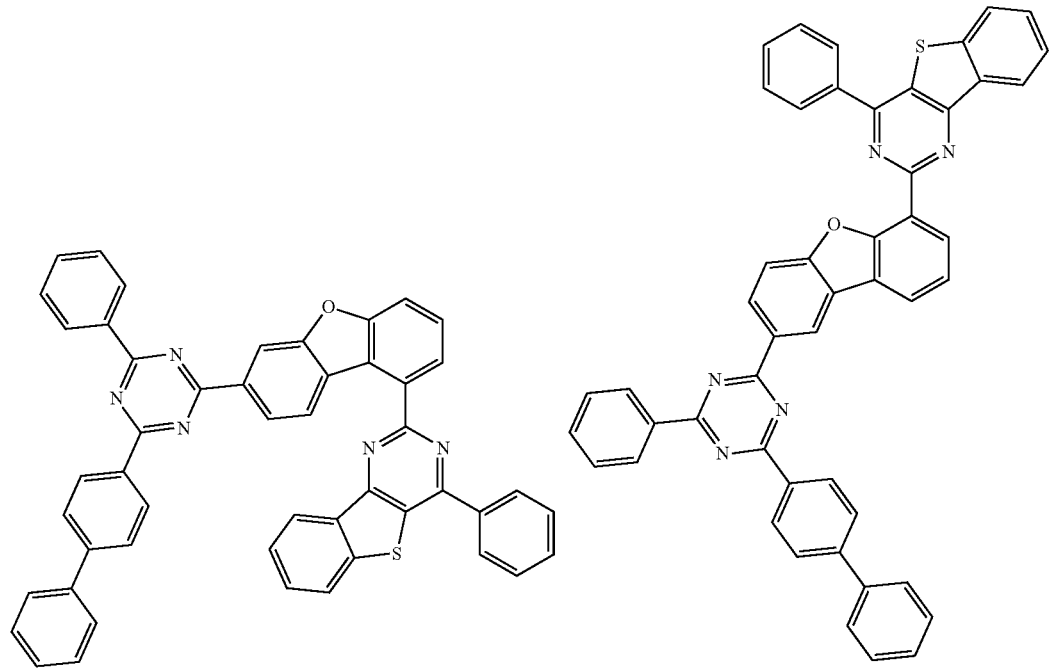
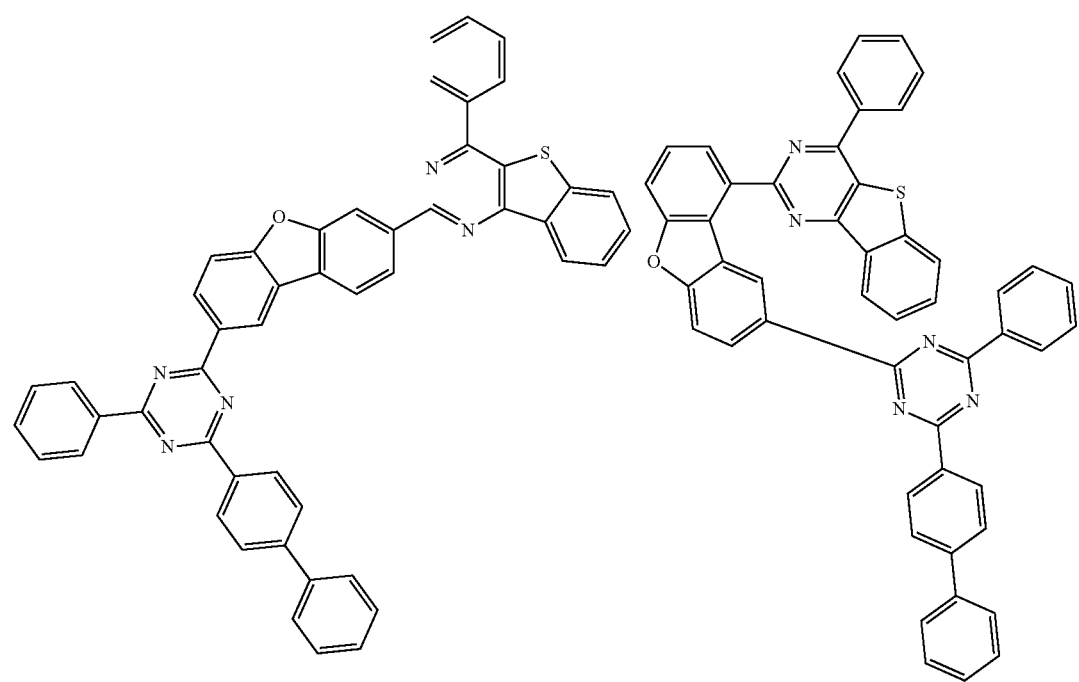

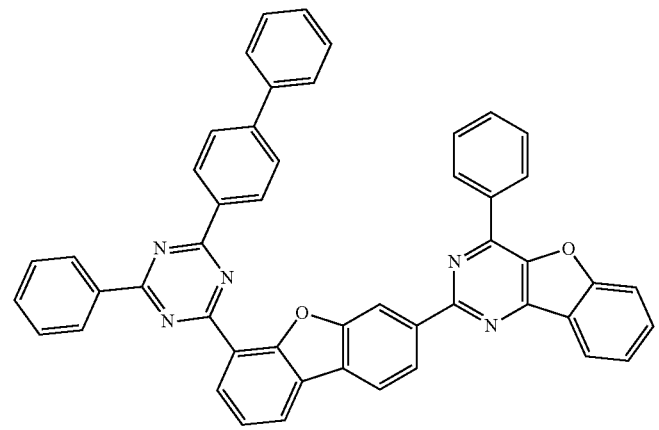
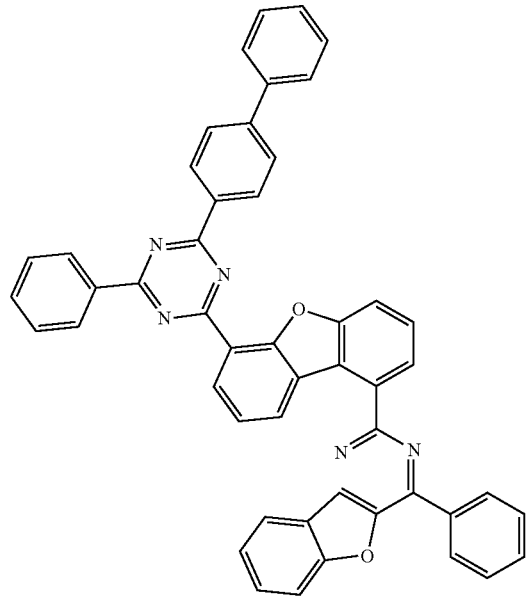
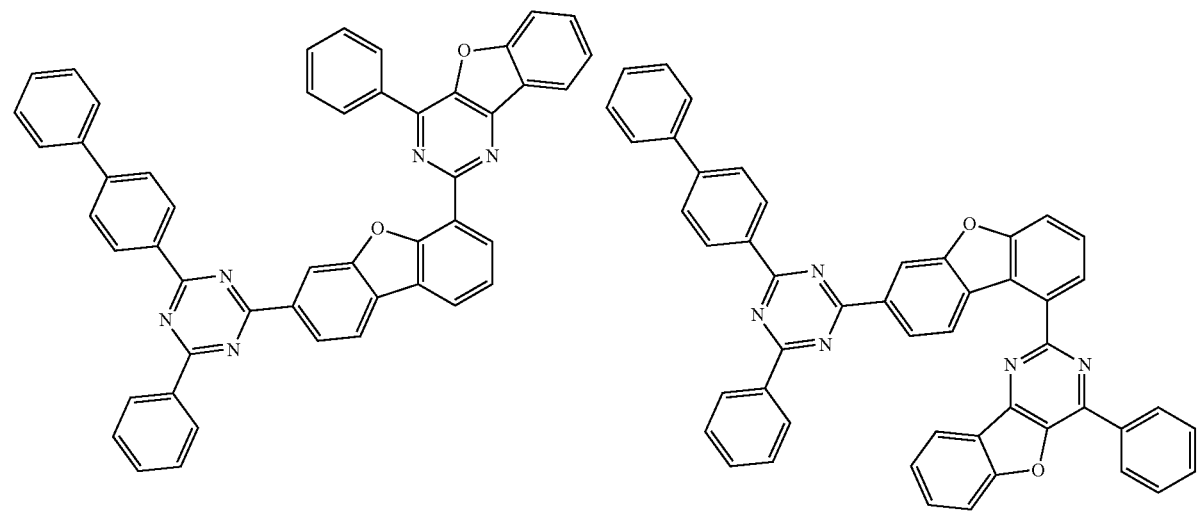

-continued
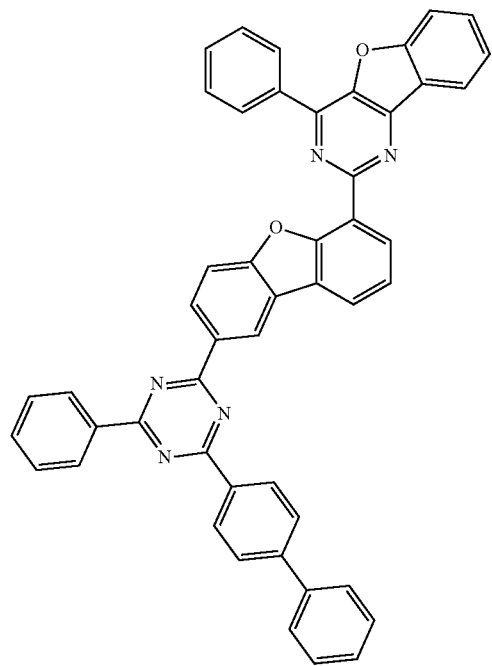
25
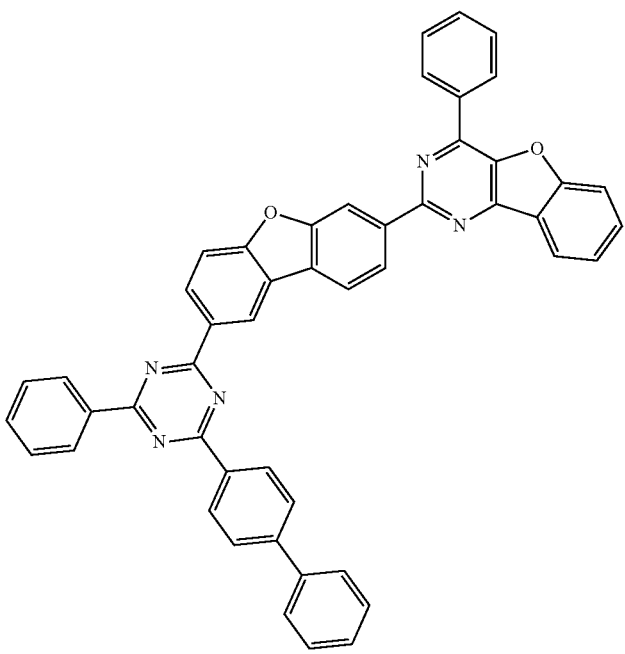
26
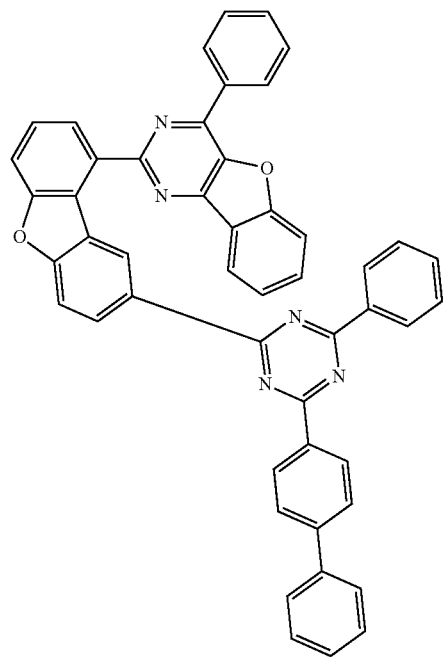
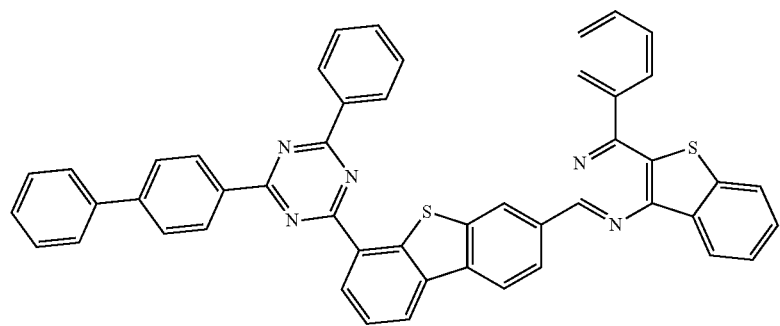

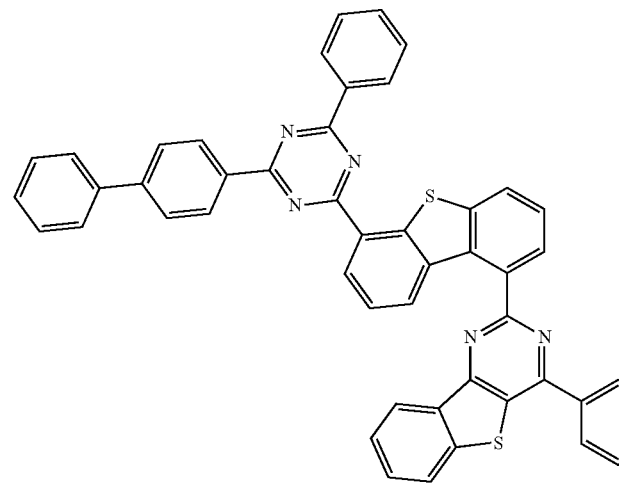
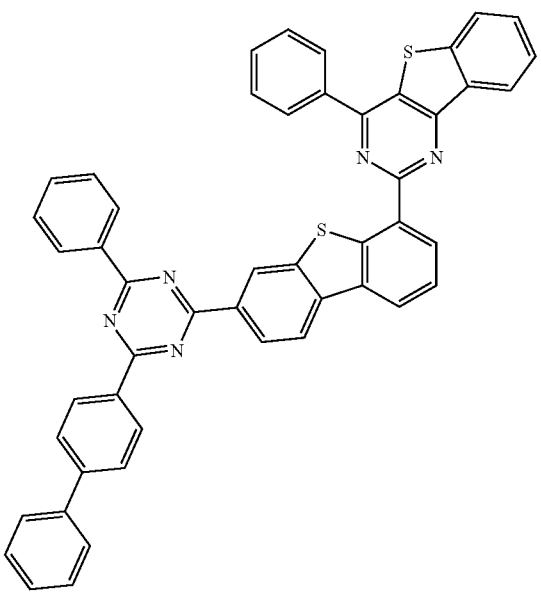
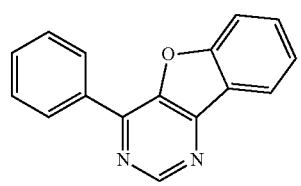
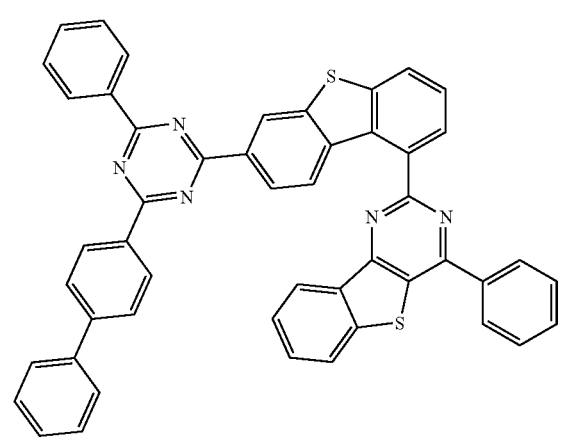

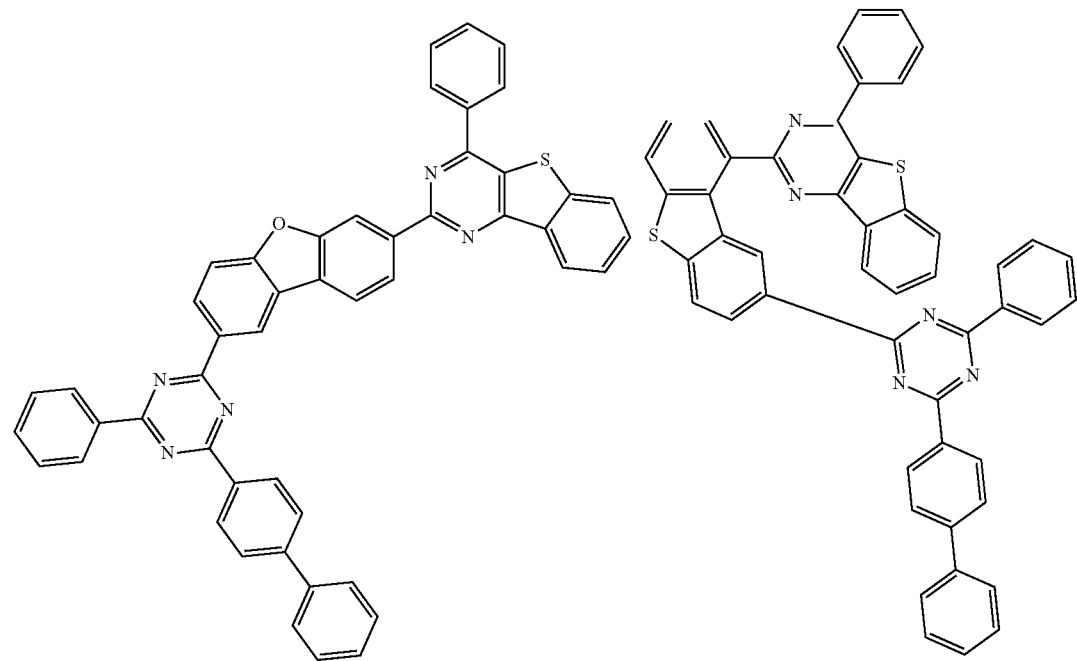
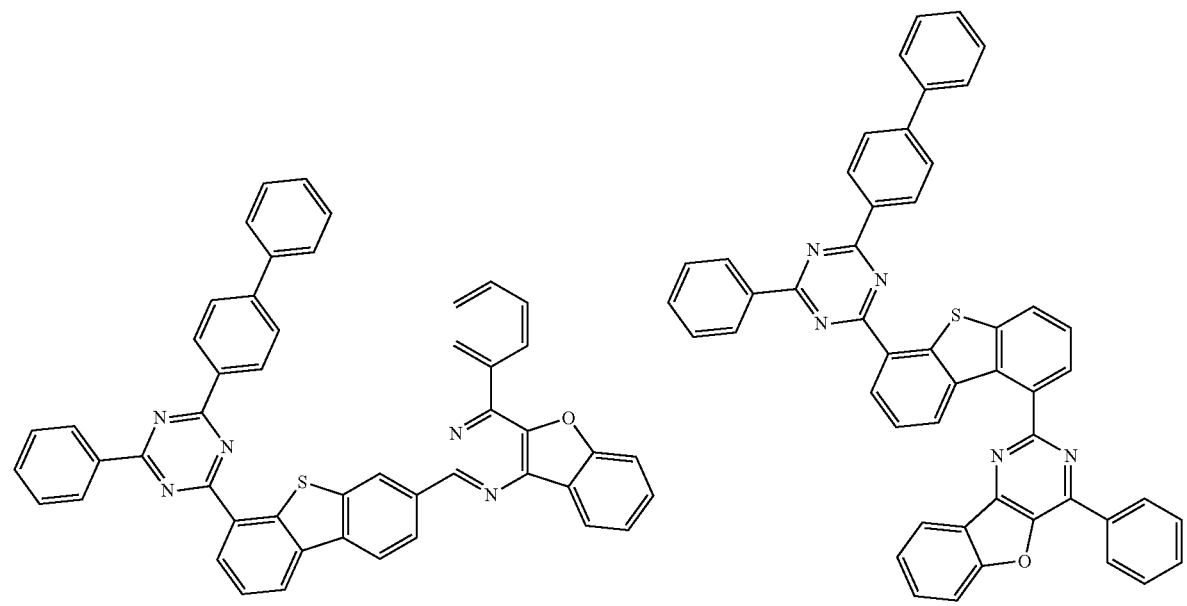

-continued
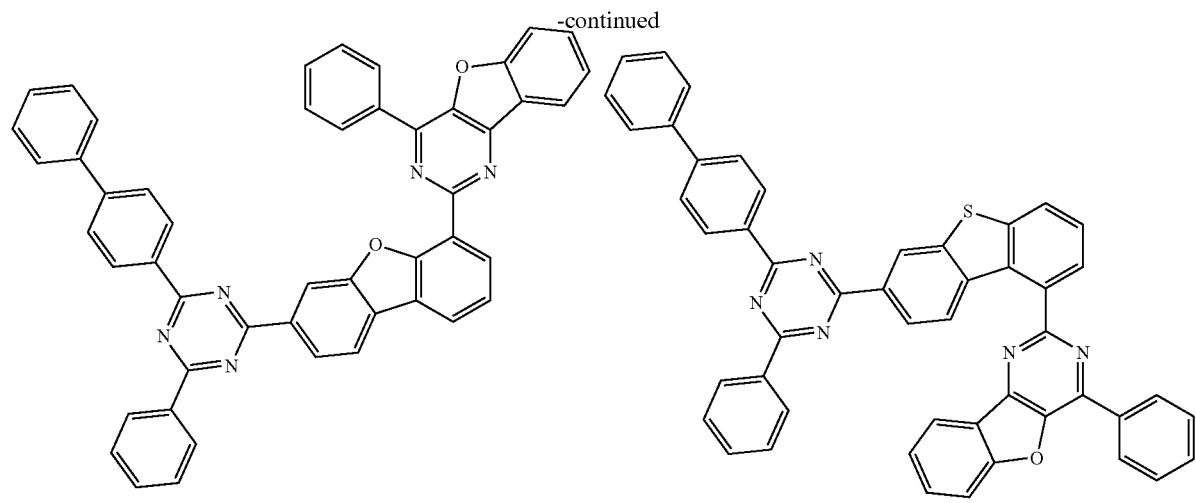
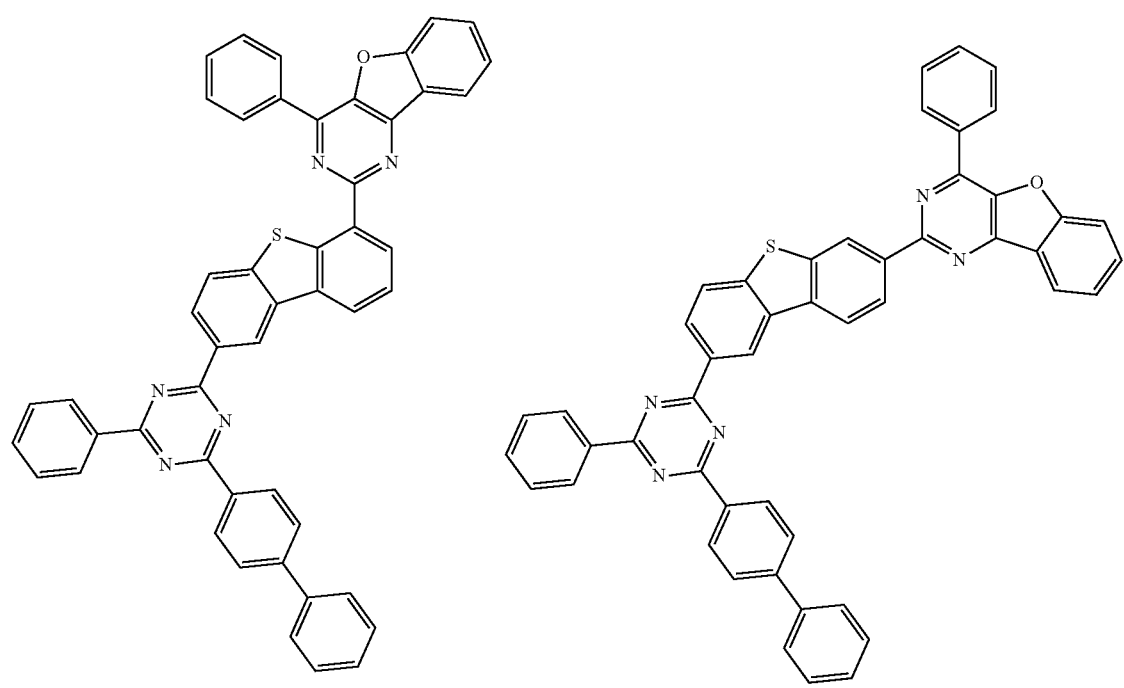

-continued
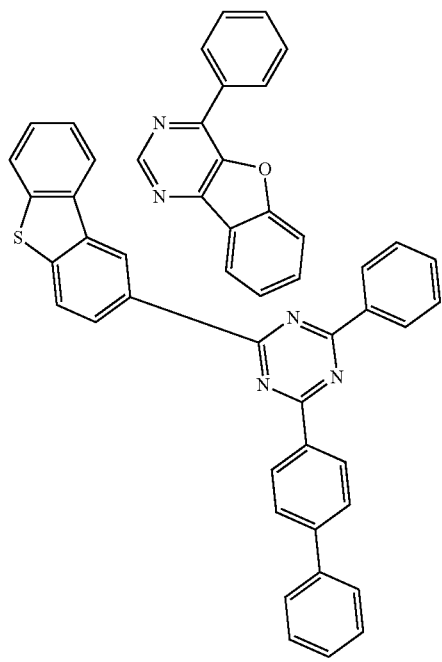
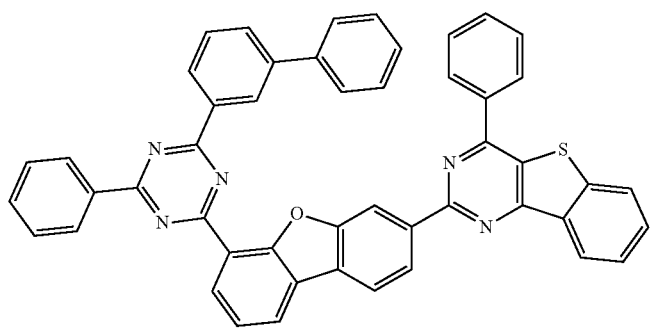
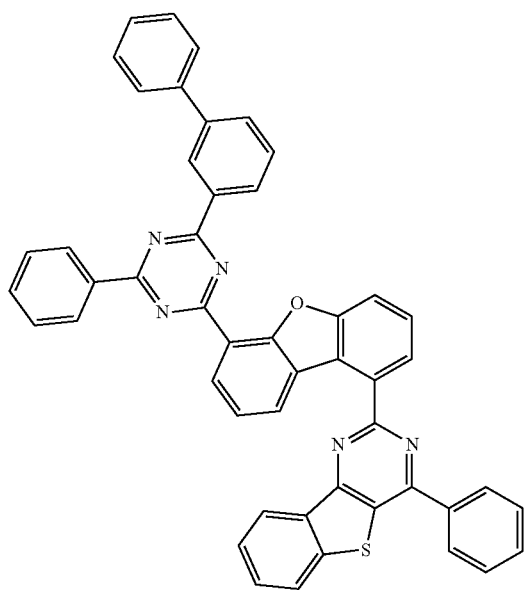
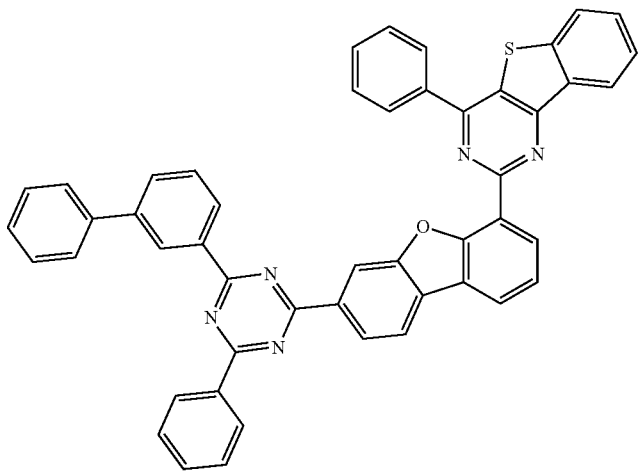
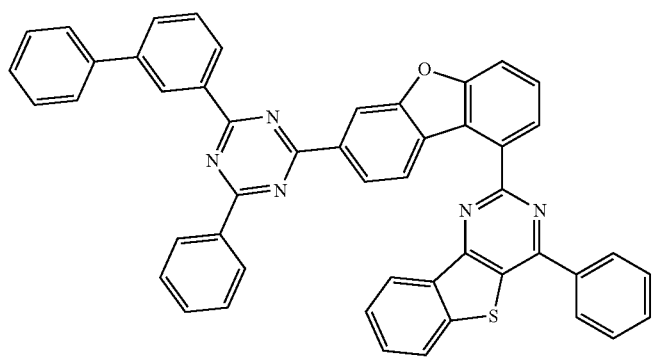

-continued
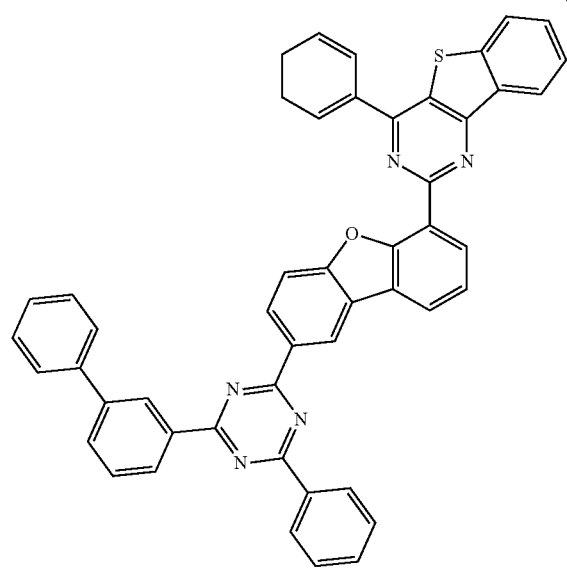
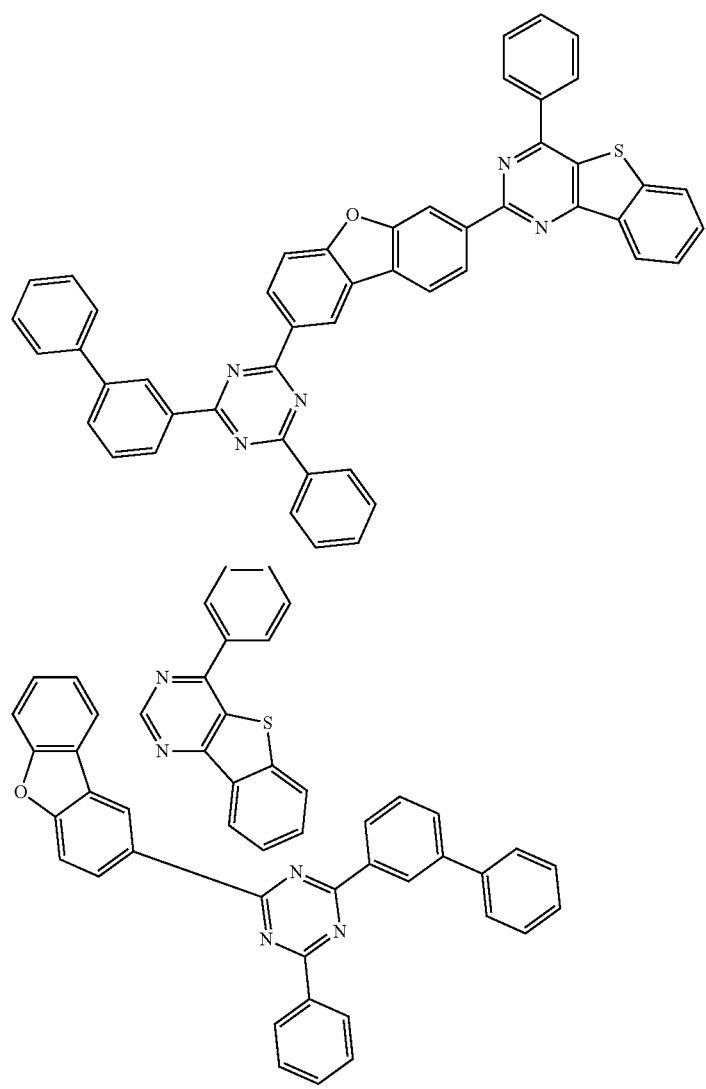

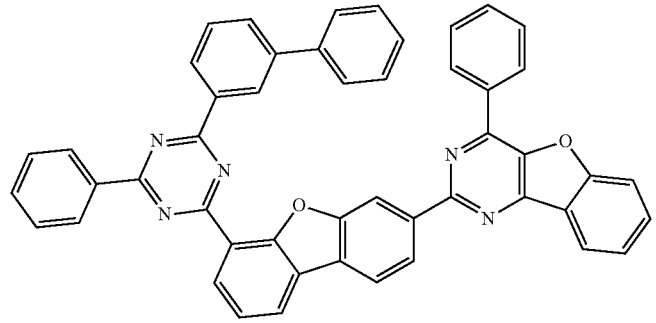
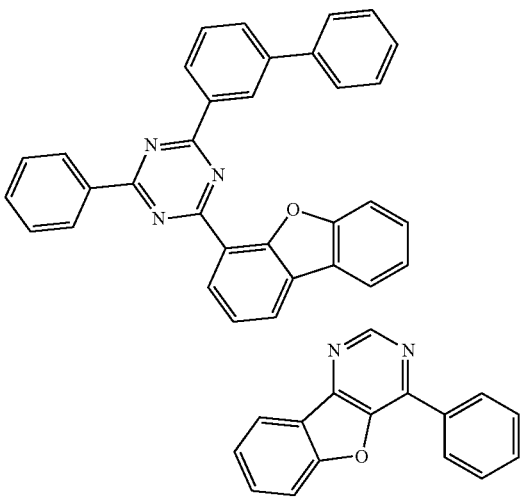
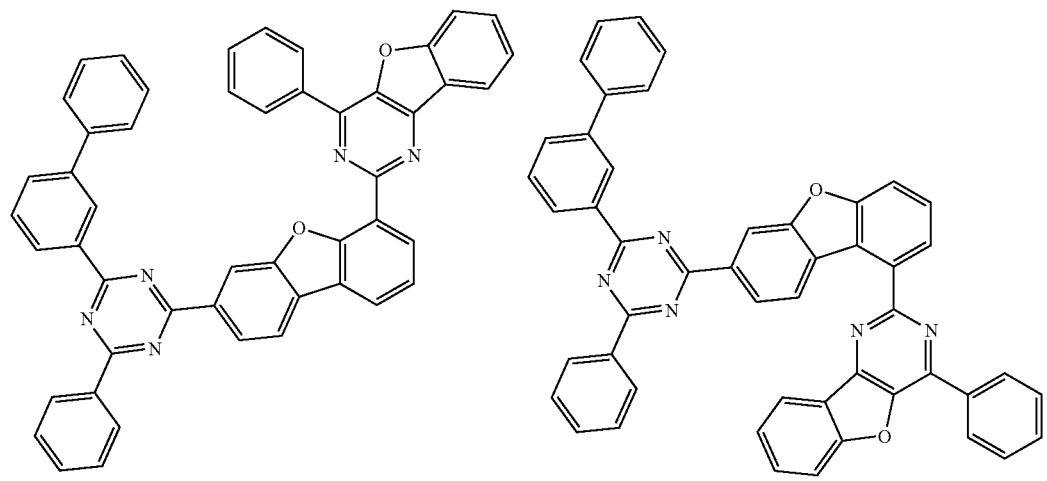
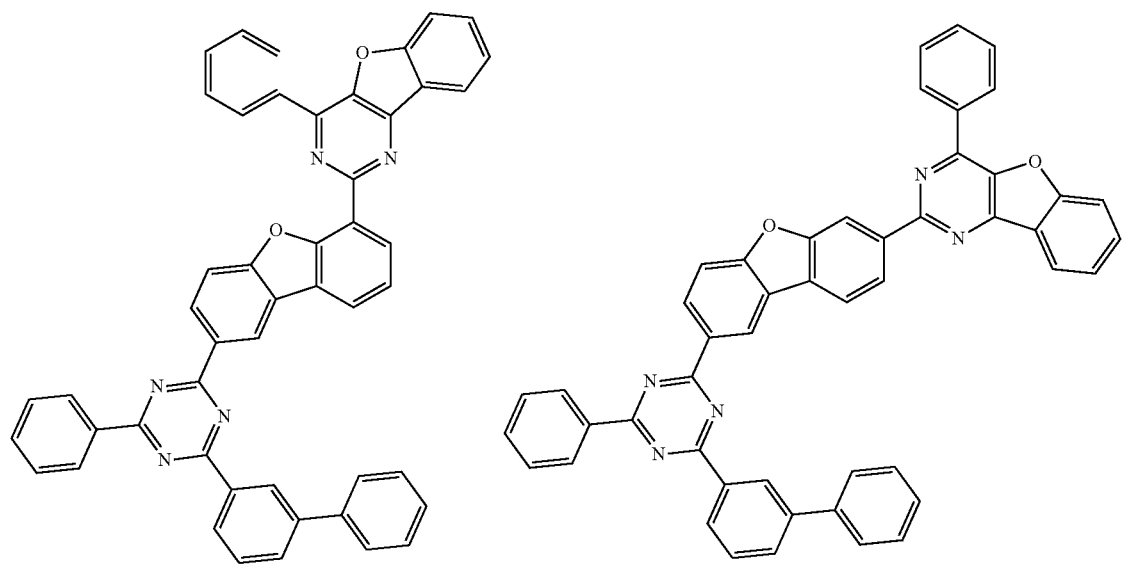

-continued
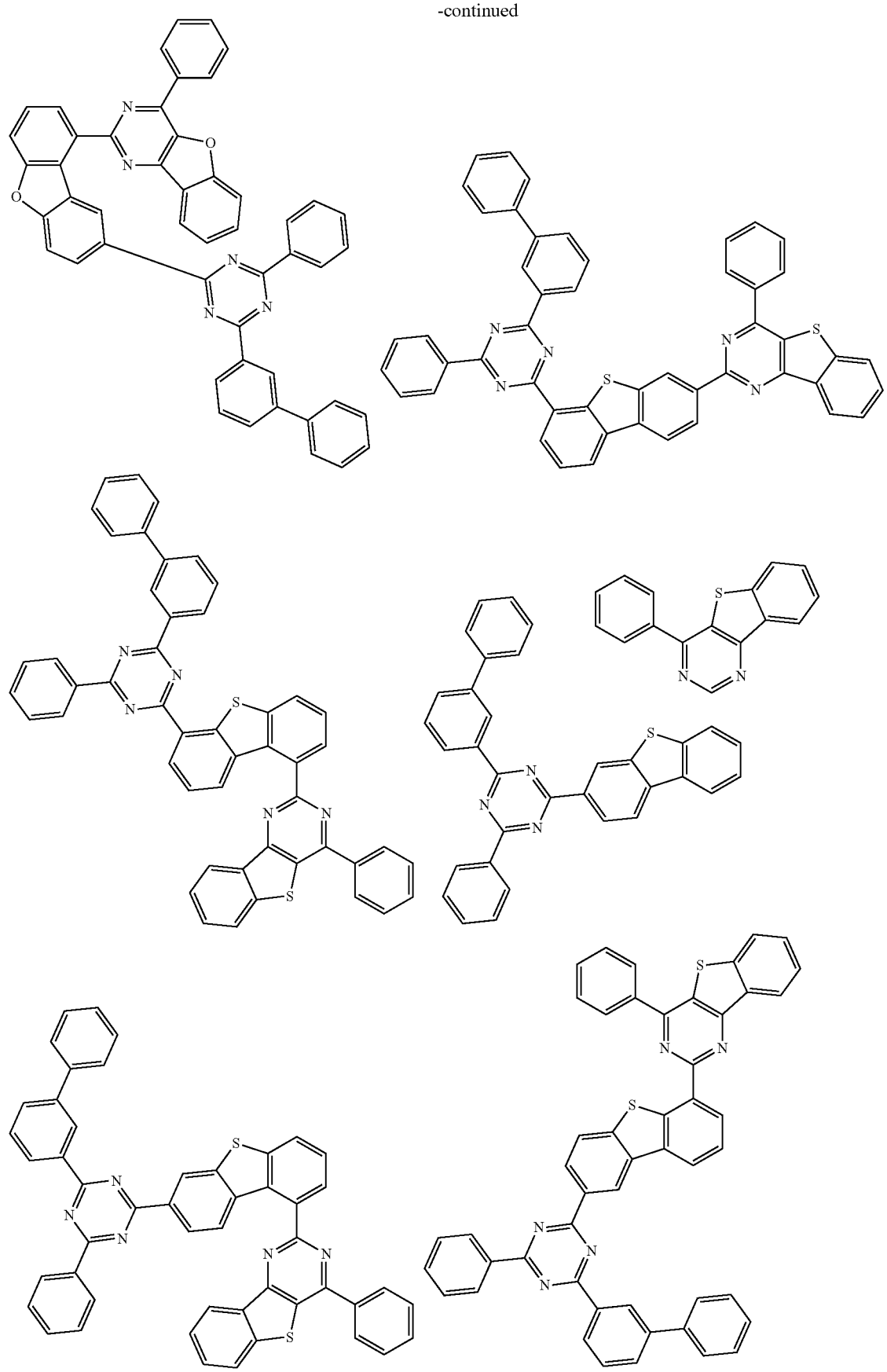

-continued
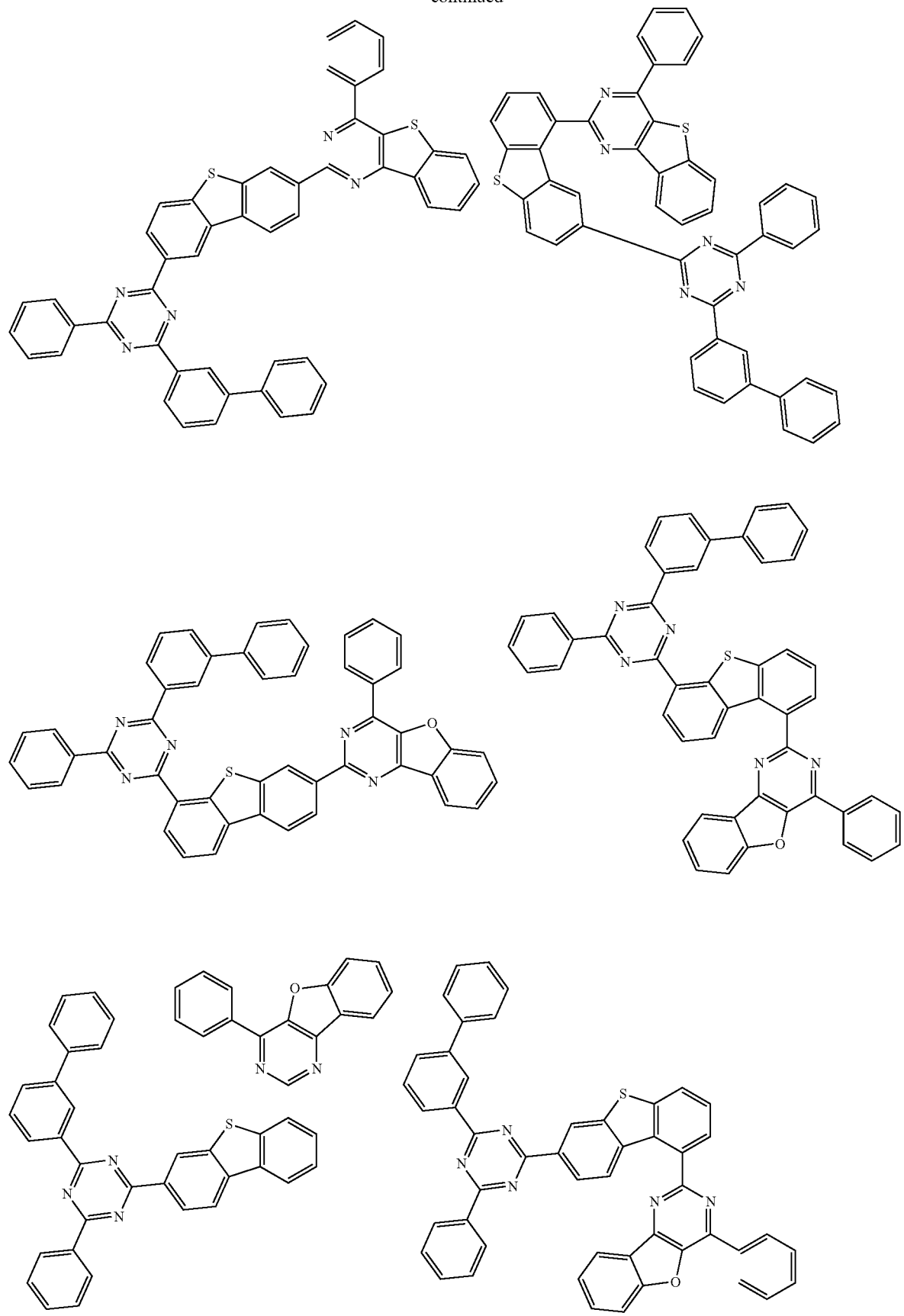

-continued
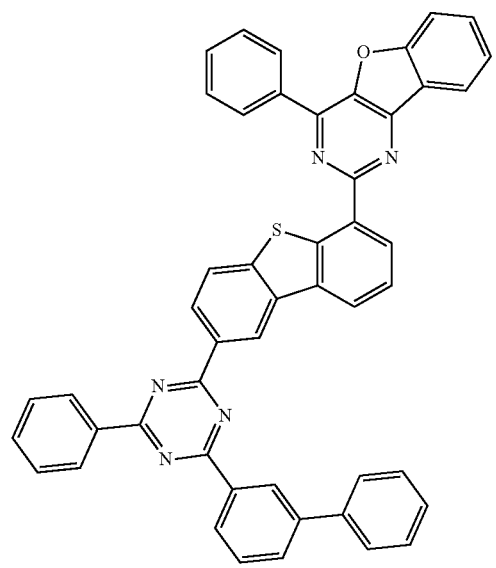
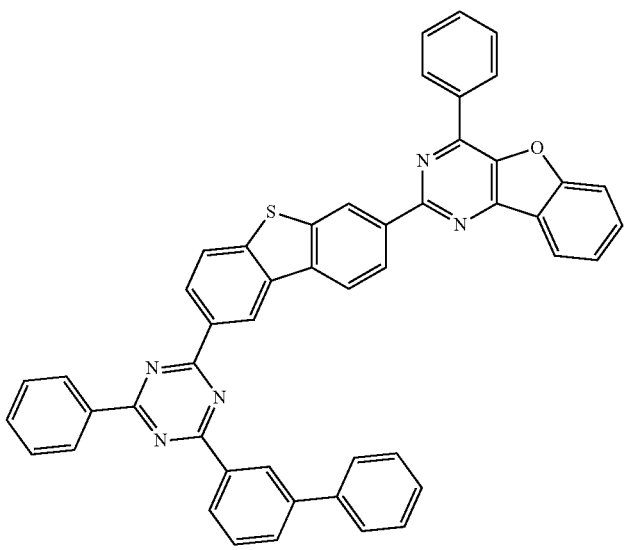
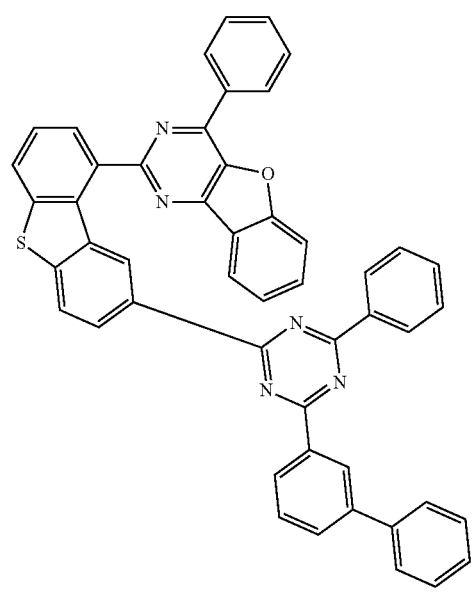
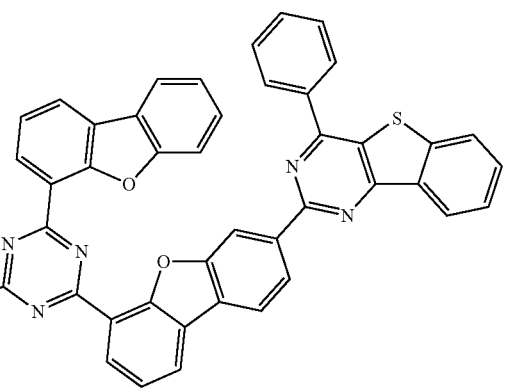
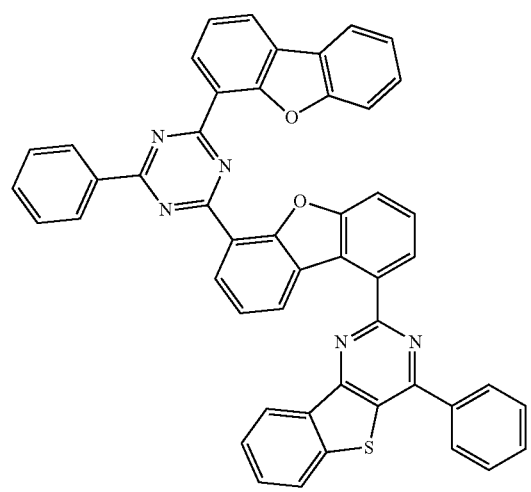
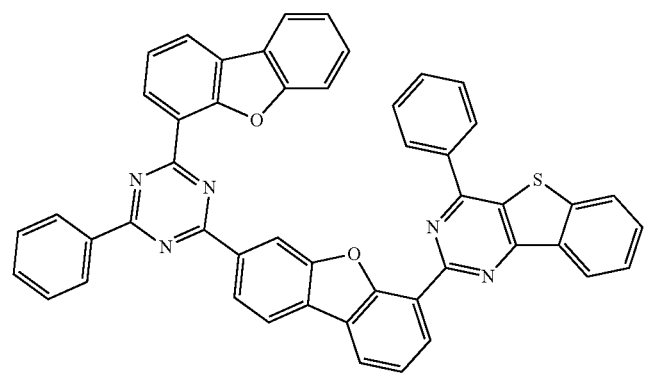

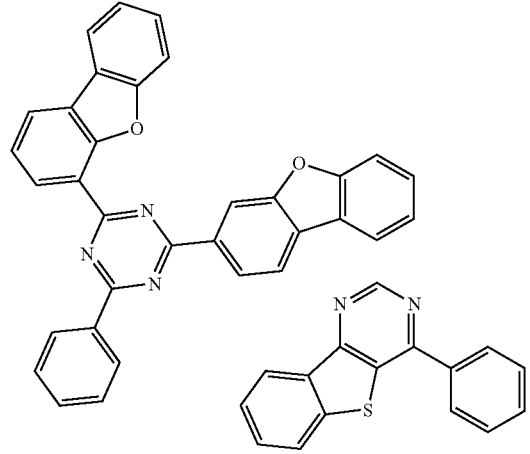
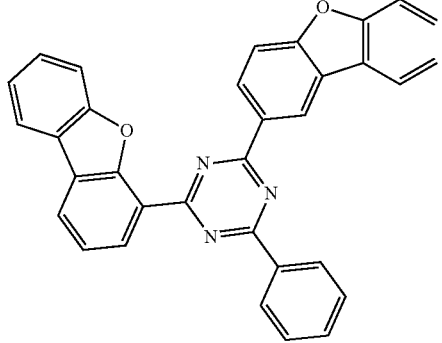
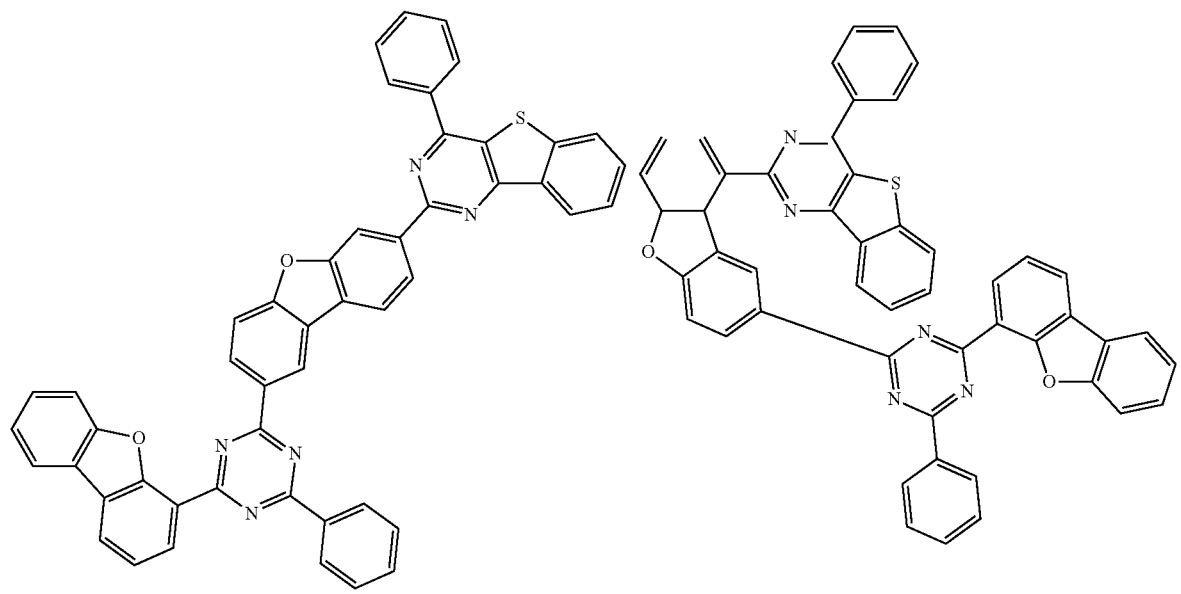
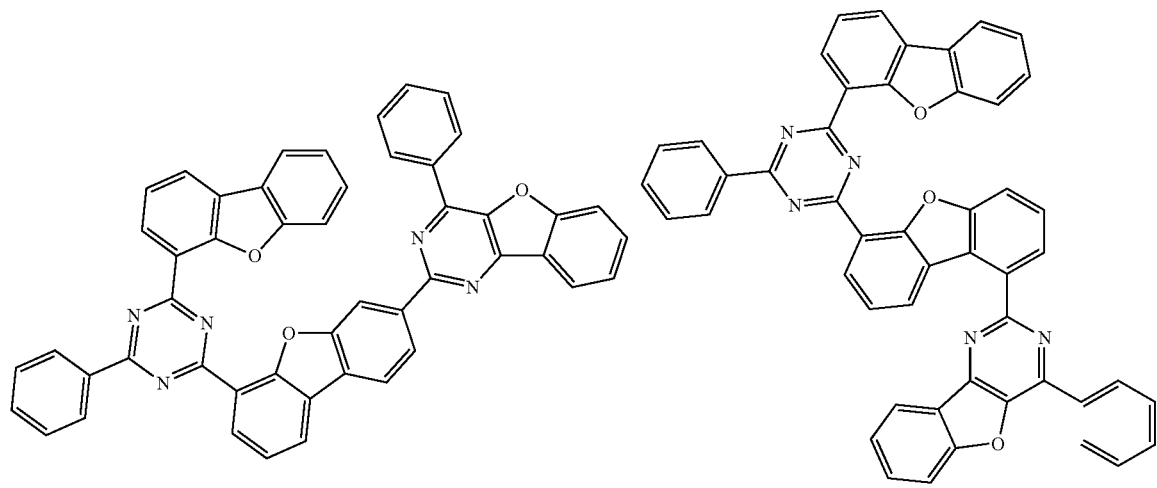

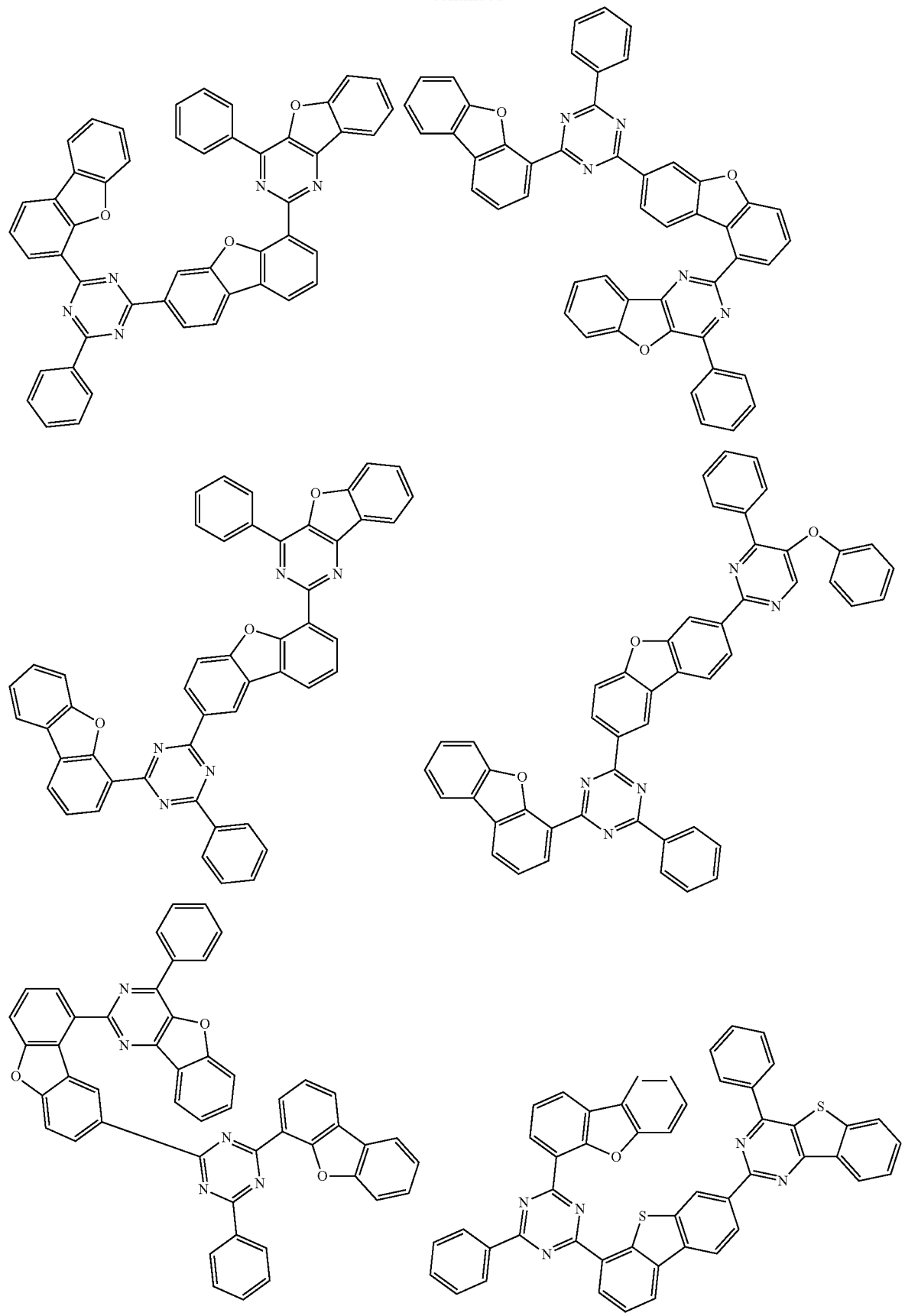

-continued
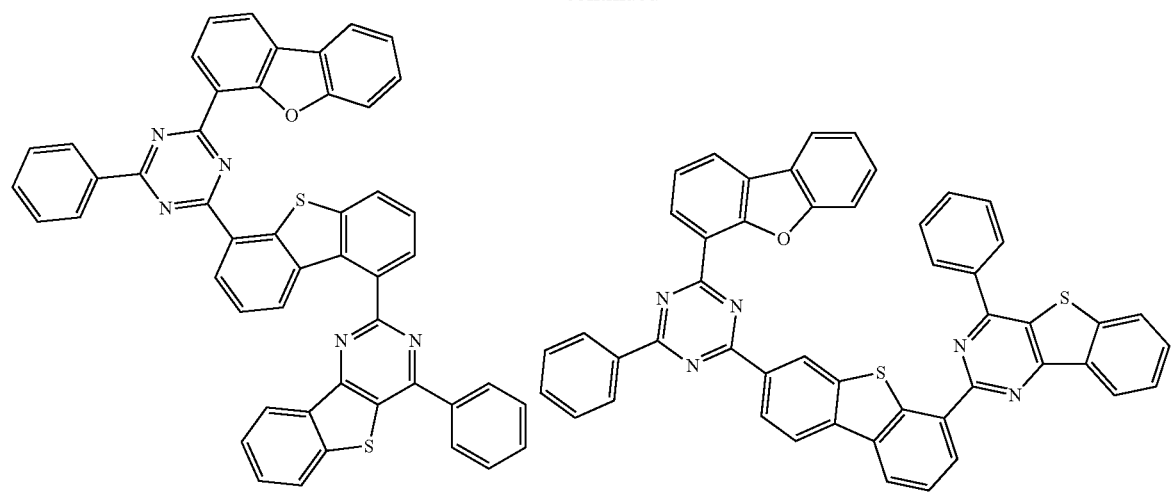
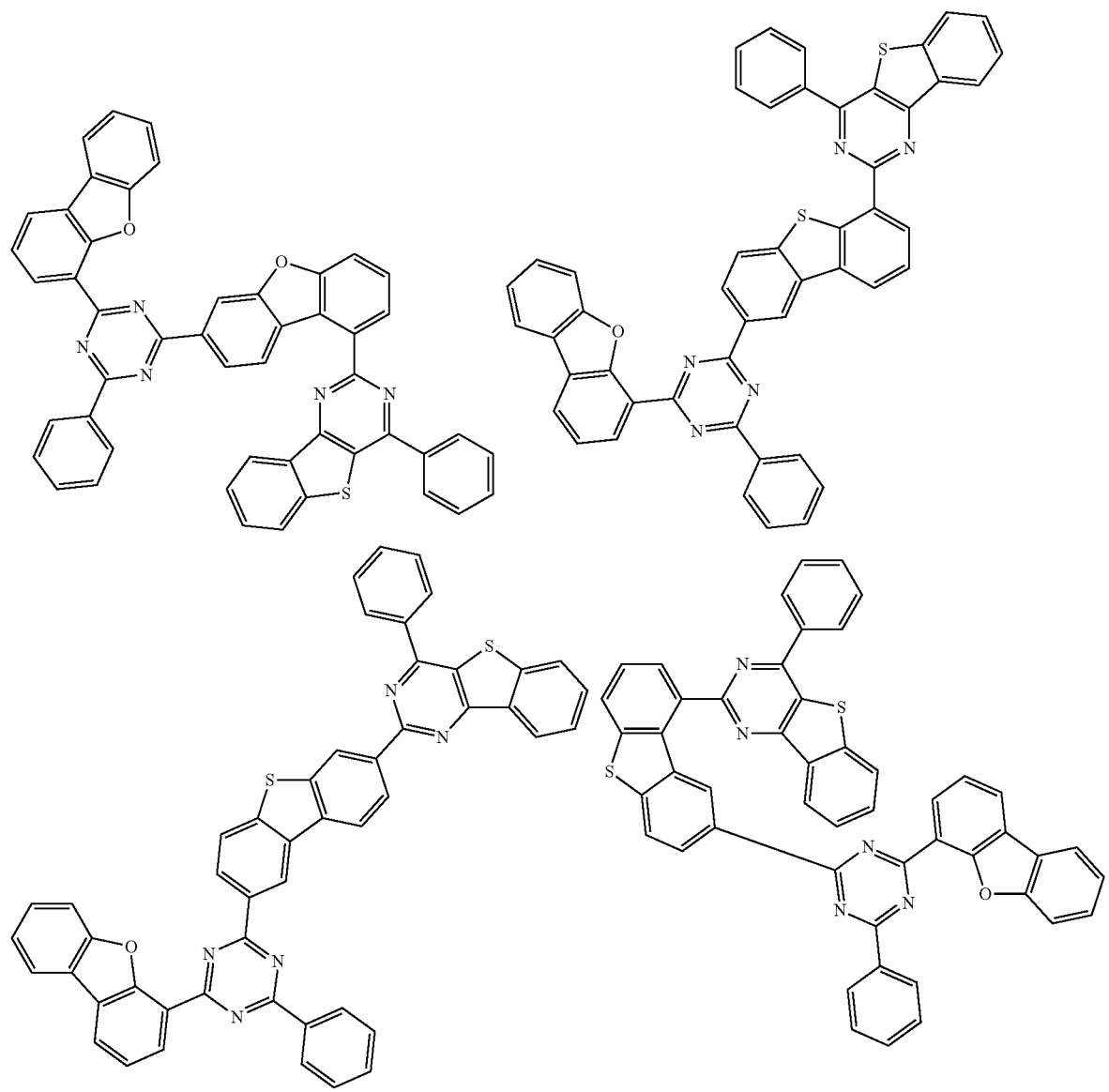

-continued
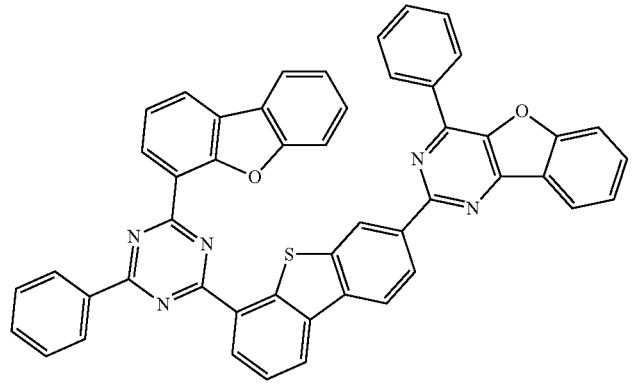
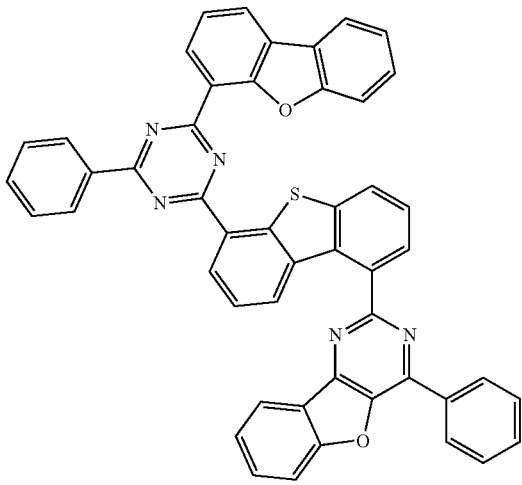
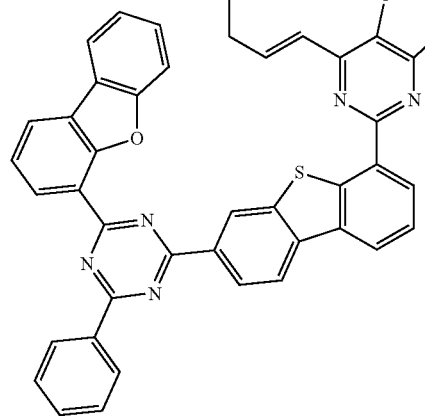
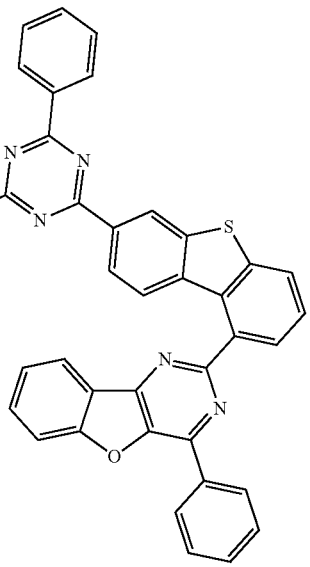
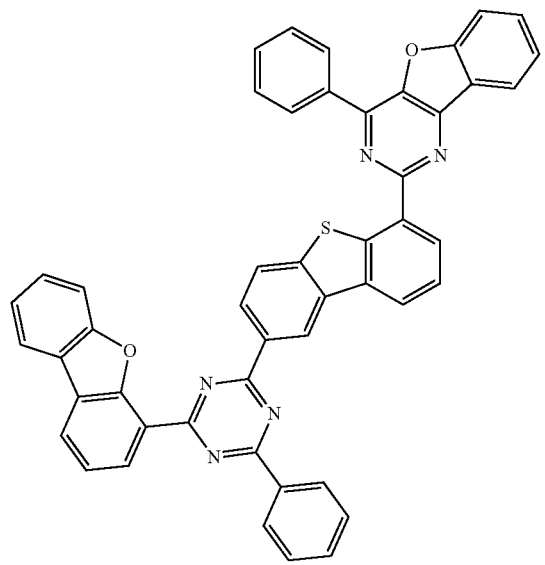
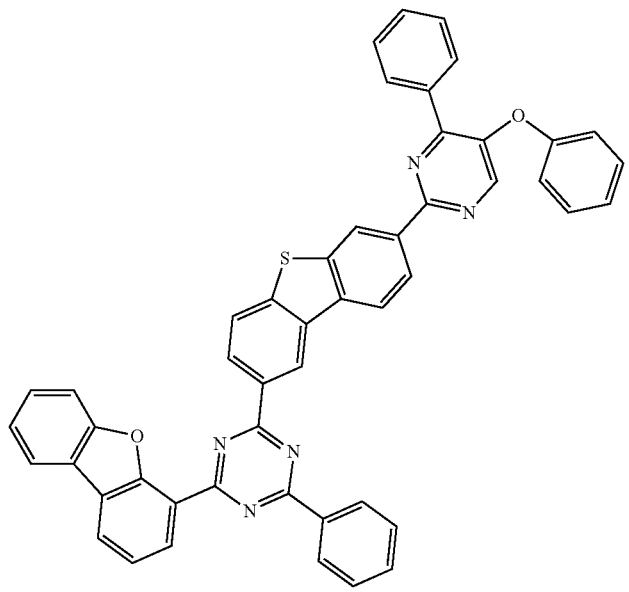

-continued
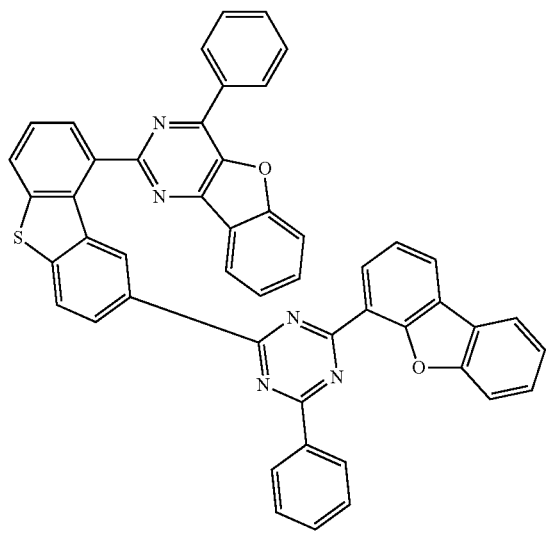
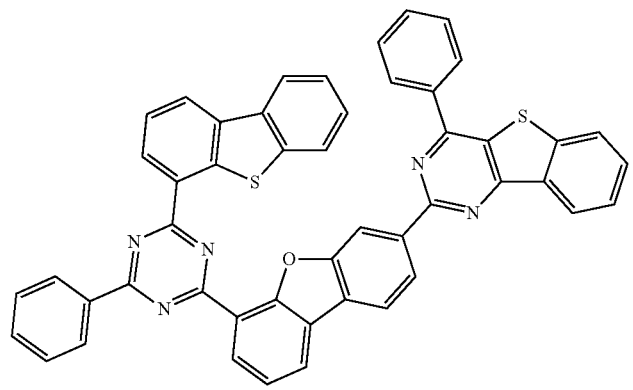
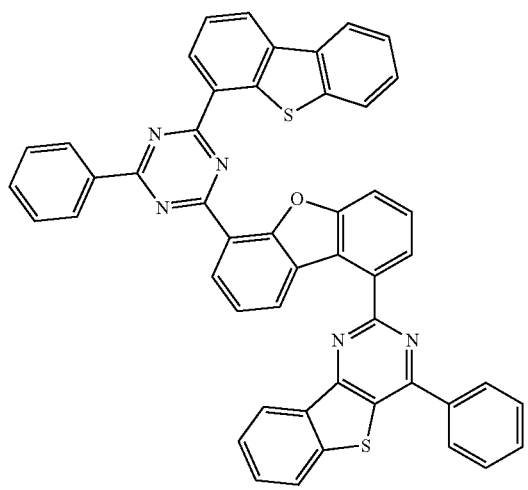
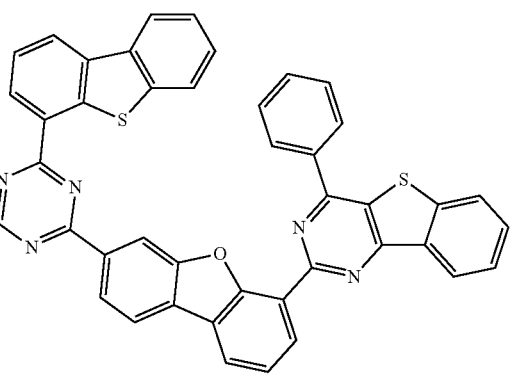
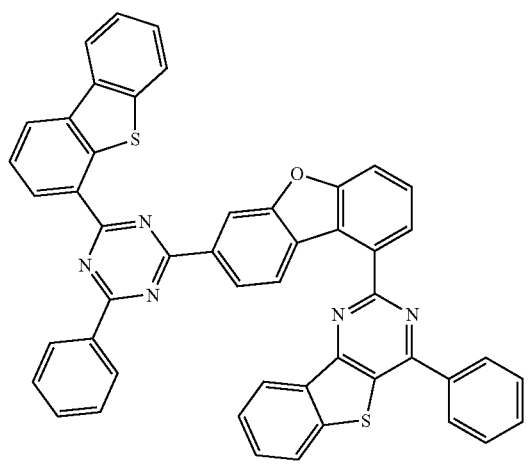
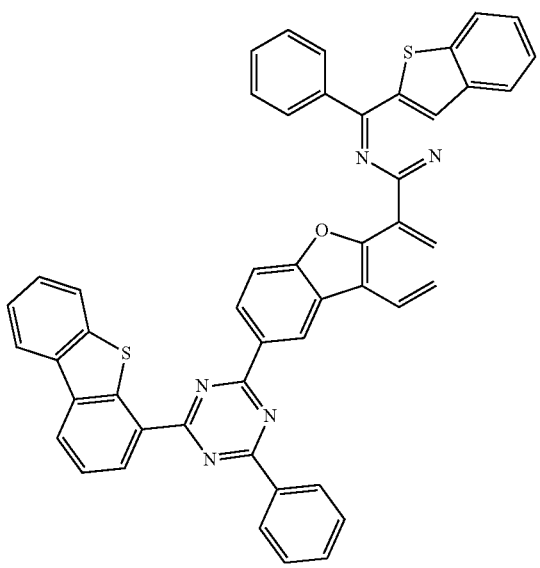

-continued
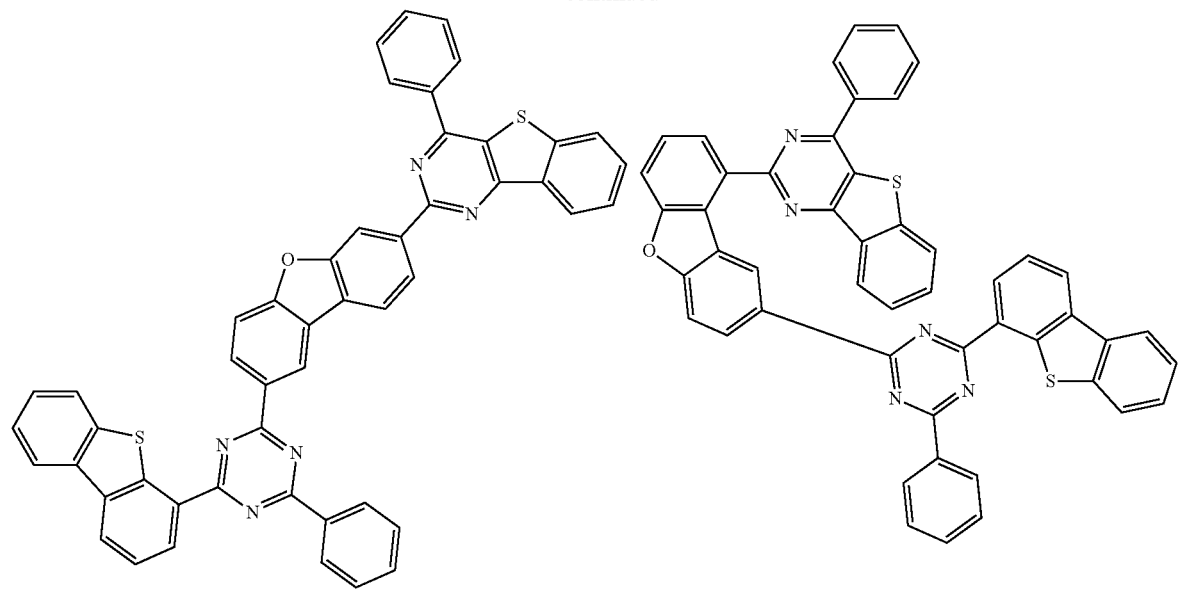
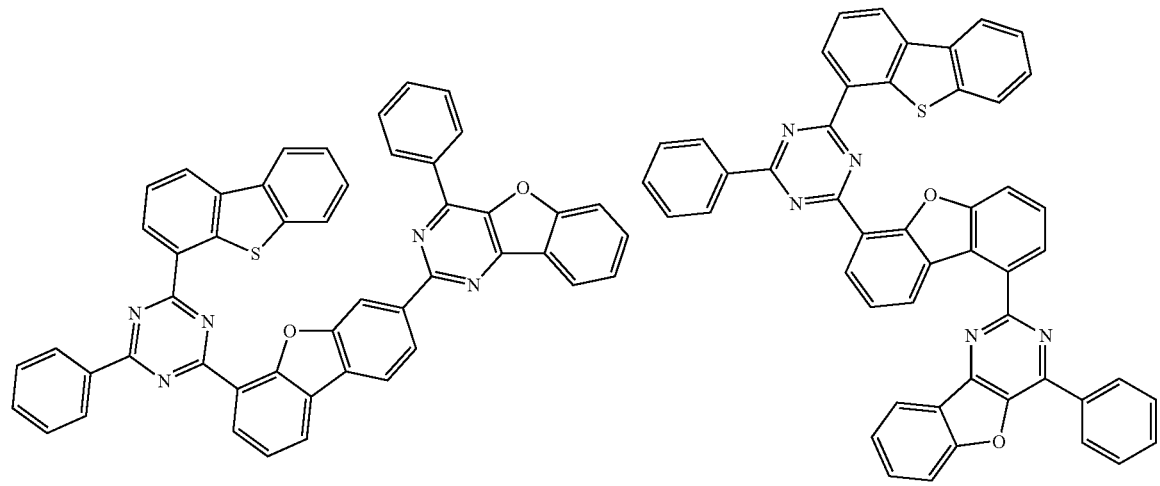
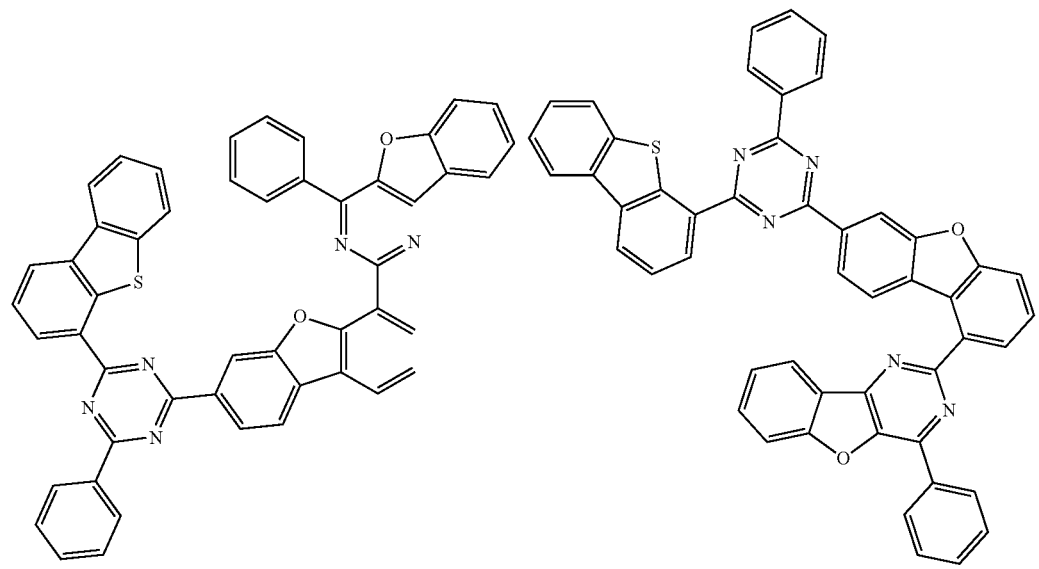

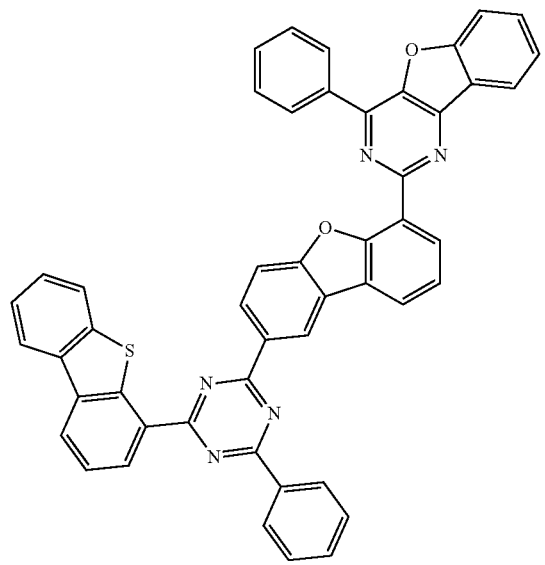
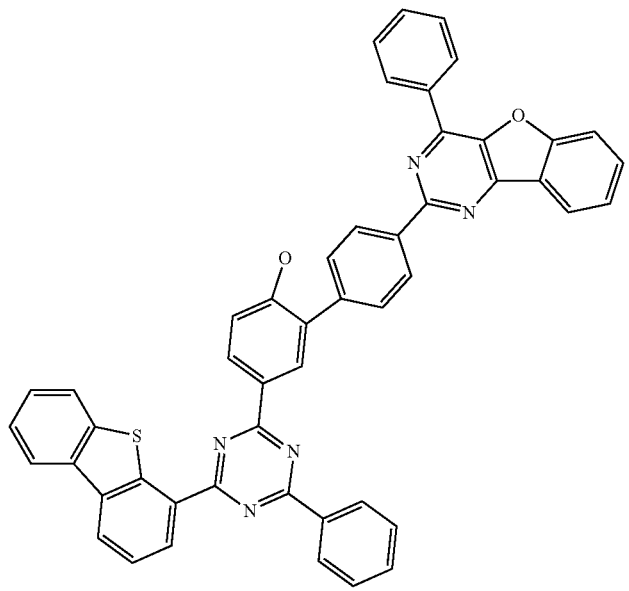
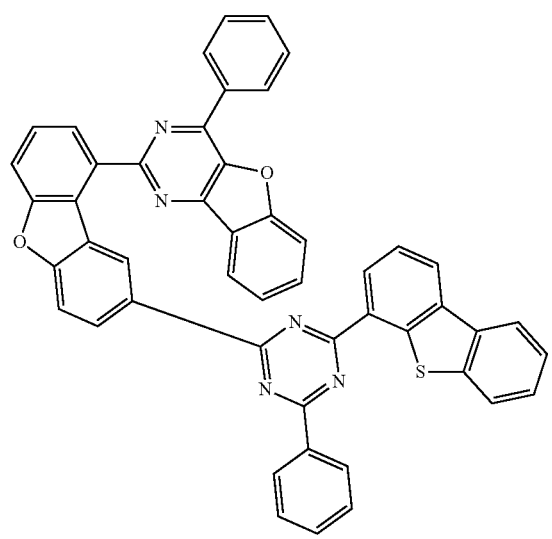
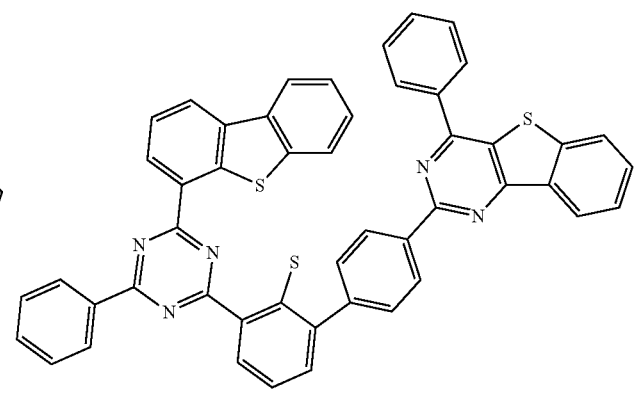
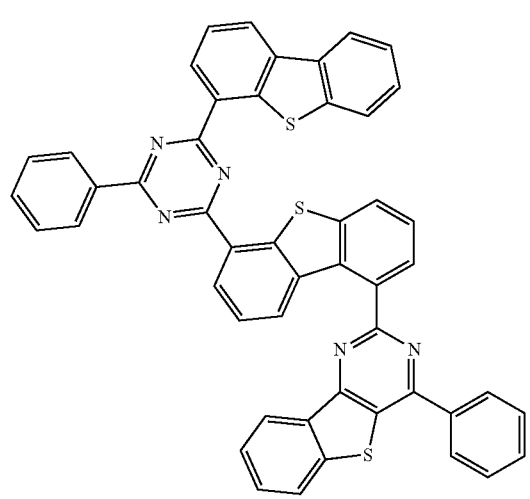
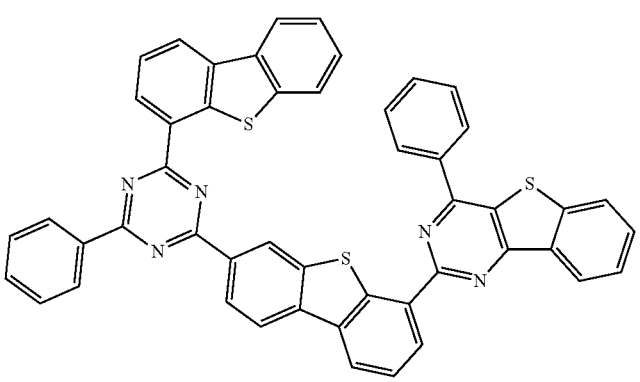

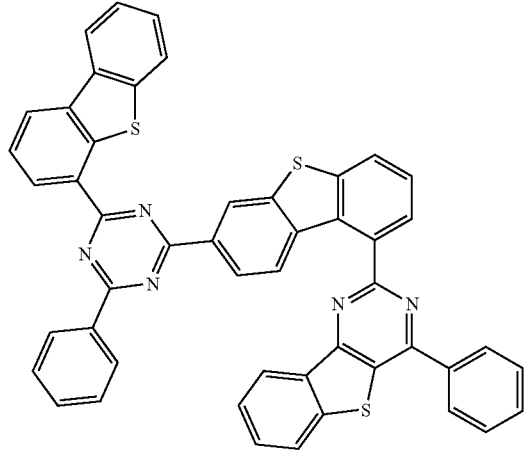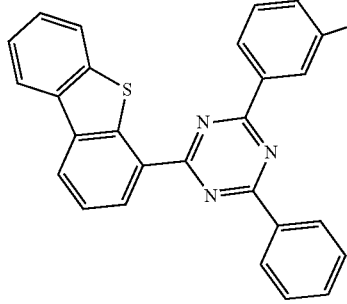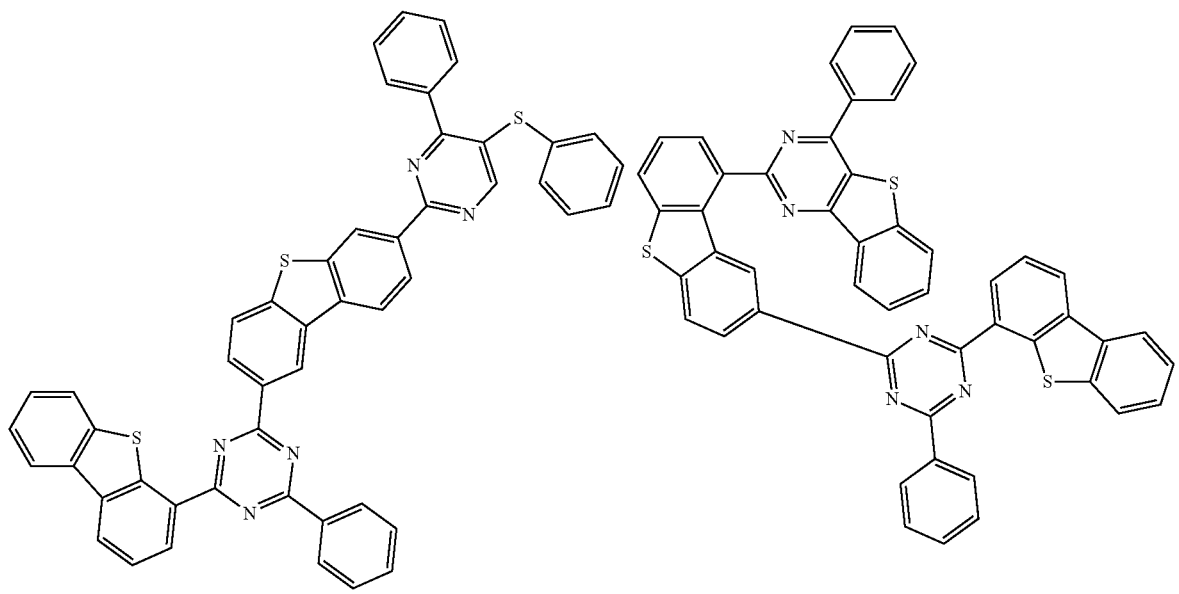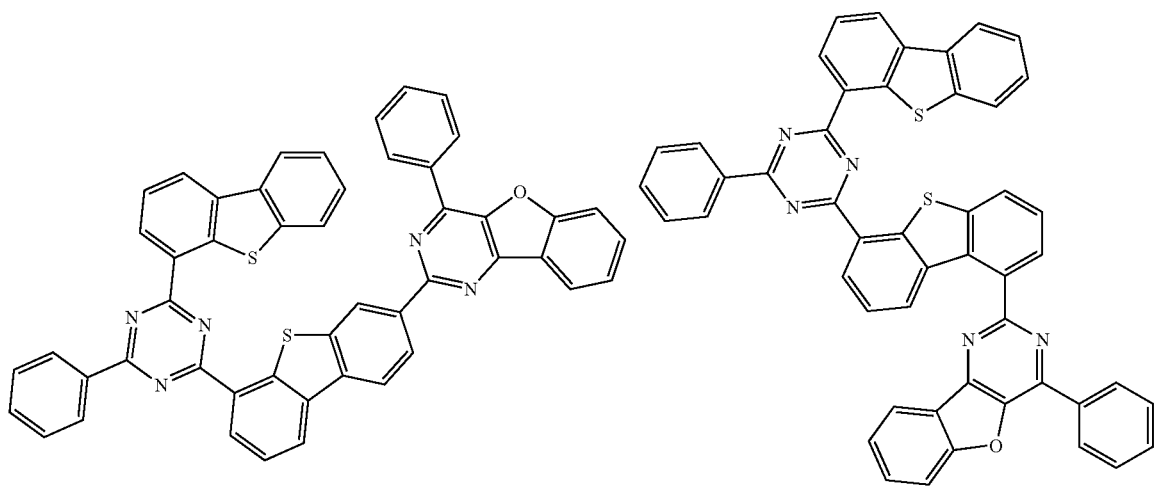

-continued
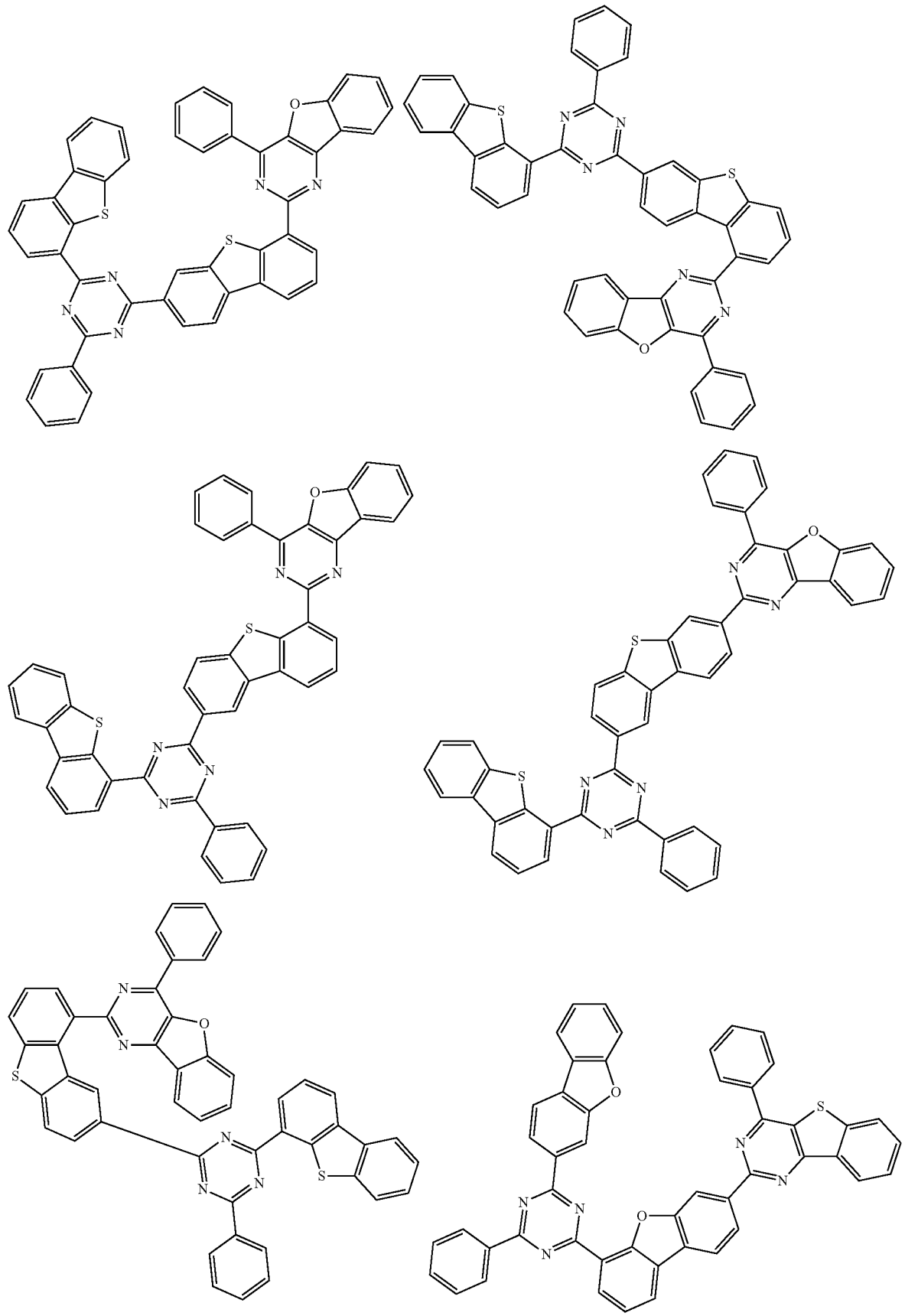

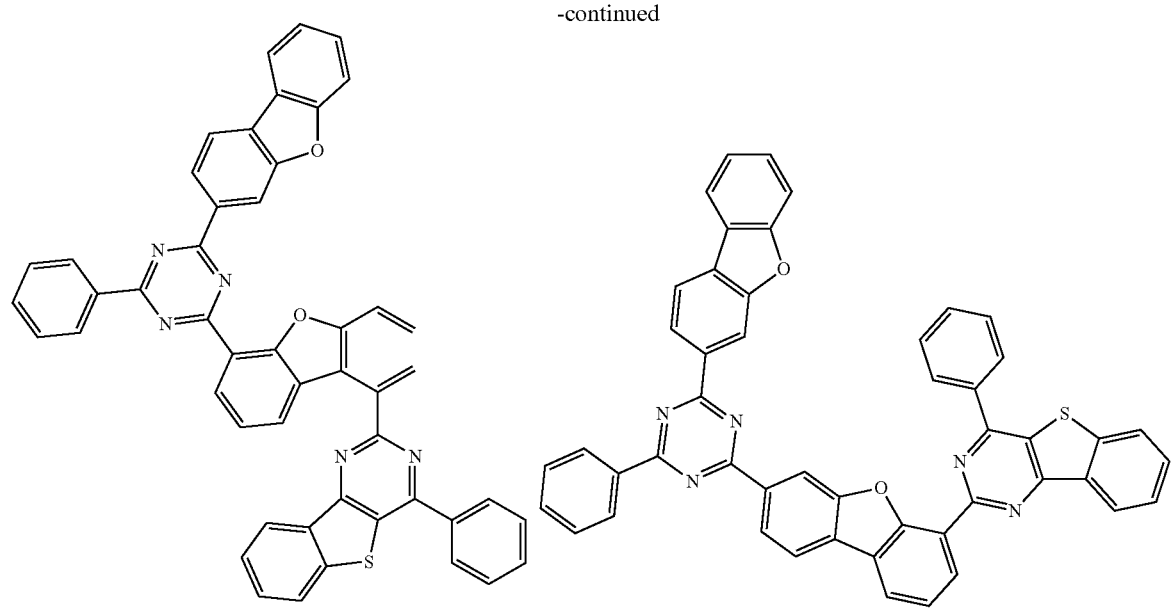
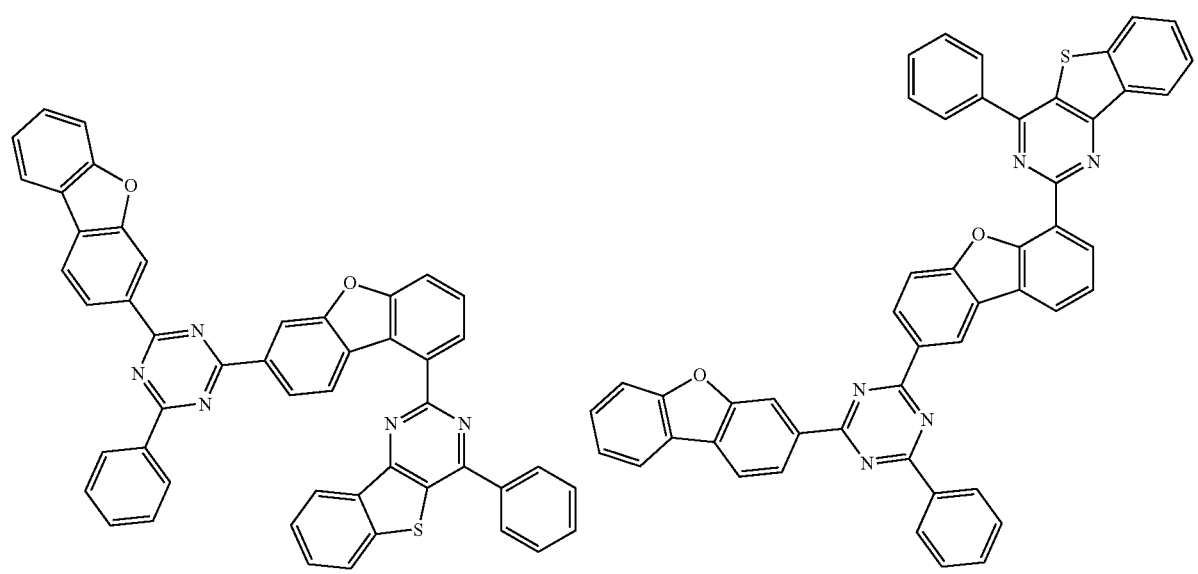

-continued
65
66
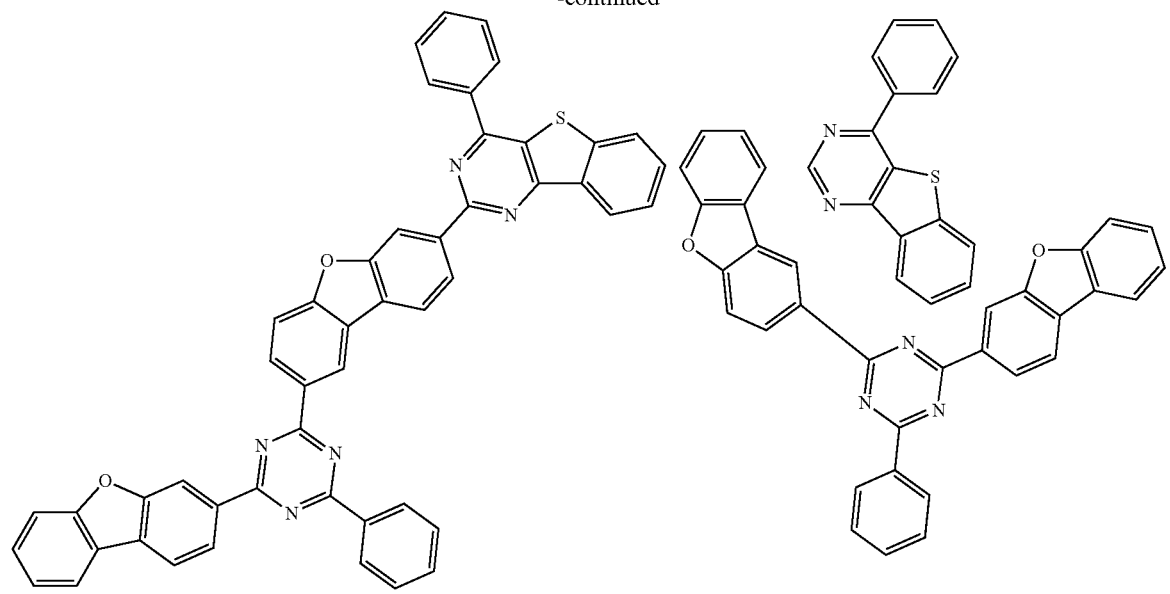
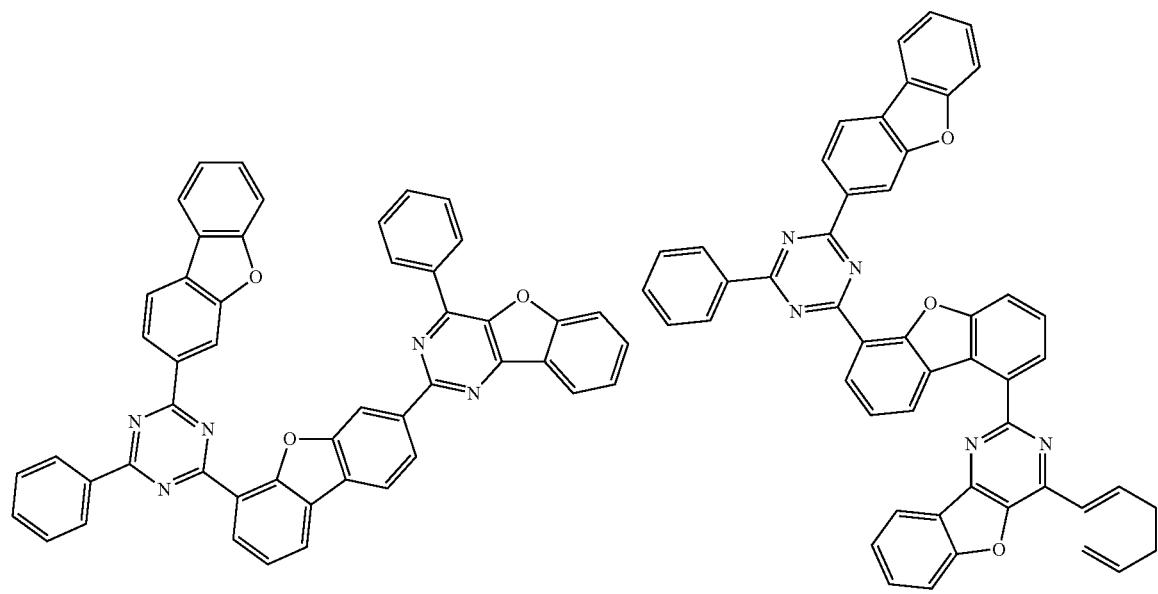

-continued
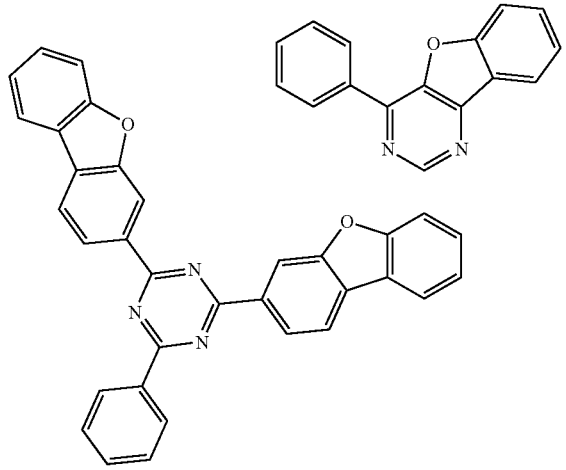
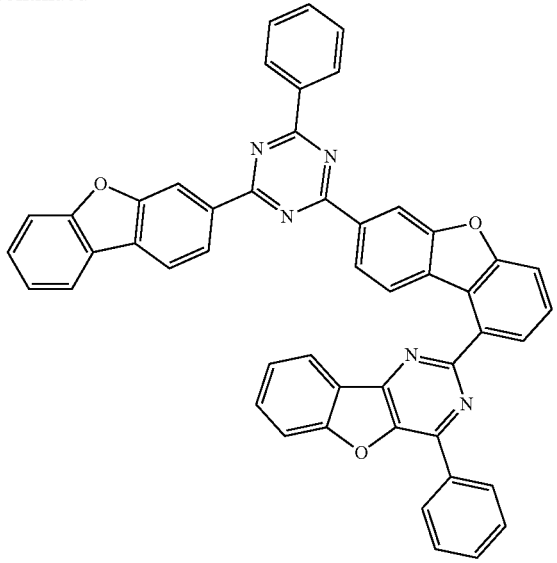
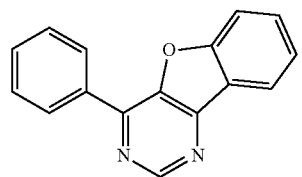
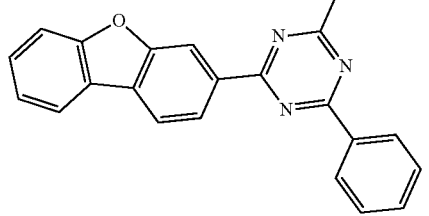
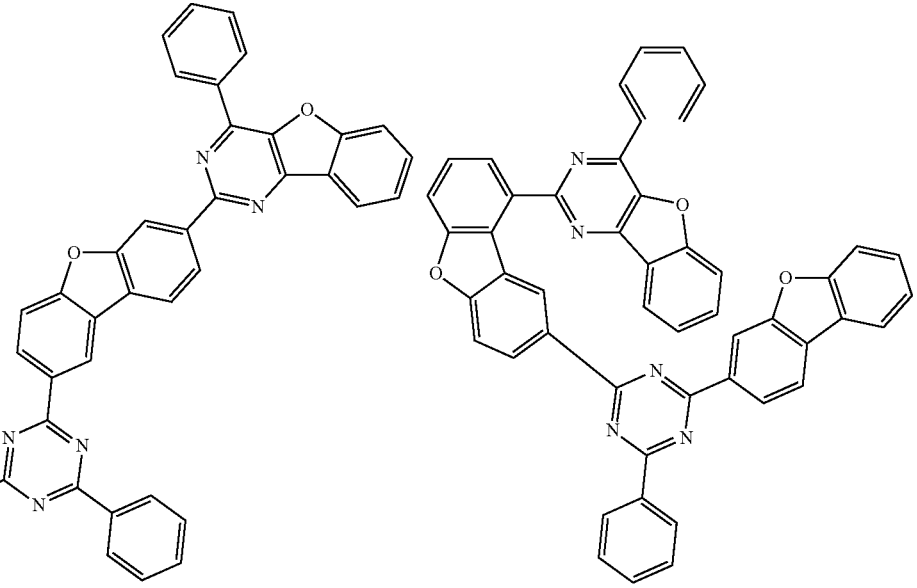

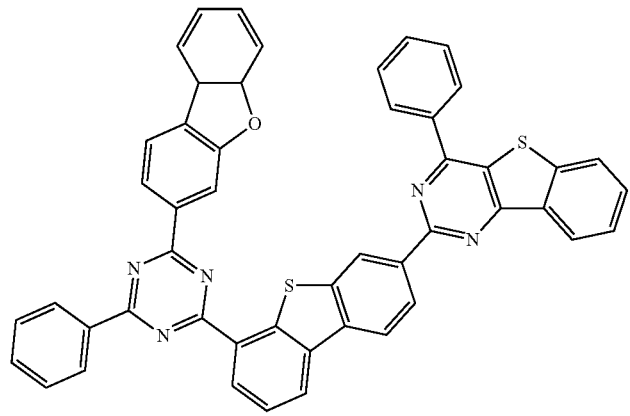
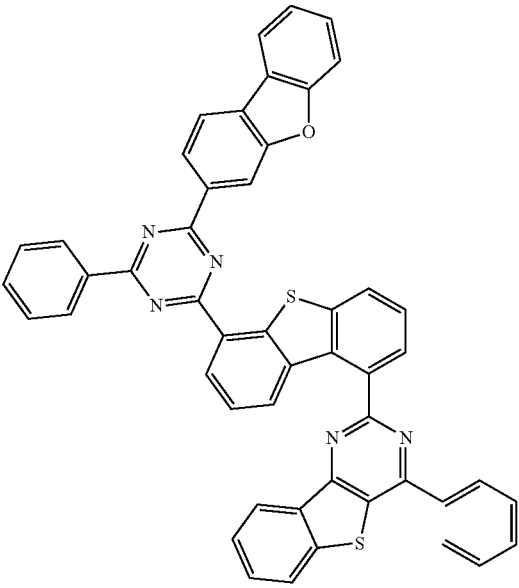
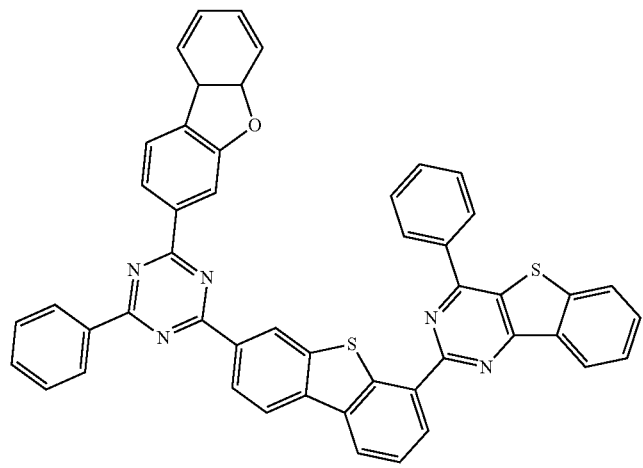
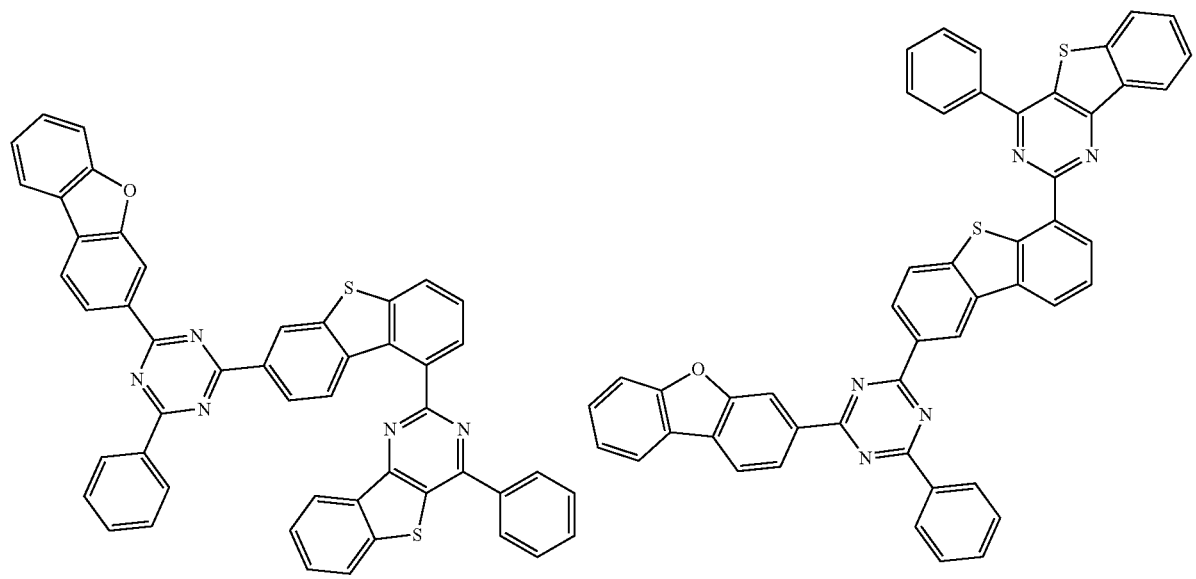

-continued
71 72
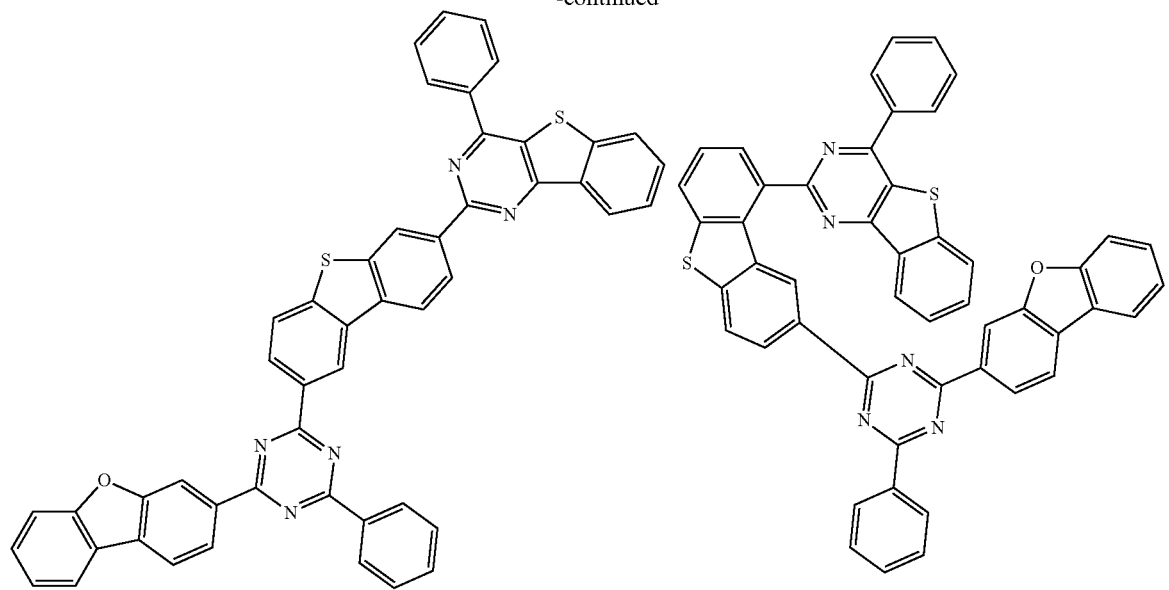
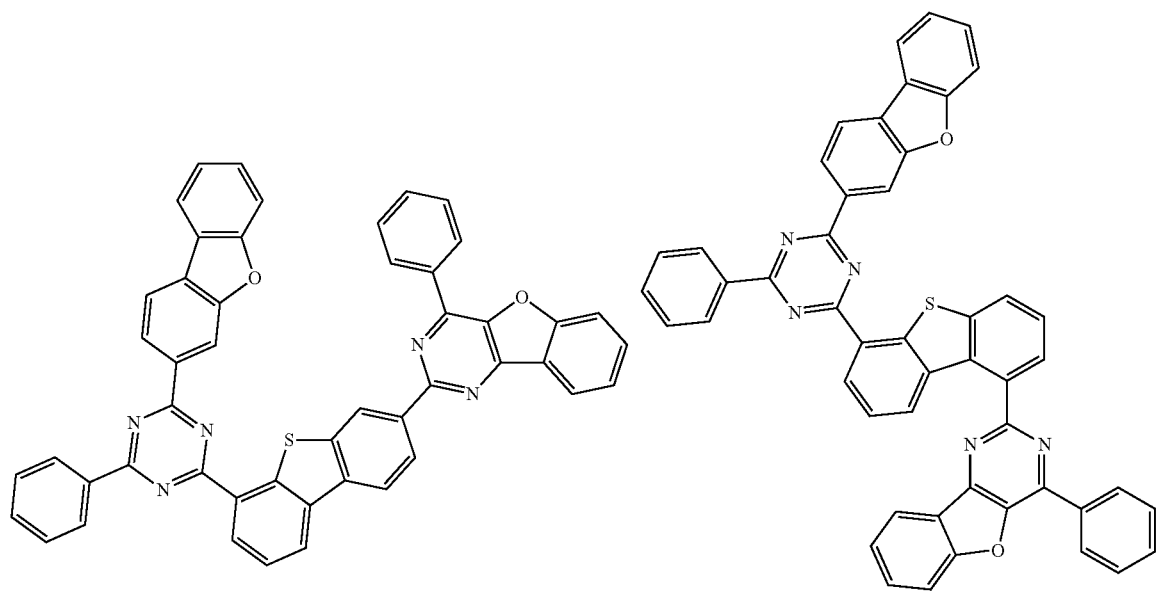

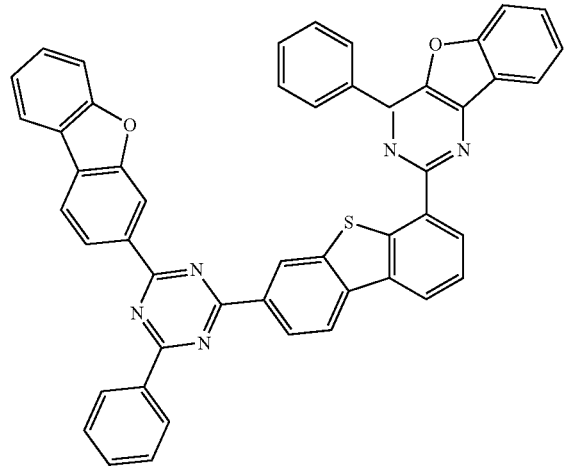
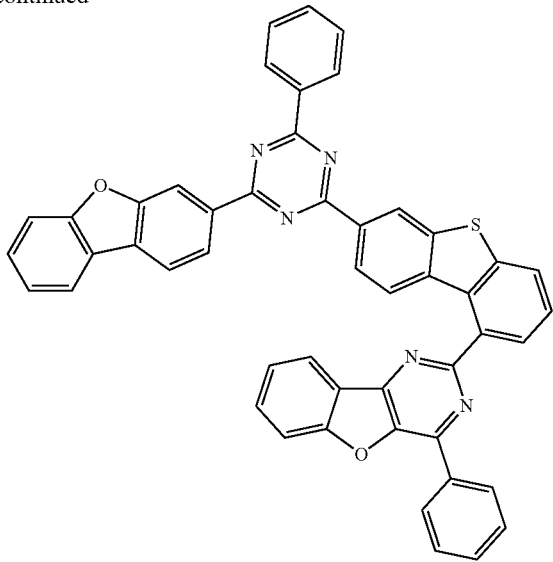
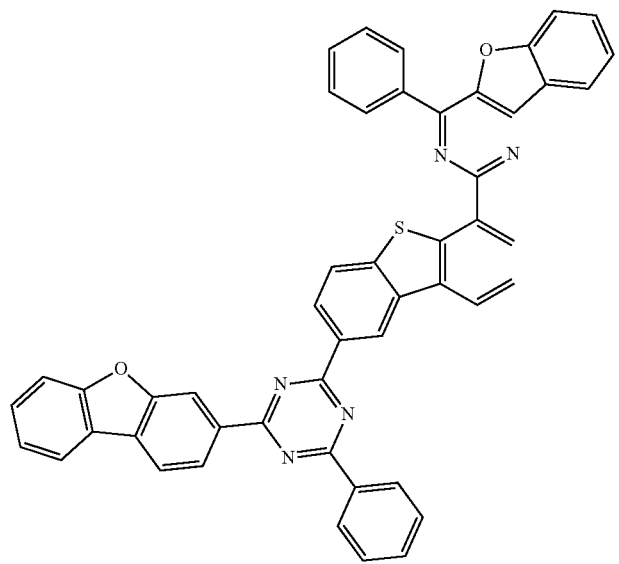
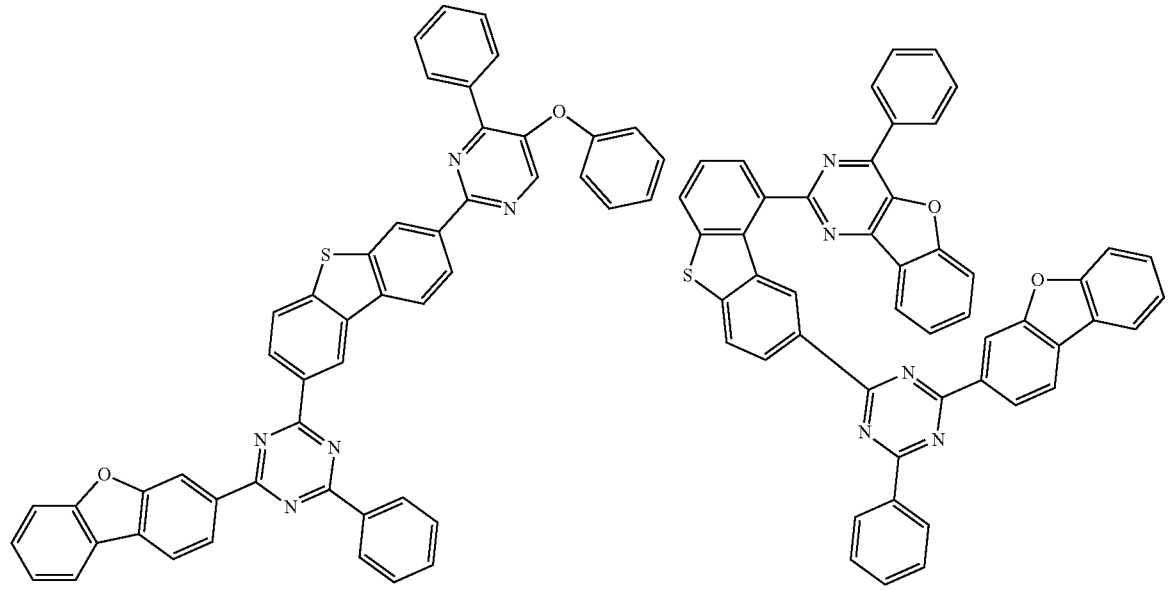

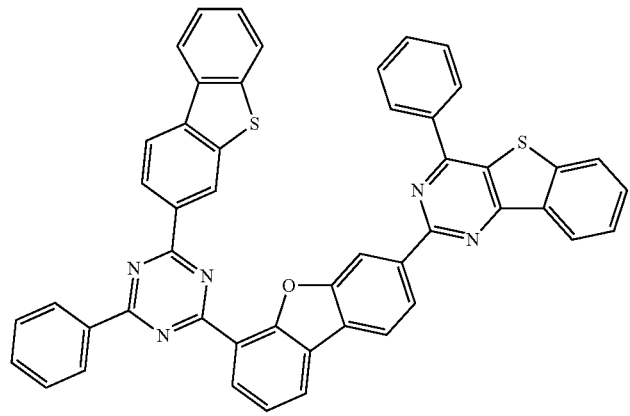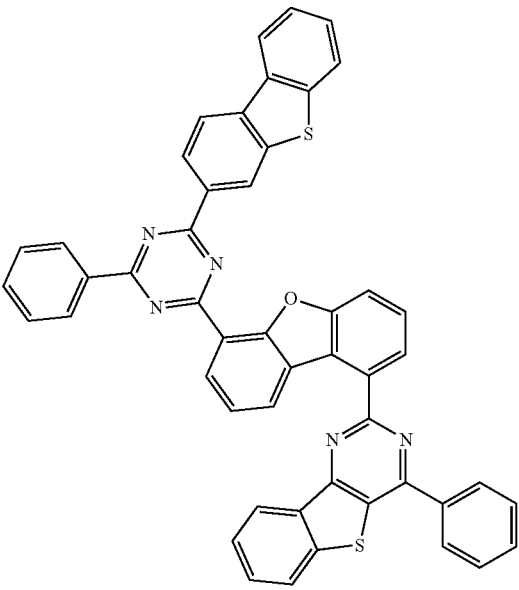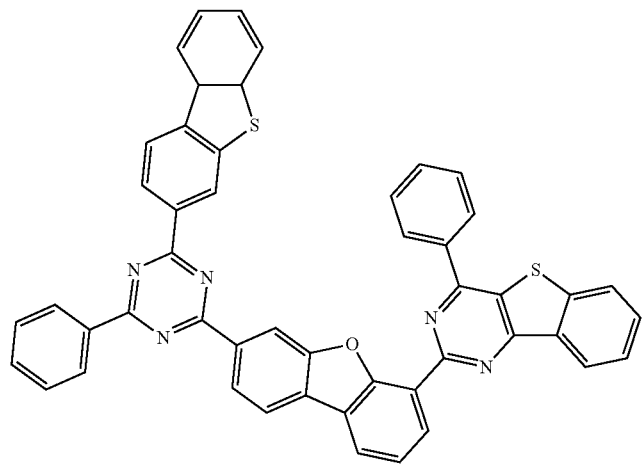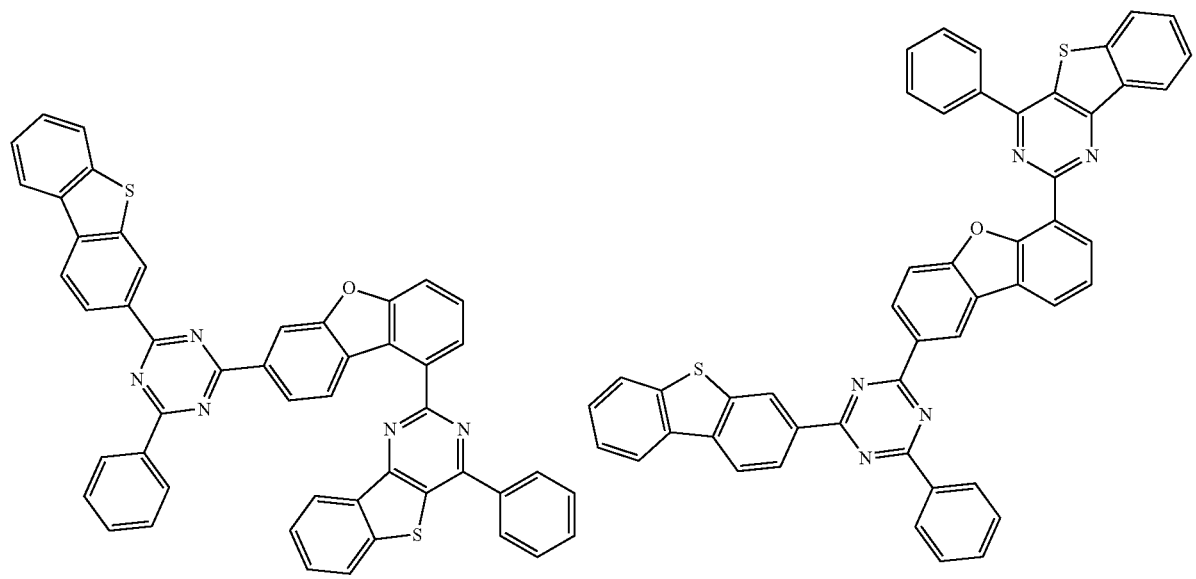

-continued
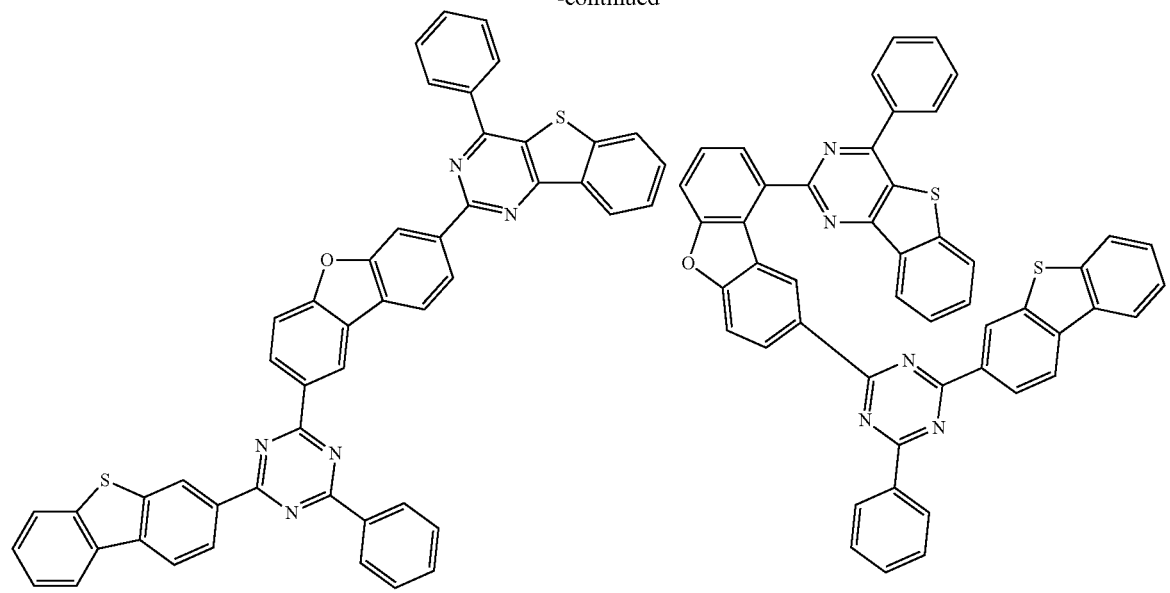
77
78
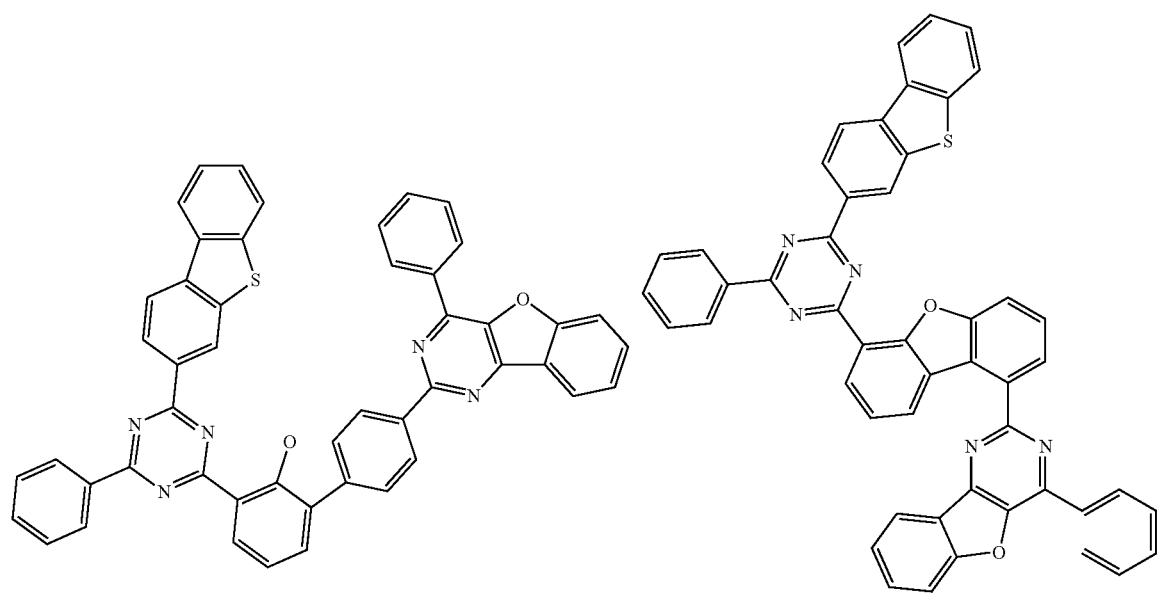

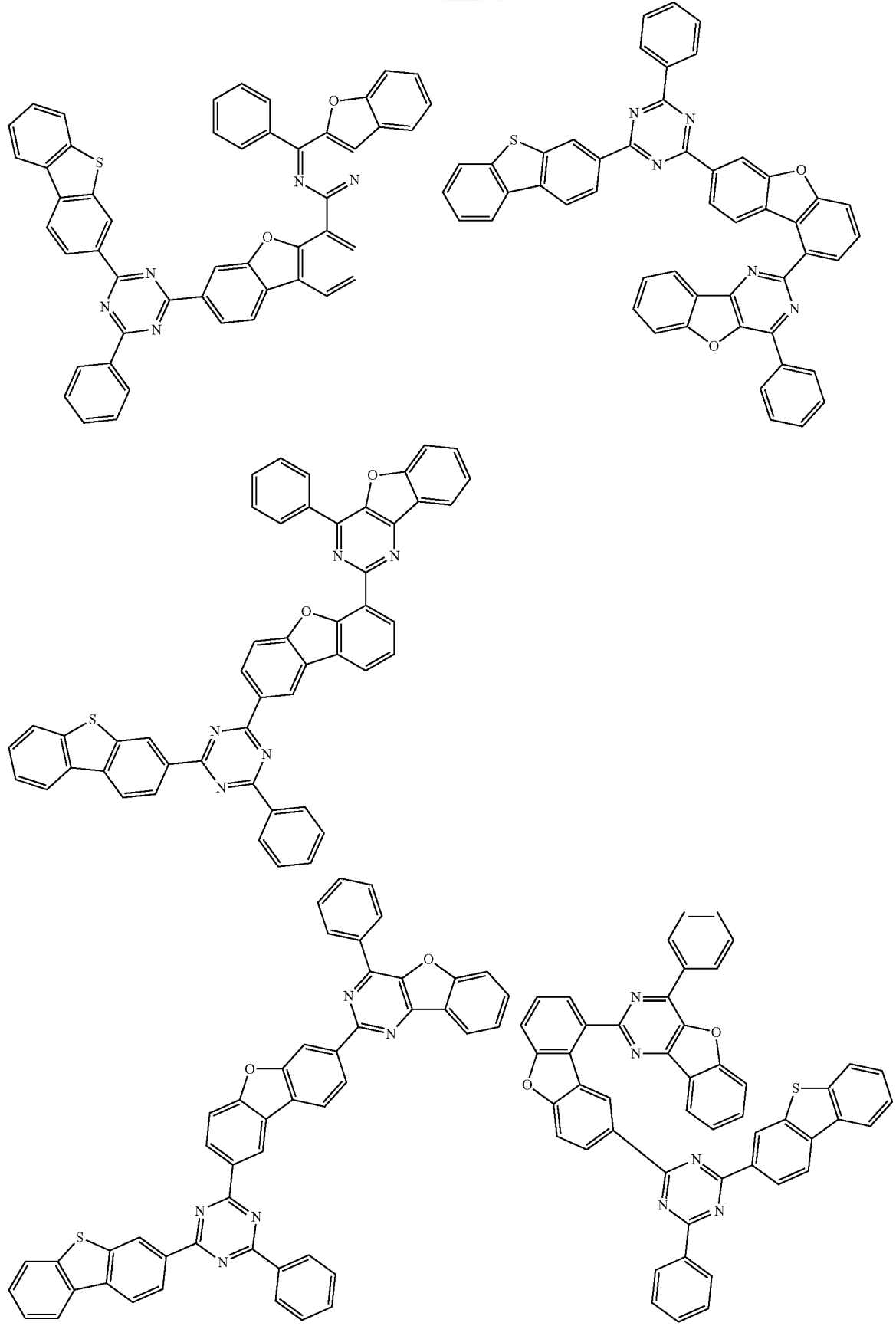

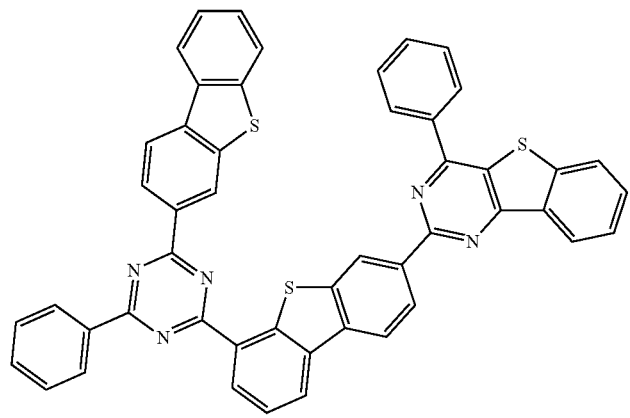
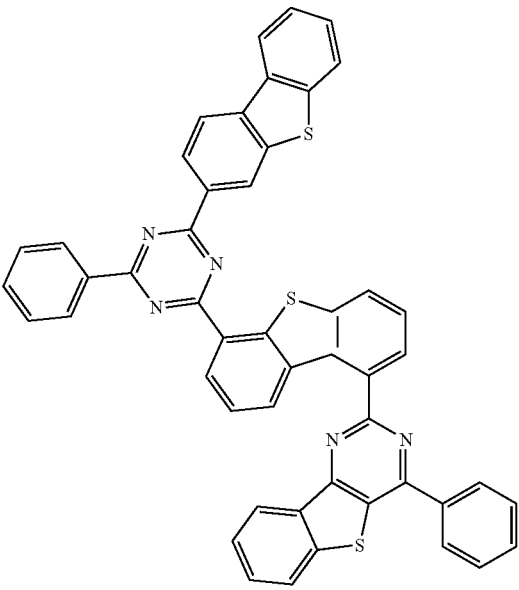
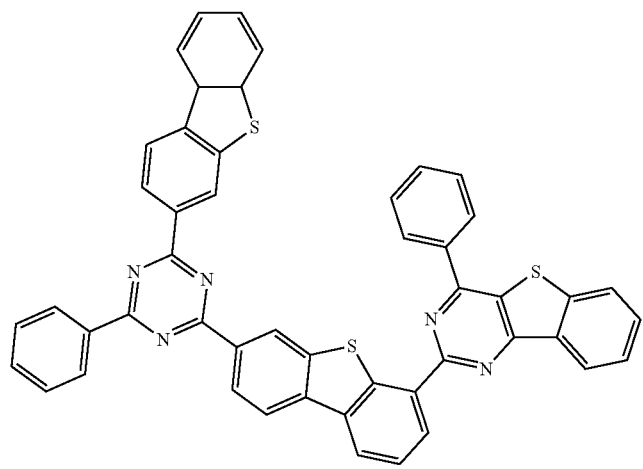
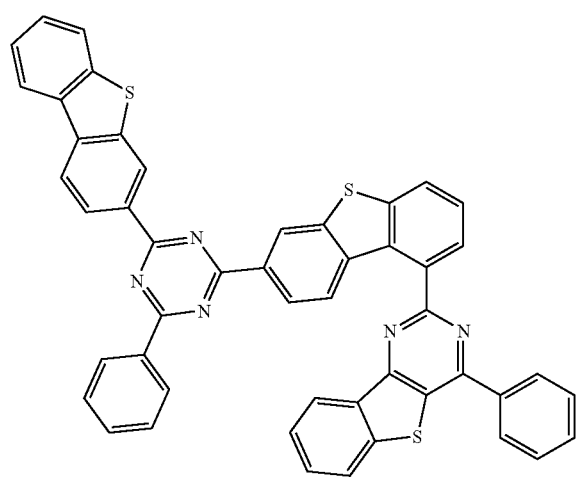
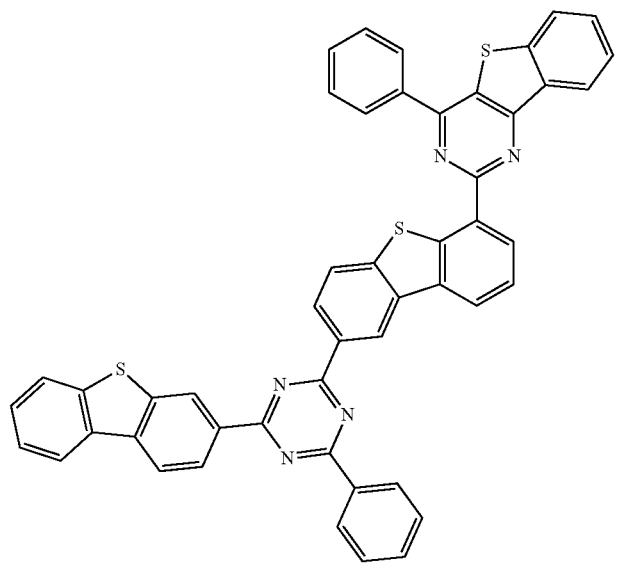

83 84
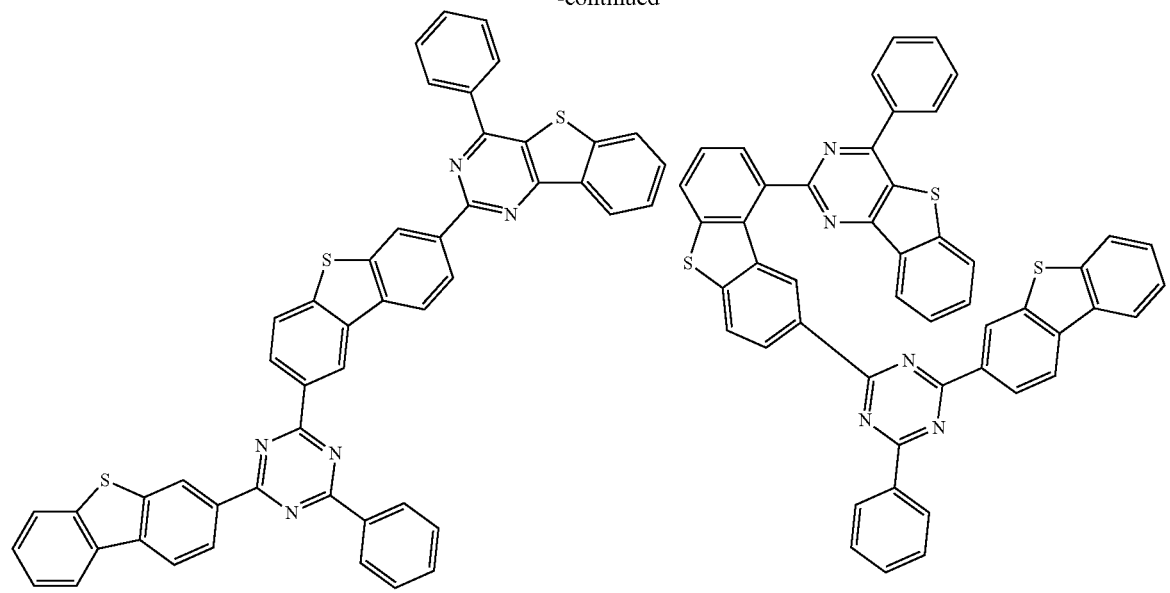
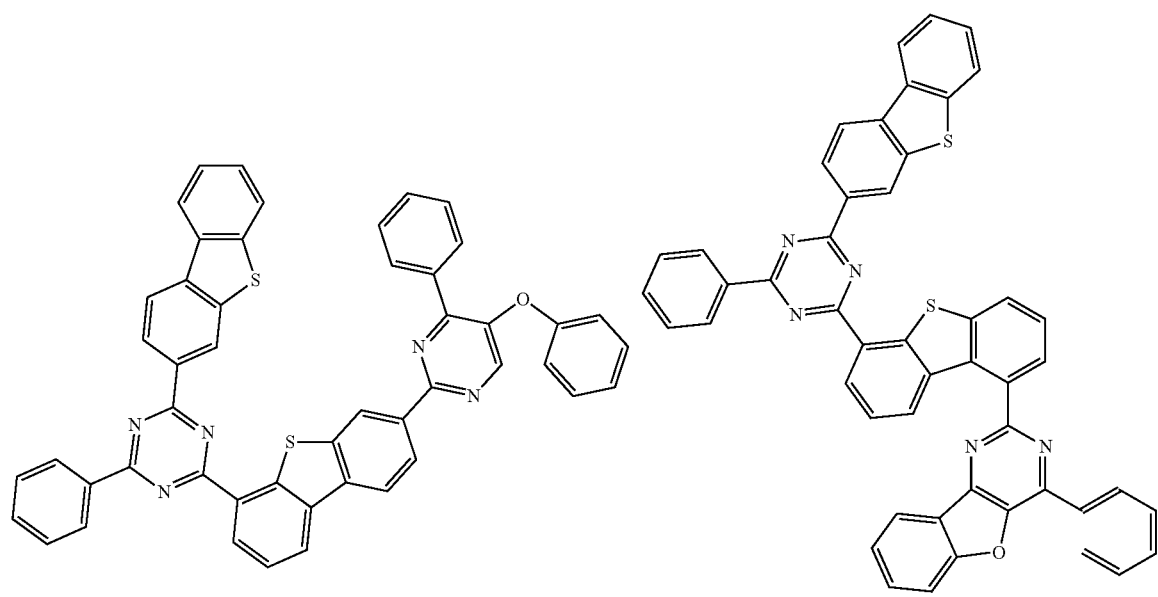

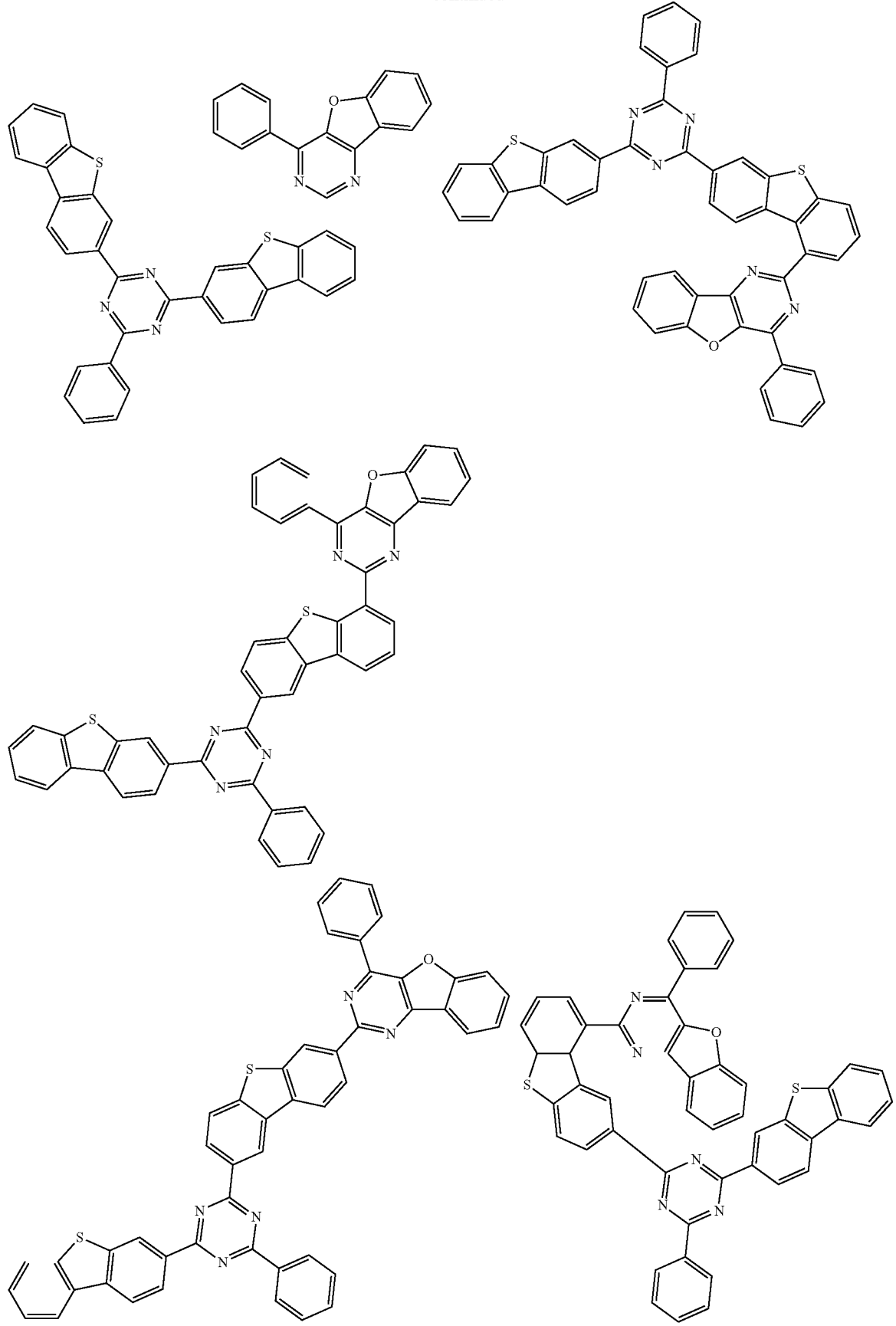

-continued
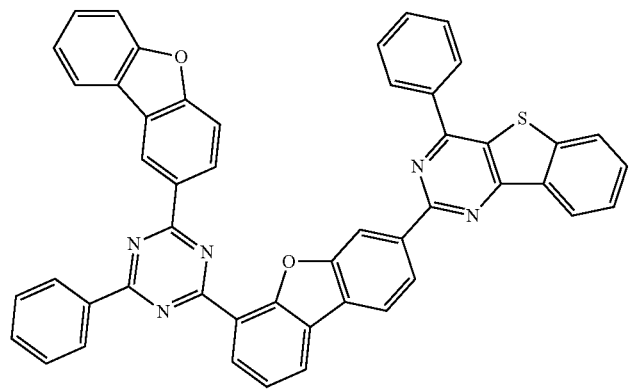
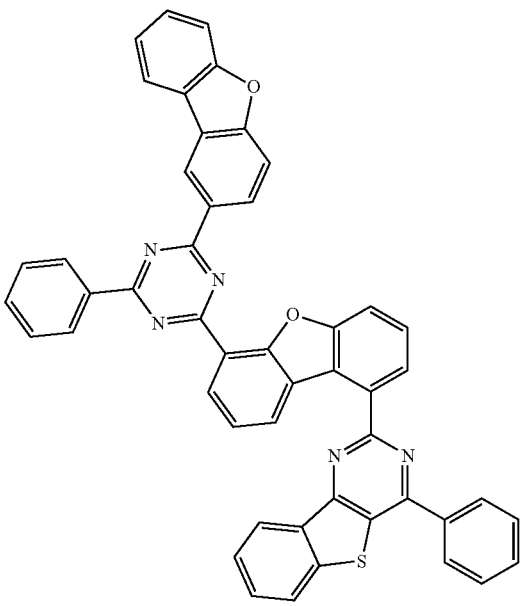
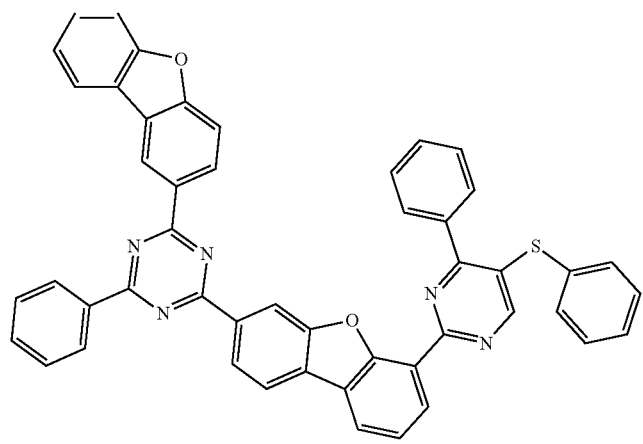
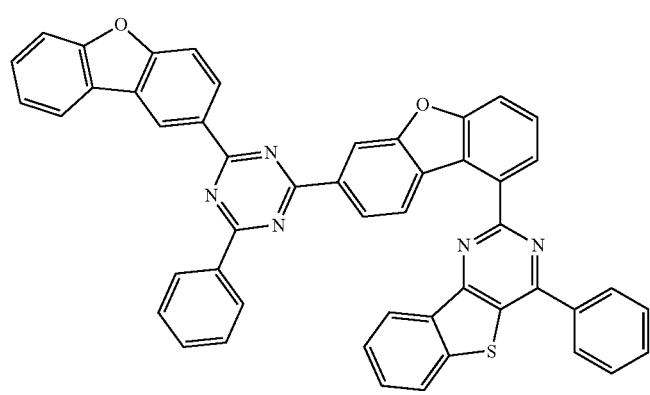

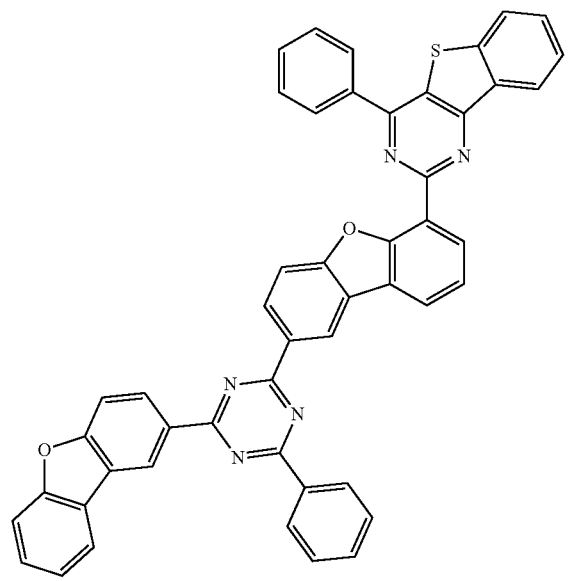
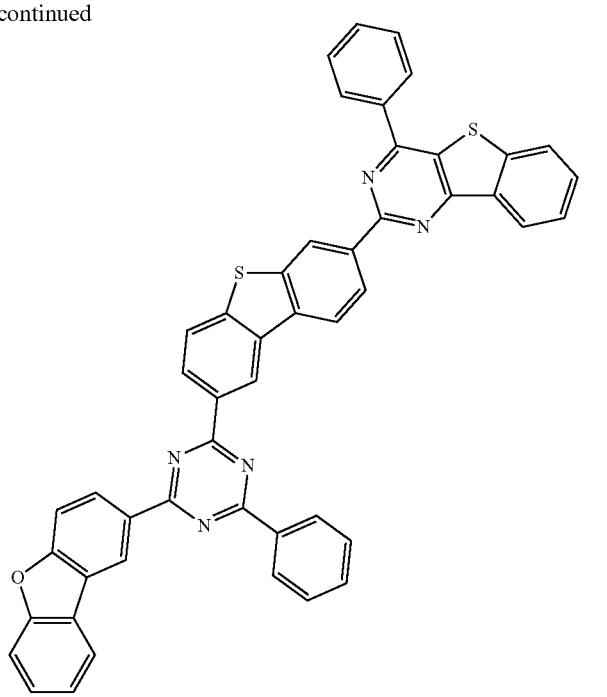
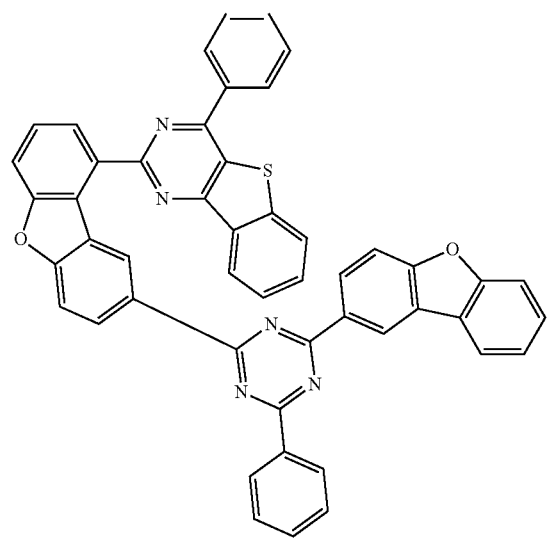
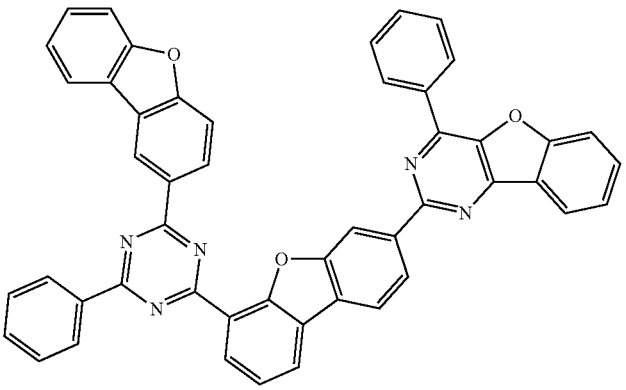
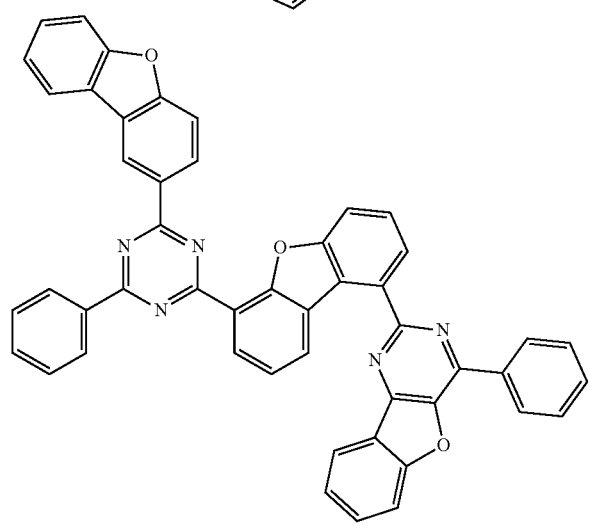

91 92
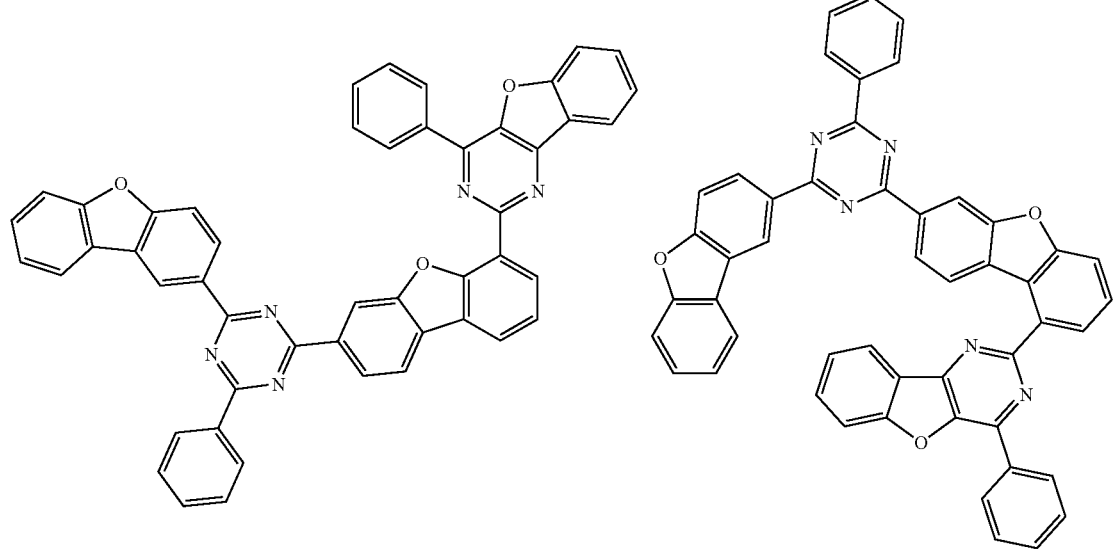
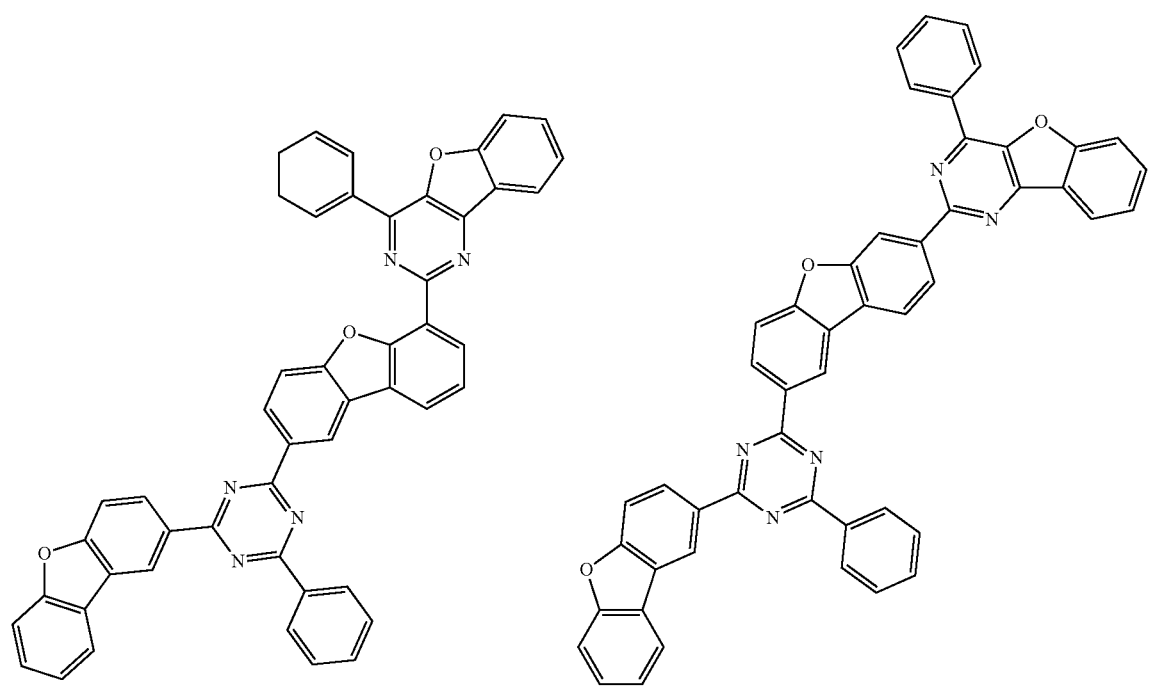

-continued
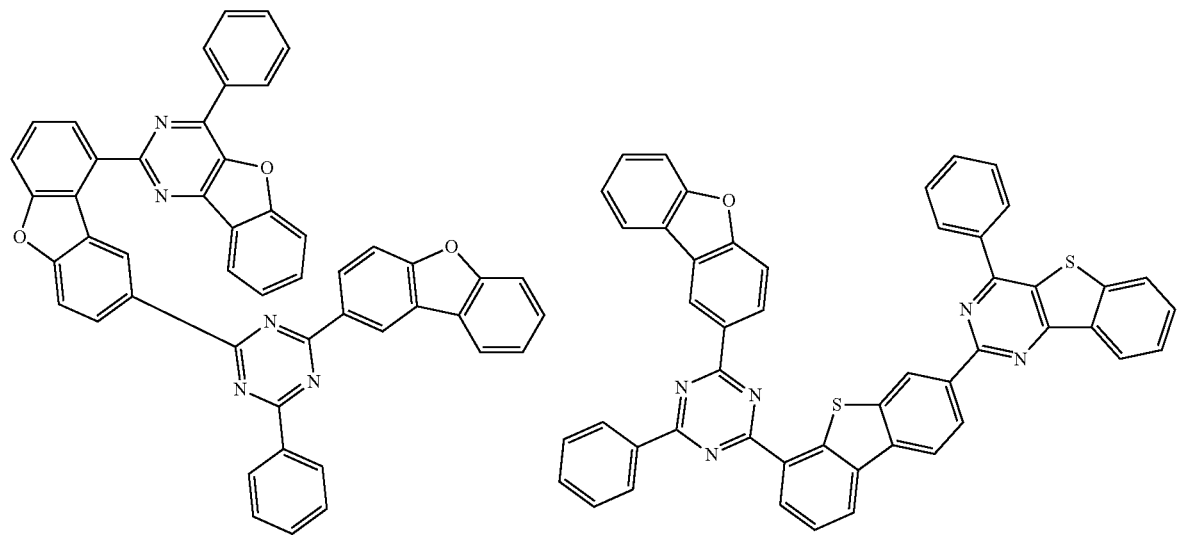
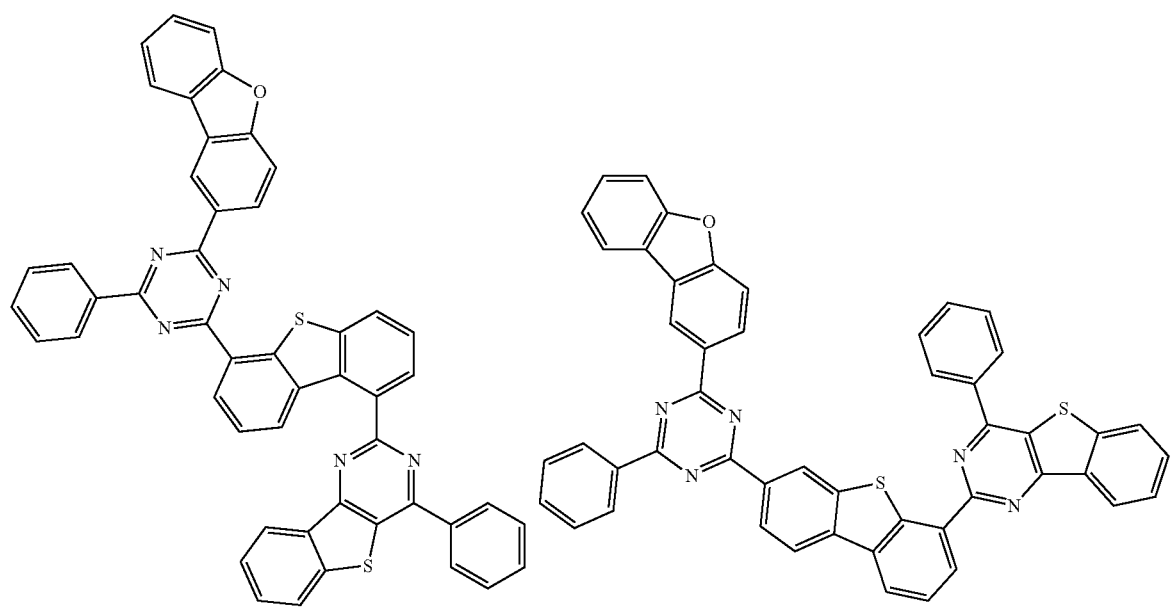
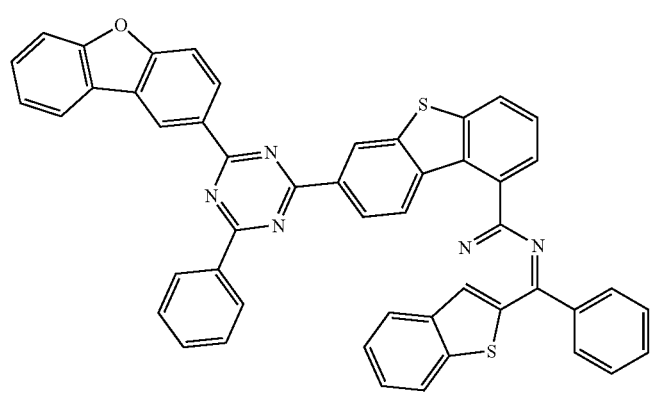

-continued
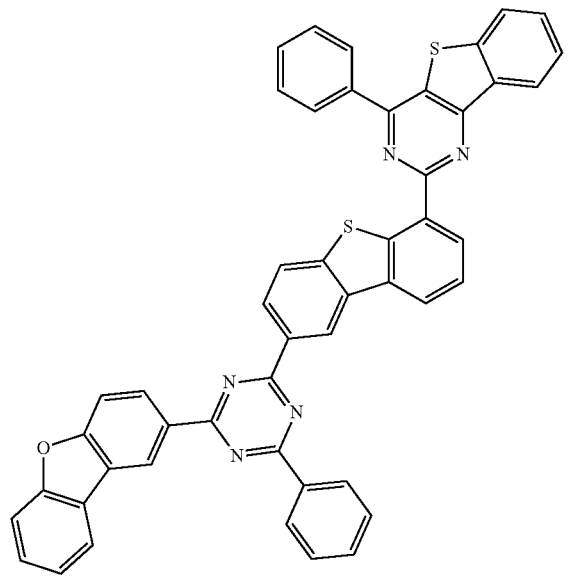
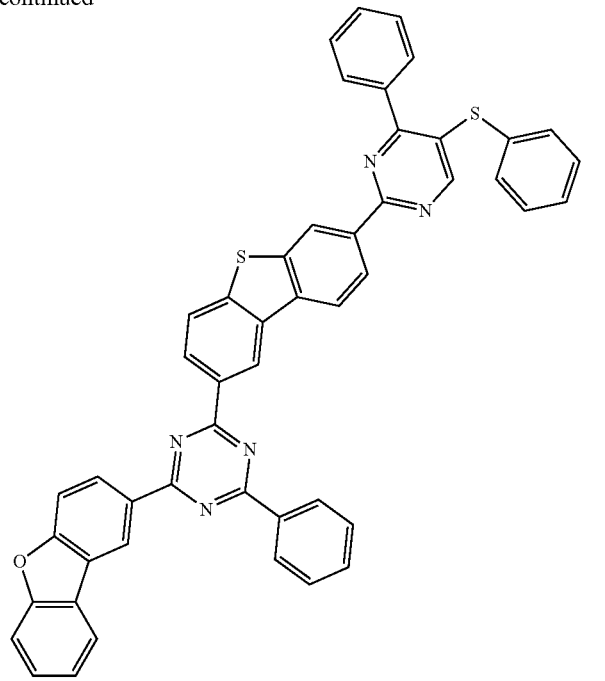
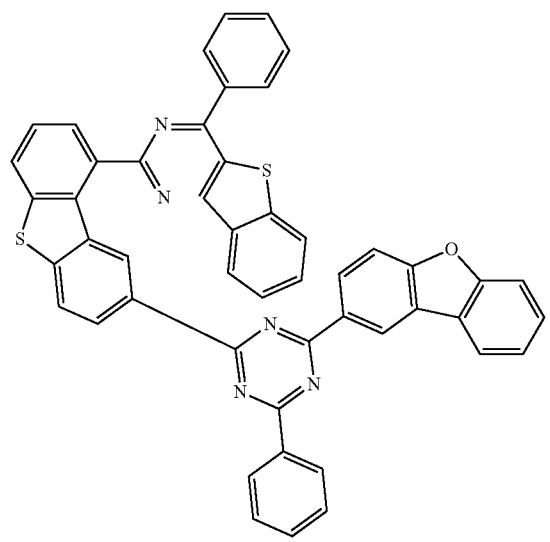
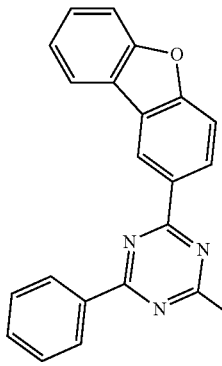
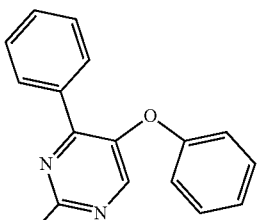
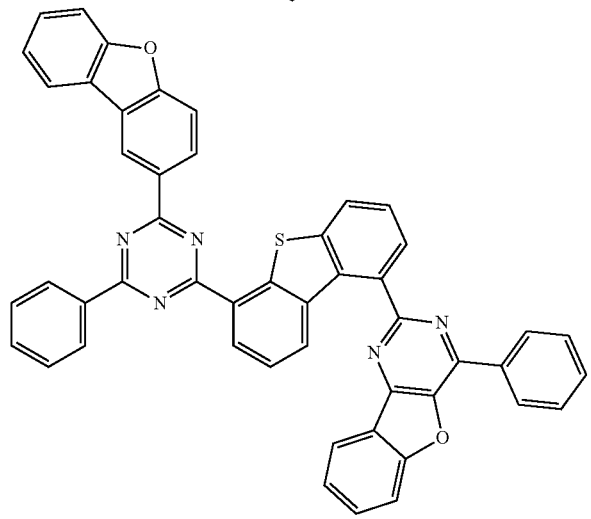

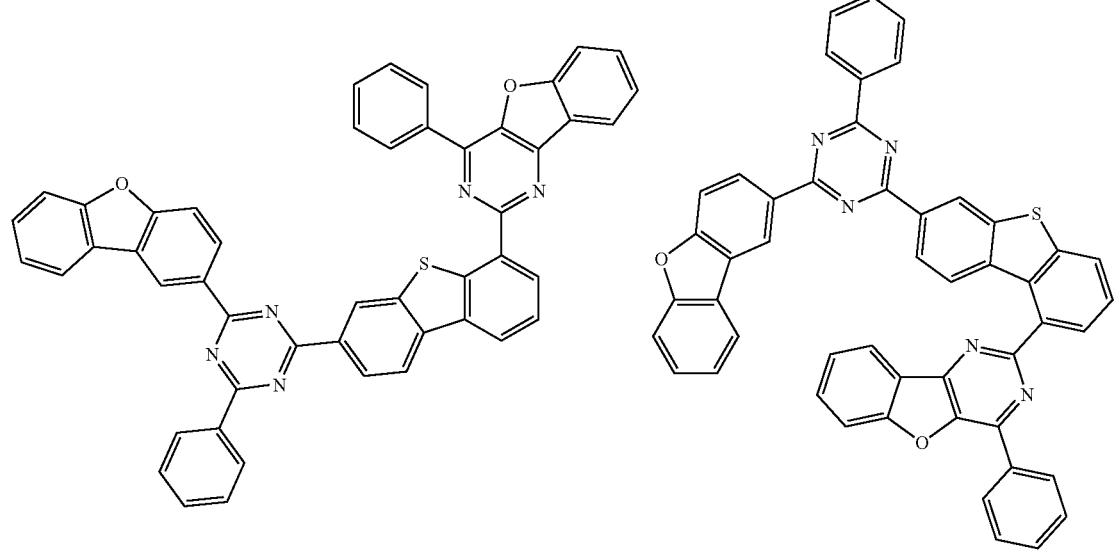
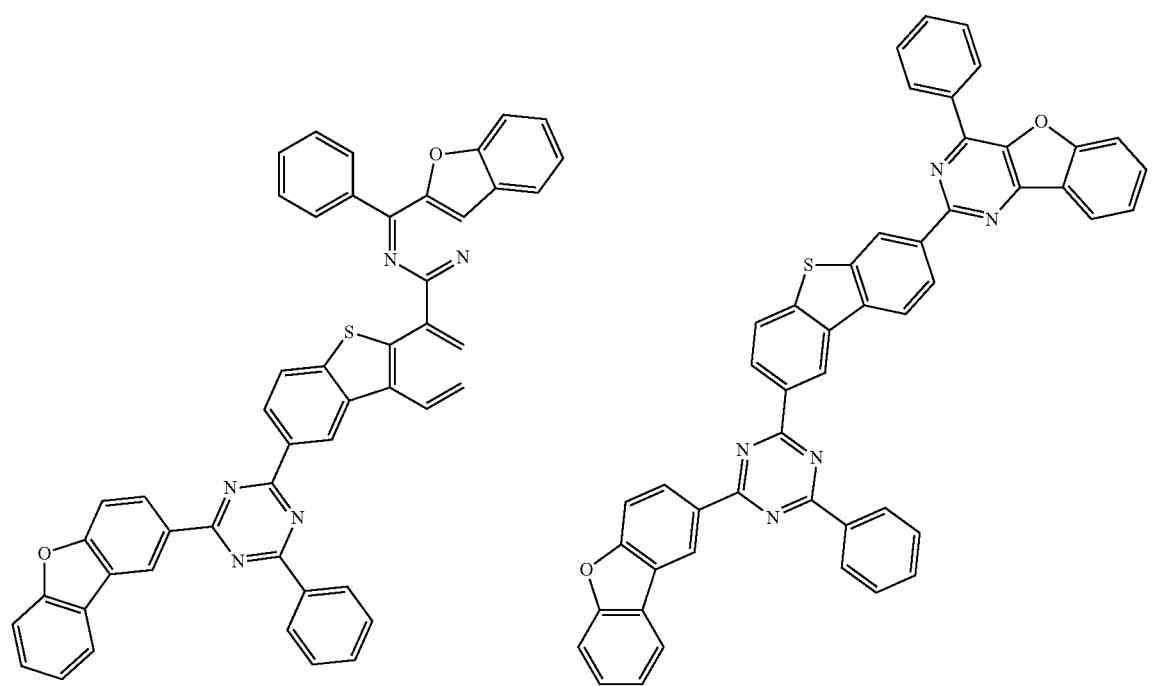

-continued
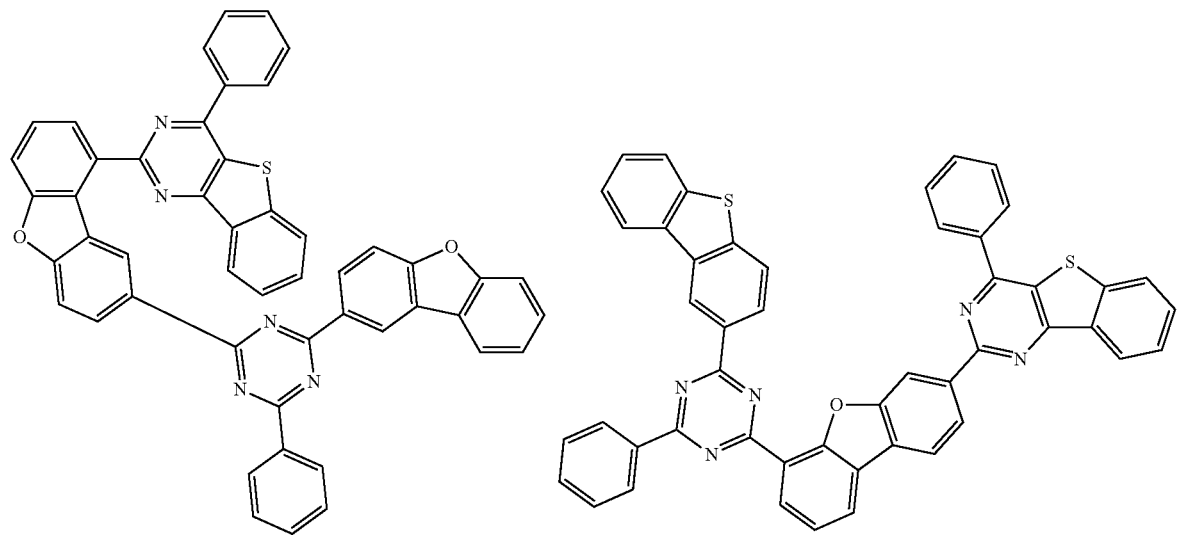
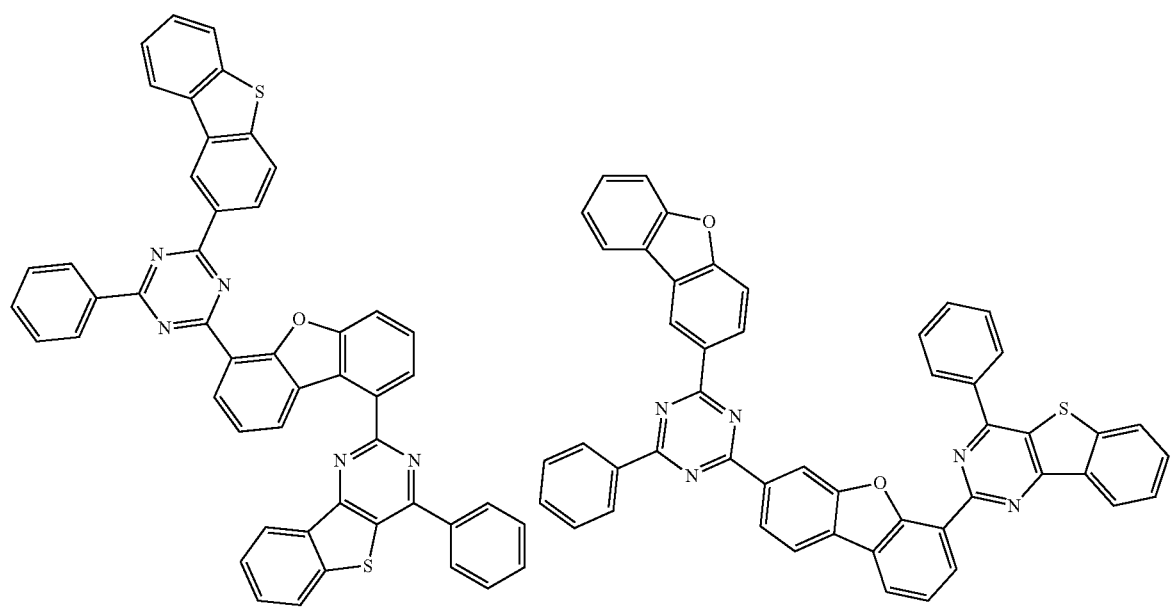
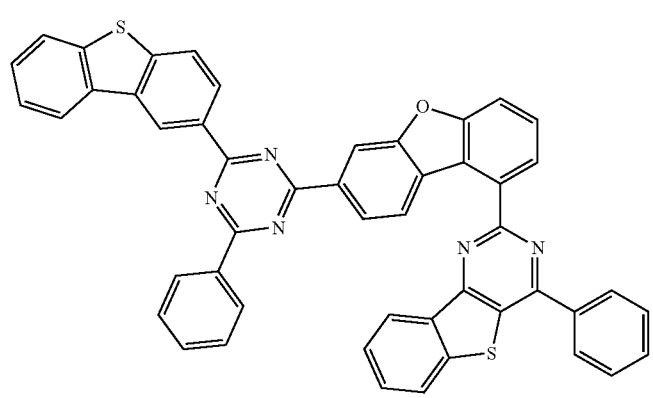

-continued
101
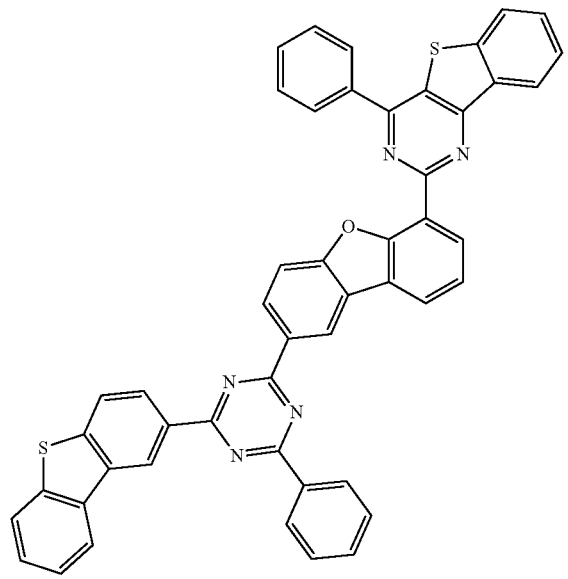
102
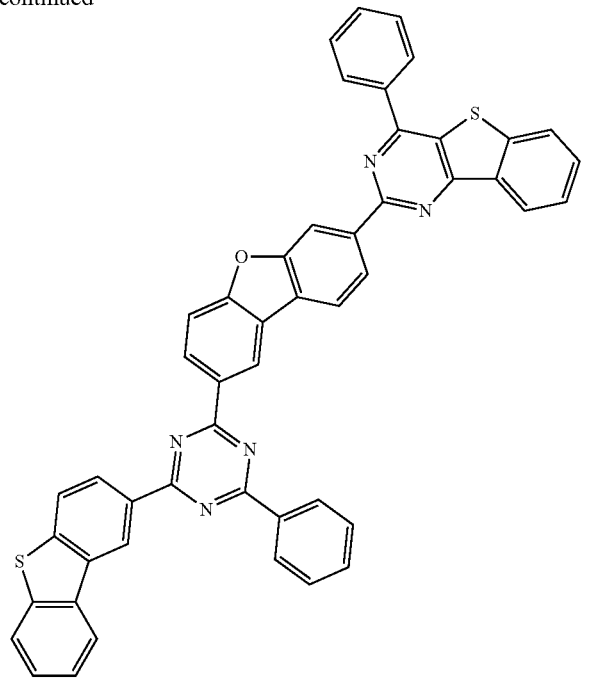
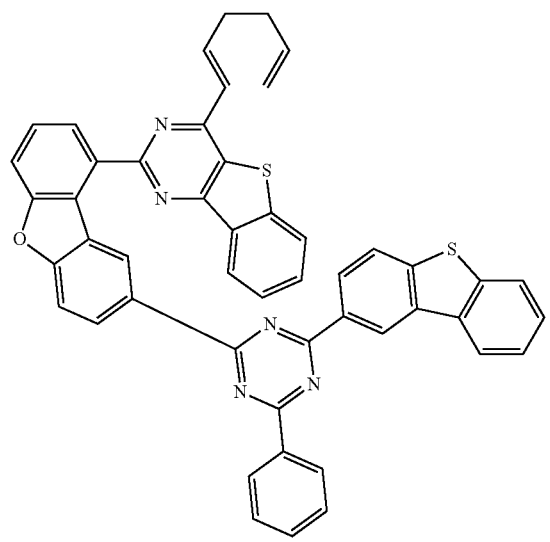
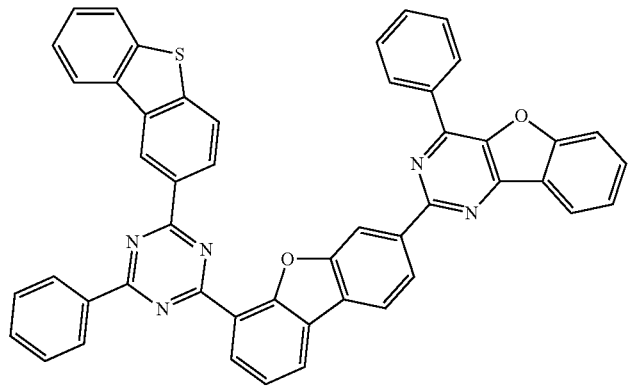
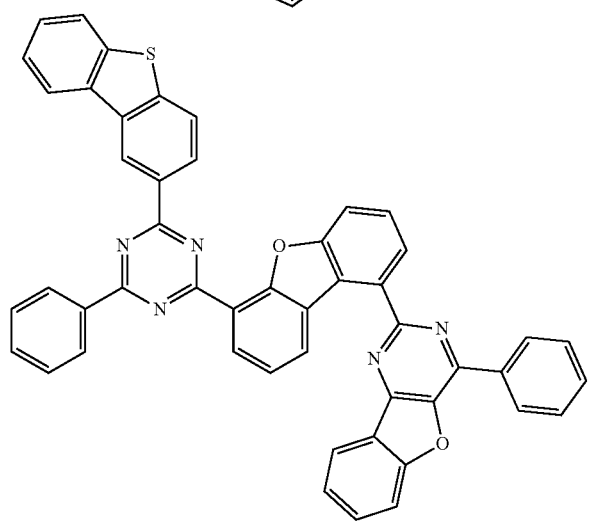

-continued
103
104
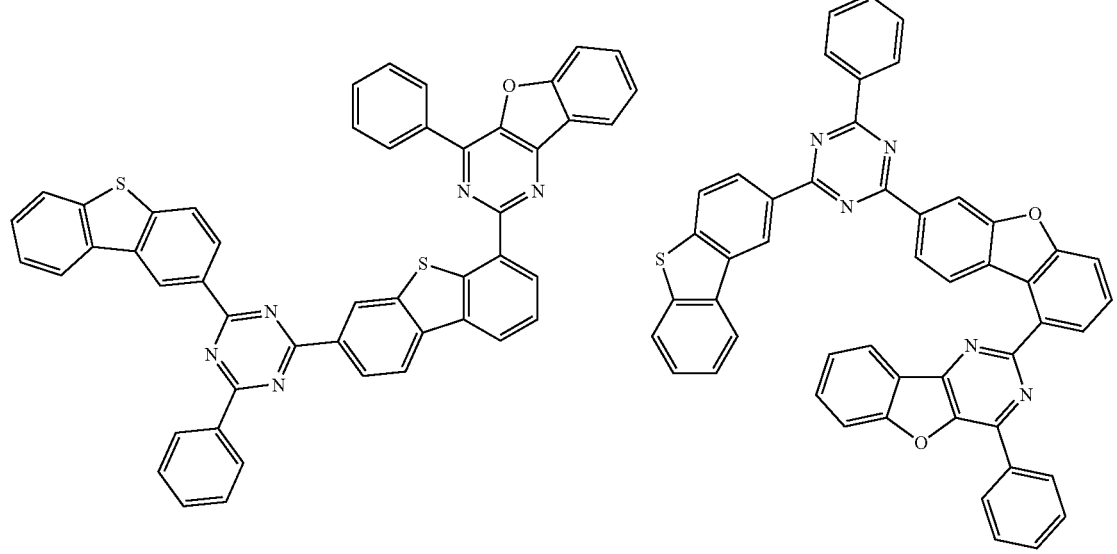
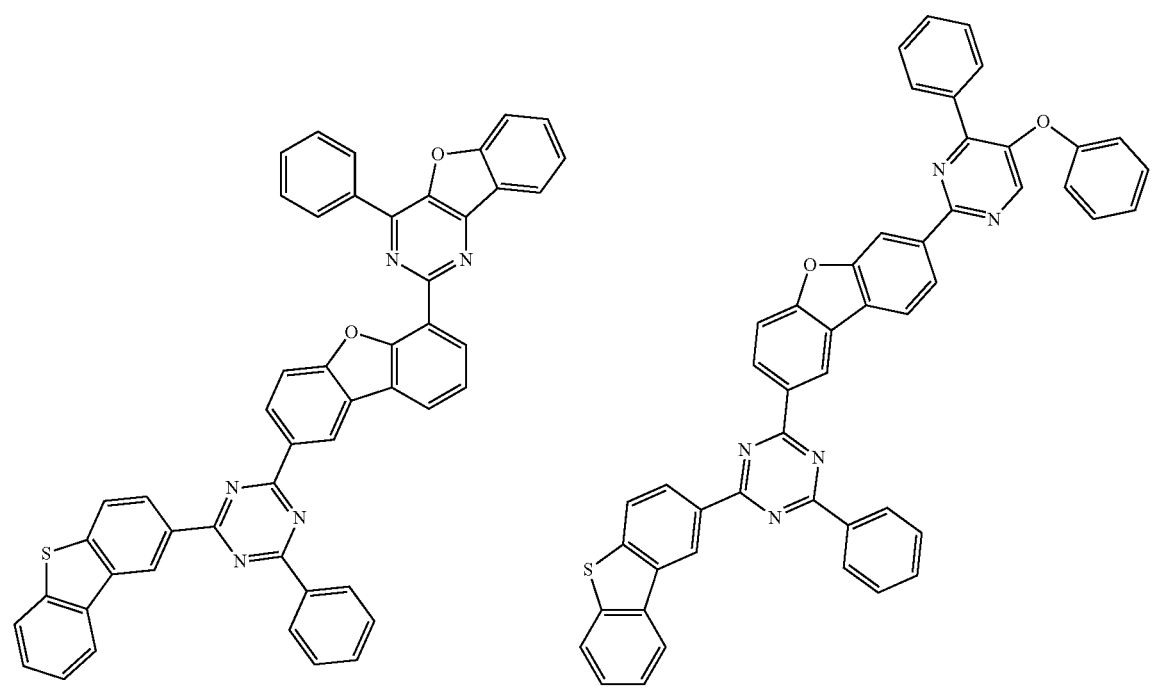

-continued
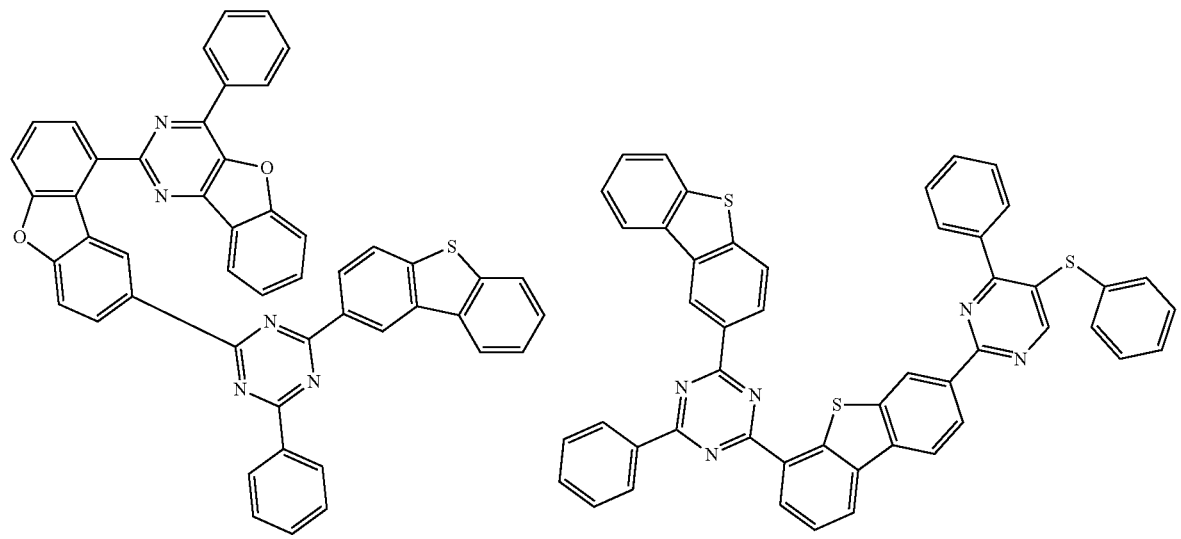
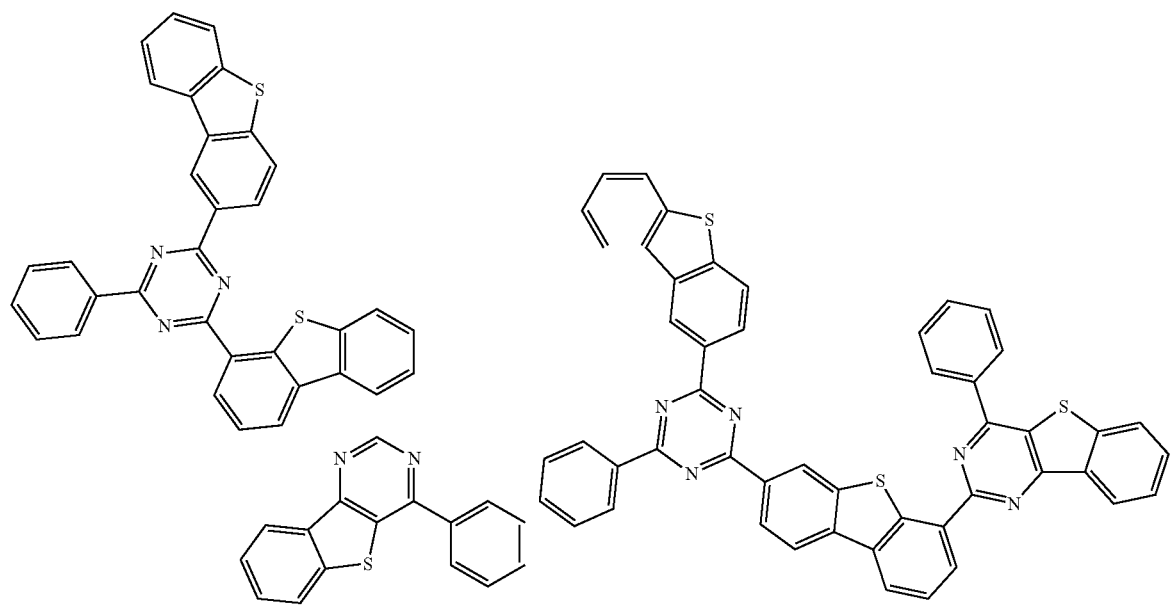
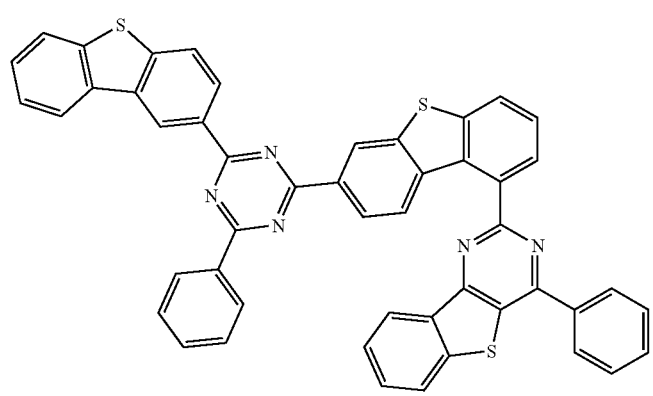

-continued
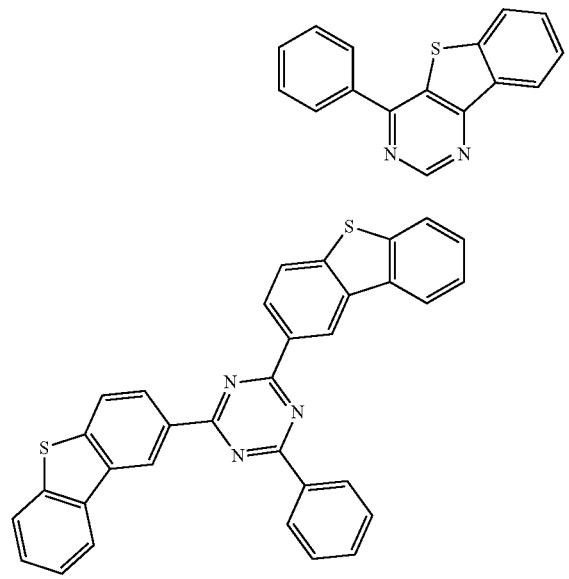
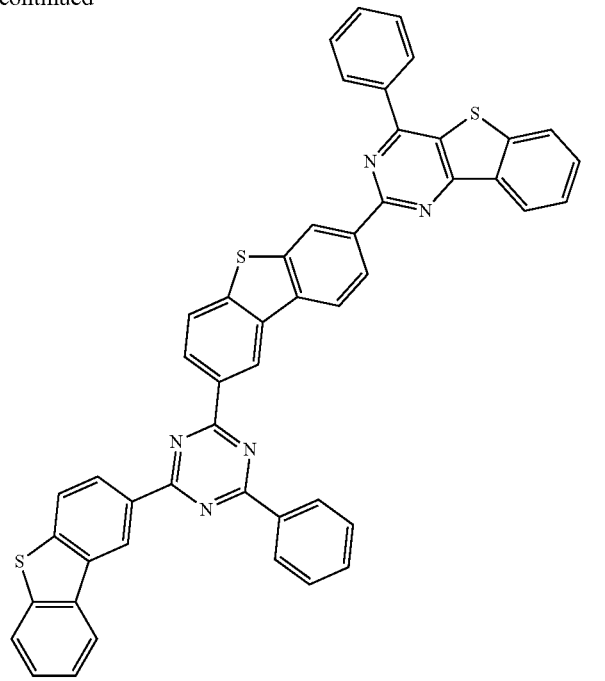
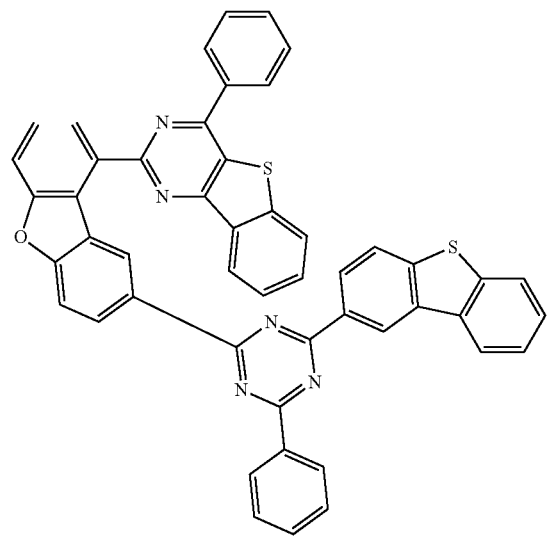
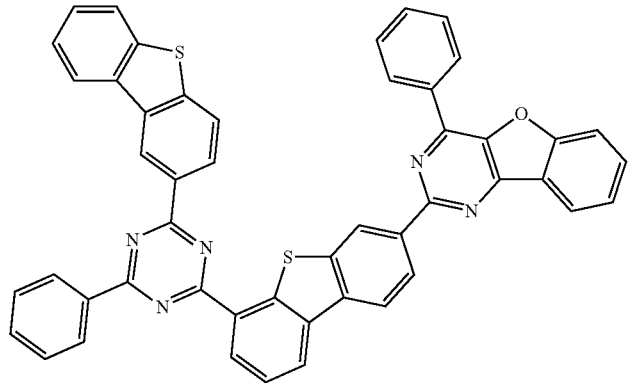
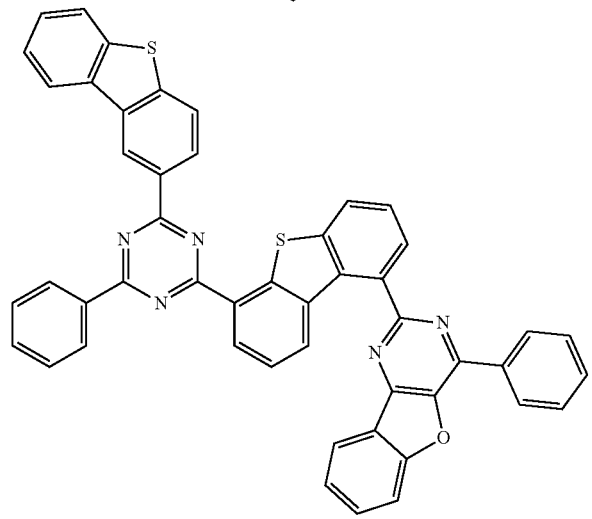

109 110
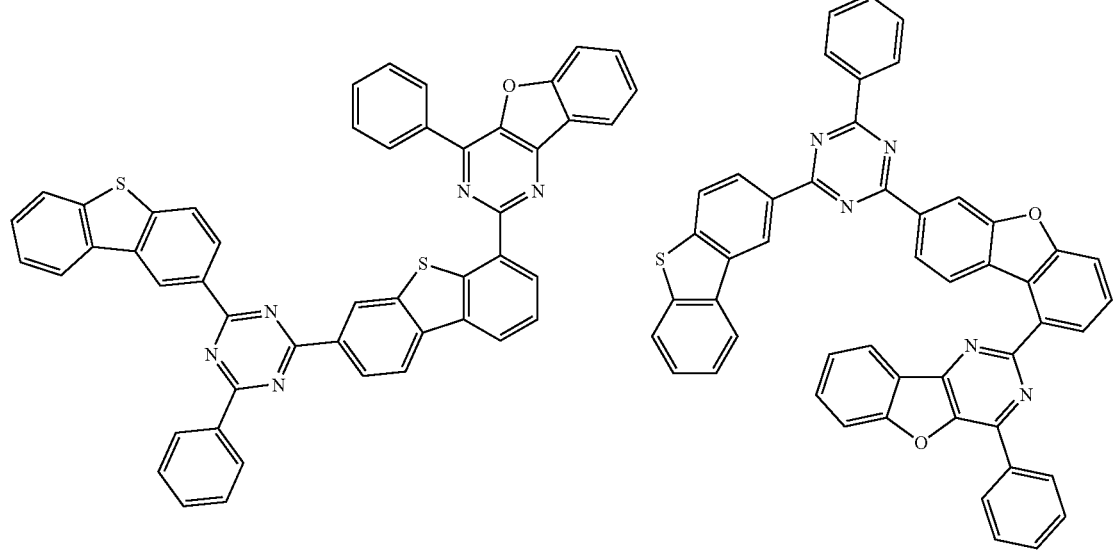
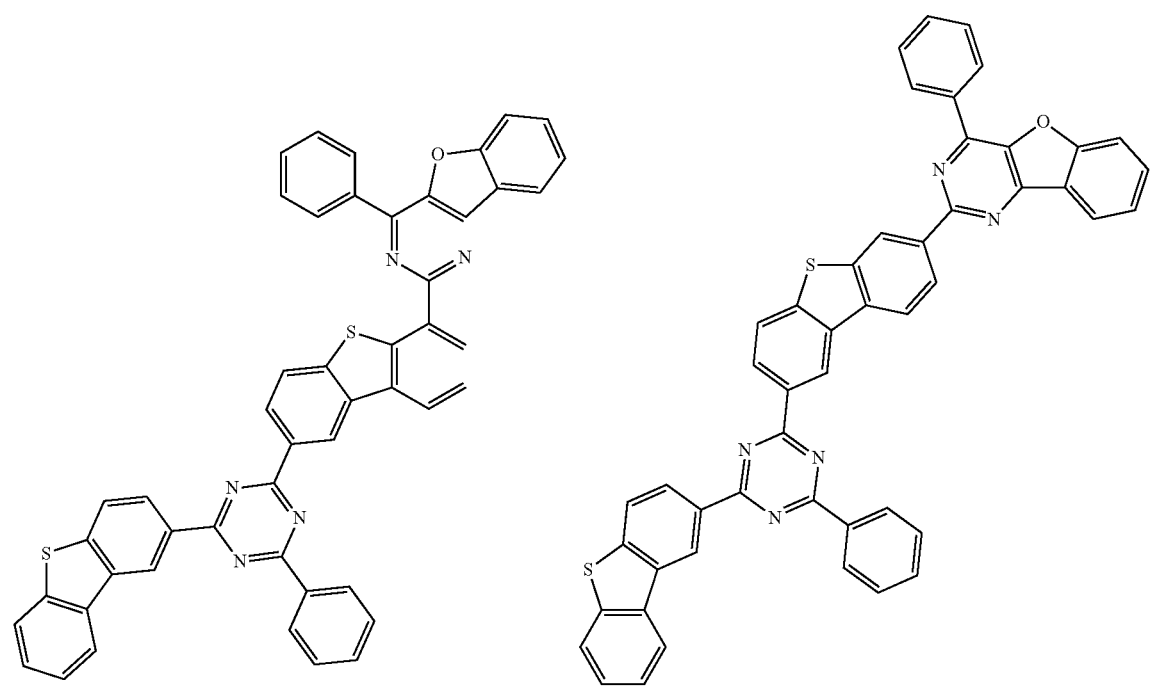

-continued
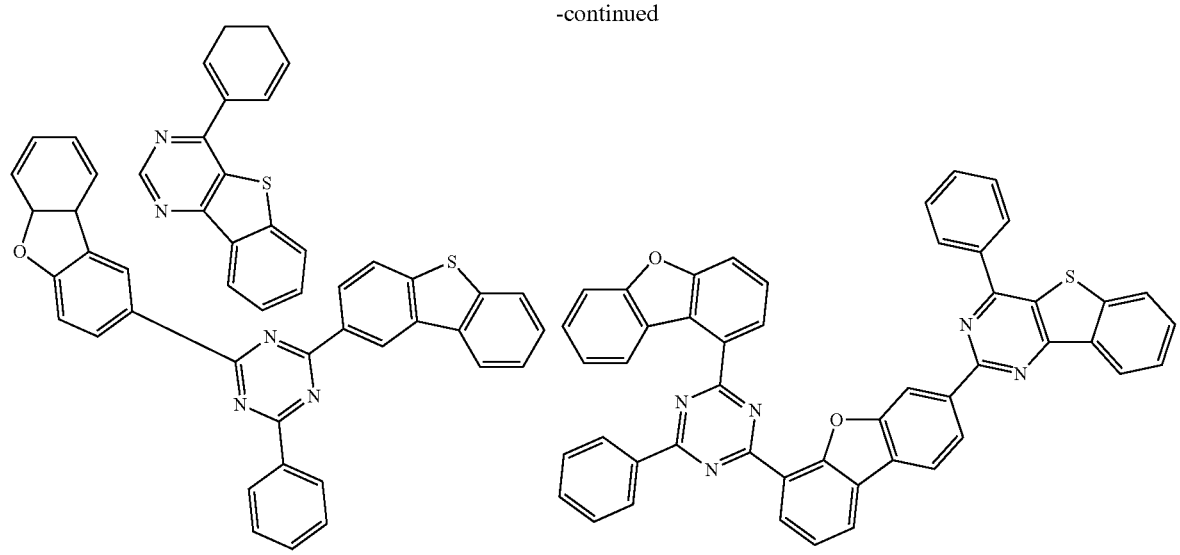
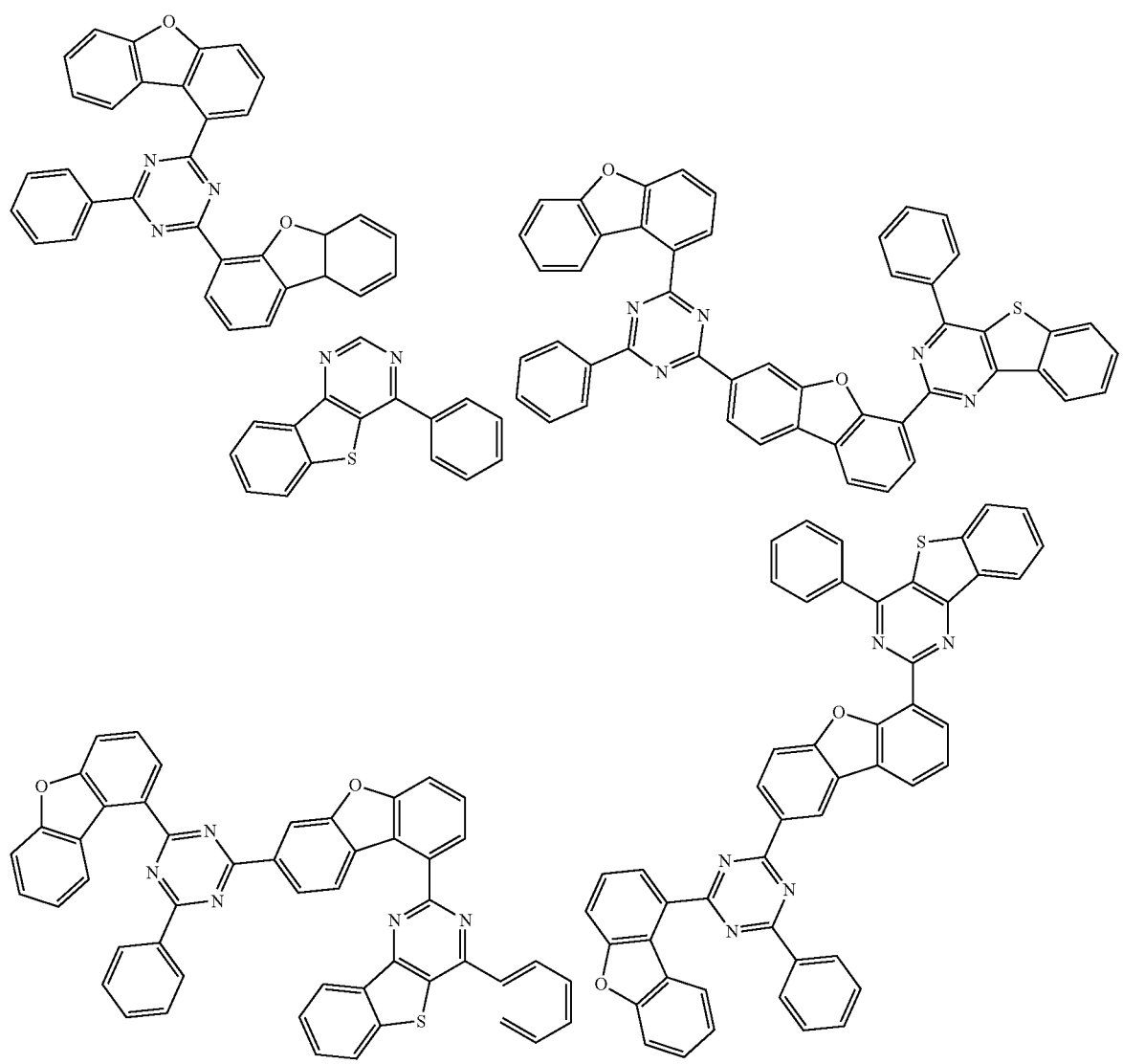

113
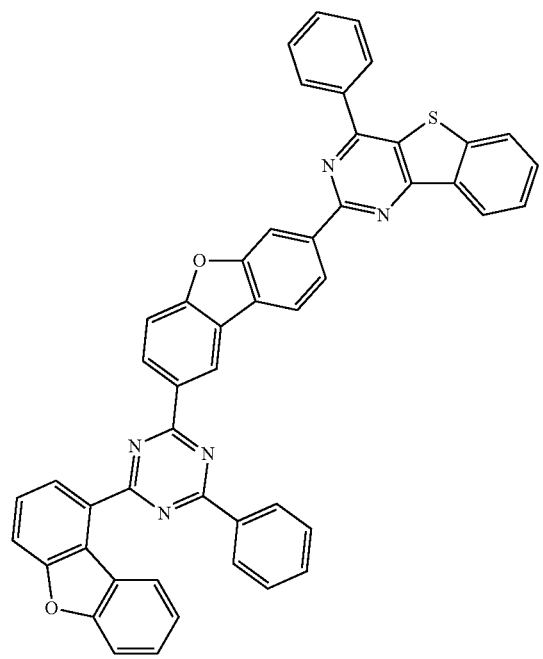
114
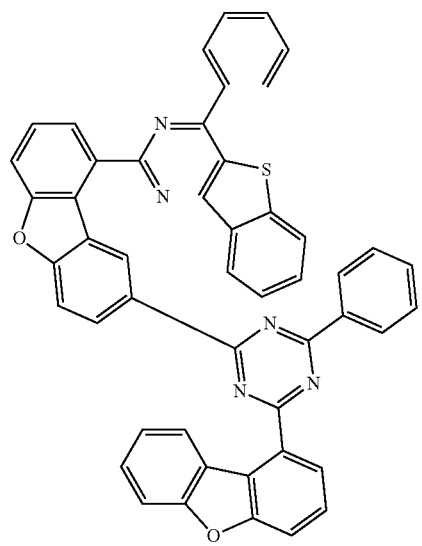
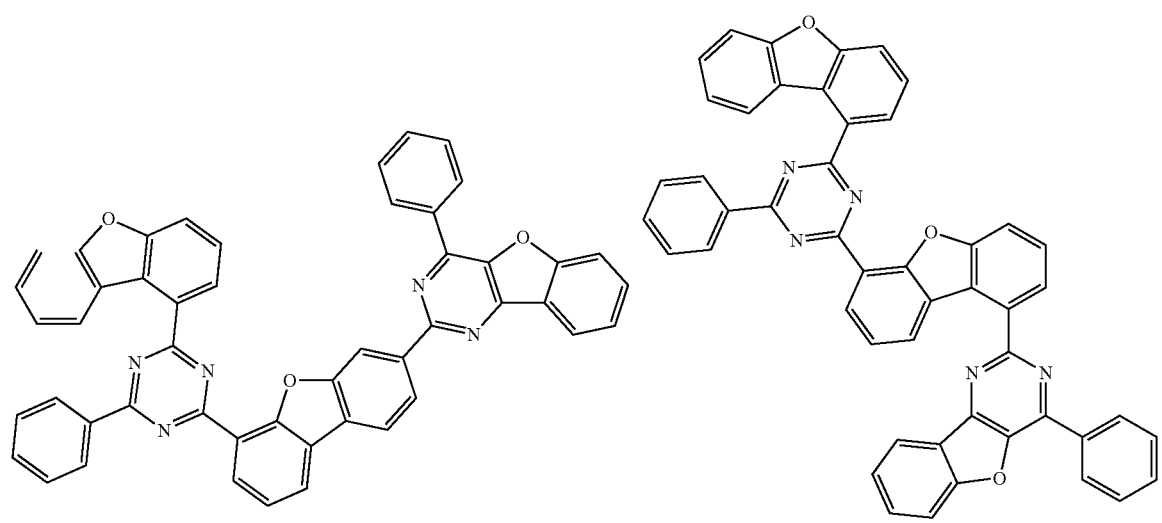

115
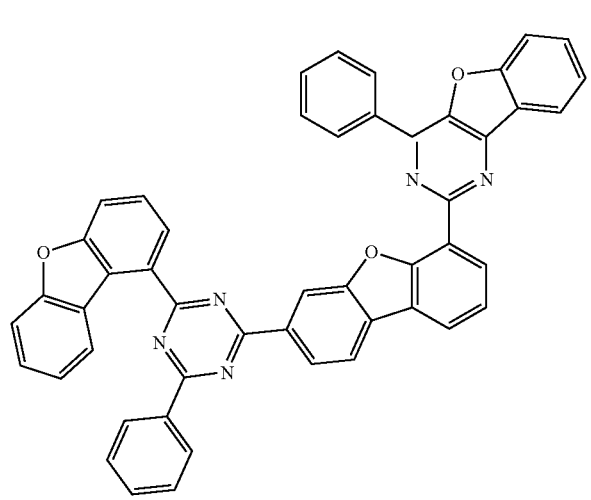
116
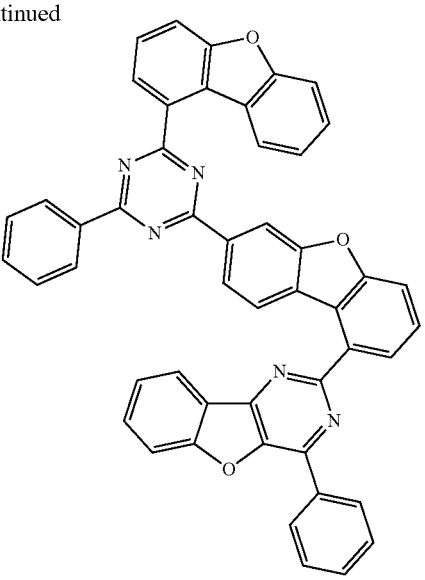
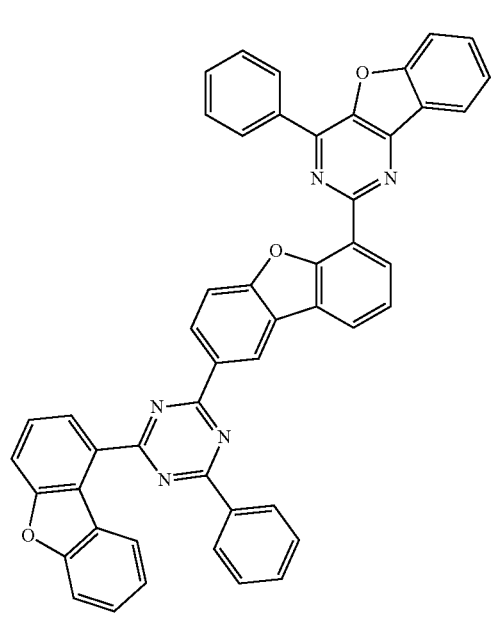
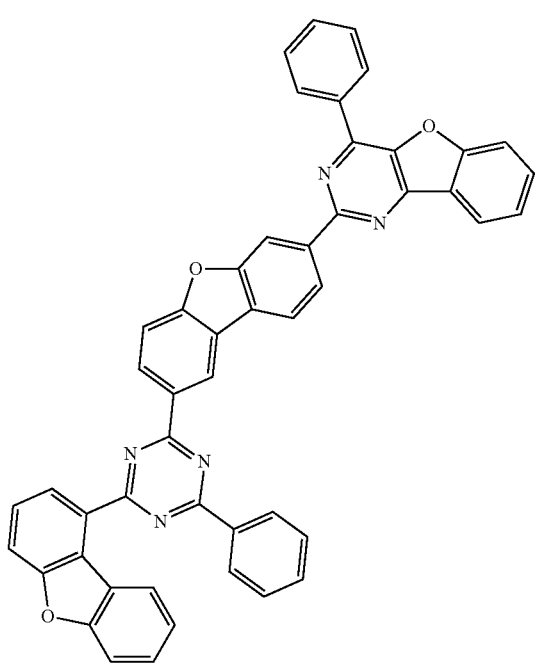

-continued
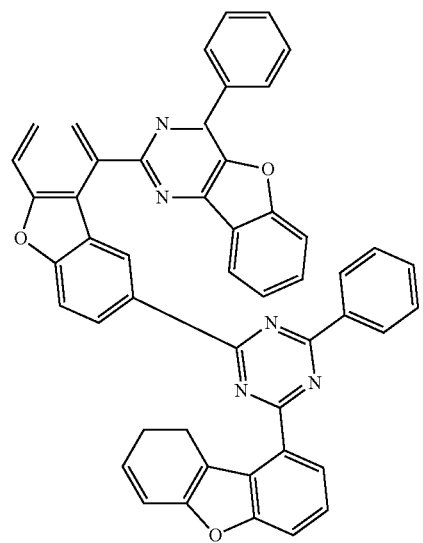
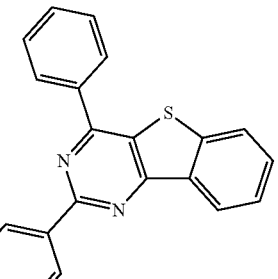
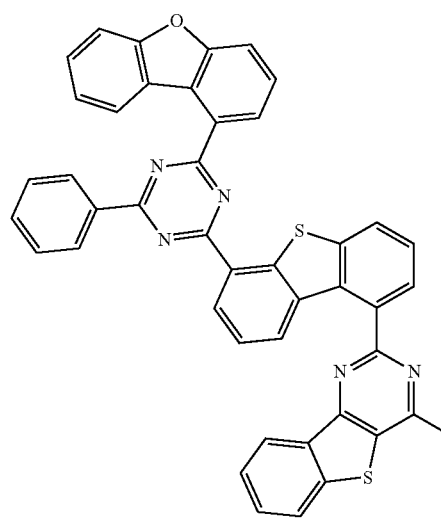
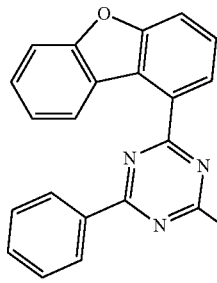
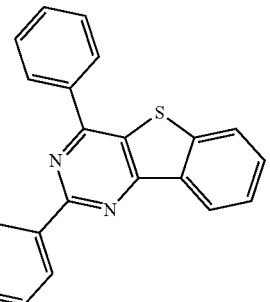
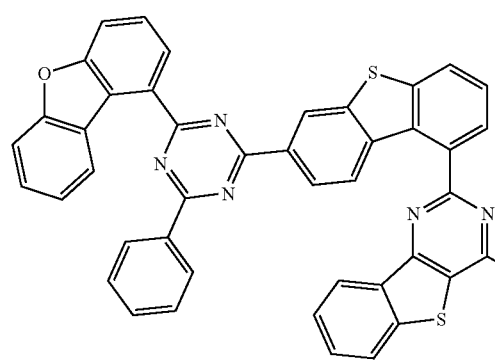
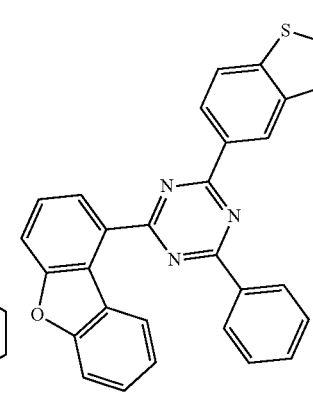

119 120
-continued
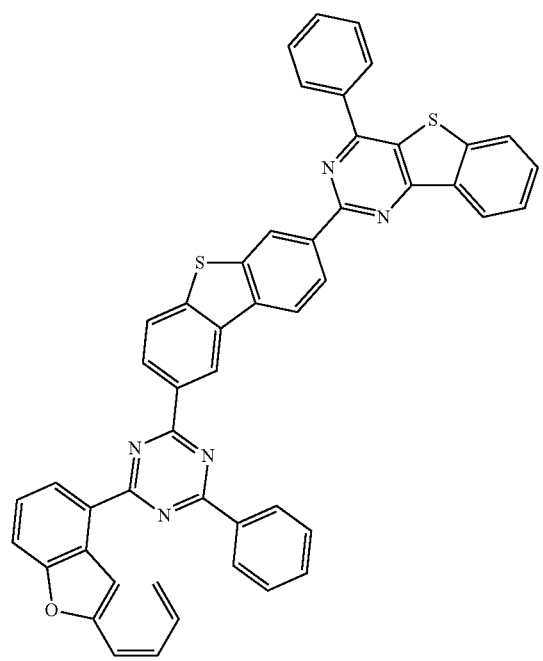
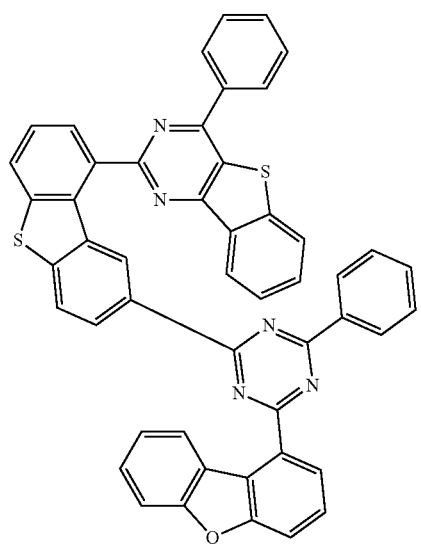
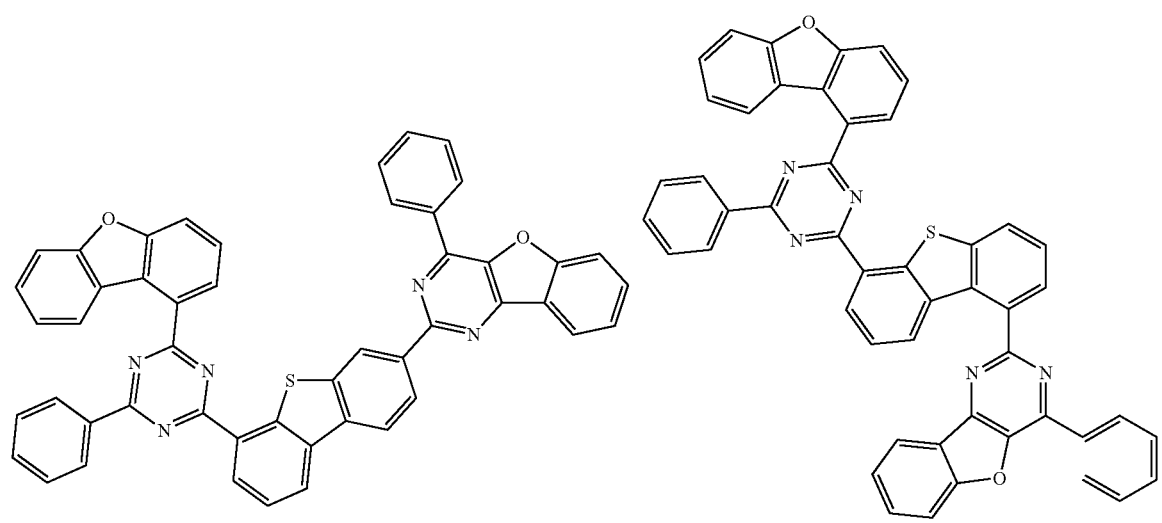

-continued
121
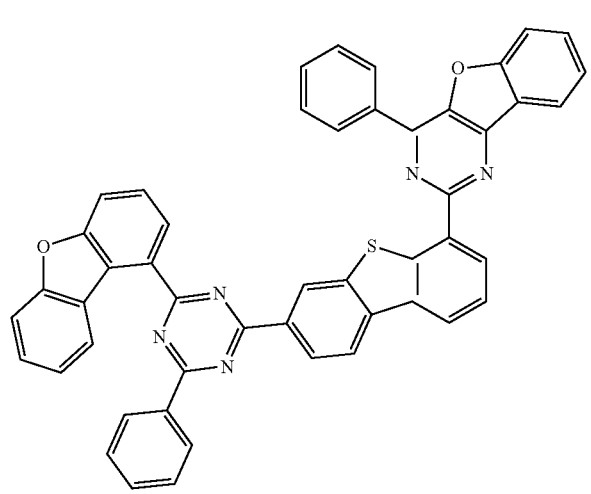
122
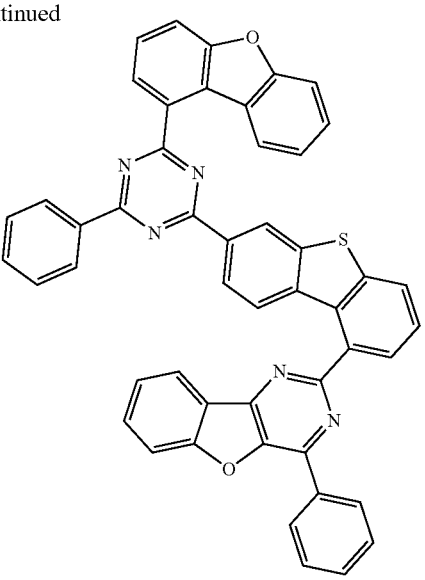
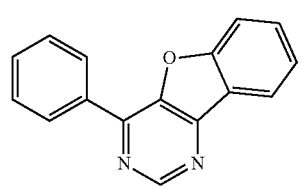
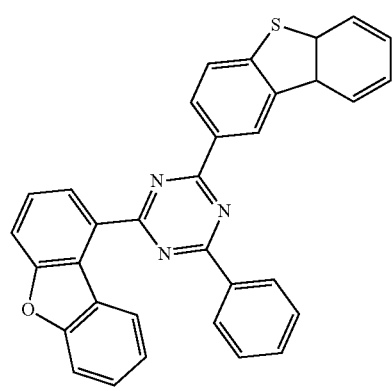
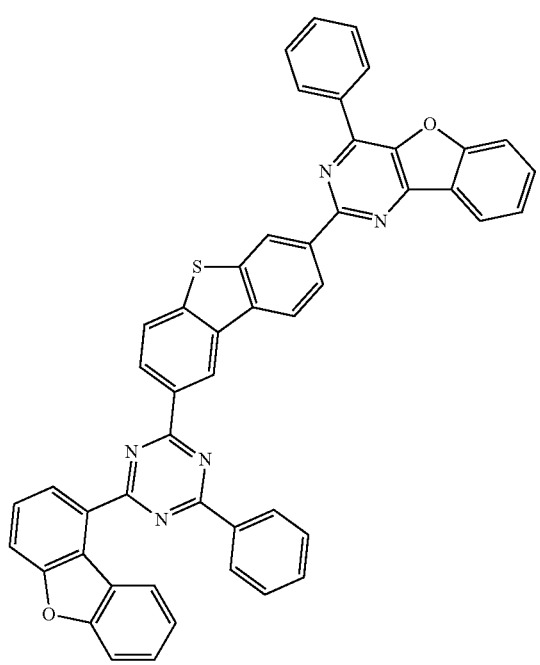

-continued
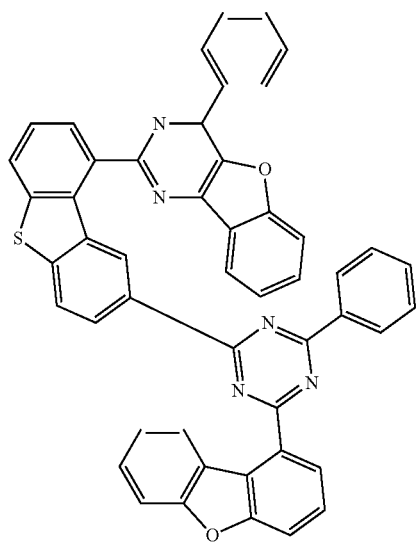
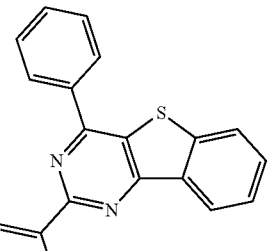
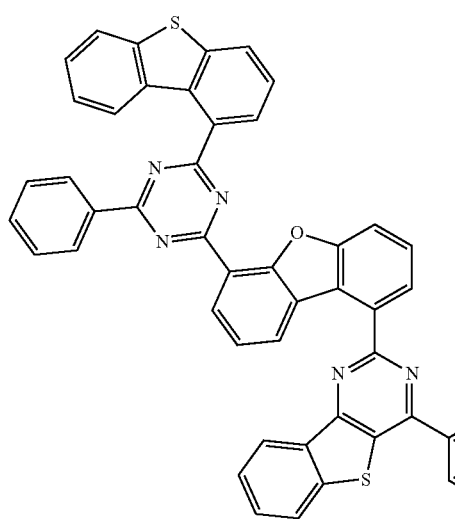
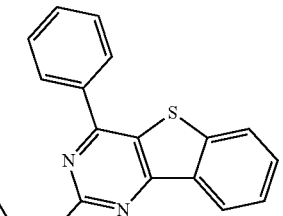
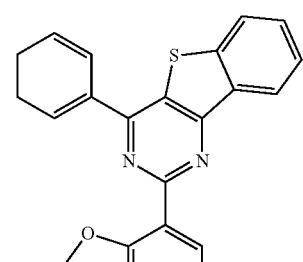
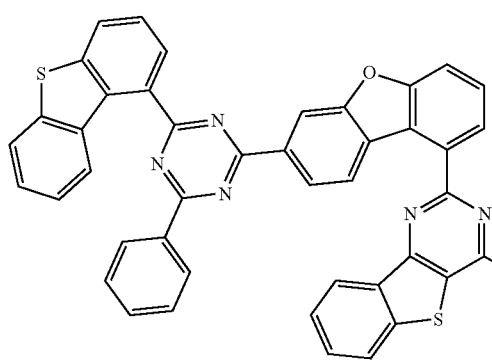
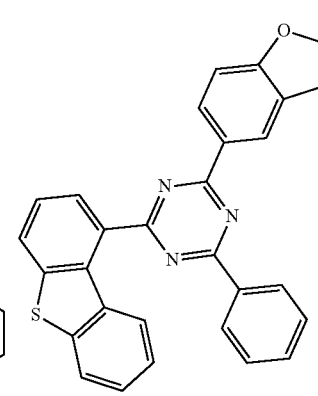

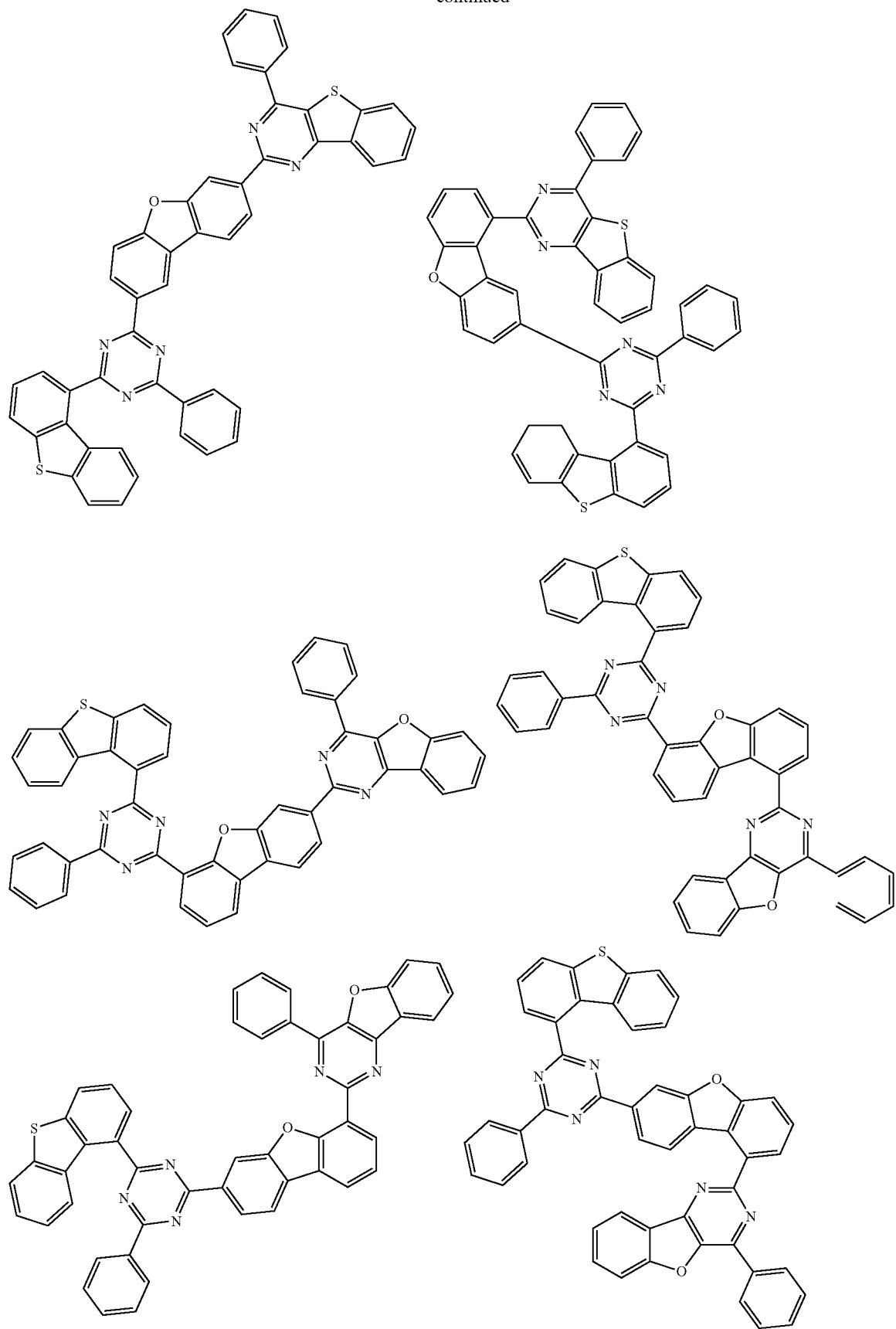

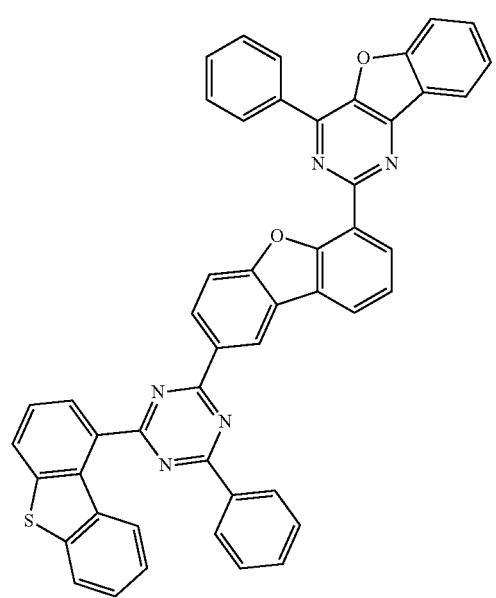
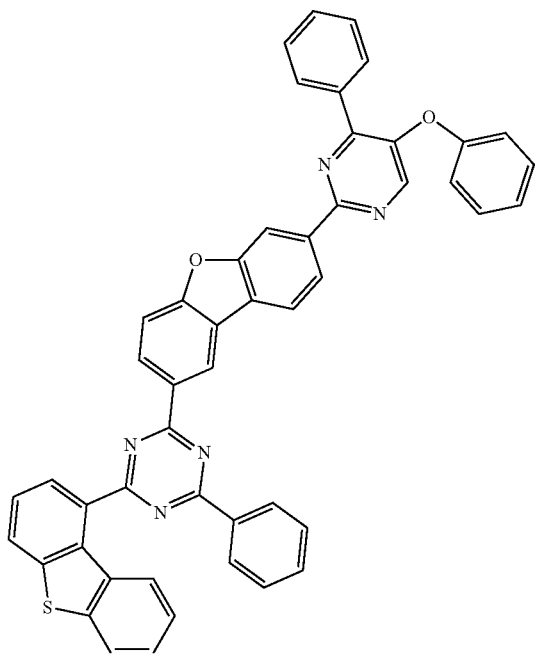
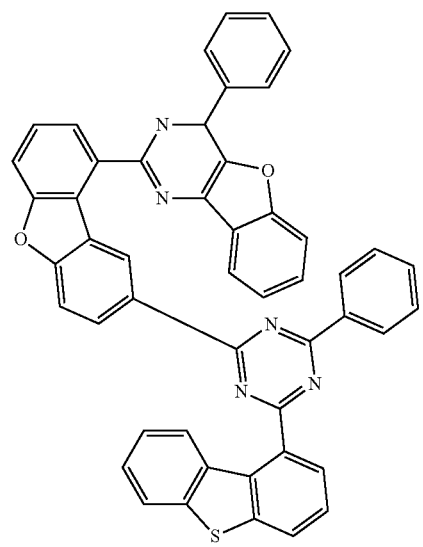
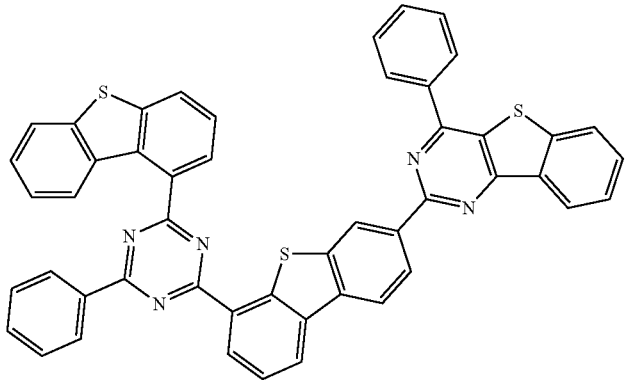
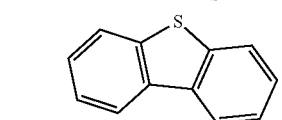
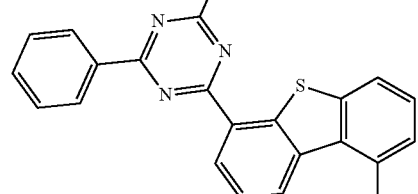
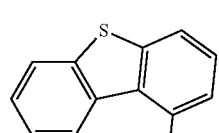
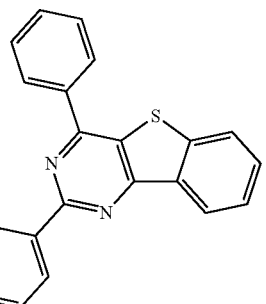
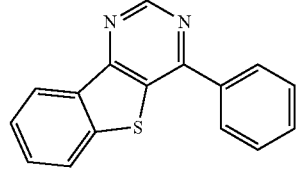

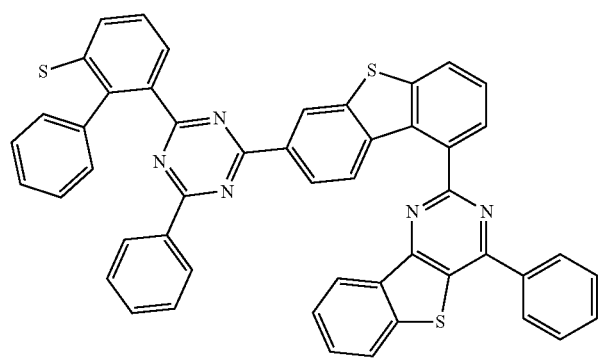
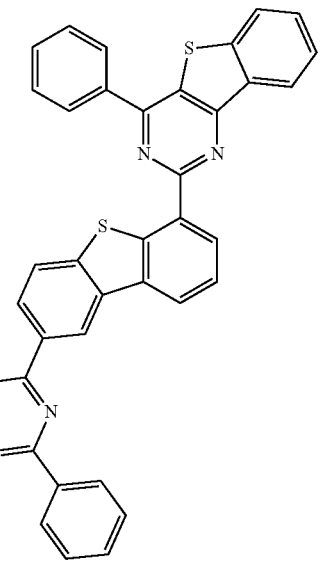
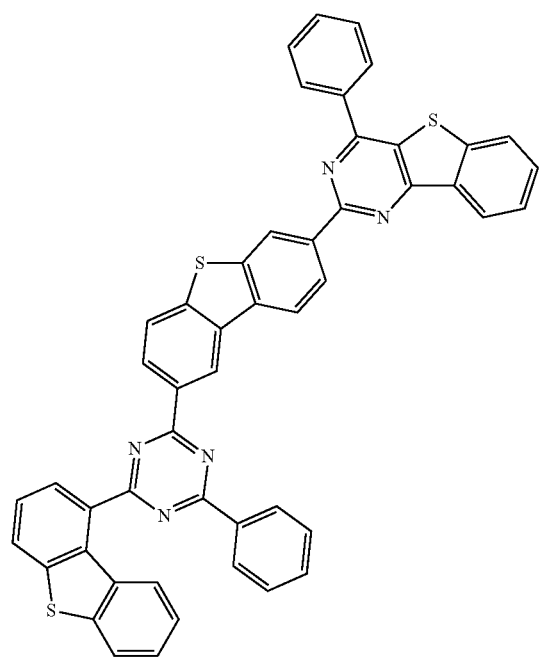

131
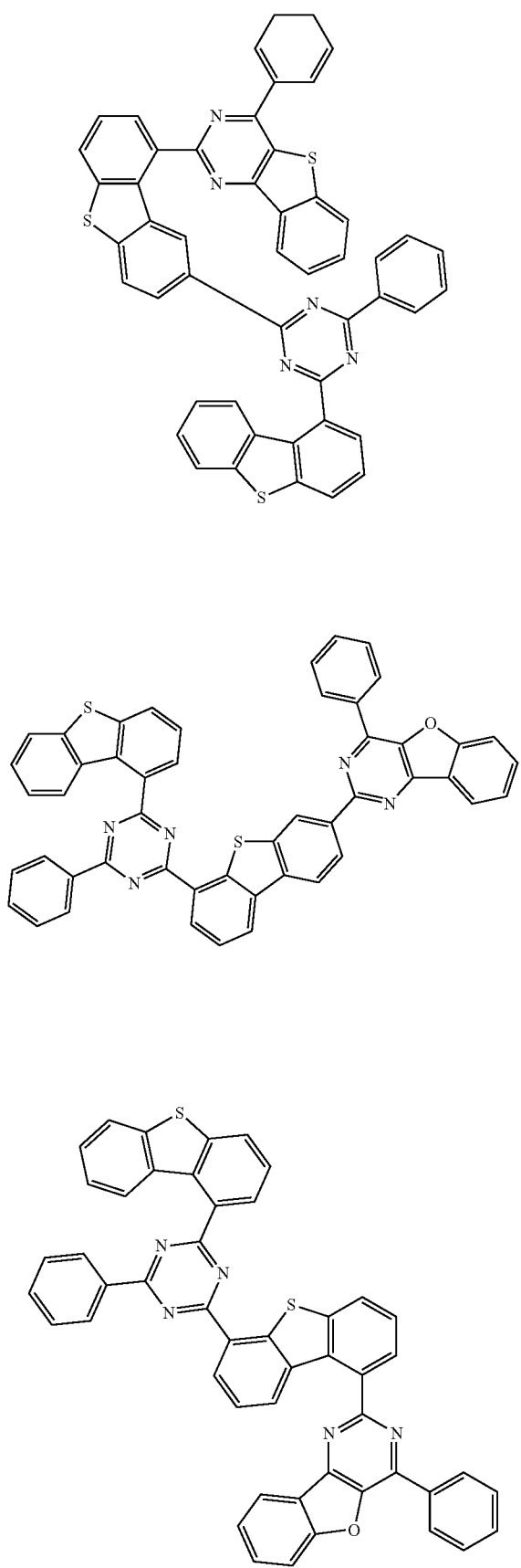
132
-continued
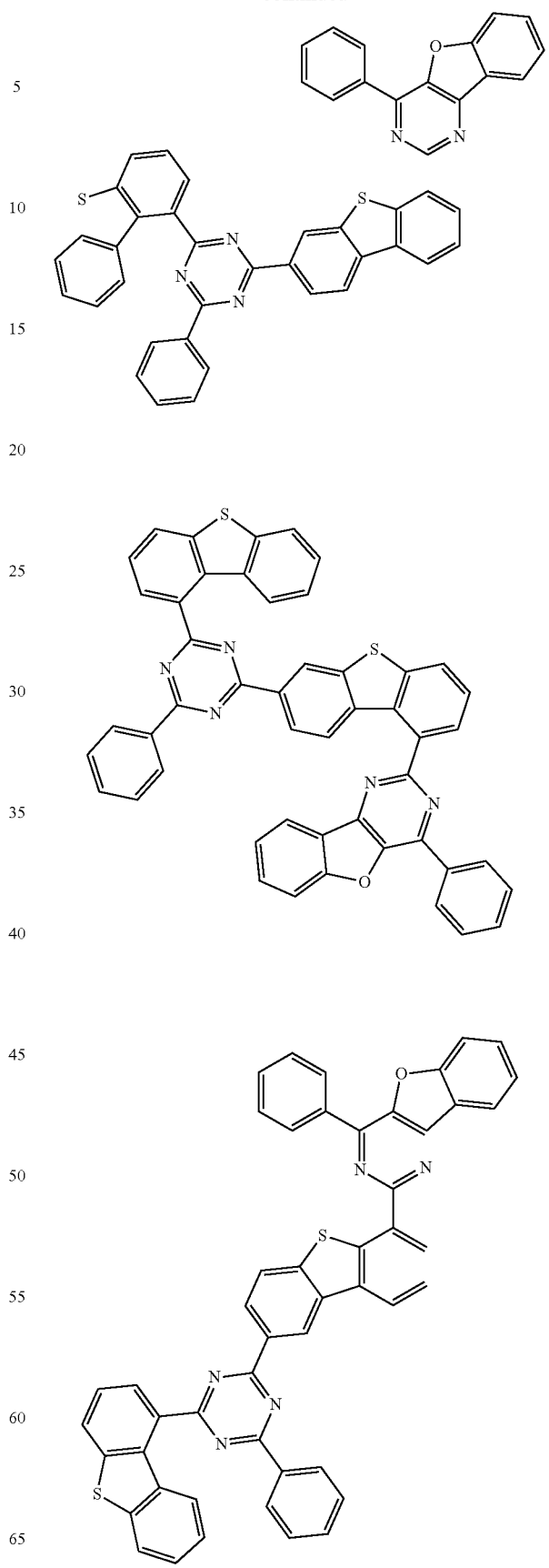

133
-continued
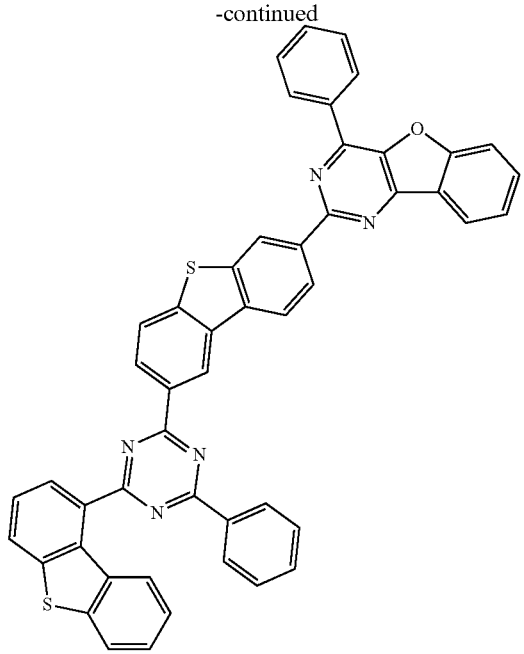
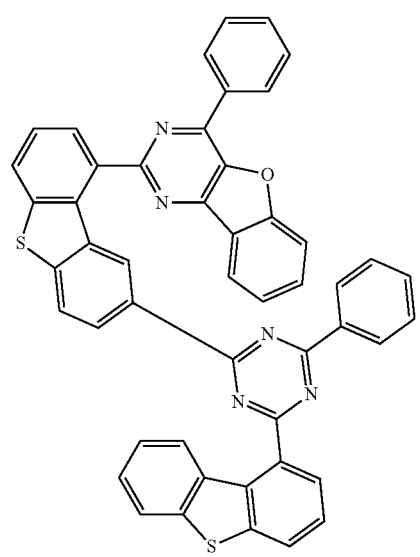
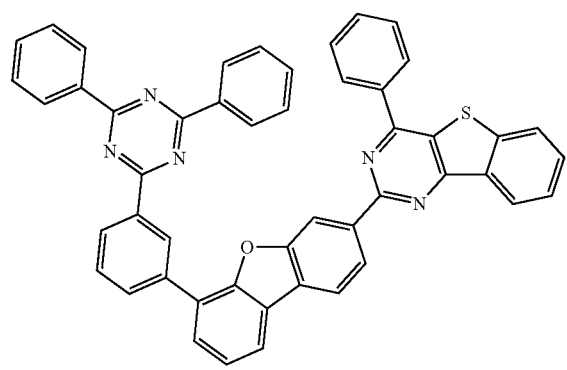
134
-continued
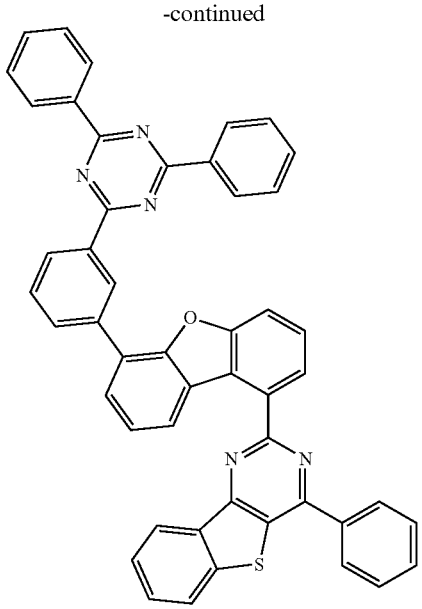
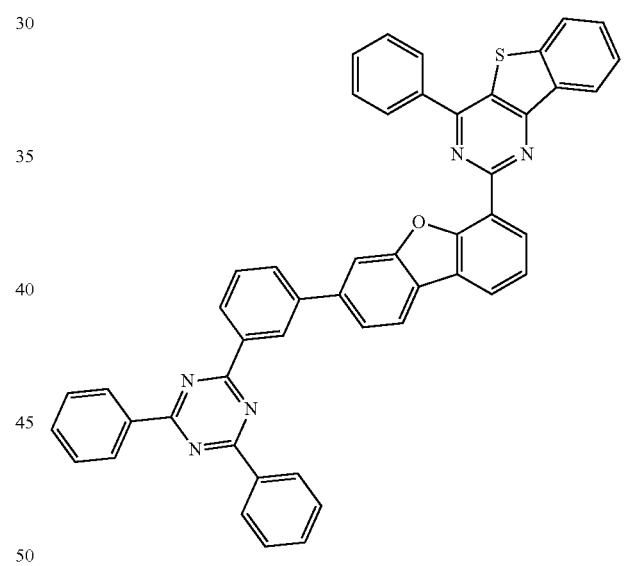
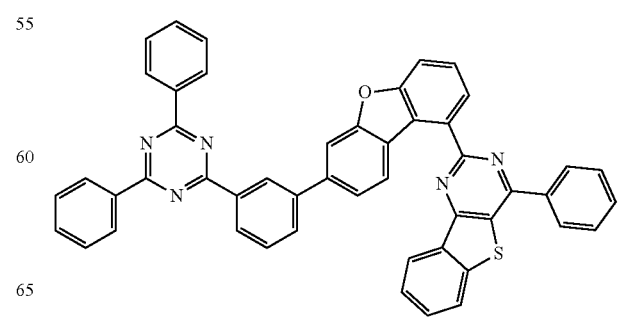

135
-continued
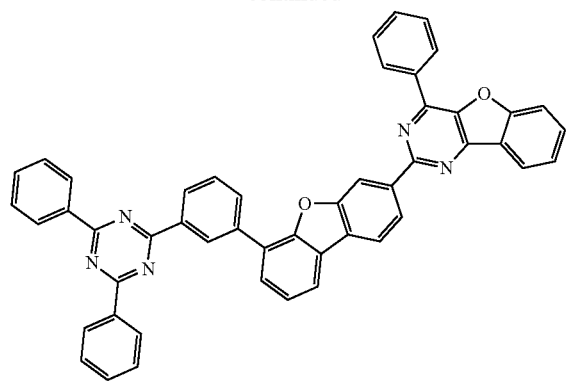
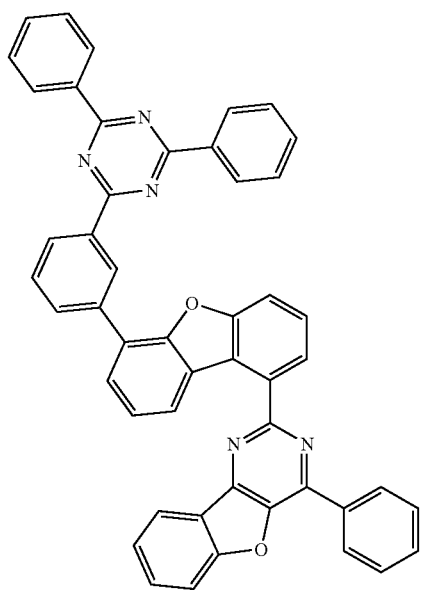
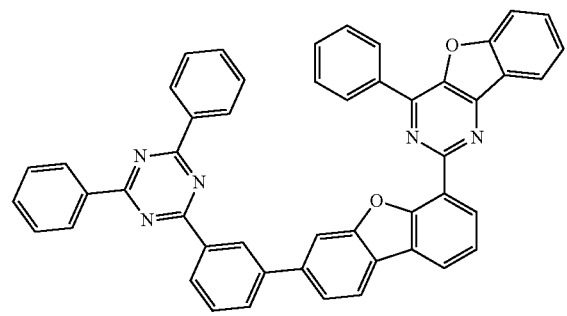
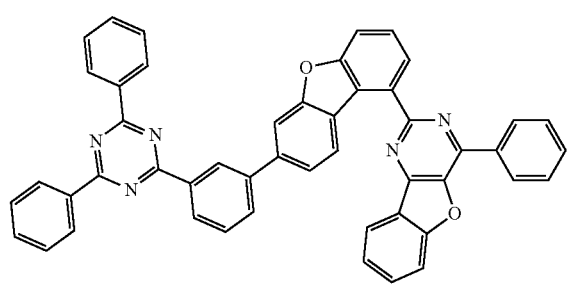
136
-continued
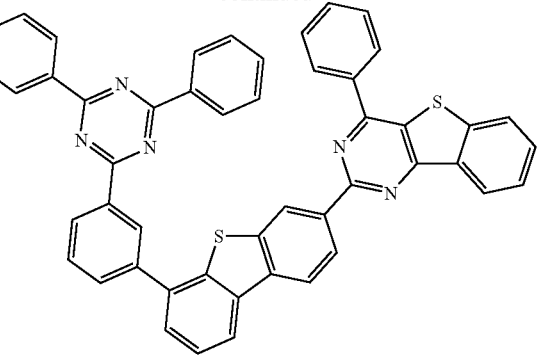
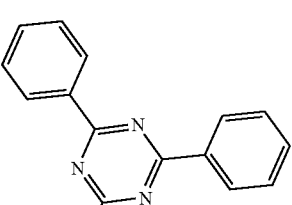
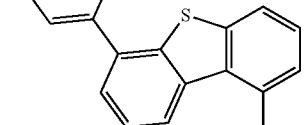
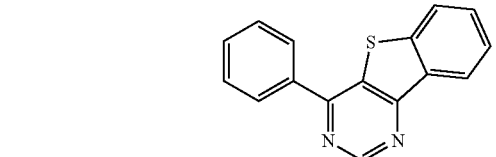
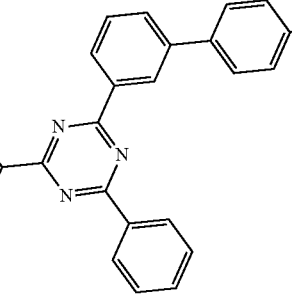

137
-continued
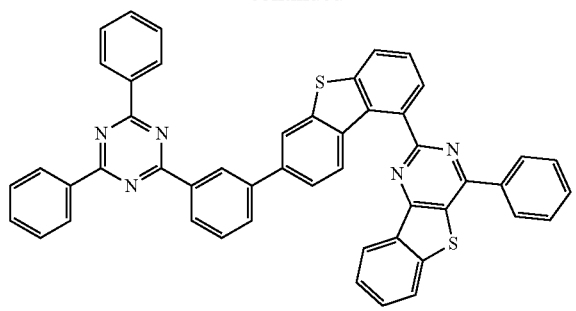
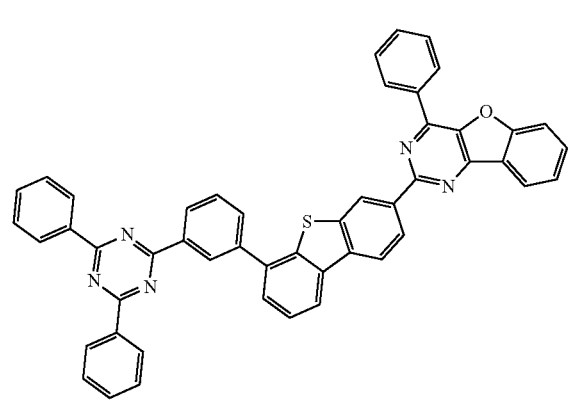
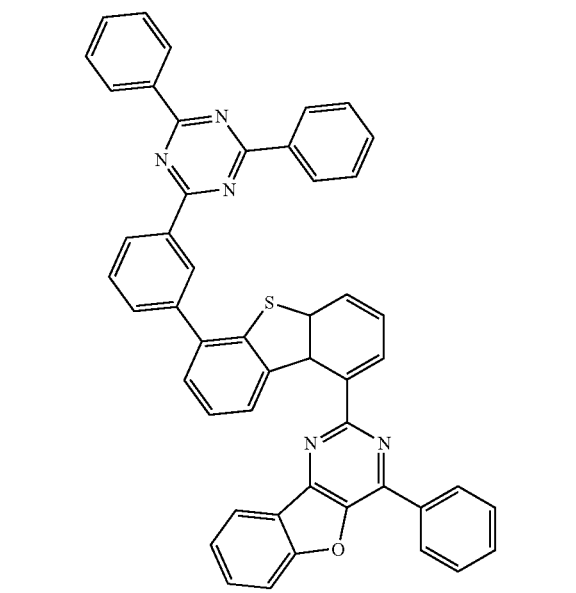
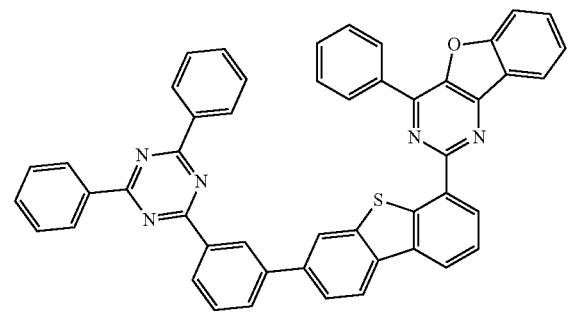
138
-continued
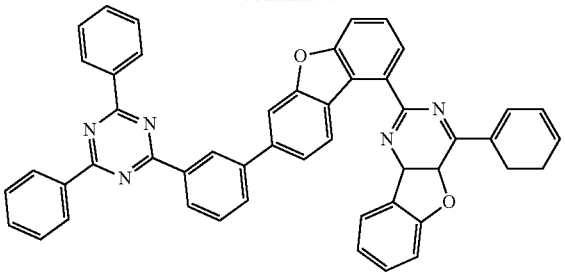
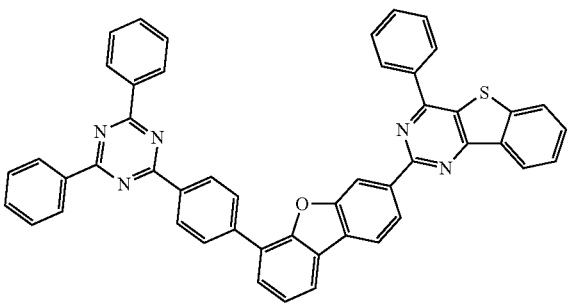
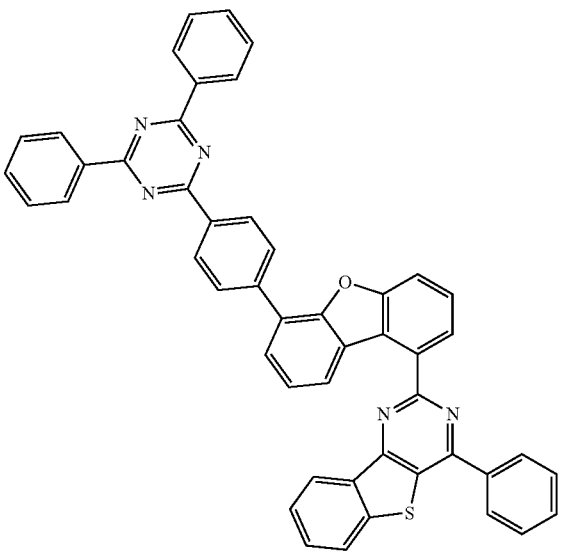

139
-continued
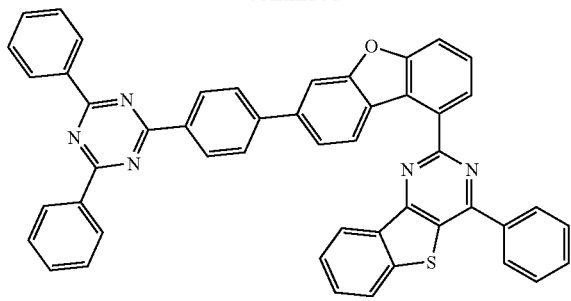
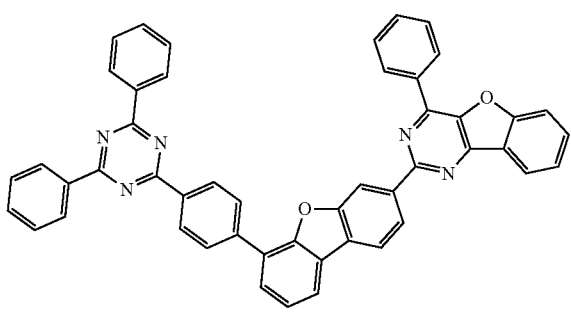
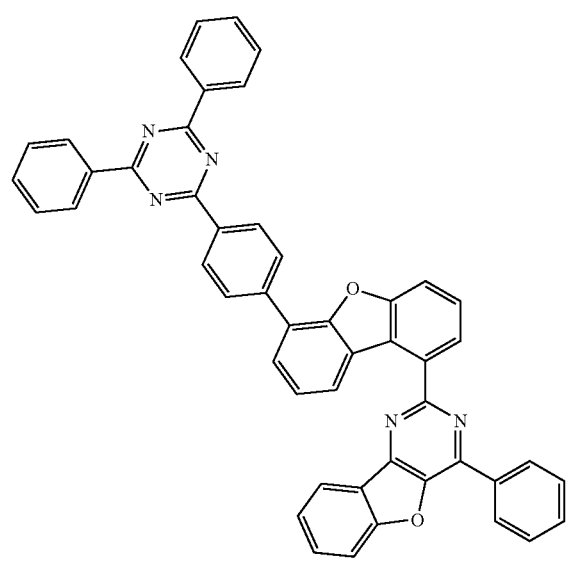
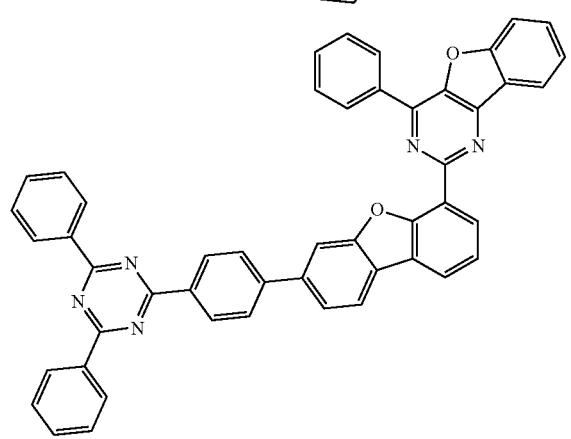
140
-continued
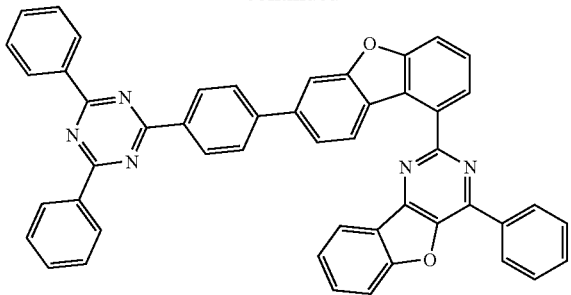
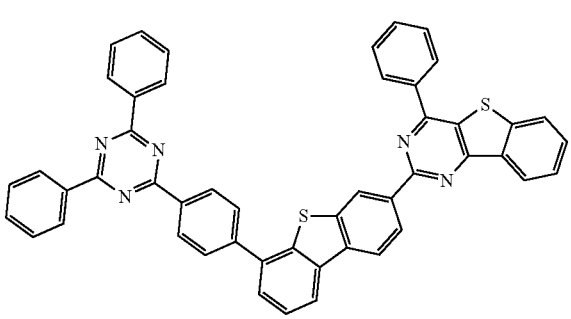
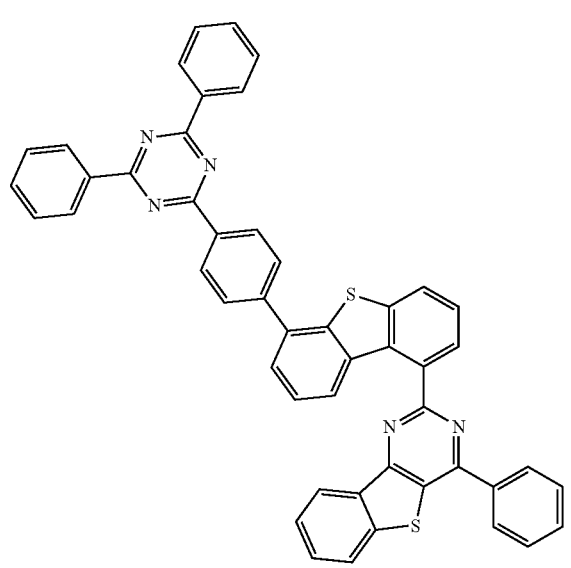
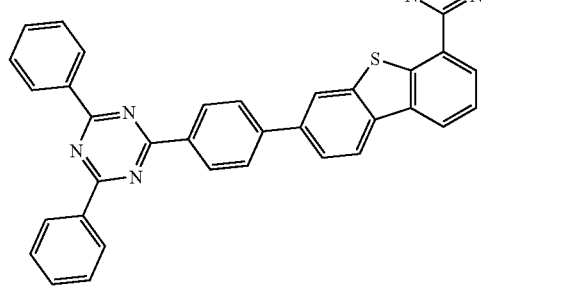

141
-continued
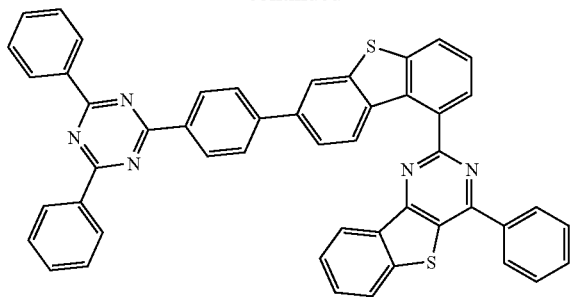
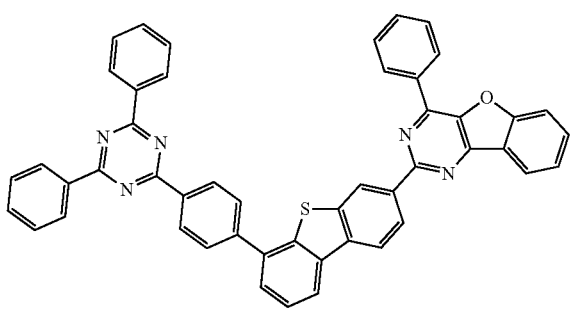
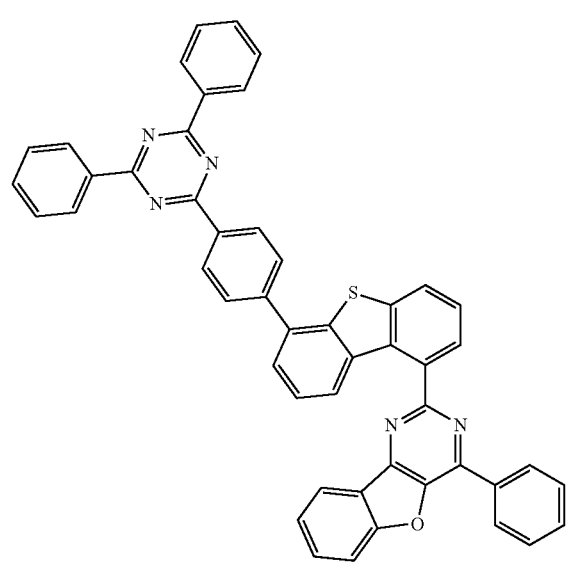
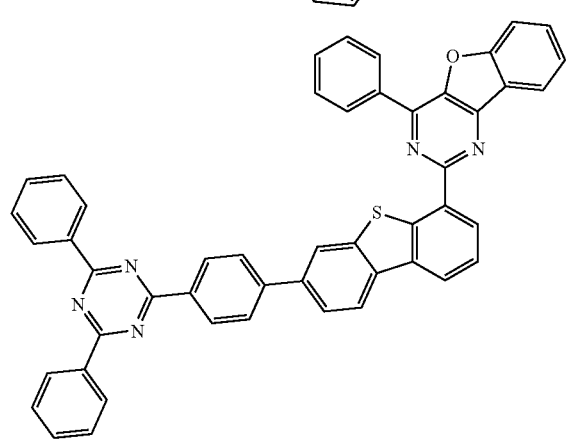
142
-continued
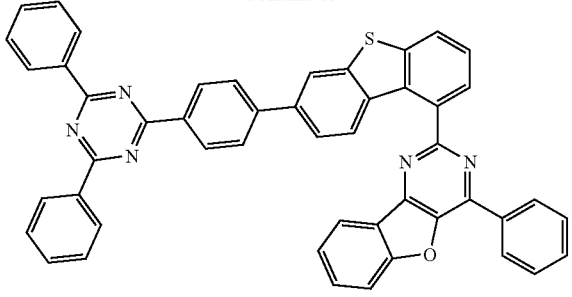

143
-continued
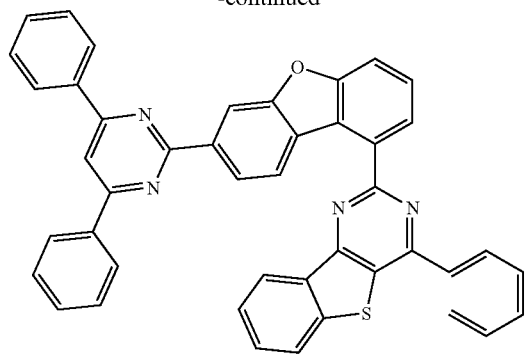
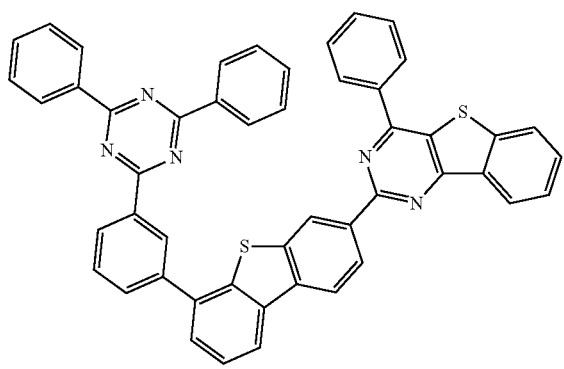
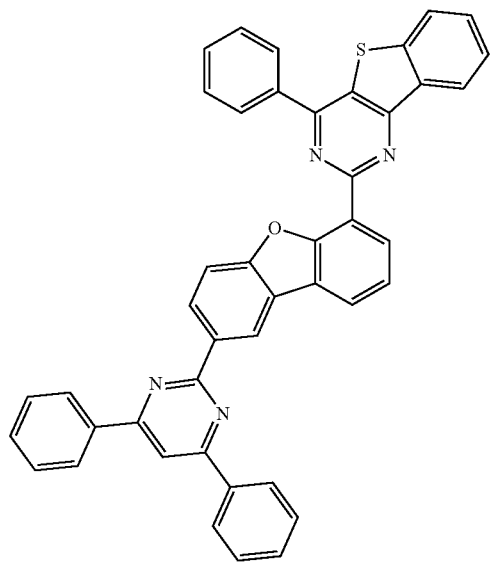
144
-continued
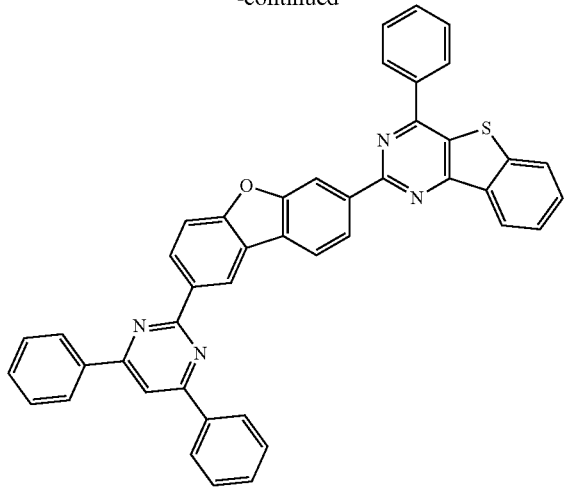
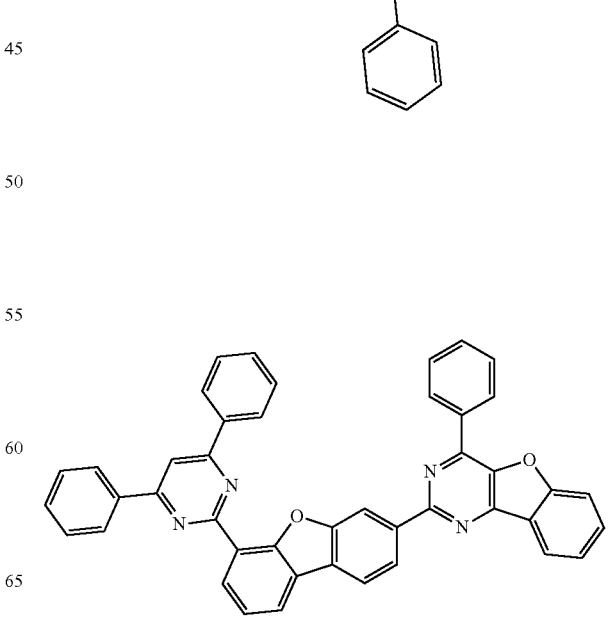

-continued
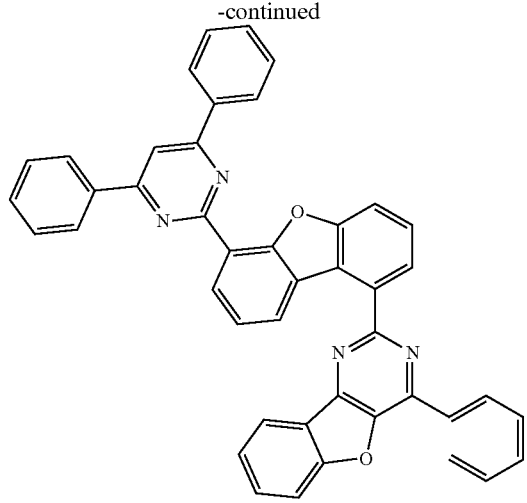
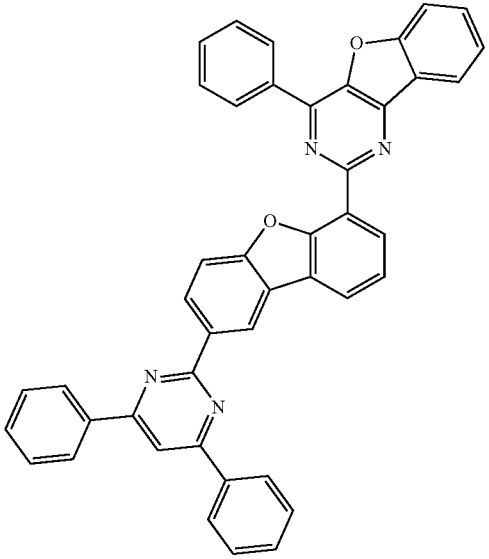
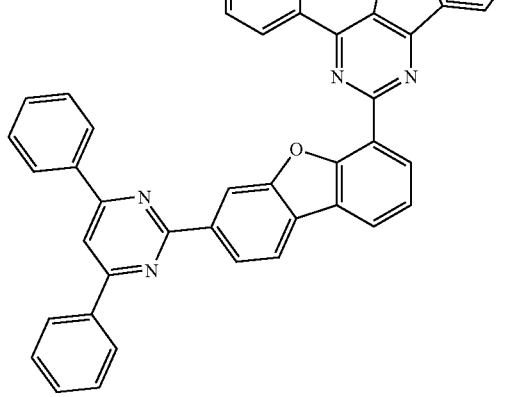
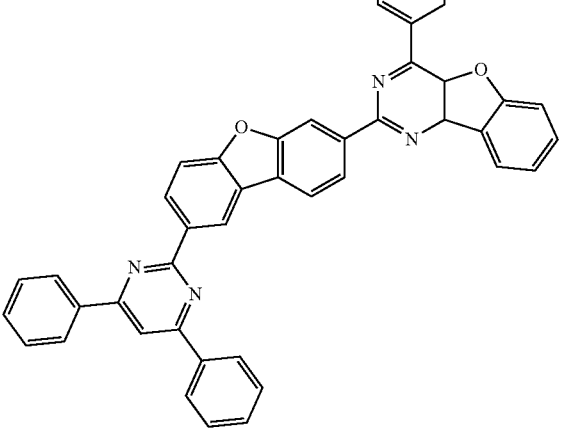
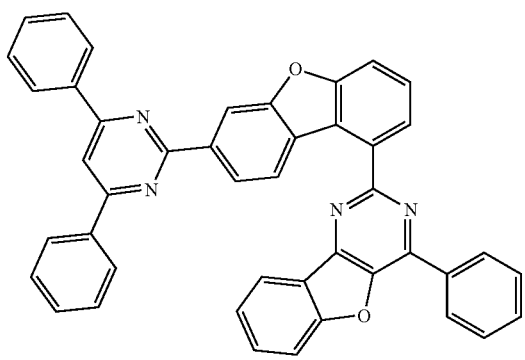
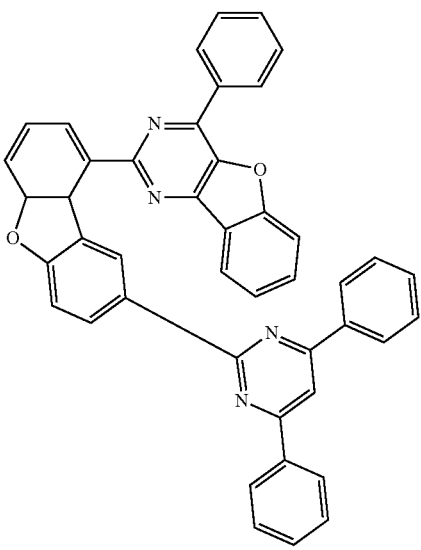

147
-continued
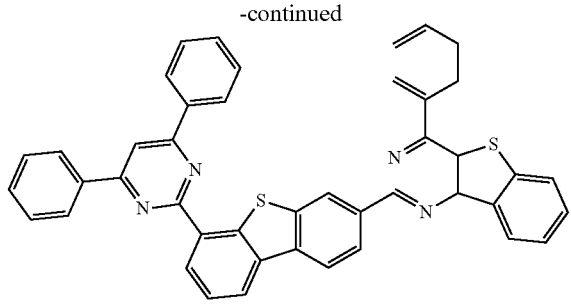
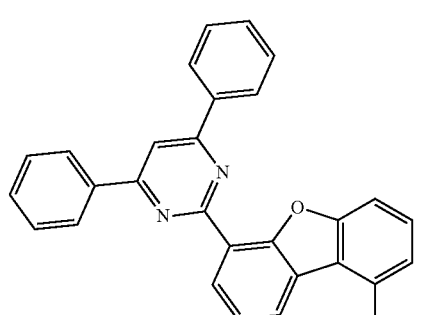
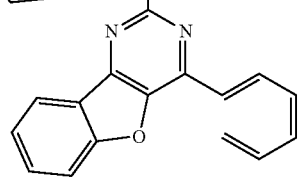
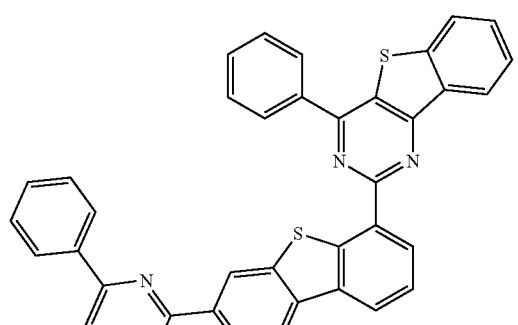
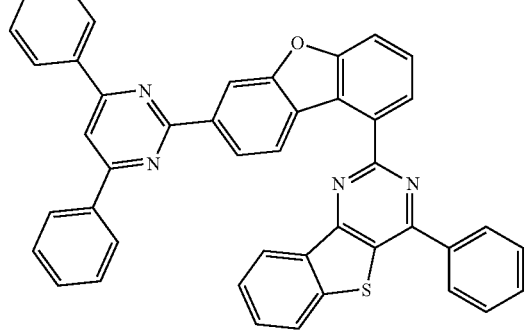
148
-continued
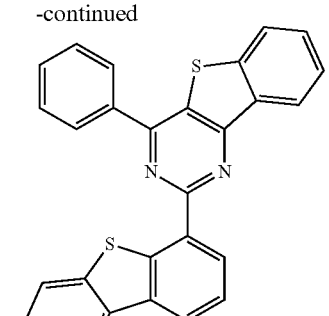
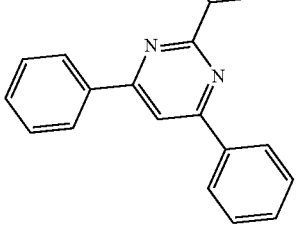
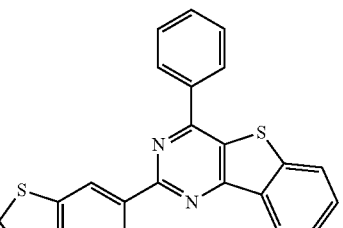
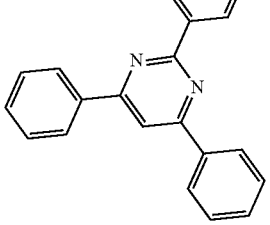
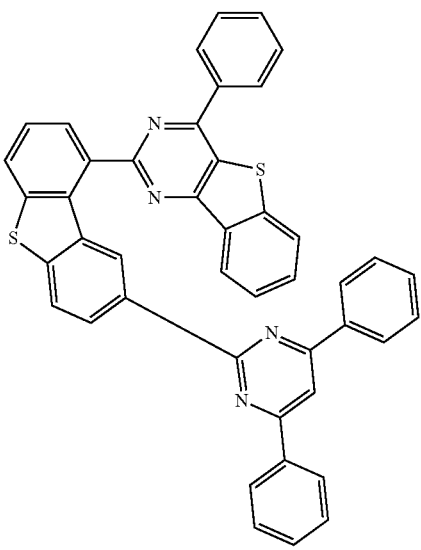

-continued
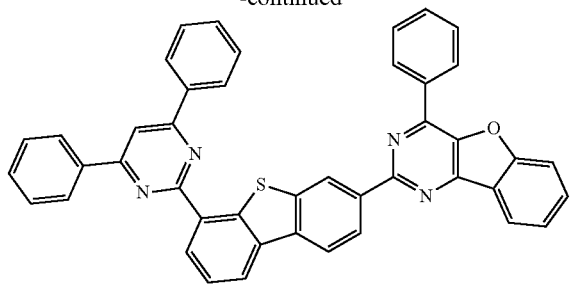
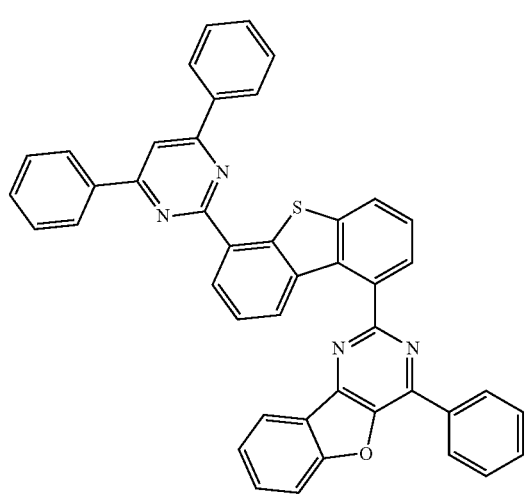
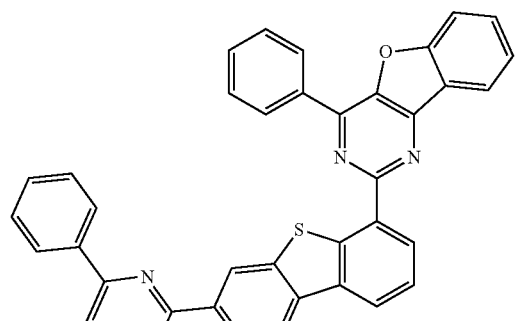
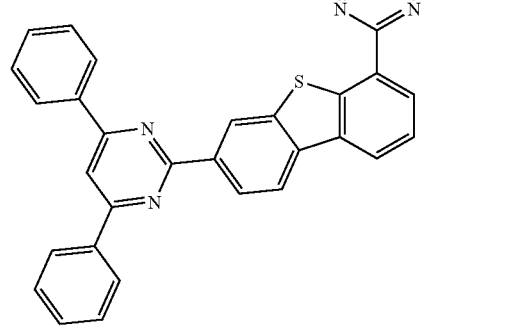
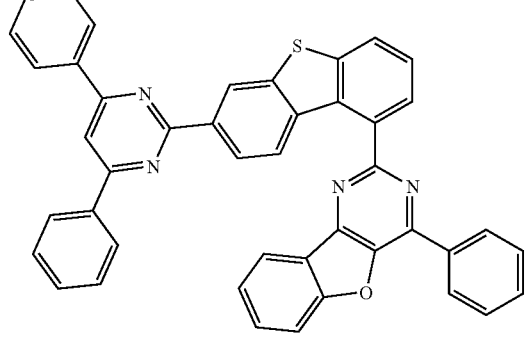
-continued
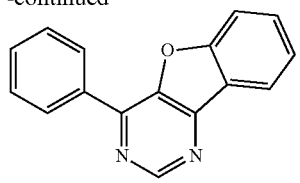
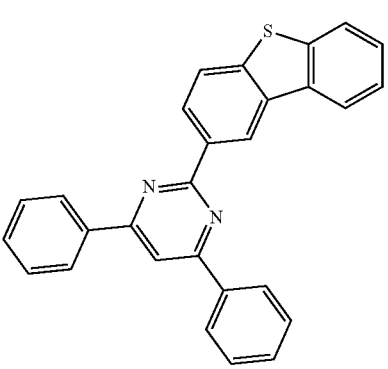
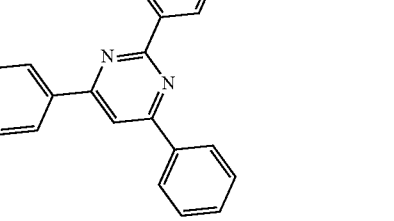
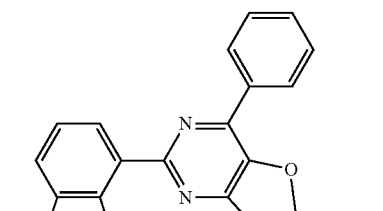
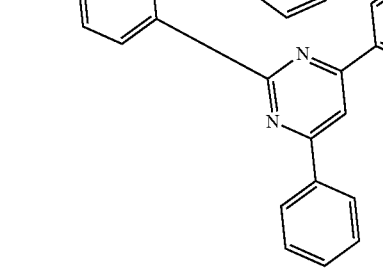

151
-continued
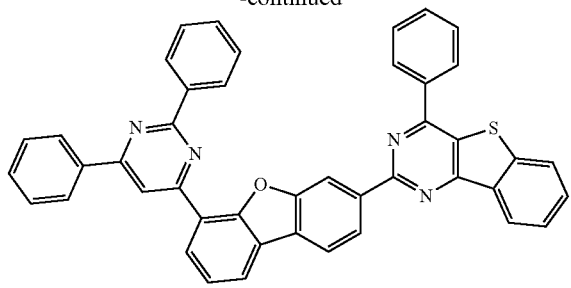
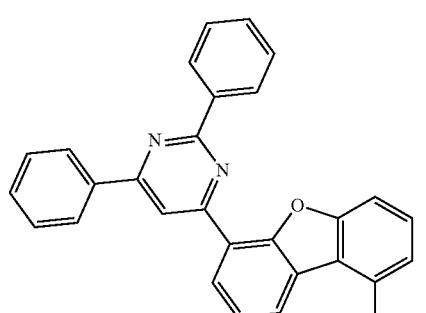
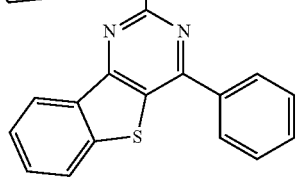
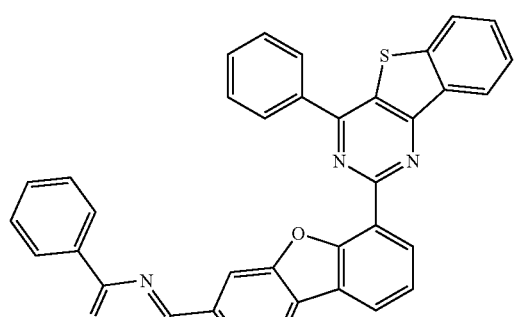
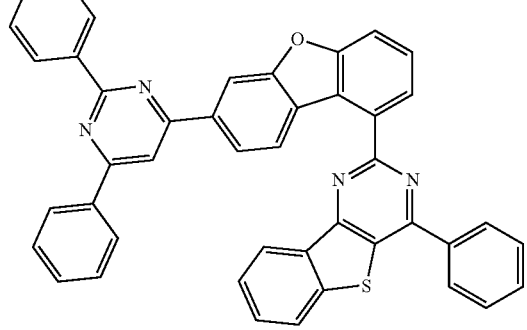
152
-continued
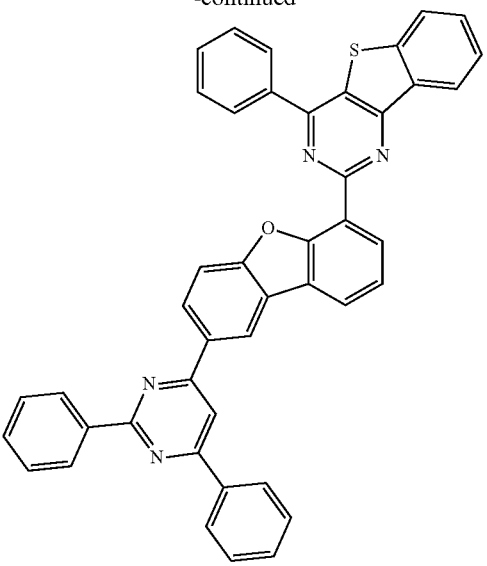
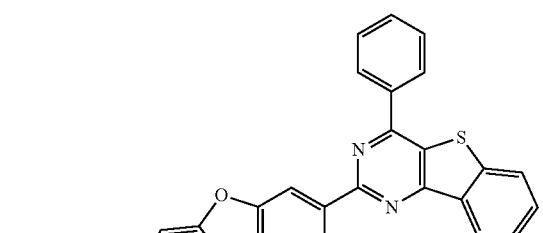
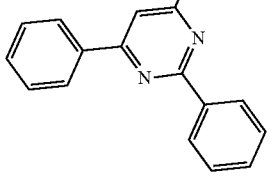
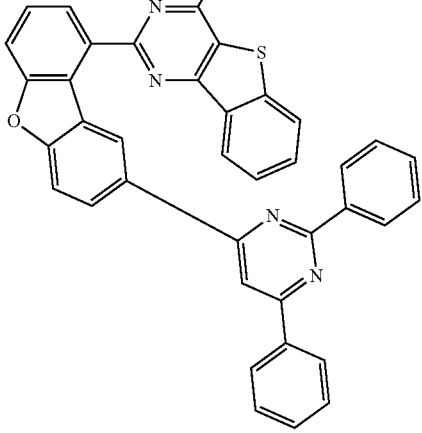

153
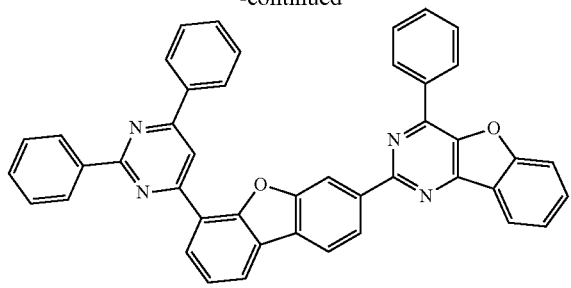
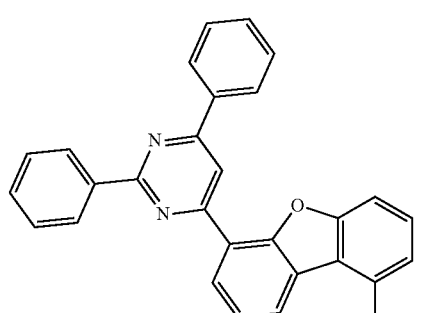
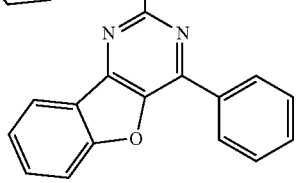
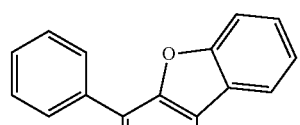
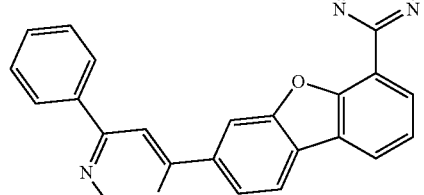
154
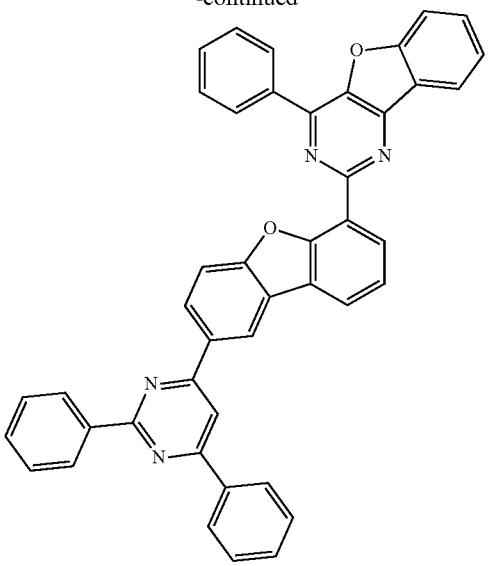
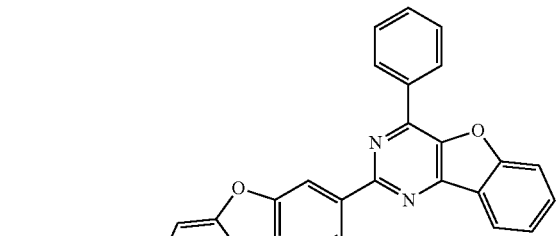
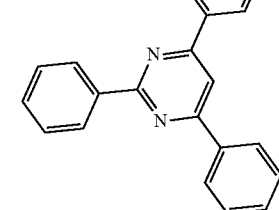
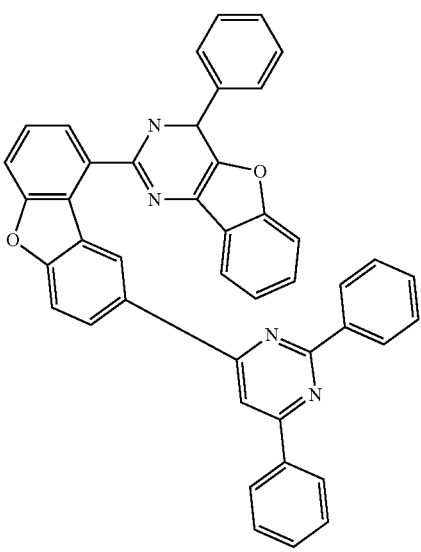

-continued
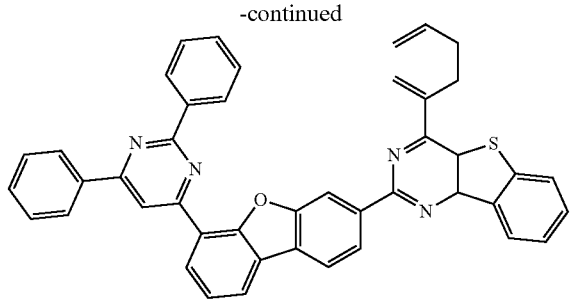
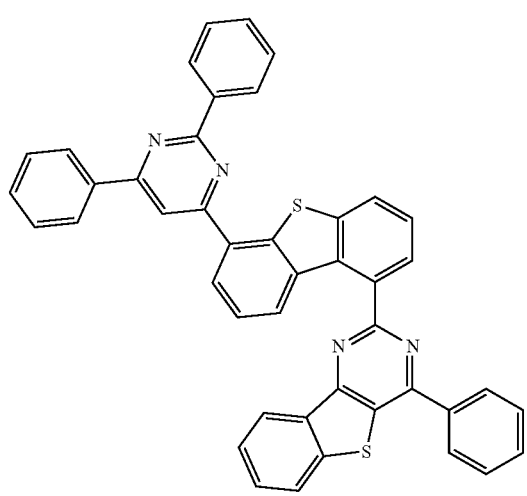
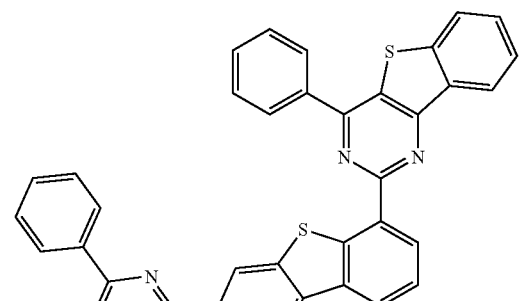
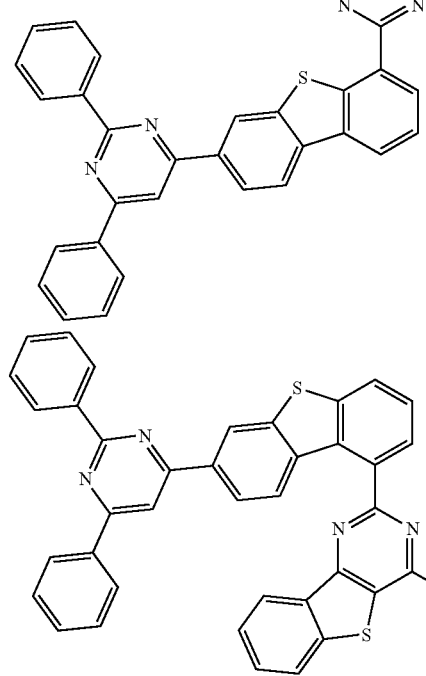
-continued
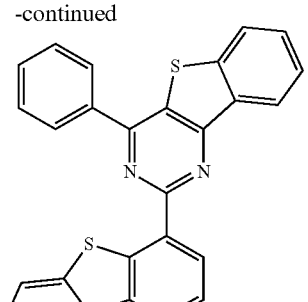
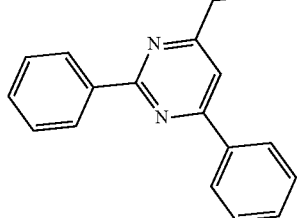
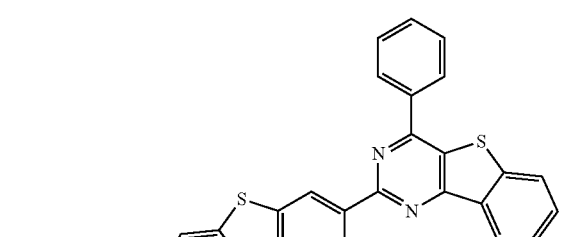
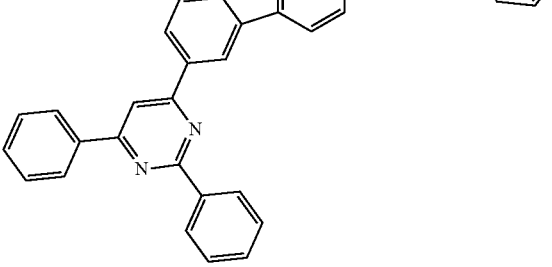
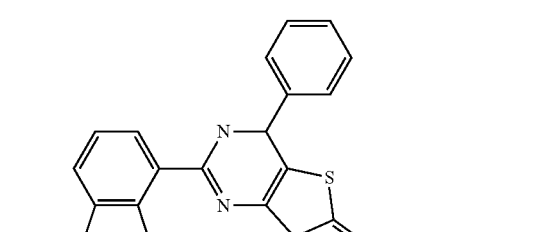
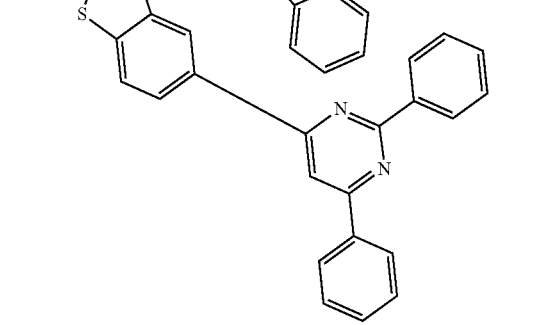

157
-continued
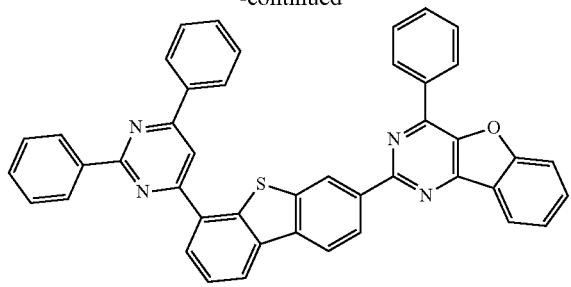
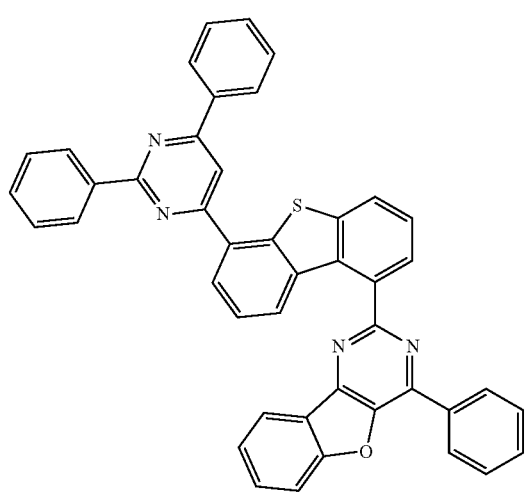
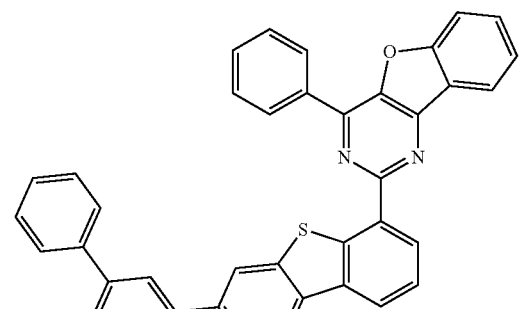
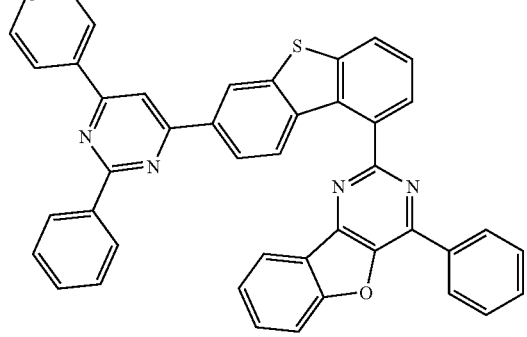
158
-continued
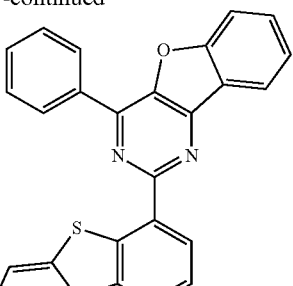
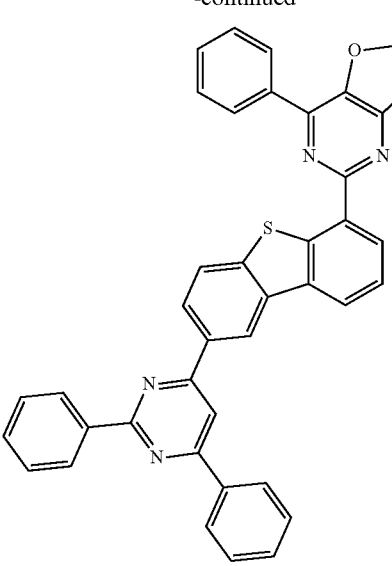
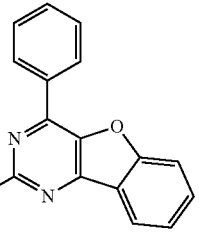
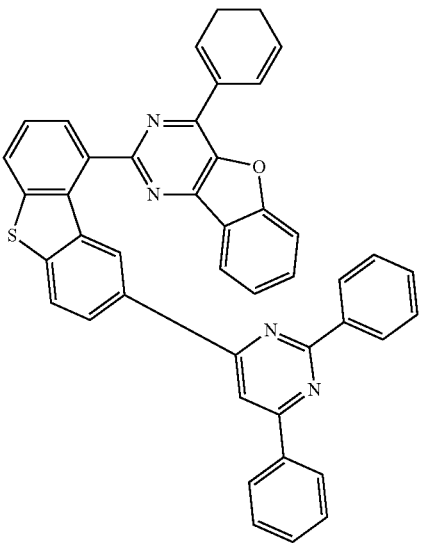

159
-continued
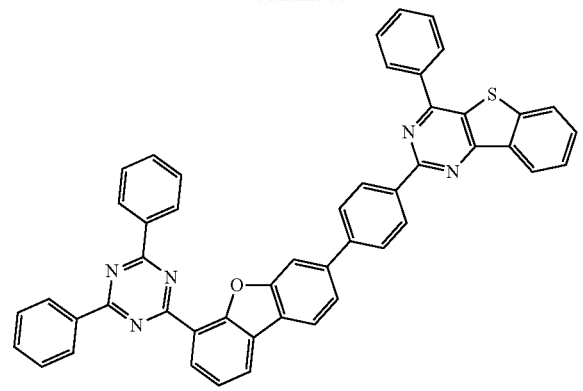
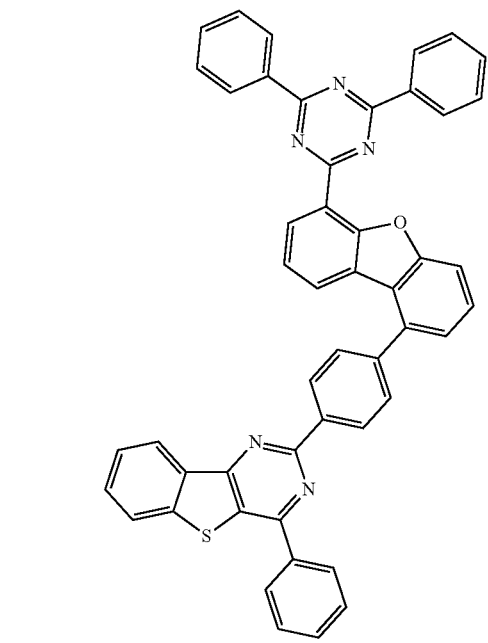
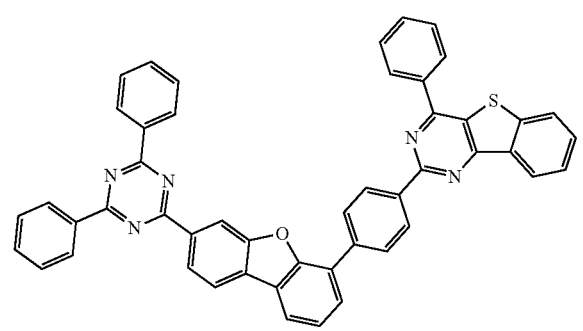
160
-continued
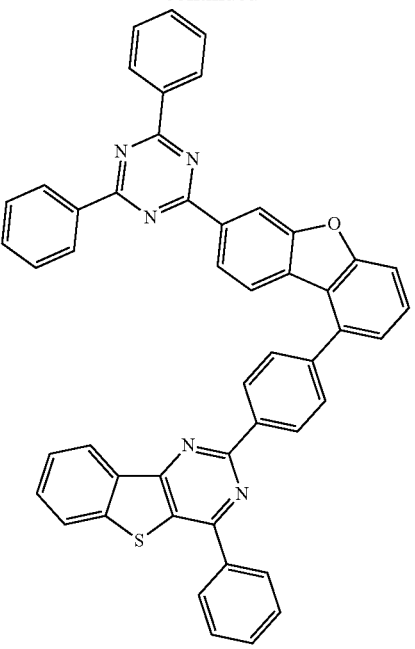
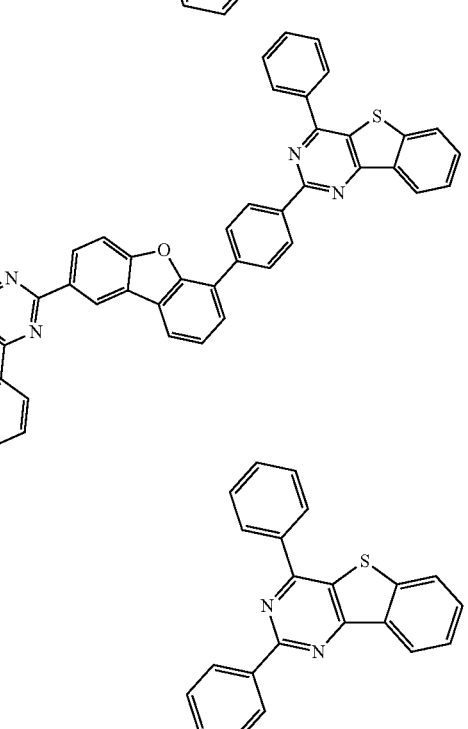

161
-continued
162
-continued
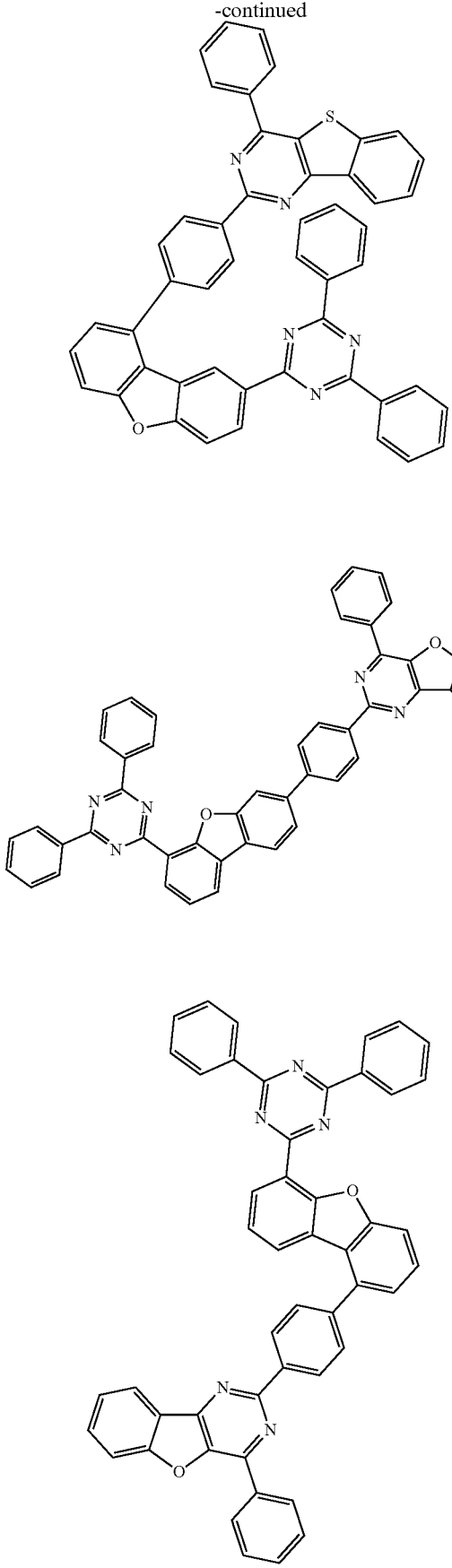
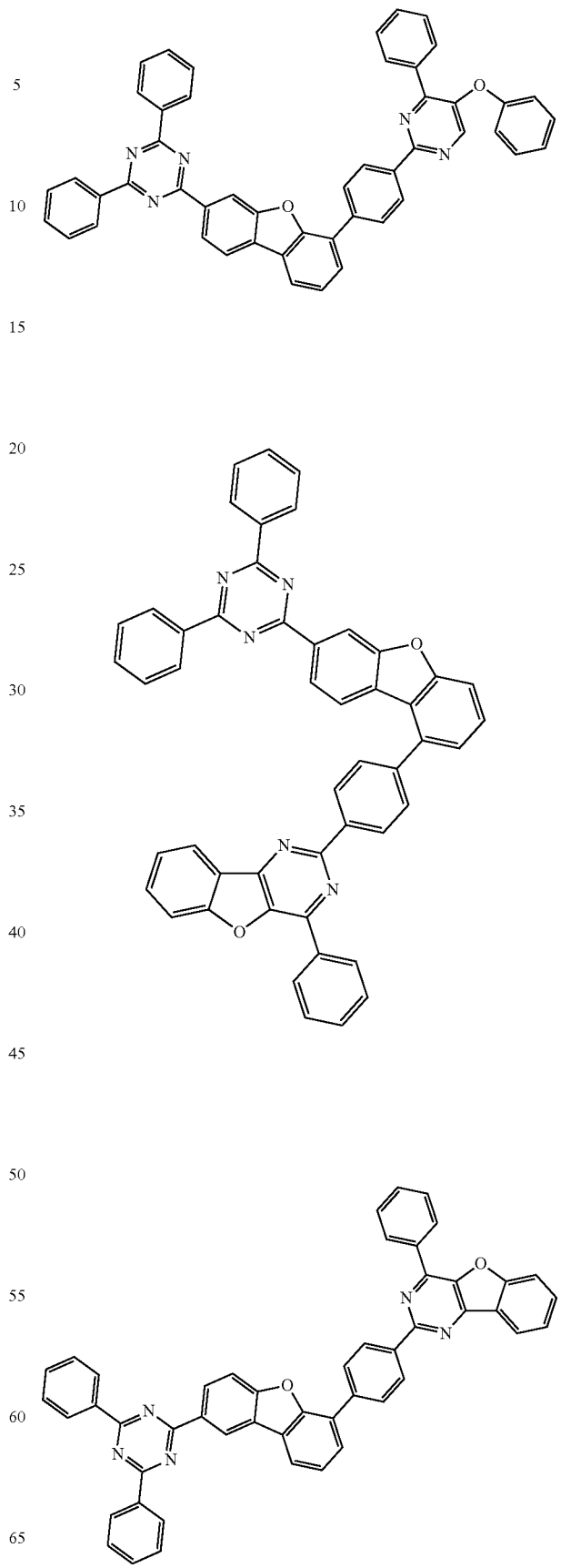

163
-continued
164
-continued
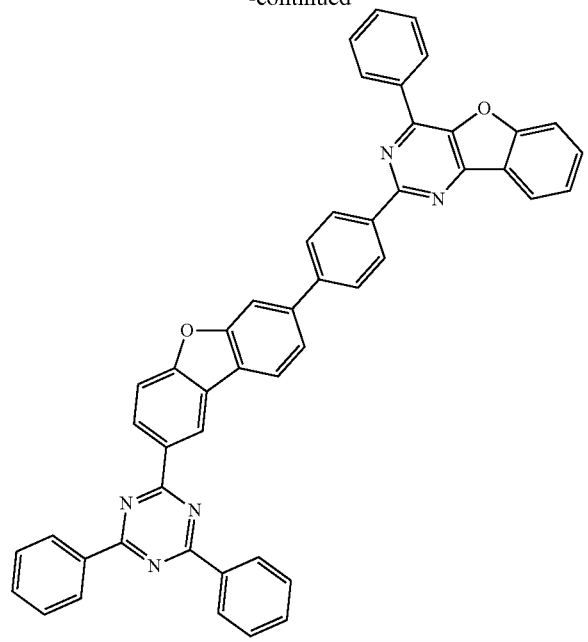
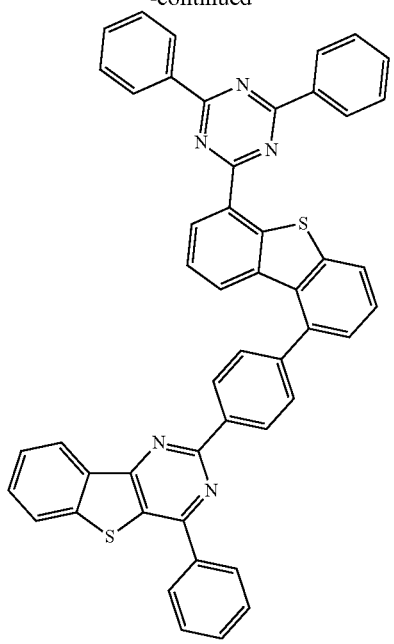
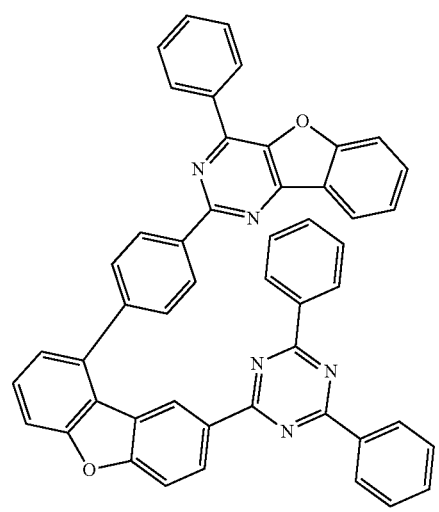
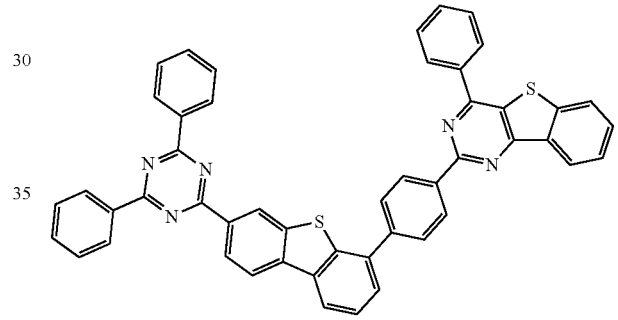
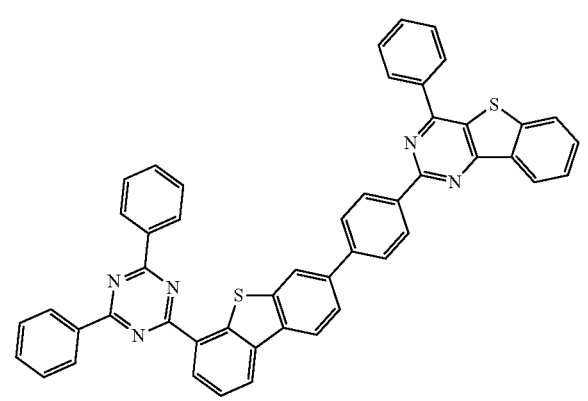
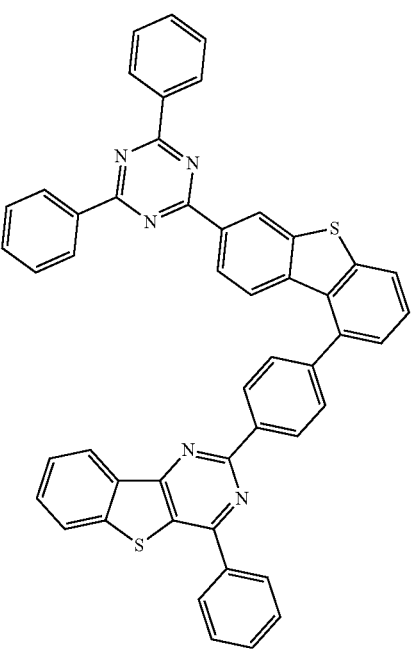

165
-continued
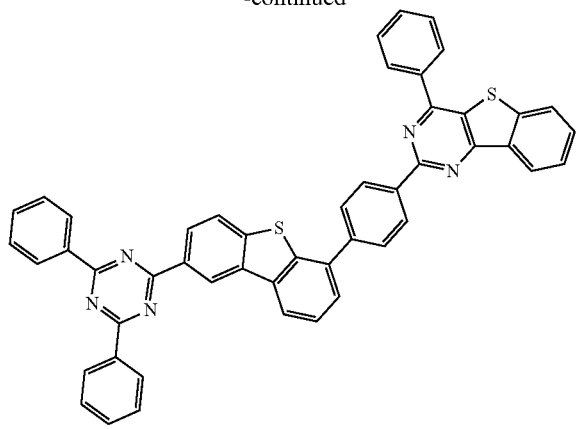
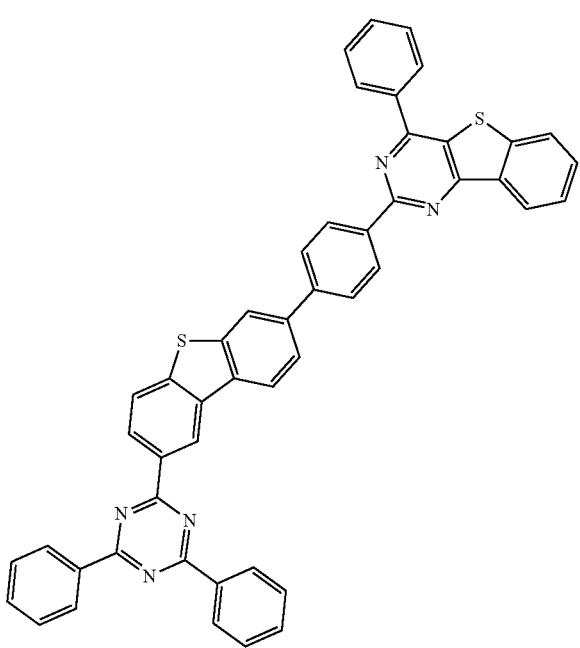
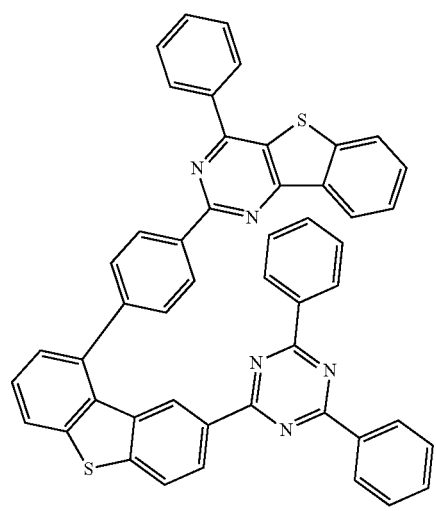
166
-continued
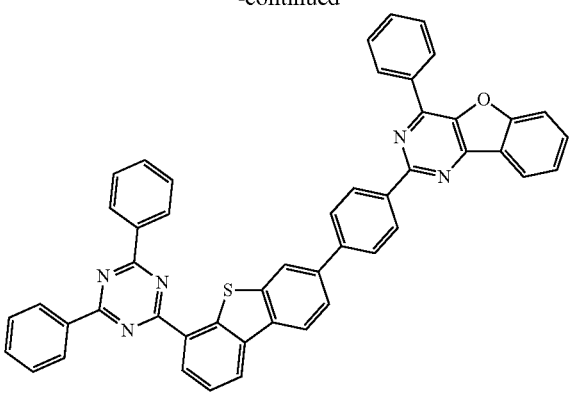
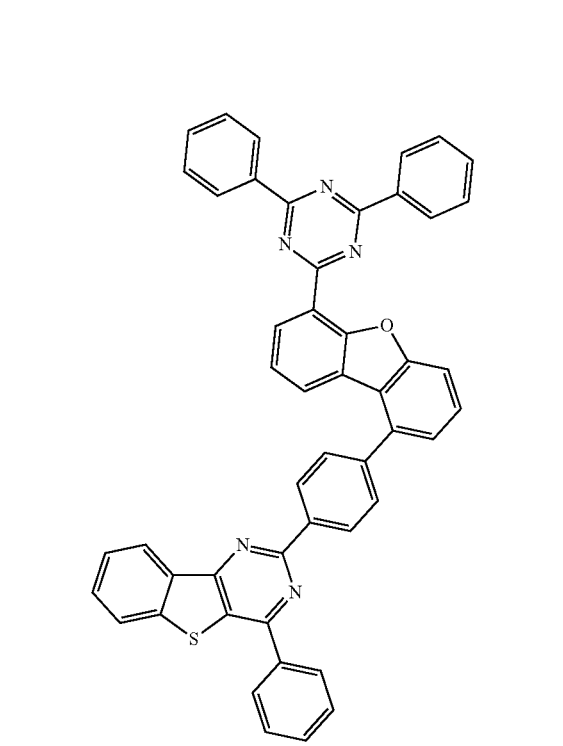
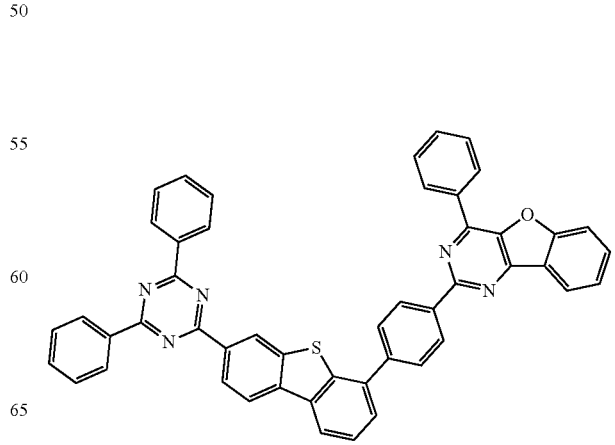

167
-continued
168
-continued
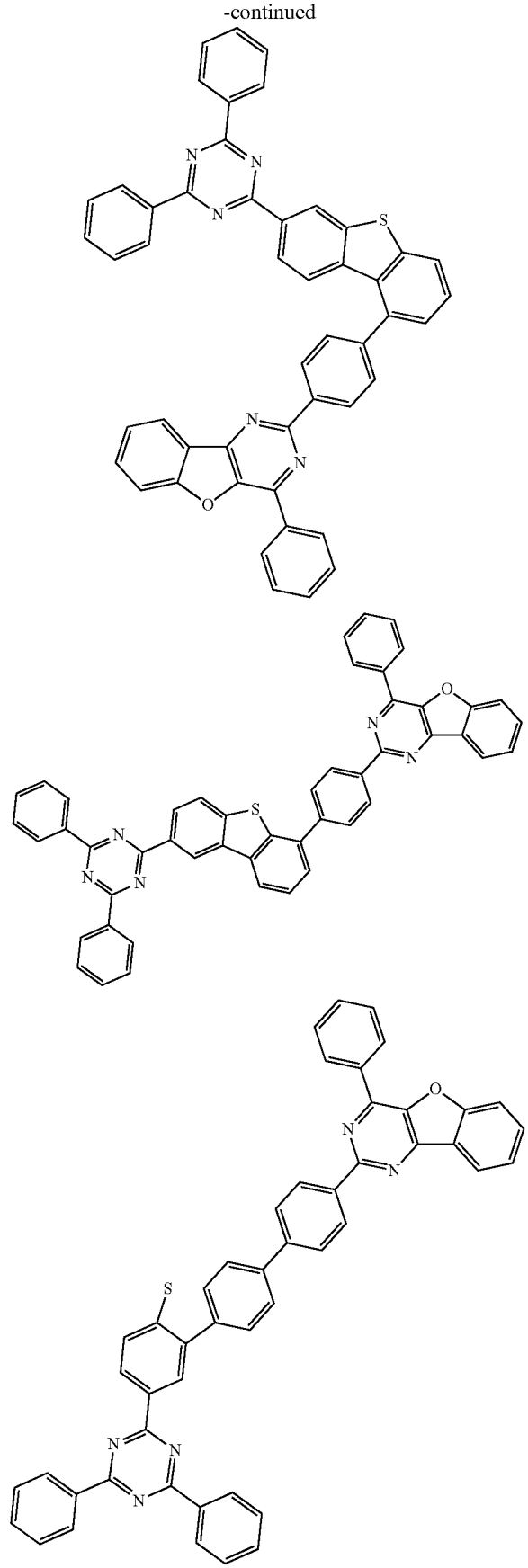
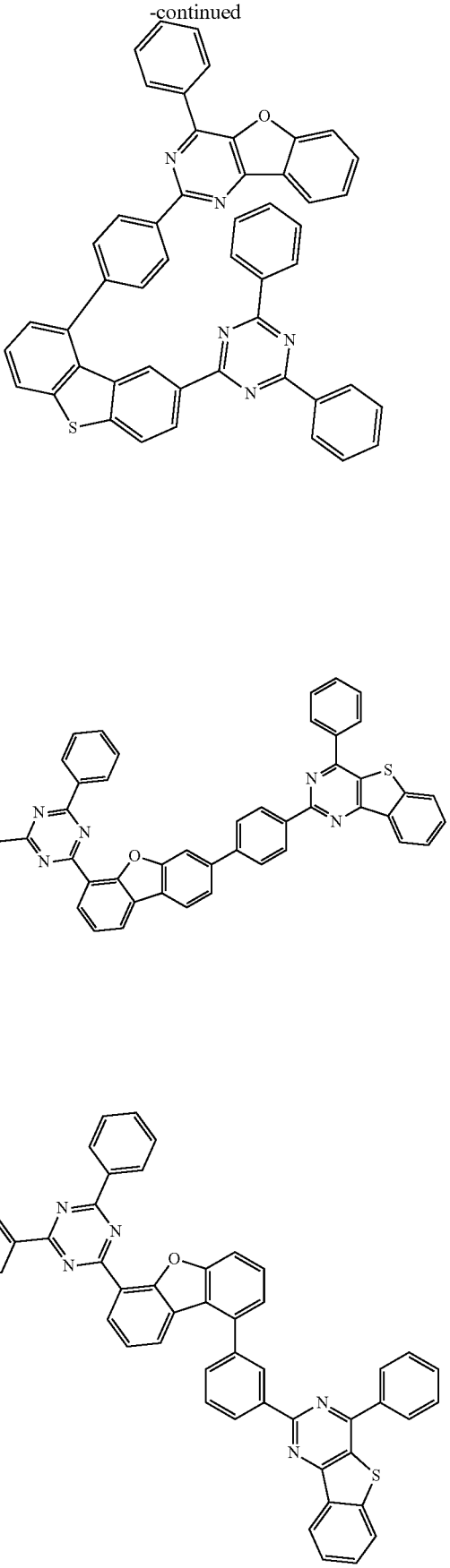

169
-continued
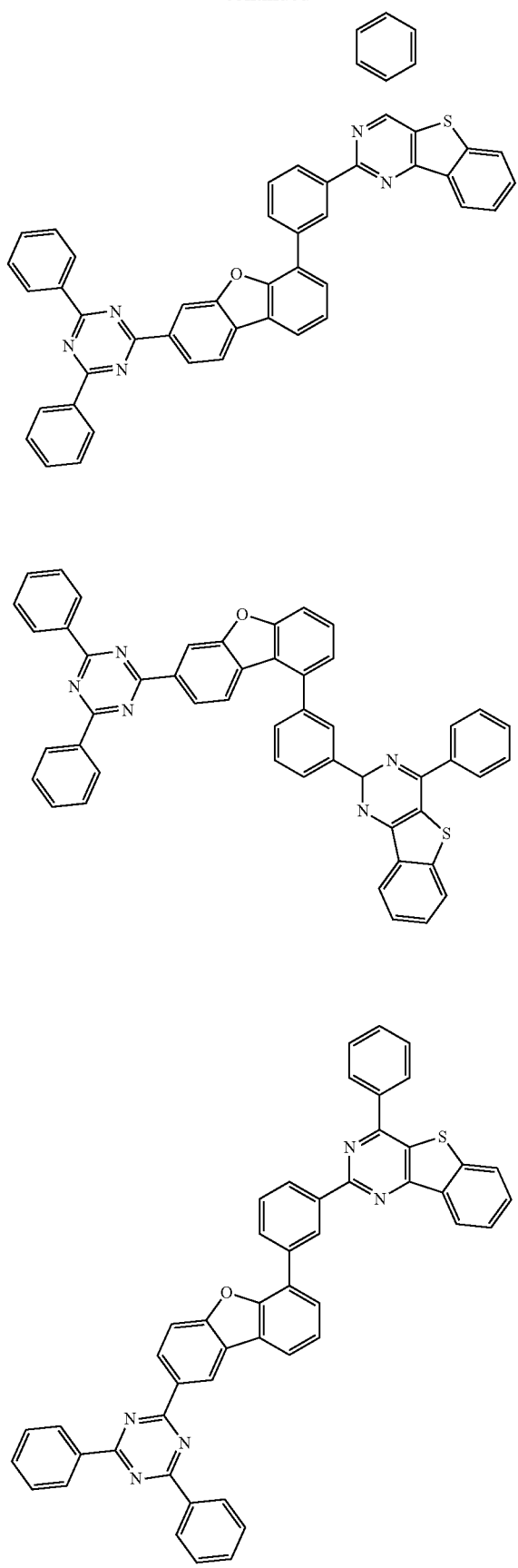
170
-continued
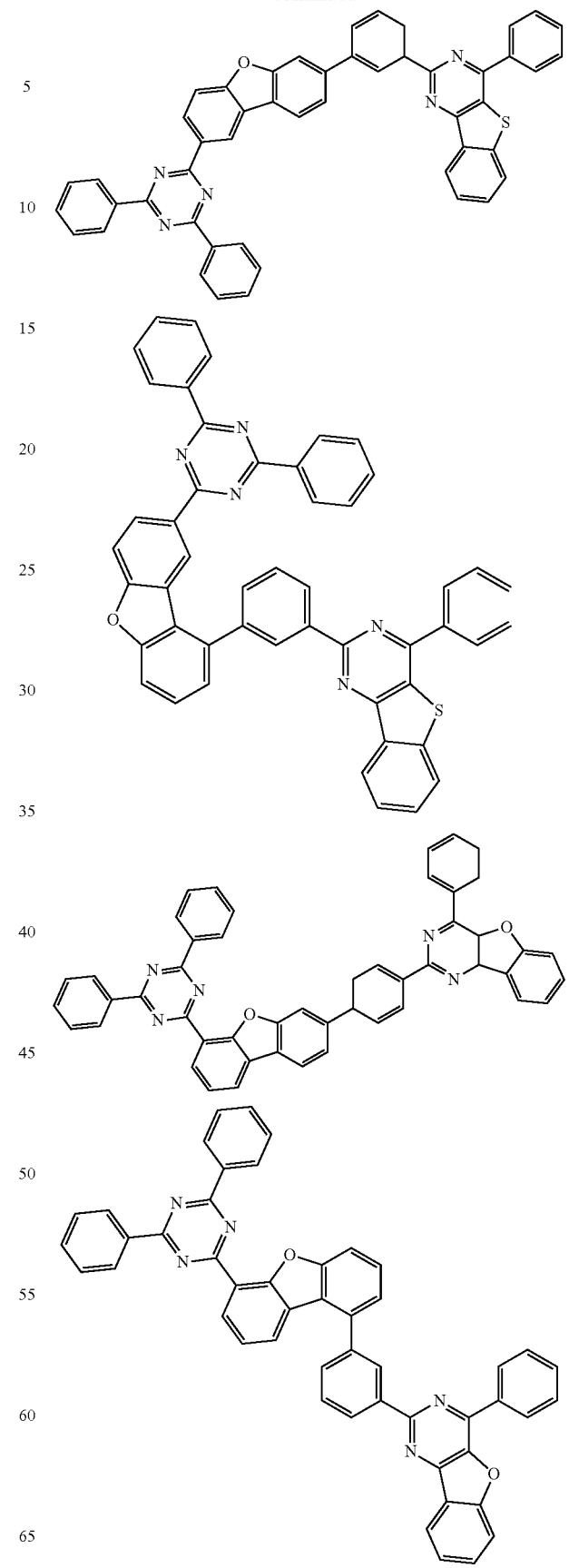

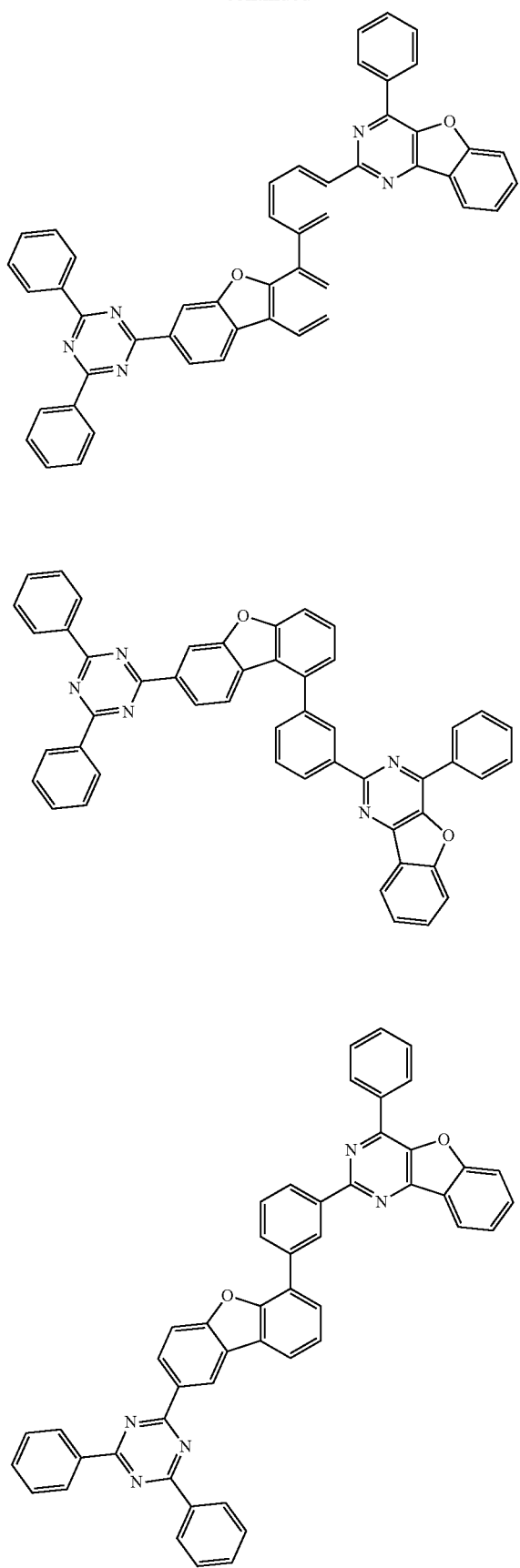
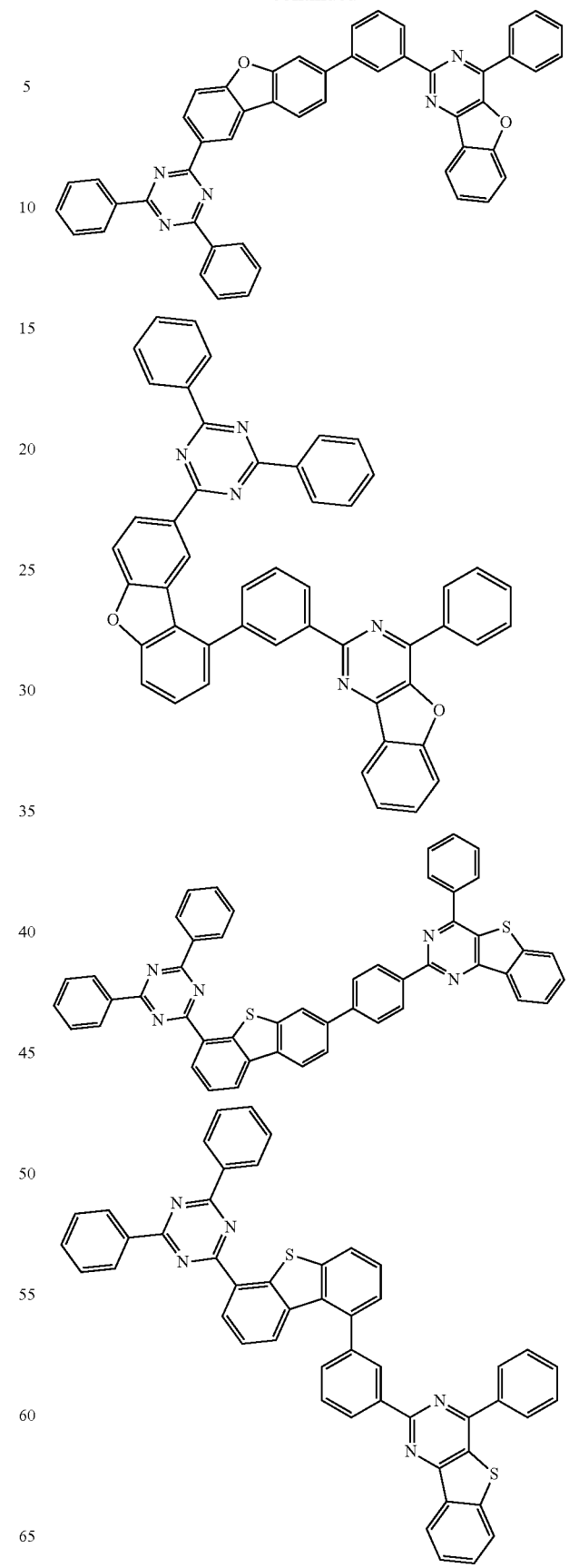

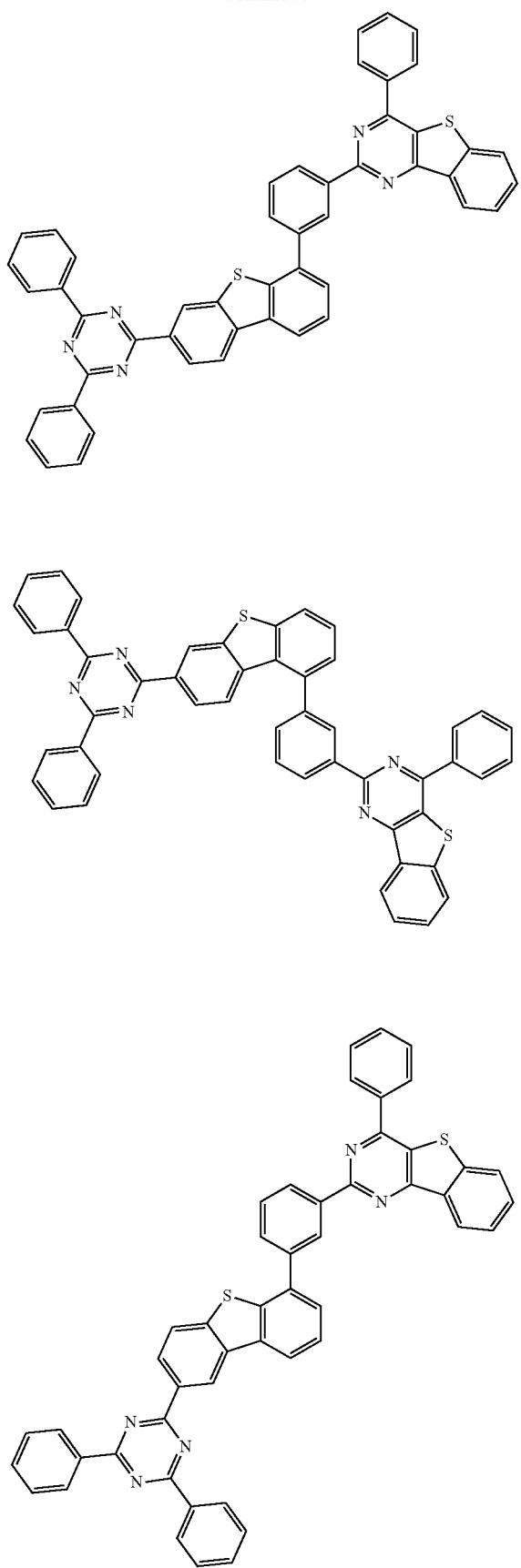
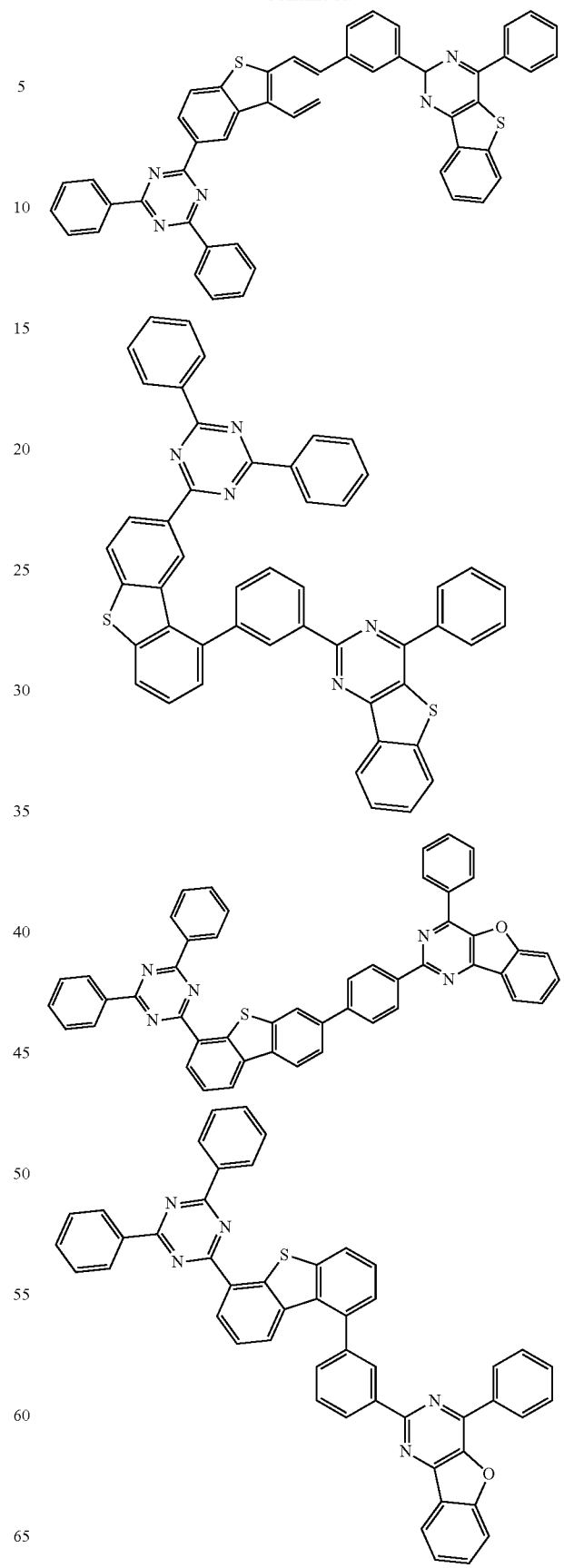

175
-continued
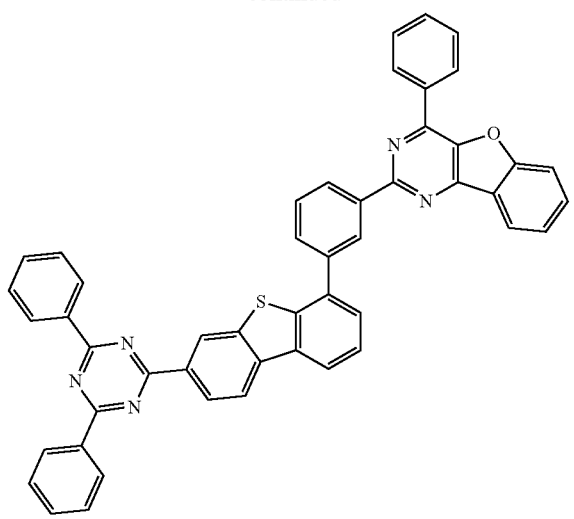
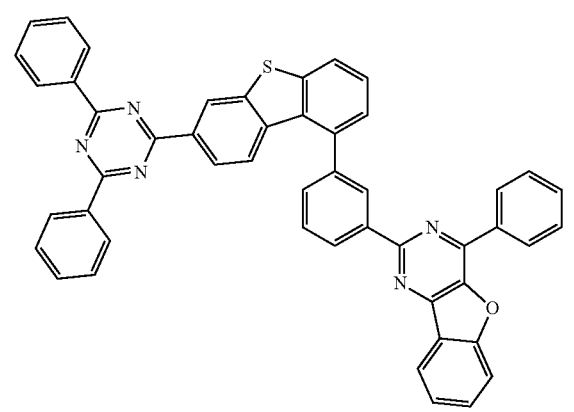
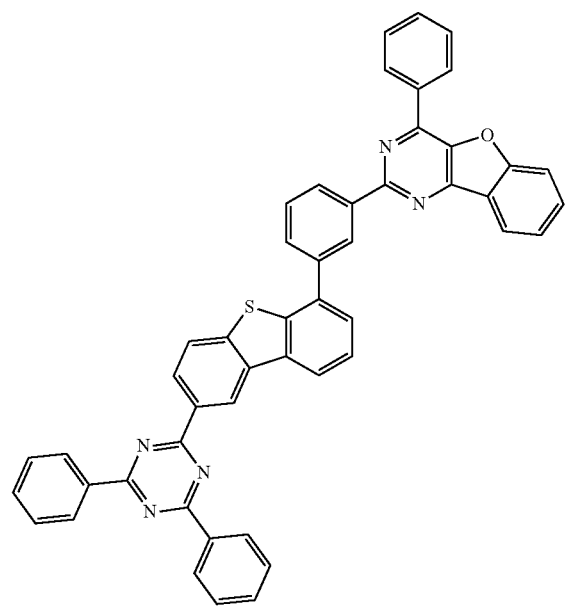
176
-continued
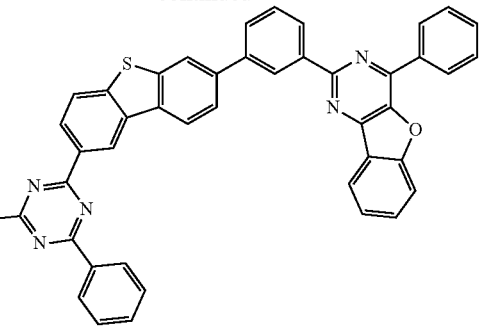
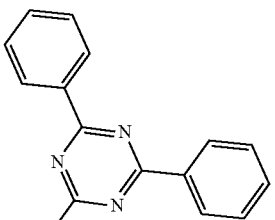
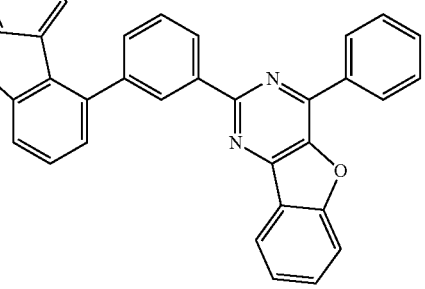
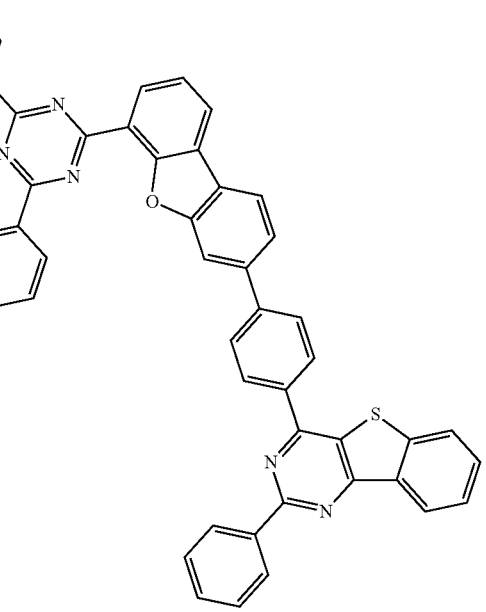

177
-continued
178
-continued
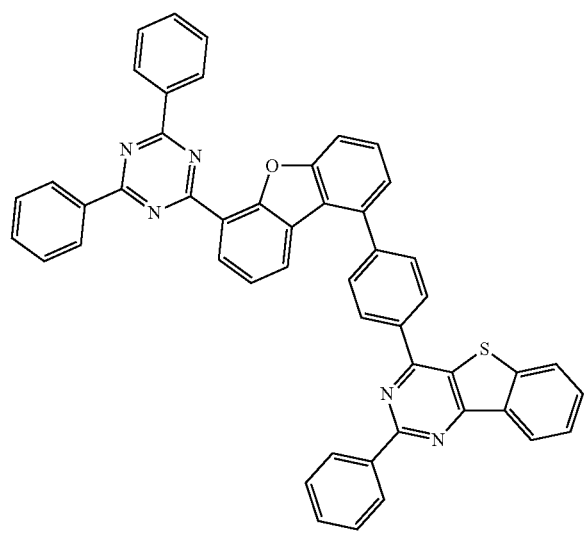
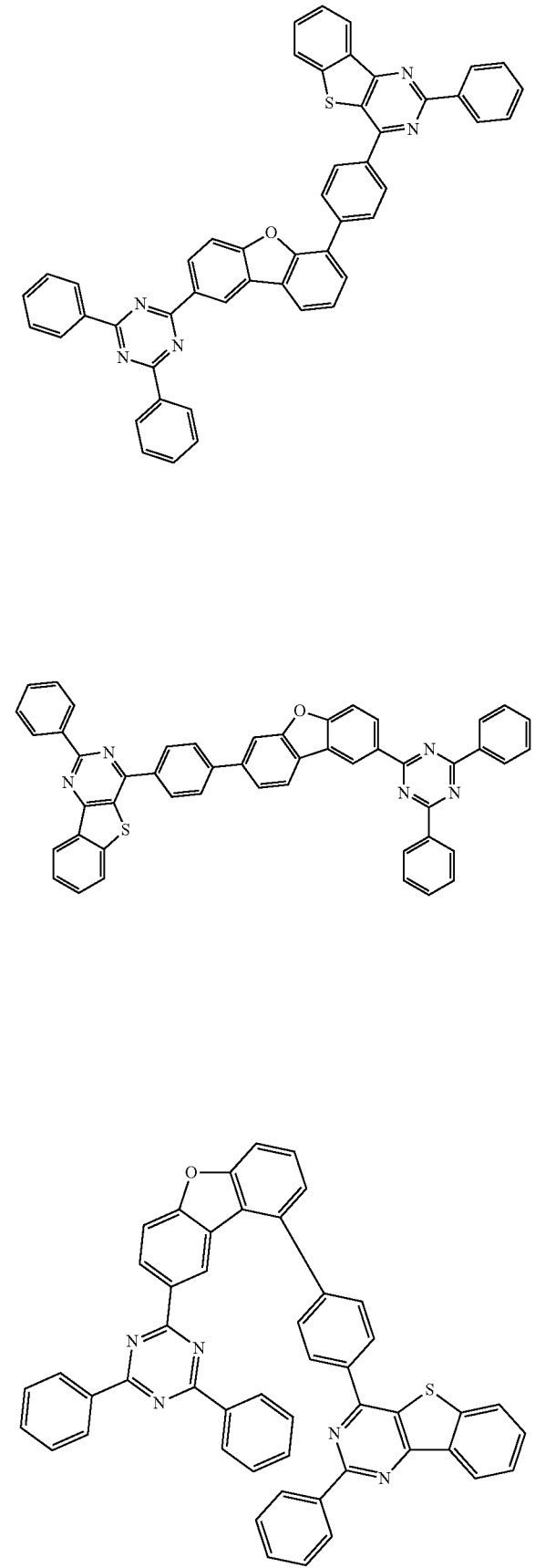

179
-continued
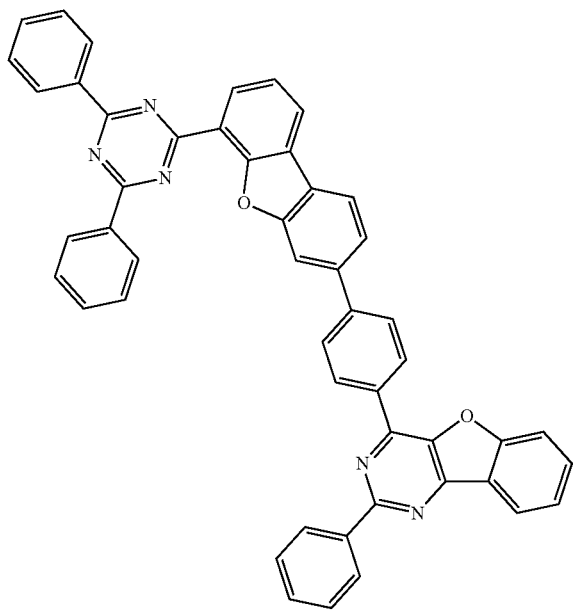
180
-continued
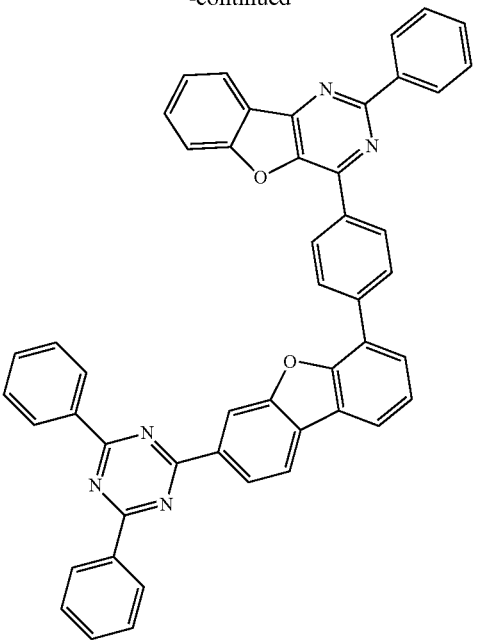
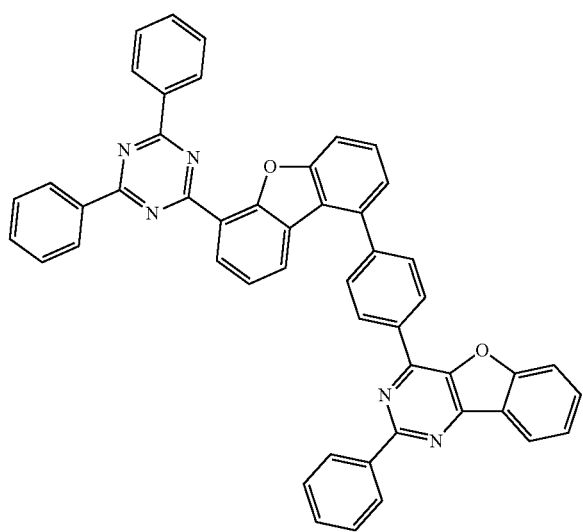
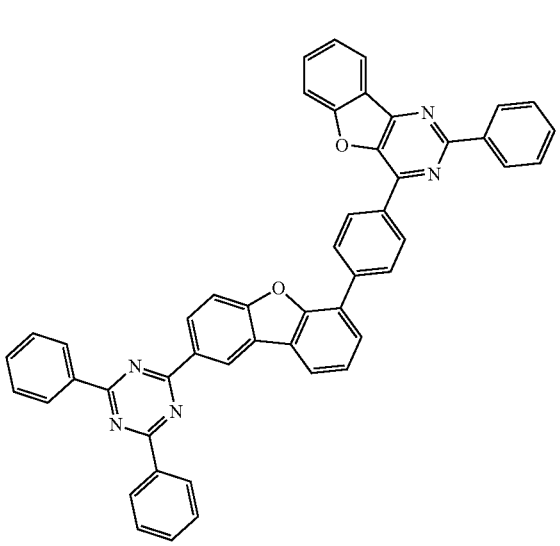

181
-continued
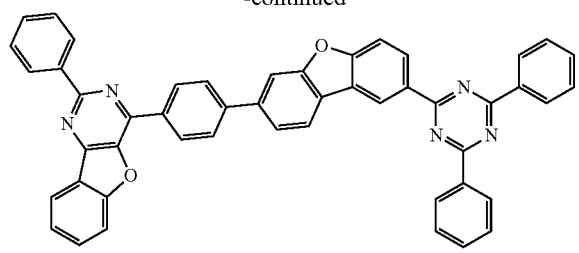
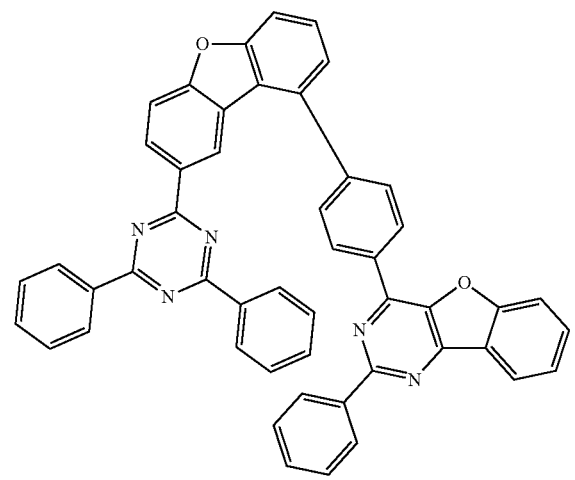
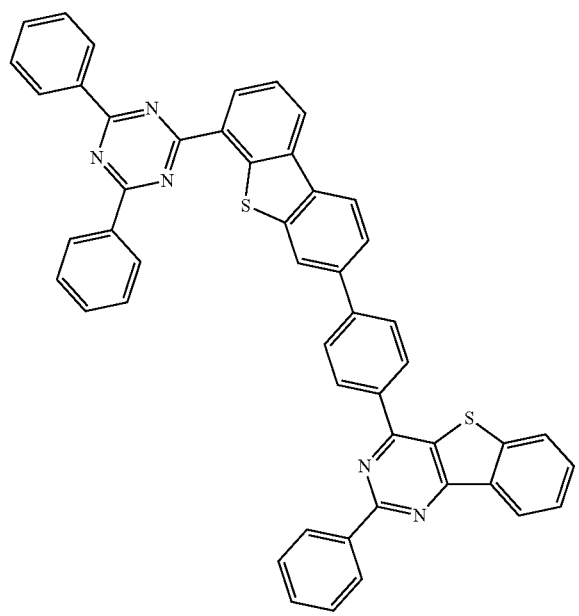
182
-continued
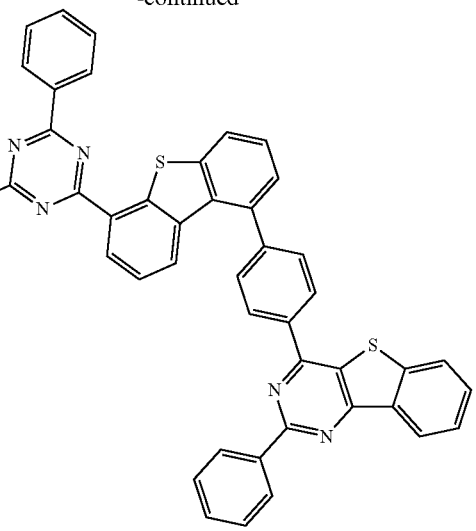
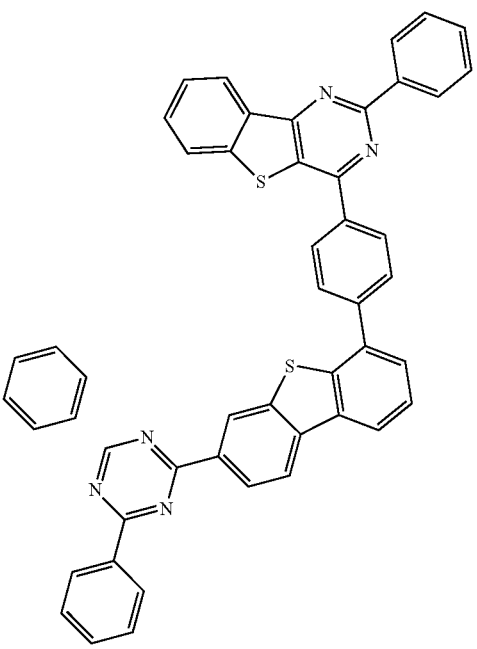
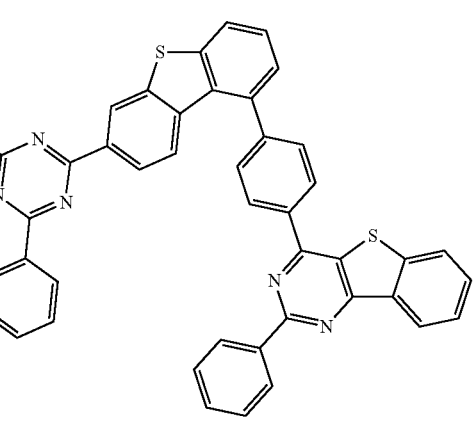

-continued
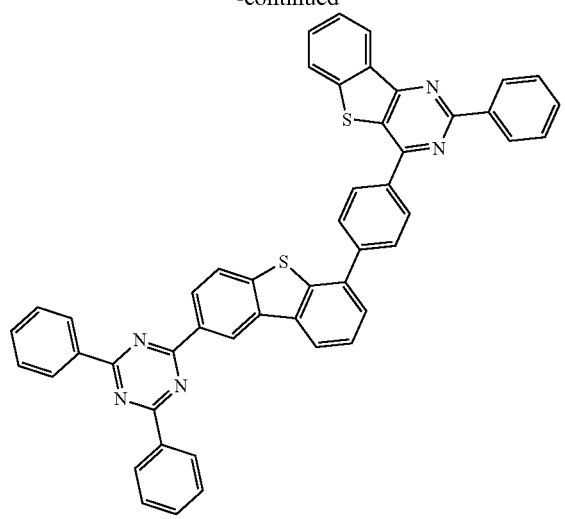
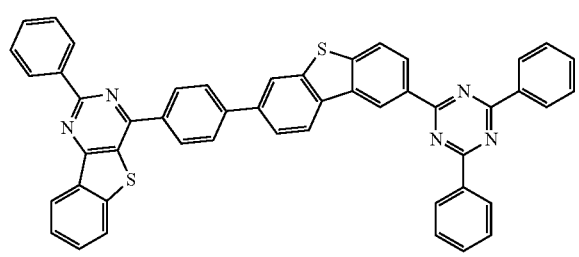
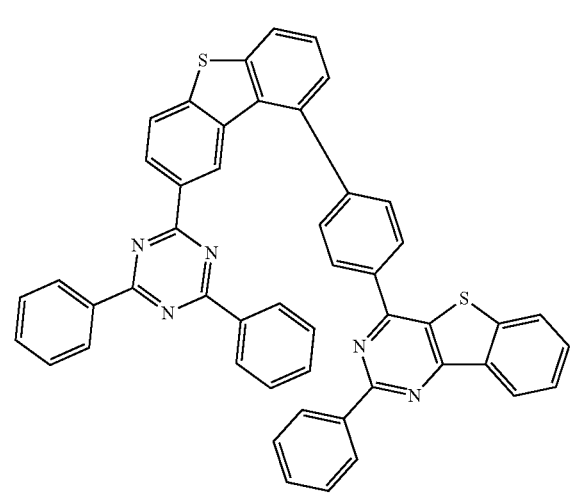
-continued
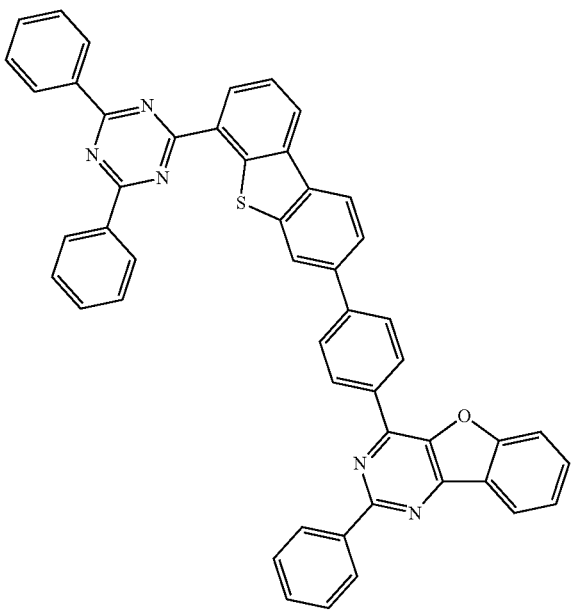
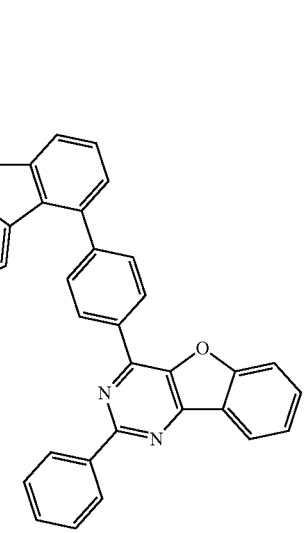

185
-continued
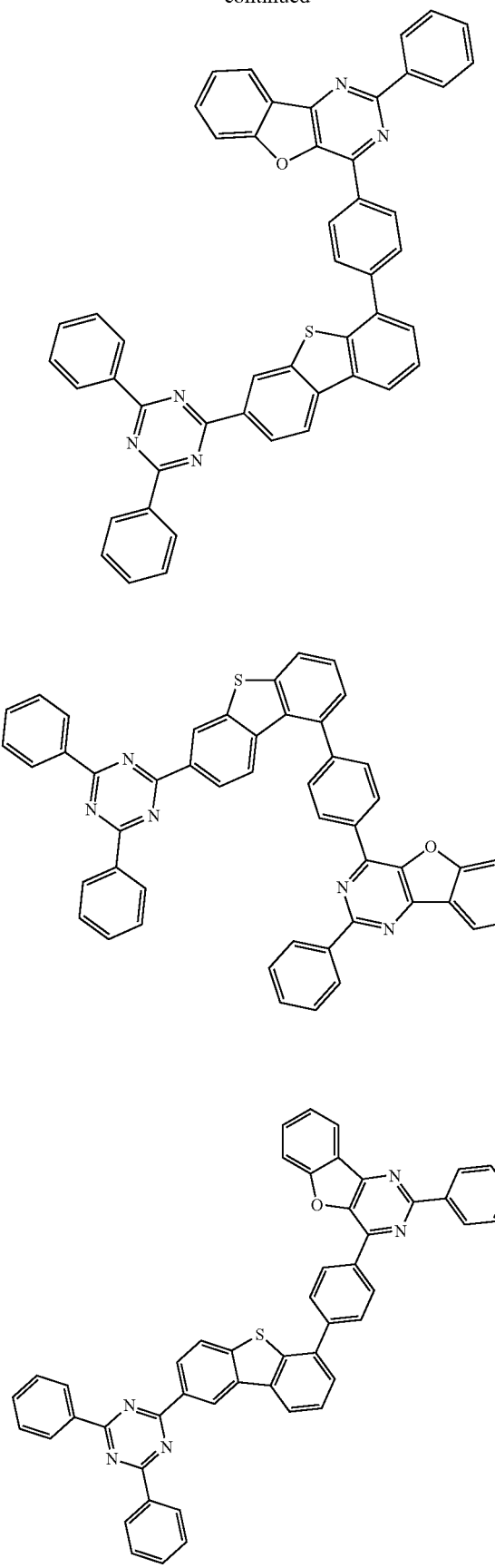
186
-continued
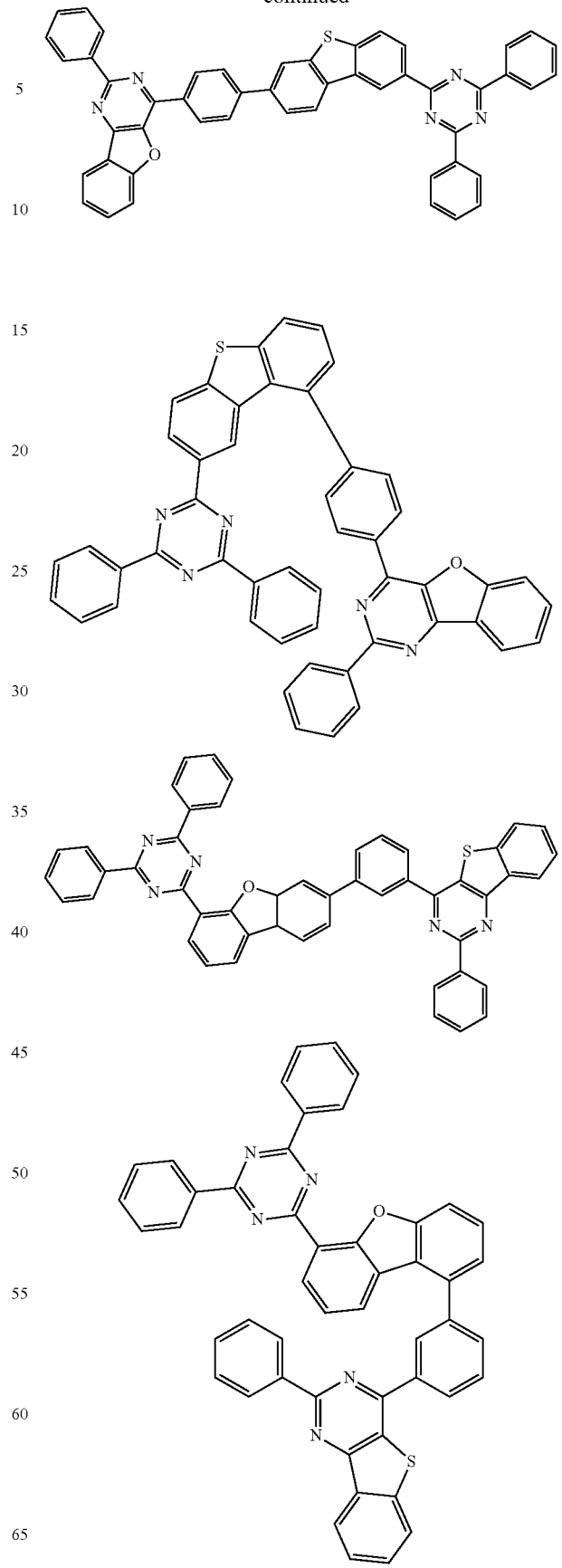

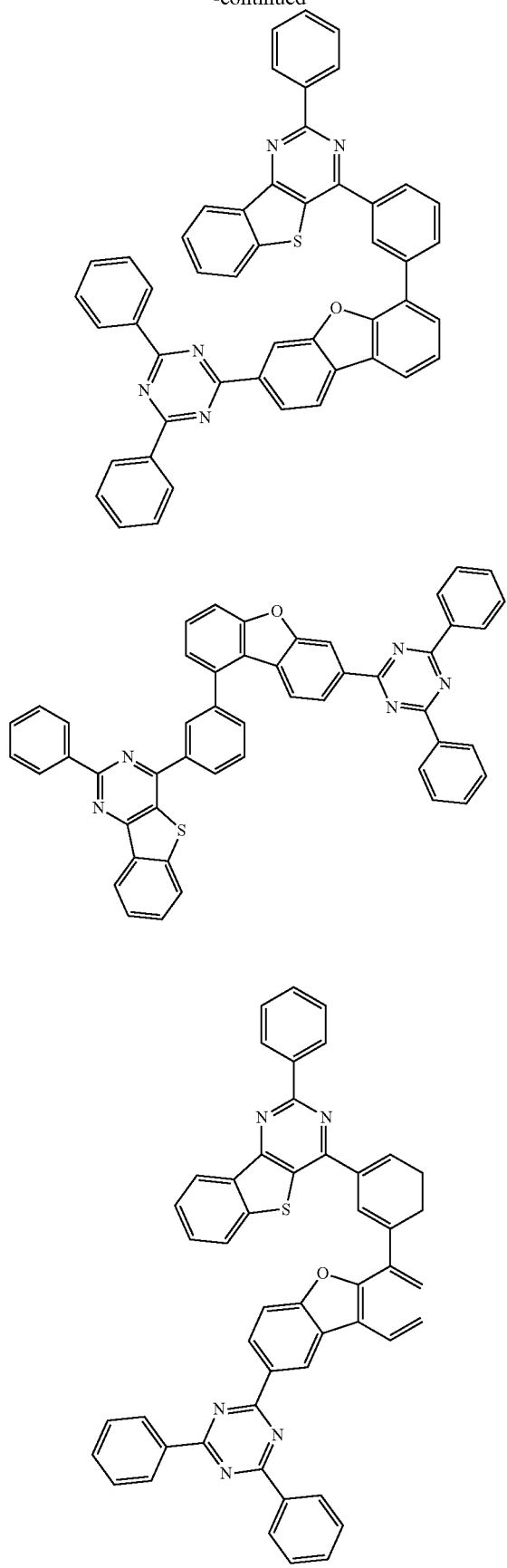
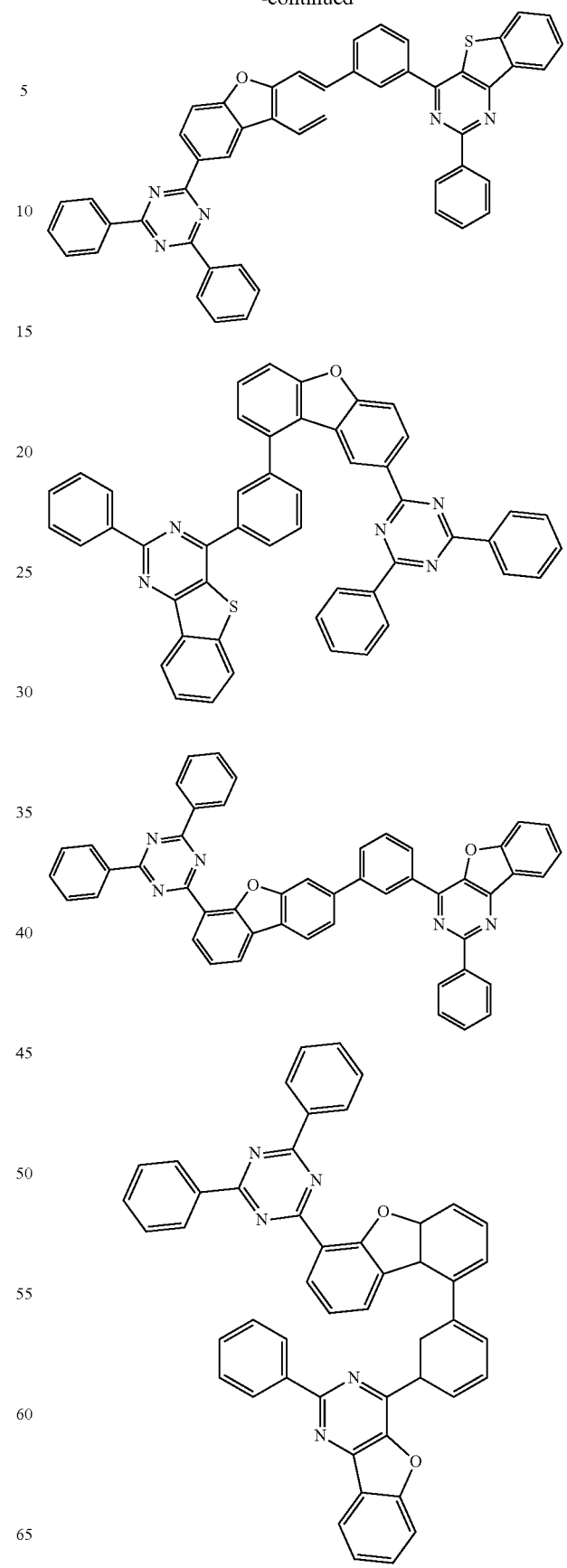

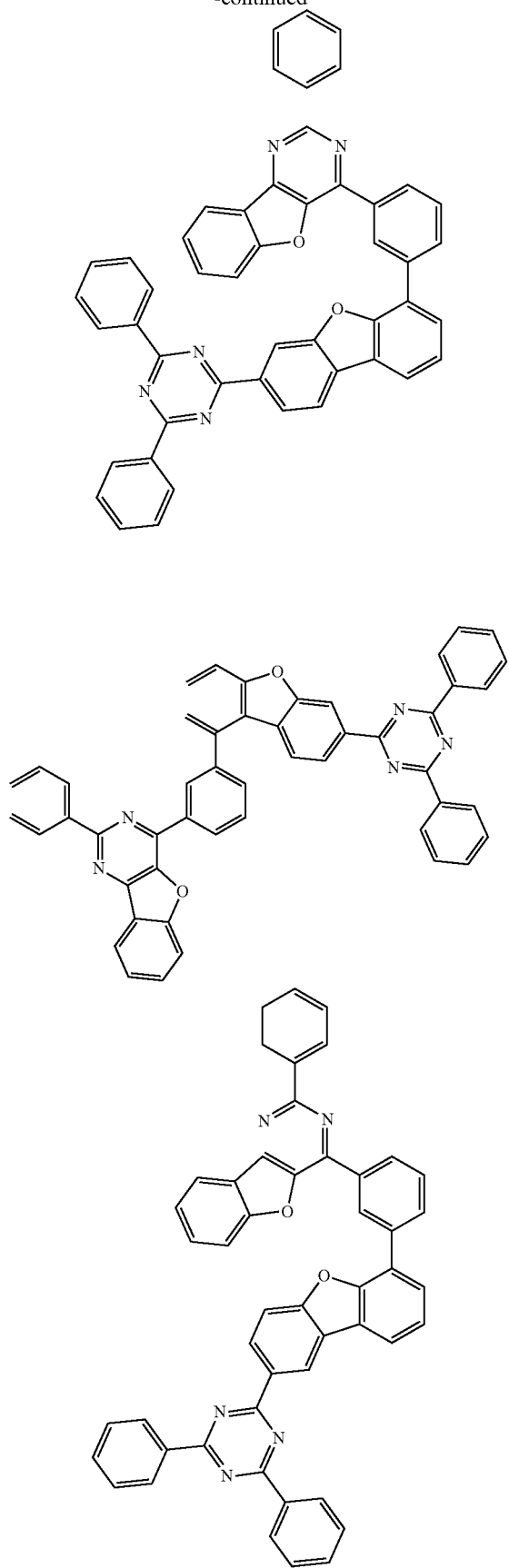
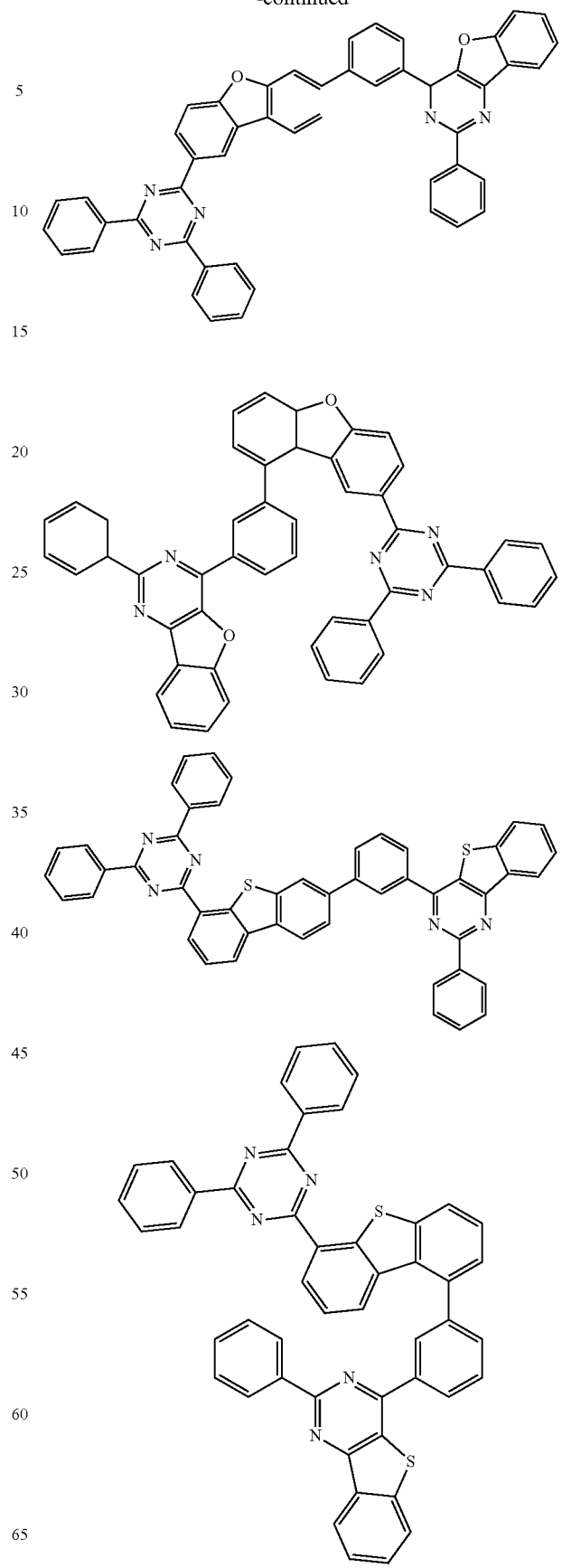

191
-continued
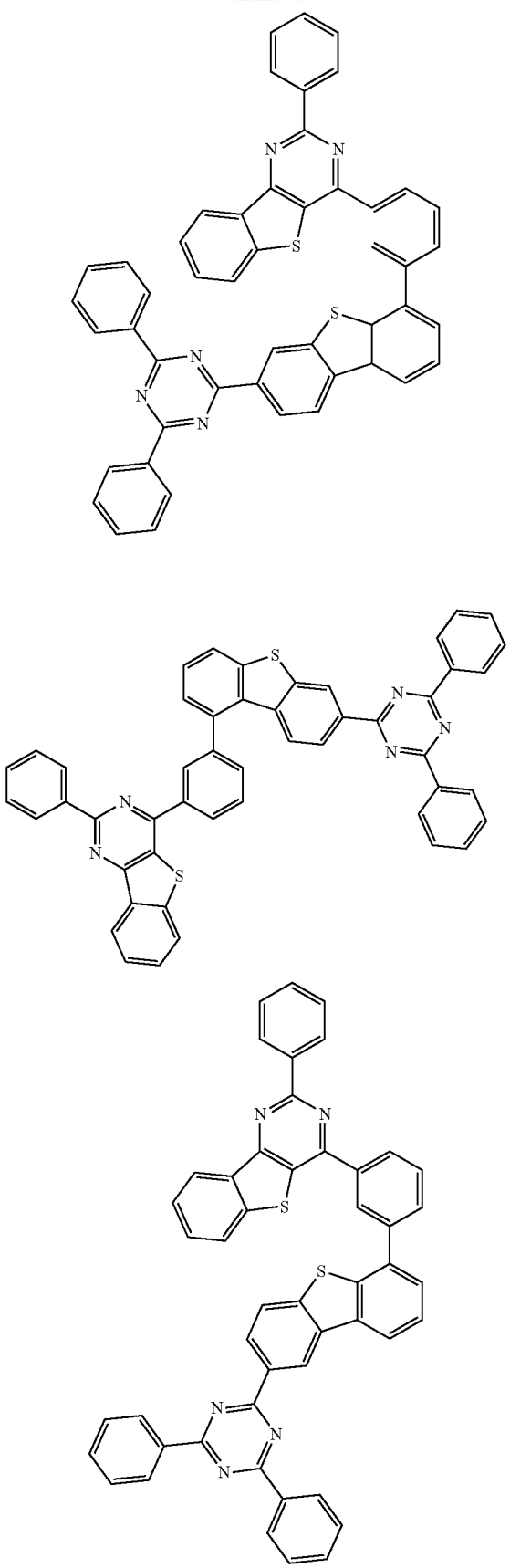
192
-continued
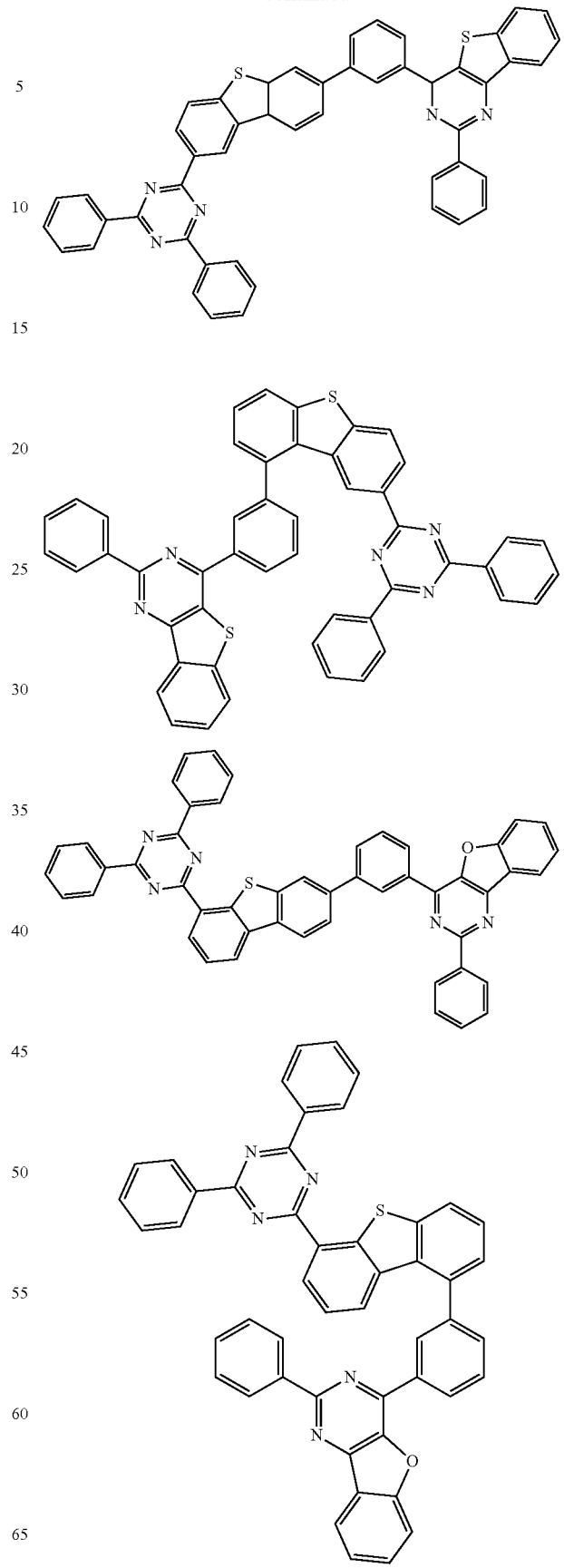

193
-continued
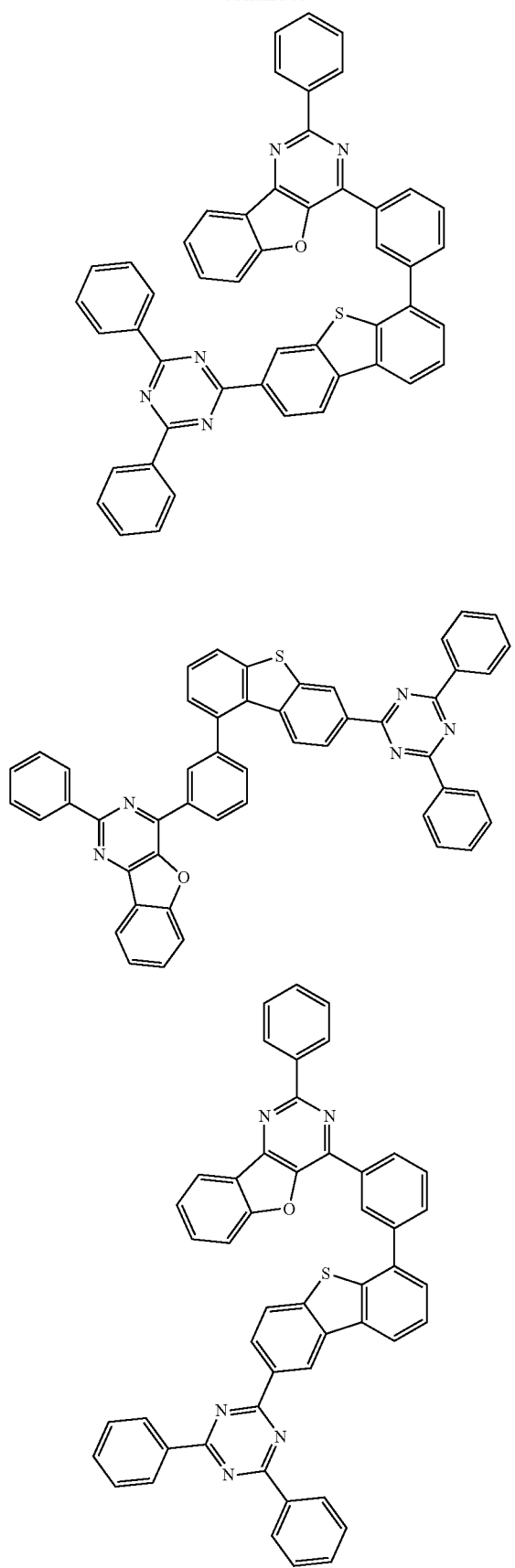
194
-continued
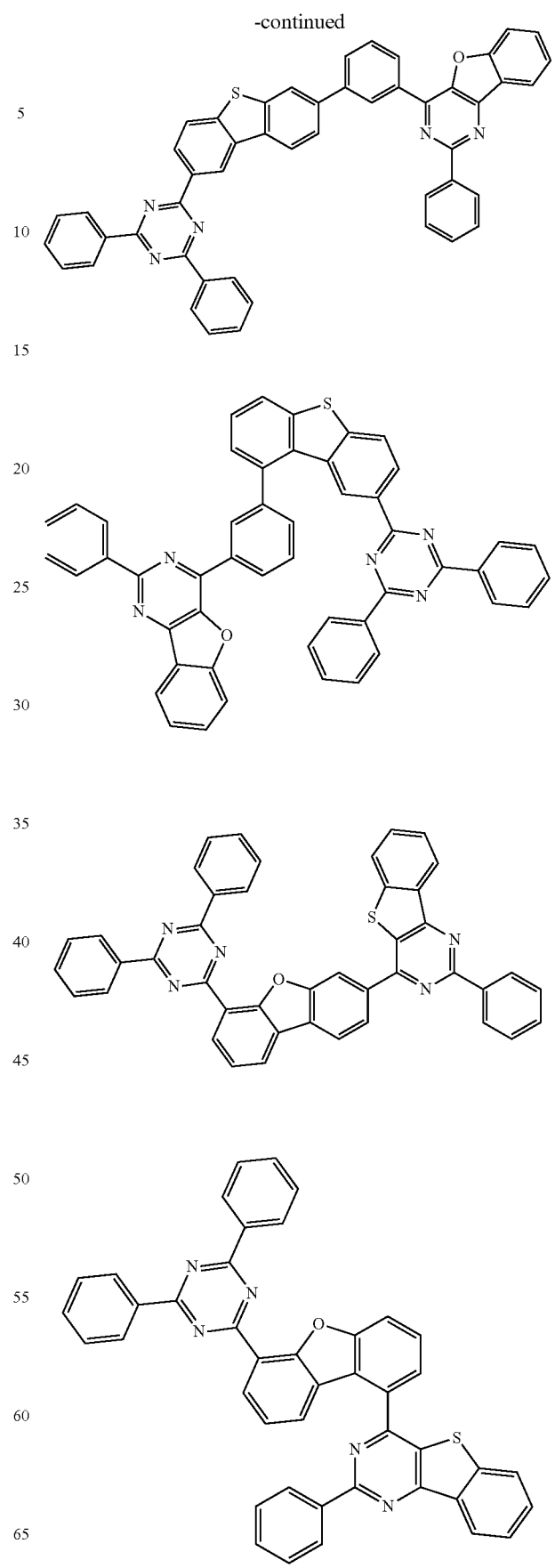

195
-continued
196
-continued
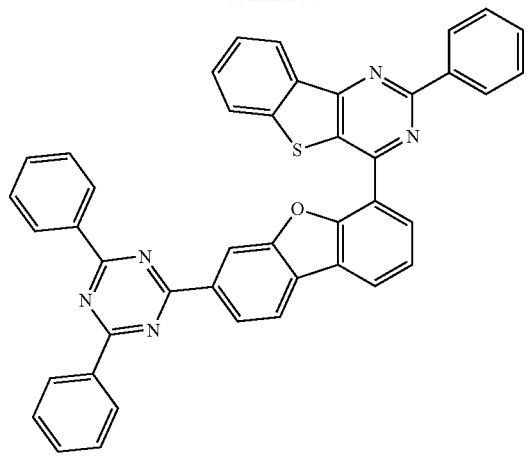
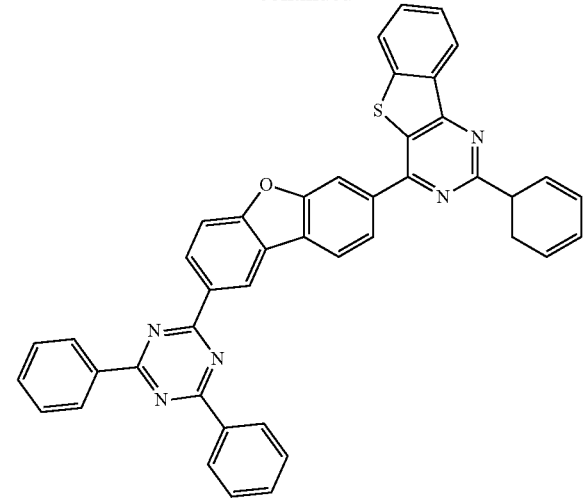
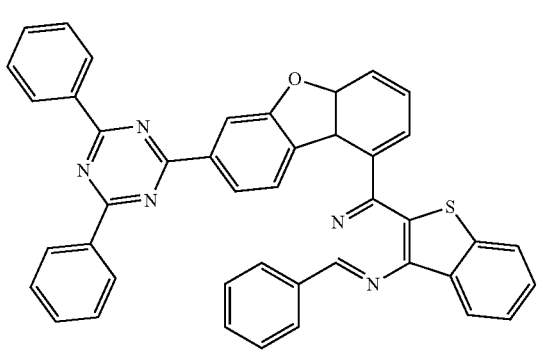
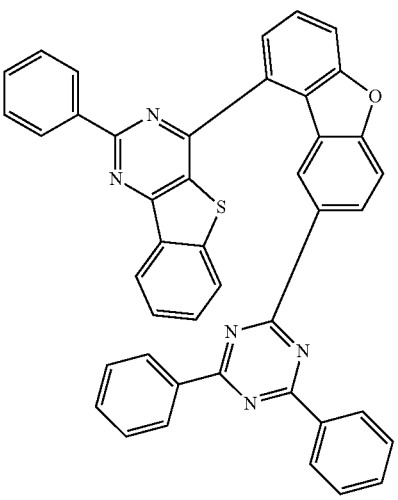
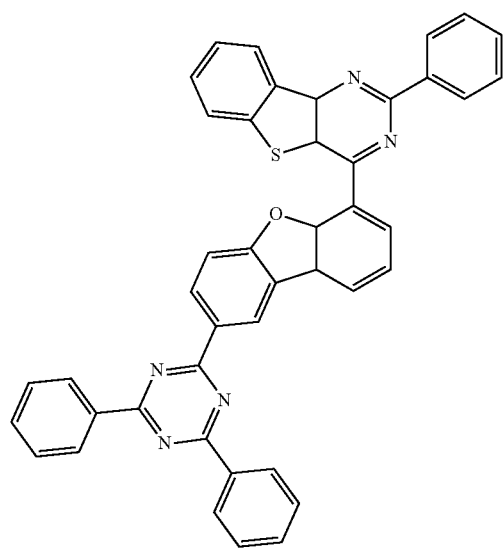

197
-continued
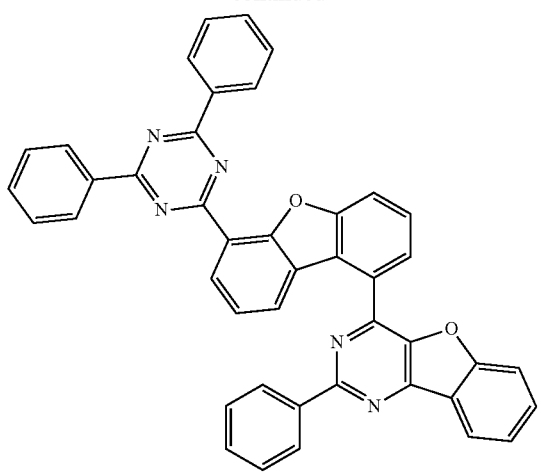
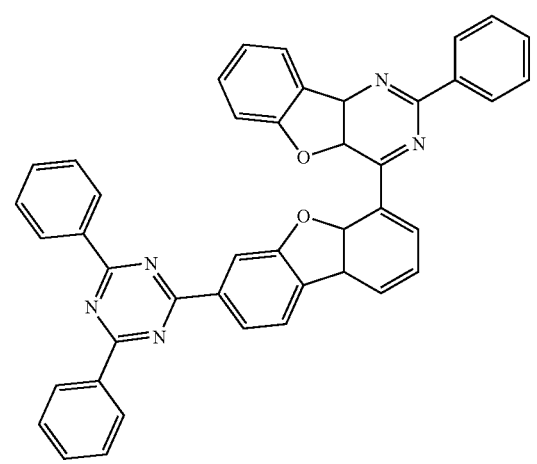
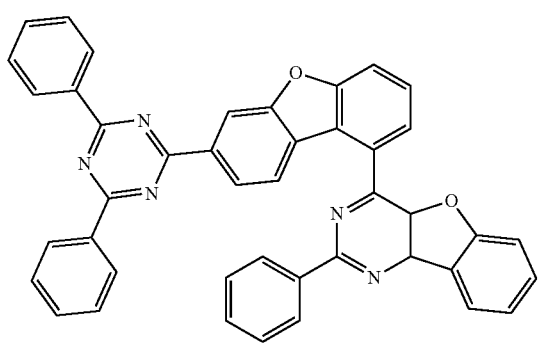
198
-continued
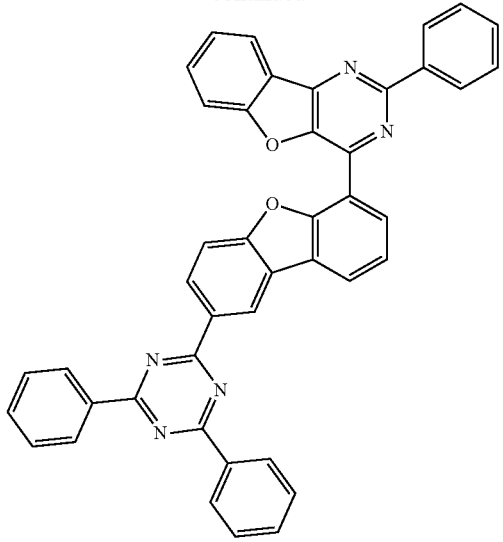
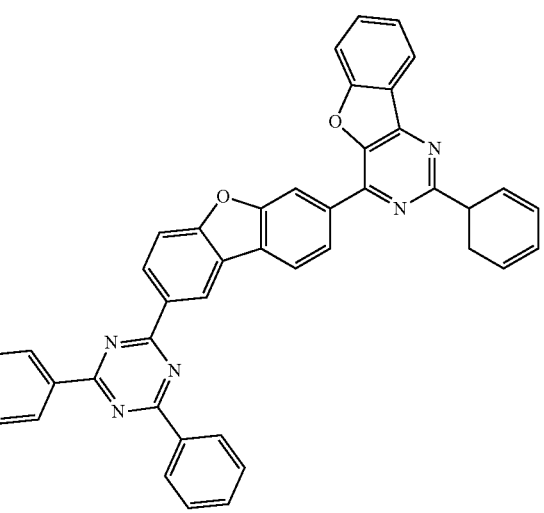
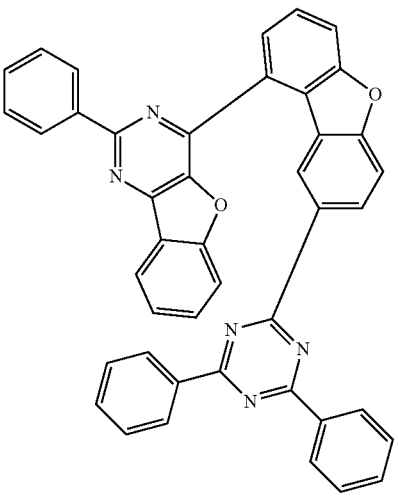

199
-continued
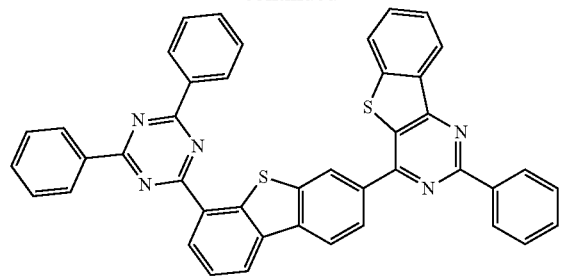
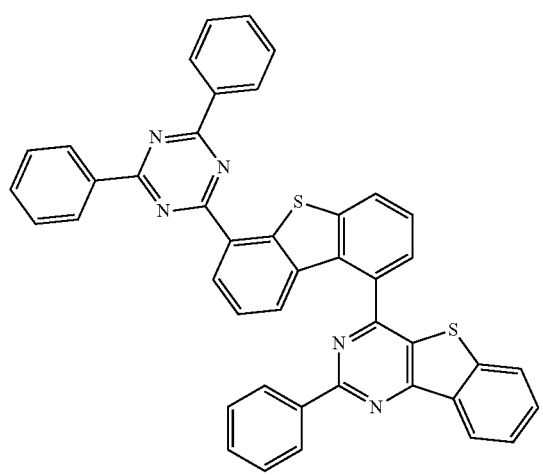
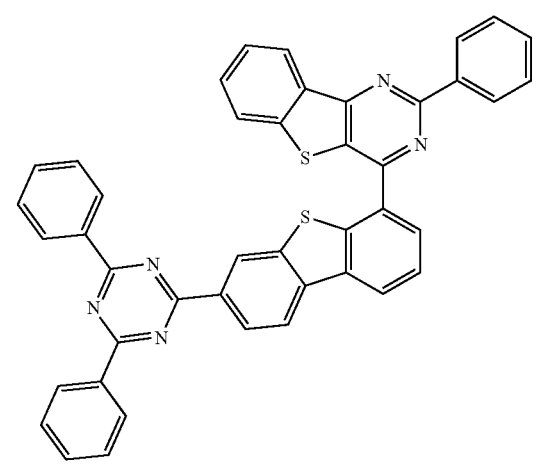

200
-continued
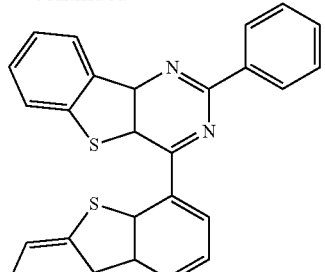
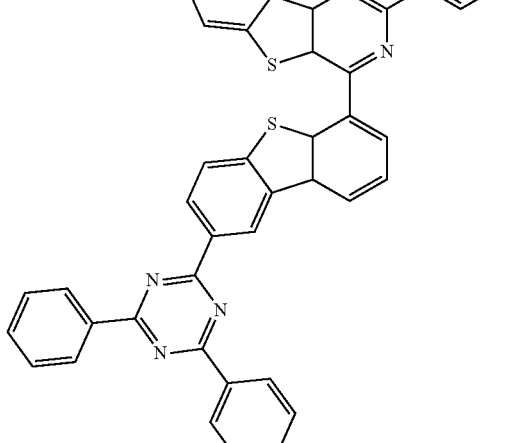
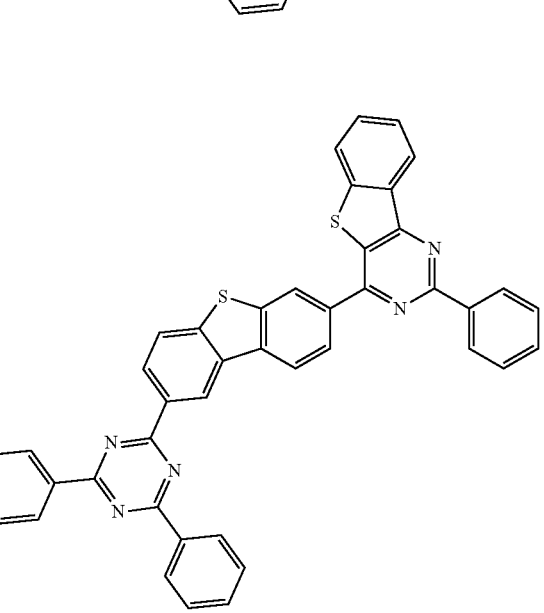
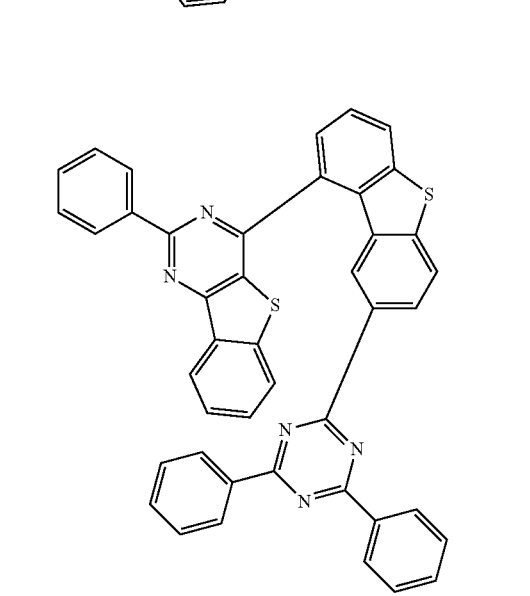

201
-continued
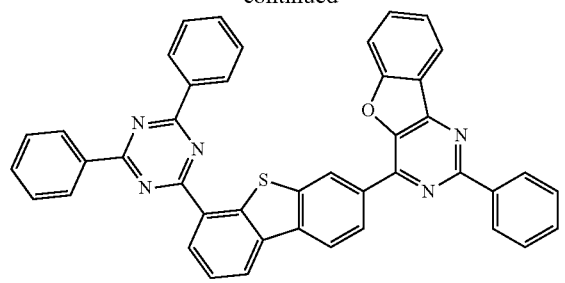
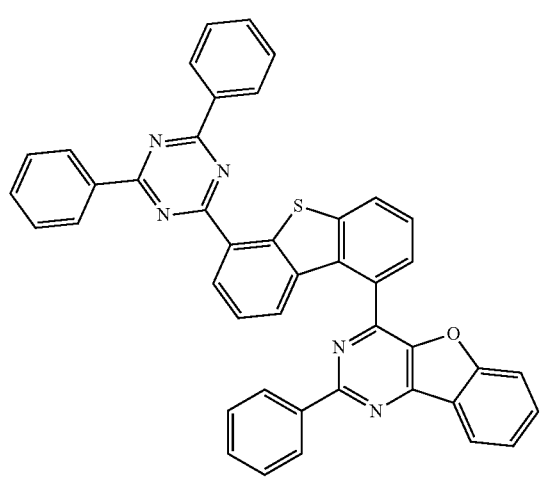
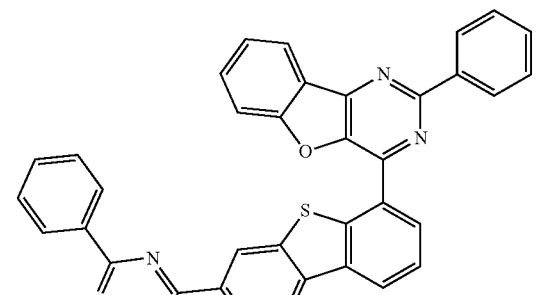
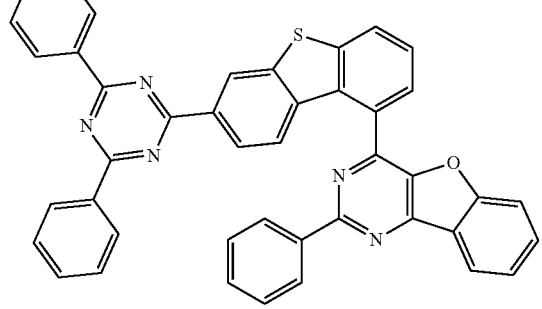
202
-continued
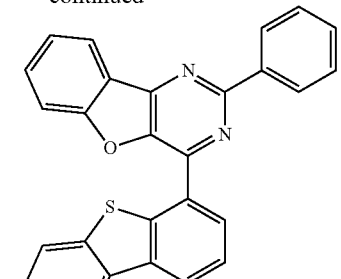
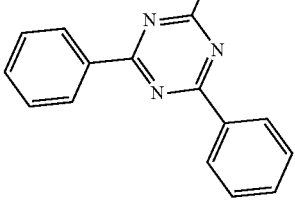
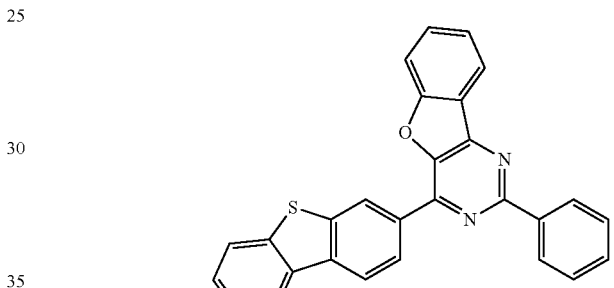
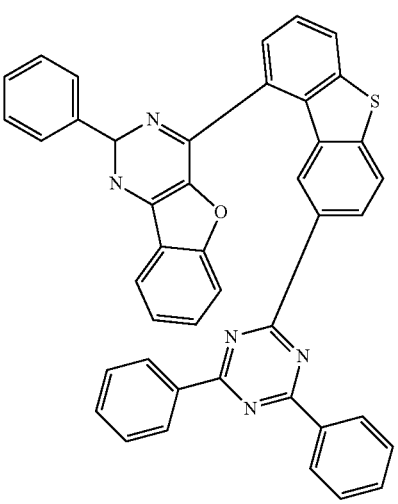

203
-continued
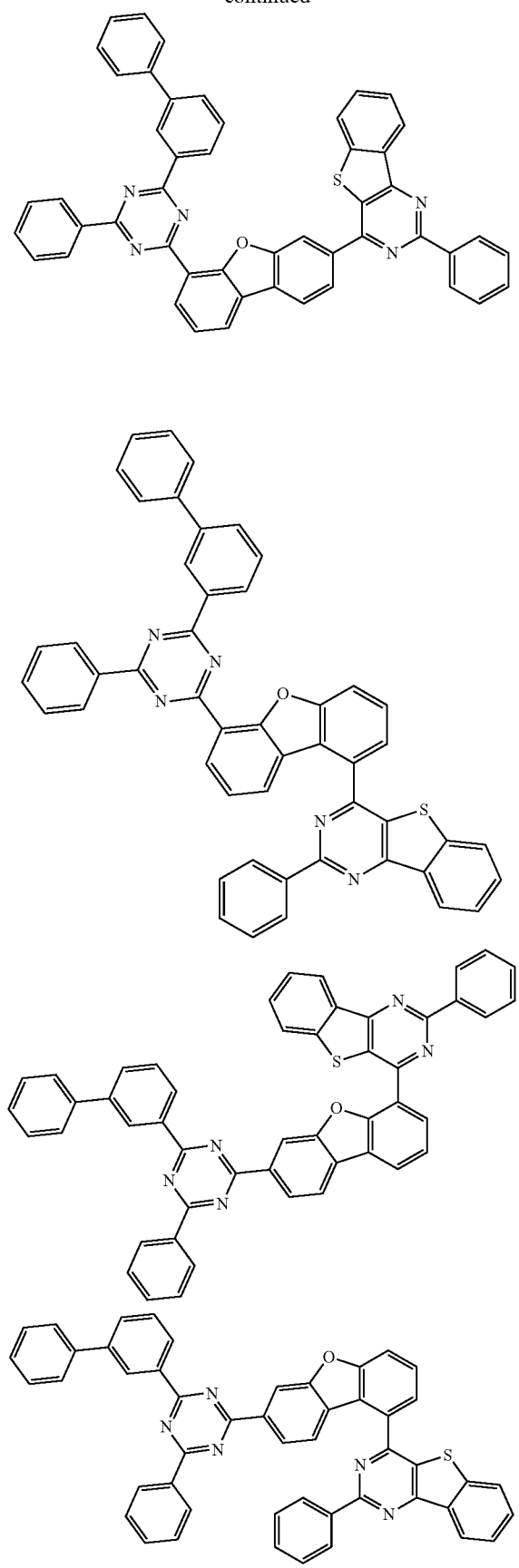
204
-continued
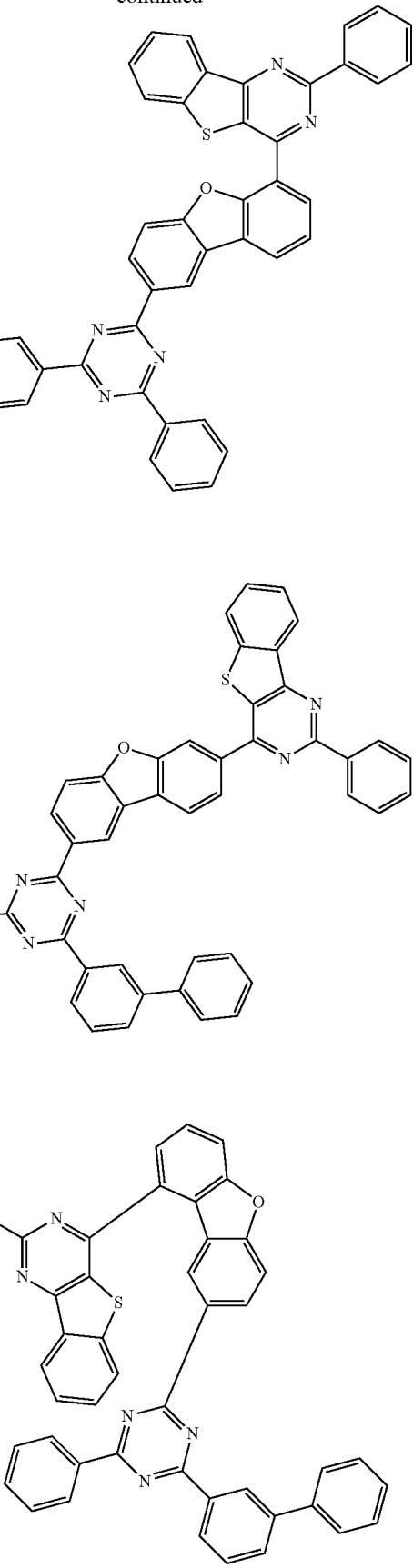

205
-continued
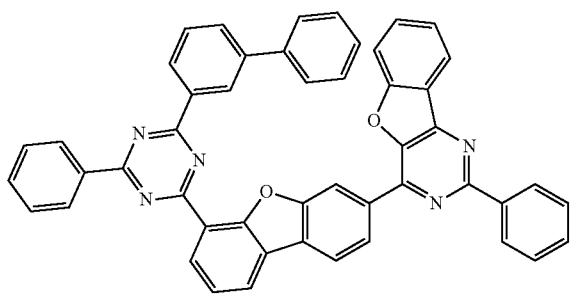
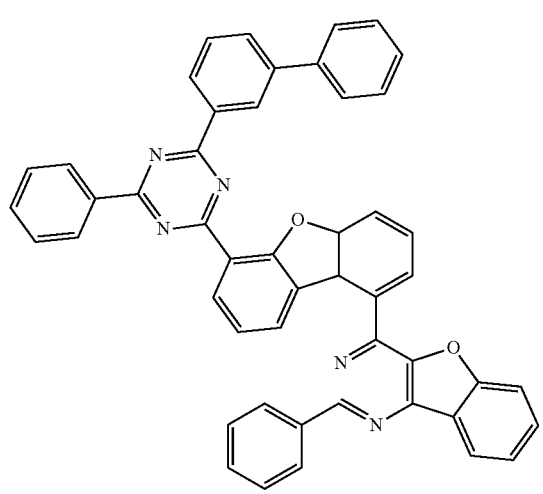
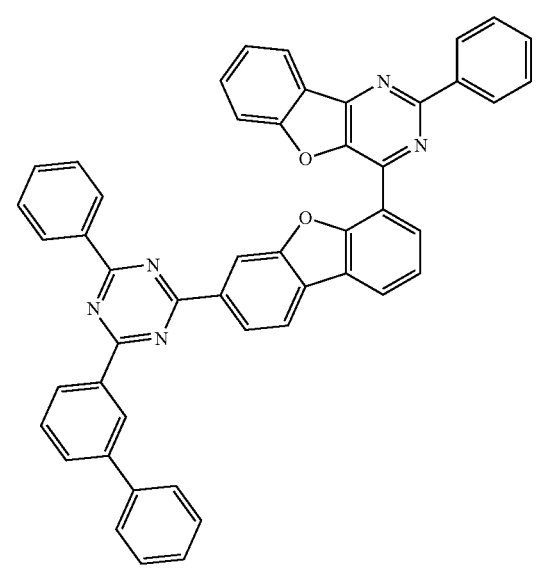
206
-continued
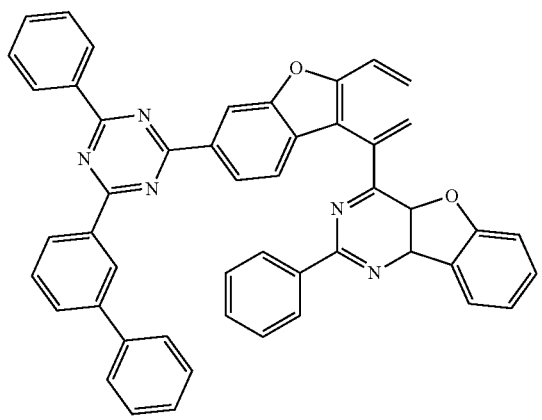
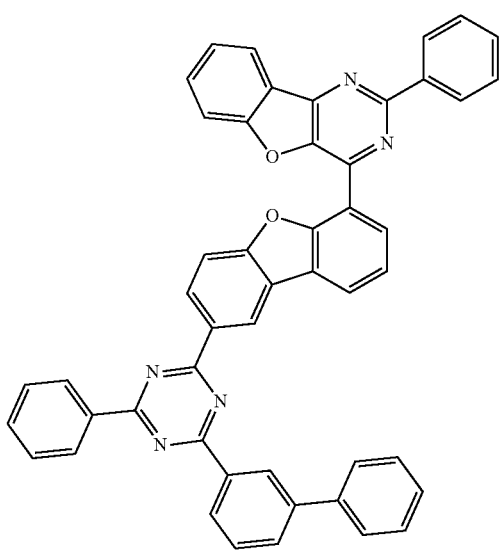
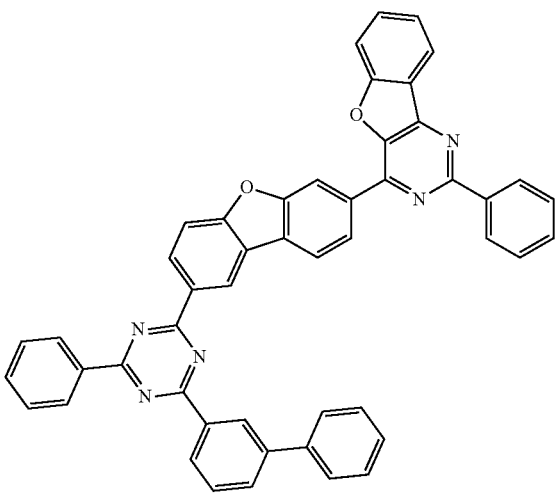

207
-continued
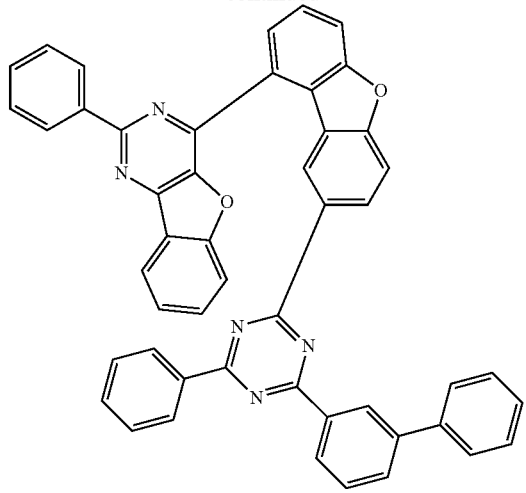
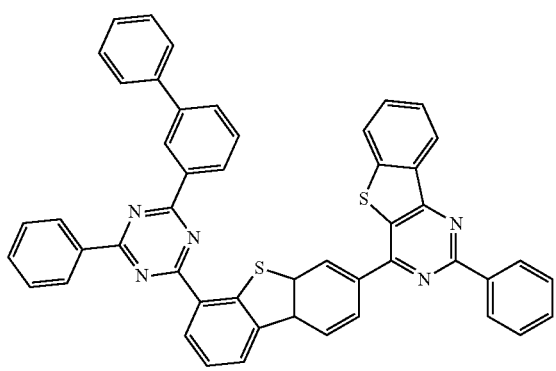
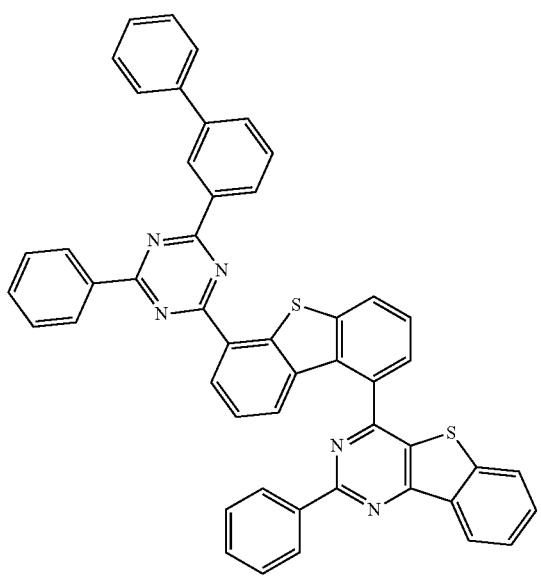
208
-continued
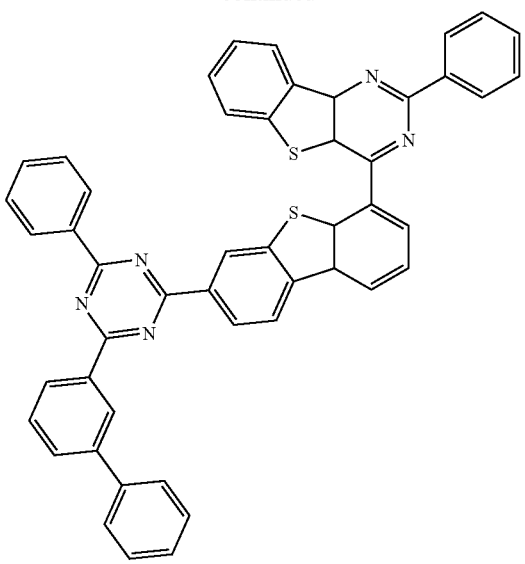
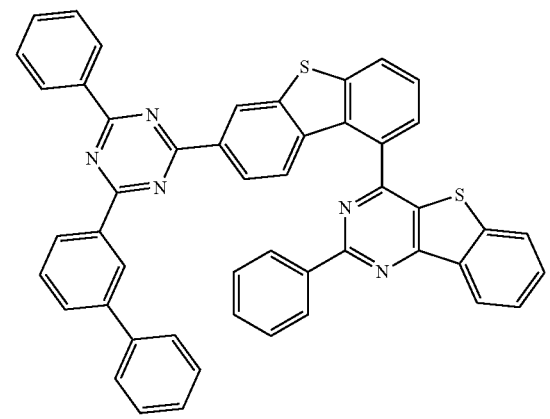
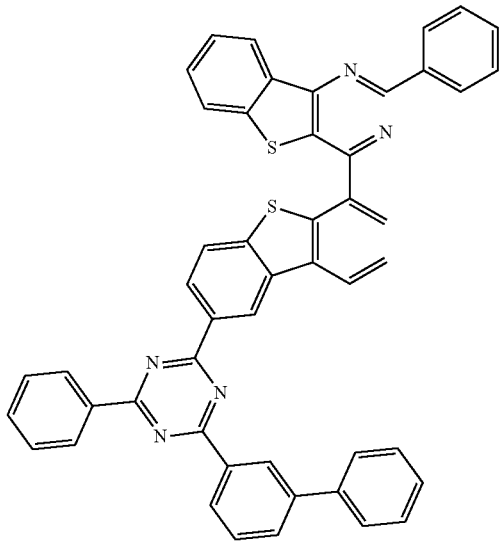

209
-continued
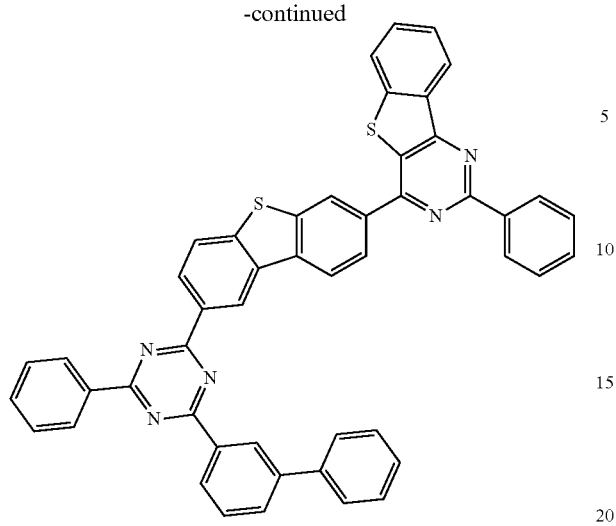
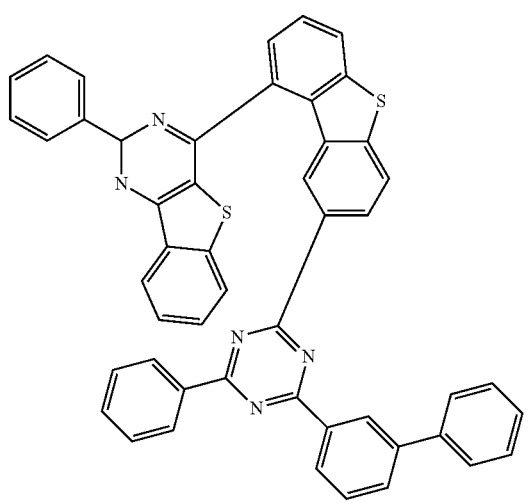
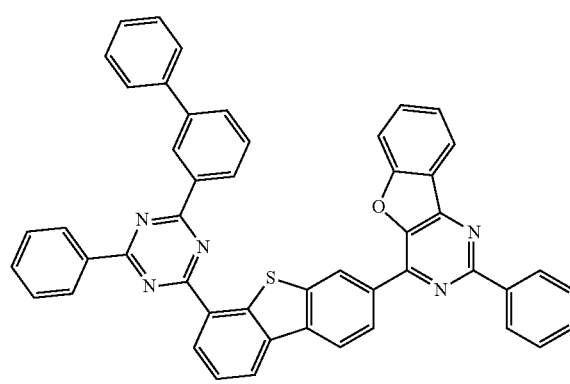
210
-continued
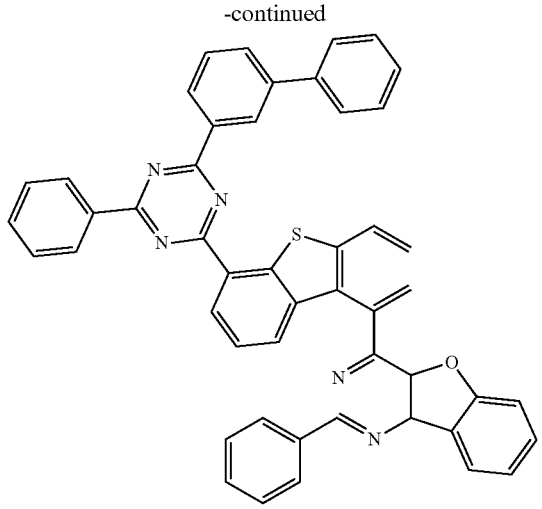
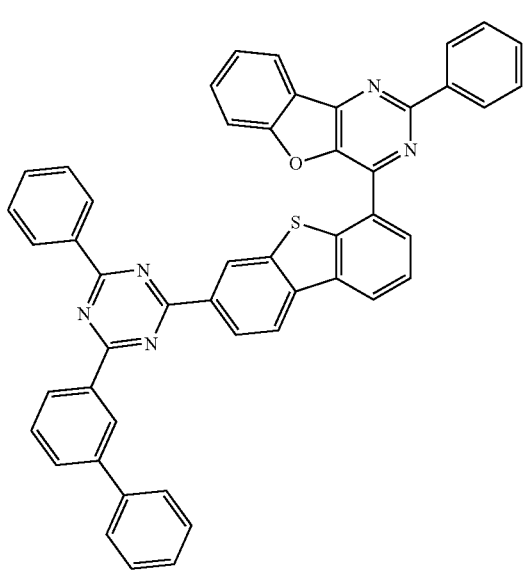
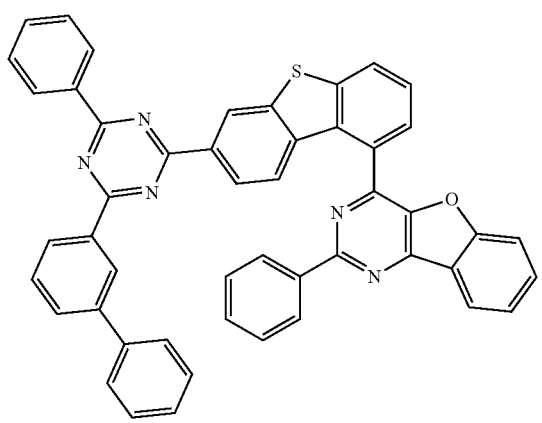

211
-continued
212
-continued
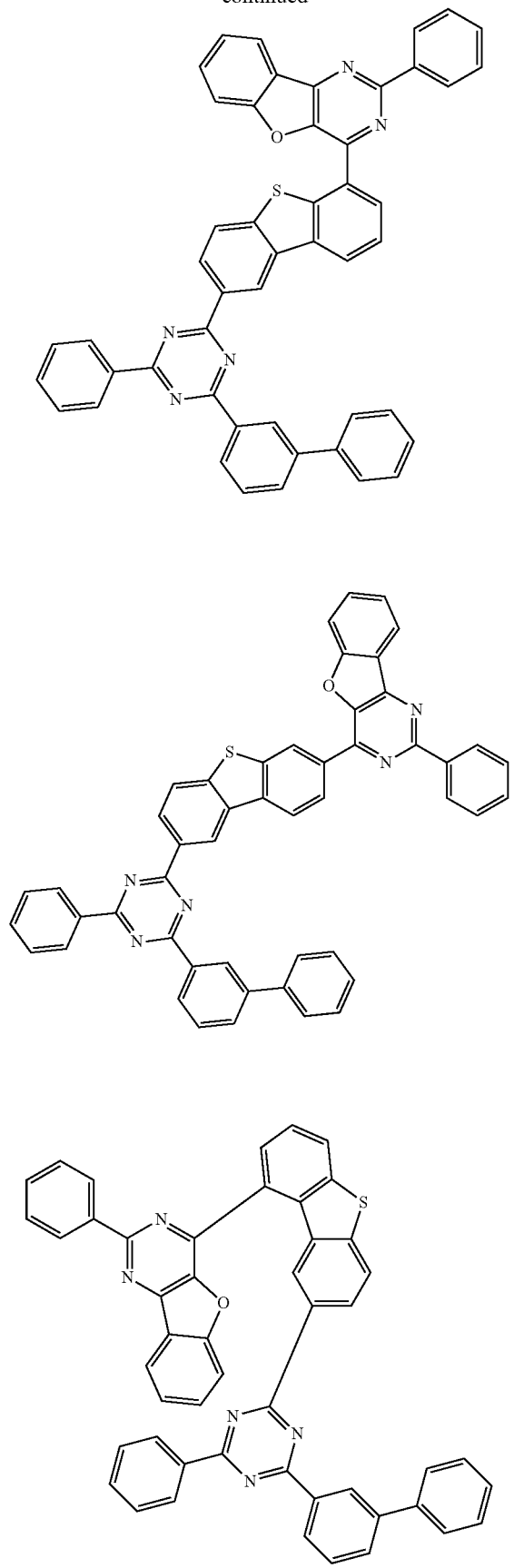
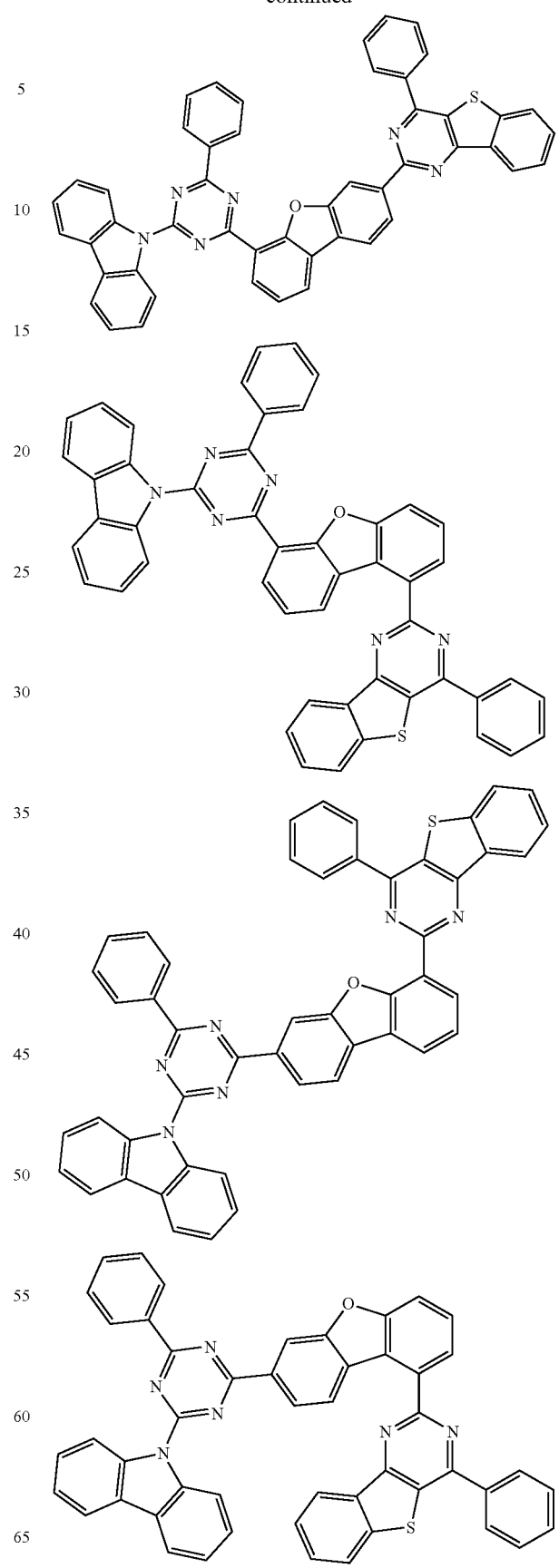

213
-continued
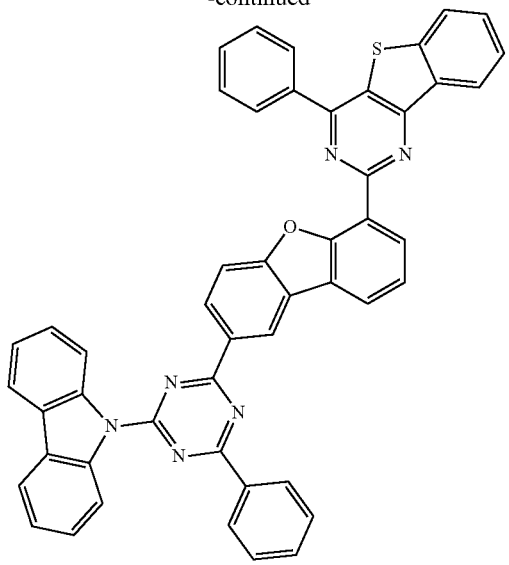
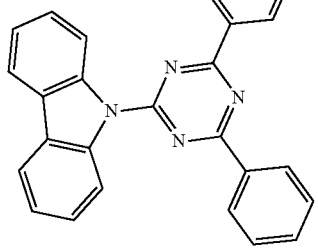
214
-continued
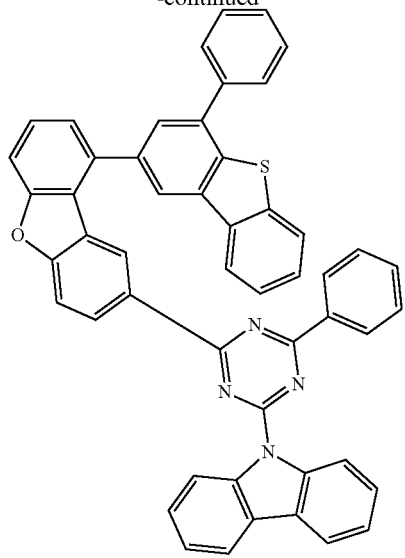
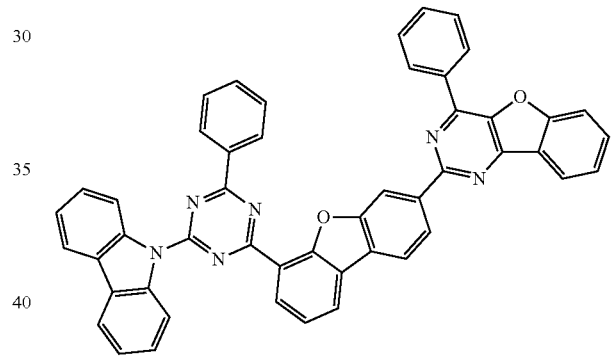
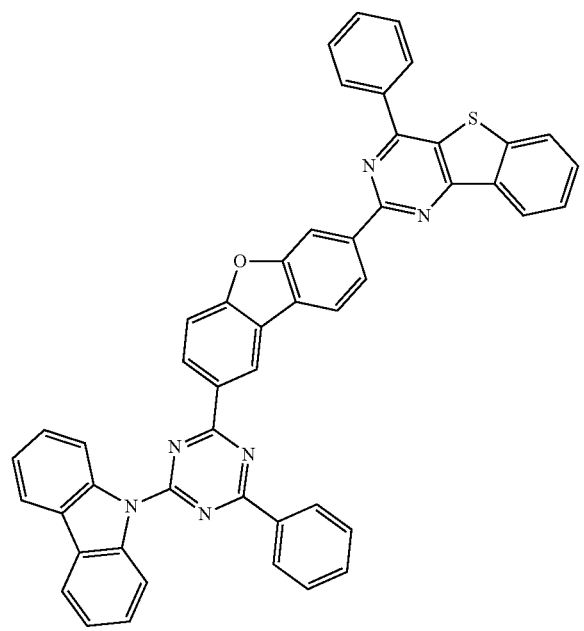
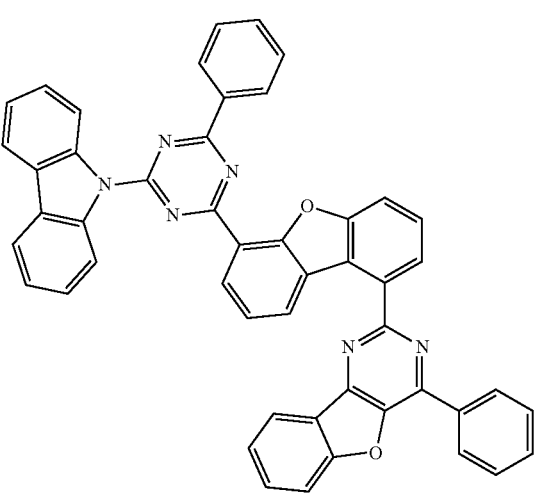

-continued
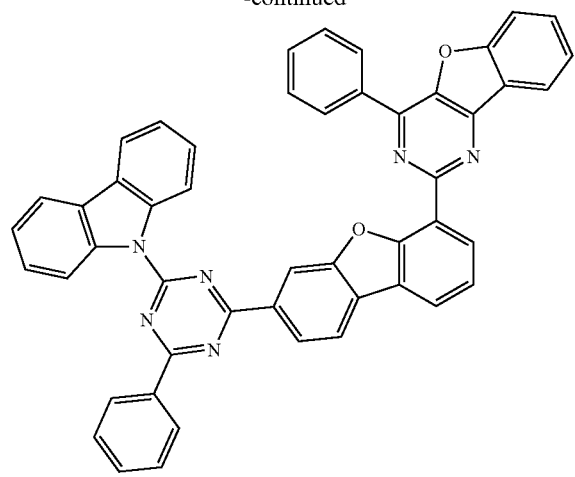
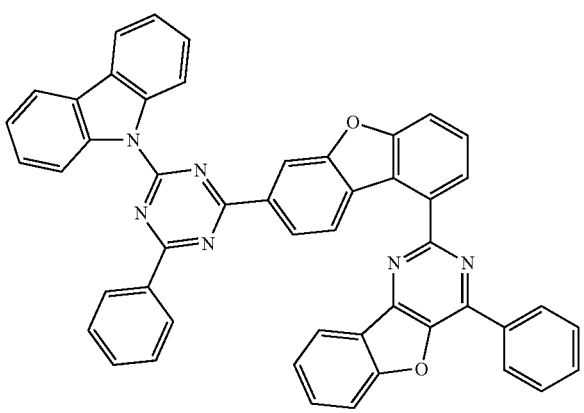
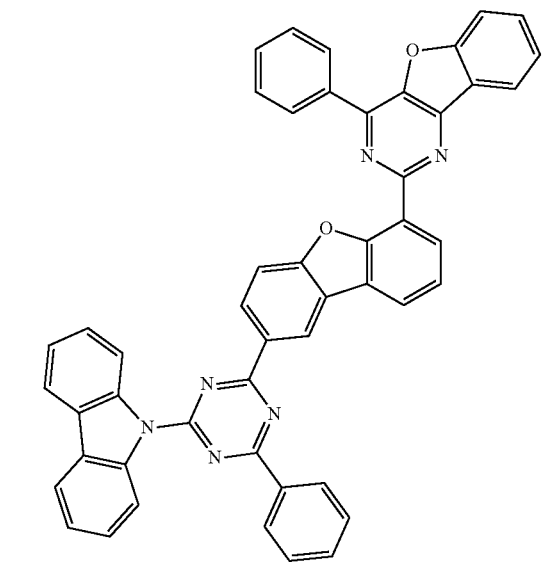
-continued
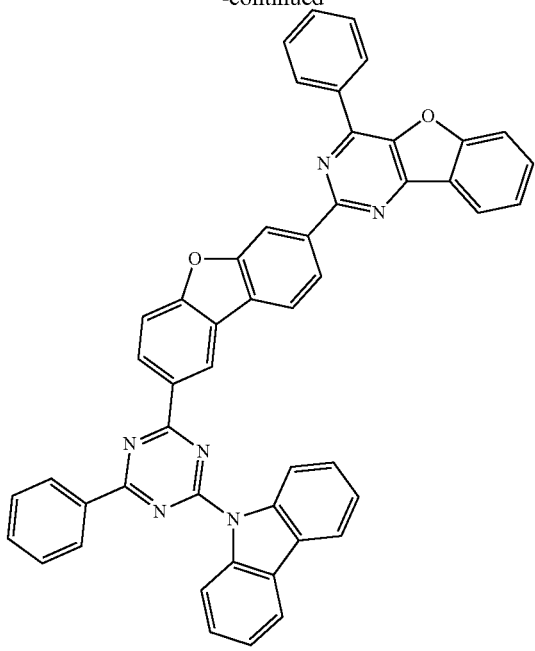
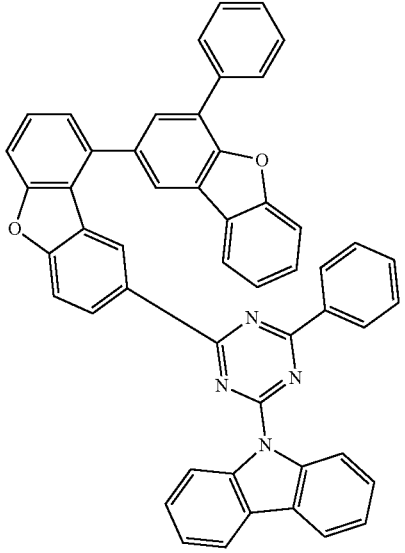
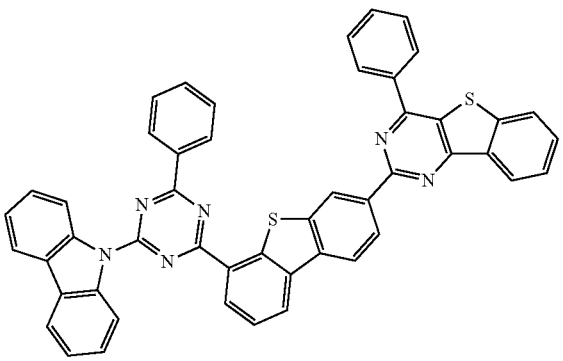

217
218
-continued
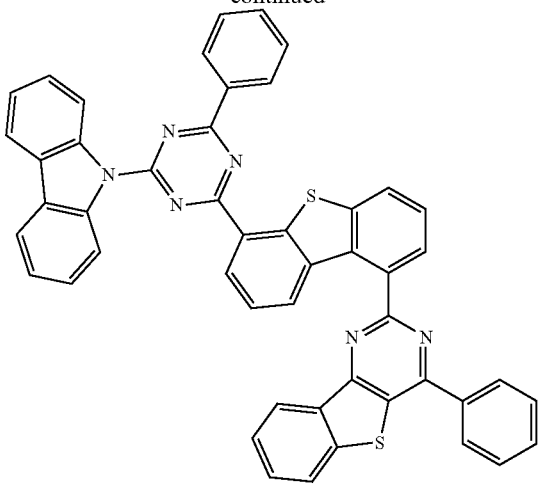
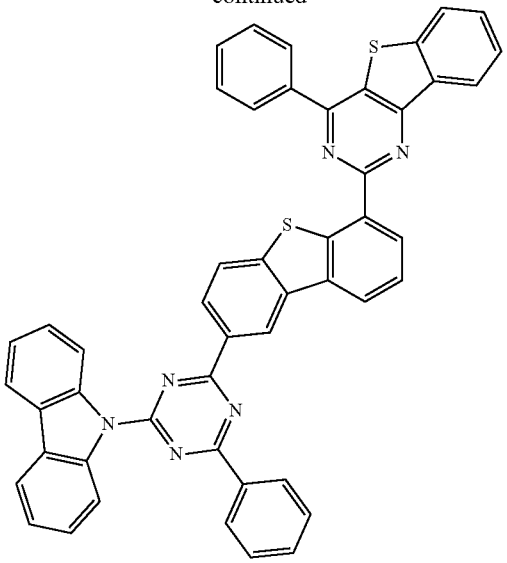
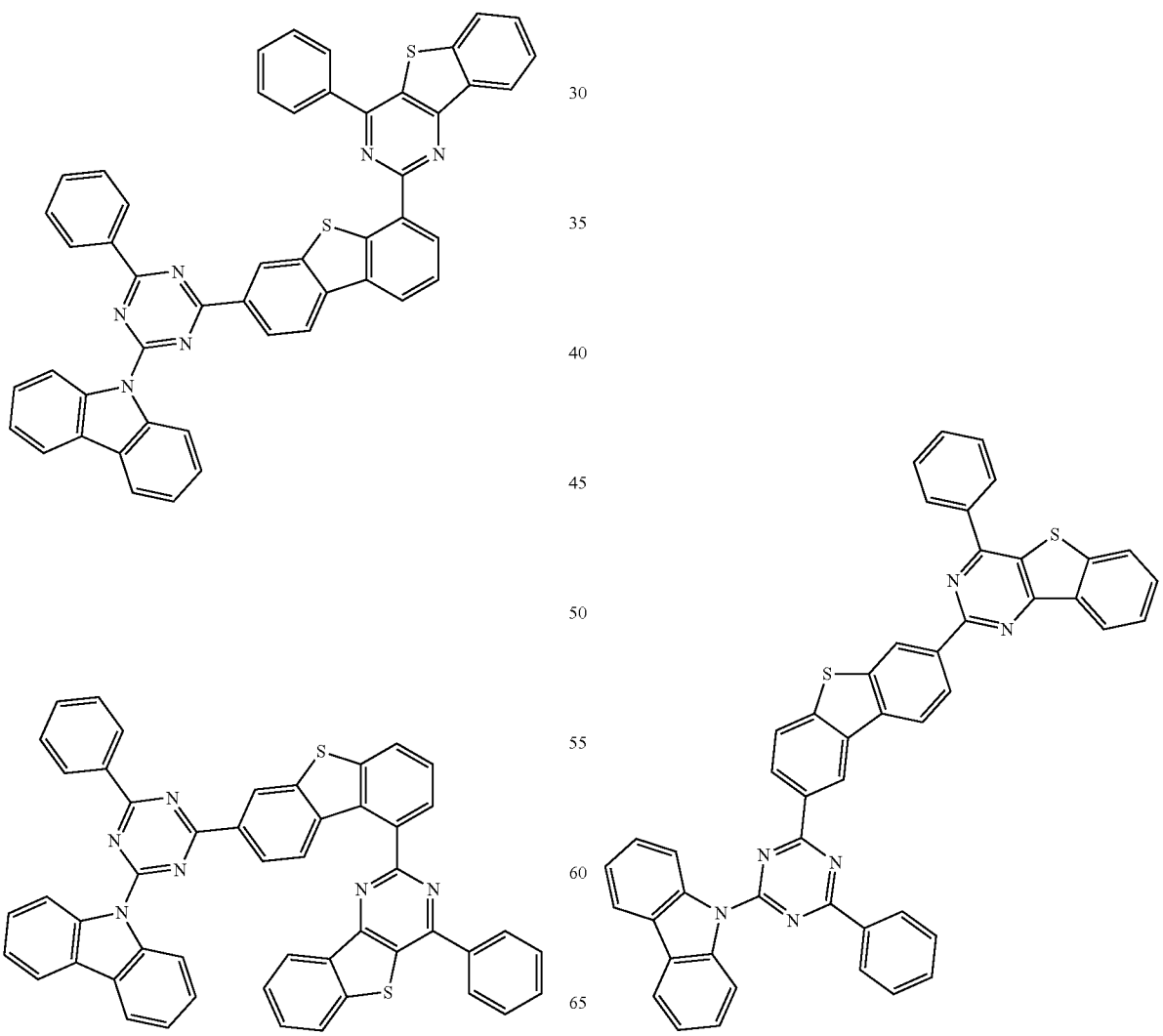

219
-continued
220
-continued
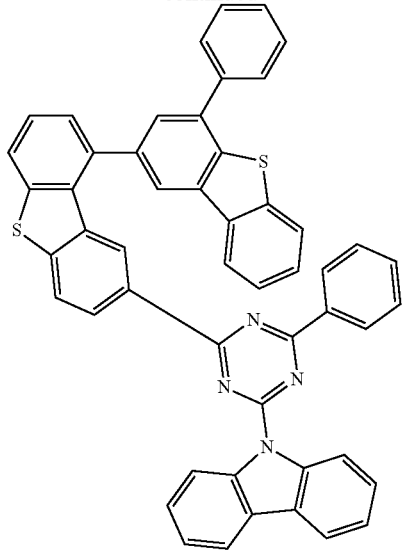
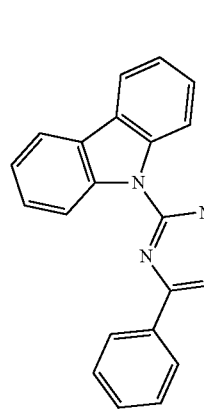
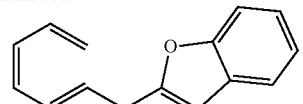
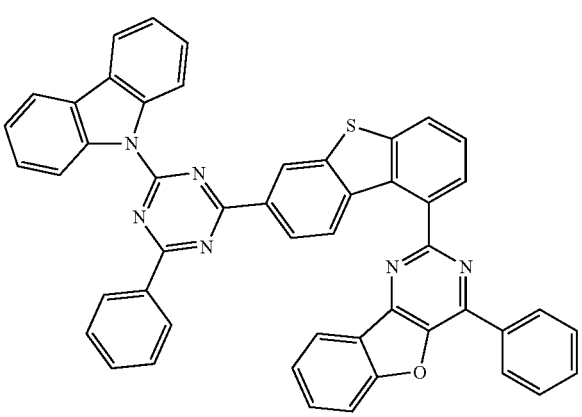
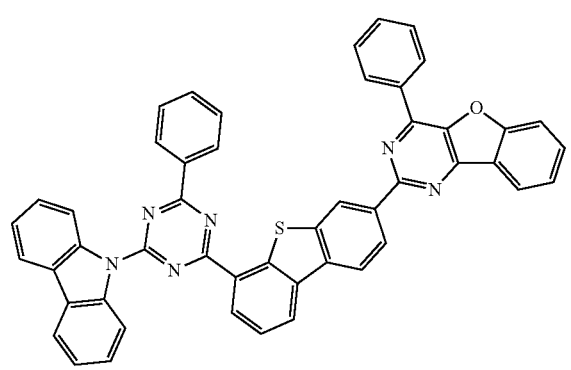
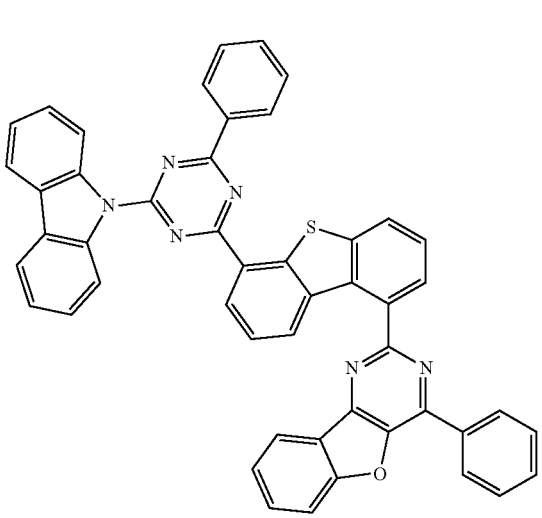
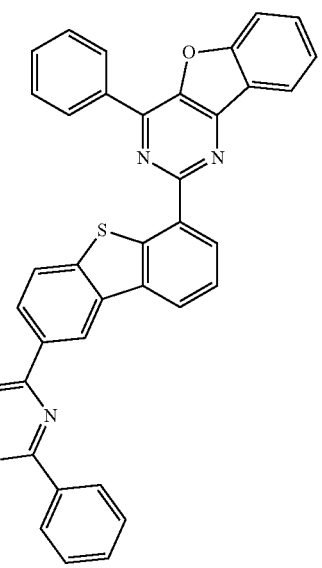

221
-continued
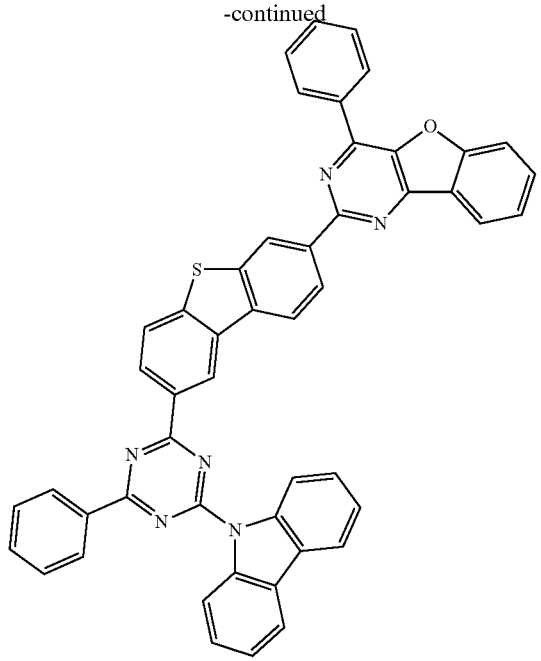
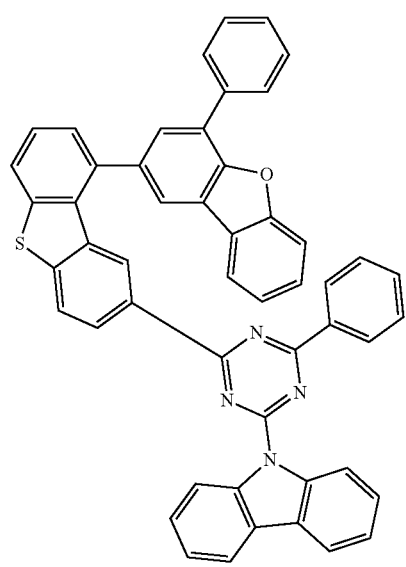
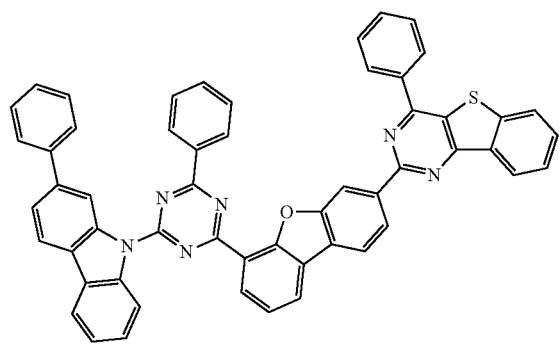 [SMILES: c1ccc(-c2ccc3c4ccccc4n(-c4nc(-c5ccccc5)nc(-c5cccc6c5oc5cc(-c7nc(-c8ccccc8)c8oc9ccccc9c8n7)ccc56)n4)c3c2)cc1]
222
-continued
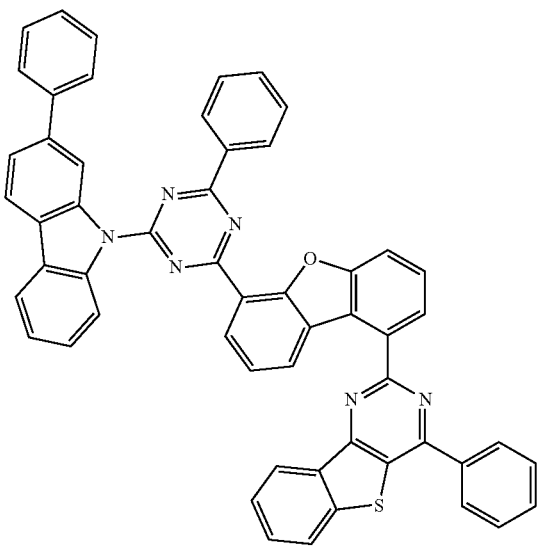
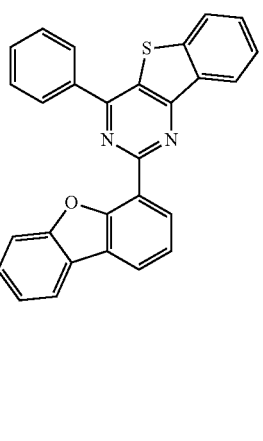
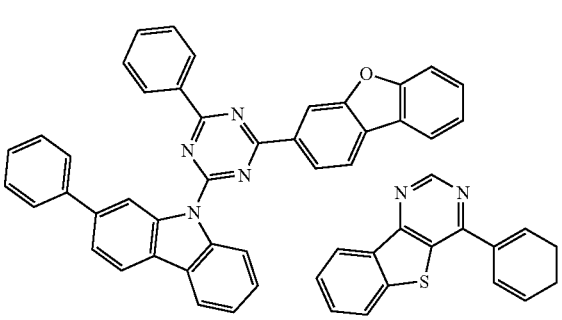

223
-continued
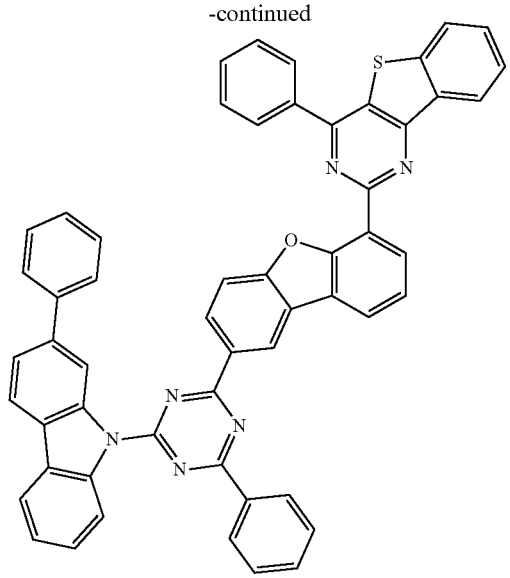
224
-continued
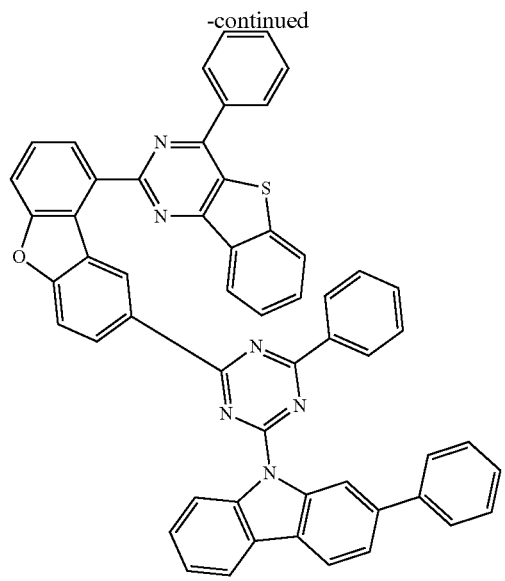
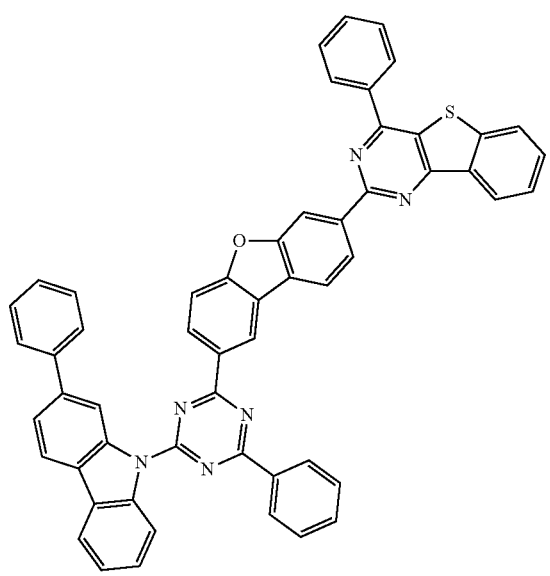
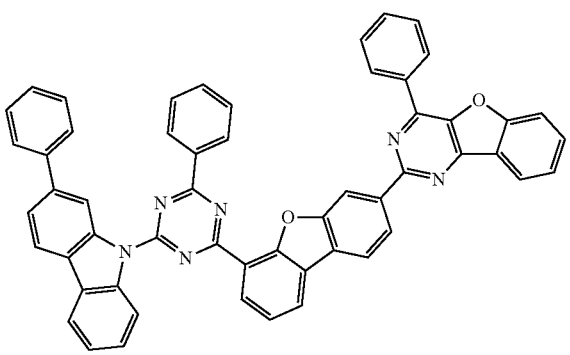

225
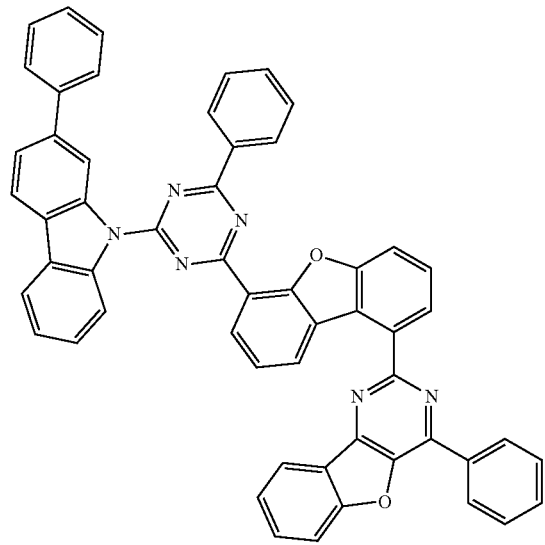
226
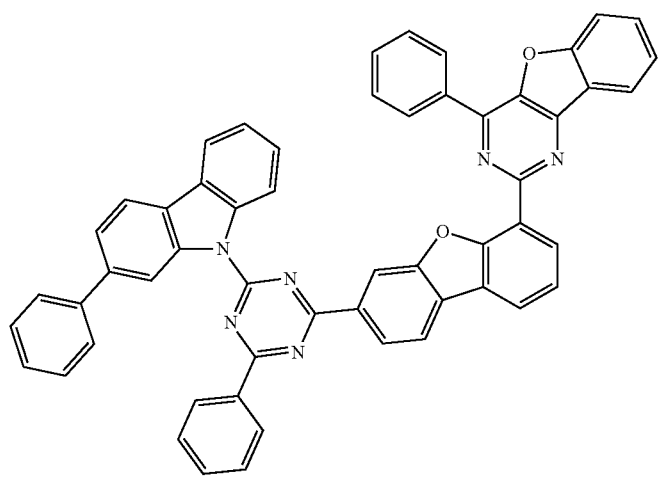
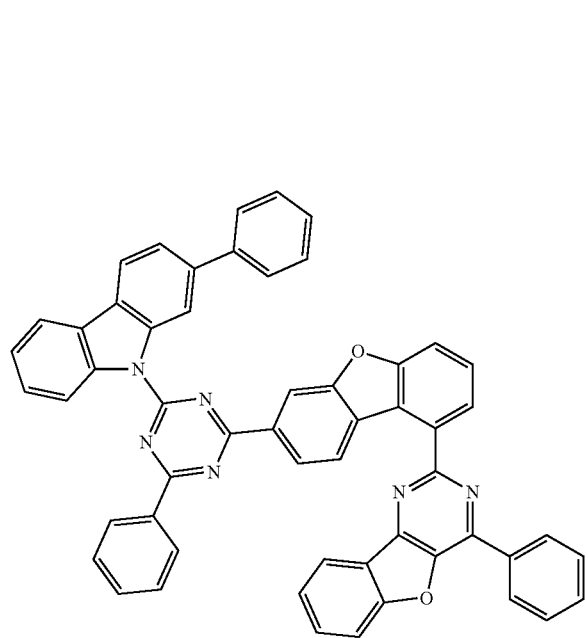
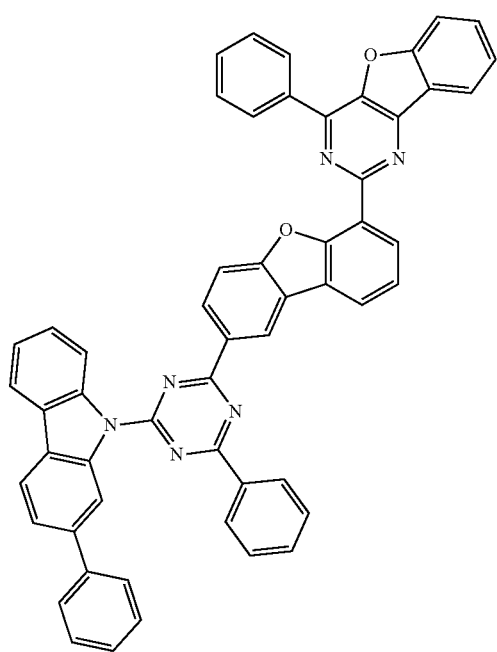

227
228
-continued
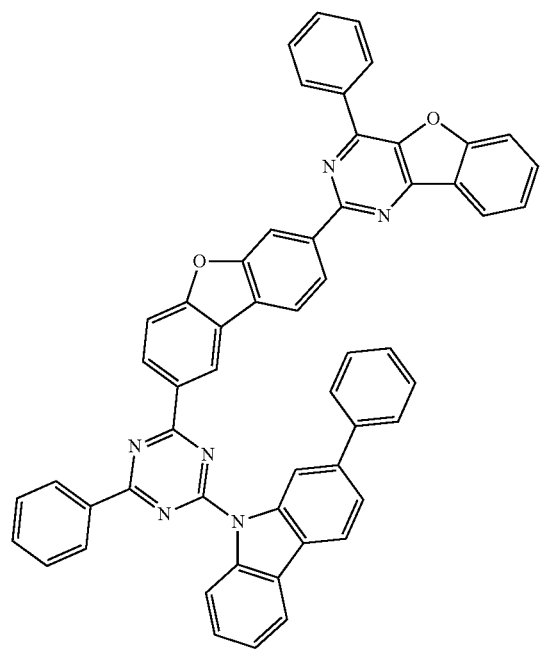
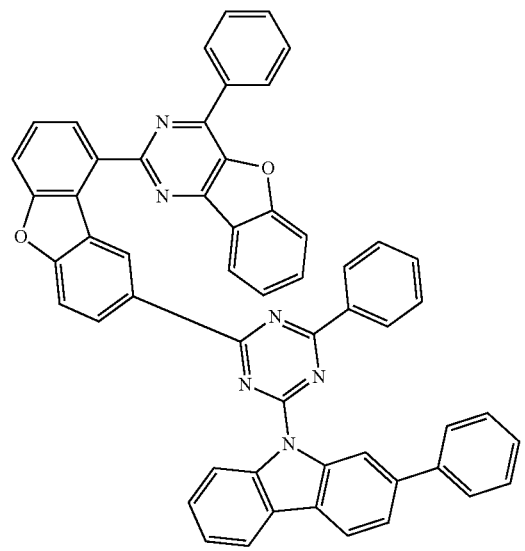
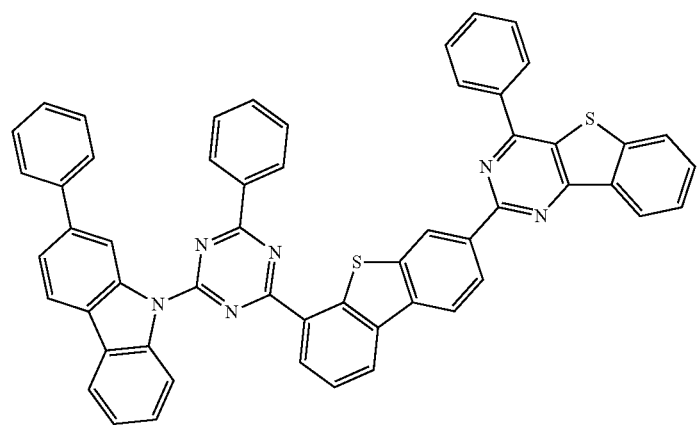
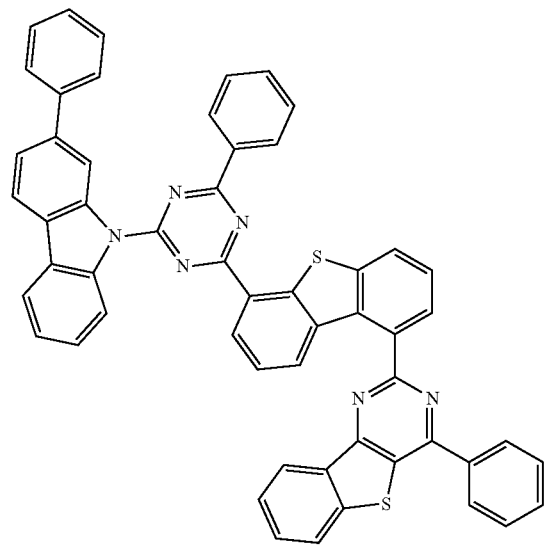
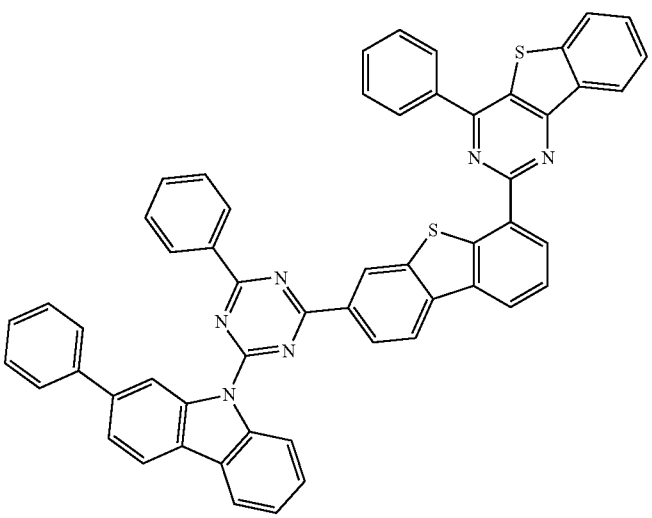

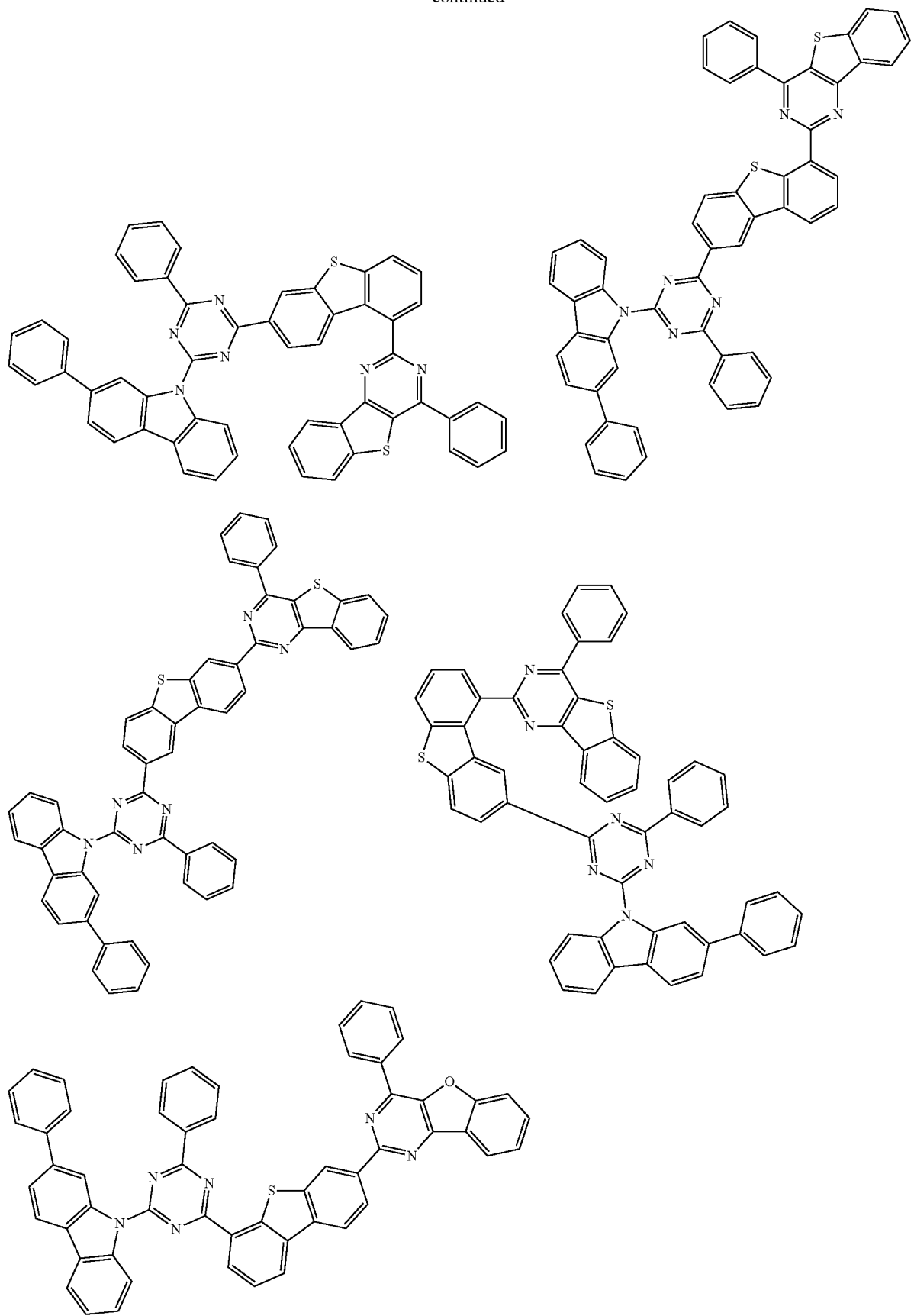

231
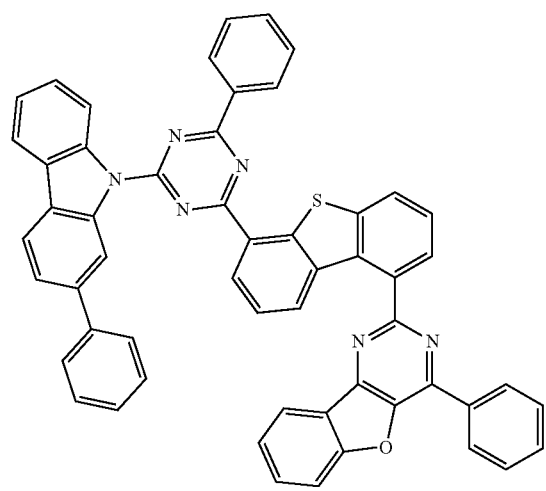
232
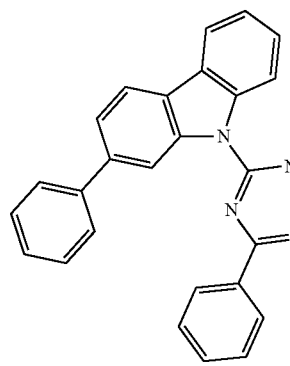
-continued
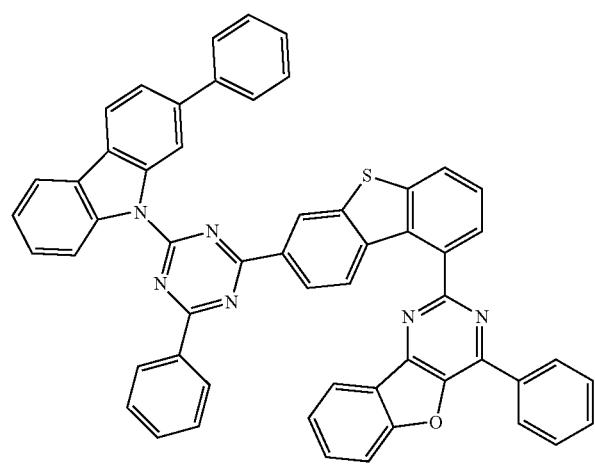
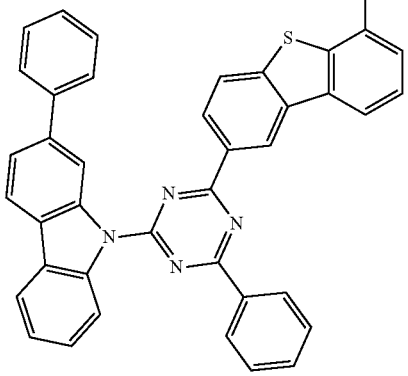
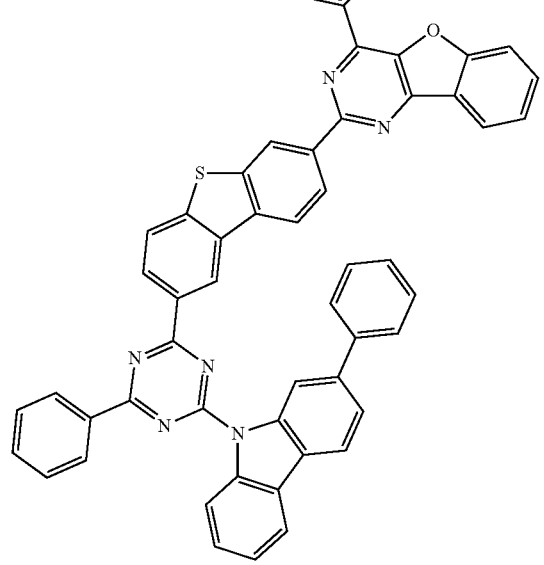
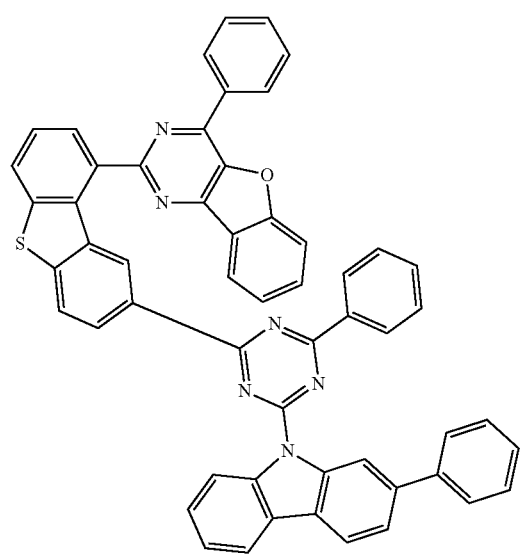

-continued
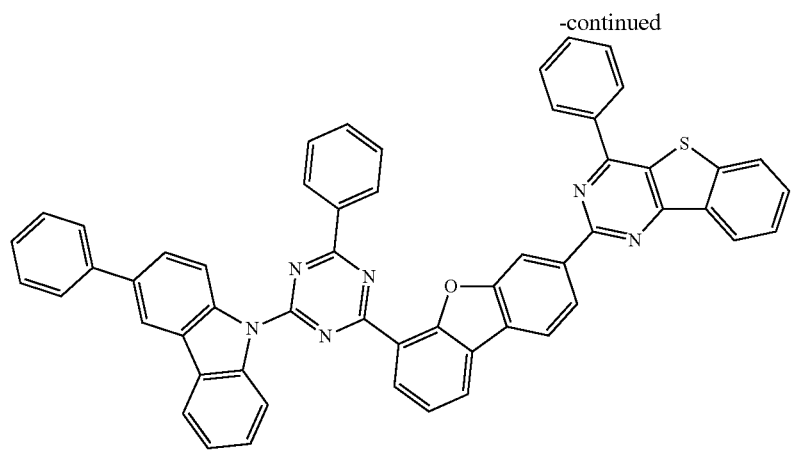
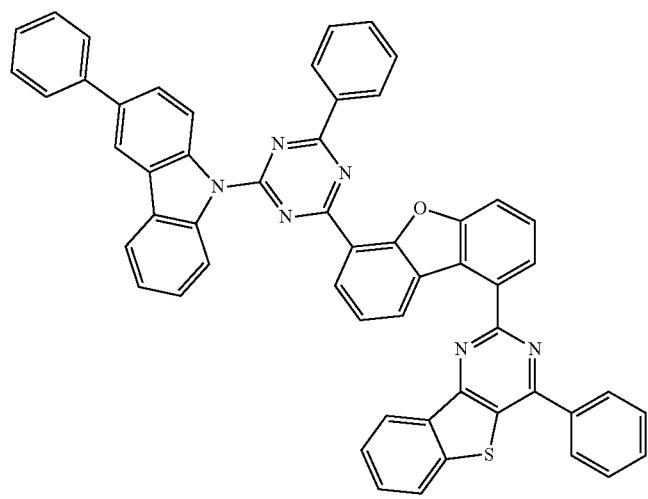
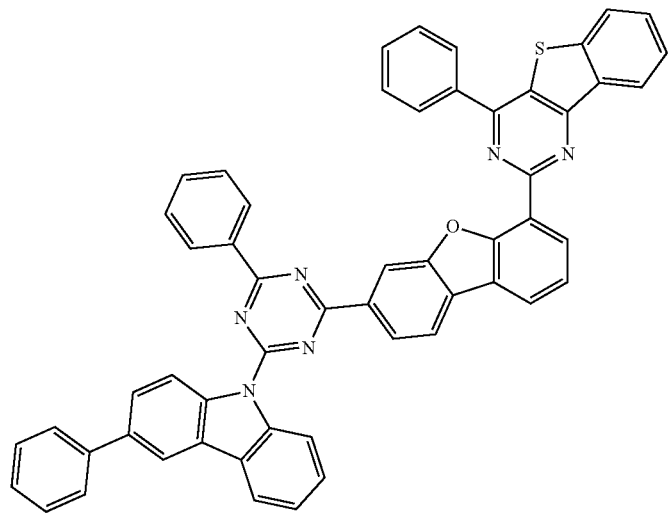

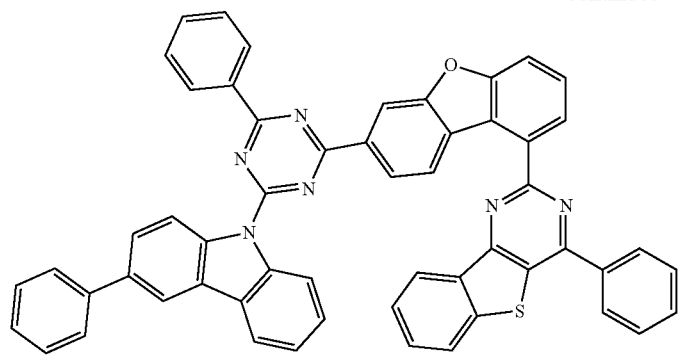
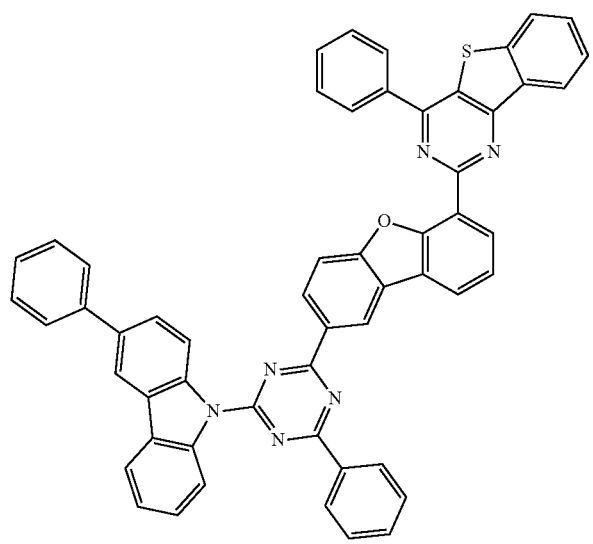
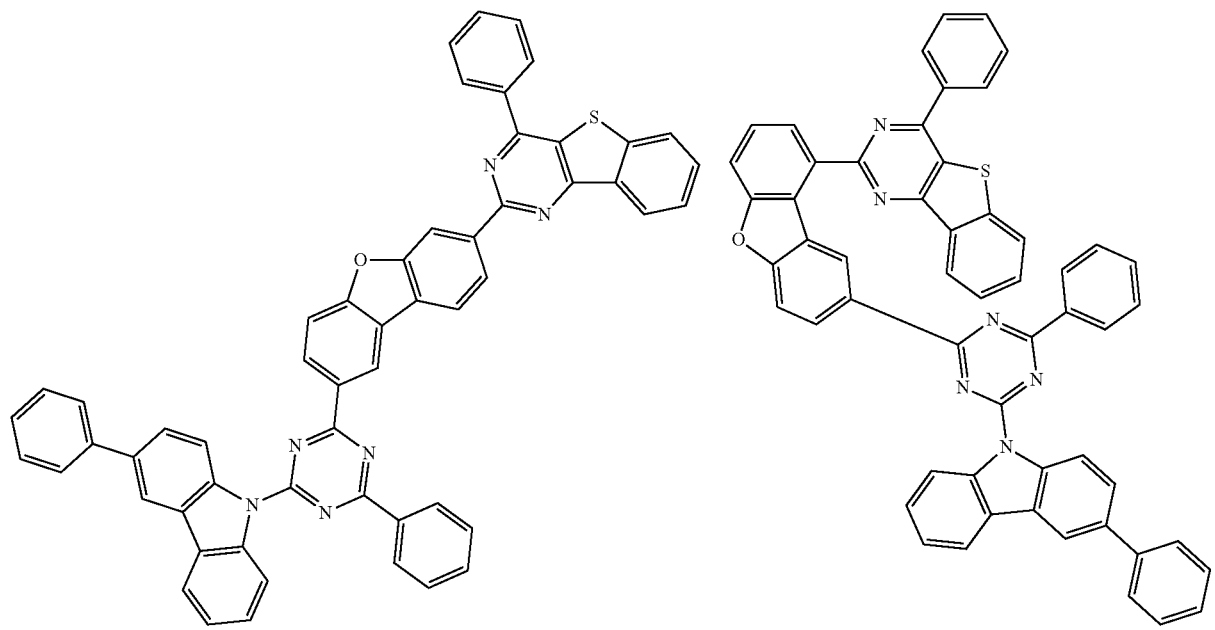

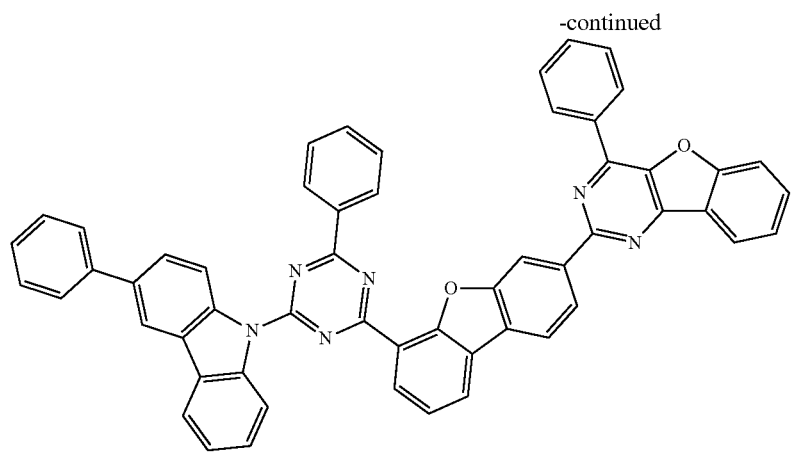
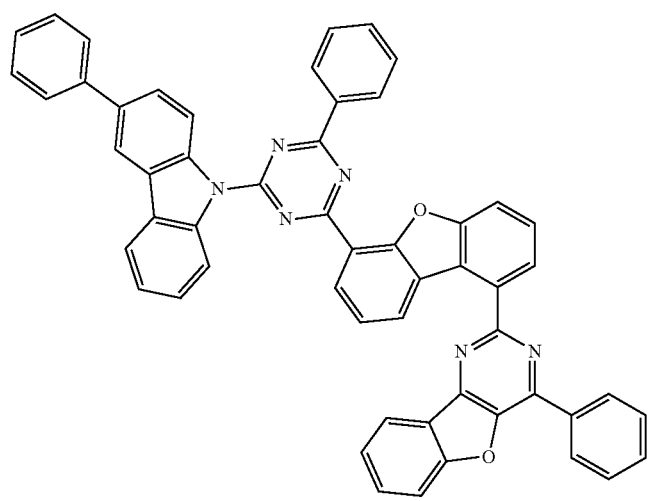
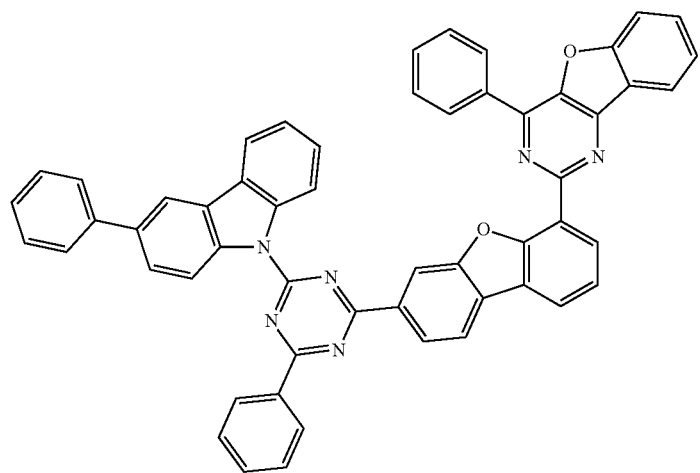

-continued
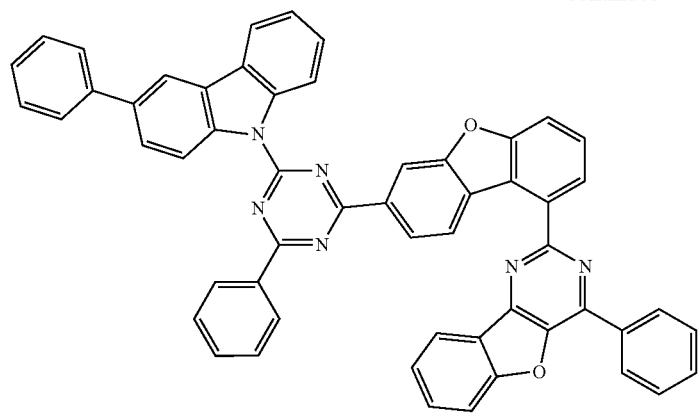
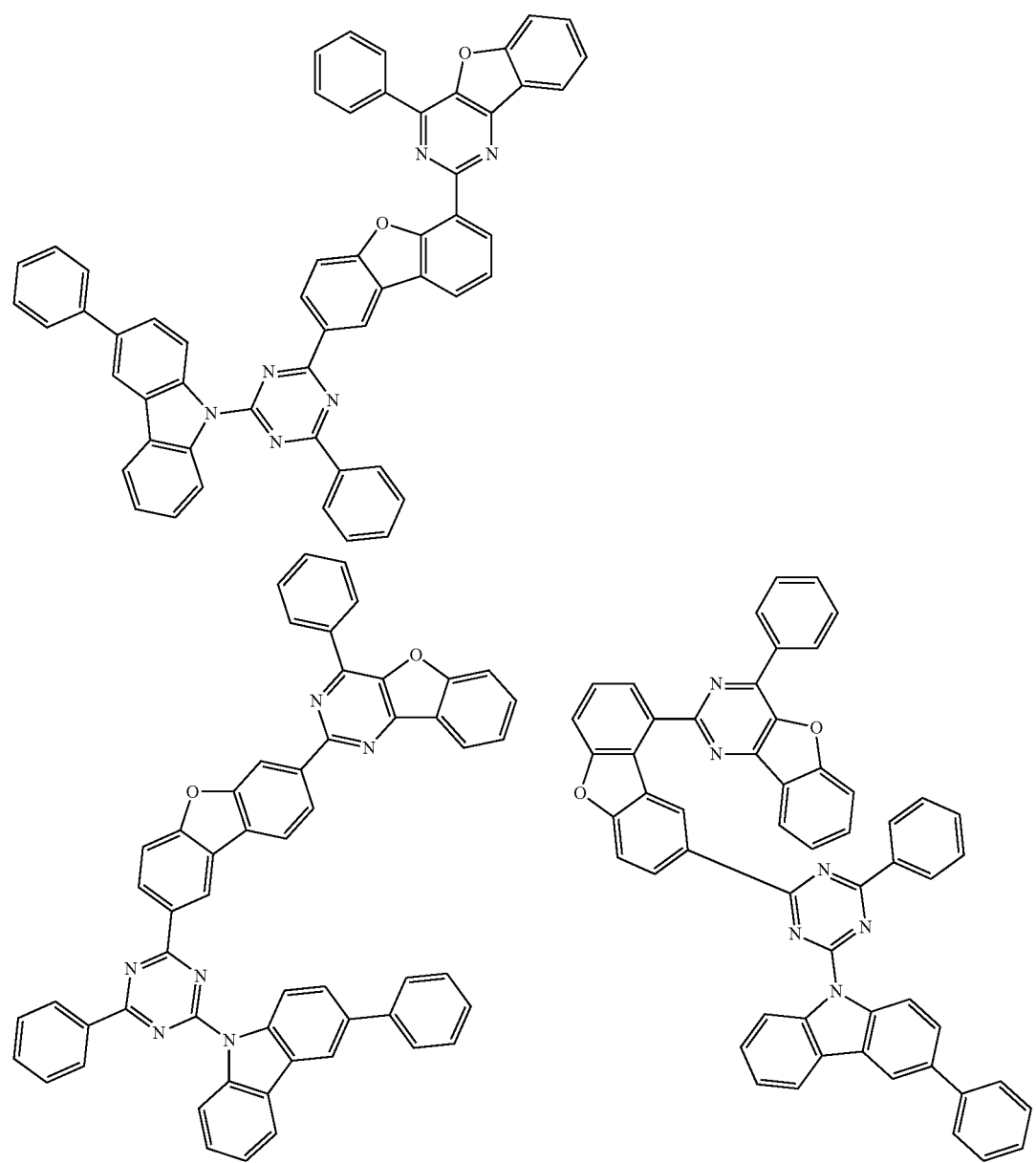

-continued
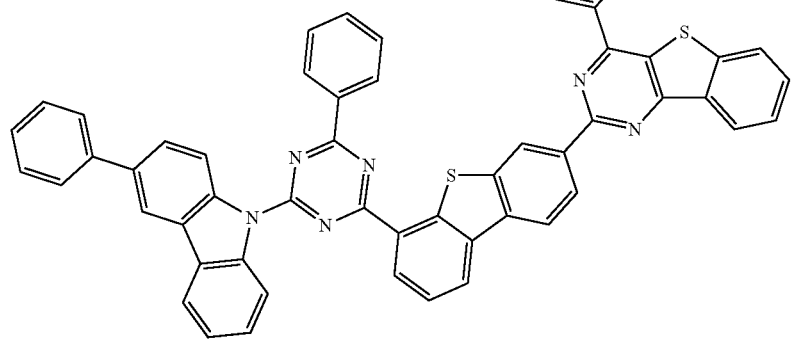
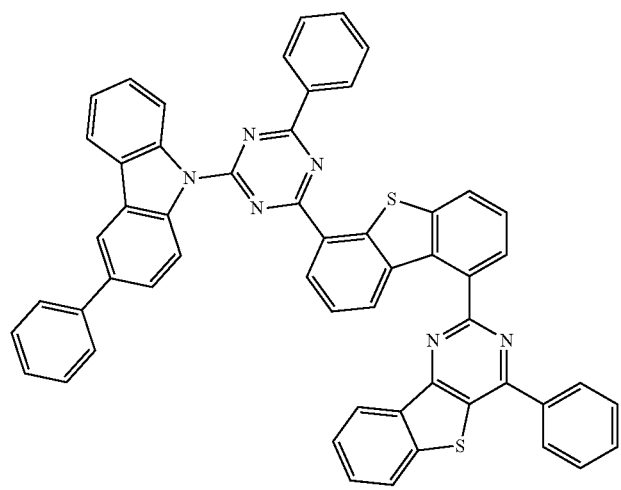
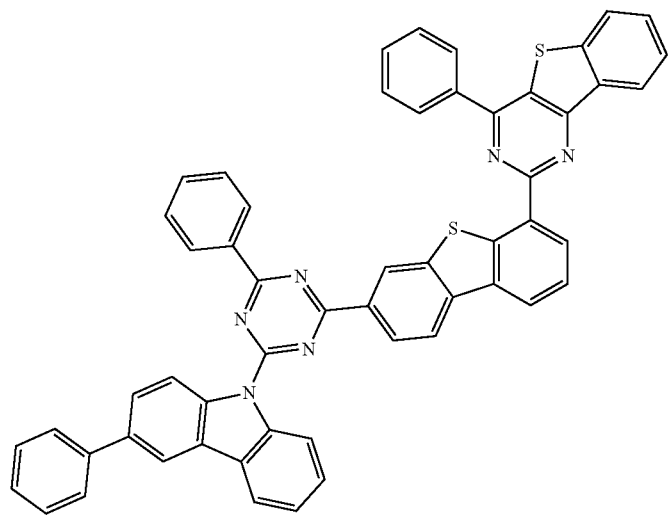

-continued
243
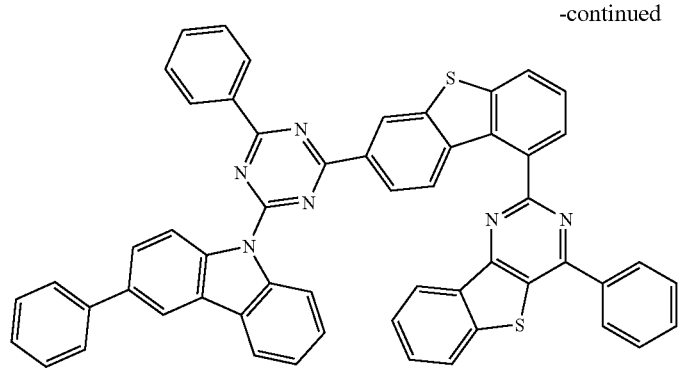
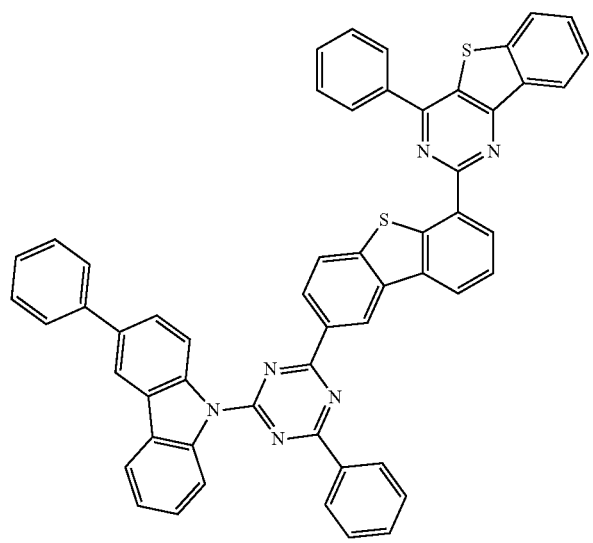
244
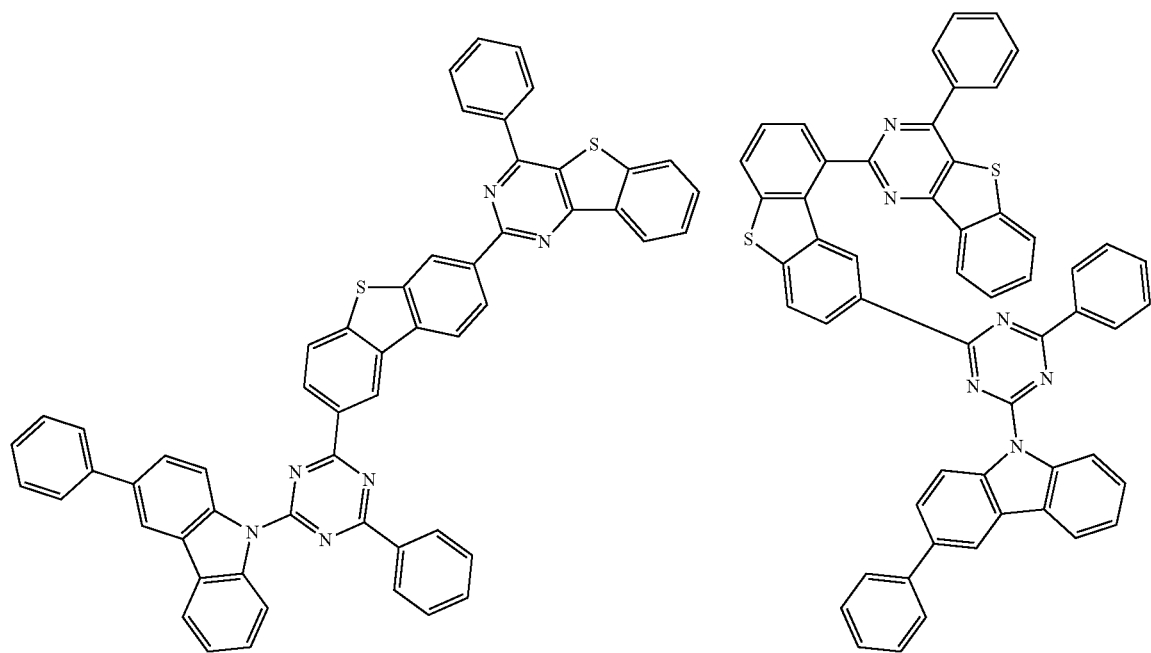

-continued
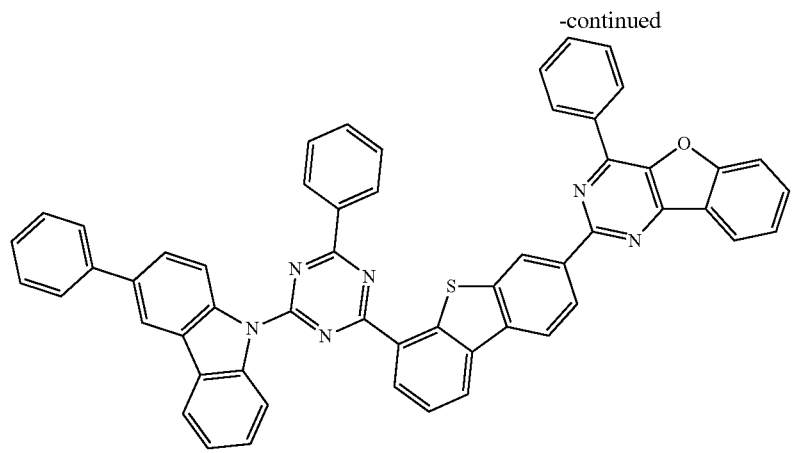
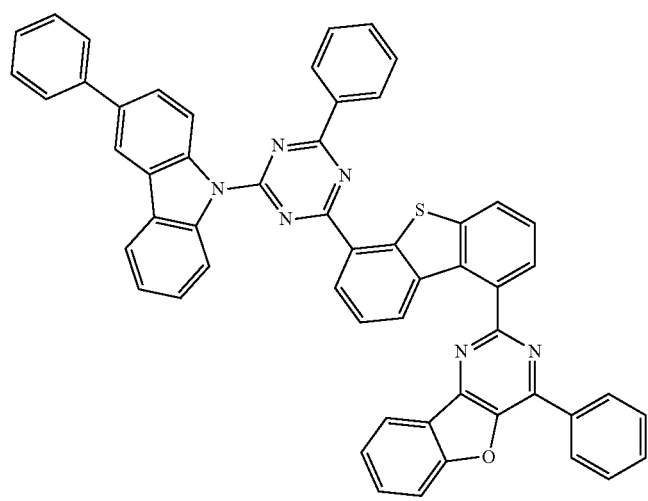
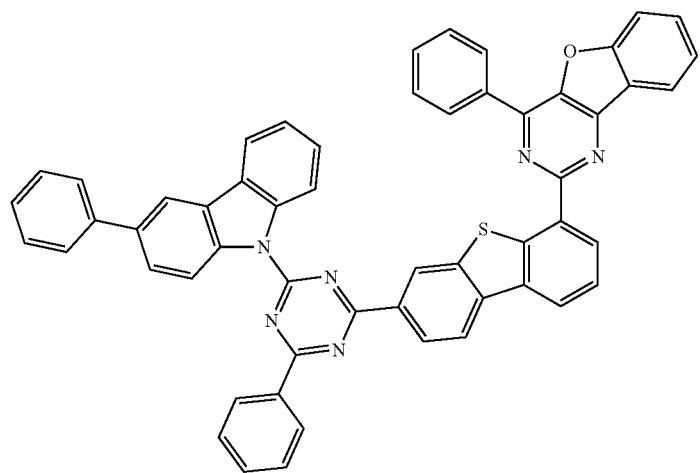

-continued
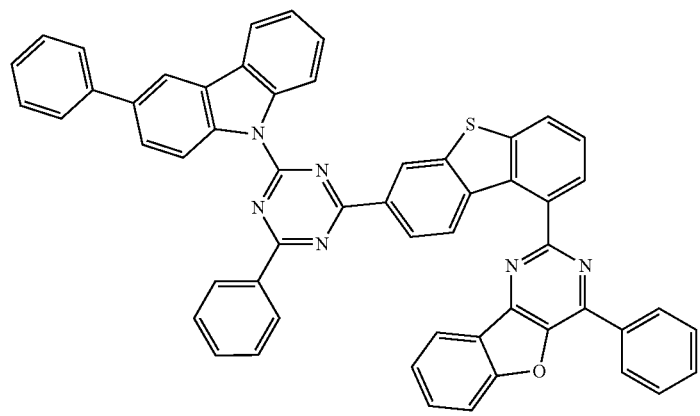
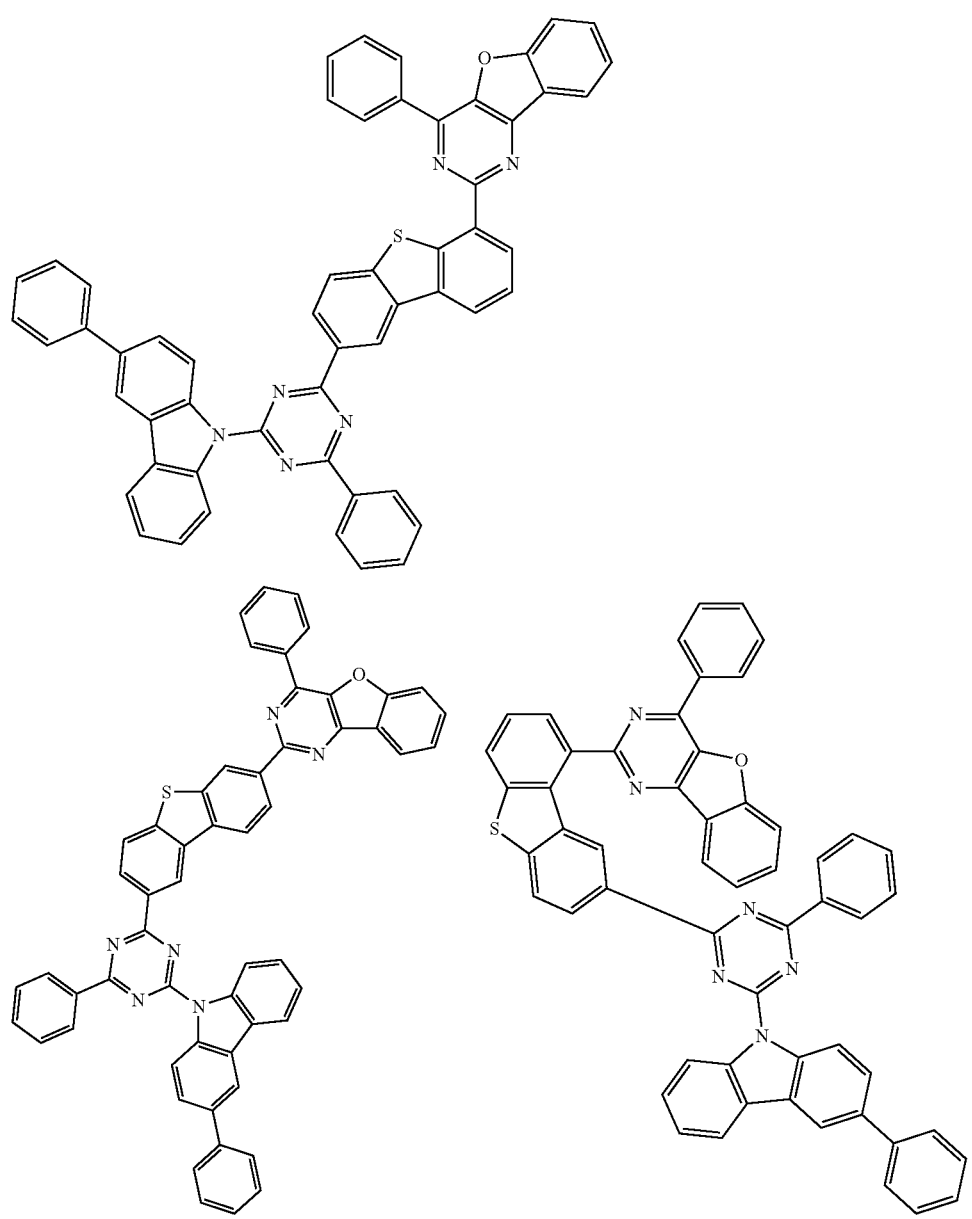

-continued
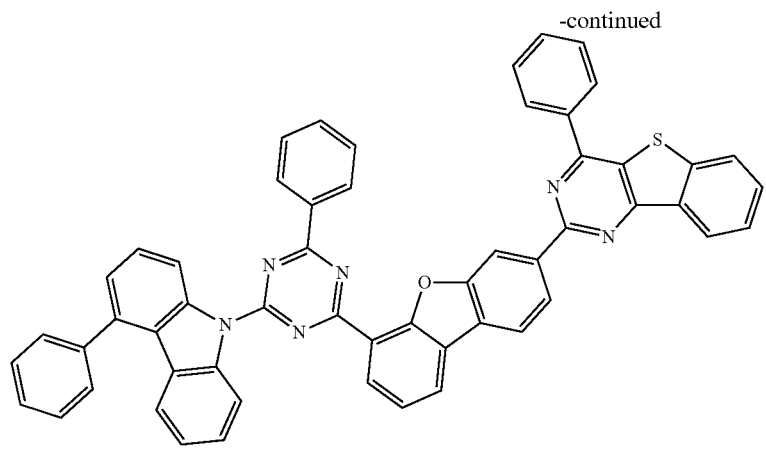
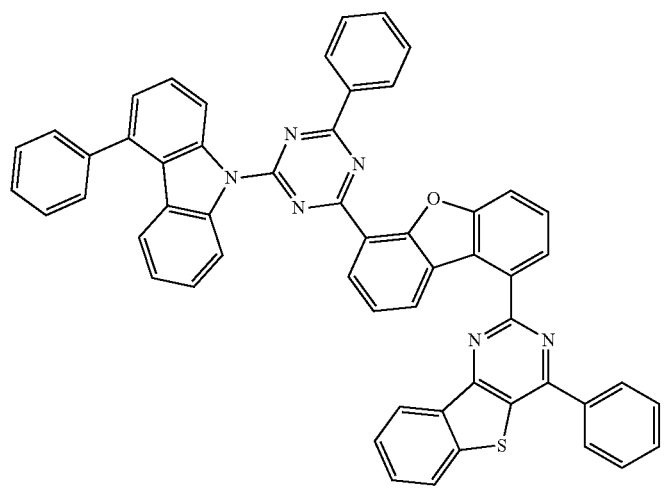
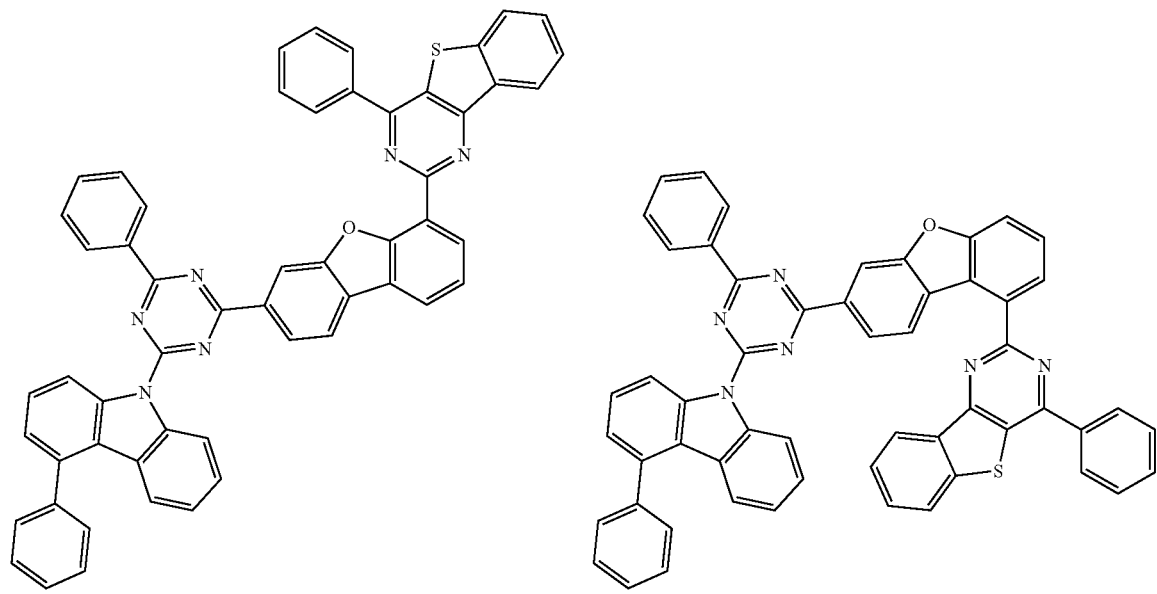

-continued
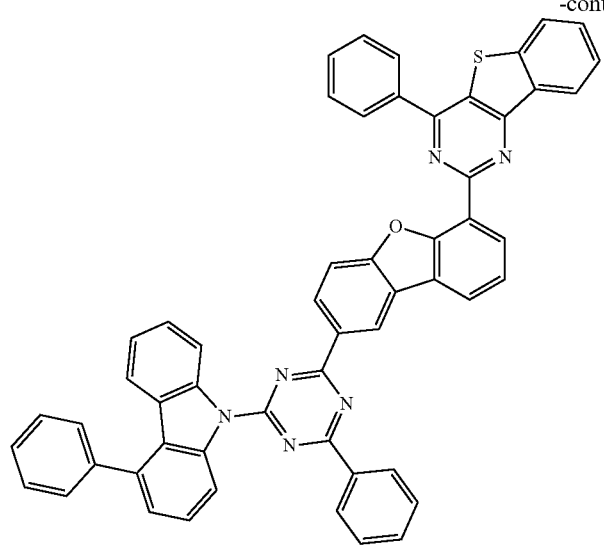
251
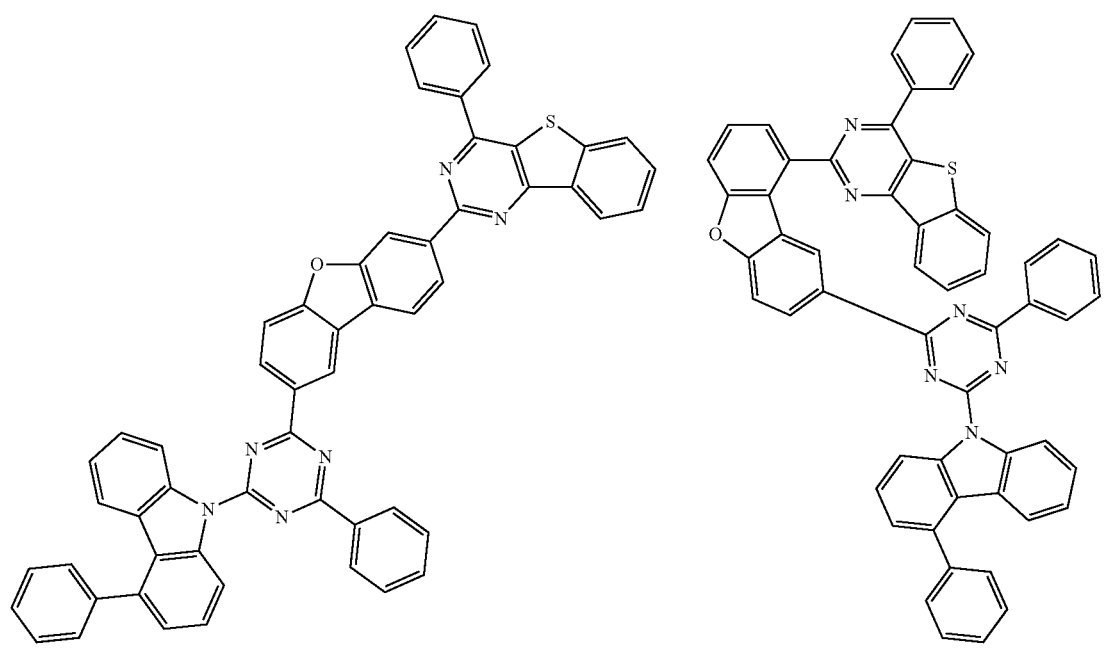
252
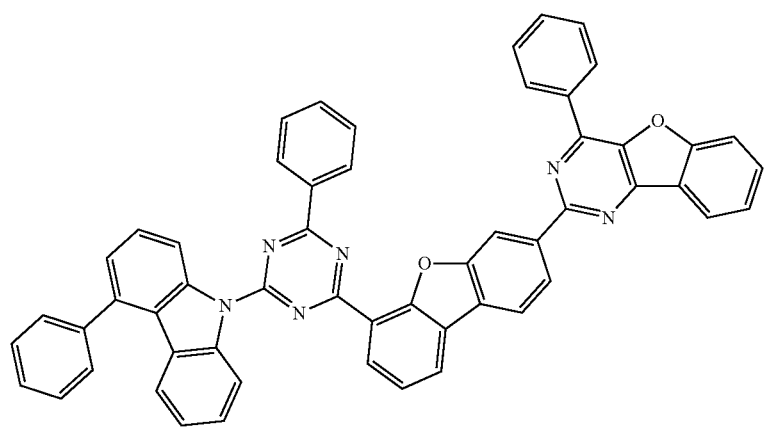

-continued
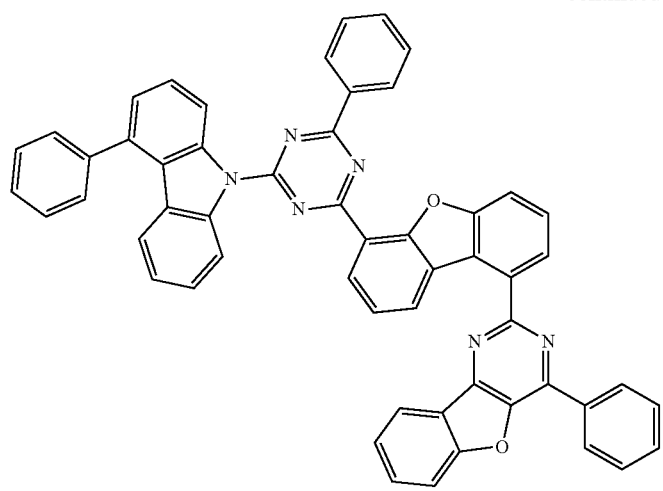
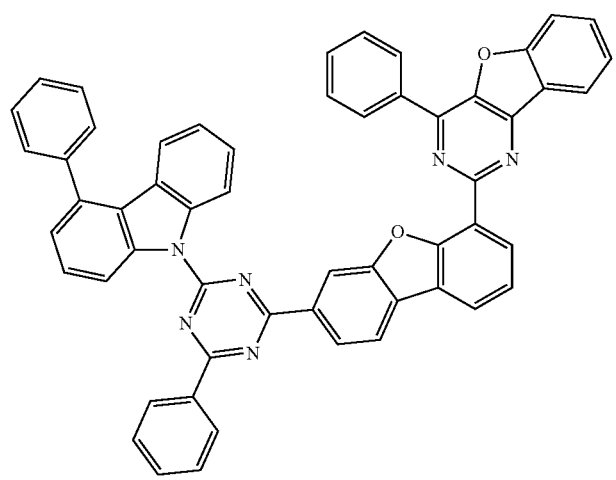
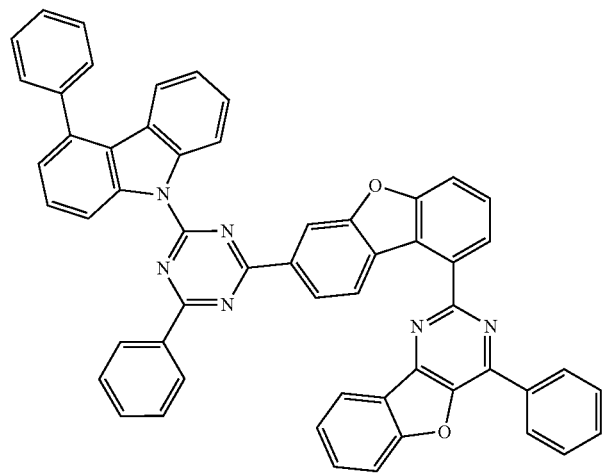

255
256
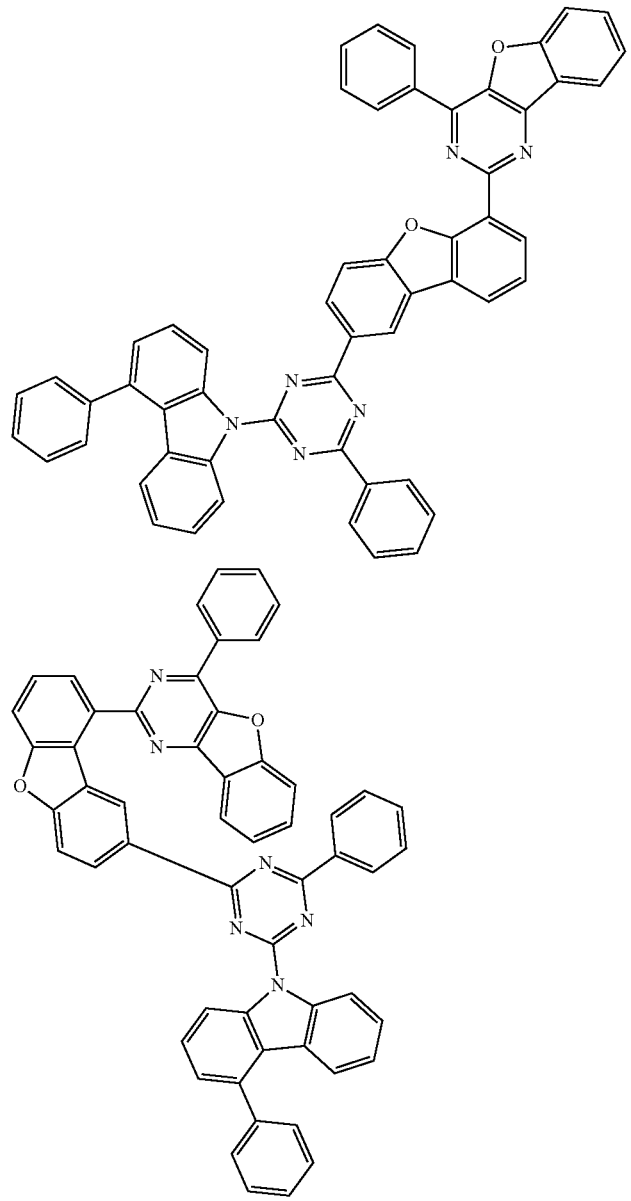
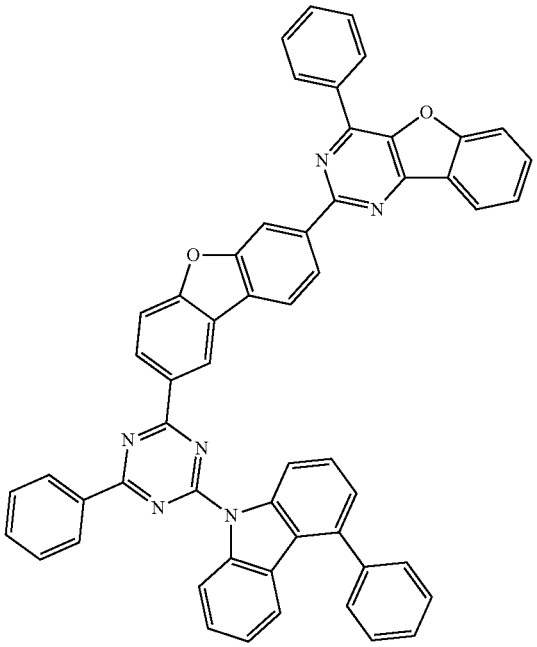
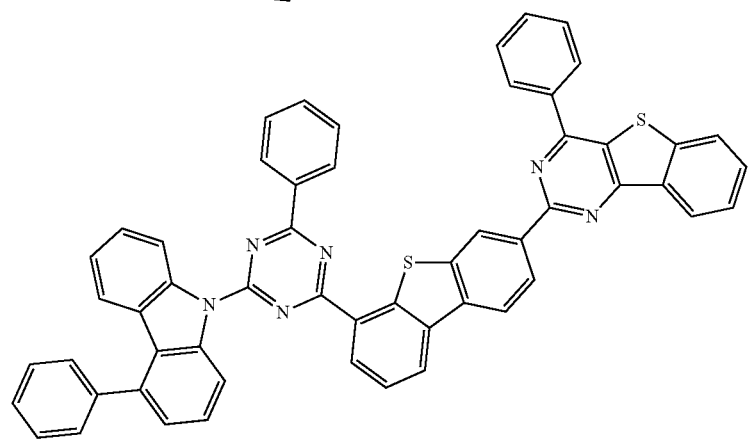

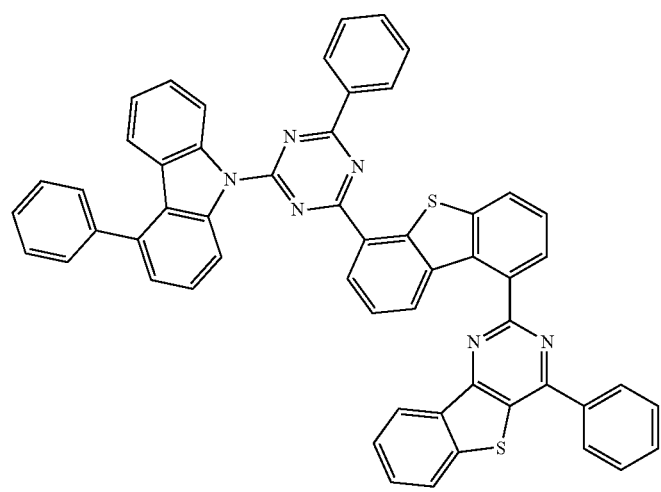
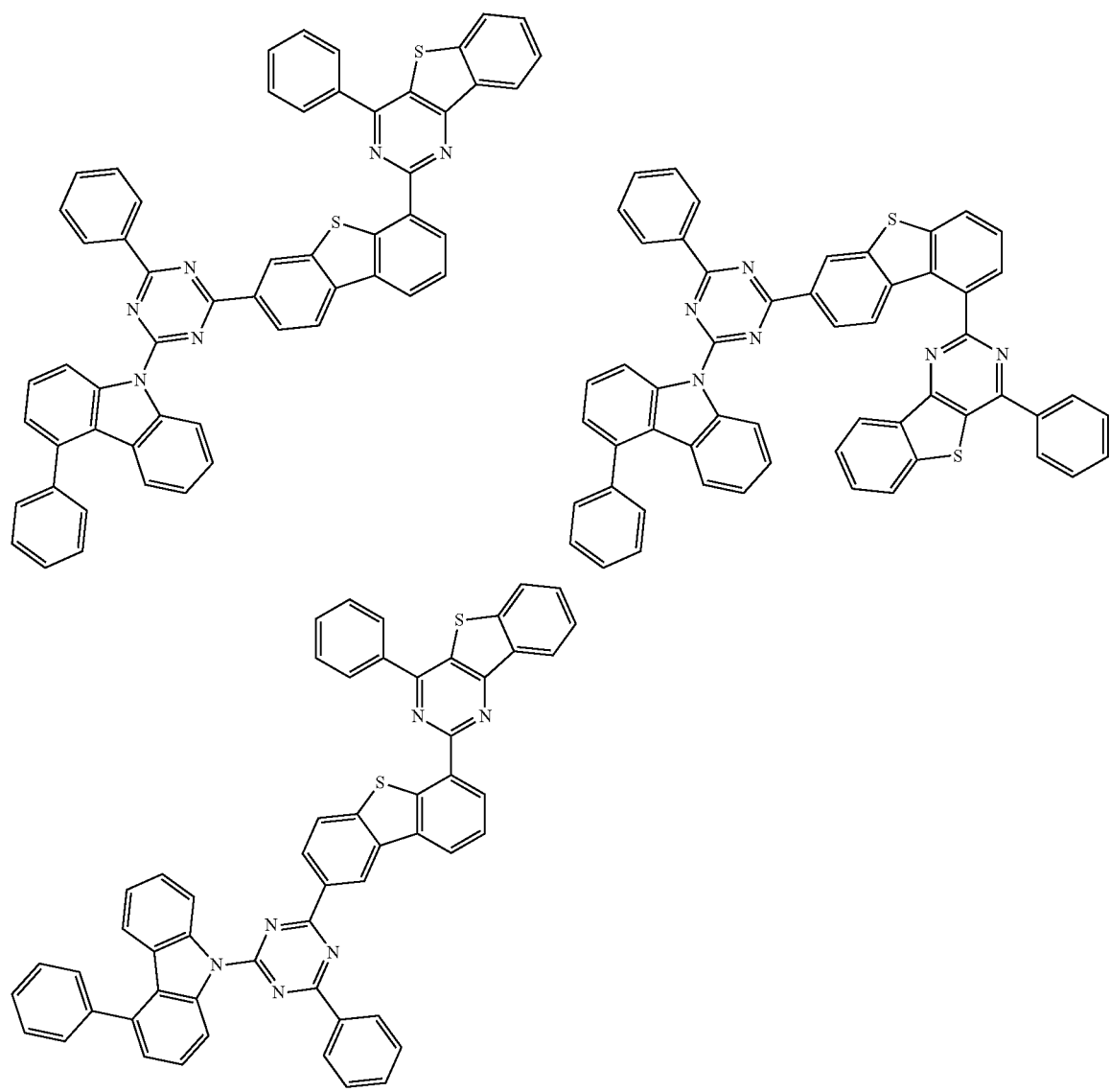

259 260
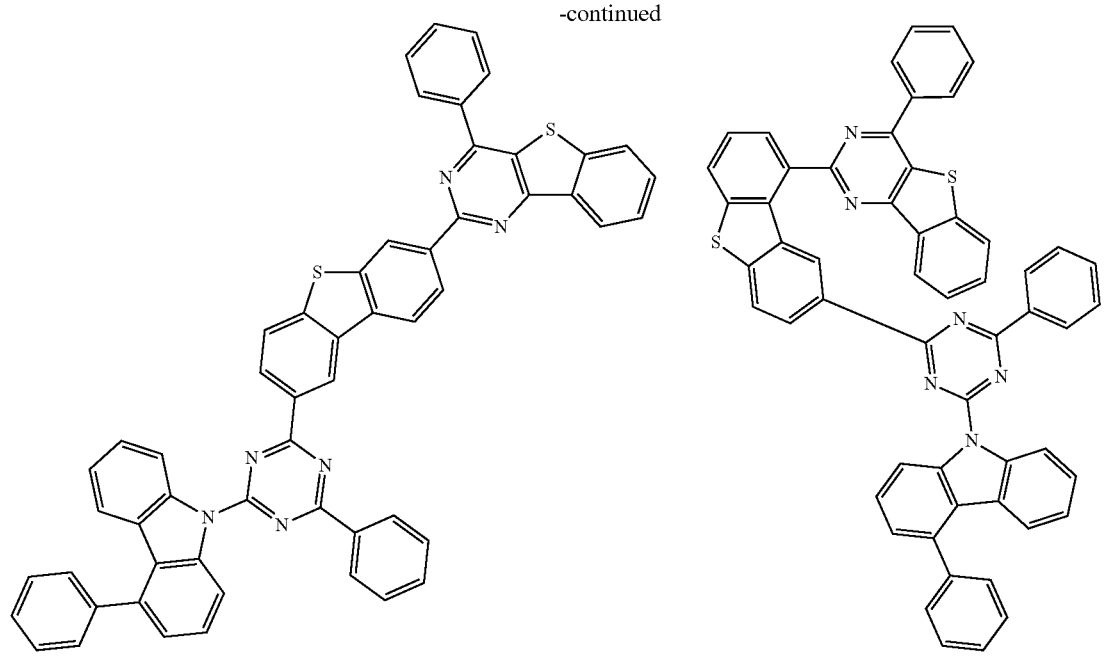
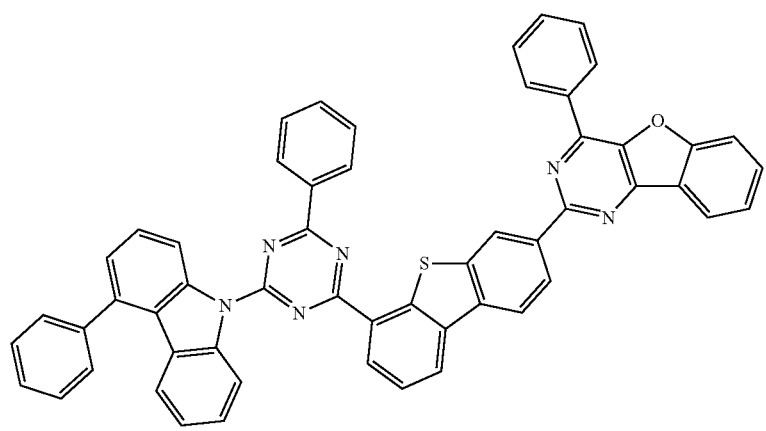
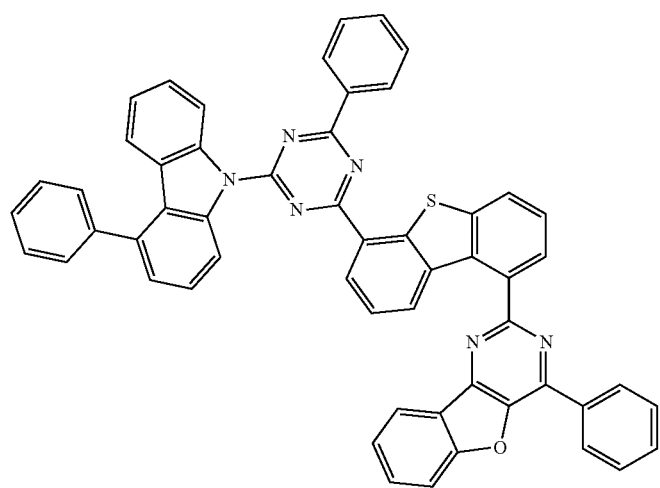

-continued
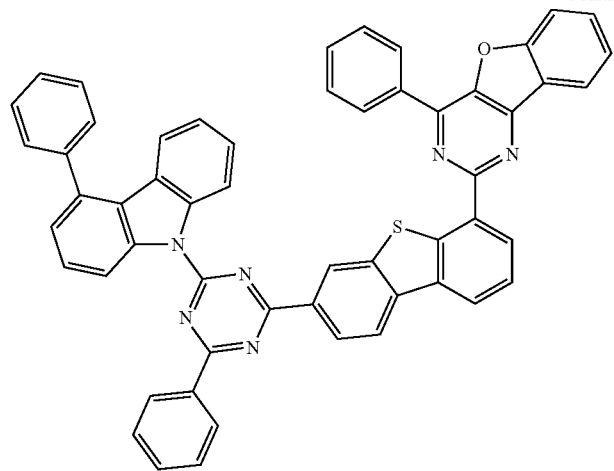
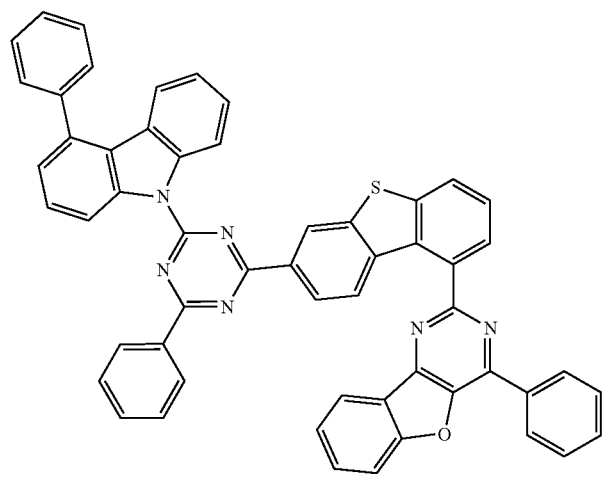
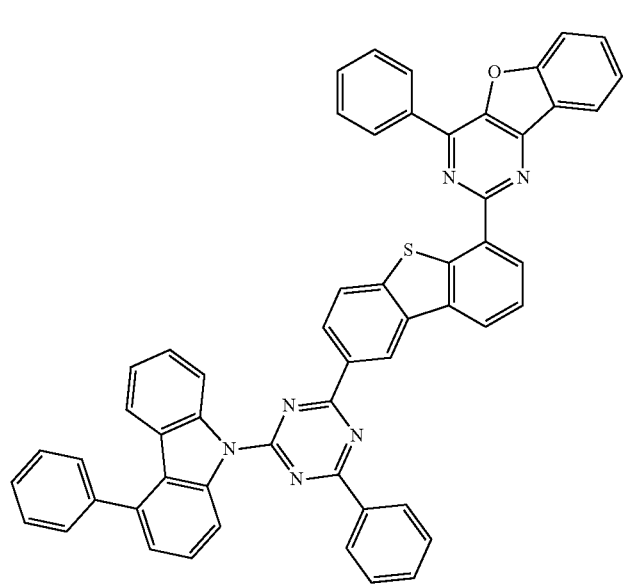
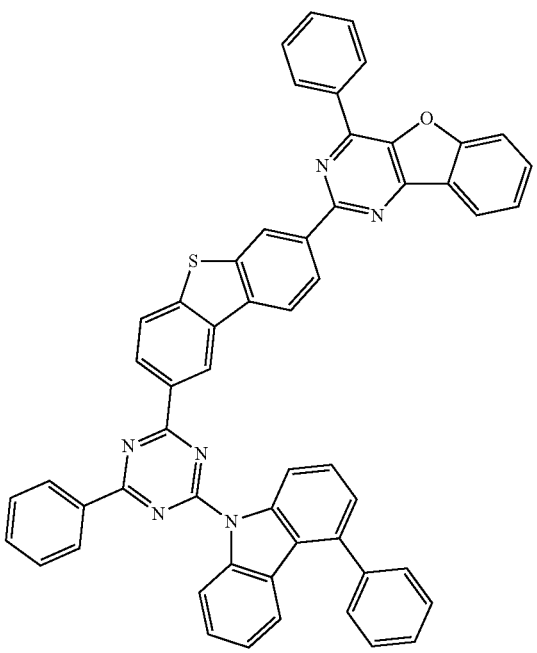

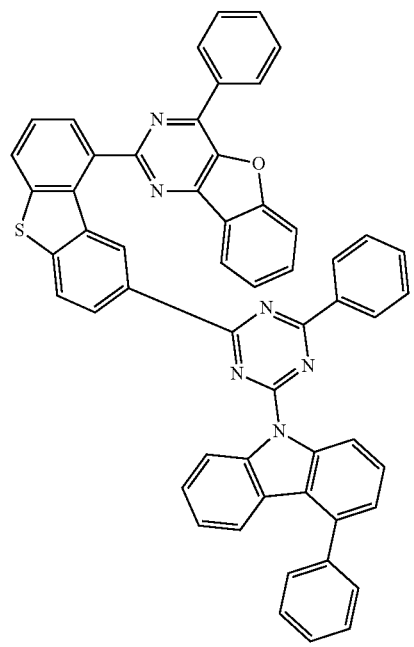
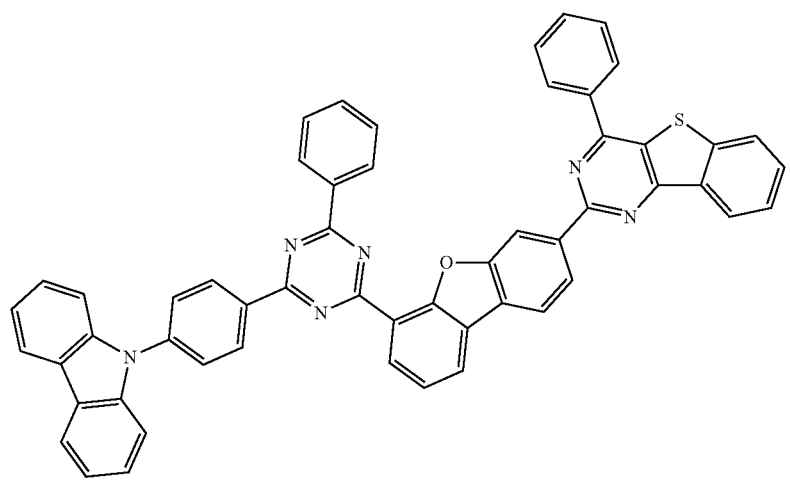
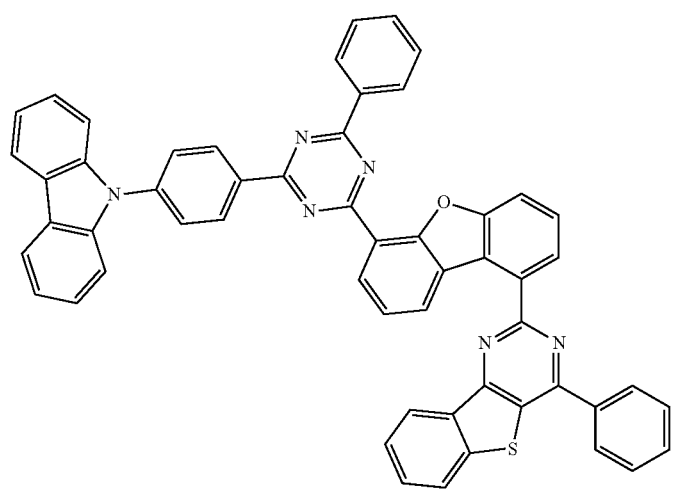

-continued
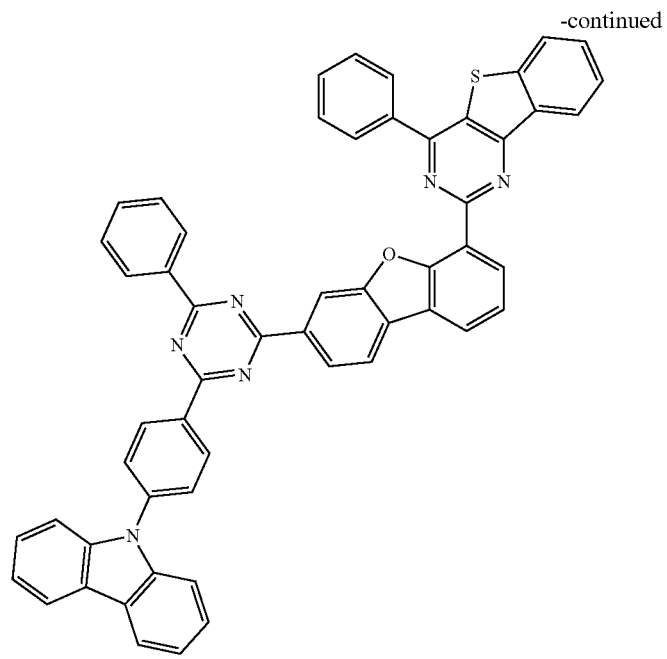
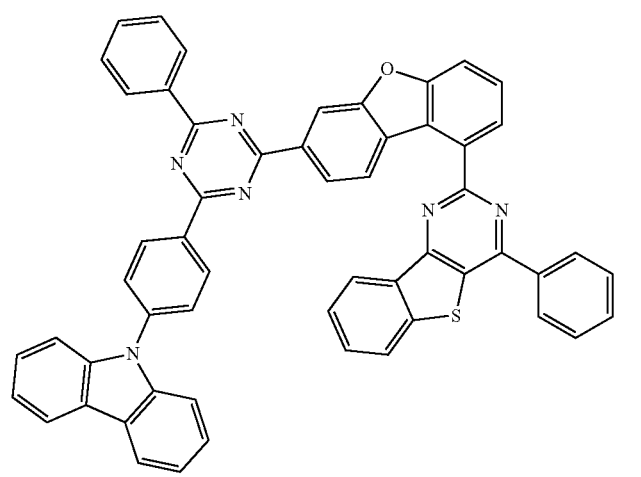
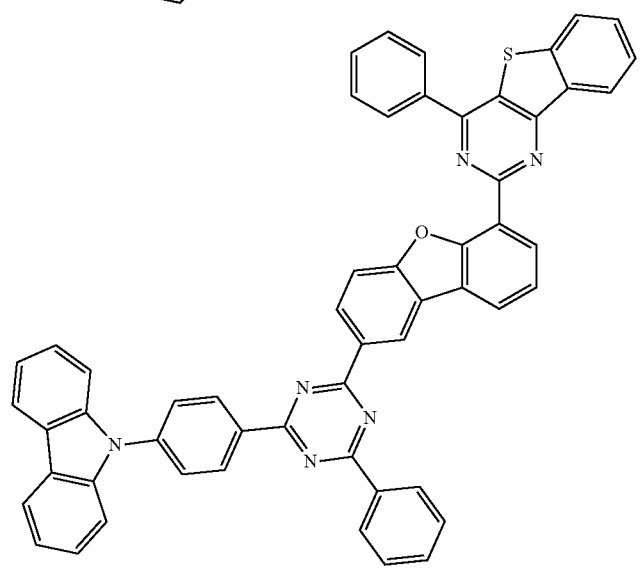

267
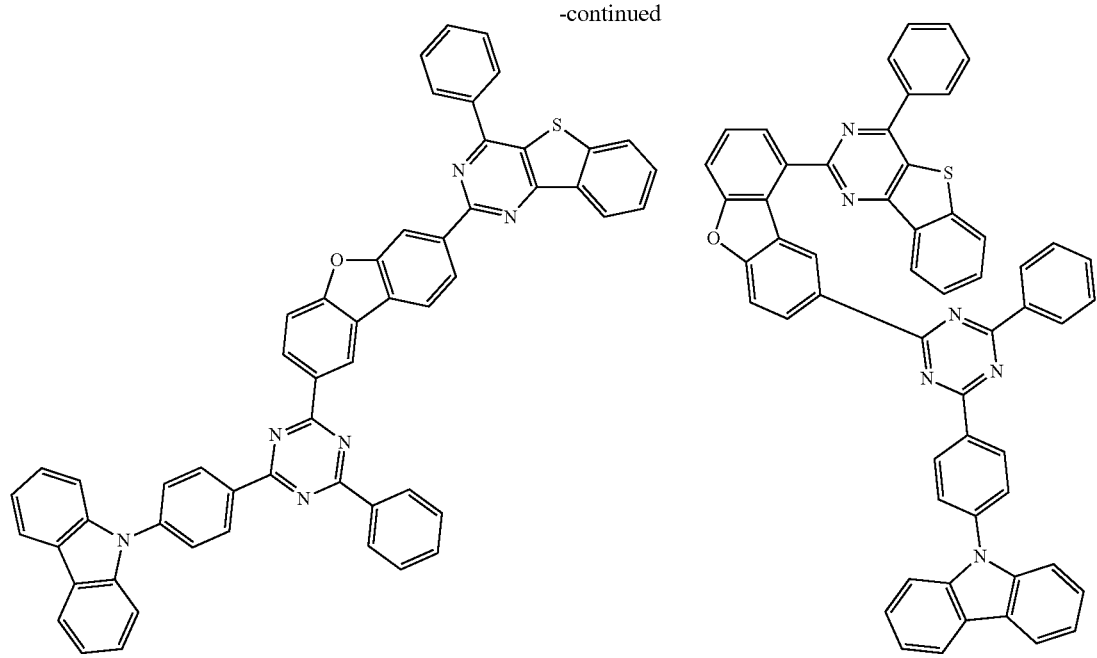
268
-continued
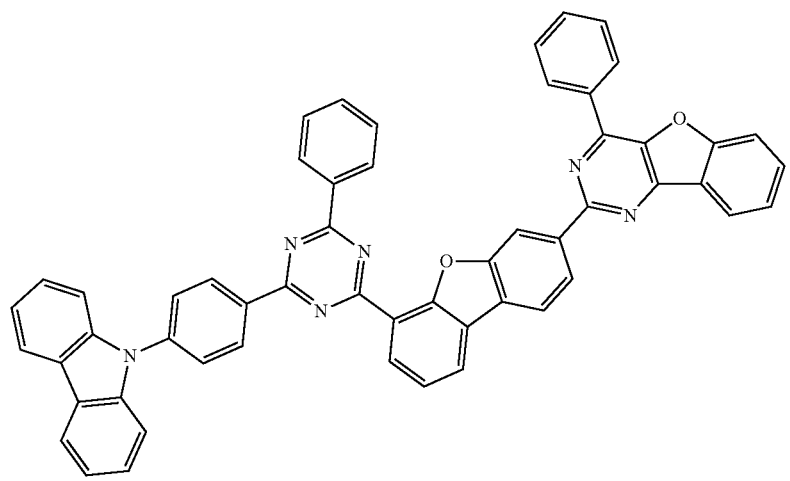
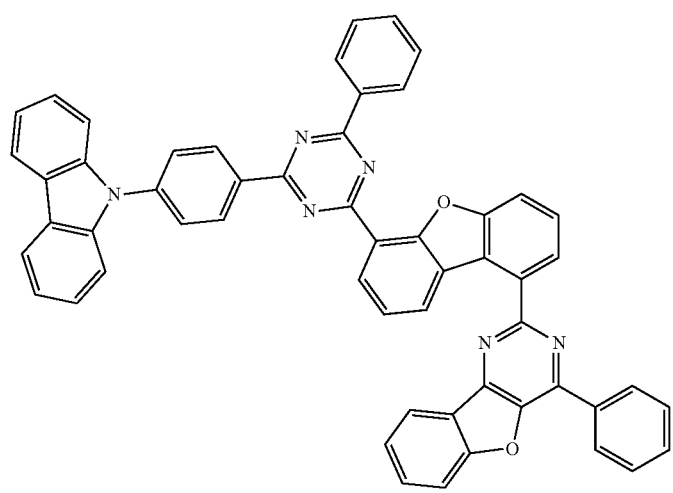

-continued
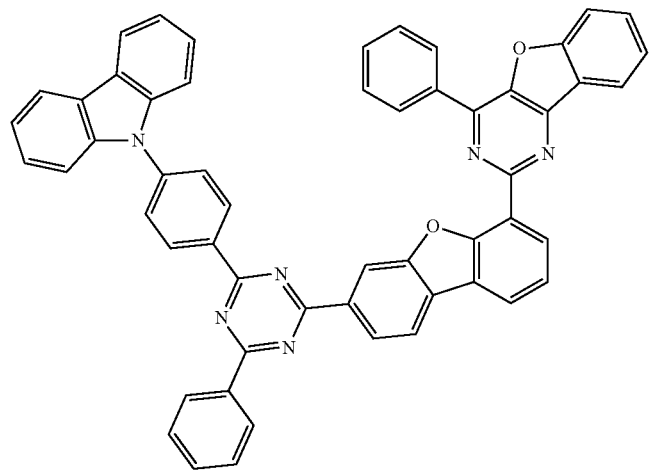
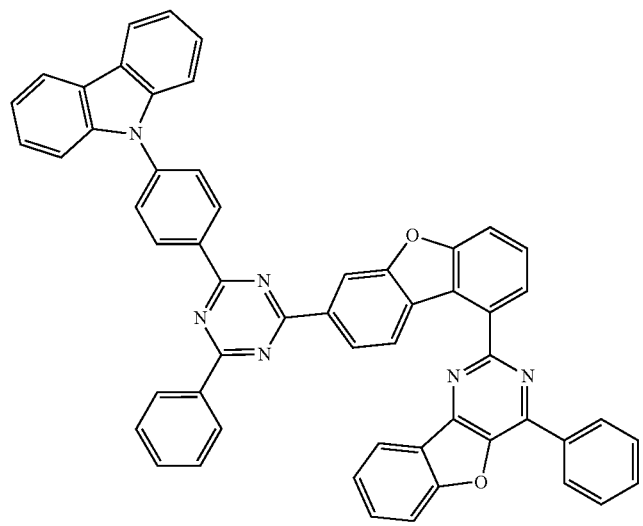
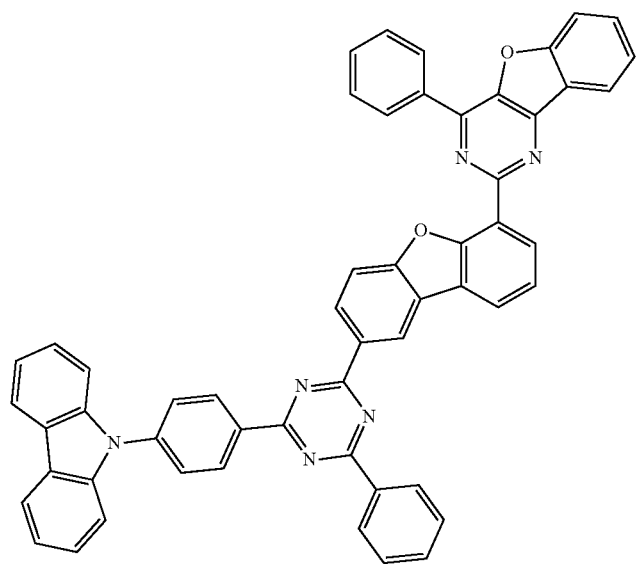

271 272
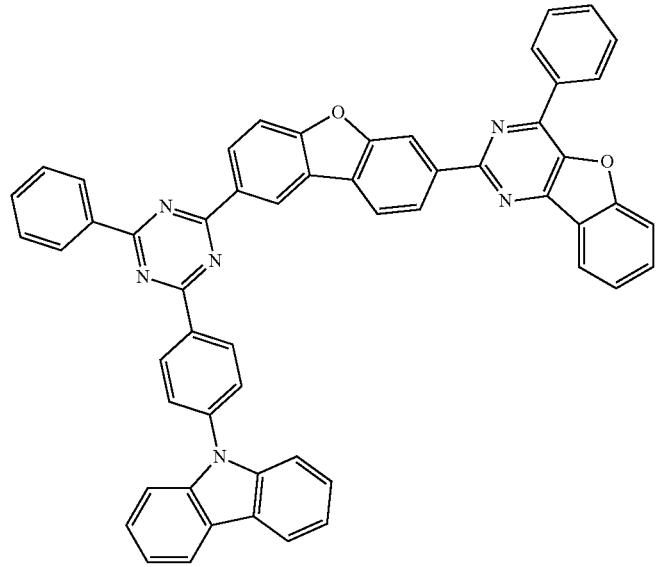
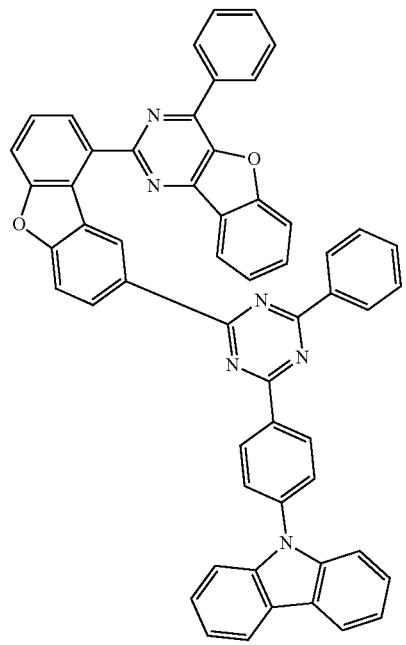
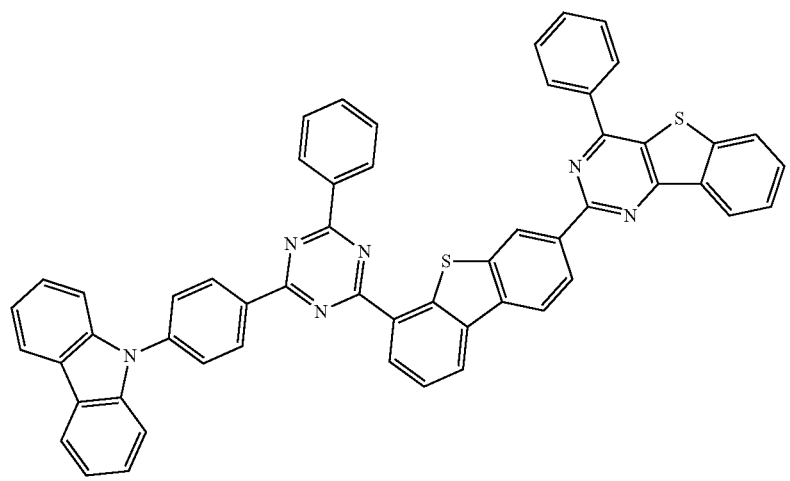
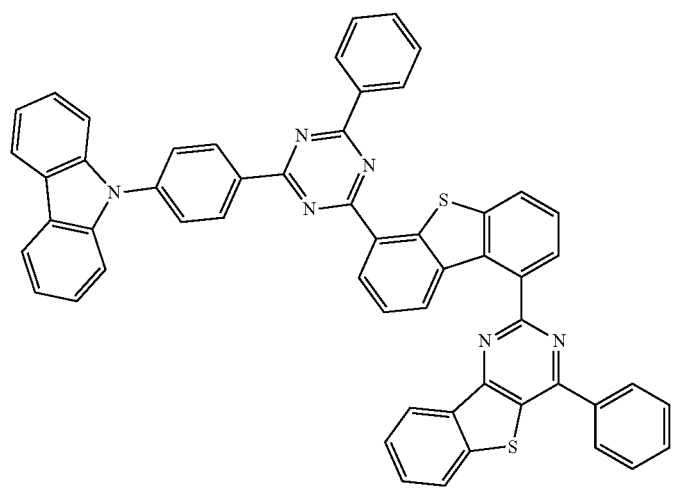

-continued
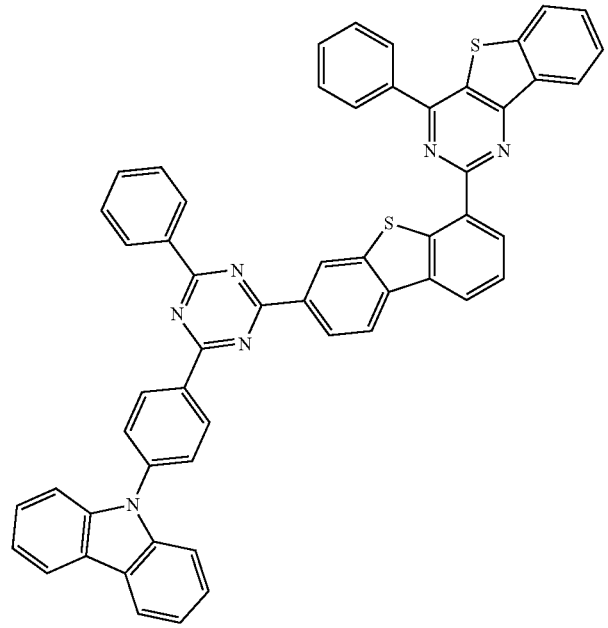
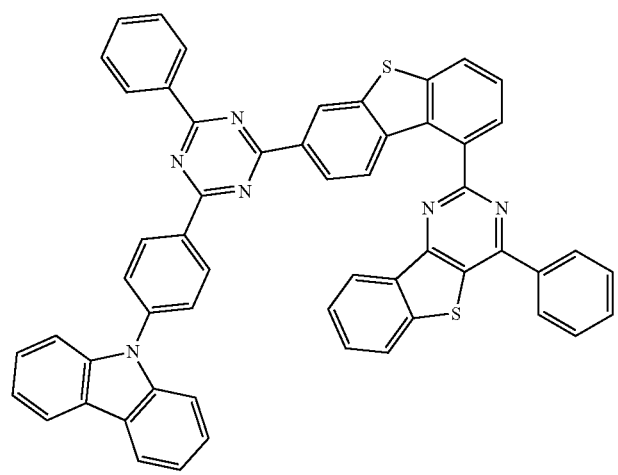
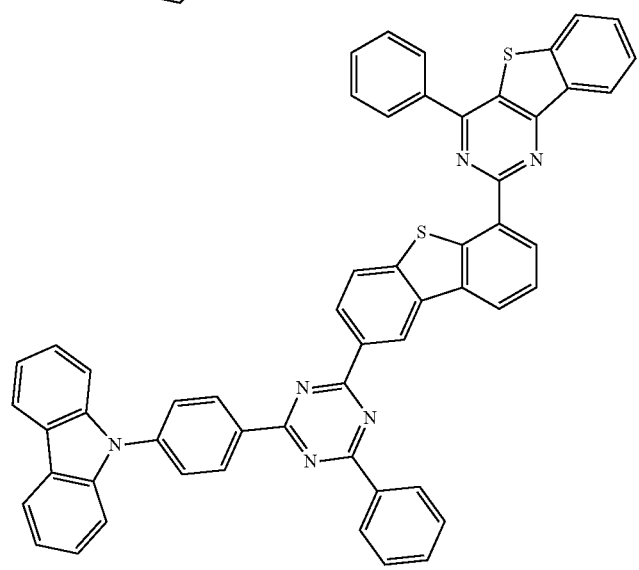

-continued
275
276
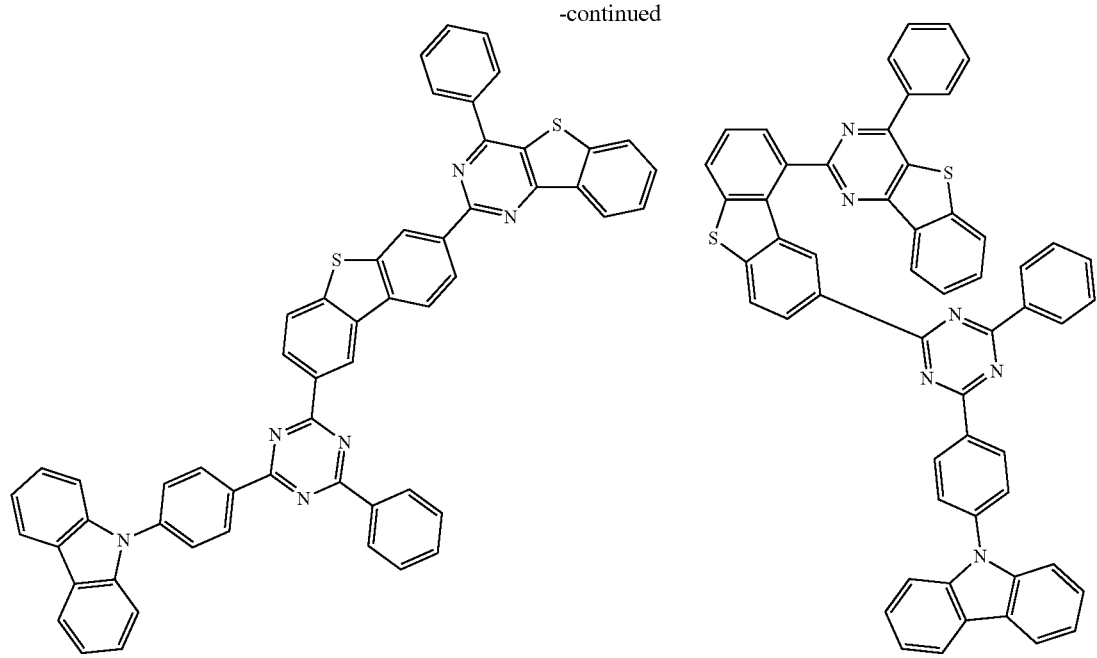
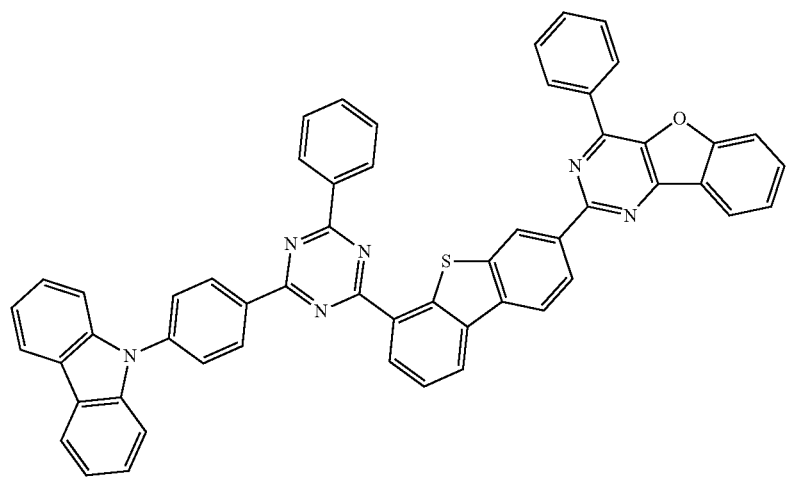
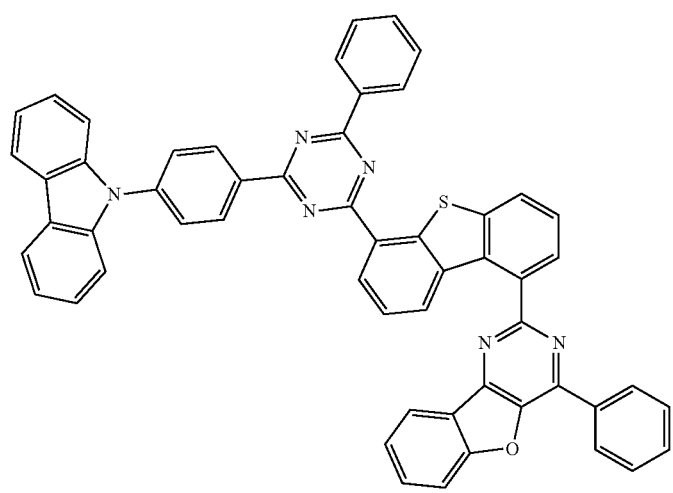

-continued
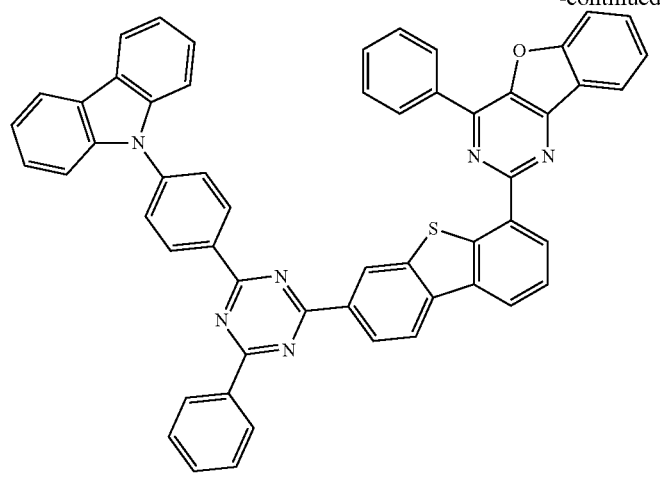
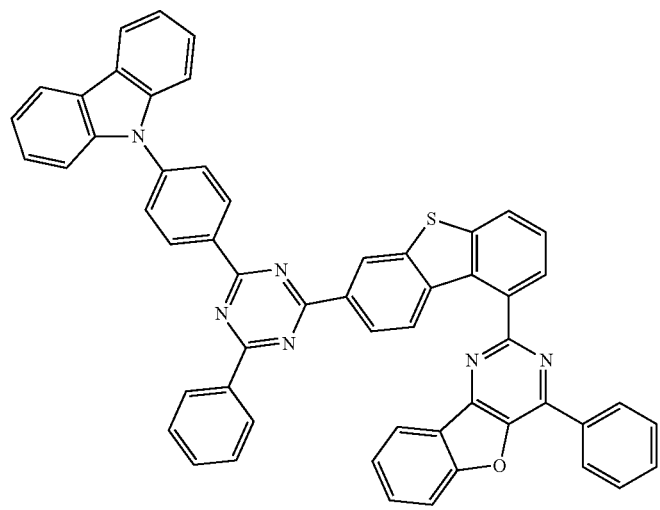
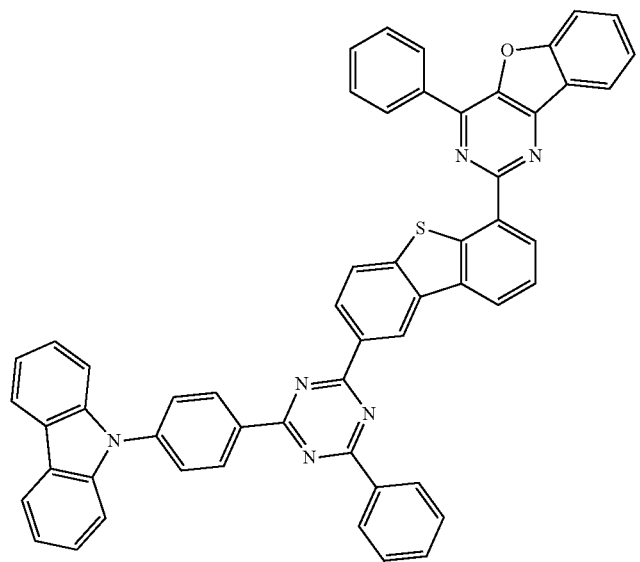

279
280
-continued
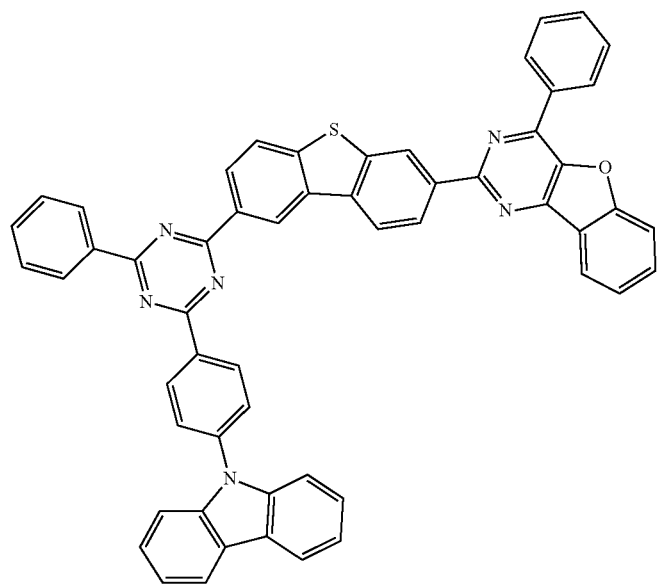
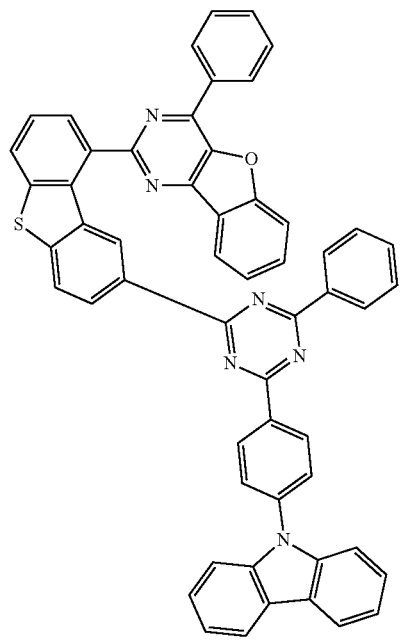
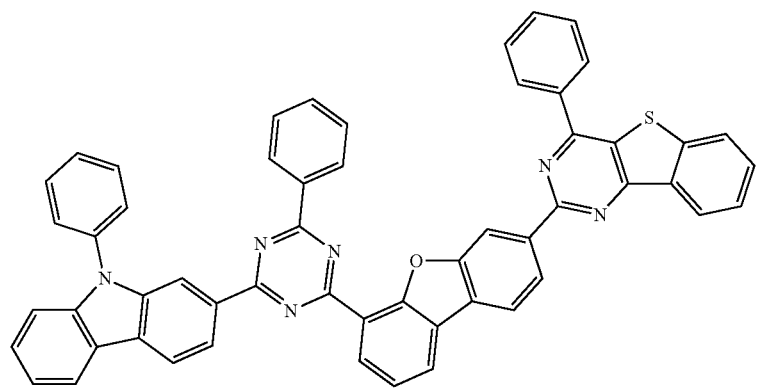
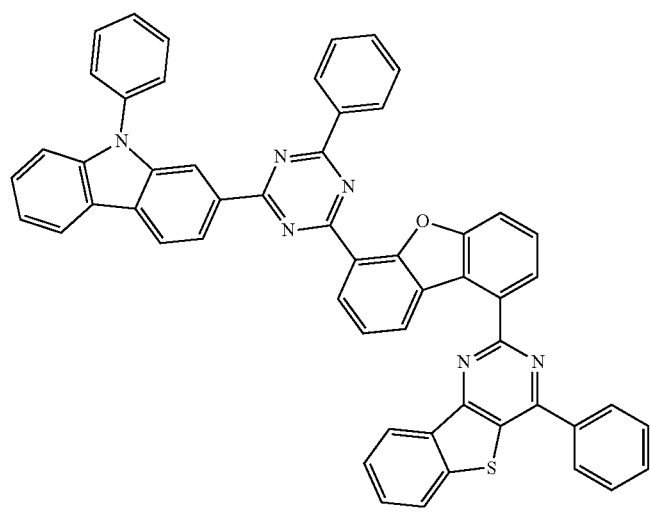

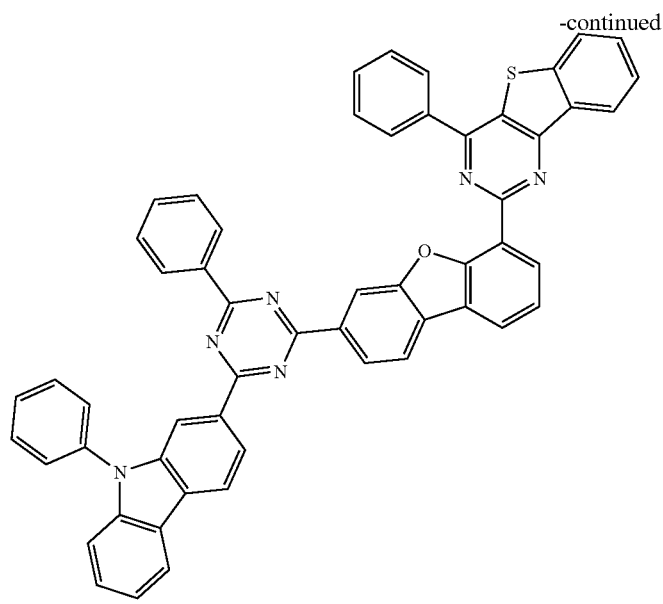
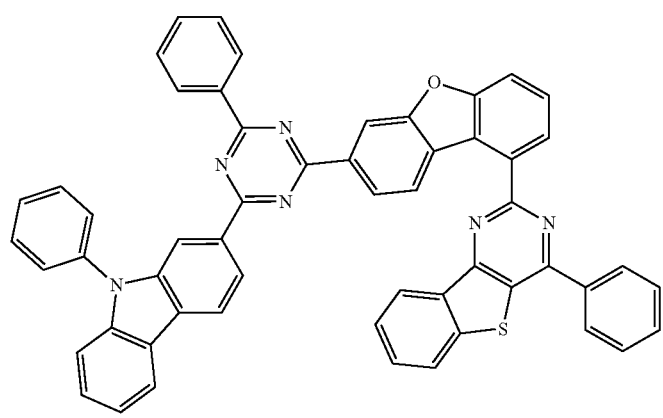
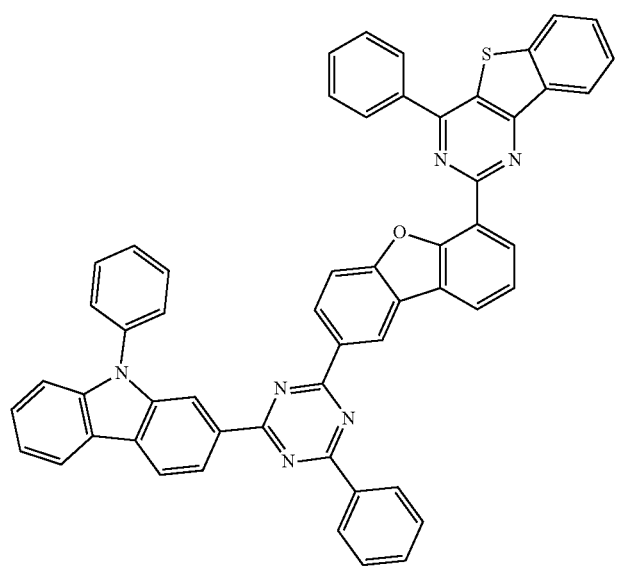

283 284
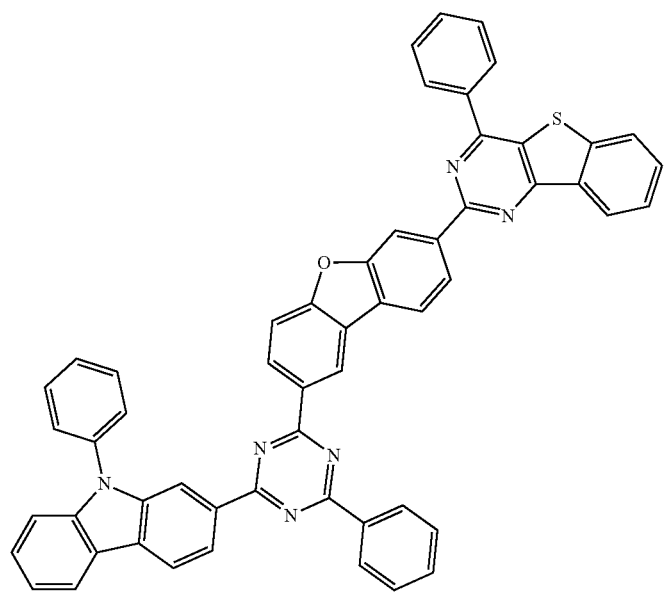 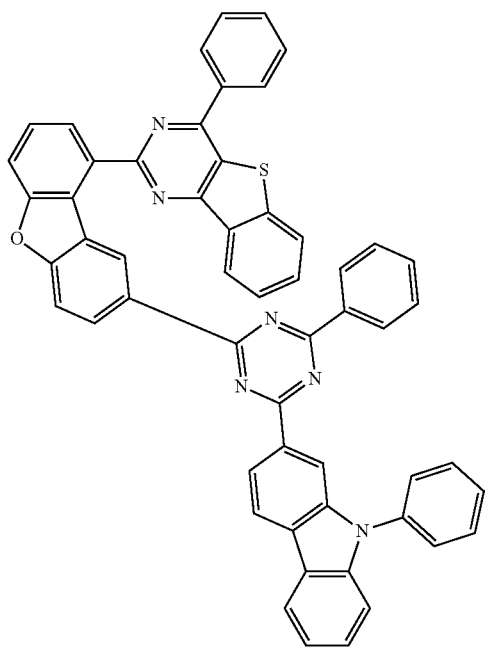
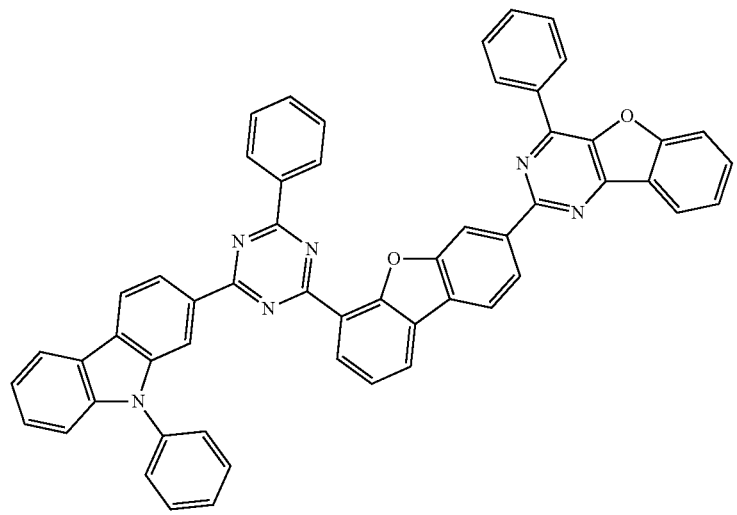
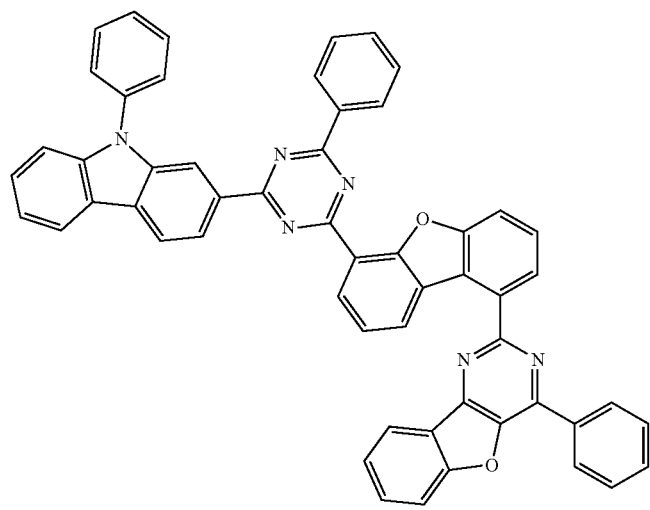

285
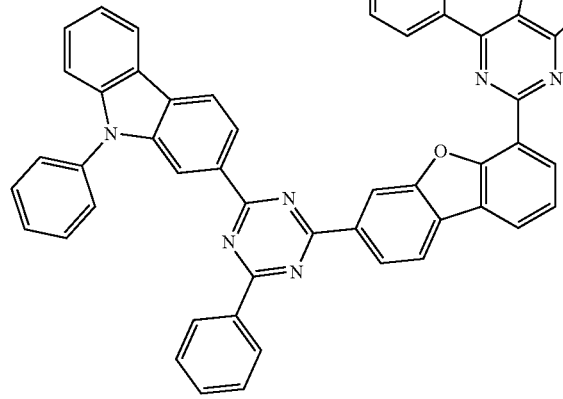
286
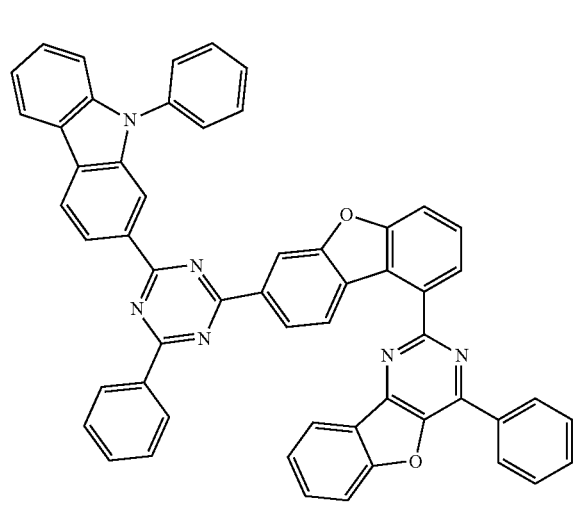
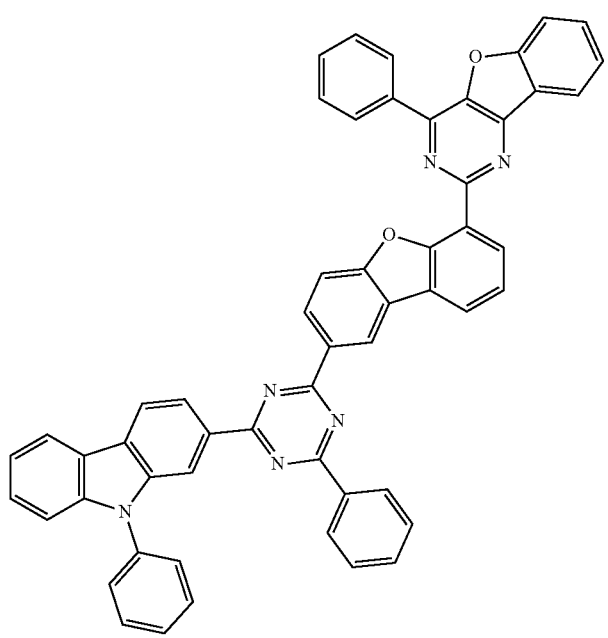

287
288
-continued
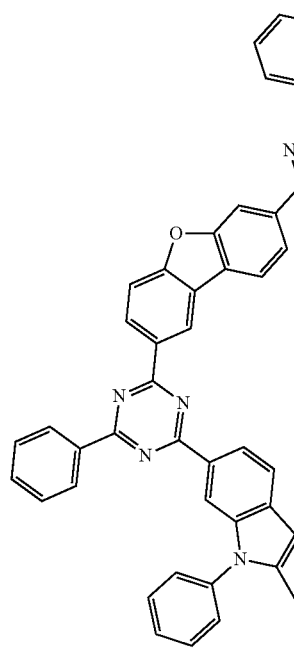
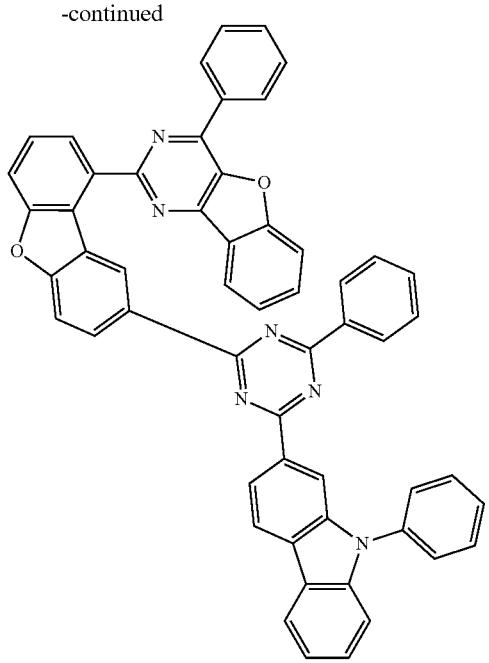
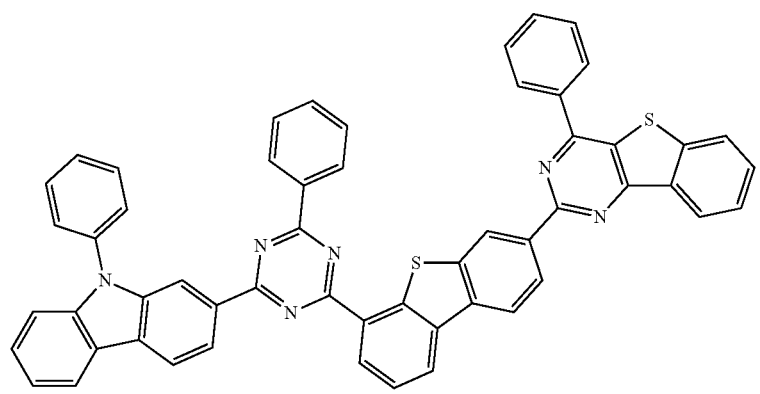
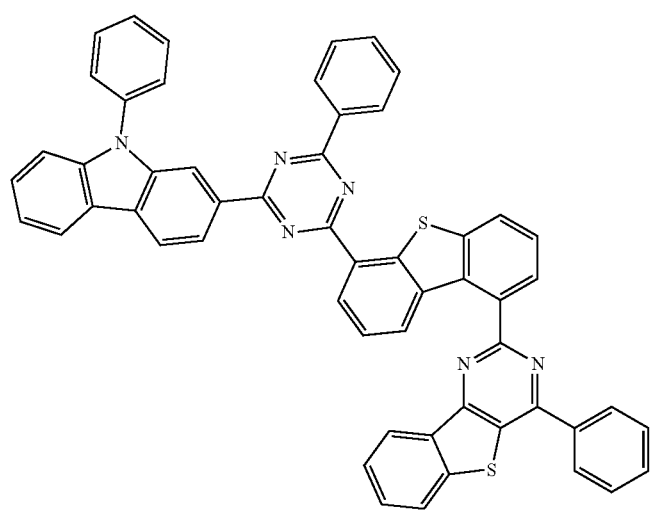

-continued
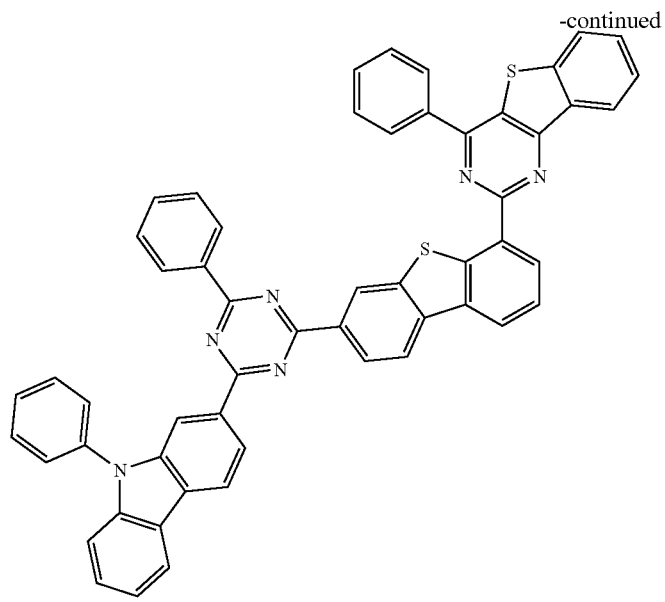
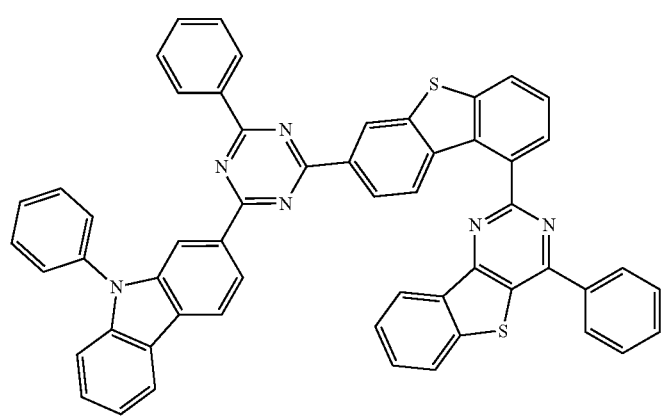
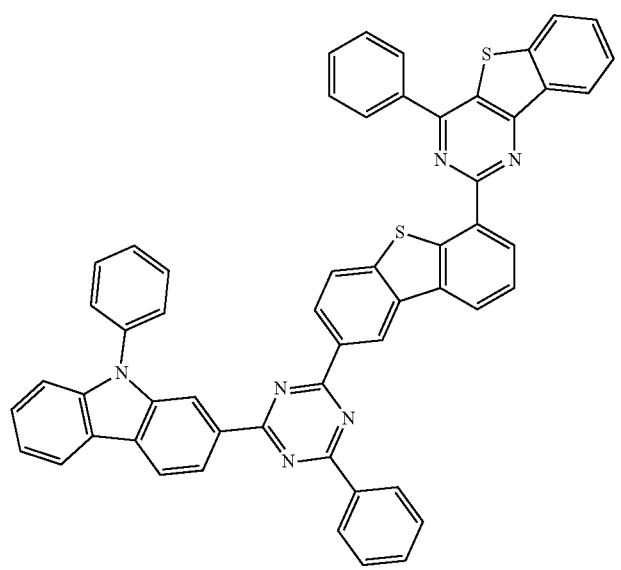

291 292
-continued
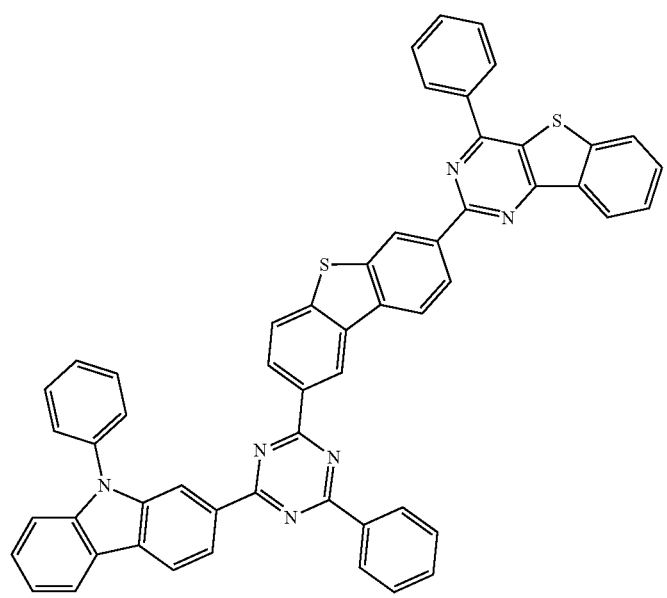
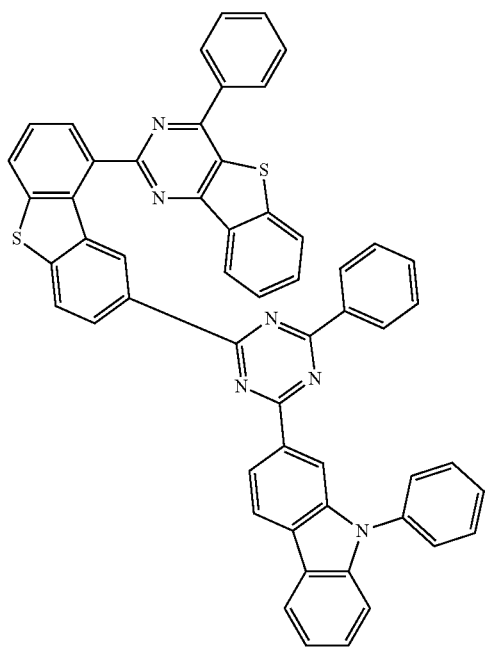
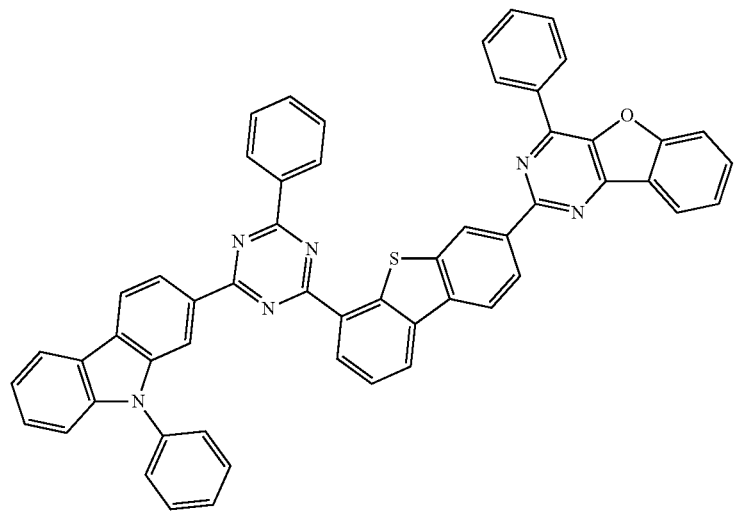
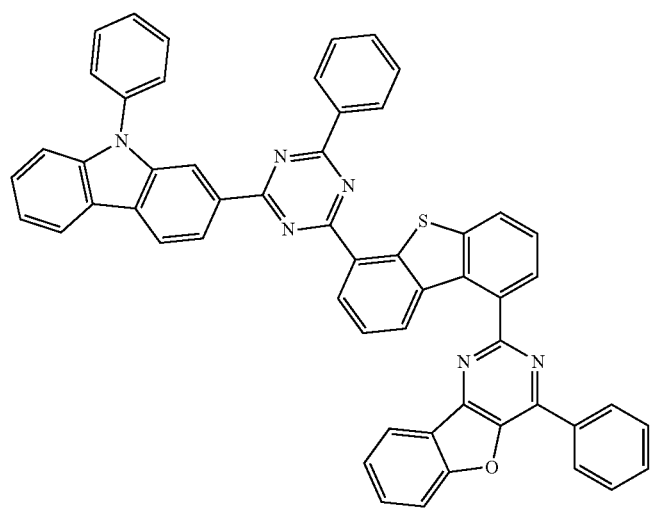

293
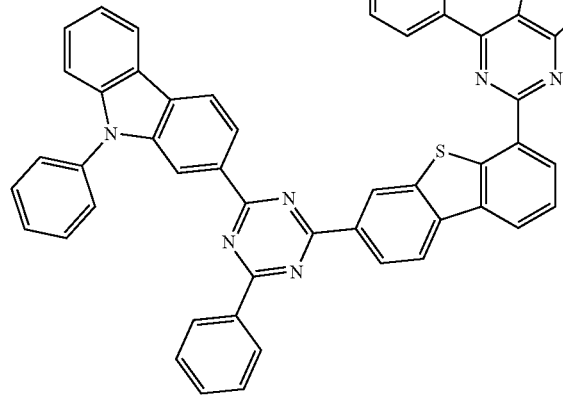
294
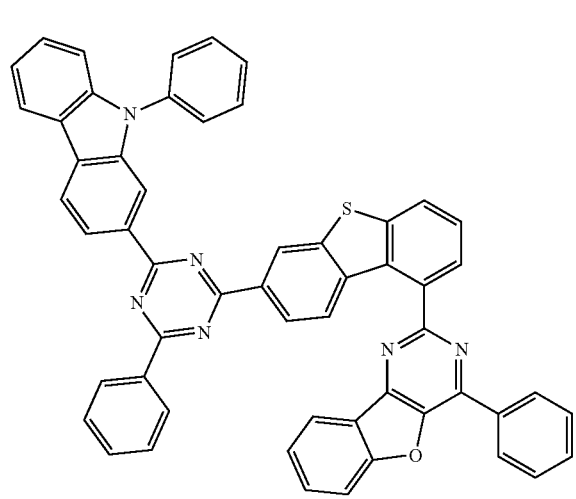
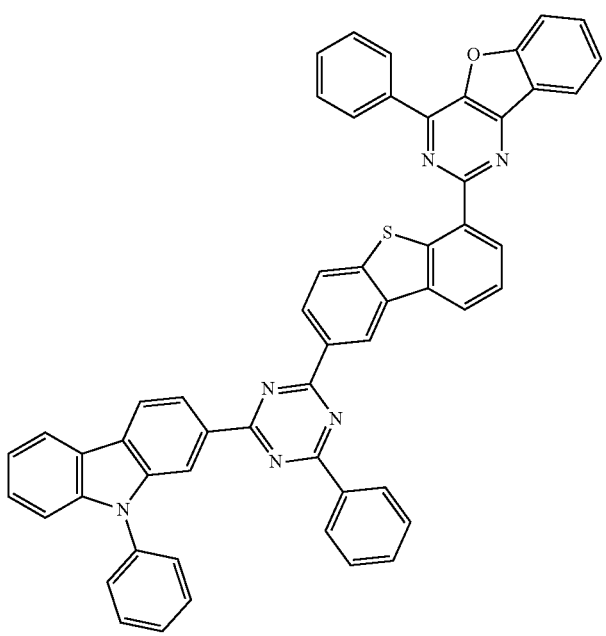

-continued
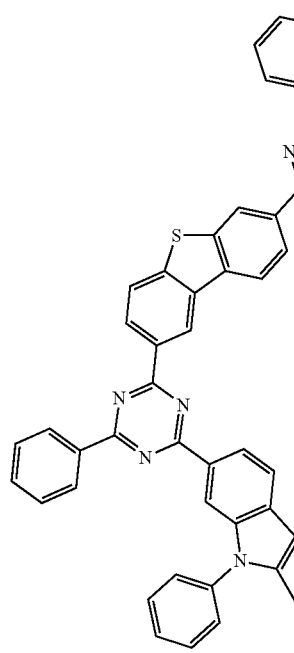
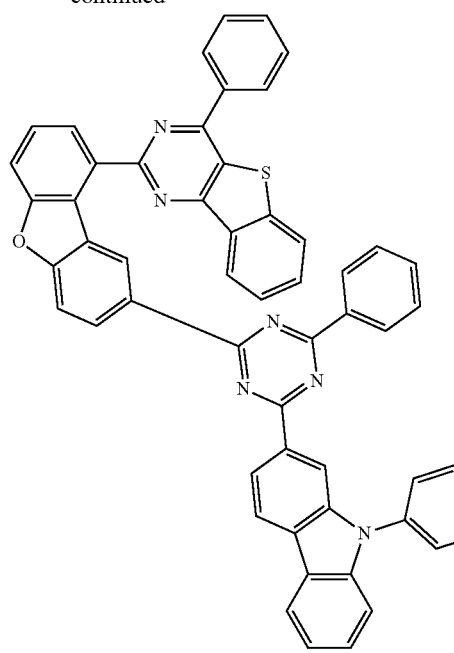
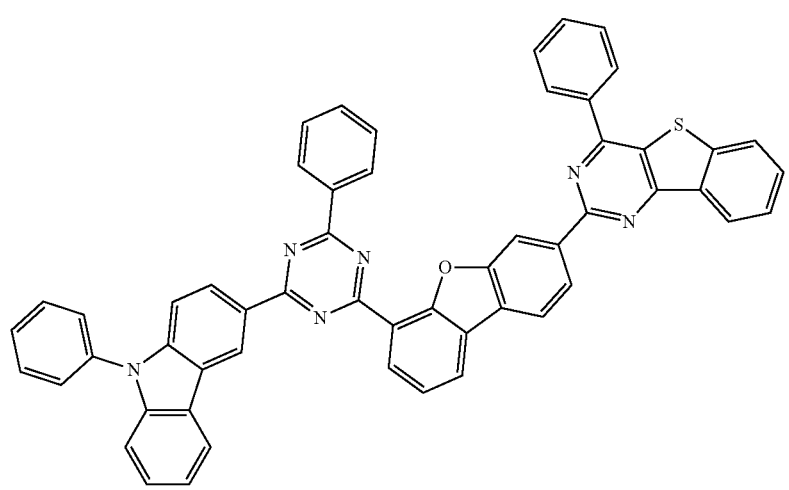
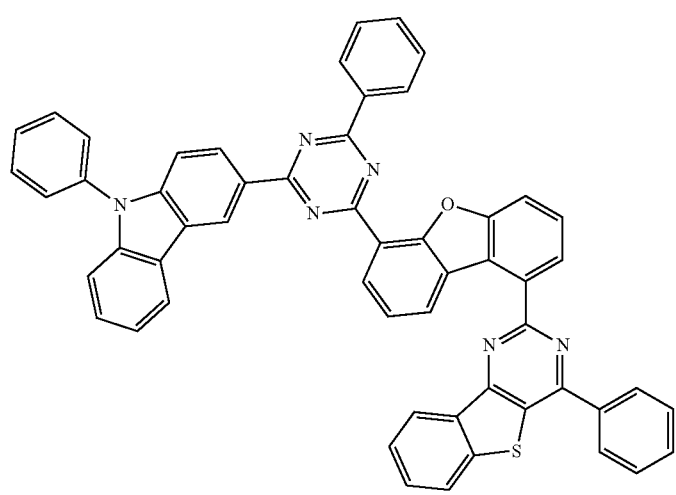

-continued
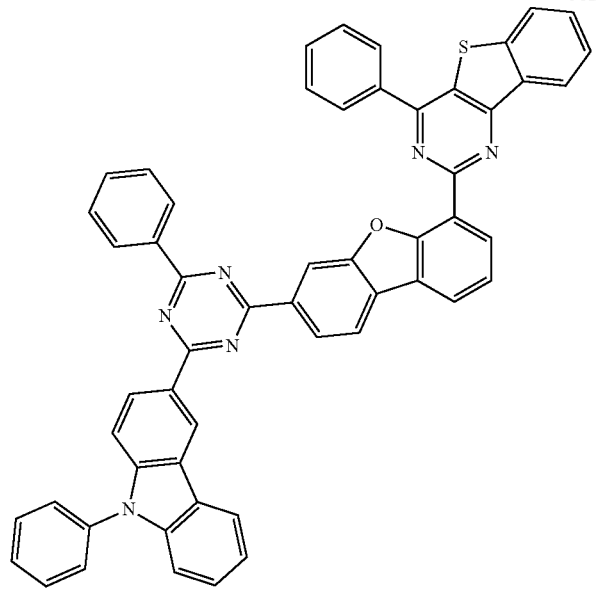
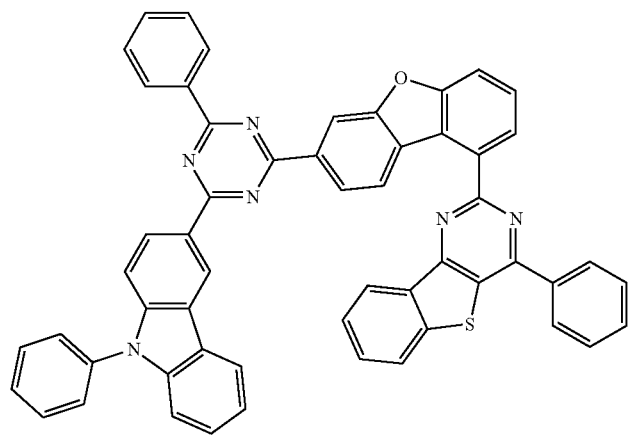
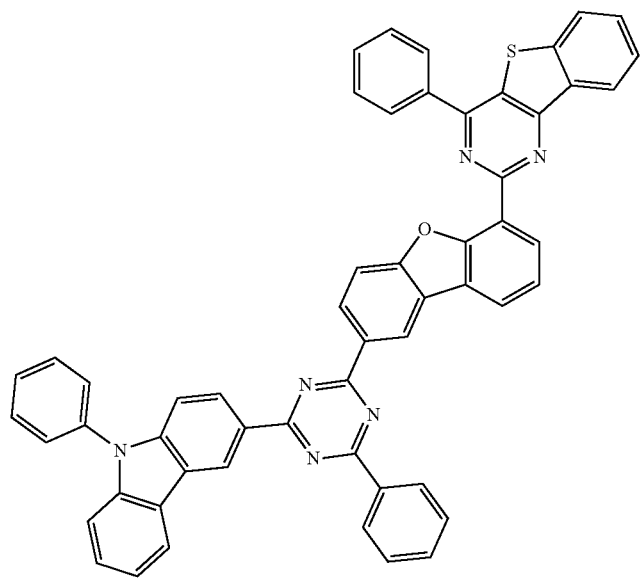

299
300
-continued
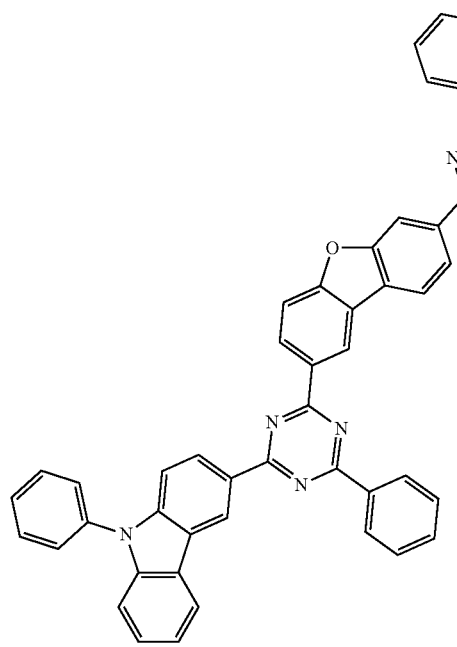
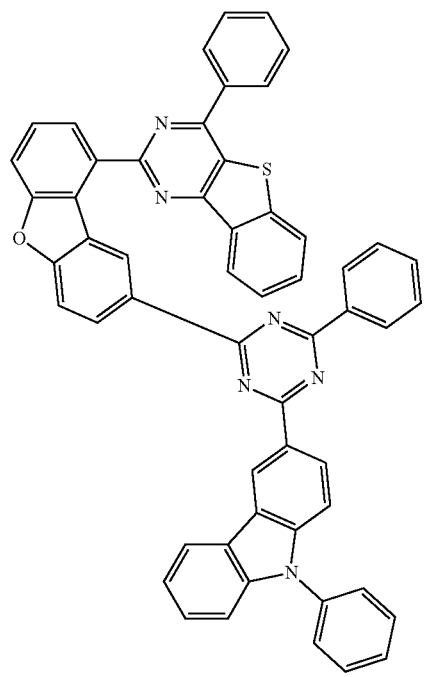
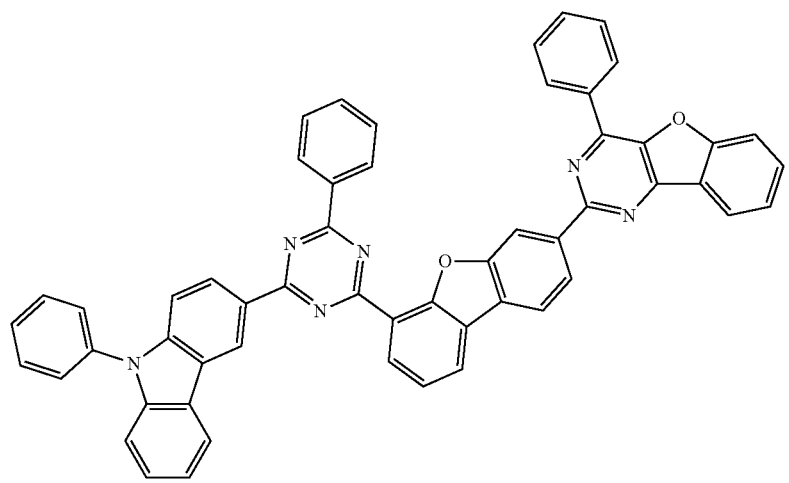
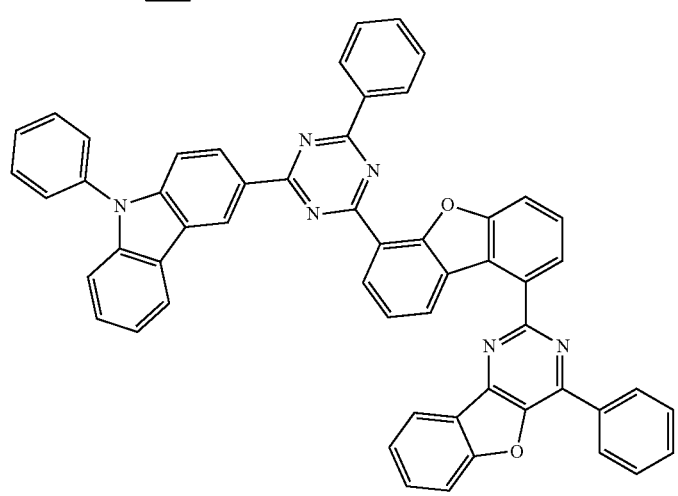

-continued
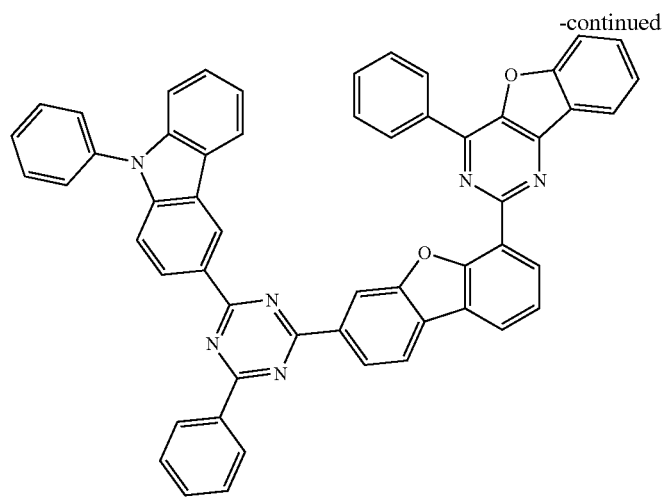
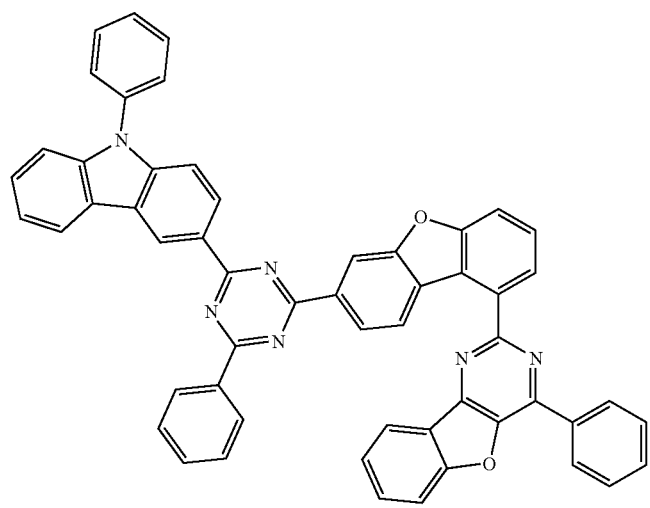
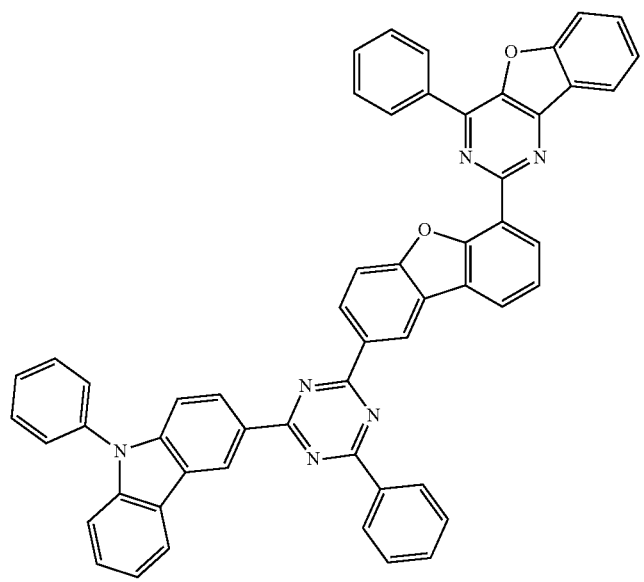

303
304
-continued
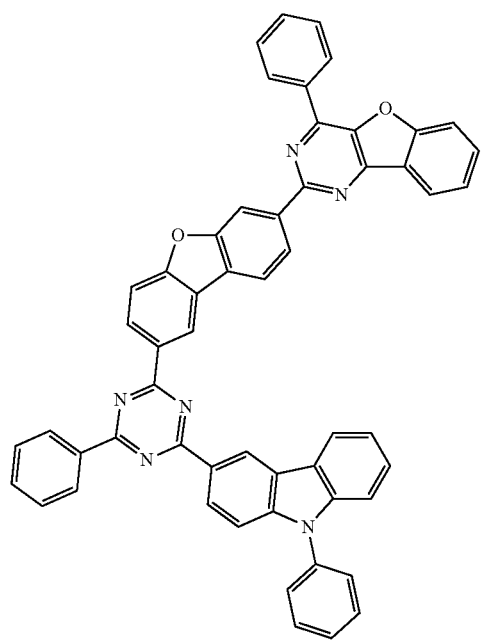
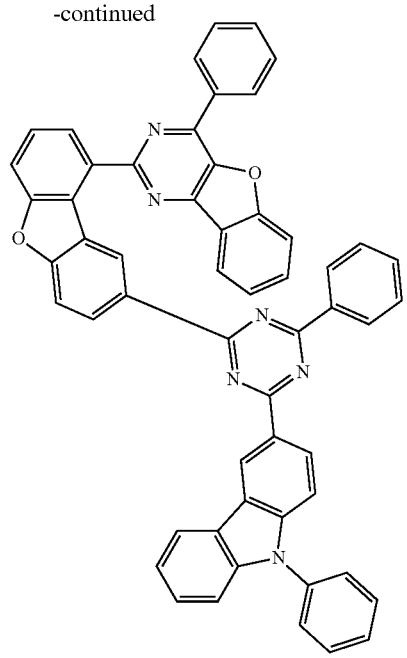
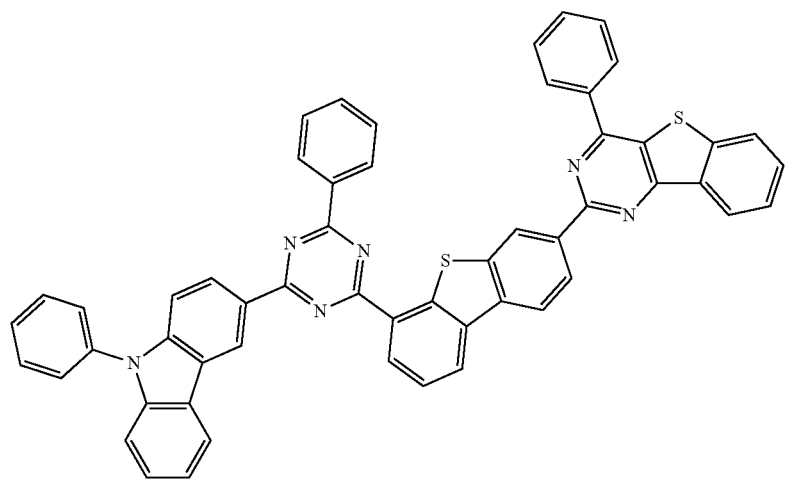
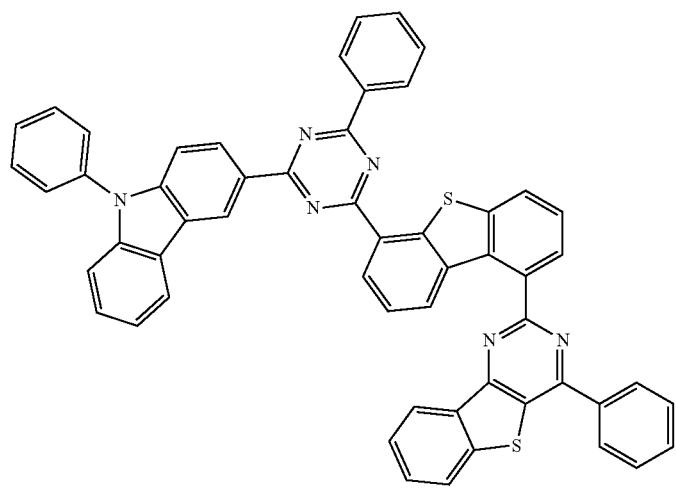

-continued
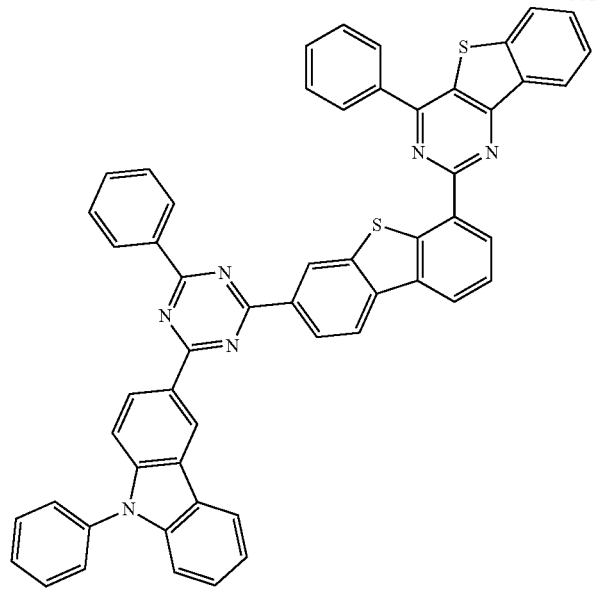
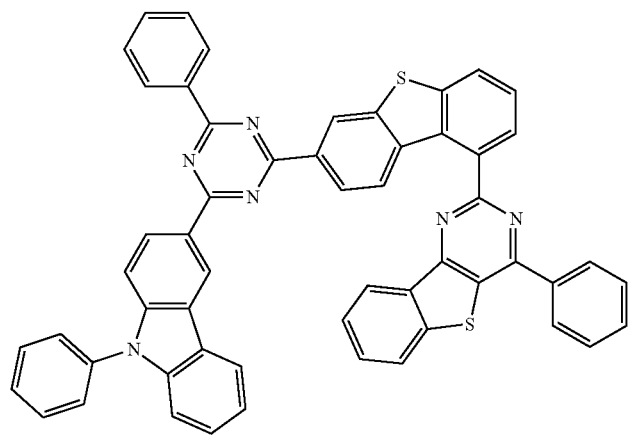
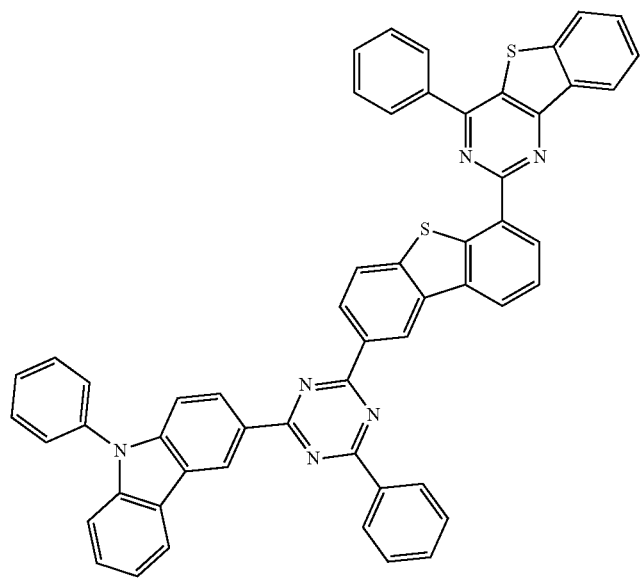

307 308
-continued
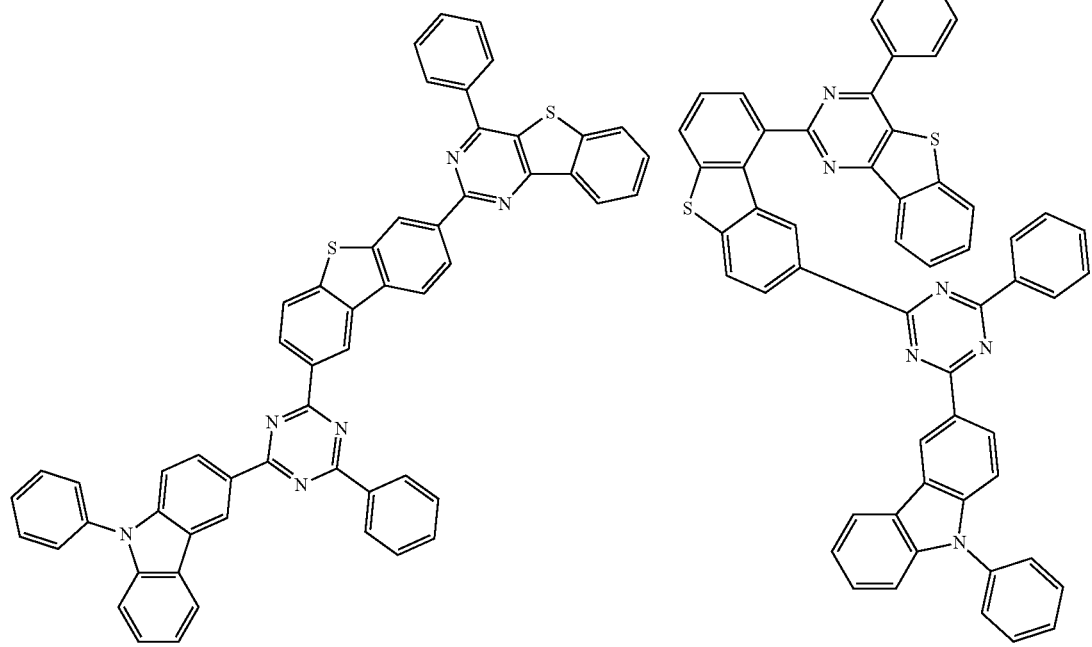
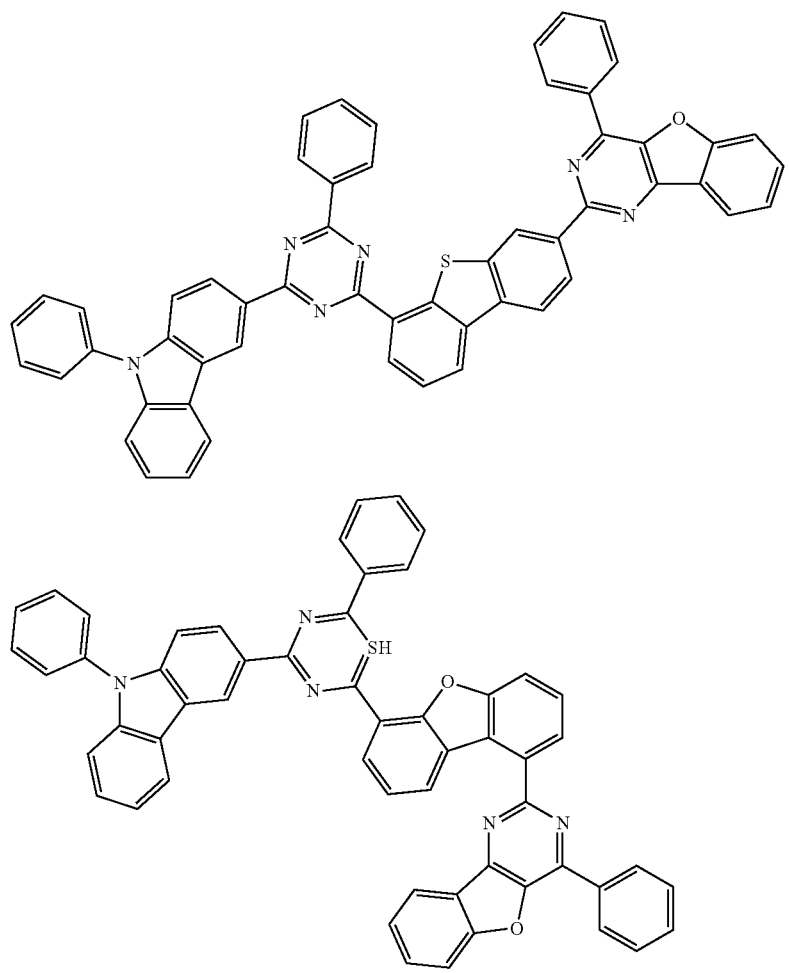

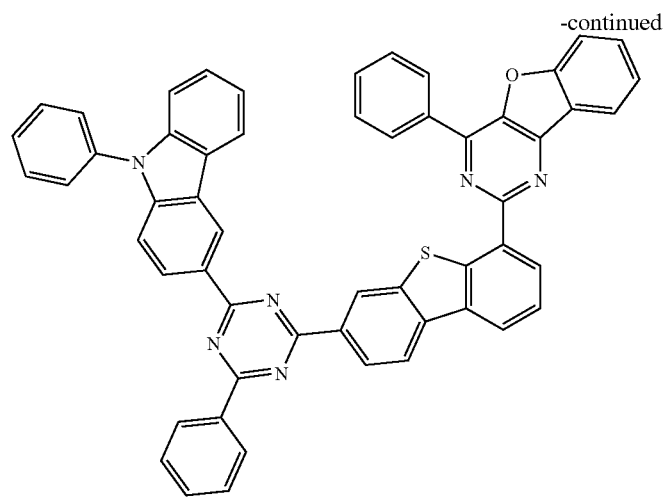
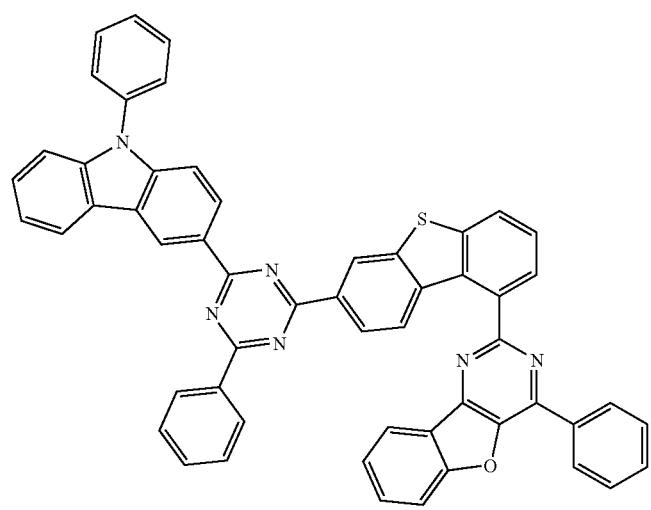
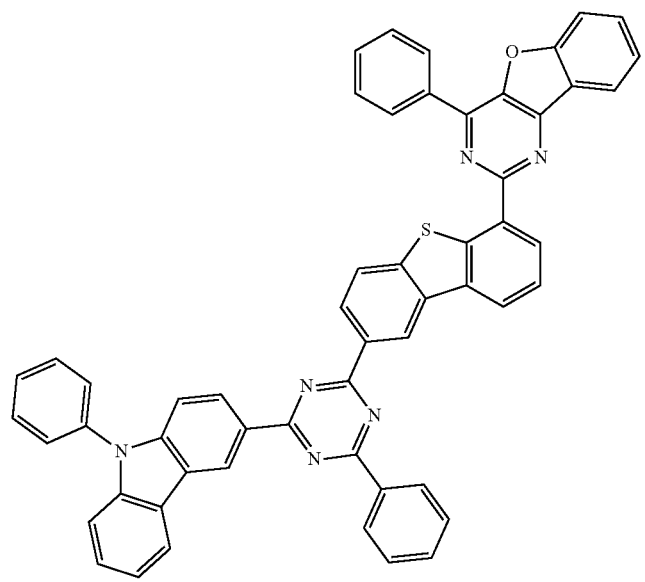

-continued
311
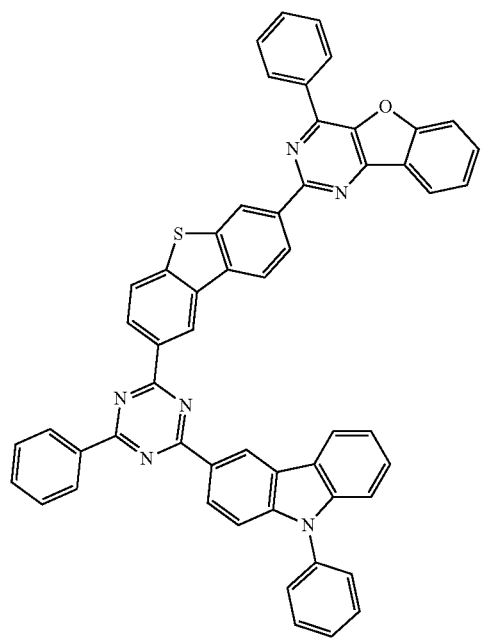
312
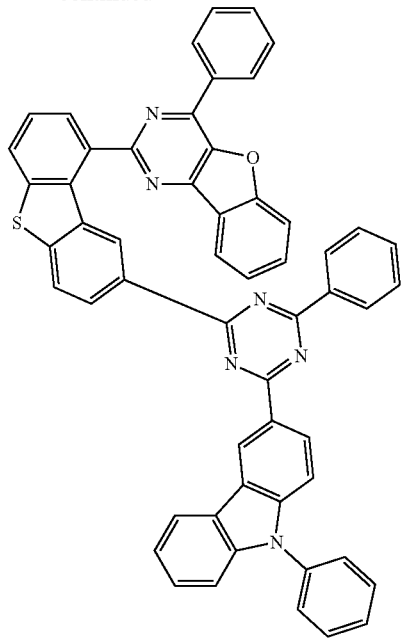
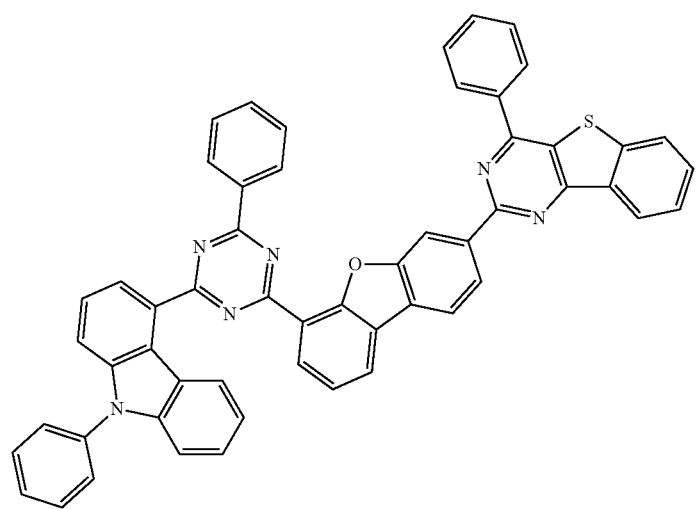

313
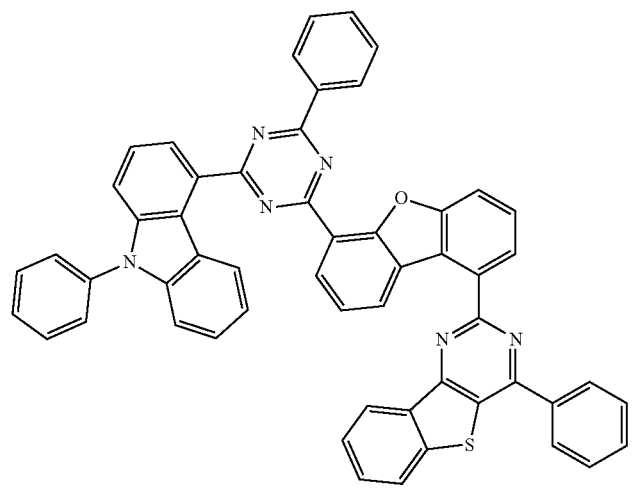
314
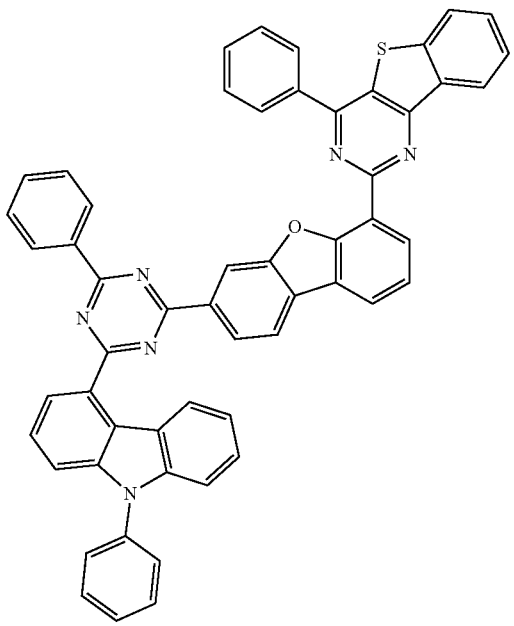
-continued
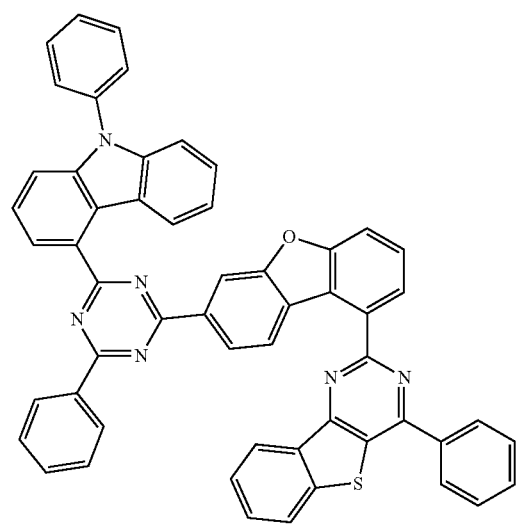
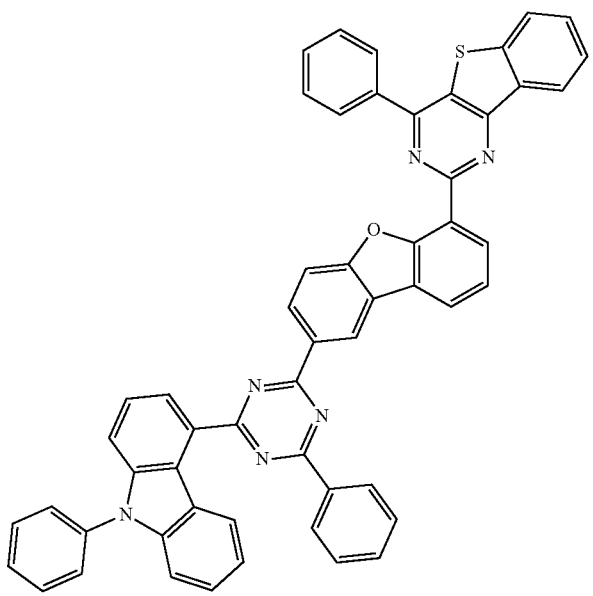

315 316
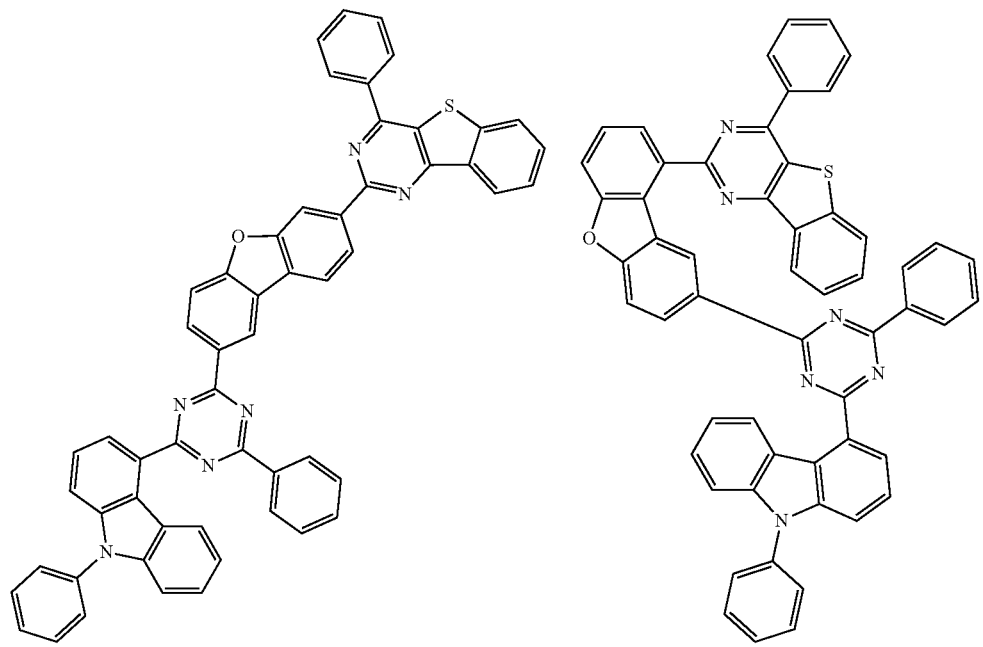
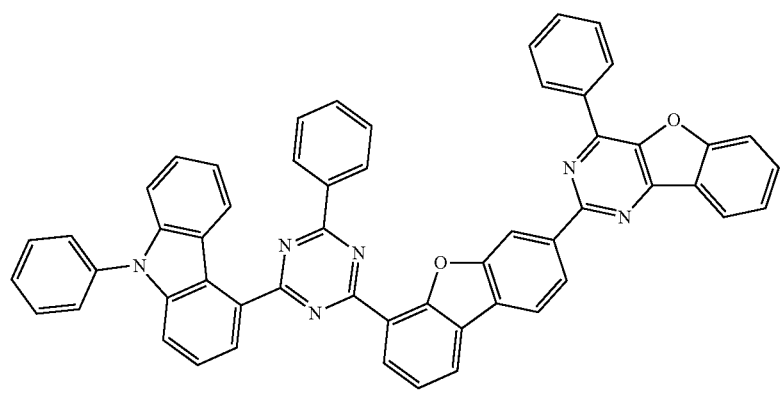
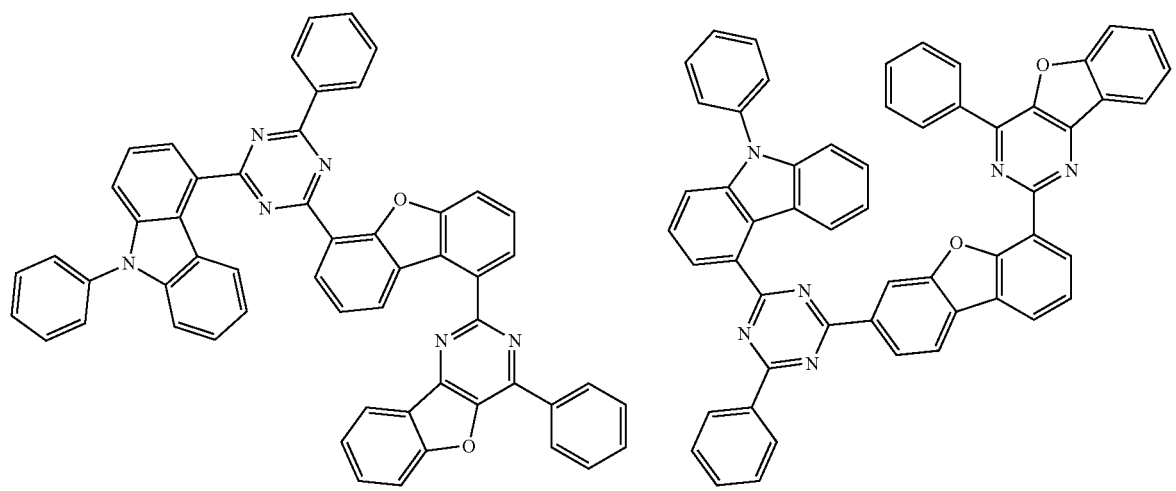

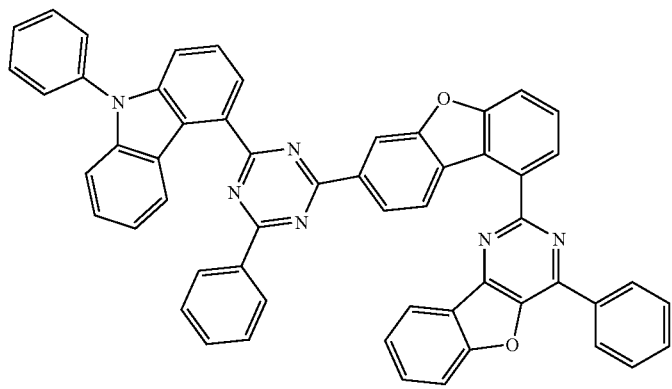
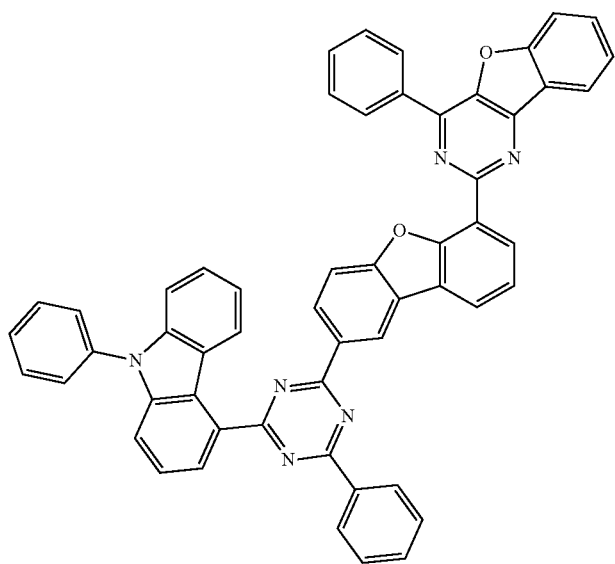
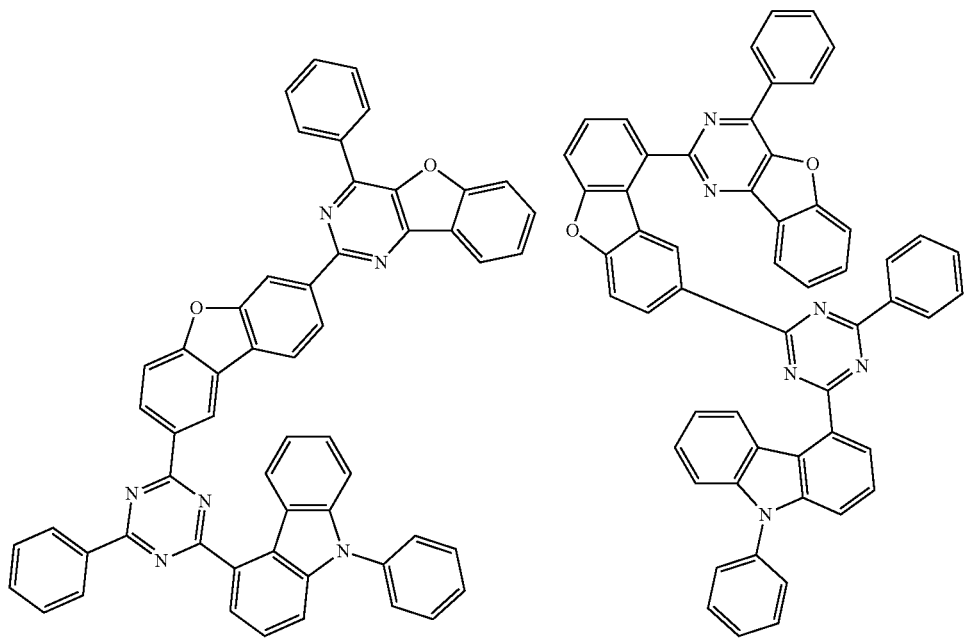

-continued
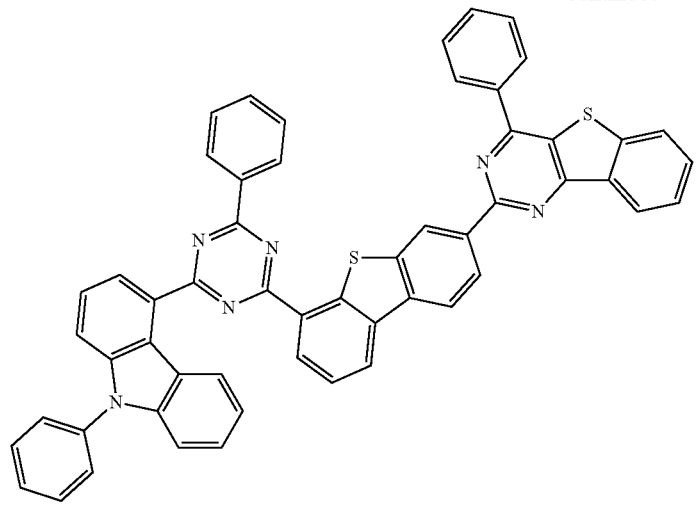
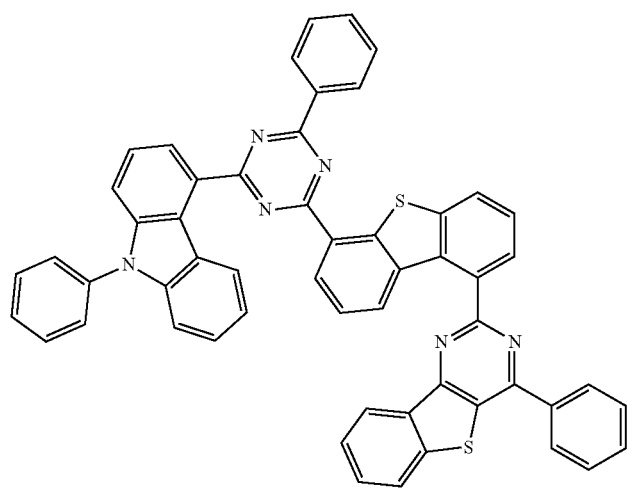
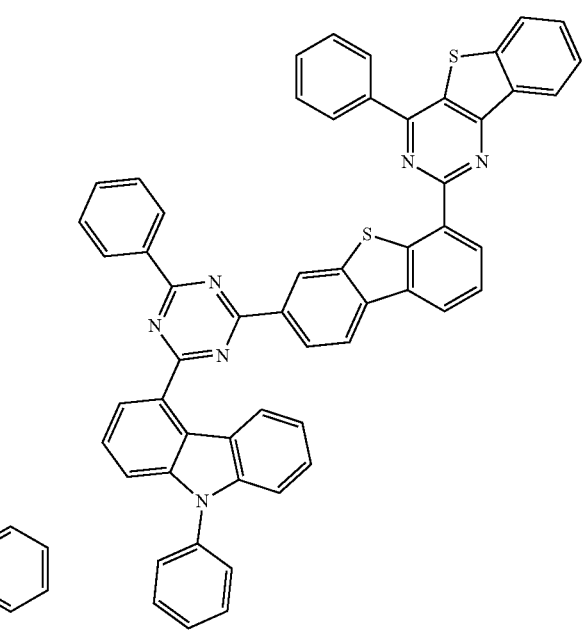
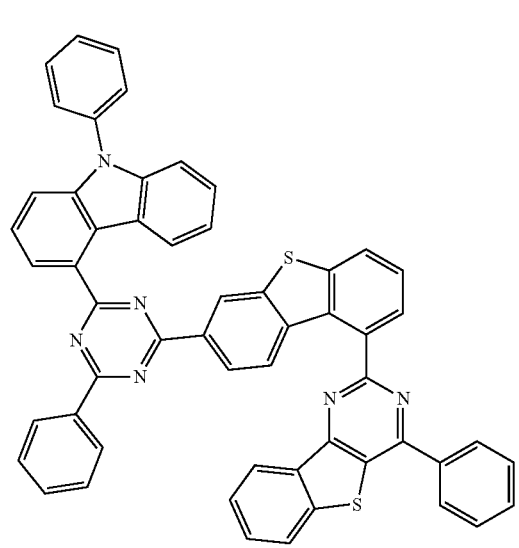
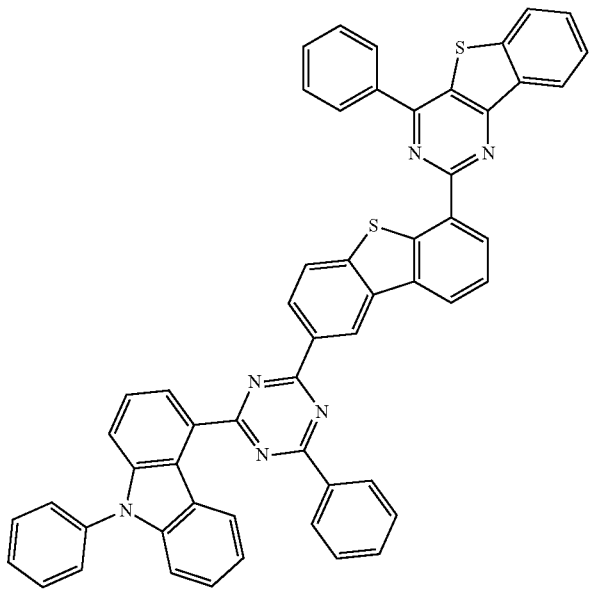

321 322
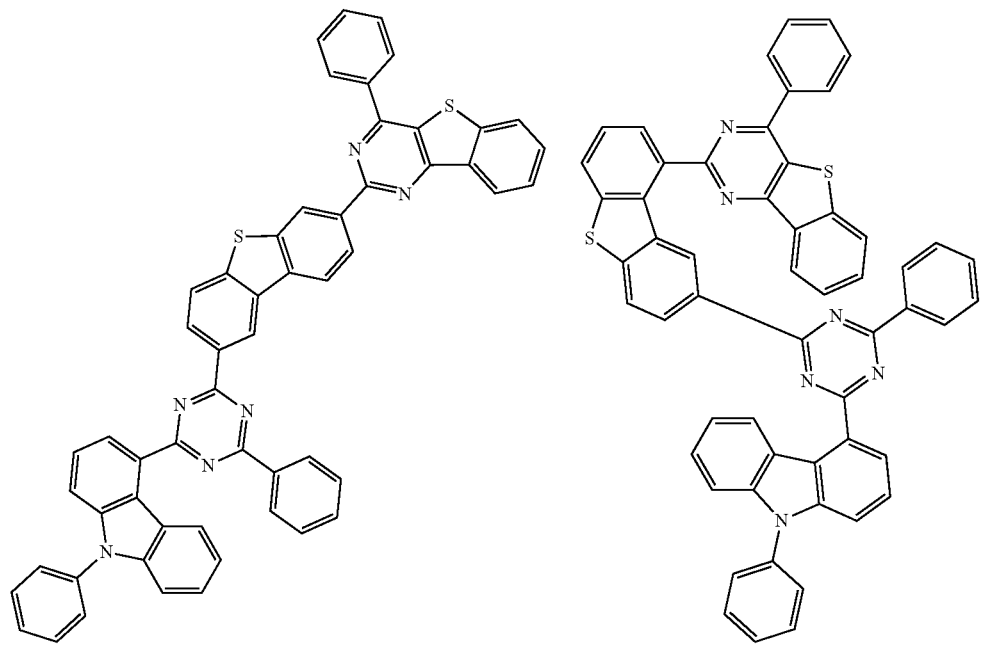
-continued
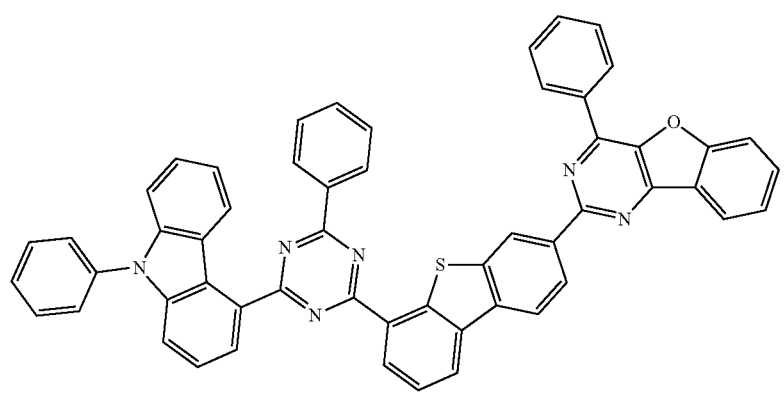
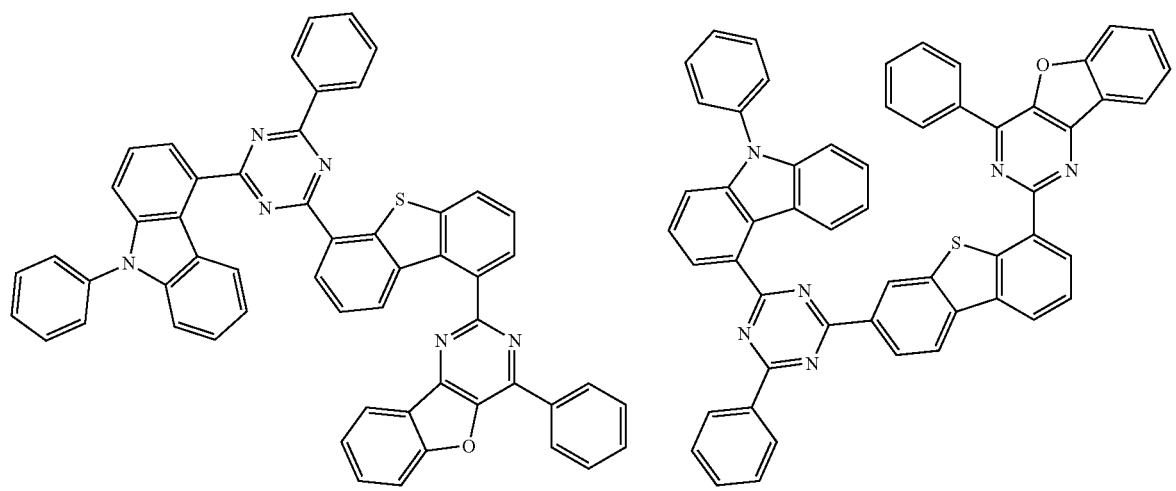

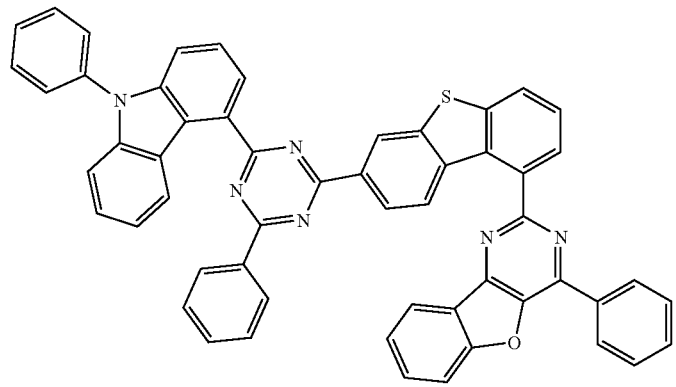
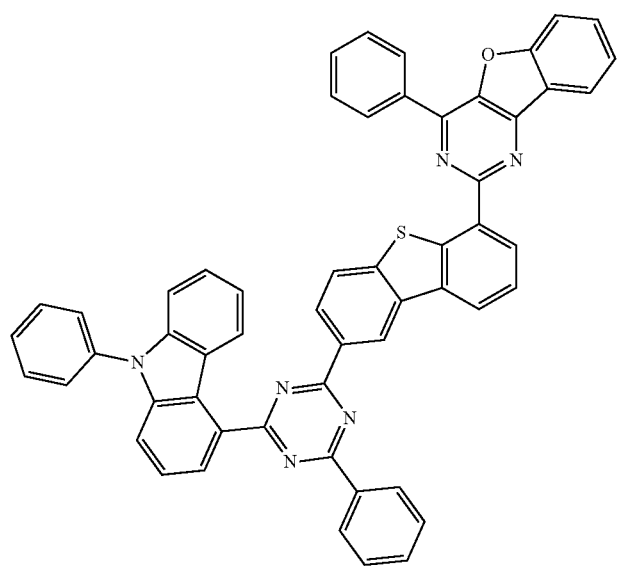
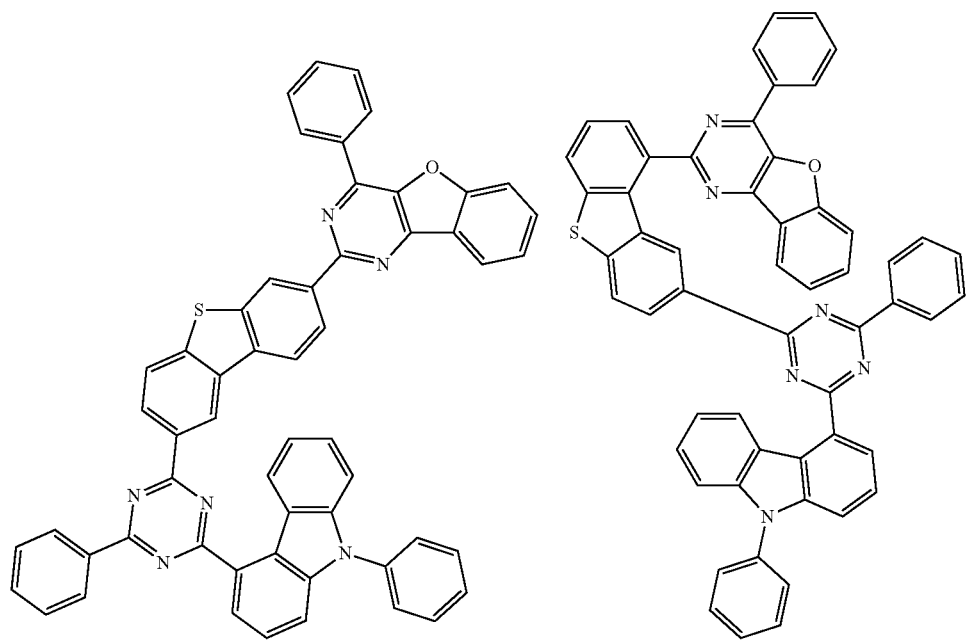

-continued

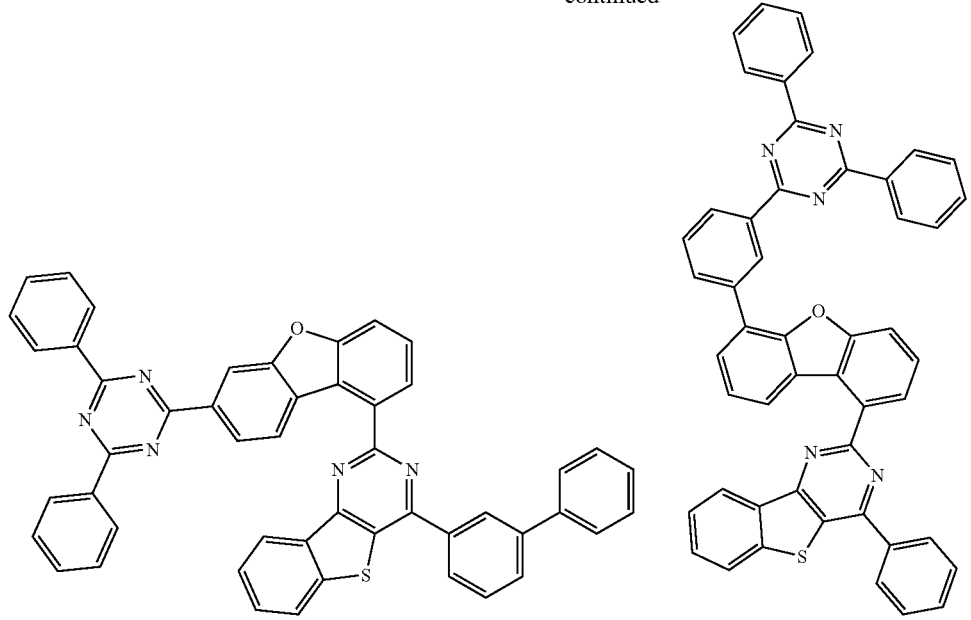

Meanwhile, the compound of Chemical Formula 1 can be prepared by the method shown in the following Reaction Scheme 1.

Reaction Scheme 1

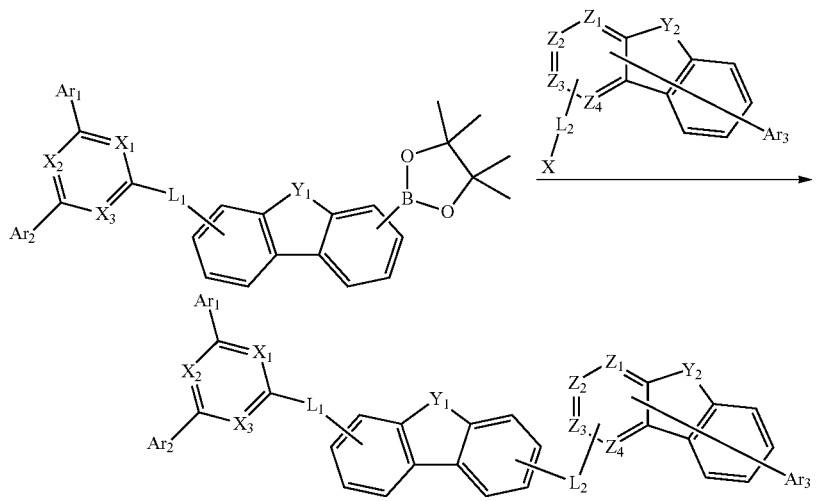

In the Reaction Scheme 1, the definition of the remaining substituents except for X is the same as defined above, and X is halogen, and more preferably, chloro or bromo. The reaction is a Suzuki coupling reaction which is preferably carried out in the presence of a palladium catalyst and a base, and a reactive group for the Suzuki coupling reaction can be modified as known in the art. The above preparation method may be further embodied in the Preparation Examples described hereinafter.

In another embodiment of the invention, there is provided an organic light emitting device including a compound of Chemical Formula 1 described above. As an example, there is provided an organic light emitting device including a first electrode; a second electrode that is provided opposite to the first electrode; and one or more organic material layers that are provided between the first electrode and the second electrode, wherein one or more layers of the organic material layers include the compound of Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic material layers.

Further, the organic material layer may include a hole injection layer, a hole transport layer, a layer for simultaneously performing hole injection and transport, wherein the hole injection layer, the hole transport layer, the layer for simultaneously performing hole injection and transport may include the compound of Chemical Formula 1.

Further, the organic material layer may include a light emitting layer, wherein the light emitting layer may include the compound of Chemical Formula 1.

Further, the organic material layer may include an electron transport layer, or an electron injection layer, wherein the electron transport layer, or the electron injection layer may include the compound of Chemical Formula 1.

Further, the electron transport layer, the electron injection layer, or the layer for simultaneously performing electron transport and electron injection may include the compound of Chemical Formula 1.

Further, the organic material layer may include a light emitting layer or an electron transport layer, wherein the electron transport layer may include the compound of Chemical Formula 1. Further, the organic light emitting device according to the present disclosure may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 may be included in the light emitting layer.

FIG. 2 shows an example of an organic light emitting device comprising a substrate 1, an anode 2, a hole injection layer 5, a hole transport layer 6, a light emitting layer 3, an electron blocking layer 7, an electron transport and injection layer 8, and a cathode 4. In such a structure, the compound of Chemical Formula 1 may be included in one or more layers of the hole injection layer, the hole transport layer, the light emitting layer and the electron transport layer.

Specifically, the organic material layer may include a light emitting layer, and the light emitting layer may include two or more kinds of host materials.

In this case, the two or more kinds of host materials may include the compound of Chemical Formula 1.

The organic light emitting device according to the present disclosure may be manufactured by materials and methods known in the art, except that one or more layers of the organic material layers include the compound of Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound of Chemical Formula 1 may be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive compound, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive compound, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound of Chemical Formula 1 may be included in an organic solar cell or an organic transistor in addition to an organic light emitting device.

The preparation of the compound of Chemical Formula 1 and the organic light emitting device comprising the same will be described in detail in the following examples. However, these examples are presented for illustrative purposes only, and are not intended to limit the scope of the present disclosure.

Preparation Example 1

Preparation Example 1-1: Preparation of Intermediate Compound A-4

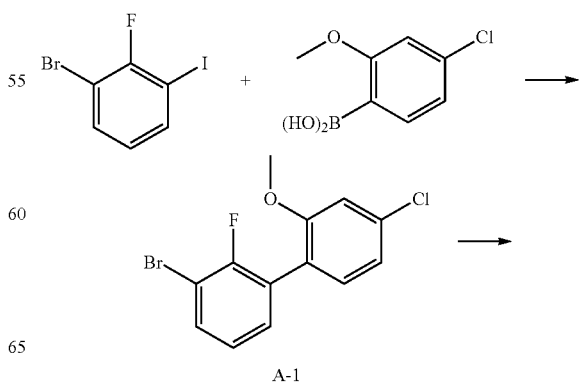

A-1

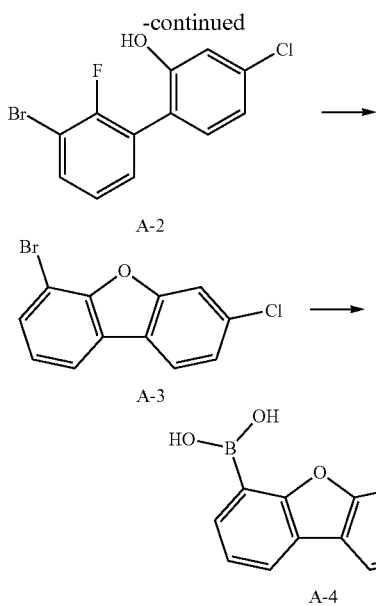

A-2

A-3

A-4

1) Preparation of Compound A-1

1-Bromo-2-fluoro-3-iodobenzene (100 g, 332.3 mmol) and (4-chloro-2-methoxyphenyl) boronic acid (61.9 g, 332.3 mmol) were added to tetrahydrofuran (2000 ml) under a nitrogen atmosphere, and the mixture was stirred and refluxed. Then, sodium carbonate (105.7 g, 997 mmol) was dissolved in water (106 ml), added thereto, sufficiently stirred, and then tetrakistriphenyl-phosphinepalladium (11.5 g, 10 mmol) was added. After reaction for 8 hours, the mixture was cooled to room temperature, the organic layer and the aqueous layer were separated, and then the organic layer was distilled. This was again added to and dissolved in chloroform (2098 ml), and washed twice with water. The organic layer was then separated, anhydrous magnesium sulfate was added, stirred and then filtered. The filtrate was distilled under reduced pressure. The concentrated compound was recrystallized from chloroform and ethanol to give solid compound A-1 (78.7 g, yield: 75%; MS: [M+H]$^+$=314).

2) Preparation of Compound A-2

Compound A-1 (78.7 g, 249.4 mmol) was dissolved in dichloromethane (800 ml) and then cooled to 0° C. Boron tribromide (26.0 ml, 274.3 mmol) was slowly added dropwise, and then stirred for 12 hours. After the reaction was completed, the mixture was washed three times with water, dried over magnesium sulfate, and filtered. The filtrate was distilled under reduced pressure and purified by column chromatography to give Compound A-2 (72.9 g, yield: 97%; MS:[M+H]$^+$=300).

3) Preparation of Compound A-3

After Compound A-2 (72.9 g, 241.8 mmol) and calcium carbonate (66.8 g, 483.5 mmol) were dissolved in N-methyl-2-pyrrolidone (500 ml), the mixture was heated and stirred for 2 hours. After lowering the temperature to room temperature, the reaction mixture was subjected to reverse precipitation in water and filtered. The result was completely dissolved in dichloromethane, washed with water, dried over anhydrous magnesium sulfate, concentrated under reduced pressure, recrystallized using ethanol and then dried to give Compound A-3 (57.1 g, yield 84%; MS:[M+H]$^+$=280).

4) Preparation of Compound A-4

After Compound A-3 (57.1 g, 202.8 mmol) was dissolved in tetrahydrofuran (600 mL), the temperature was lowered to −78° C. and 2.5 M tert-butyllithium (t-BuLi) (85.1 mL, 213.0 mmol) was added slowly. The mixture was stirred at the same temperature for 1 hour, and then triisopropylborate (70.2 mL, 304.2 mmol) was added thereto, and stirred for 2.5 hours while gradually raising the temperature to room temperature. To the reaction mixture was added a 2N aqueous hydrochloric acid solution (450 mL) and the mixture was stirred at room temperature for 1.5 hours. The resulting precipitate was filtered, washed with water and ethyl ether, and then vacuum dried to give Compound A-4 (44.9 g, yield 90%; MS:[M+H]$^+$=247).

Preparation Example 1-2: Preparation of Intermediate Compound B-5

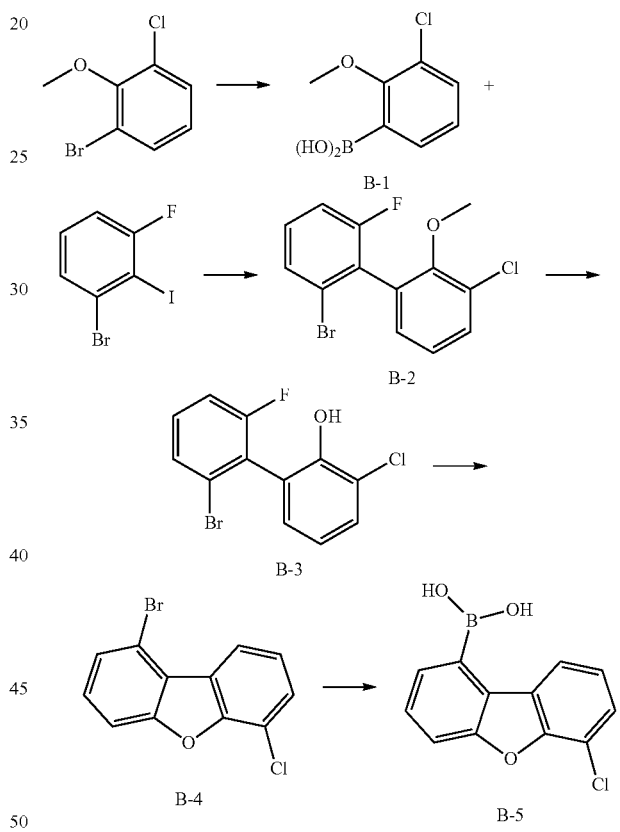

1) Preparation of Compound B-1

After 1-bromo-3-fluoro-2-methoxybenzene (100.0 g, 451.5 mmol) was dissolved in tetrahydrofuran (1000 mL), the temperature was lowered to −78° C. and 2.5 M tert-butyl lithium (t-BuLi) (182.4 mL, 456.0 mmol) was slowly added dropwise. The mixture was stirred at the same temperature for 1 hour, and then triisopropylborate (B(OiPr)$_3$) (156.3 mL, 677.3 mmol) was added thereto and stirred for 3 hours while gradually raising the temperature to room temperature. To the reaction mixture was added a 2N aqueous hydrochloric acid solution (150 mL) and the mixture was stirred at room temperature for 1.5 hours. The resulting precipitate was filtered, washed sequentially with water and ethyl ether, and then vacuum dried. After drying, it was recrystallized from chloroform and ethyl acetate and dried to give Compound B-1 (84.2 g, yield 90%; MS: [M+H]$^+$=230).

2) Preparation of Compound B-2

Compound B-2 (74.6 g, yield 52%; MS:[M+H]$^+$=314) was prepared in the same manner as in the Preparation of Compound A-1 of Preparation Example 1, except that Compound B-1 (84.2 g, 451.7 mmol) was used instead of (4-chloro-2-methoxyphenyl) boronic acid, and 1-bromo-3-fluoro-2-iodobenzene was used instead of 1-bromo-2-fluoro-3-iodobenzene.

3) Preparation of Compound B-3

Compound B-3 (60.3 g, yield 85%; MS:[M+H]$^+$=300) was prepared in the same manner as in the Preparation of Compound A-2, except that Compound B-2 (74.6 g, 236.4 mmol) was used instead of Compound A-1.

4) Preparation of Compound B-4

Compound B-4 (48.1 g, yield 85%; MS:[M+H]$^+$=280) was prepared in the same manner as in the Preparation of Compound A-3, except that Compound B-3 (60.3 g, 199.9 mmol) was used instead of Compound A-2.

5) Preparation of Compound B-5

Compound B-5 (40.1 g, yield 95%; MS:[M+H]$^+$=247) was prepared in the same manner as in the Preparation of Compound A-4, except that Compound B-4 (48.1 g, 170.9 mmol) was used instead of Compound A-3.

Preparation Example 1-3: Synthesis of Intermediate Compound C-4

1) Preparation of Compound C-1

Compound C-1 (60.1 g, yield 76%; MS:[M+H]$^+$=314) was prepared in the same manner as in the Preparation of Compound A-1 of Preparation Example 1, except that 1-bromo-3-fluoro-2-iodobenzene (75.0 g, 249.3 mmol) was used instead of 1-bromo-2-fluoro-3-iodobenzene.

2) Preparation of Compound C-2

Compound C-2 (54.0 g, yield 94%; MS:[M+H]$^+$=300) was prepared in the same manner as in the Preparation of Compound A-2, except that Compound C-1 (60.1 g, 190.4 mmol) was used instead of Compound A-1.

3) Preparation of Compound C-3

Compound C-3 (42.2 g, yield 83%; MS:[M+H]$^+$=280) was prepared in the same manner as in the Preparation of Compound A-3, except that Compound C-2 (54.0 g, 179.1 mmol) was used instead of Compound A-2.

4) Preparation of Compound C-4

Compound C-4 (34.1 g, yield 92%; MS:[M+H]$^+$=247) was prepared in the same manner as in the Preparation of Compound A-4, except that Compound C-3 (42.2 g, 170.9 mmol) was used instead of Compound A-3.

Preparation Example 1-4: Synthesis of Intermediate Compound D-4

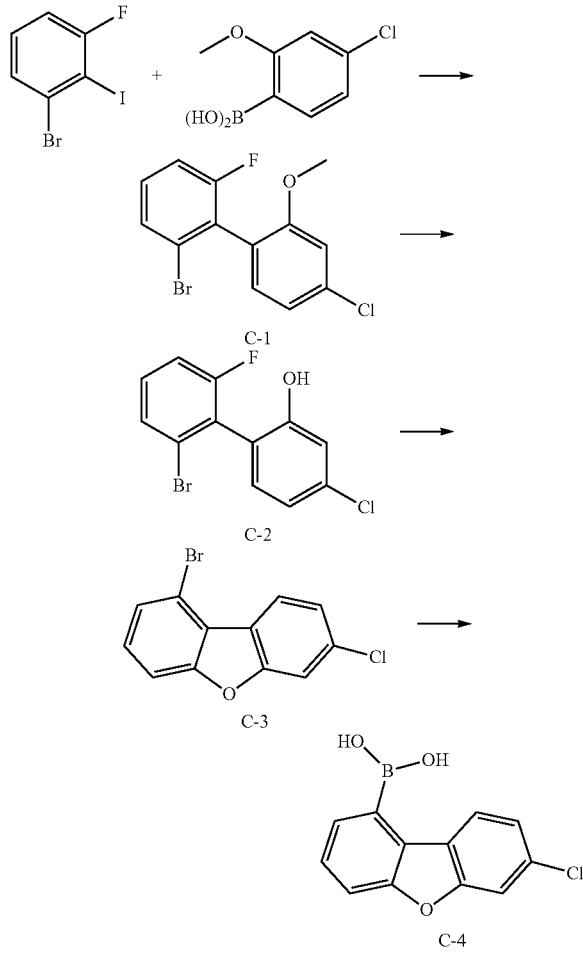

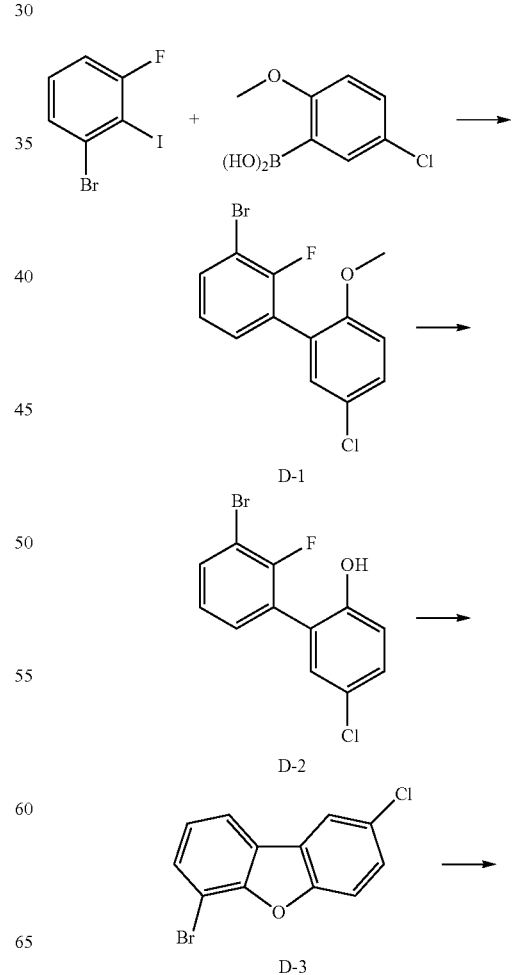

-continued

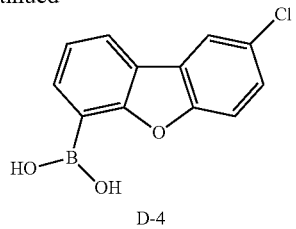
D-4

1) Preparation of Compound D-1

Compound D-1 (55 g, yield 70%; MS:[M+H]$^+$=315) was prepared in the same manner as in the Preparation of Compound A-1 of Preparation Example 1, except that (5-chloro-2-methoxyphenyl)boronic acid was used instead of (4-chloro-2-methoxyphenyl) boronic acid.

2) Preparation of Compound D-2

Compound D-2 (48.1 g, yield 91%; MS:[M+H]$^+$=300) was prepared in the same manner as in the Preparation of Compound A-2, except that Compound D-1 (55 g, 174.6 mmol) was used instead of Compound A-1.

3) Preparation of Compound D-3

Compound D-3 (41.3 g, yield 92%; MS:[M+H]$^+$=280) was prepared in the same manner as in the Preparation of Compound A-3, except that Compound D-2 (48.1 g, 159.5 mmol) was used instead of Compound A-2.

4) Preparation of Compound D-4

Compound D-4 (33.1 g, yield 92%; MS:[M+H]$^+$=247) was prepared in the same manner as in the Preparation of Compound A-4, except that Compound D-3 (41.3 g, 146.7 mmol) was used instead of Compound A-3.

Preparation Example 1-5: Preparation of Intermediate Compound E-4

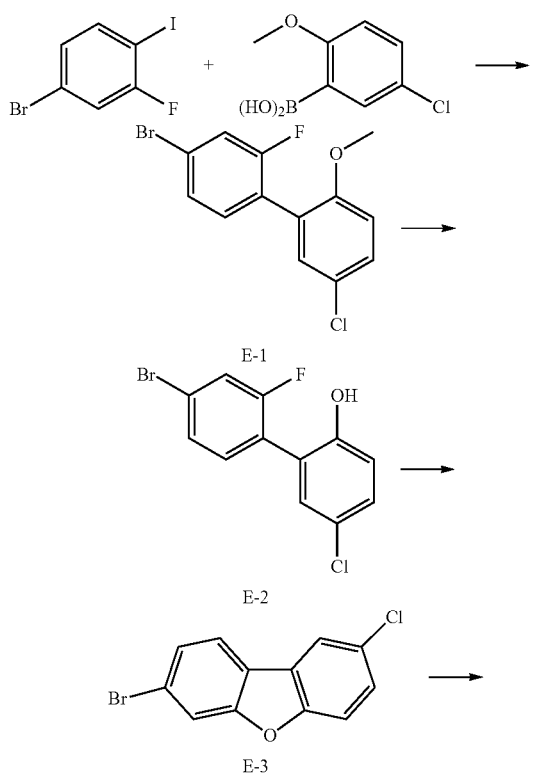

-continued

E-4

1) Preparation of Compound E-1

Compound E-1 (62.3 g, yield 79%; MS:[M+H]$^+$=315) was prepared in the same manner as in the Preparation of Compound A-1 of Preparation Example 1, except that 4-bromo-2-fluoro-1-iodobenzene was used instead of 1-bromo-2-fluoro-3-iodobenzene, and (5-chloro-2-methoxyphenyl)boronic acid was used instead of (4-chloro-2-methoxyphenyl)boronic acid.

2) Preparation of Compound E-2

Compound E-2 (51.7 g, yield 87%; MS:[M+H]$^+$=300) was prepared in the same manner as in the Preparation of Compound A-2, except that Compound E-1 (62.3 g, 197.4 mmol) was used instead of Compound A-1.

3) Preparation of Compound E-3

Compound E-3 (41.8 g, yield 87%; MS:[M+H]$^+$=280) was prepared in the same manner as in the Preparation of Compound A-3, except that Compound E-2 (51.7 g, 171.5 mmol) was used instead of Compound A-2.

4) Preparation of Compound E-4

Compound E-4 (31.2 g, yield 85%; MS:[M+H]$^+$=247) was prepared in the same manner as in the Preparation of Compound A-4, except that Compound E-3 (41.8 g, 148.5 mmol) was used instead of Compound A-3.

Preparation Example 1-6: Preparation of Intermediate Compound F-4

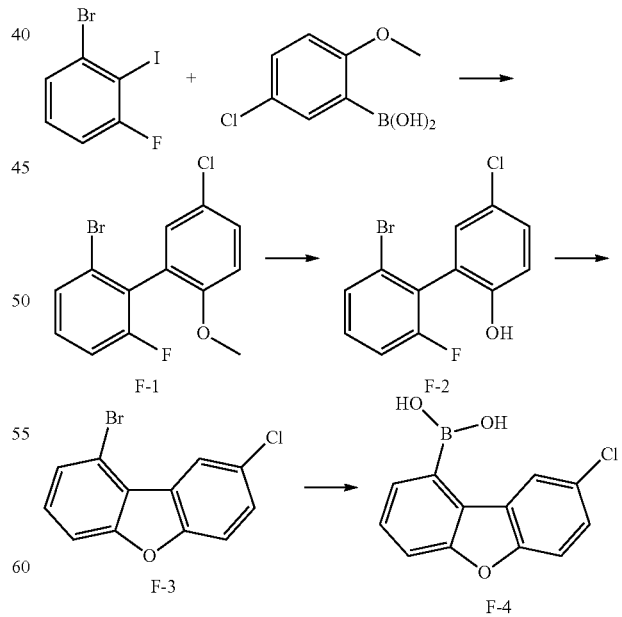

1) Preparation of Compound F-1

Compound F-1 (59.5 g, yield 76%; MS:[M+H]$^+$=315) was prepared in the same manner as in the Preparation of Compound A-1, except that 1-bromo-3-fluoro-2-iodobenzene was used instead of 1-bromo-2-fluoro-3-iodobenzene, and (5-chloro-2-methoxyphenyl)boronic acid was used instead of (4-chloro-2-methoxyphenyl)boronic acid.

2) Preparation of Compound F-2

Compound F-2 (50.8 g, yield 89%; MS:[M+H]$^+$=300) was prepared in the same manner as in the Preparation of Compound A-2, except that Compound F-1 (59.5 g, 189 mmol) was used instead of Compound A-1.

3) Preparation of Compound F-3

Compound F-3 (42.8 g, yield 90%; MS:[M+H]$^+$=280) was prepared in the same manner as in the Preparation of Compound A-3, except that Compound F-2 (50.8 g, 168.5 mmol) was used instead of Compound A-2.

4) Preparation of Compound F-4

Compound F-4 (30.3 g, yield 81%; MS:[M+H]$^+$=247) was prepared in the same manner as in the Preparation of Compound A-4, except that Compound F-3 (42.8 g, 147 mmol) was used instead of Compound A-3.

Preparation Example 1-7: Preparation of Intermediate Compound G-5

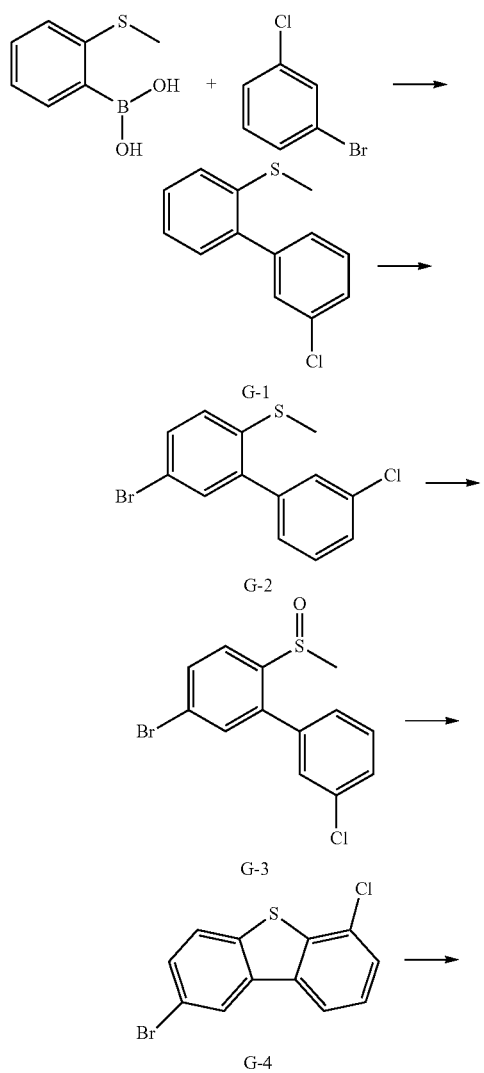

-continued

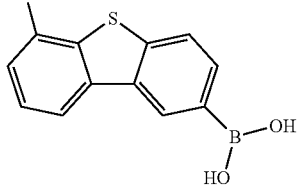

G-5

1) Preparation of Compound G-1

Compound G-1 (49 g, yield 79%; MS:[M+H]$^+$=235) was prepared in the same manner as in the Preparation of Compound A-1, except that 1-bromo-3-chlorobenzene was used instead of 1-bromo-2-fluoro-3-iodobenzene, and (2-(methylthio)phenyl)boronic acid was used instead of (4-chloro-2-methoxyphenyl)boronic acid.

2) Preparation of Compound G-2

Acetic acid (420 ml) was added to Compound G-1 (49.0 g, 148.5 mmol) under a nitrogen atmosphere, to which bromine (13.9 ml, 271 mmol) was added and stirred at 65° C. for 3 hours. After cooling, water was added to the mixture, and the precipitated solid was filtered and washed three times with water. The filtered filtrate was recrystallized from acetonitrile and toluene to give Compound G-2 (50.3 g, yield 77%; MS:[M+H]$^+$=314).

3) Preparation of Compound G-3

Acetic acid (530 ml) was added to Compound G-2 (50.3 g, 160 mmol), to which 35% hydrogen peroxide (16.4 g) was added, and the mixture was stirred at room temperature for 5 hours. NaOH aqueous solution was added to the reaction, which was stirred for 20 minutes, ethyl acetate was added, and the aqueous layer was removed. The reaction mixture was dried over anhydrous magnesium sulfate, concentrated under reduced pressure, recrystallized using a mixed solution of tetrahydrofuran and ethyl acetate, and then dried to give Compound G-3 (43.2 g, yield 87%, MS:[M+H]$^+$=308).

4) Preparation of Compound G-4

Compound G-3 (43.2 g, 160 mmol) was added to sulfuric acid (220 mL) and then stirred at room temperature for 5 hours. Aqueous NaOH solution was added to the reaction mixture, which was stirred for 30 minutes, chloroform was added thereto, the layers were separated, and then washed three times with water. Ethyl acetate was added and the aqueous layer was removed. The reaction mixture was dried over anhydrous magnesium sulfate, concentrated under reduced pressure, and recrystallized using a mixed solution of tetrahydrofuran and ethyl acetate to give Compound G-4 (30.6 g, yield: 74%, MS:[M+H]$^+$=296).

5) Preparation of Compound G-5

Compound G-5 (20.4 g, yield: 75%; MS:[M+H]$^+$=263) was prepared in the same manner as in the Preparation of Compound A-4, except that Compound G-4 (42.0 g, 148.5 mmol)[JSS1] was used instead of Compound A-3.

Preparation Example 1-8: Preparation of Intermediate Compound H-5

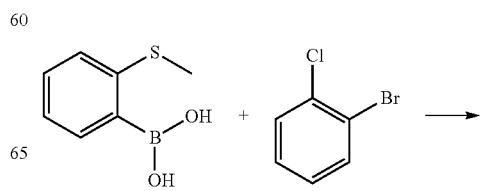

-continued

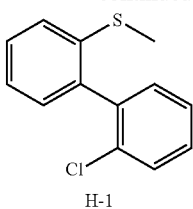
H-1

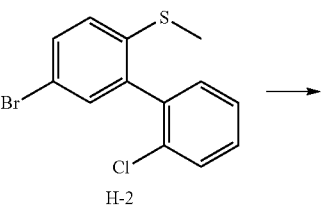
H-2

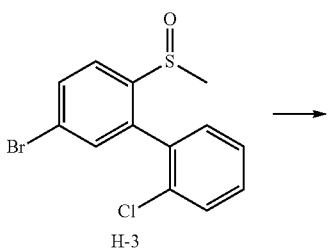
H-3

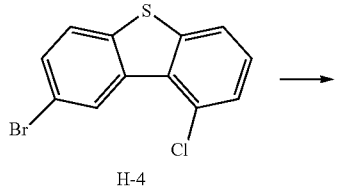
H-4

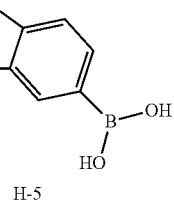
H-5

Compound H-5 (42 g, MS:[M+H]⁺=235 was prepared in the same manner as in the Preparation of Compound G-5 of Preparation Example 1-7, except that 1-bromo-2-chlorobenzene was used instead of 1-bromo-3-chlorobenzene.

Preparation Example 2

Preparation Example 2-1: Preparation of Intermediate Compound I-1

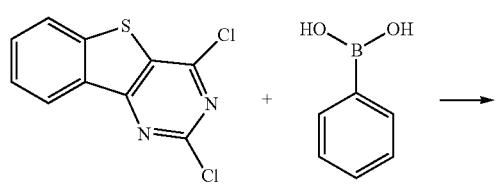

-continued

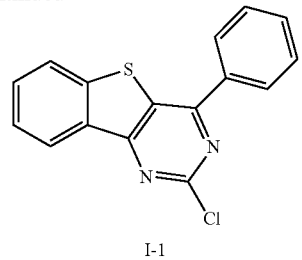
I-1

After 2,4-dichlorobenzothieno[3,2-d]pyrimidine (15 g, 57.8 mmol) and phenylboronic acid (7.9 g, 64.7 mmol) were dissolved in tetrahydrofuran (250 ml), 1.5 M aqueous potassium carbonate solution (120 ml) was added and tetrakis-(triphenylphosphine)palladium (1.4 g, 1.28 mmol) was added, and then the mixture was heated and stirred for 7 hours. After lowering the temperature to room temperature, the aqueous layer was separated and removed, dried over anhydrous magnesium sulfate, concentrated under reduced pressure, recrystallized from chloroform and ethanol and then dried to give Compound I-1 (14.1 g, yield 83%, MS:[M+H]⁺=297).

Preparation Example 2-2: Preparation of Intermediate Compound I-2

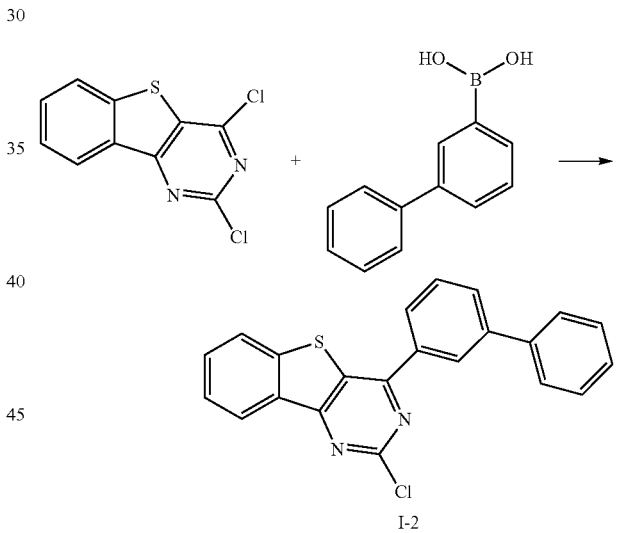
I-2

Compound I-2 was prepared in the same manner as the Preparation of Compound I-1, except that [1,1'-biphenyl]-3-ylboronic acid was used instead of phenylboronic acid.

Preparation Example 2-3: Preparation of Intermediate Compound I-3

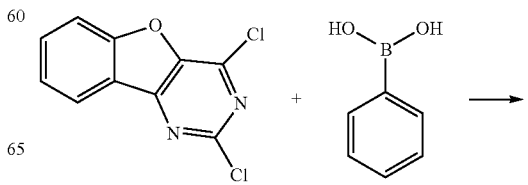

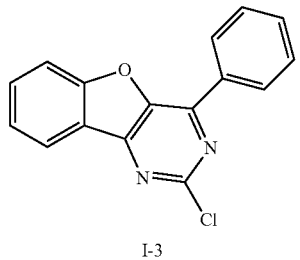

I-3

Compound I-3 was prepared in the same manner as in the Preparation of Compound 1-1, except that 2,4-dichlorobenzofuro[3,2-d]pyrimidine was used instead of 2,4-dichlorobenzothieno[3,2-d]pyrimidine.

Preparation Example 2-4: Preparation of Intermediate Compound I-4

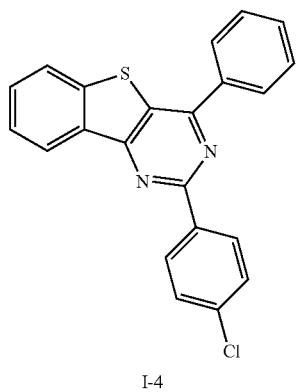

I-4

After Compound I-1 (15.0 g, 0.05 mol) and (4-chlorophenyl)boronic acid (21.4 g, 0.06 mol) were dissolved in dioxane (200 ml), $K_3PO_4$ (21.4 g, 0.1 mol) was added and bis(tri-t-butylphosphine)palladium(0) (0.26 g, 0.5 mmol) was added, and then the mixture was heated and stirred for 13 hours. After lowering the temperature to room temperature, the aqueous layer was separated and removed, dried over anhydrous magnesium sulfate, concentrated under reduced pressure, recrystallized with ethyl acetate, and then dried to give Compound I-4 (14.1 g, yield 81%, MS: $[M+H]^+=373$).

Preparation Example 2-5: Preparation of Intermediate Compound I-5

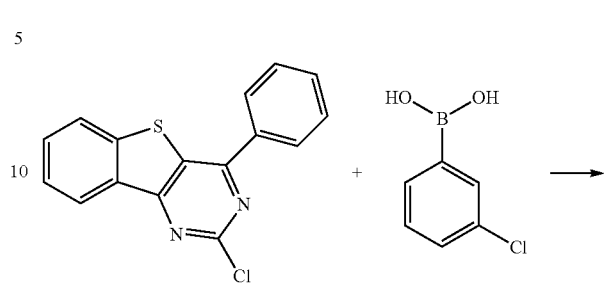

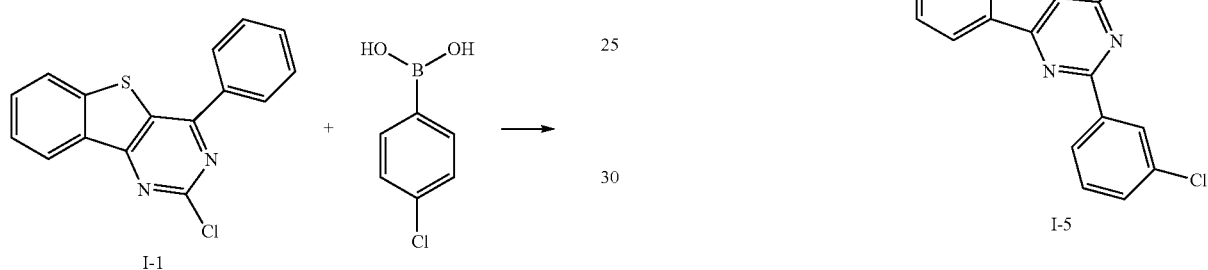

I-5

Compound I-5 was prepared in the same manner as the Preparation of Compound I-4, except that (3-chlorophenyl)boronic acid was used instead of (4-chlorophenyl)boronic acid.

EXAMPLE

Example 1: Preparation of Compound 1

1) Preparation of Compound 1-1

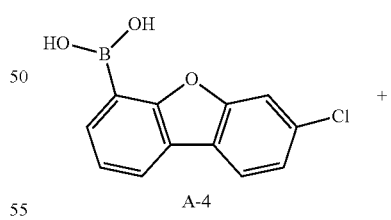

A-4

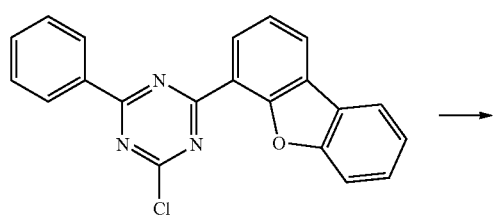

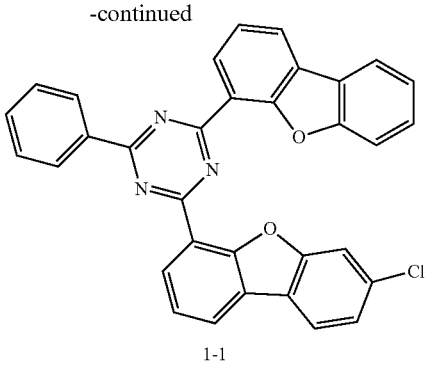

1-1

Compound A-4 (10 g, 40.6 mmol) and 2-chloro-4-(dibenzofuran-4-yl)-6-phenyl-1,3,5-triazine (14.5 g, 40.6 mmol) were added to tetrahydrofuran (200 ml) under a nitrogen atmosphere, and the mixture was stirred and refluxed. Then, potassium carbonate (16.8 g, 121.7 mmol) was dissolved in water (17 ml), added thereto, sufficiently stirred, and then tetrakistriphenyl-phosphinepalladium (1.4 g, 1.2 mmol) was added. After reaction for 8 hours, the mixture was cooled to room temperature, the organic layer and the aqueous layer were separated, and then the organic layer was distilled. This was again added to and dissolved in chloroform (424 ml), and washed twice with water. The organic layer was then separated, anhydrous magnesium sulfate was added, stirred and then filtered. The filtrate was distilled under reduced pressure. The concentrated compound was recrystallized from chloroform and ethanol to give solid compound I-1 (17.8 g, yield: 84%; MS: [M+H]$^+$=524).

2) Preparation of Compound 1-2

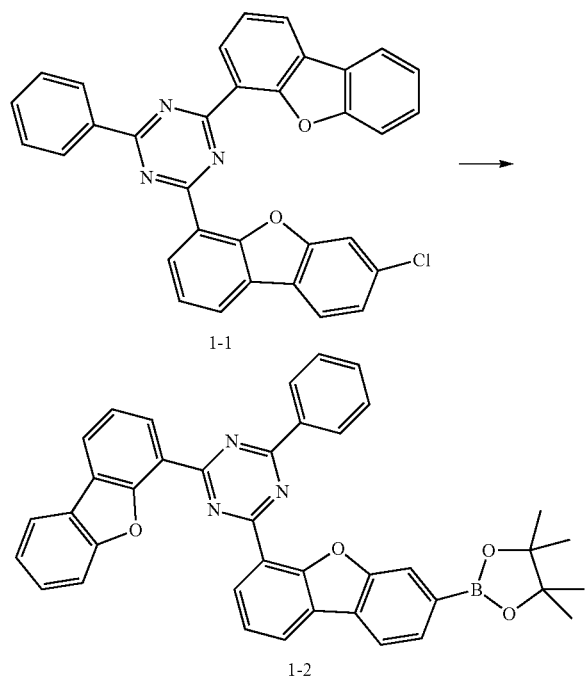

Compound 1-1 (17.8 g, 34 mmol) and bis(pinacolato)diboron (17.3 g, 68.1 mmol) were added to dioxane (356 ml) under a nitrogen atmosphere, and the mixture was stirred and refluxed. Then, potassium acetate (9.8 g, 102.1 mmol) was added thereto and sufficiently stirred, and then tetrakistriphenyl-phosphinepalladium (0.6 g, 1 mmol) and tricyclohexylphosphine (0.6 g, 2 mmol) were added. After reaction for 6 hours, the reaction mixture was cooled to room temperature, the organic layer was subjected to filtration treatment to remove a salt, and then the filtered organic layer was distilled. This was added again to and dissolved in chloroform (209 ml), and washed twice with water. The organic layer was then separated, anhydrous magnesium sulfate was added, stirred and then filtered. The filtrate was distilled under reduced pressure. The concentrated compound was recrystallized from chloroform and ethanol to give a solid compound 1-2 (16.8 g, yield 80%, MS: [M+H]$^+$= 616.2).

3) Preparation of Compound 1

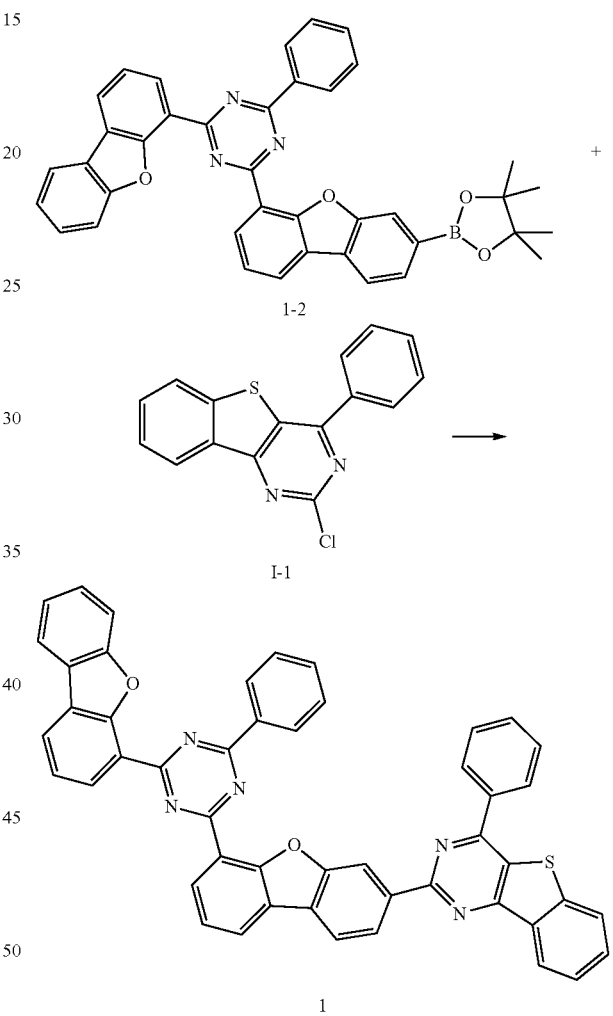

Compound 1-2 (16.8 g, 27.3 mmol) and Compound I-1 (8.1 g, 27.3 mmol) were added to tetrahydrofuran (336 ml) under a nitrogen atmosphere, and the mixture was stirred and refluxed. Then, potassium carbonate (11.3 g, 81.9 mmol) was dissolved in water (11 ml), added thereto and sufficiently stirred, and then bis(tri-tert-butylphosphine)palladium (0.4 g, 0.8 mmol) was added. After the reaction for 8 hours, the reaction mixture was cooled to room temperature, the organic layer and the aqueous layer were separated, and the organic layer was distilled. This was added again to and dissolved in chloroform (409 ml), and washed twice with water. The organic layer was then separated, anhydrous magnesium sulfate was added, stirred and then filtered. The filtrate was distilled under reduced pressure. The concentrated compound was recrystallized from chloroform and ethyl acetate to give a solid compound I (14.5 g, yield 71%, MS: [M+H]⁺=750.2).

Example 2: Preparation of Compound 2

1) Preparation of Compound 2-1

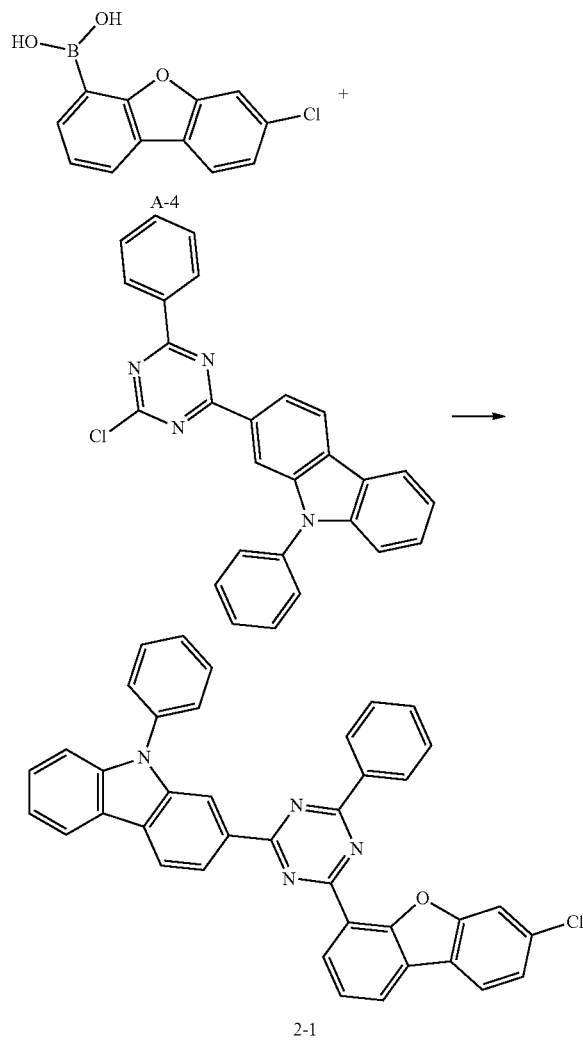

Compound 2-1 (14.6 g, yield 60%, MS:[M+H]⁺=599) was prepared in the same manner as in the Preparation of Compound 1-1, except that 2-(4-chloro-6-phenyl-1,3,5-triazin-2-yl)9-phenyl-9H-carbazole was used instead of 2-chloro-4-(dibenzofuran-4-yl)-6-phenyl-1,3,5-triazine.

2) Preparation of Compound 2-2

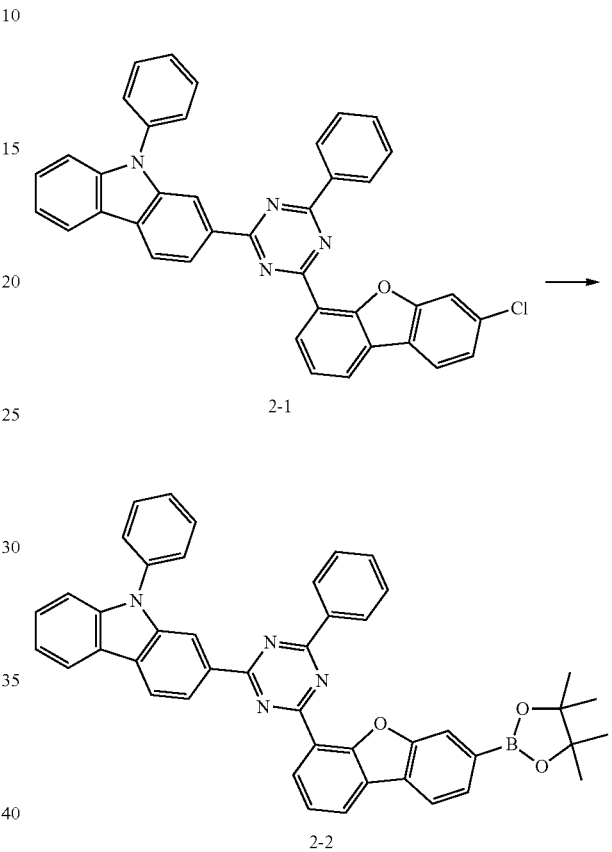

Compound 2-2 (12.6 g, yield 75%, MS:[M+H]⁺=691) was prepared in the same manner as in the Preparation of Compound 1-2, except that Compound 2-1 was used instead of Compound 1-1.

3) Preparation of Compound 2

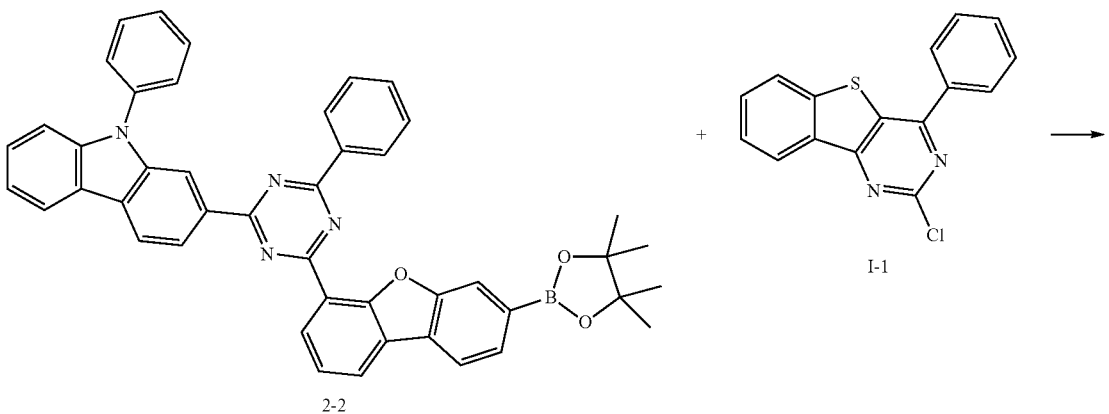

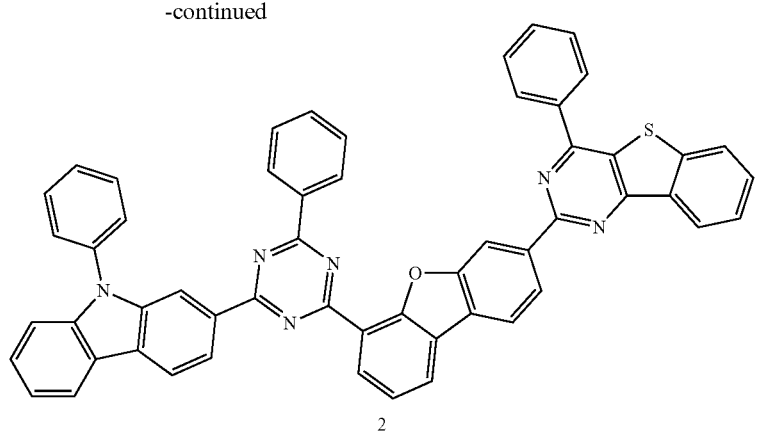

Compound 2 (7.7 g, yield 51%, MS:[M+H]$^+$=825) was prepared in the same manner as in the Preparation of Compound 1, except that Compound 2-2 was used instead of Compound 1-2.

Example 3: Preparation of Compound 3

1) Preparation of Compound 3-1

Compound 3-1 (13.8 g, yield 67%, MS:[M+H]$^+$=540) was prepared in the same manner as in the Preparation of Compound 1-1, except that Compound G-5 and 2-chloro-4-(dibenzofuran-1-yl)-6-phenyl-1,3,5-triazine were instead of Compound A-4 and 2-chloro-4-(dibenzofuran-4-yl)-6-phenyl-1,3,5-triazine.

2) Preparation of Compound 3-2

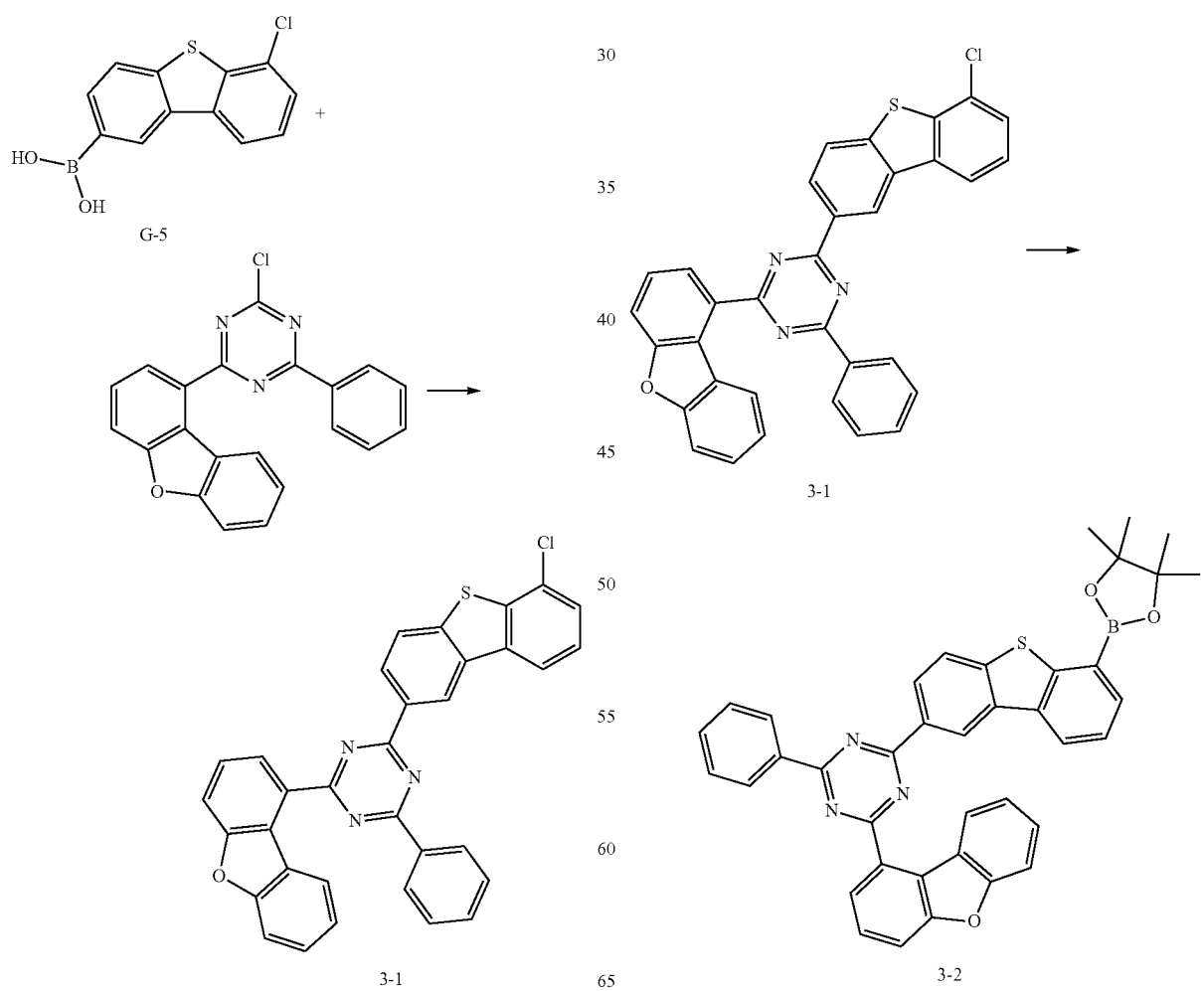

Compound 3-2 (11.2 g, yield 77%, MS:[M+H]$^+$=632) was prepared in the same manner as in the Preparation of Compound 1-2, except that compound 3-1 was used instead of compound 1-1.

3) Preparation of Compound 3

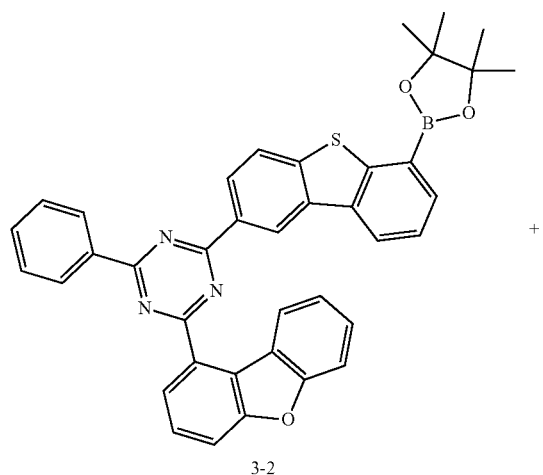
3-2

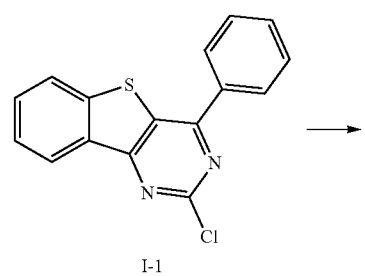
I-1

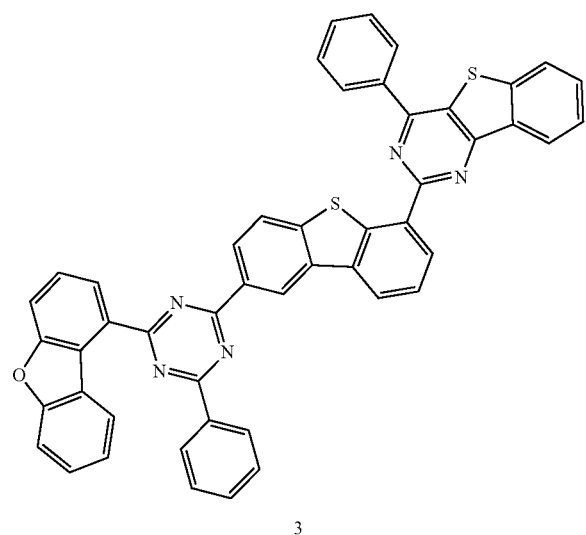
3

Compound 3 (9.7 g, yield 78%, MS:[M+H]$^+$=766) was prepared in the same manner as the Preparation of Compound 1, except that Compound 3-2 was used instead of Compound 1-2.

Example 4: Preparation of Compound 4

1) Preparation of Compound 4-1

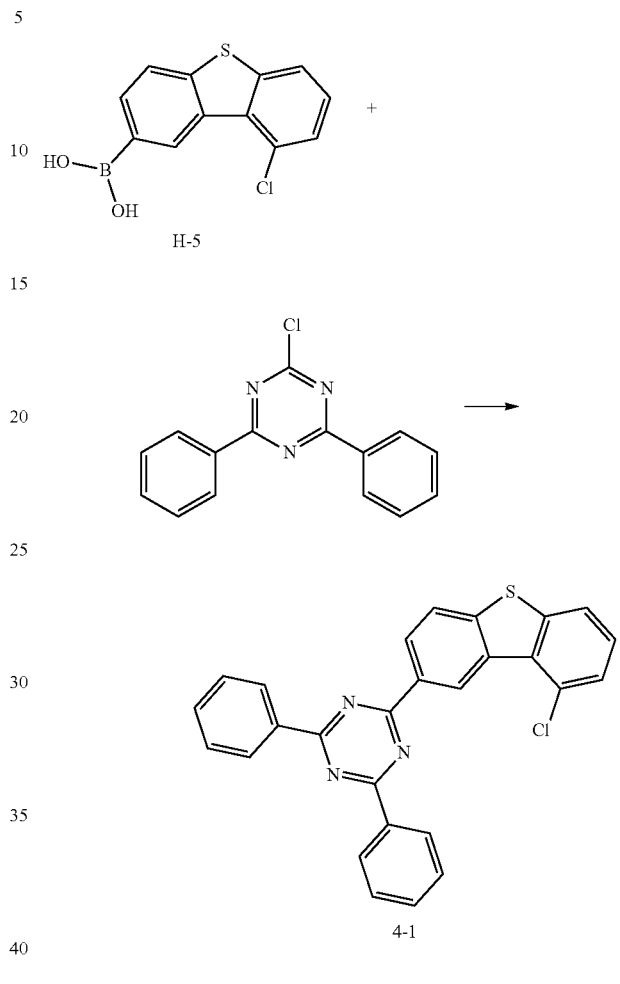
4-1

Compound 4-1 (11.6 g, yield 68%, MS:[M+H]$^+$=450) was prepared in the same manner as the Preparation of Compound 1-1, except that Compound H-5 and 2-chloro-4,6-diphenyl-1,3,5-triazine were used instead of Compound A-4 and 2-chloro-4-(dibenzofuran-4-yl)-6-phenyl-1,3,5-triazine.

2) Preparation of Compound 4-2

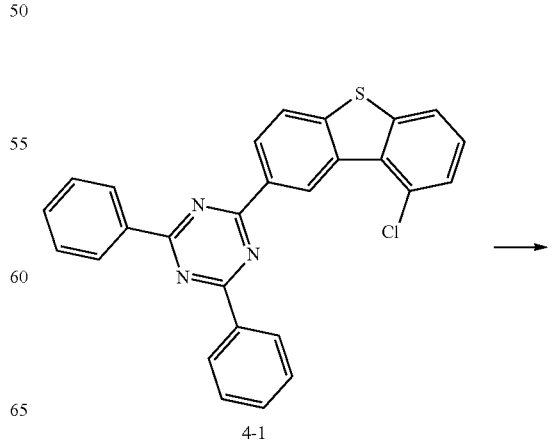
4-1

-continued

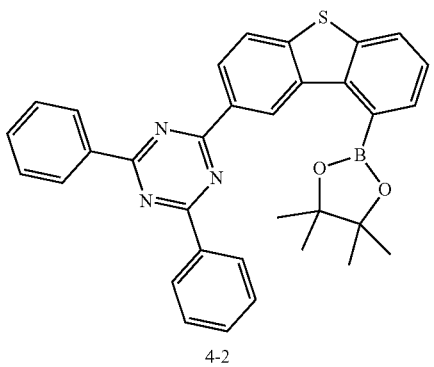
4-2

Compound 4-2 (11.0 g, yield 79%, MS:[M+H]⁺=542) was prepared in the same manner as in the Preparation of Compound 1-2, except that Compound 4-1 was used instead of Compound 1-1.

3) Preparation of Compound 4

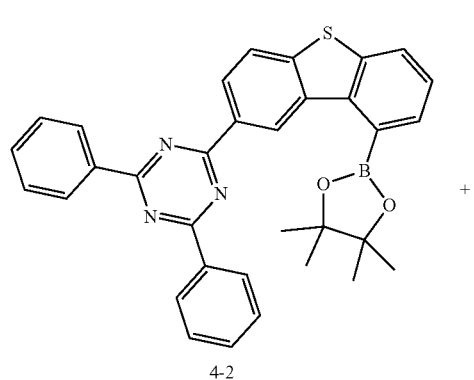
4-2

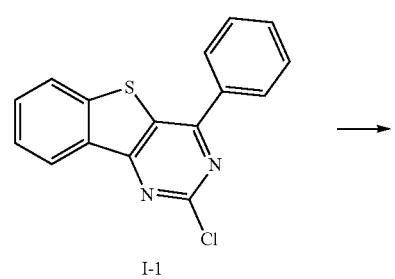
I-1

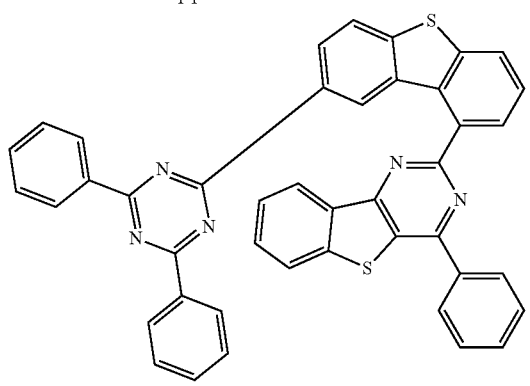
4

Compound 4 (8.5 g, yield 62%, MS:[M+H]⁺=676) was prepared in the same manner as in the Preparation of Compound 1, except that Compound 4-2 was used instead of Compound 1-2.

Example 5: Preparation of Compound 5

1) Preparation of Compound 5-1

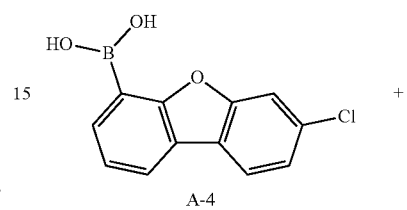
A-4

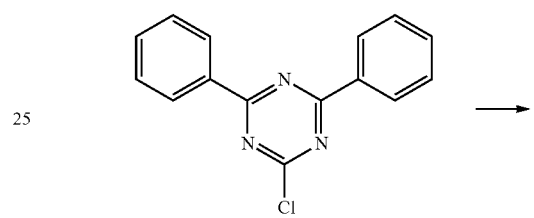

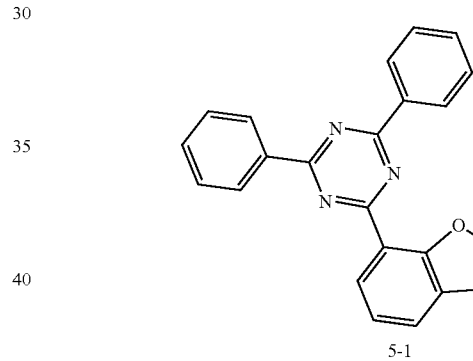
5-1

Compound 5-1 (11.6 g, yield 66%, MS:[M+H]⁺=434) was prepared in the same manner as in the Preparation of Compound 1-1, except that 2-chloro-4,6-diphenyl-1,3,5-triazine was used instead of 2-chloro-4-(dibenzofuran-4-yl)-6-phenyl-1,3,5-triazine.

2) Preparation of Compound 5-2

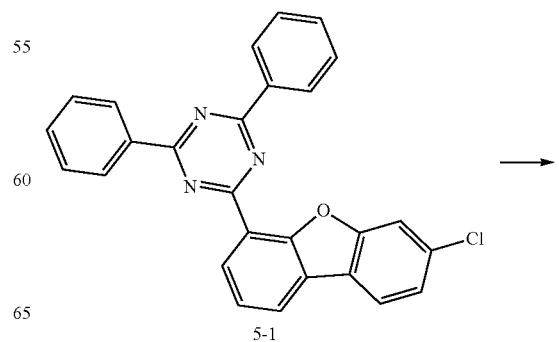
5-1

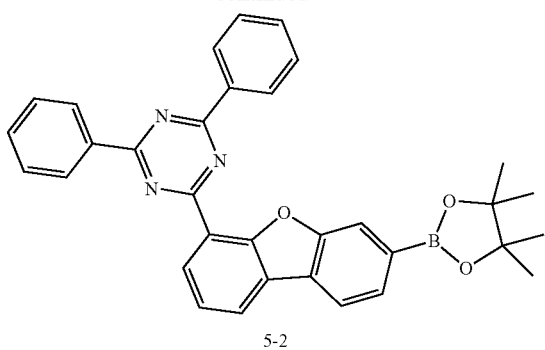

5-2

Compound 5-2 (9.4 g, yield 67%, MS:[M+H]$^+$=526) was prepared in the same manner as in the Preparation of Compound 1-2, except that Compound 5-1 was used instead of Compound 1-1.

3) Preparation of Compound 5-3

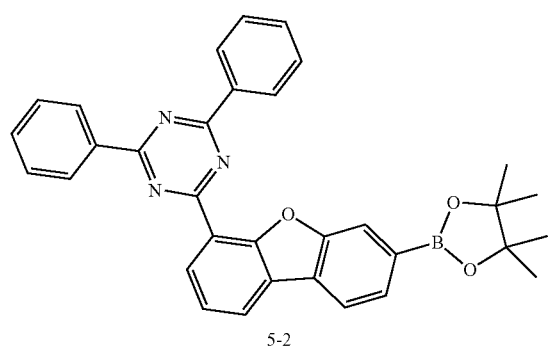

5-2

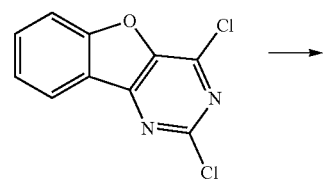

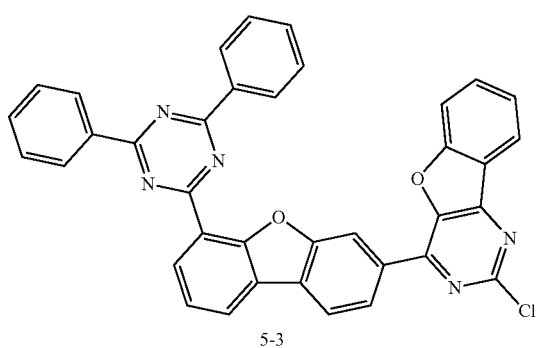

5-3

Compound 5-3 (7.7 g, yield 72%, MS:[M+H]$^+$=602) was prepared in the same manner as in the Preparation of Compound 1, except that Compound 5-2 and 2,4-dichlorobenzofuro[3,2-d]pyrimidine were used instead of Compound 1-2 and Compound I-1.

4) Preparation of Compound 5

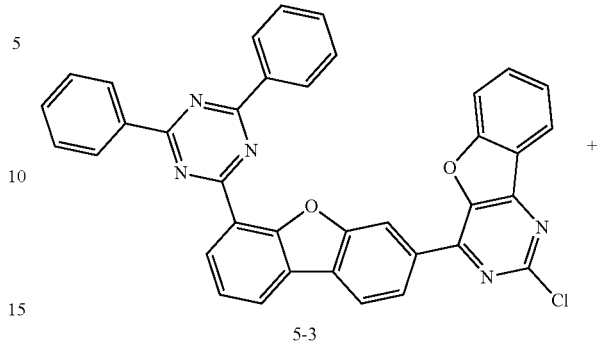

5-3

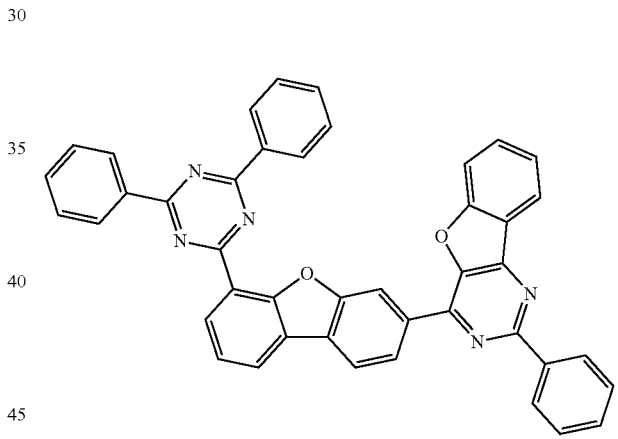

5

Compound 5-3 (7.7 g, 12.8 mmol) and phenylboronic acid (1.6 g, 12.8 mmol) were added to dioxane (154 ml) under a nitrogen atmosphere, and the mixture was stirred and refluxed. Then, tribasic potassium phosphate (8.2 g, 38.4 mmol) was dissolved in water (8 ml) and stirred sufficiently, and then dibenzylideneacetonepalladium (0.2 g, 0.4 mmol) and tricyclohexylphosphine (0.2 g, 0.8 mmol) were added. After the reaction for 6 hours, the reaction mixture was cooled to room temperature, and then the resulting solid was filtered. The solid was added to and dissolved in dichlorobenzene (247 ml), washed twice with water, and the organic layer was separated, anhydrous magnesium sulfate was added, stirred, and filtered. The filtrate was distilled under reduced pressure. The concentrated compound was recrystallized from tetrahydrofuran and toluene to give a solid compound 5 (4.4 g, yield 54%, MS: [M+H]$^+$=644).

Example 6: Preparation of Compound 6

1) Preparation of Compound 6-1

2) Preparation of Compound 6-2

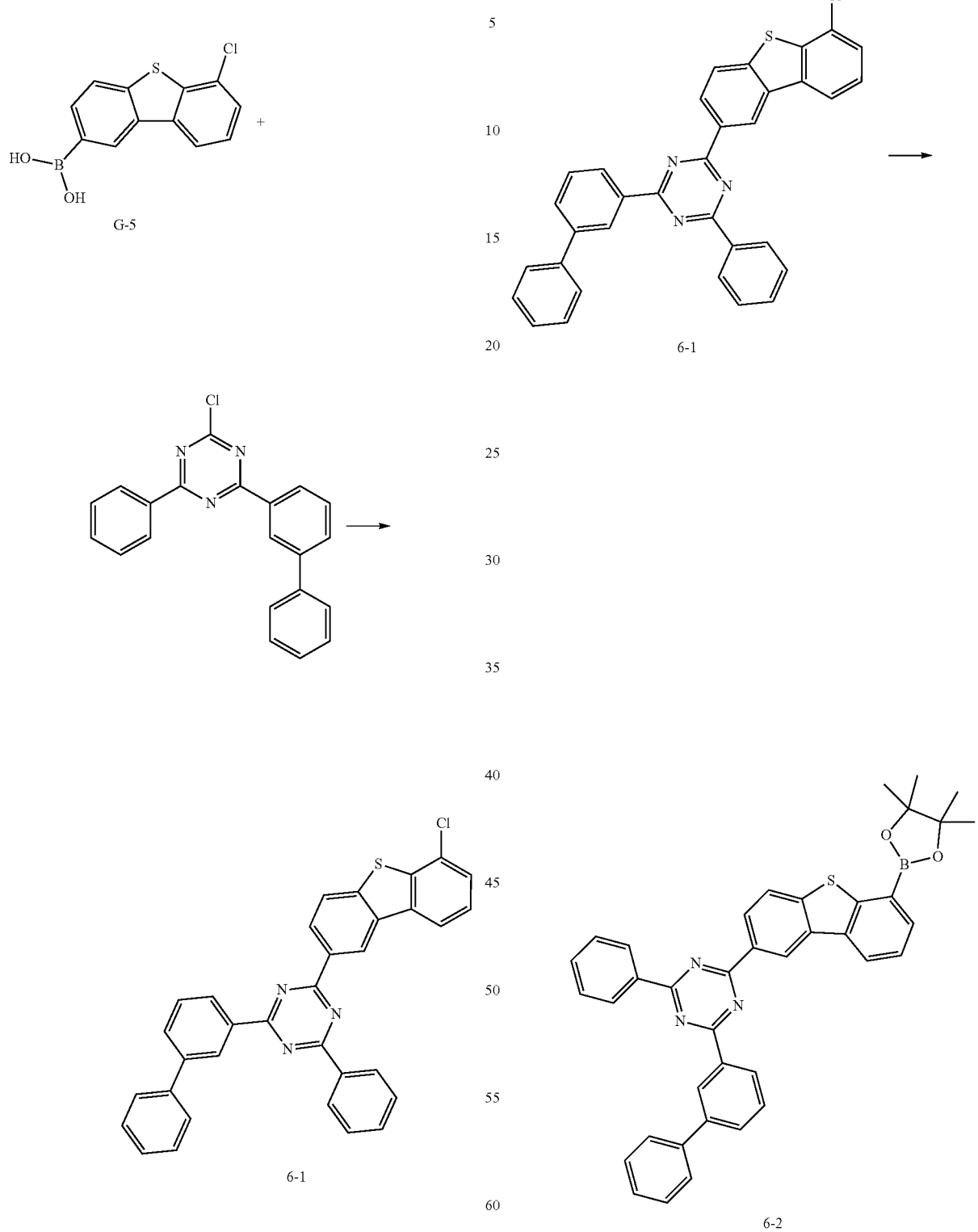

Compound 6-1 (15.4 g, yield 77%, MS:[M+H]$^+$=526) was prepared in the same manner as in the Preparation of Compound 1-1, except that Compound G-5 and 2-{[1,1'-biphenyl]-3-yl}-4-chloro-6-phenyl-1,3,5-triazine were used instead of Compound A-4 and 2-chloro-4-(dibenzofuran-4-yl)-6-phenyl-1,3,5-triazine.

Compound 6-2 (13.0 g, yield 72%, MS:[M+H]$^+$=618) was prepared in the same manner as in the Preparation of Compound 1-2, except that Compound 6-1 was used instead of Compound 1-1.

3) Preparation of Compound 6-3

4) Preparation of Compound 6

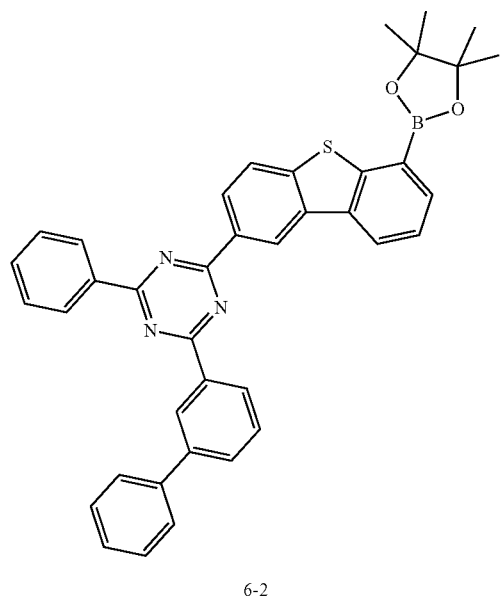

6-2

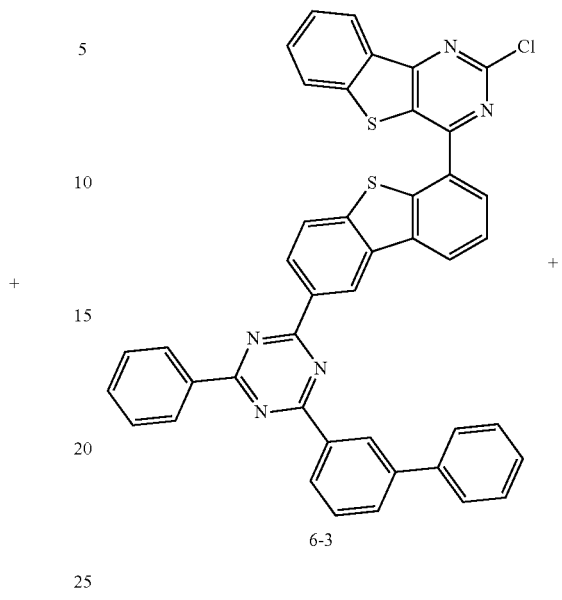

6-3

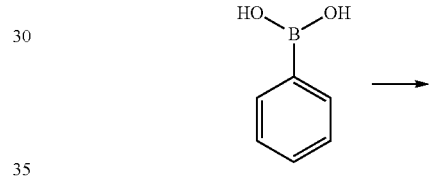

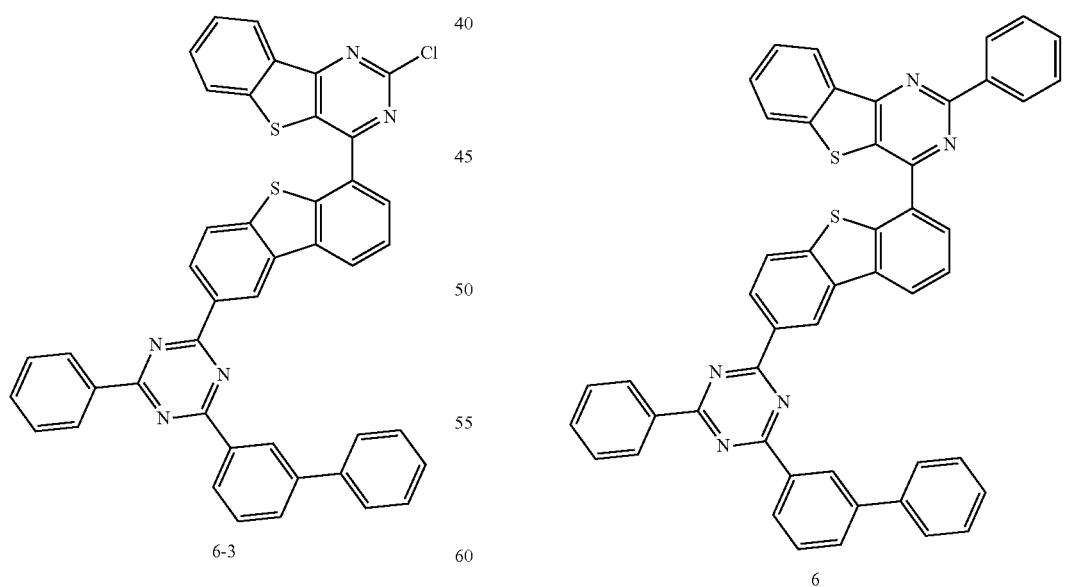

6-3

6

Compound 6-3 (11.1 g, yield 74%, MS:[M+H]$^+$=710) was prepared in the same manner as in the Preparation of Compound 1, except that Compound 6-2 and 2,4-dichlorobenzothieno[3,2-d]pyrimidine was used instead of Compound 1-2 and Compound I-1.

Compound 6 (6.9 g, yield 59%, MS:[M+H]$^+$=752) was prepared in the same manner as in the Preparation of Compound 5, except that Compound 6-3 was used instead of Compound 5-3.

Example 7: Preparation of Compound 7

1) Preparation of Compound 7-1

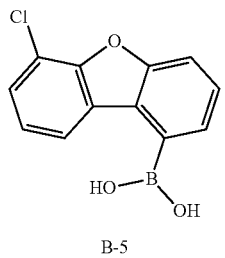

B-5

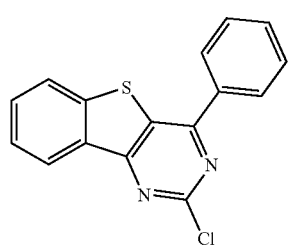

I-1

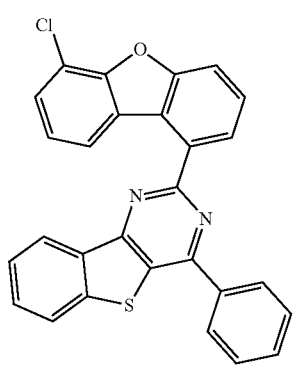

7-1

Compound B-5 (9 g, 36.5 mmol) and Compound 1-1 (10.8 g, 36.5 mmol) were added to tetrahydrofuran (180 ml) under a nitrogen atmosphere, and the mixture was stirred and refluxed. Then, potassium carbonate (15.1 g, 109.6 mmol) was dissolved in water (15 ml), added thereto and sufficiently stirred, and then tetrakistriphenyl-phosphinepalladium (1.3 g, 1.1 mmol) was added. After reaction for 8 hours, the mixture was cooled to room temperature, and then the resulting solid was filtered. The solid was added to and dissolved in chloroform (337 ml), and washed twice with water. The organic layer was then separated, anhydrous magnesium sulfate was added, stirred and then filtered. The filtrate was distilled under reduced pressure. The concentrated compound was recrystallized from a mixed solution of chloroform and ethanol to give a solid compound 7-1 (14.7 g, 87%, MS: [M+H]$^+$=463)

2) Preparation of Compound 7-2

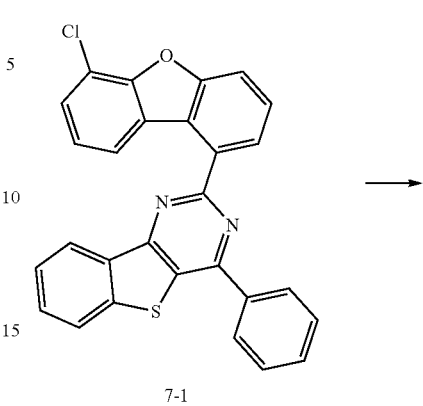

7-1

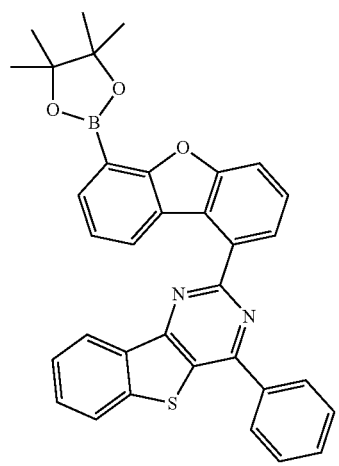

7-2

Compound 7-1 (14.7 g, 31.8 mmol) and bis(pinacolato)diboron (16.2 g, 63.6 mmol) were added to dioxane (294 ml) under a nitrogen atmosphere, and the mixture was stirred and refluxed. Then, potassium carbonate (9.2 g, 95.4 mmol) was added thereto, sufficiently stirred, and then palladium dibenzylideneacetonepalladium (0.5 g, 1 mmol) and tricyclohexylphosphine (0.5 g, 1.9 mmol) were added. After the reaction for 6 hours, the reaction mixture was cooled to room temperature, the organic layer and then the organic layer was subjected to filtration treatment to remove a salt, and then the filtered organic layer was distilled. This was added again to and dissolved in chloroform (176 ml), and washed twice with water. The organic layer was then separated, anhydrous magnesium sulfate was added, stirred and then filtered. The filtrate was distilled under reduced pressure. The concentrated compound was recrystallized from chloroform and ethanol to give a solid compound 7-2 (13.7 g, yield 78%, MS: [M+H]$^+$=555).

3) Preparation of Compound 7

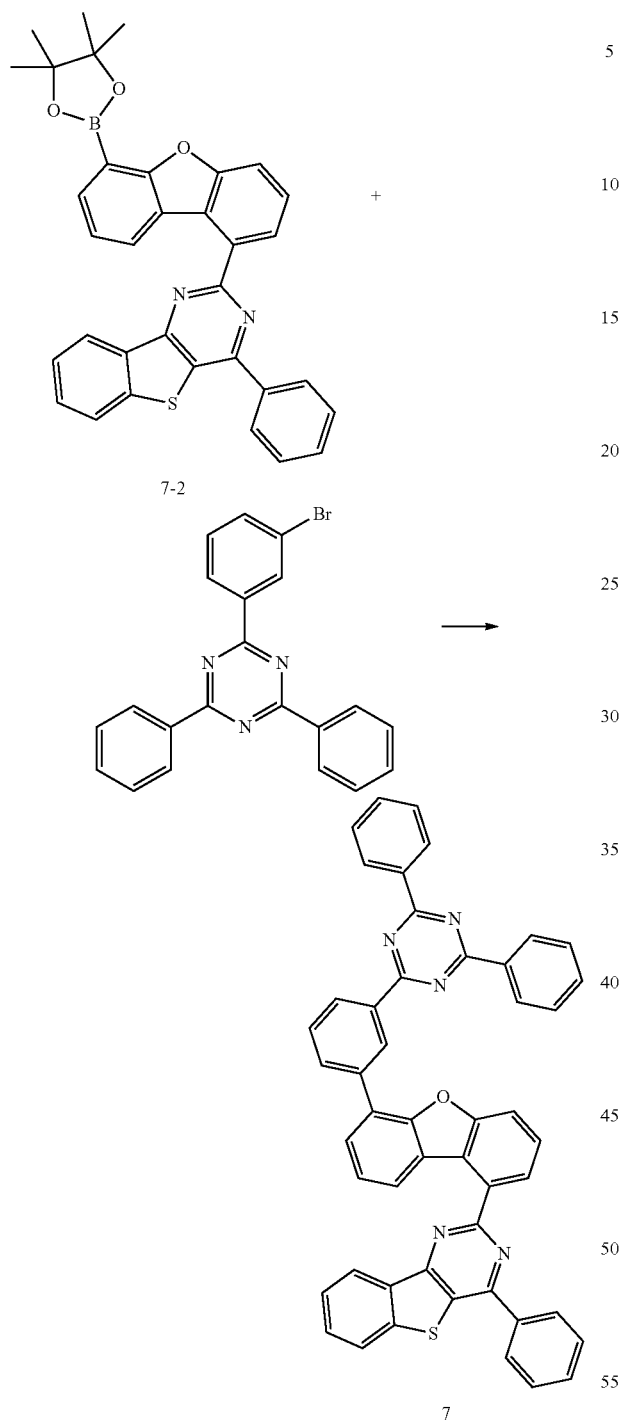

After Compound 7-2 (13.7 g, 24.7 mmol) and 2-(3-bromophenyl)-4,6-diphenyl-1,3,5-triazine (8.4 g, 24.7 mmol) were added to tetrahydrofuran. (274 ml) under a nitrogen atmosphere, and the mixture was stirred and refluxed. Then, potassium carbonate (10.3 g, 74.2 mmol) was dissolved in and added to water (10 ml), sufficiently stirred, and then bis(tri-tert-butylphosphine)palladium (0.4 g, 0.7 mmol) was added. After the reaction for 8 hours, the reaction mixture was cooled to room temperature, and the resulting solid was filtered. The solid was added to and dissolved in chloroform (364 ml), washed twice with water, and the organic layer was separated, anhydrous magnesium sulfate was added thereto, stirred and then filtered. The filtrate was distilled under reduced pressure. The concentrated compound was recrystallized from tetrahydrofuran and toluene to give a solid compound 7 (13.3 g, yield 73%, MS: $[M+H]^+$=736).

Example 8: Preparation of Compound 8

1) Preparation of Compound 8-1

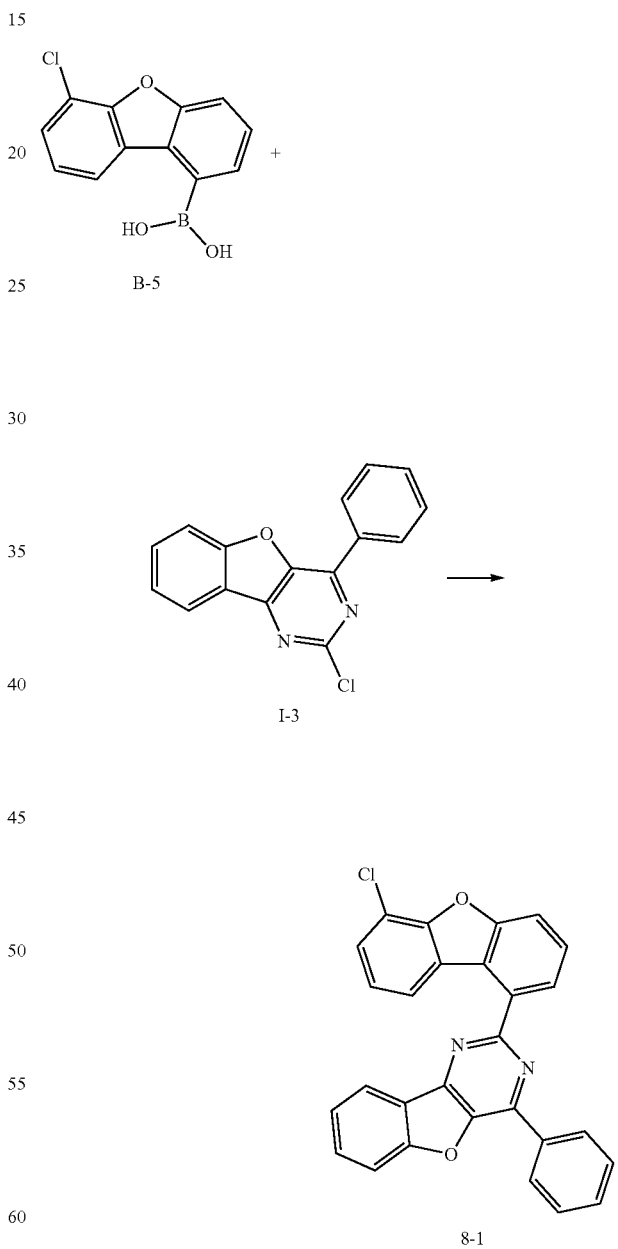

Compound 8-1 (12.7 g, yield 78%, MS:$[M+H]^+$=447) was prepared in the same manner as in the Preparation of Compound 7-1, except that Compound 1-3 was used instead of Compound I-1.

2) Preparation of Compound 8-2

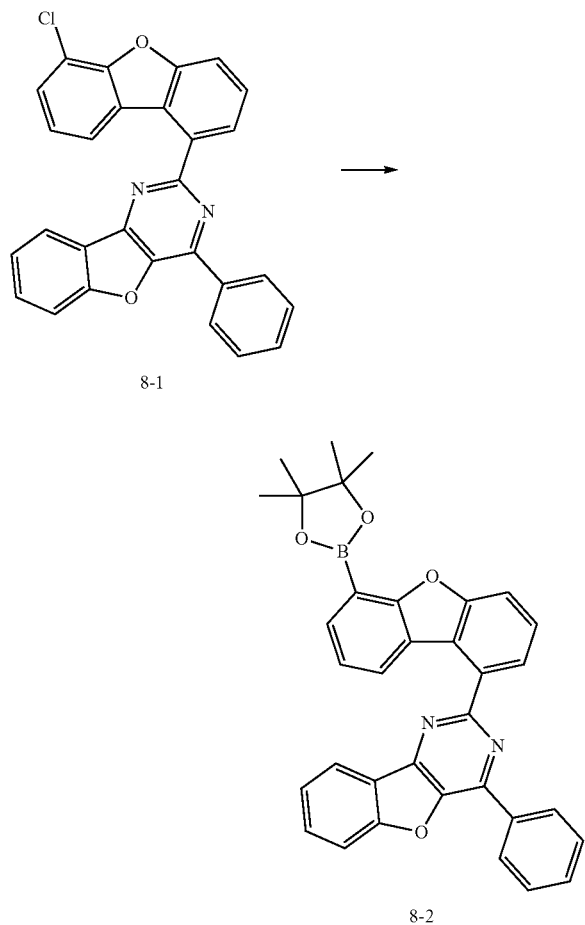

8-1

8-2

Compound 8-2 (12.0 g, yield 78%, MS:[M+H]$^+$=539) was prepared in the same manner as in the Preparation of Compound 7-2, except that Compound 8-1 was used instead of Compound 7-1.

3) Preparation of Compound 8

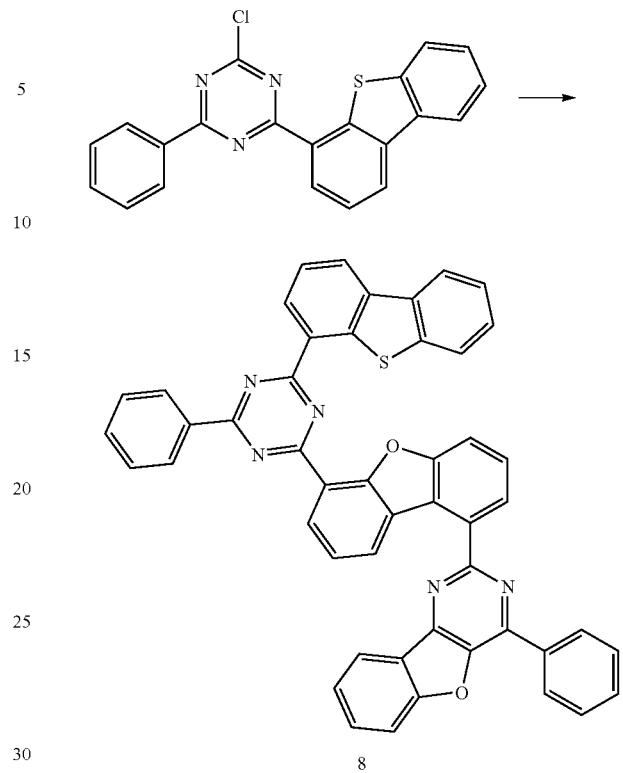

8

Compound 8 (11.3 g, yield 68%, MS:[M+H]$^+$=750) was prepared in the same manner as in the Preparation of Compound 7, except that Compound 8-2 and 2-chloro-4-(dibenzothiophen-4-yl)-6-phenyl-1,3,5-triazine were used instead of Compound 7-2 and 2-(3-bromophenyl)-4,6-diphenyl-1,3,5-triazine.

Example 9: Preparation of Compound 9

1) Preparation of Compound 9-1

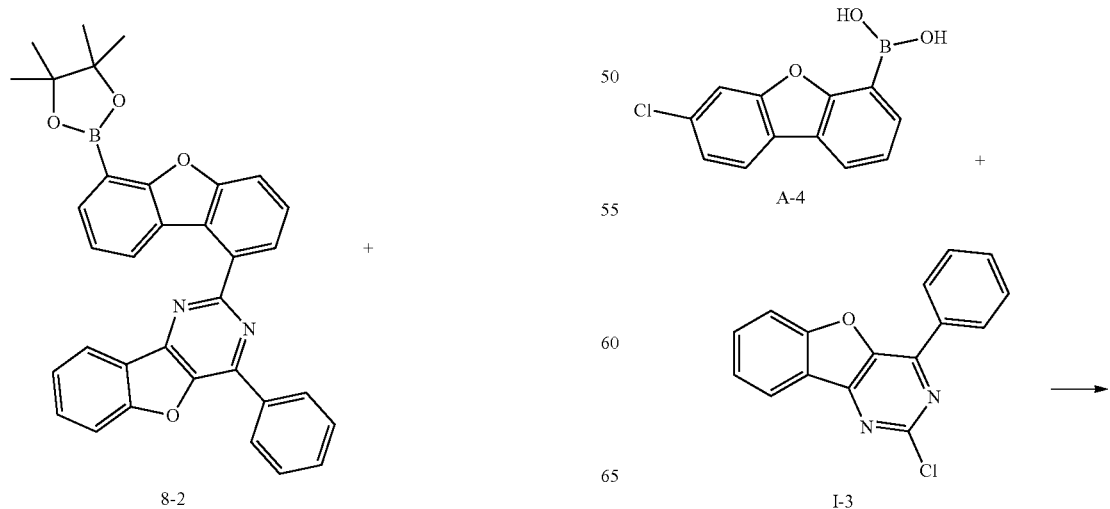

A-4

I-3

3) Preparation of Compound 9

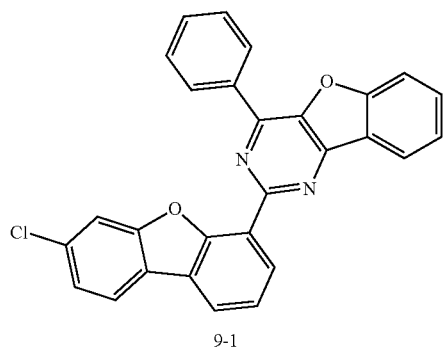

9-1

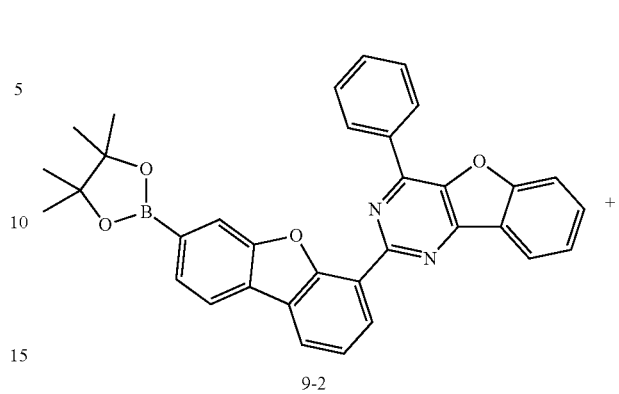

9-2

Compound 9-1 (13.4 g, yield 82%, MS:[M+H]$^+$=447) was prepared in the same manner as in the Preparation of Compound 7-1, except that Compound A-4 and Compound 1-3 were used instead of Compound B-5 and Compound I-1.

2) Preparation of Compound 9-2

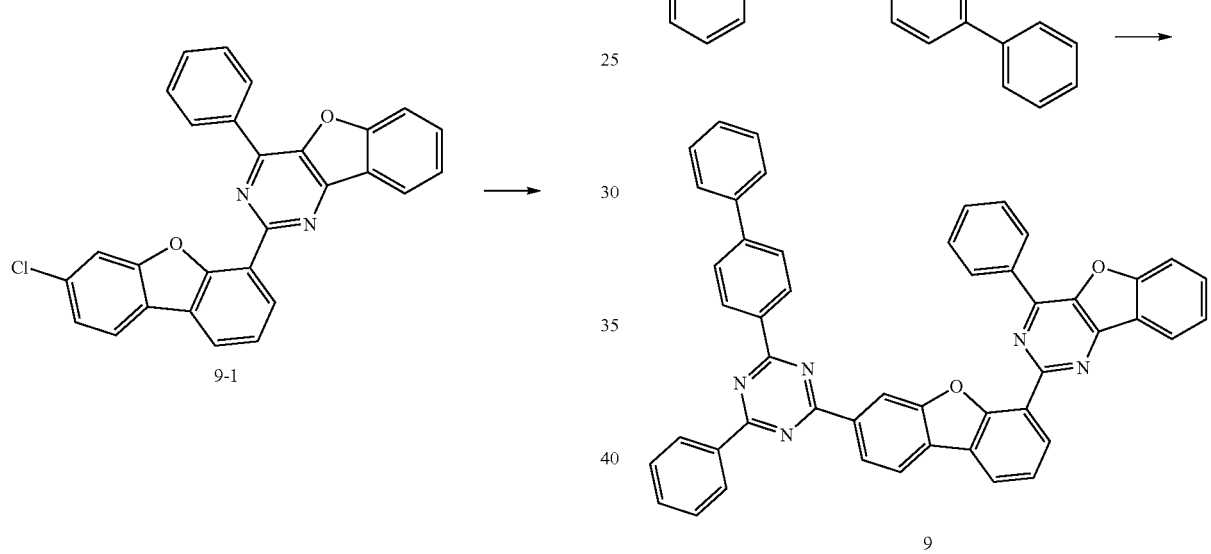

9

Compound 9 (9.5 g, yield 61%, MS:[M+H]$^+$=720) was prepared in the same manner as in the Preparation of Compound 7, except that Compound 9-2 and 2-{[1,1'-biphenyl]-4-yl}-4-chloro-6-phenyl-1,3,5-triazine were used instead of Compound 7-2 and 2-(3-bromophenyl)-4,6-diphenyl-1,3,5-triazine.

Example 10: Preparation of Compound 10

1) Preparation of Compound 10-1

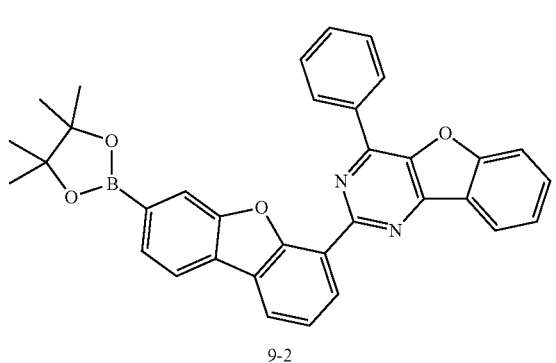

9-2

Compound 9-2 (11.6 g, yield 72%, MS:[M+H]$^+$=539) was prepared in the same manner as in the Preparation of Compound 7-2, except that Compound 9-1 was used instead of Compound 7-1.

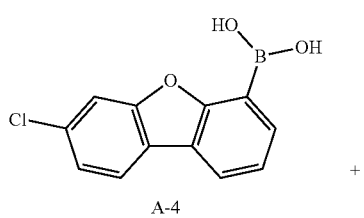

A-4

-continued

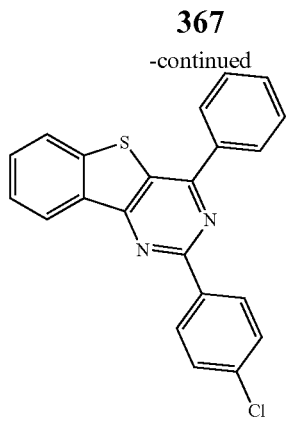

I-4

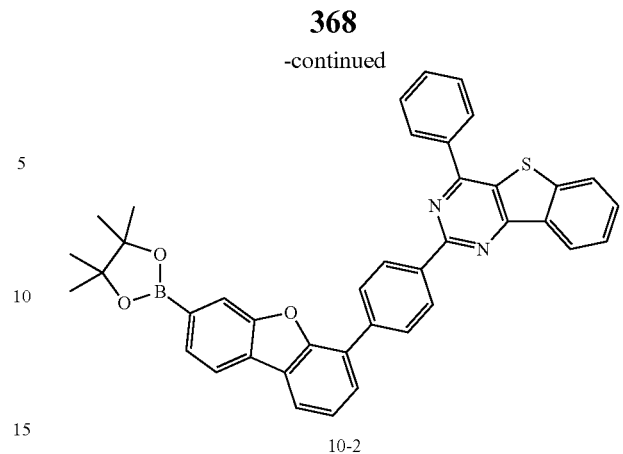

10-2

Compound 10-2 (13.4 g, yield 74%, MS:[M+H]$^+$=631) was prepared in the same manner as in the Preparation of Compound 7-2, except that Compound 10-1 was used instead of Compound 7-1.

3) Preparation of Compound 10

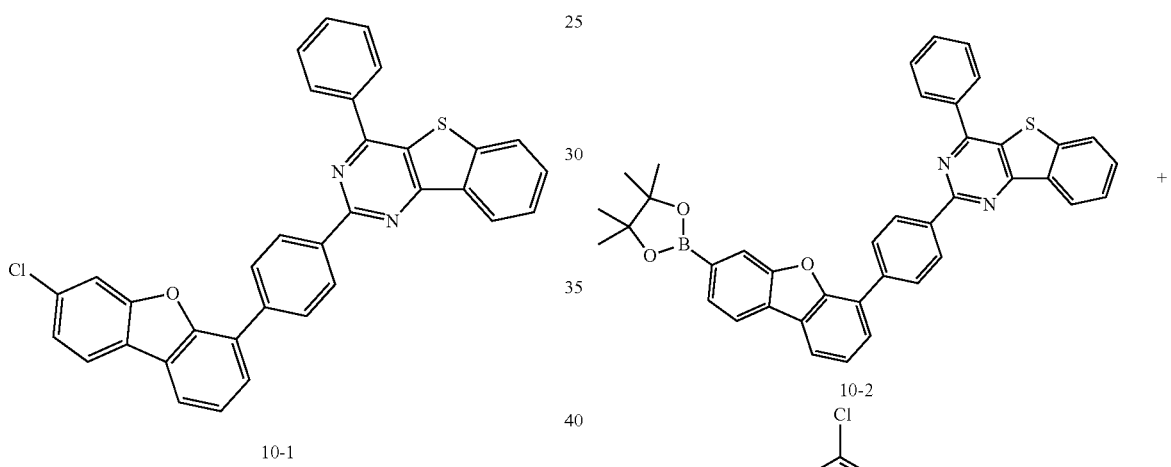

10-1

Compound 10-1 (15.5 g, yield 79%, MS:[M+H]$^+$=539) was prepared in the same manner as in the Preparation of Compound 7-1, except that Compound A-4 and Compound I-4 were used instead of Compound B-5 and Compound I-1.

2) Preparation of Compound 10-2

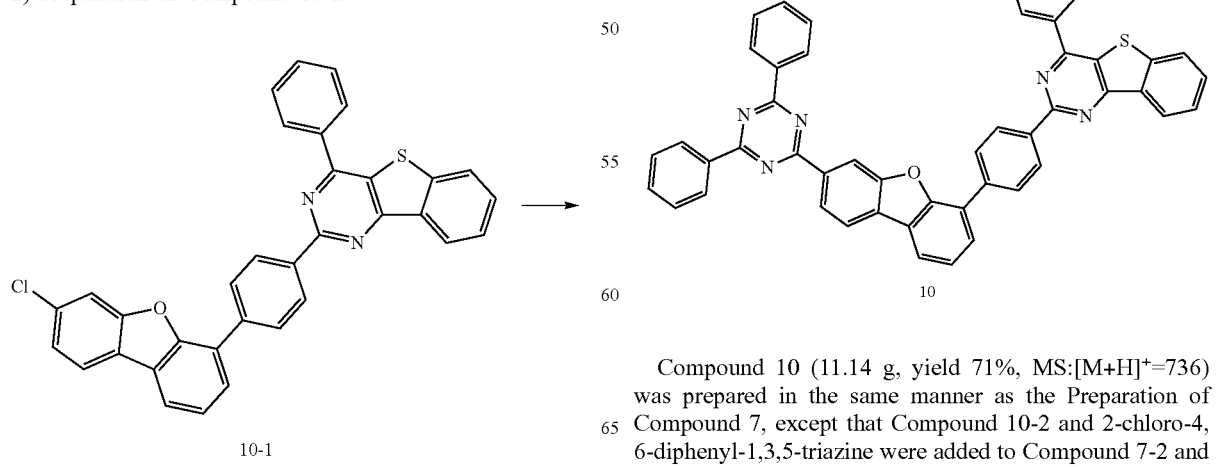

10

Compound 10 (11.14 g, yield 71%, MS:[M+H]$^+$=736) was prepared in the same manner as the Preparation of Compound 7, except that Compound 10-2 and 2-chloro-4,6-diphenyl-1,3,5-triazine were added to Compound 7-2 and 2-(3-bromophenyl)-4,6-diphenyl-1,3,5-triazine.

Example 11: Preparation of Compound 11

1) Preparation of Compound 11-1

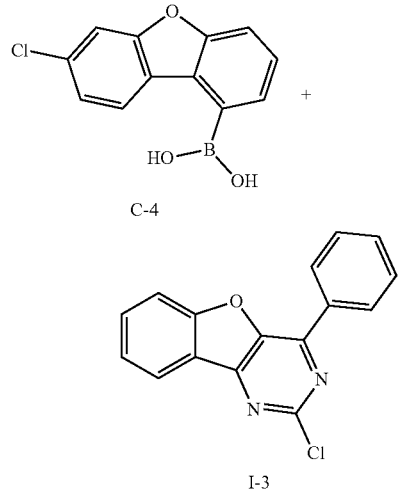

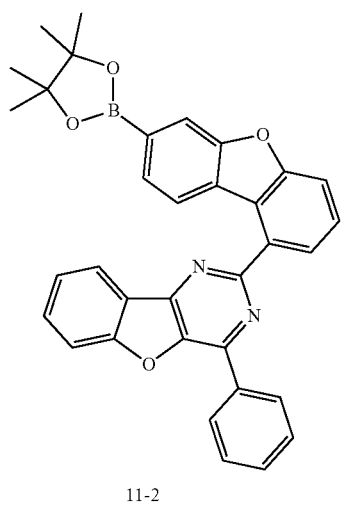

Compound 11-2 (14.0 g, yield 80%, MS:[M+H]$^+$=539) was prepared in the same manner as in the Preparation of Compound 7-2, except that compound 11-1 was used instead of compound 7-1.

3) Preparation of Compound 11

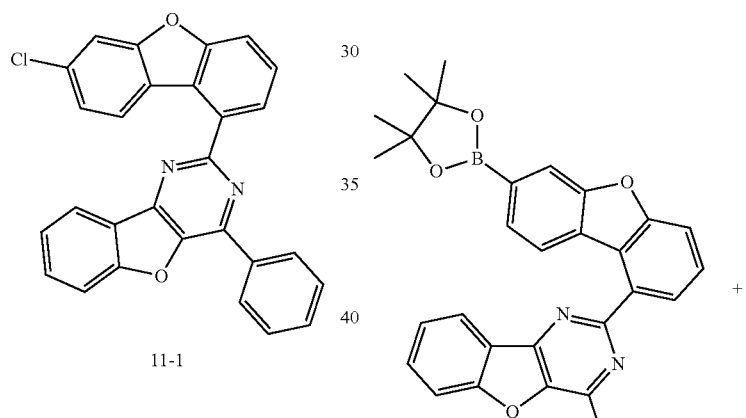

Compound 11-1 (14.5 g, yield 89%, MS:[M+H]$^+$=447) was prepared in the same manner as in the Preparation of Compound 7-1, except that Compound C-4 and Compound I-3 were used instead of Compound B-5 and Compound I-1.

2) Preparation of Compound 11-2

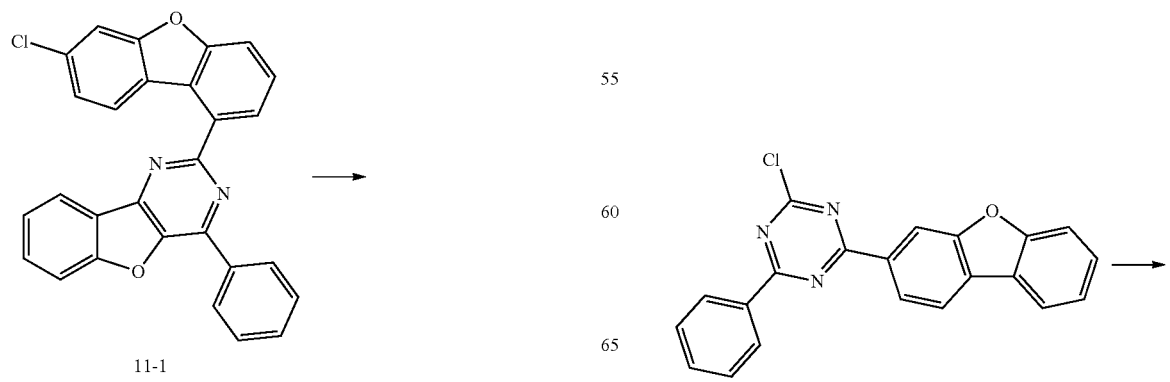

-continued

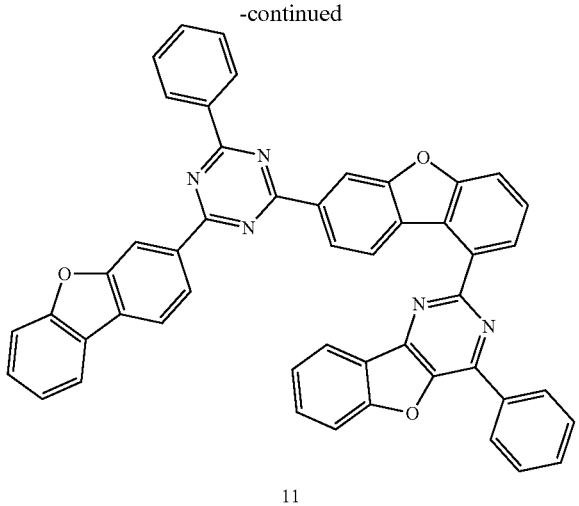

11

Compound 11 (10.5 g, yield 55%, MS:[M+H]$^+$=734) was prepared in the same manner as in the Preparation of Compound 7, except that Compound 11-2 and 2-chloro-4-(dibenzofuran-3-yl)-6-phenyl-1,3,5-triazine were used instead of Compound 7-2 and 2-(3-bromophenyl)-4,6-diphenyl-1,3,5-triazine.

Example 12: Preparation of Compound 12

1) Preparation of Compound 12-1

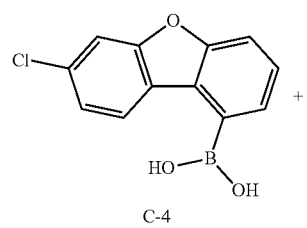
C-4

+

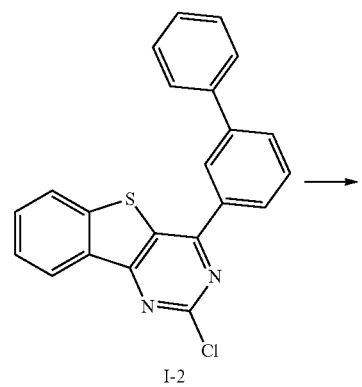
I-2

→

-continued

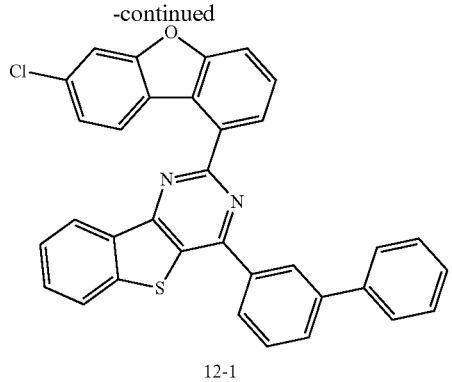
12-1

Compound 12-1 (14.9 g, yield 77%, MS:[M+H]$^+$=539) was prepared in the same manner as in the Preparation of Compound 7-1, except that Compound C-4 and Compound 1-2 were used instead of Compound B-5 and Compound I-1.

2) Preparation of Compound 12-2

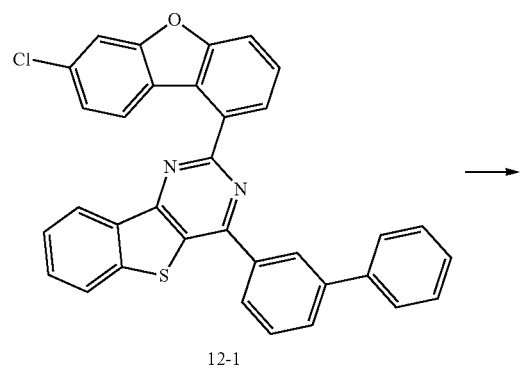
12-1

→

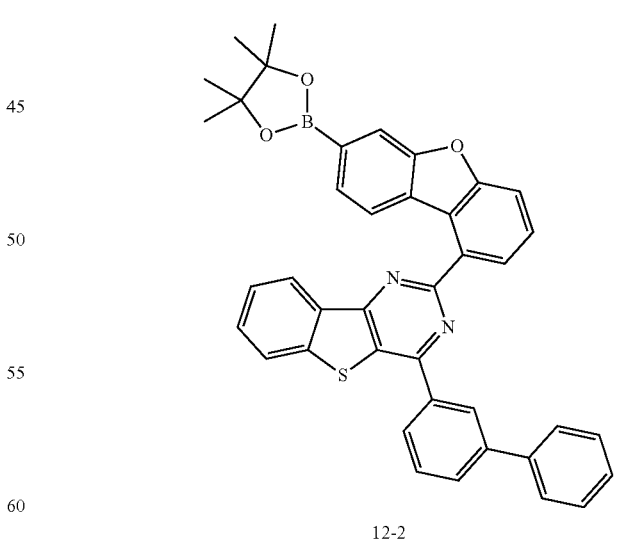
12-2

Compound 12-2 (12.2 g, yield 70%, MS:[M+H]$^+$=631) was prepared in the same manner as in the Preparation of Compound 7-2, except that Compound 12-1 was used instead of Compound 7-1.

3) Preparation of Compound 12

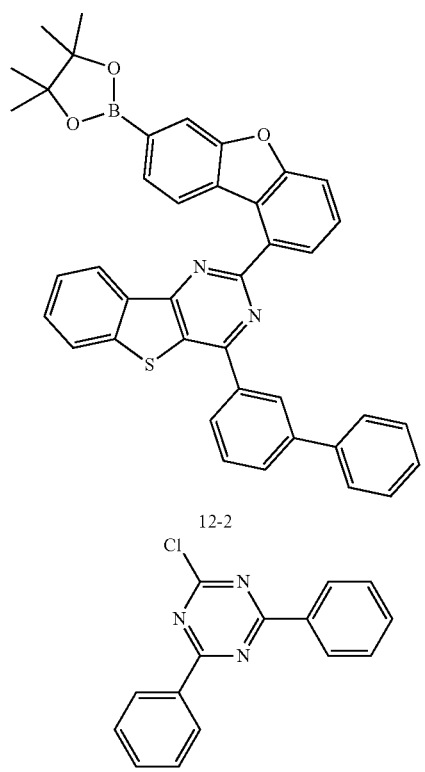

12-2

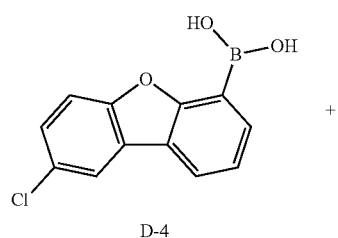

12

Compound 12 (9.0 g, yield 63%, MS:[M+H]$^+$=736) was prepared in the same manner as in the Preparation of Compound 7, except that Compound 12-2 and 2-chloro-4,6-diphenyl-1,3,5-triazine were used instead of Compound 7-2 and 2-(3-bromophenyl)-4,6-diphenyl-1,3,5-triazine.

Example 13: Preparation of Compound 13

1) Preparation of Compound 13-1

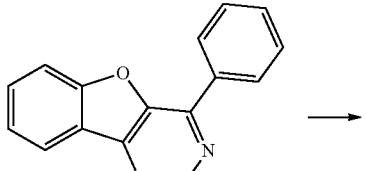

D-4

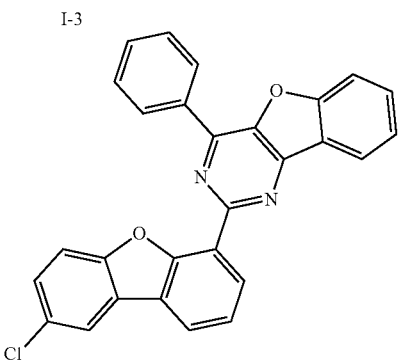

I-3

13-1

Compound 13-1 (12.7 g, yield 78%, MS:[M+H]$^+$=447) was prepared in the same manner as in the Preparation of Compound 7-1, except that Compound D-4 and Compound I-3 were used instead of Compound B-5 and Compound I-1.

2) Preparation of Compound 13-2

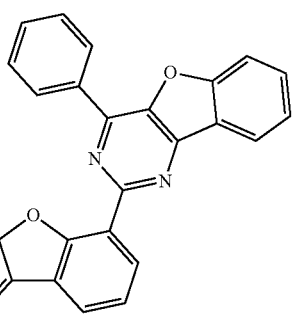

13-1

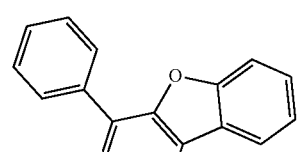

13-2

Compound 13-2 (11.2 g, yield 73%, MS:[M+H]$^+$=539) was prepared in the same manner as in the Preparation of Compound 7-2, except that Compound 13-1 was used instead of Compound 7-1.

3) Preparation of Compound 13

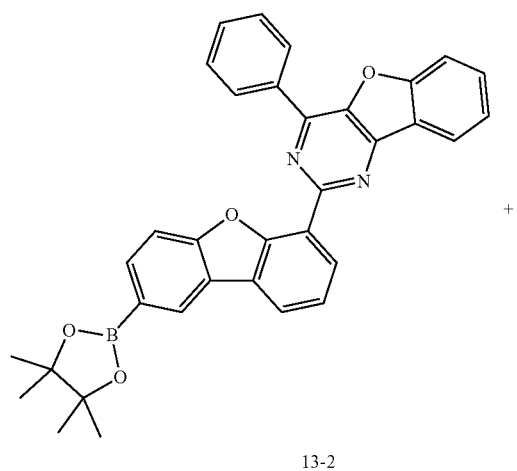

13-2

13

Compound 13 (11.1 g, yield 73%, MS:[M+H]$^+$=734) was prepared in the same manner as in the Preparation of Compound 7, except that Compound 13-2 and 2-chloro-4-(dibenzofuran-2-yl)-6-phenyl-1,3,5-triazine were used instead of Compound 7-2 and 2-(3-bromophenyl)-4,6-diphenyl-1,3,5-triazine.

Example 14: Preparation of Compound 14

1) Preparation of Compound 14-1

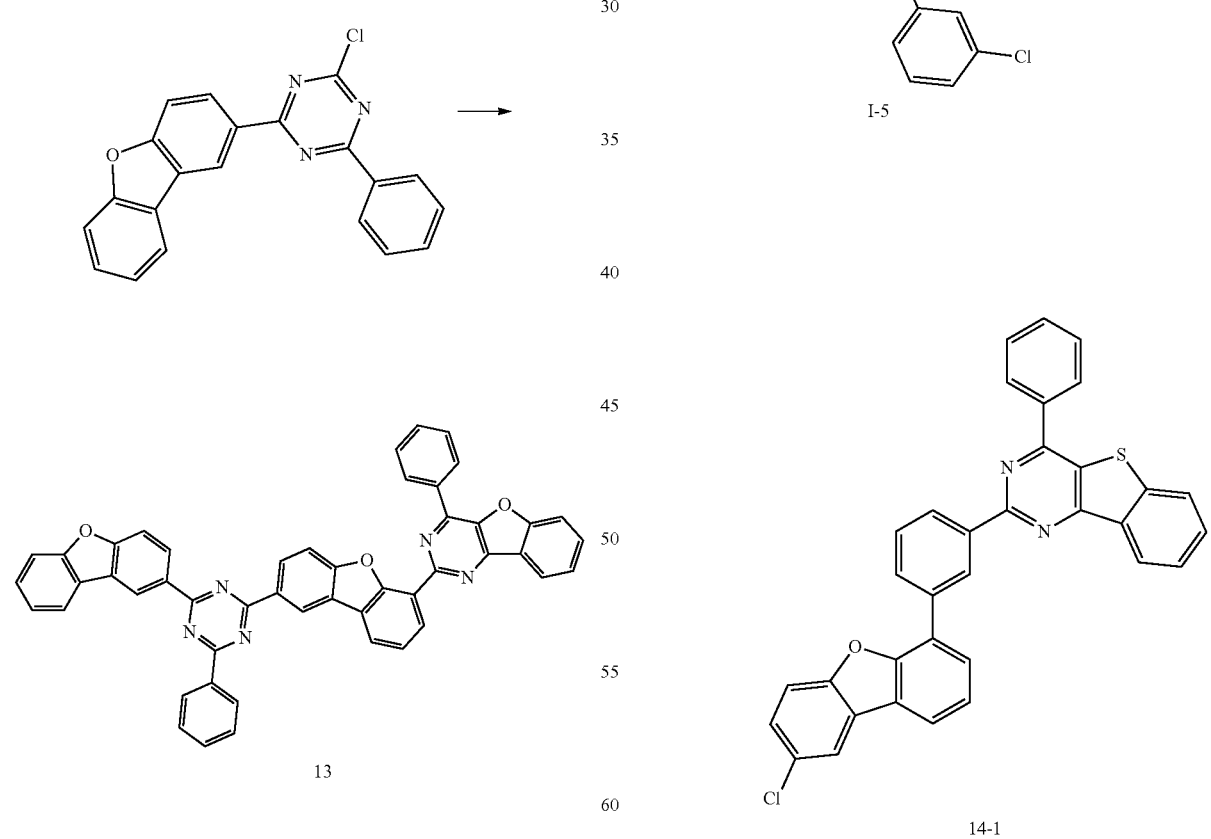

D-4

I-5

14-1

Compound 14-1 (14.3 g, yield 73%, MS:[M+H]$^+$=539) was prepared in the same manner as in the Preparation of Compound 7-1, except that Compound D-4 and Compound I-5 were used instead of Compound B-5 and Compound I-1.

2) Preparation of Compound 14-2

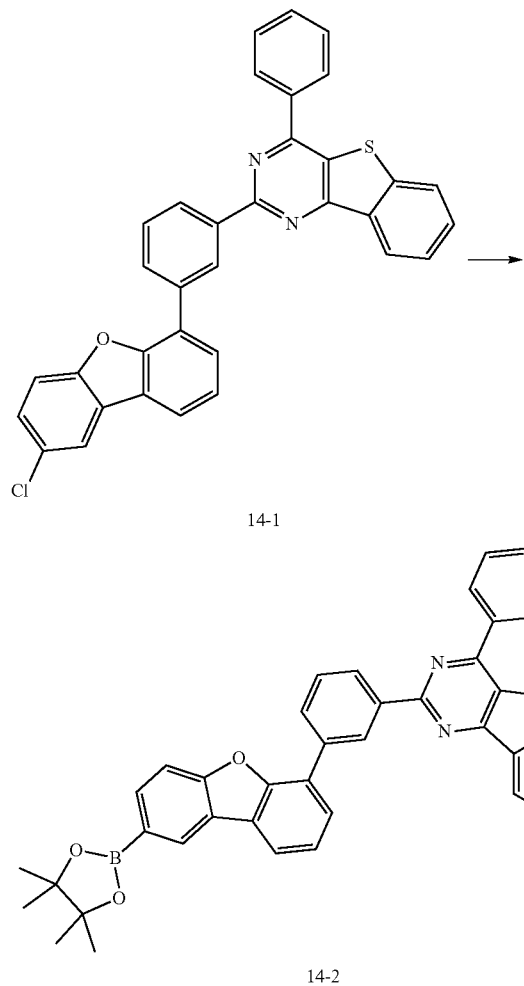

14-1

14-2

Compound 14-2 (12.1 g, yield 72%, MS:[M+H]$^+$=631) was prepared in the same manner as the Preparation of Compound 7-2, except that Compound 14-1 was used instead of Compound 7-1.

3) Preparation of Compound 14

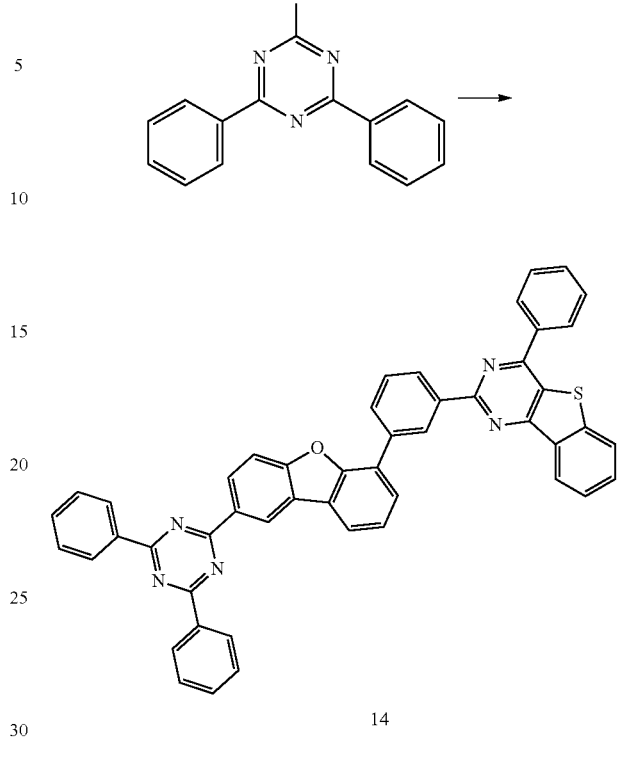

14

Compound 14 (8.5 g, yield 60%, MS:[M+H]$^+$=736) was prepared in the same manner as in the Preparation of Compound 7, except that Compound 14-2 and 2-chloro-4,6-diphenyl-1,3,5-triazine were used instead of Compound 7-2 and 2-(3-bromophenyl)-4,6-diphenyl-1,3,5-triazine.

Example 15: Preparation of Compound 15

1) Preparation of Compound 15-1

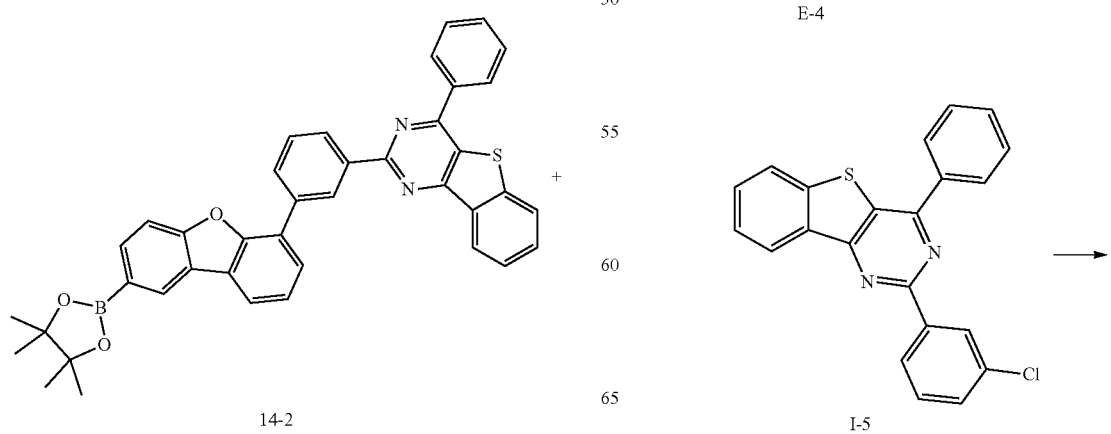

E-4

I-5

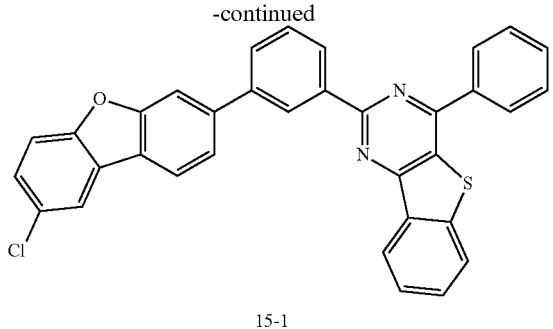

15-1

Compound 15-1 (14.7 g, yield 75%, MS:[M+H]$^+$=539) was prepared in the same manner as the Preparation of Compound 7-1, except that Compound E-4 and Compound 1-5 were used instead of Compound B-5 and Compound I-1.

2) Preparation of Compound 15-2

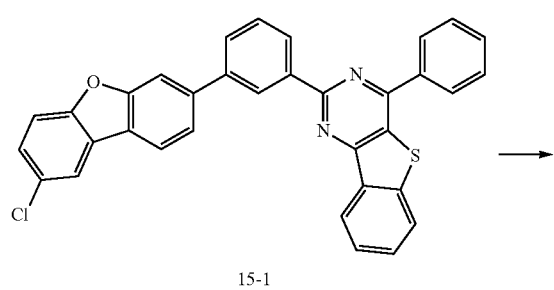

15-1

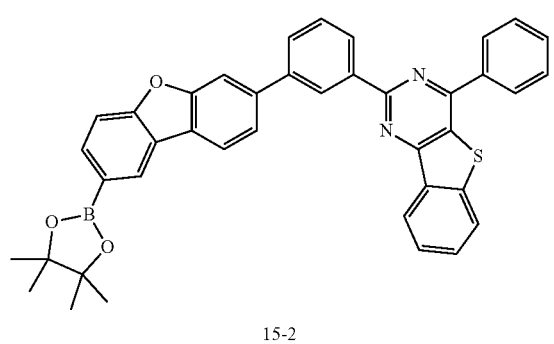

15-2

Compound 15-2 (13.1 g, yield 76%, MS:[M+H]$^+$=631) was prepared in the same manner as the Preparation of Compound 7-2, except that Compound 15-1 was used instead of Compound 7-1.

3) Preparation of Compound 15

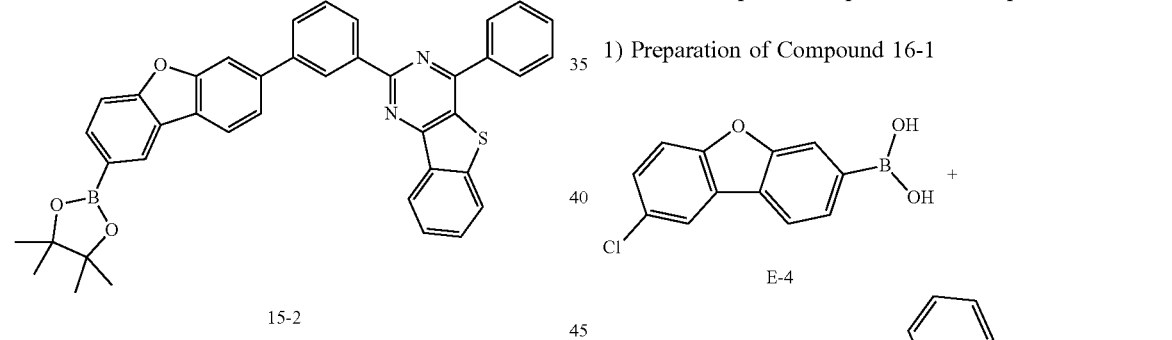

15-2

Compound 15 (7.8 g, yield 51%, MS:[M+H]$^+$=736) was prepared in the same manner as in the Preparation of Compound 7, except that Compound 15-2 and 2-chloro-4,6-diphenyl-1,3,5-triazine were used instead of Compound 7-2 and 2-(3-bromophenyl)-4,6-diphenyl-1,3,5-triazine.

Example 16: Preparation of Compound 16

1) Preparation of Compound 16-1

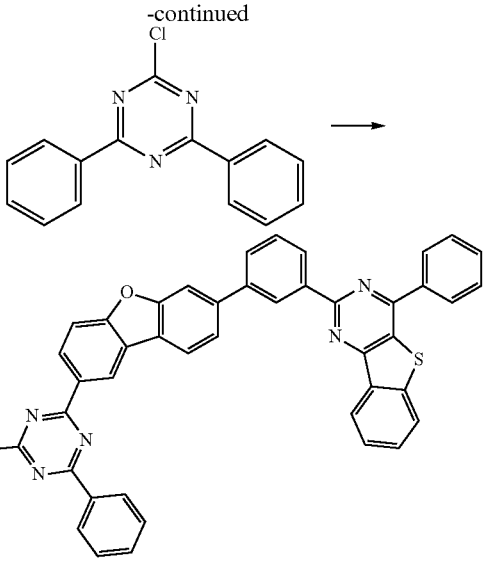

E-4

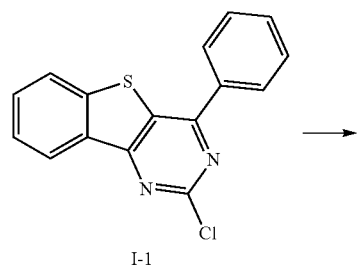

I-1

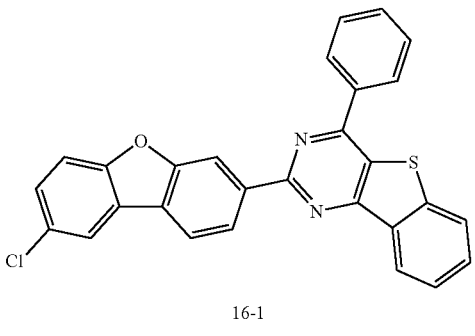

16-1

Compound 16-1 (12.0 g, yield 70%, MS:[M+H]$^+$=463) was prepared in the same manner as in the Preparation of Compound 7-1, except that Compound E-4 was used instead of Compound B-5.

2) Preparation of Compound 16-2

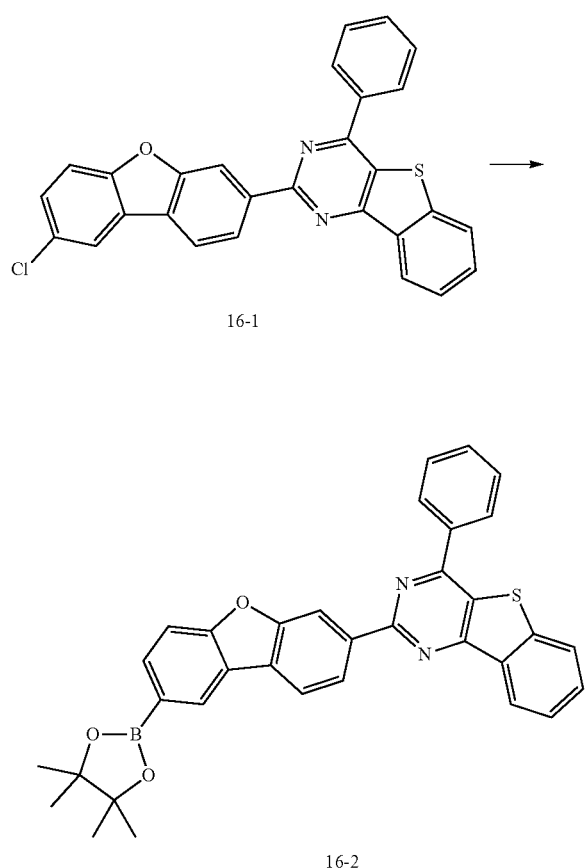

16-1

16-2

Compound 16-2 (9.2 g, yield 64%, MS:[M+H]$^+$=555) was prepared in the same manner as in the Preparation of Compound 7-2, except that Compound 16-1 was used instead of Compound 7-1.

3) Preparation of Compound 16

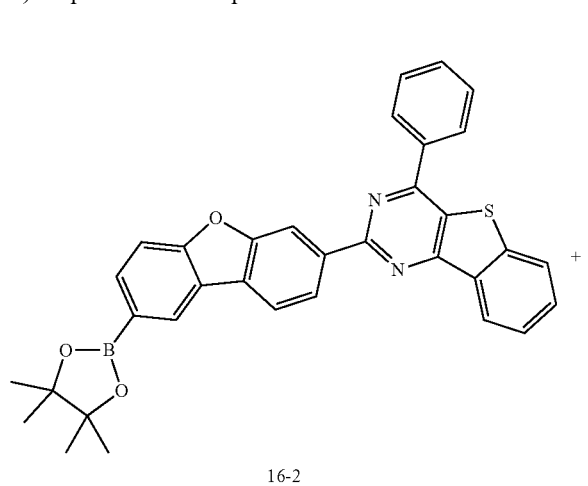

16-2

-continued

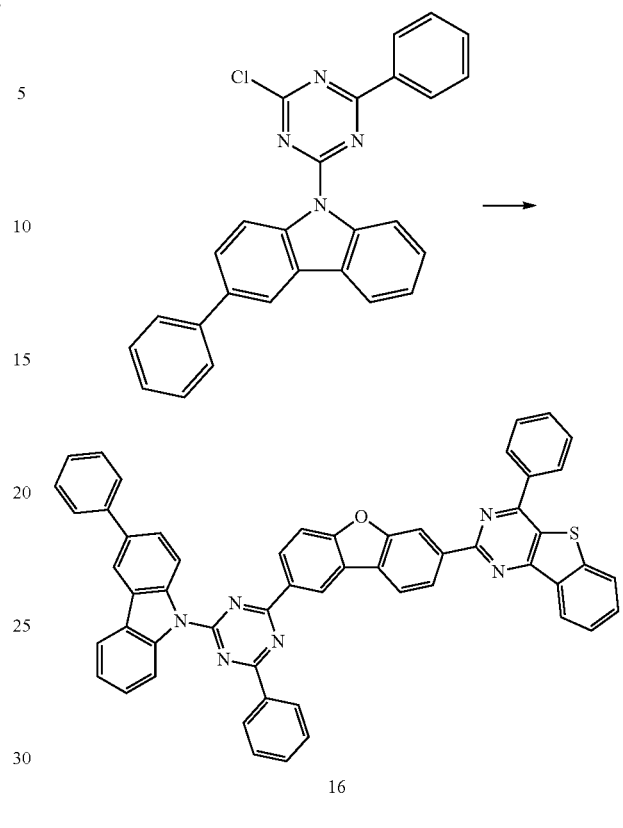

16

Compound 16 (7.5 g, yield 55%, MS:[M+H]$^+$=824) was prepared in the same manner as in the Preparation of Compound 7, except that Compound 16-2 and 9-(4-chloro-6-phenyl-1,3,5-triazine-2-yl)-3-phenyl-9H-carbazole were used instead of Compound 7-2 and 2-(3-bromophenyl)-4,6-diphenyl-1,3,5-triazine.

Example 17: Preparation of Compound 17

1) Preparation of Compound 17-1

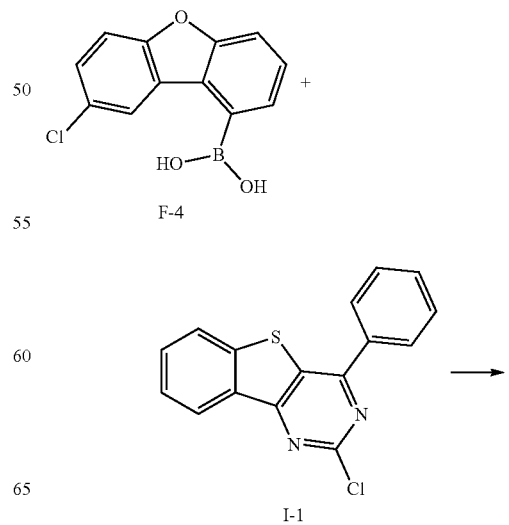

F-4

I-1

383

-continued

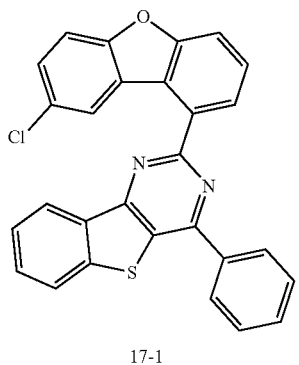

17-1

Compound 17-1 (13.0 g, yield 77%, MS:[M+H]⁺=463) was prepared in the same manner as the Preparation of Compound 7-1, except that Compound F-4 was used instead of compound B-5.

2) Preparation of Compound 17-2

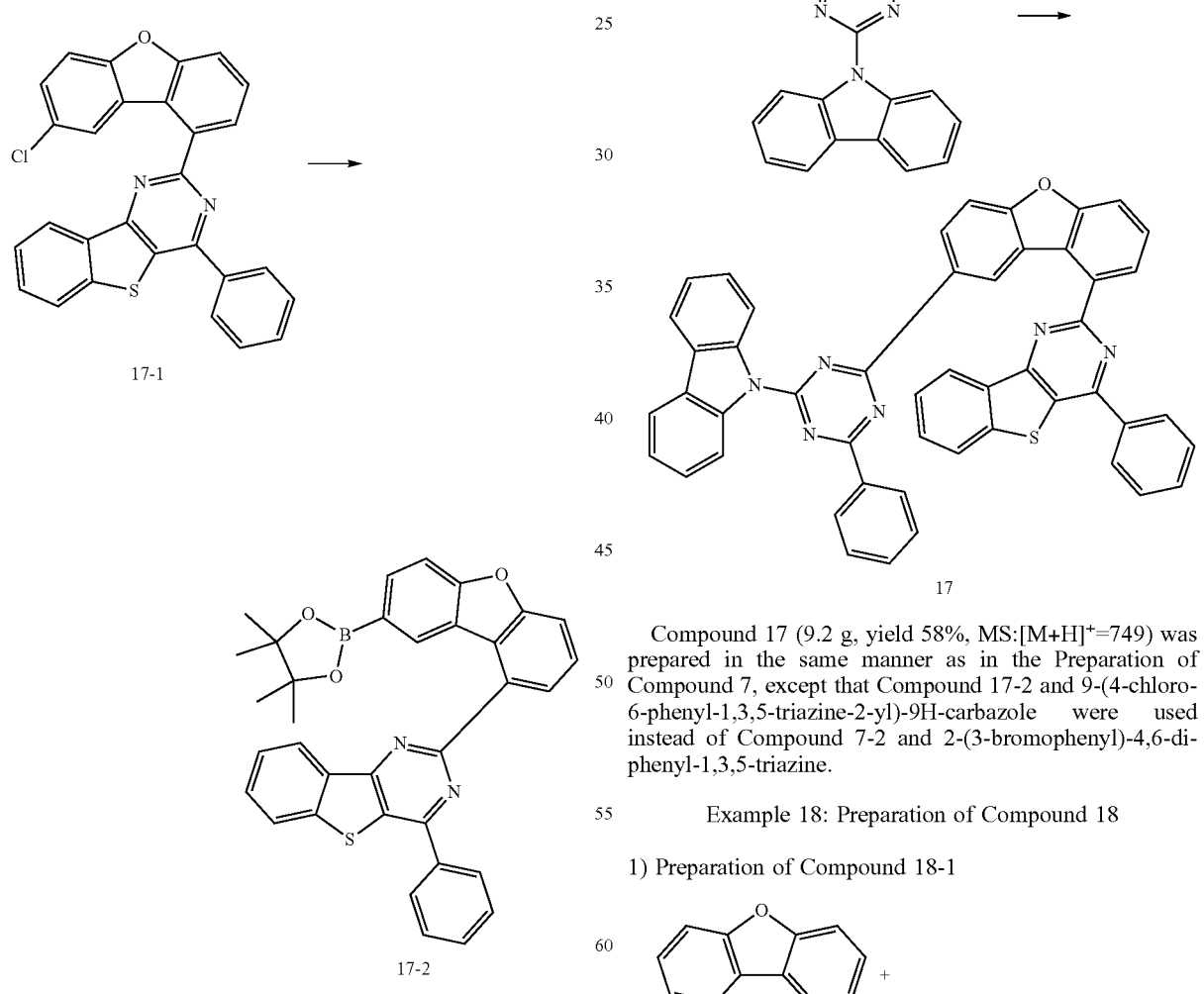

17-1

17-2

Compound 17-2 (11.8 g, yield 76%, MS:[M+H]⁺=555) was prepared in the same manner as in the Preparation of Compound 7-2, except that Compound 17-1 was used instead of Compound 7-1.

384

3) Preparation of Compound 17

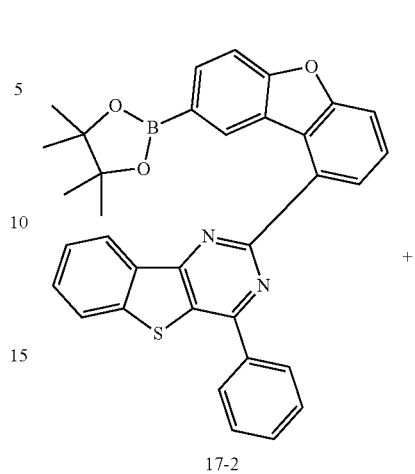

17-2

+

17

Compound 17 (9.2 g, yield 58%, MS:[M+H]⁺=749) was prepared in the same manner as in the Preparation of Compound 7, except that Compound 17-2 and 9-(4-chloro-6-phenyl-1,3,5-triazine-2-yl)-9H-carbazole were used instead of Compound 7-2 and 2-(3-bromophenyl)-4,6-diphenyl-1,3,5-triazine.

Example 18: Preparation of Compound 18

1) Preparation of Compound 18-1

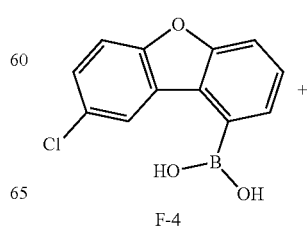

F-4

-continued

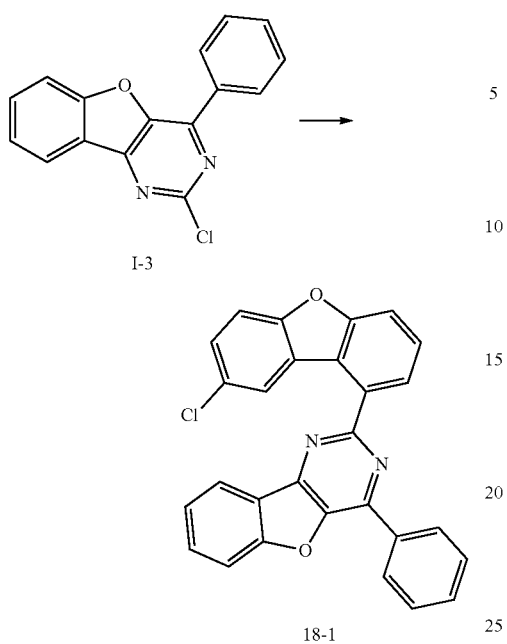
I-3

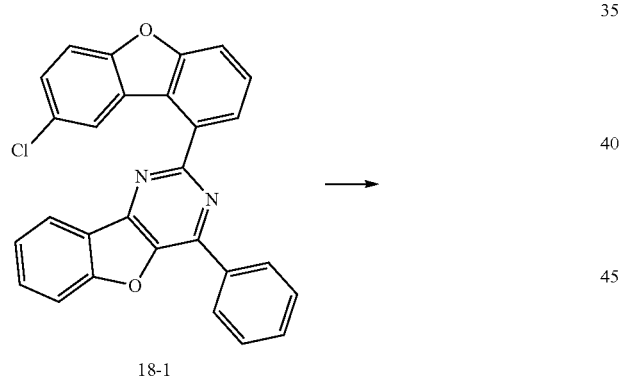
18-1

Compound 18-1 (12.9 g, yield 79%, MS:[M+H]⁺=447 was prepare in the same manner as in the Preparation of Compound 7-1, except that Compound F-4 and Compound I-3 were used instead of Compound B-5 and Compound 1-1.

2) Preparation of Compound 18-2

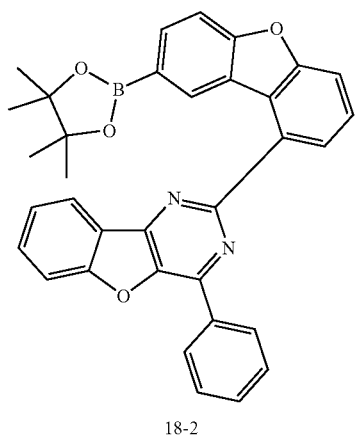
18-2

Compound 18-2 (12.4 g, yield 80%, MS:[M+H]⁺=539) was prepared in the same manner as in the Preparation of Compound 7-2, except that Compound 18-1 was used instead of Compound 7-1.

3) Preparation of Compound 18

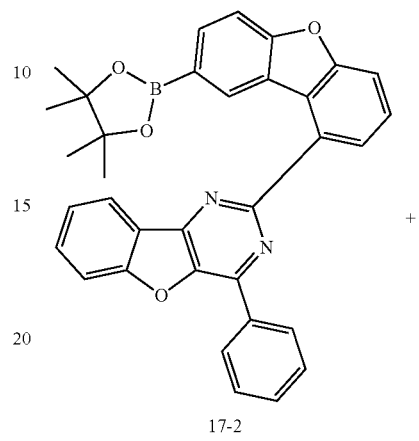
17-2

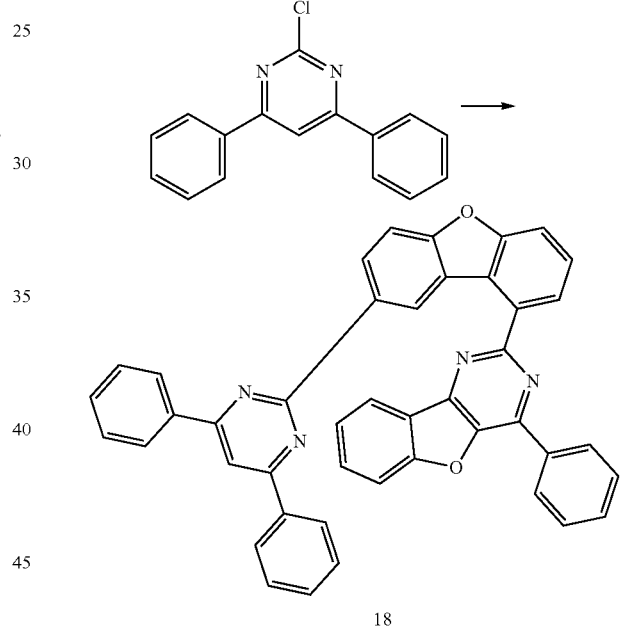
18

Compound 18 (9.0 g, yield 61%, MS:[M+H]₊=643) was prepared in the same manner as in the Preparation of Compound 7, except that Compound 18-2 and 2-chloro-4,6-diphenylpyrimidine were used instead of Compound 7-2 and 2-(3-bromophenyl)-4,6-diphenyl-1,3,5-triazine.

Experimental Examples

Experimental Example 1

A glass substrate coated with a thin film of ITO (indium tin oxide) in a thickness of 1,300 Å was put into distilled water containing the detergent dissolved therein and washed by the ultrasonic wave. In this case, the detergent which is a product commercially available from Fisher Co. was used, and the distilled water which had been twice filtered by a filter commercially available from Millipore Co. was used. The ITO was washed for 30 minutes, and ultrasonic washing was then repeated twice for 10 minutes by using the distilled water. After washing with the distilled water, the substrate was washed by ultrasonic washing with solvents of isopropyl alcohol, acetone, and methanol, then was dried and transported to a plasma cleaner. Then, the substrate was cleaned with oxygen plasma for 5 minutes, and then transferred to a vacuum evaporator.

On the ITO transparent electrode thus prepared, a compound HI-A below was thermal vacuum-deposited to a thickness of 100 Å to form a hole injection layer. Then, only a compound HT-A below was thermal vacuum-deposited to a thickness of 800 Å, and sequentially a compound HT-B below was vacuum-deposited to a thickness of 500 Å to form a hole transport layer. Then, a compound 1 as a first host of the light emitting layer and a compound H1 below as a second host in the weight ratio of 40:60, and 6 wt % of a compound GD below based on the sum of the weight of the first and second host were vacuum-deposited to a thickness of 350 Å. Then, a compound ET-A below was vacuum-deposited to a thickness of 50 Å to form a hole blocking layer. Then, a compound ET-B below and Liq were thermal vacuum-deposited in a ratio of 1:1 to a thickness of 250 Å and LiF was subsequently vacuum-deposited to a thickness of 30 Å, to form an electron transport and injection layer. Aluminum was deposited to a thickness of 1000 Å on the electron transport and injection layer to form a cathode, thereby an organic light emitting device was prepared.

HI-A

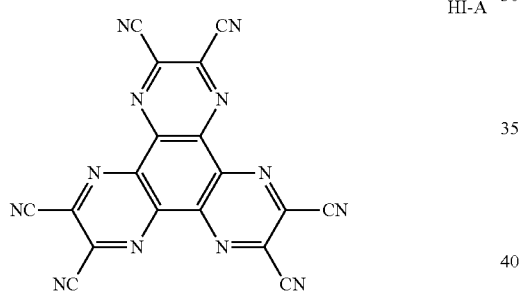

HT-A

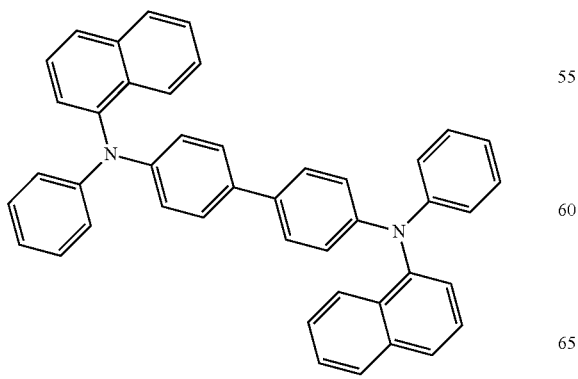

HT-B

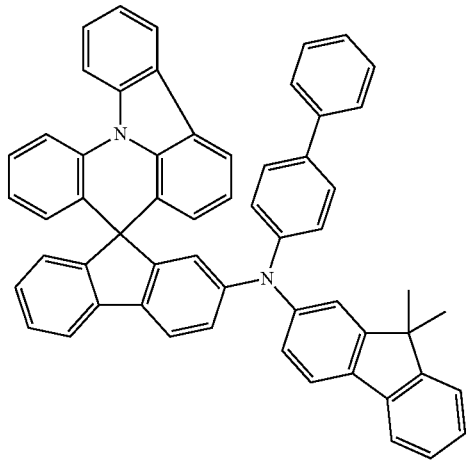

-continued

H1

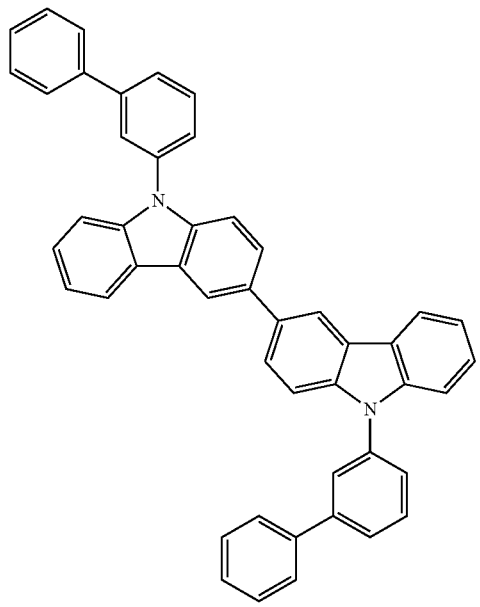

GD

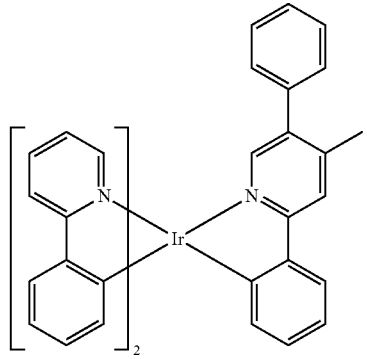

ET-A

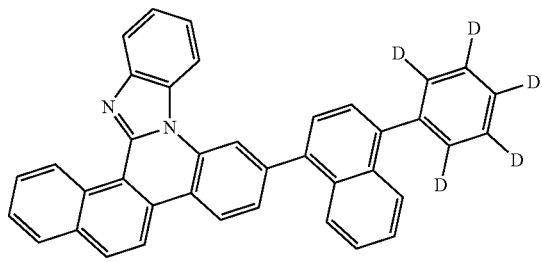

ET-B

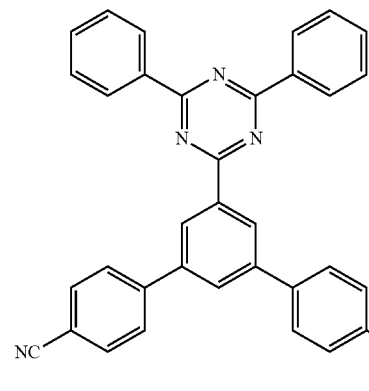

Liq

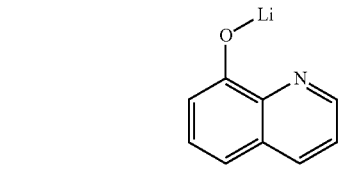

Experimental Examples 2 to 18 and Comparative Examples 1 to 2

The organic light emitting devices of Experimental Examples 2 to 18 and Comparative Examples 1 to 2 were manufactured in the same manner as in Experimental Example 1, except that the host materials were changed as shown in Table 1 below.

C1

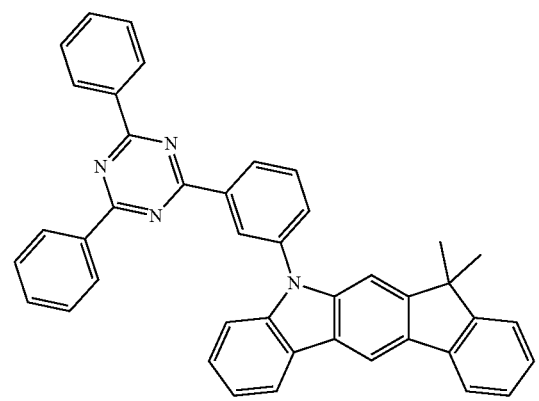

C2

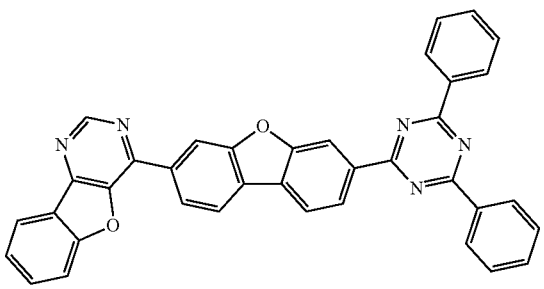

The voltage, efficiency and lifetime ($T_{95}$) were measured by applying a current to the organic light emitting devices manufactured in Experimental Examples 1 to 18 and Comparative Examples 1 to 2, and the results are shown in Table 1 below. At this time, the voltage and efficiency were measured by applying a current density of 10 mA/cm$^2$, and the lifetime was measured by applying a current density of 50 mA/cm$^2$. At this time, $T_{95}$ means the time required for the luminance to be reduced to 95% of the initial luminance at a current density of 50 mA/cm$^2$.

TABLE 1

| | Host material | Voltage (V, @ 10 mA/cm$^2$) | Efficiency (cd/A, @ 10 mA/cm$^2$) | Lifetime ($T_{95}$, hr, @ 50 mA/cm$^2$) |
|---|---|---|---|---|
| Experimental Example 1 | Compound 1 | 4.0 | 68 | 78 |
| Experimental Example 2 | Compound 2 | 4.1 | 71 | 75 |
| Experimental Example 3 | Compound 3 | 4.4 | 76 | 70 |
| Experimental Example 4 | Compound 4 | 4.4 | 77 | 71 |
| Experimental Example 5 | Compound 5 | 4.2 | 74 | 73 |
| Experimental Example 6 | Compound 6 | 4.4 | 76 | 77 |
| Experimental Example 7 | Compound 7 | 4.1 | 71 | 80 |
| Experimental Example 8 | Compound 8 | 4.0 | 74 | 78 |
| Experimental Example 9 | Compound 9 | 4.0 | 71 | 95 |
| Experimental Example 10 | Compound 10 | 4.1 | 74 | 93 |
| Experimental Example 11 | Compound 11 | 4.2 | 74 | 91 |
| Experimental Example 12 | Compound 12 | 4.2 | 77 | 95 |
| Experimental Example 13 | Compound 13 | 4.1 | 73 | 92 |
| Experimental Example 14 | Compound 14 | 4.2 | 75 | 95 |
| Experimental Example 15 | Compound 15 | 4.2 | 71 | 87 |
| Experimental Example 16 | Compound 16 | 4.2 | 72 | 90 |
| Experimental Example 17 | Compound 17 | 4.1 | 70 | 93 |
| Experimental Example 18 | Compound 18 | 4.2 | 68 | 81 |
| Comparative Example 1 | Compound C1 | 4.4 | 62 | 65 |
| Comparative Example 2 | Compound C2 | 4.8 | 55 | 57 |

As shown in Table 1, it can be seen that when an organic light emitting device is manufactured by using the compound according to the present disclosure as a host of the light emitting layer, it exhibits excellent performance in terms of voltage, efficiency and lifetime as compared with the organic light emitting device of Comparative Examples.

In particular, it was confirmed that the organic light emitting devices according to Experimental Examples have the characteristics of low voltage, high efficiency, and long lifetime, as they exhibit the voltage reduced by up to 9%, the efficiency increased by up to 24%, and the lifetime increased by from 20% up to 45%, as compared with the organic light emitting device according to Comparative Example 1 using the compound C1 which is a commonly used fluorescent host material.

In addition, comparing the compound C2 according to Comparative Example 2 and the compound of the present disclosure, it can be seen that the compound of the present invention disclosure exhibits excellent performance in terms of driving voltage and efficiency.

DESCRIPTION OF SYMBOLS

1: substrate
2: anode
3: light emitting layer
4: cathode
5: hole injection layer
6: hole transport layer
7: electron blocking layer
8: electron transport and injection layer

The invention claimed is:

1. A compound of the following Chemical Formulas 1-1 to 1-7:

Chemical Formula 1-1

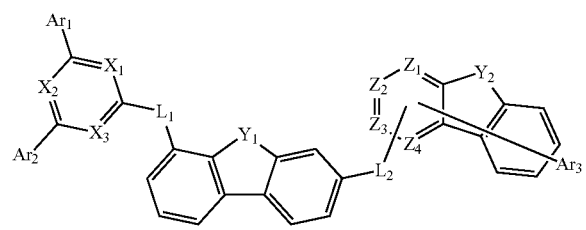

Chemical Formula 1-2

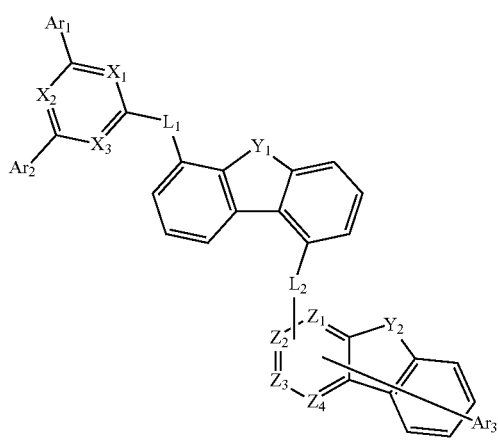

Chemical Formula 1-3

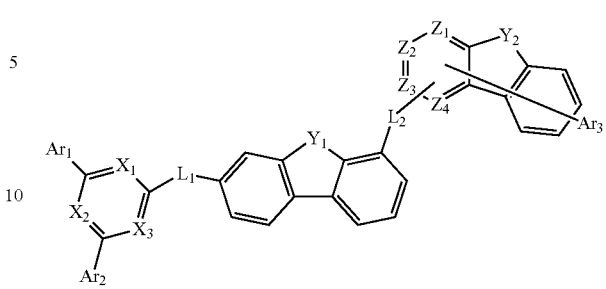

Chemical Formula 1-4

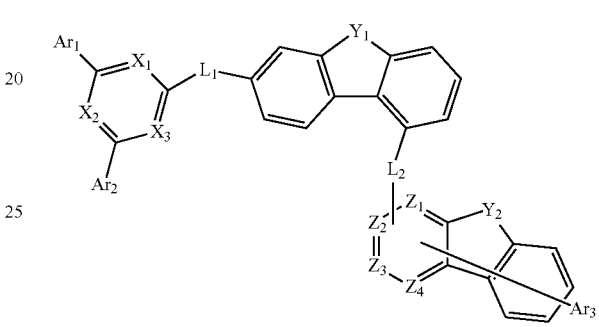

Chemical Formula 1-5

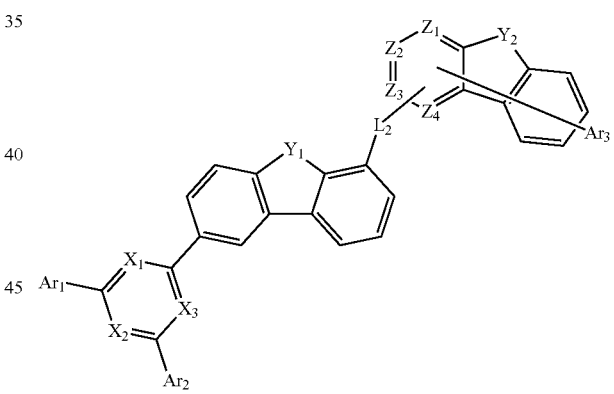

Chemical Formula 1-6

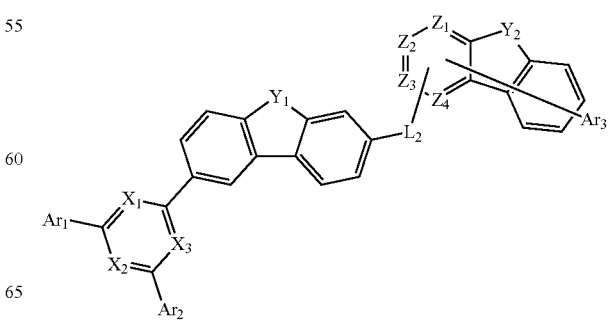

Chemical Formula 1-7

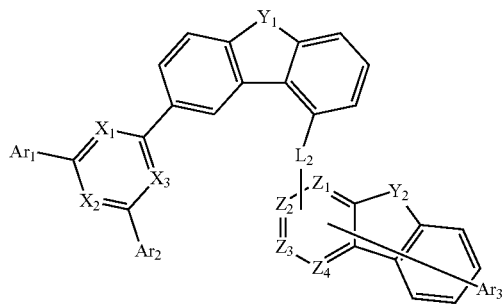

wherein, in the Chemical Formulas 1-1 to 1-7,
Y$_1$ is O or S,
L$_1$ and L$_2$ are each independently a single bond or phenylene,
X$_1$ to X$_3$ are each independently N or CH, provided that at least one of them is N,
Ar$_1$ and Ar$_2$ are each independently a substituted or unsubstituted C$_{6-60}$ aryl; or a substituted or unsubstituted C$_{5-60}$ heteroaryl containing at least one heteroatom selected from the group consisting of N, O and S,
Y$_2$ is O or S,
Z$_1$ to Z$_4$ are each independently N or CH, provided that at least two of them are N,
Ar$_3$ is hydrogen; a substituted or unsubstituted C$_{1-60}$ alkyl; or a substituted or unsubstituted C$_{6-60}$ aryl, and
the group of

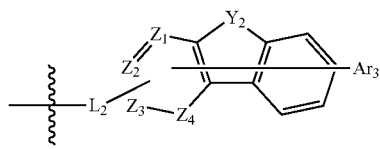

is any one selected from the following groups:

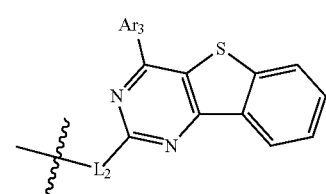

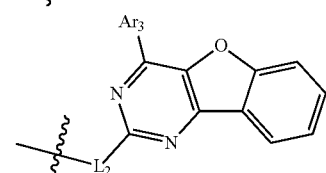

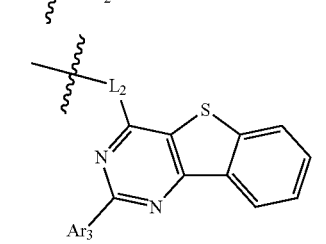

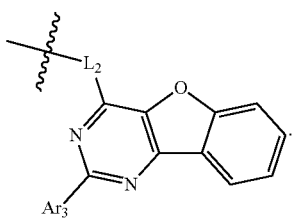

2. The compound of claim 1, wherein Ar$_1$ and Ar$_2$ are each independently phenyl; biphenyl; dibenzofuranyl; dibenzothiophenyl; carbazolyl; or carbazolyl substituted with phenyl.

3. The compound of claim 1, wherein Ar$_3$ is phenyl.

4. The compound of claim 1, wherein the compound of Chemical Formulas 1-1 to 1-7 is any one selected from the group consisting of the following compounds:

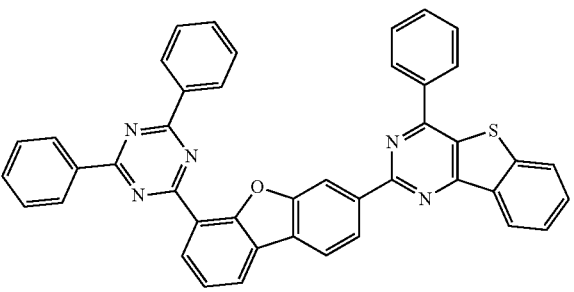

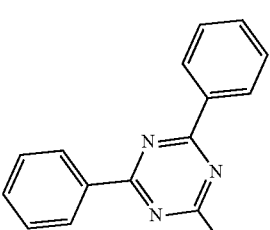

395
-continued
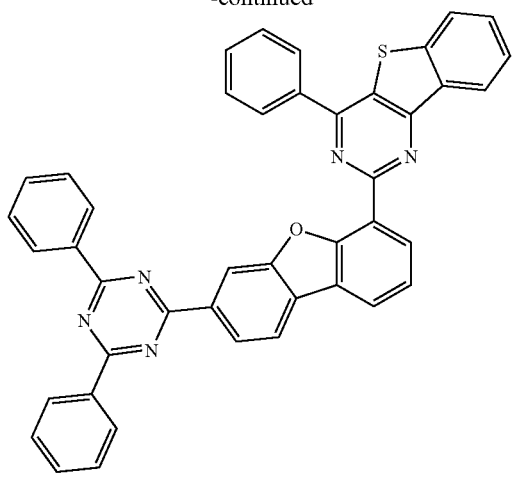
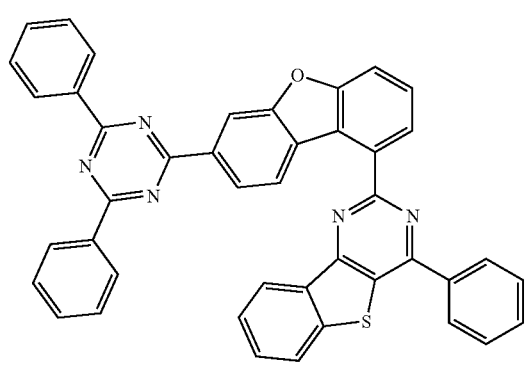
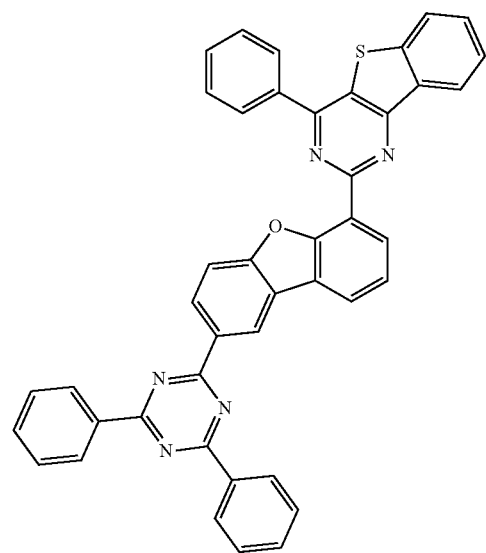
396
-continued
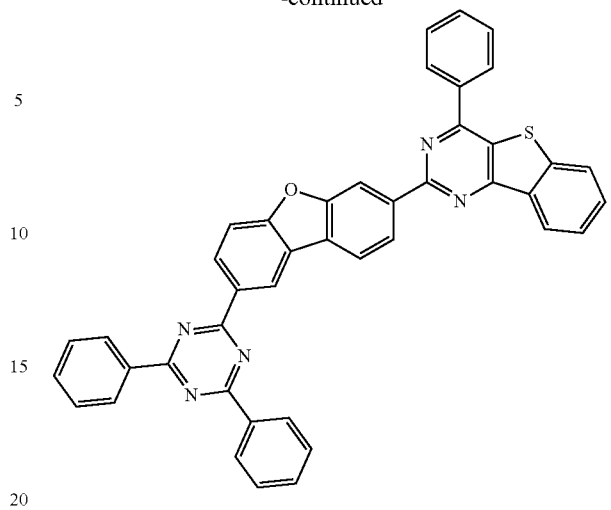
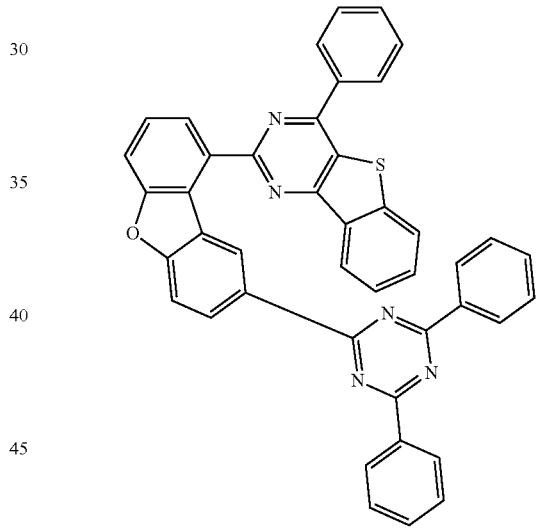
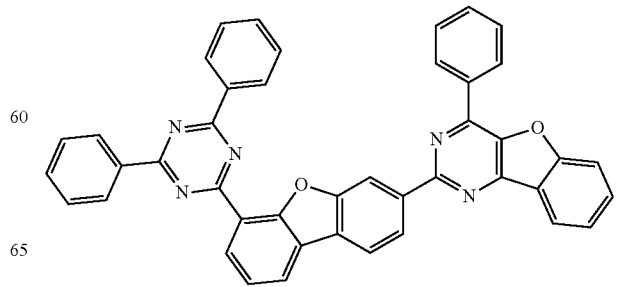

397
-continued
398
-continued
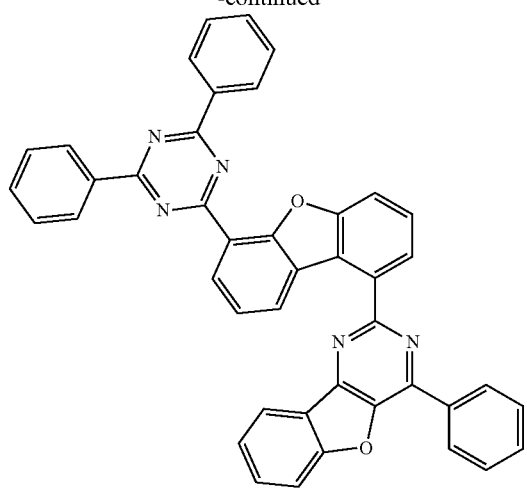
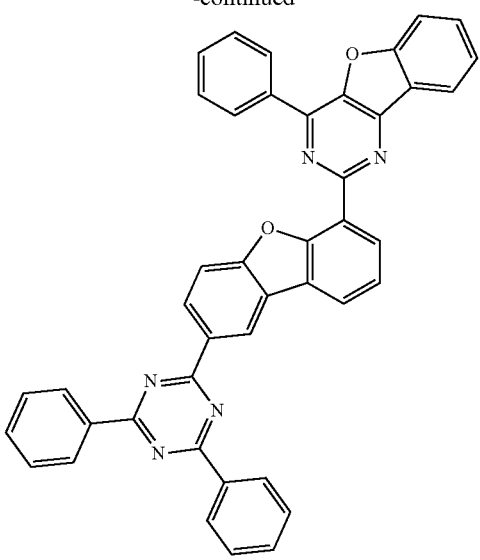
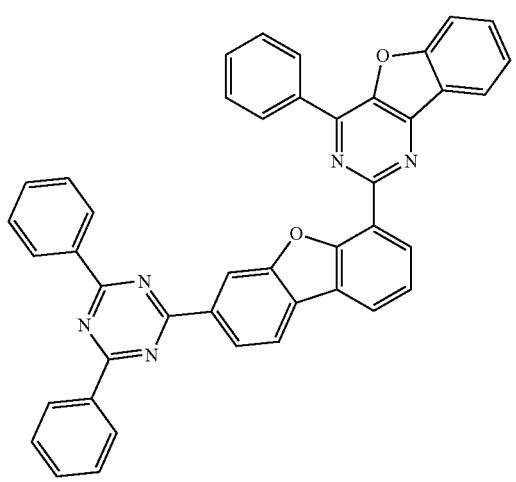
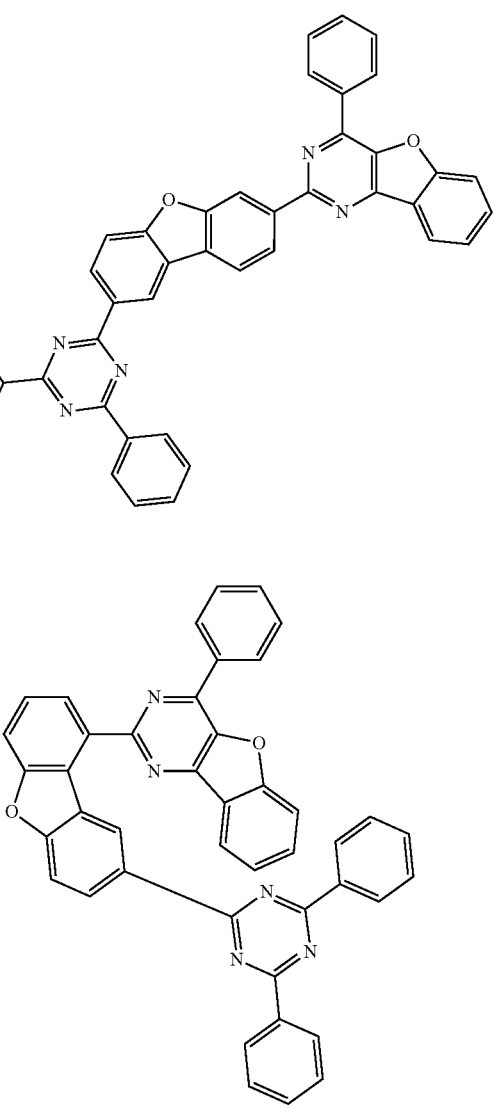
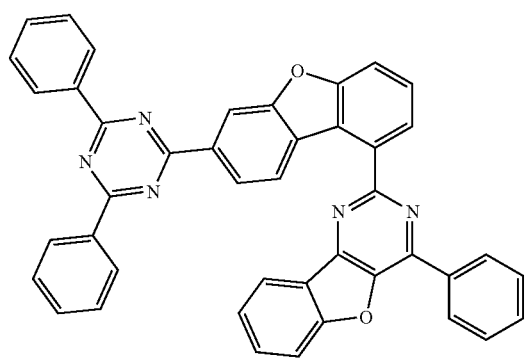

399
-continued
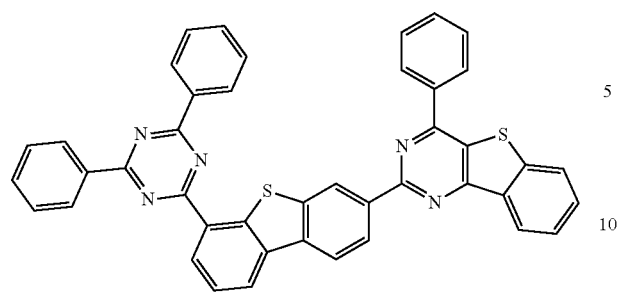
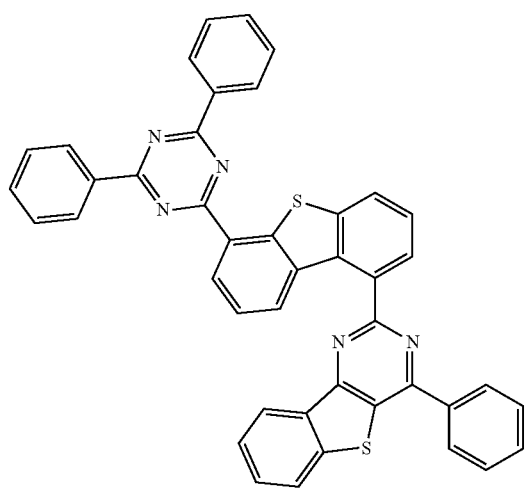
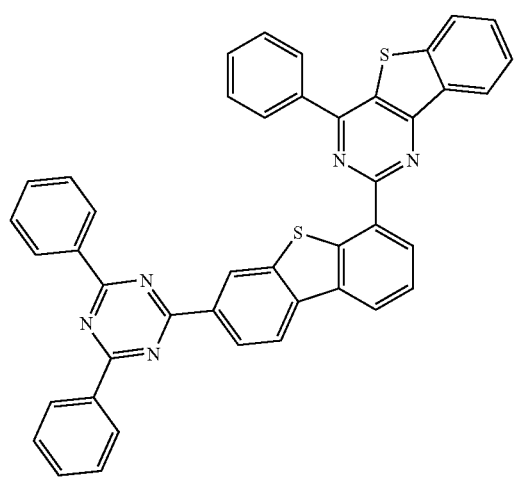
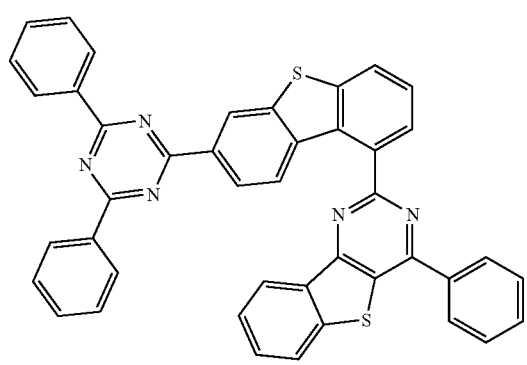
400
-continued
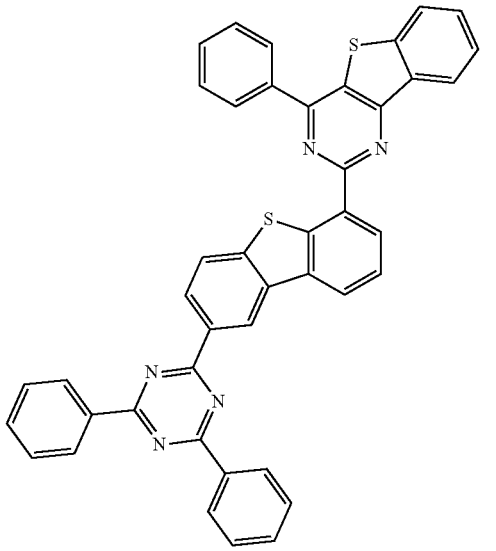
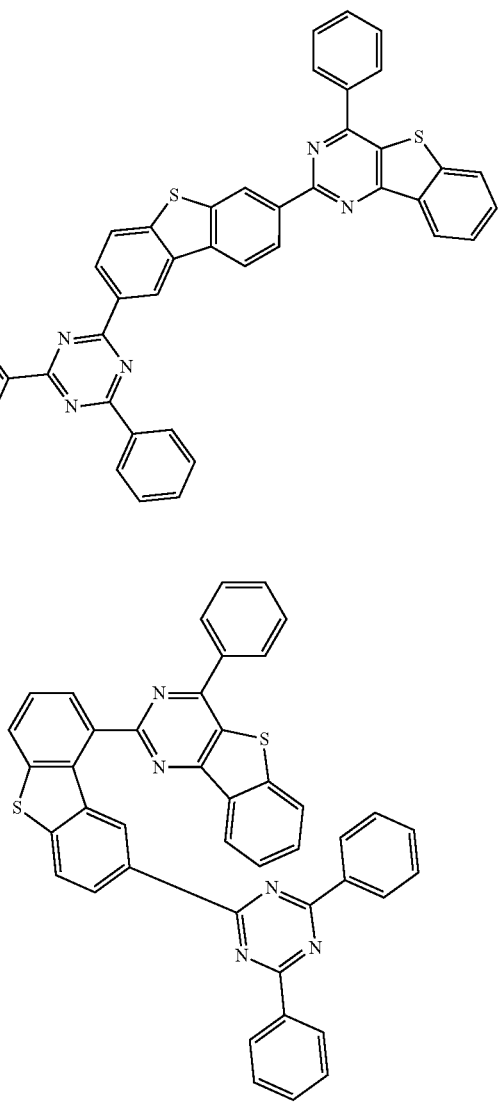

401
-continued
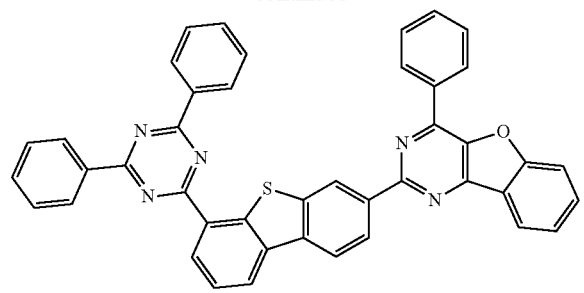
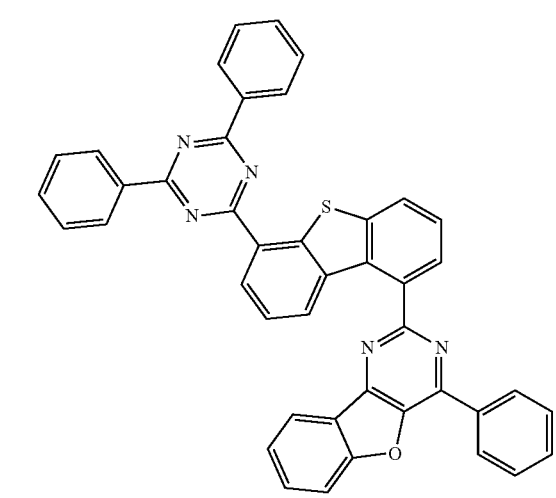
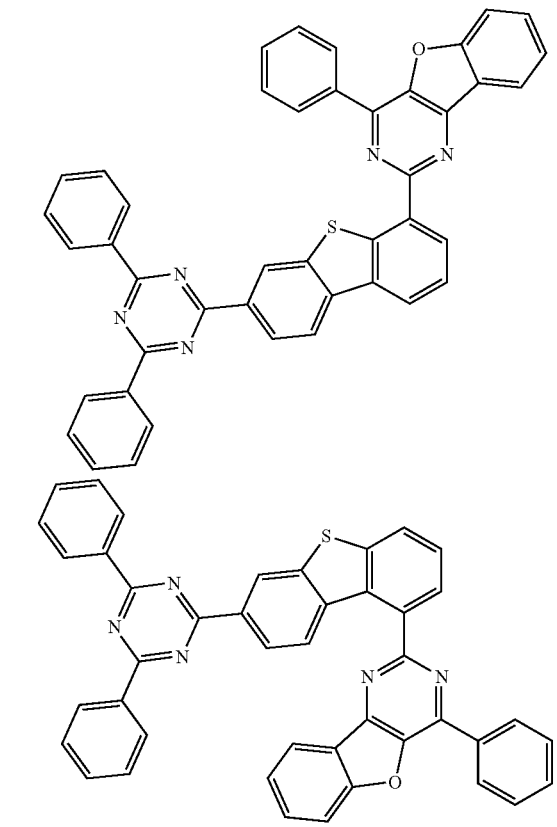
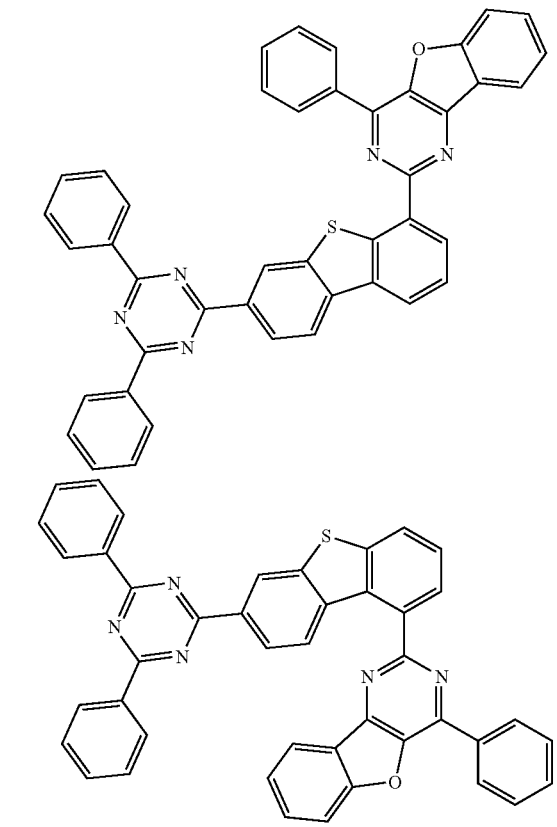
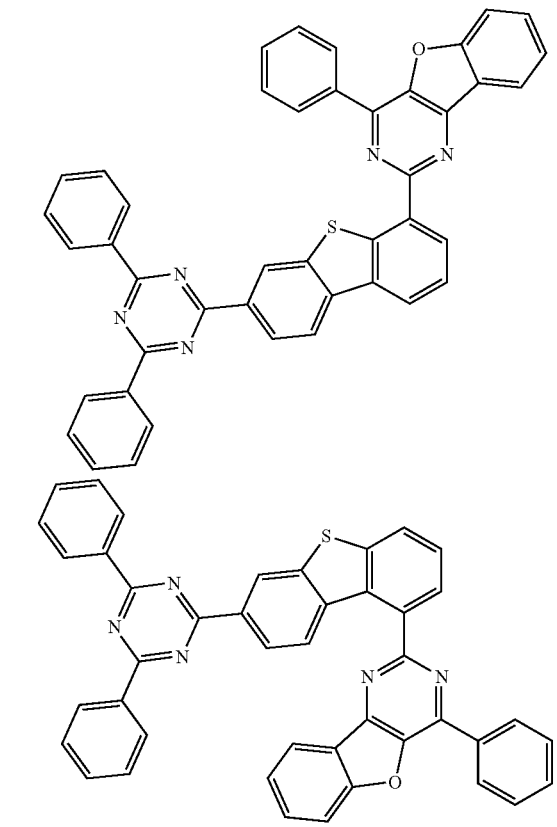
402
-continued
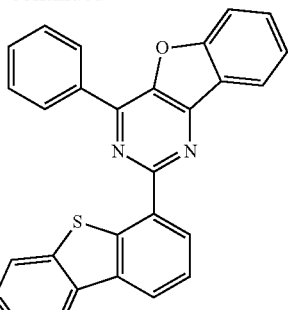
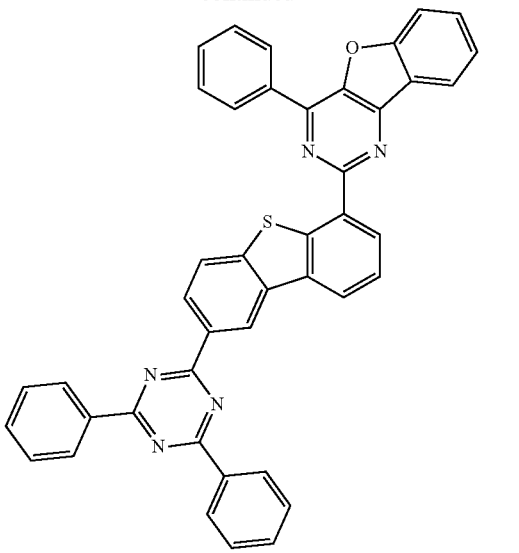
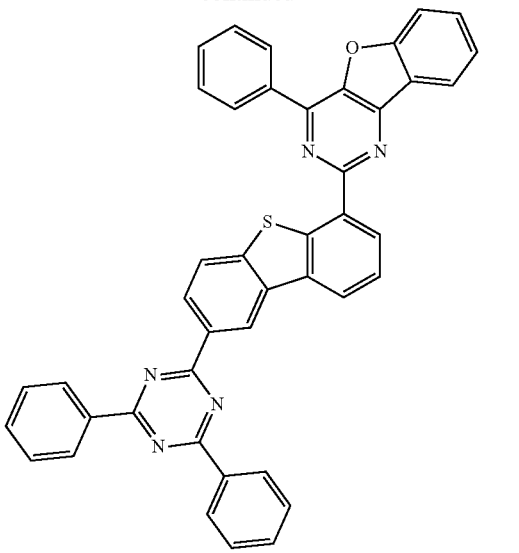
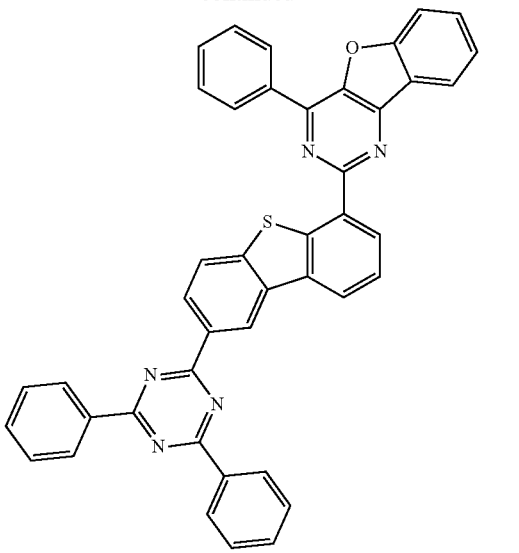

403
-continued
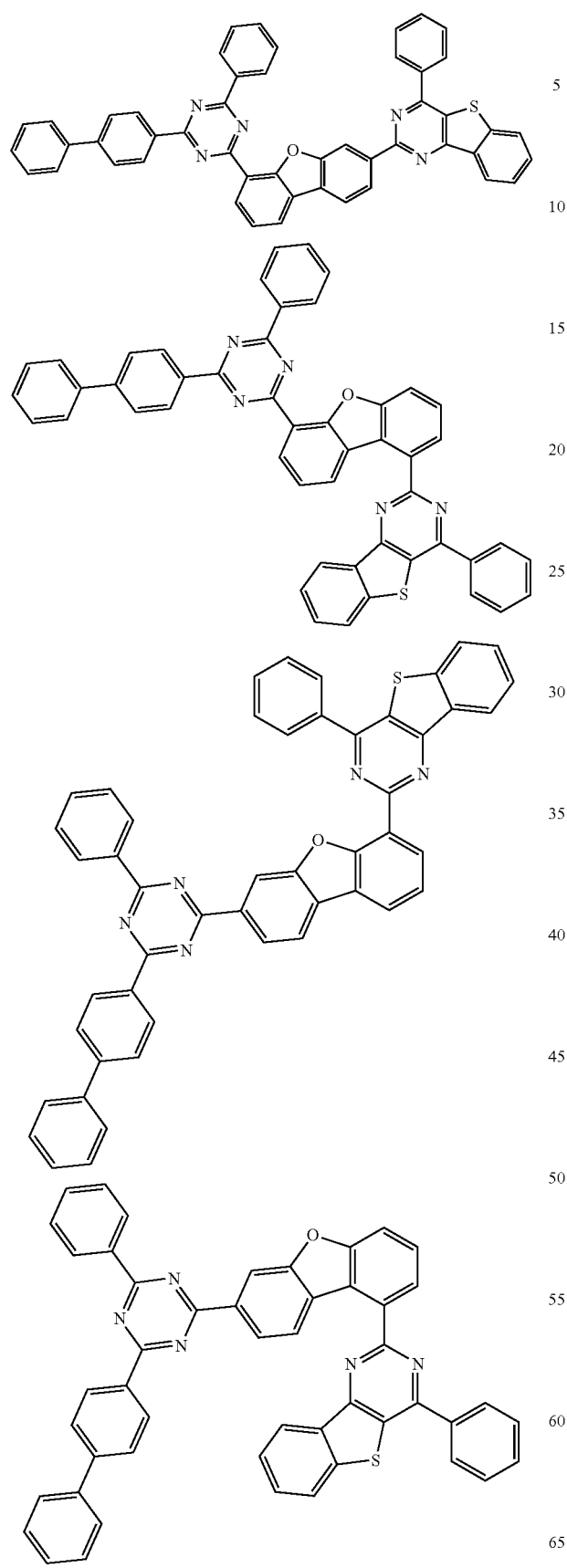
404
-continued
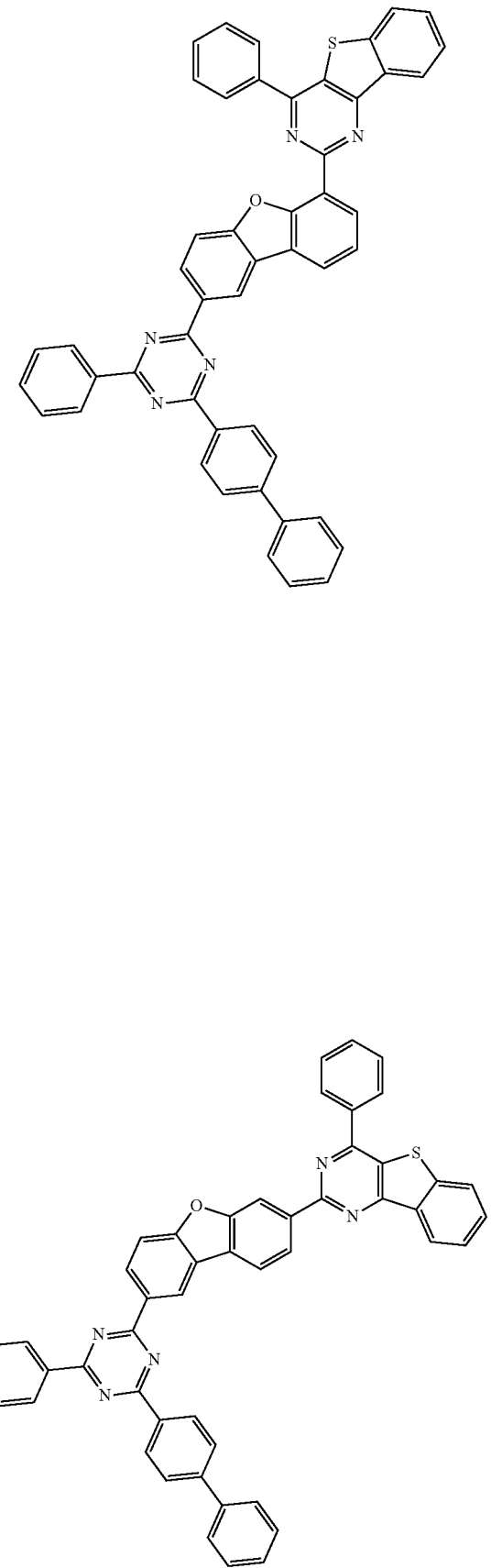

405
-continued
406
-continued
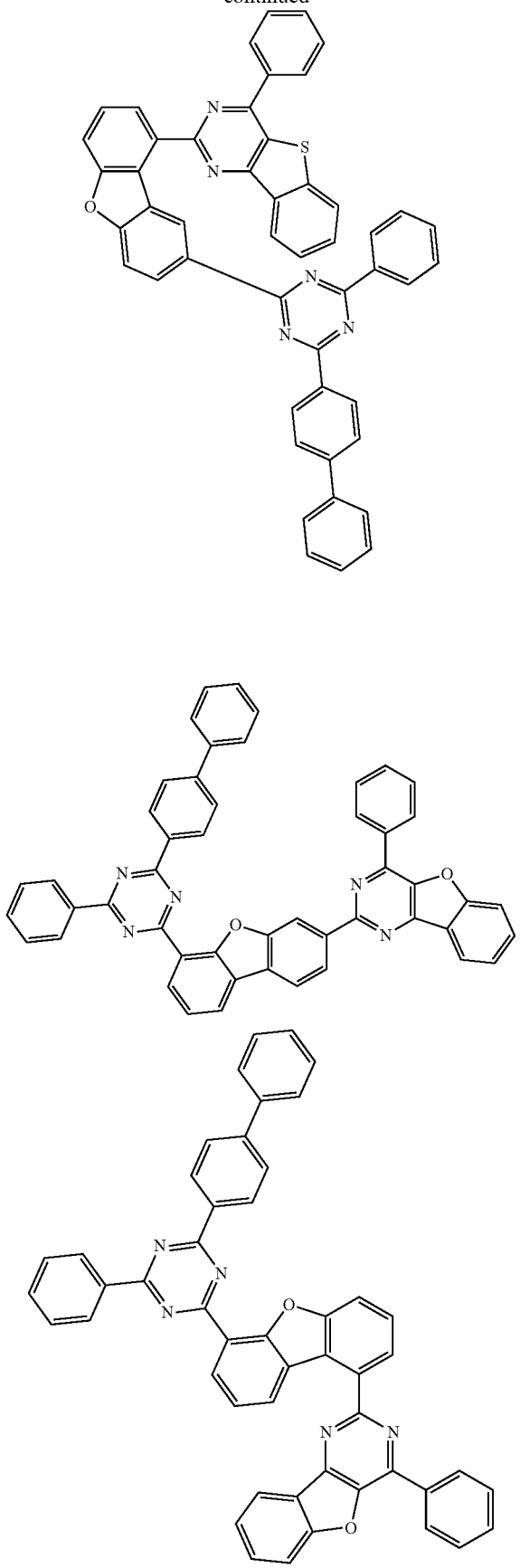
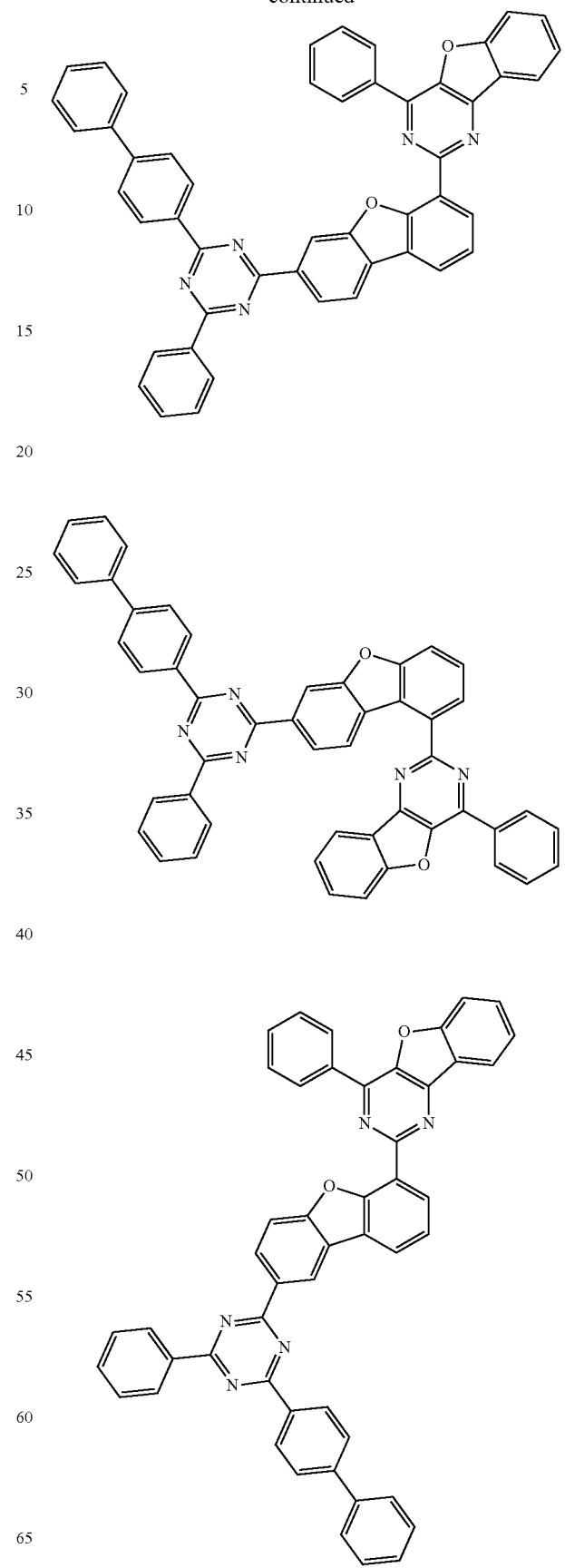

407
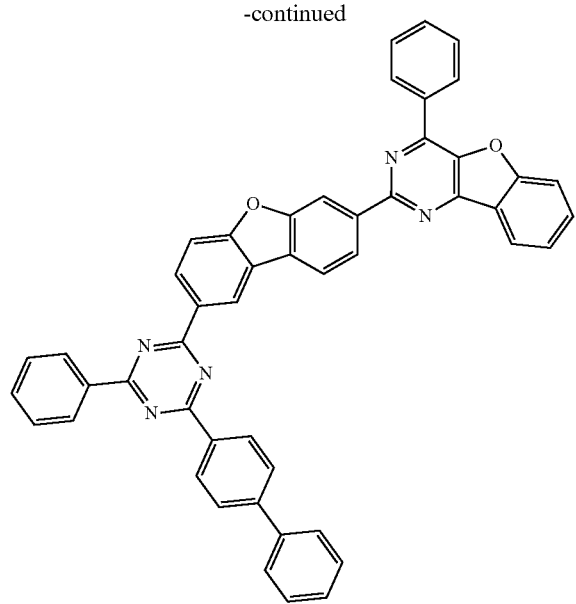
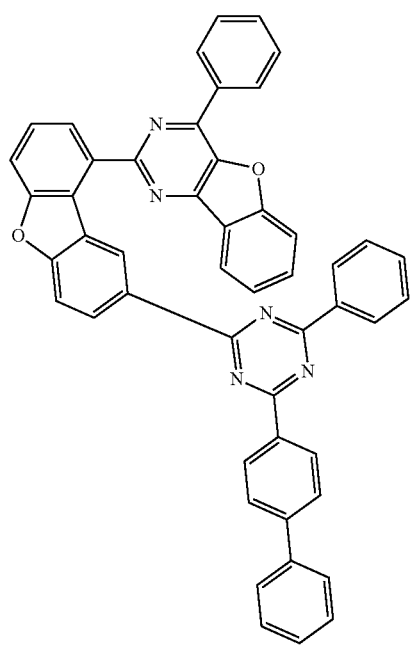
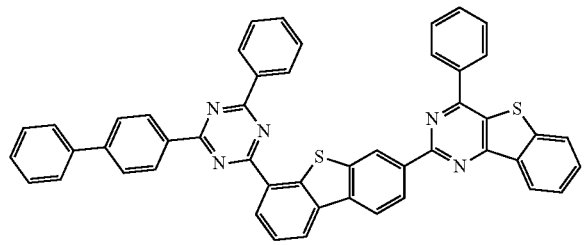
408
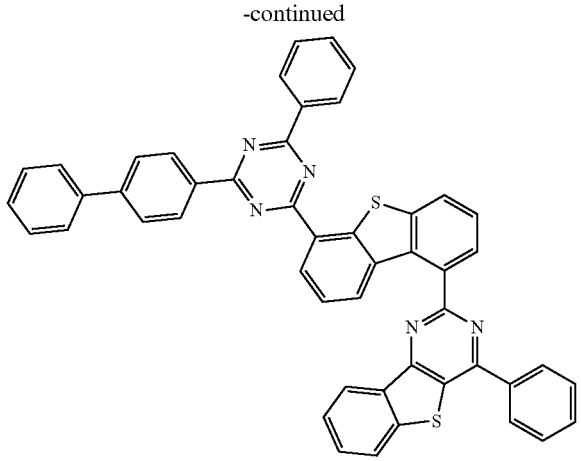
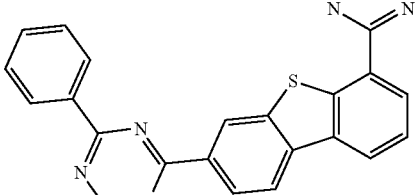
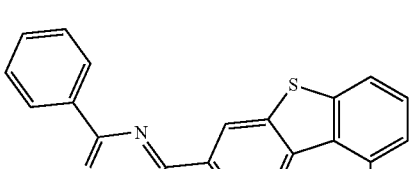

409
-continued
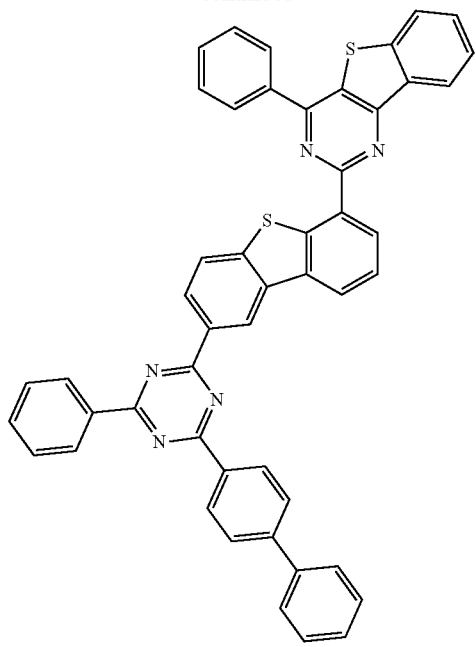
410
-continued
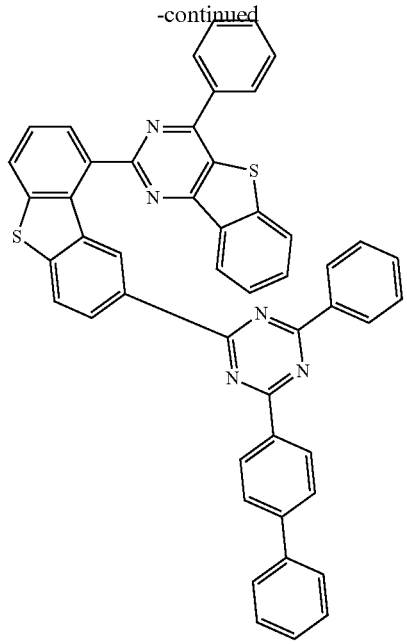
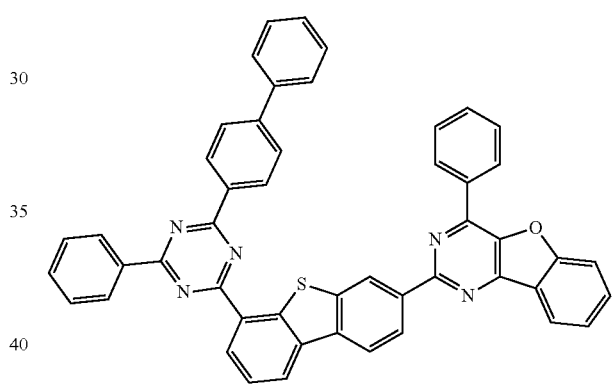
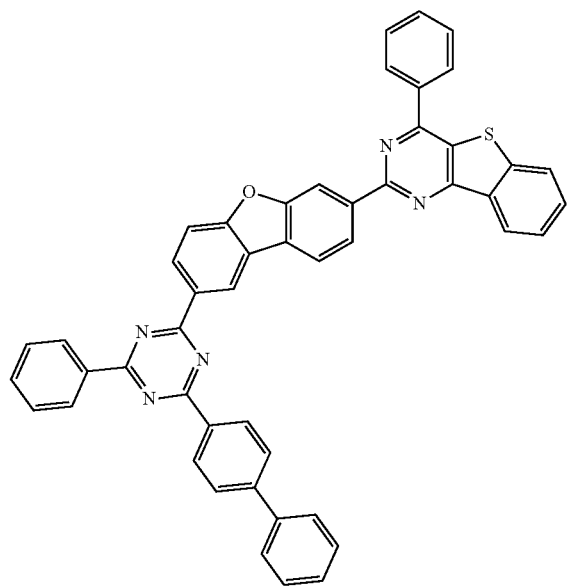

411
-continued
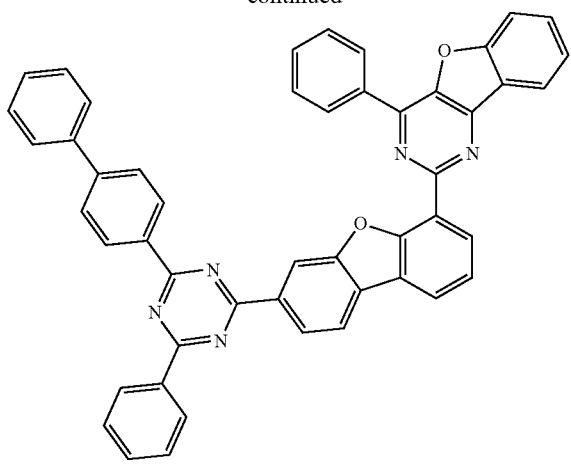
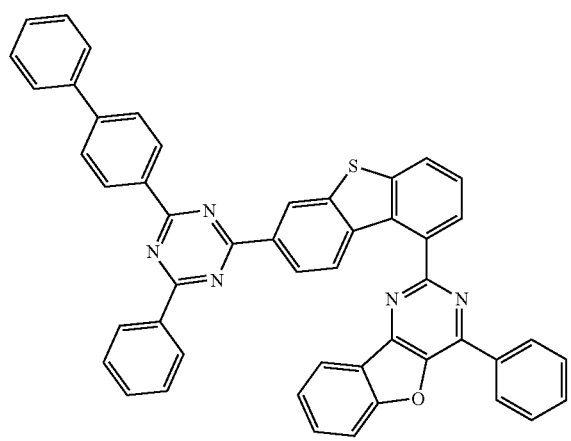
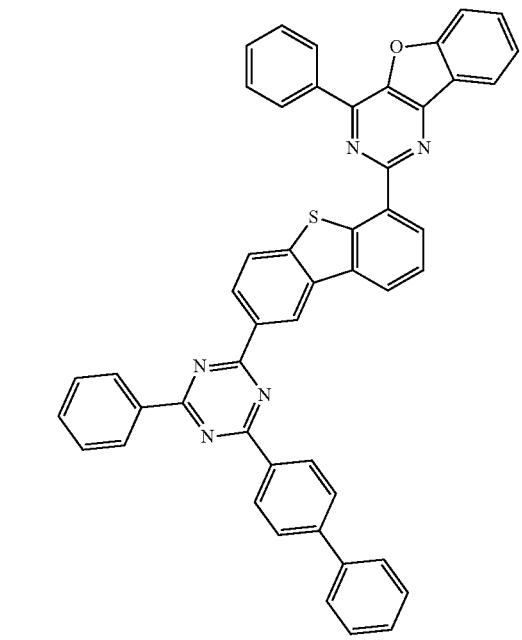
412
-continued
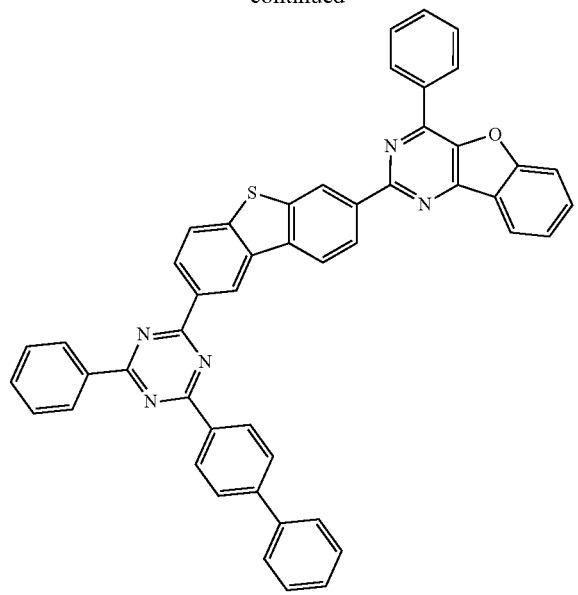
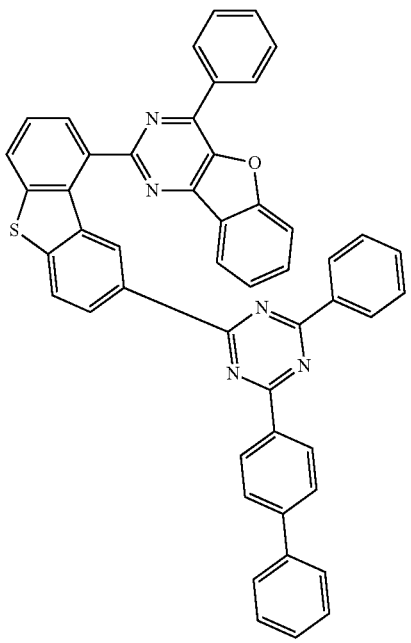
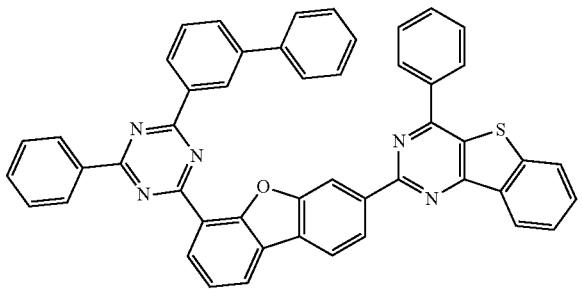

413
-continued
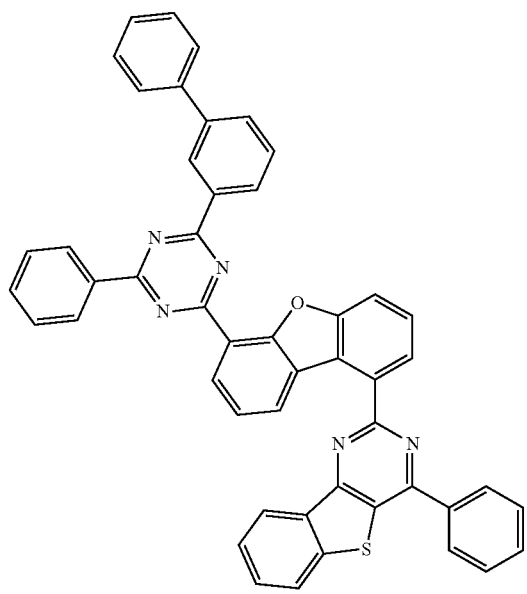
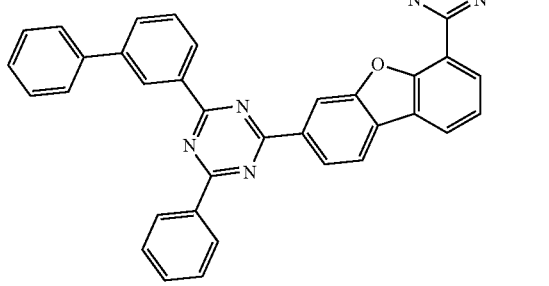
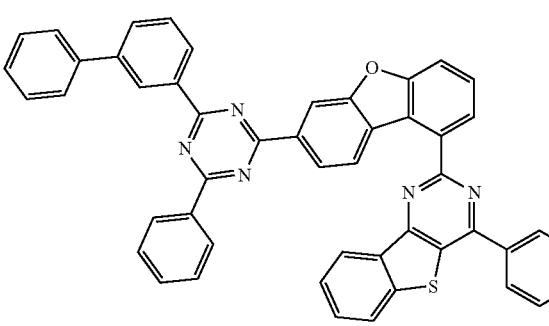
414
-continued
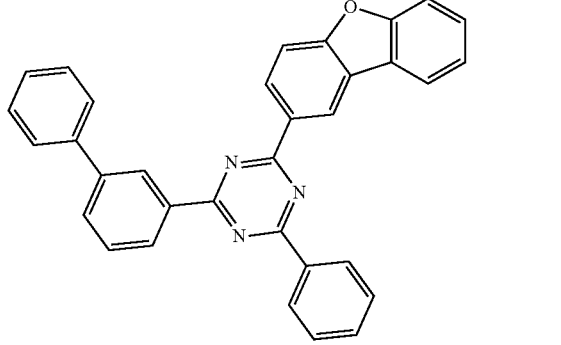
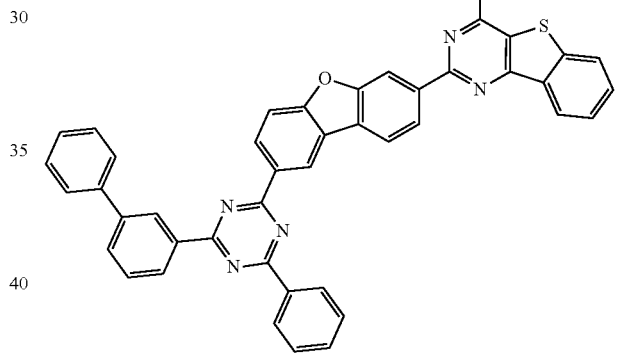
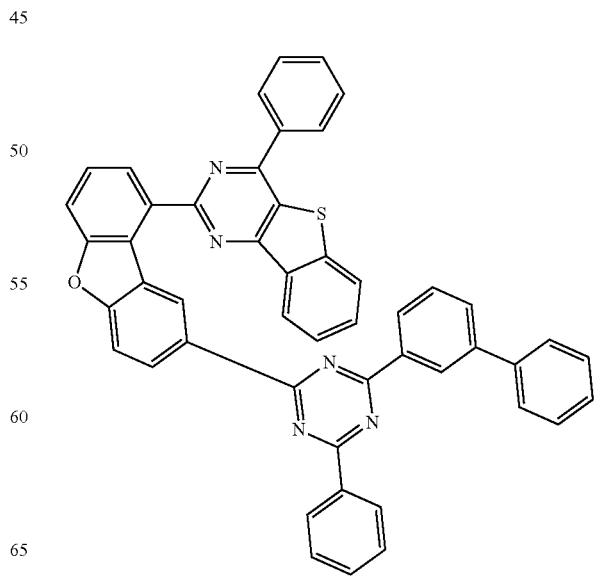

415
-continued
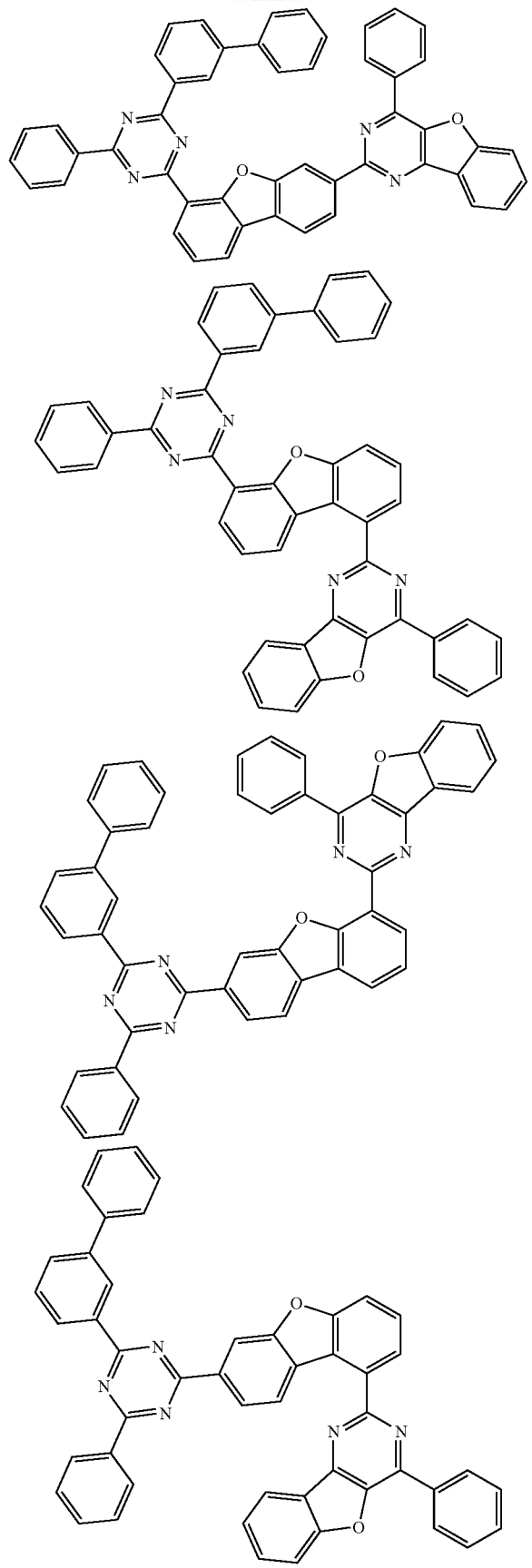
416
-continued
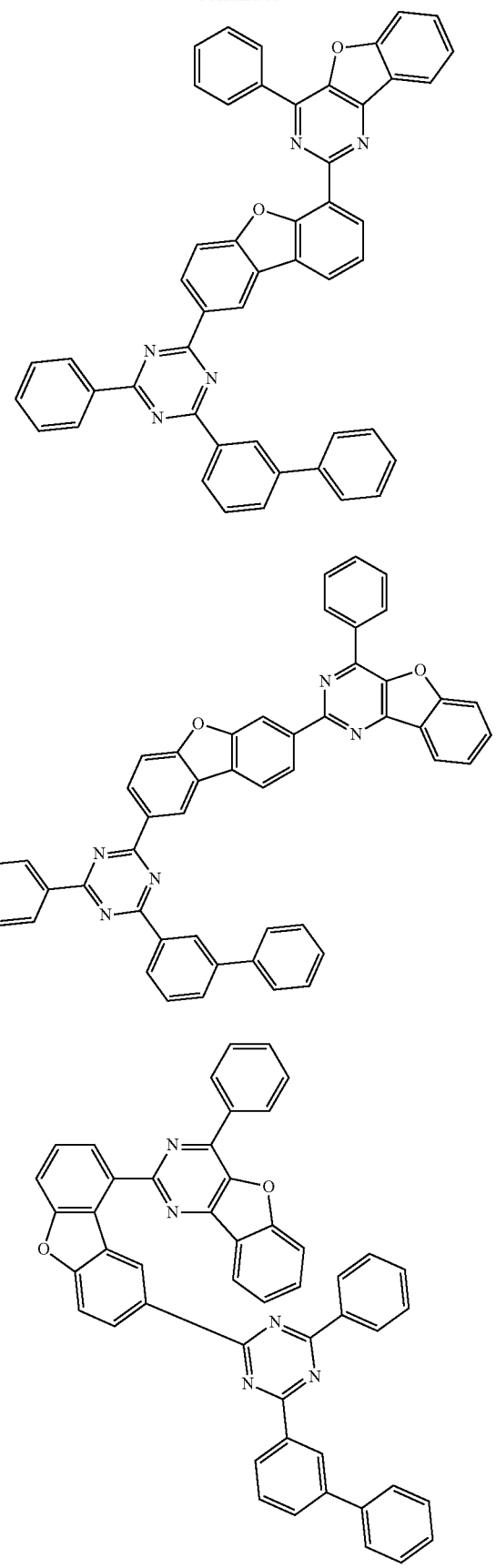

417
-continued
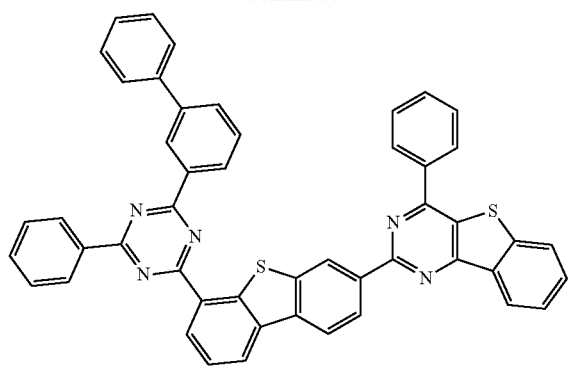
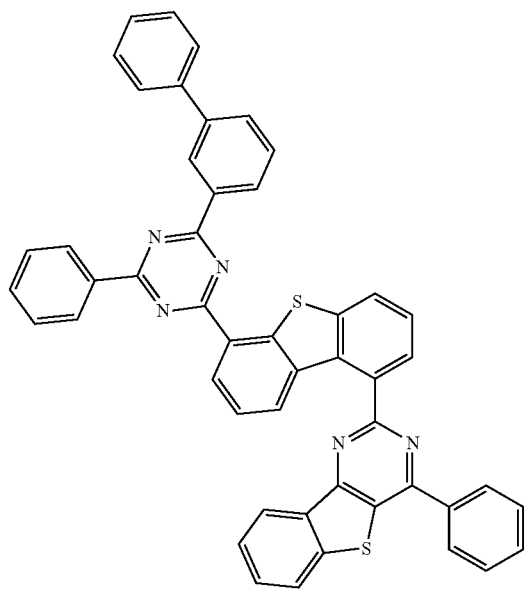
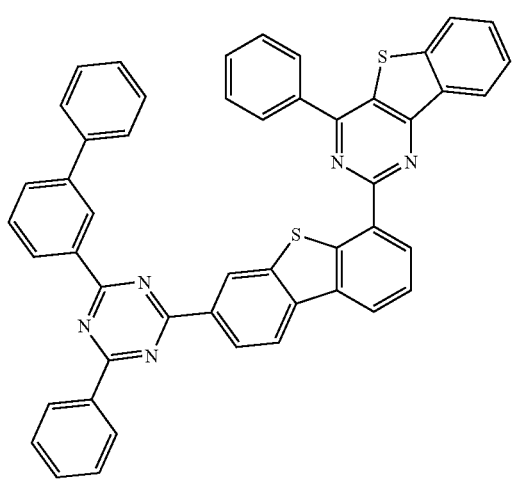
418
-continued
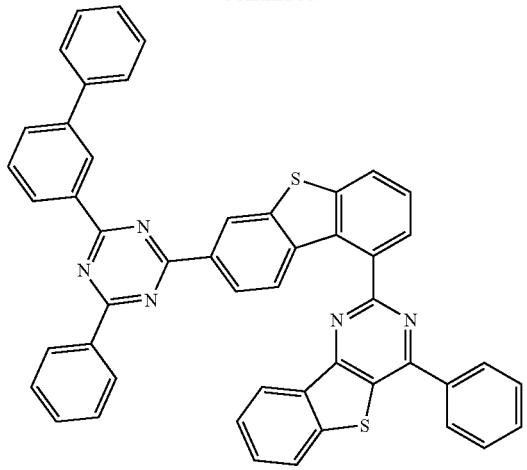
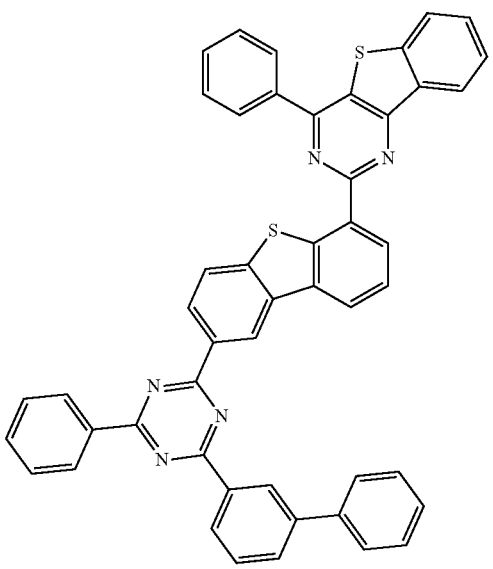
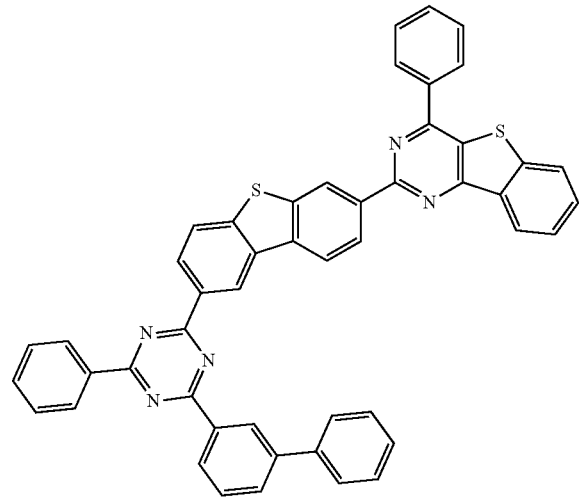

419
-continued
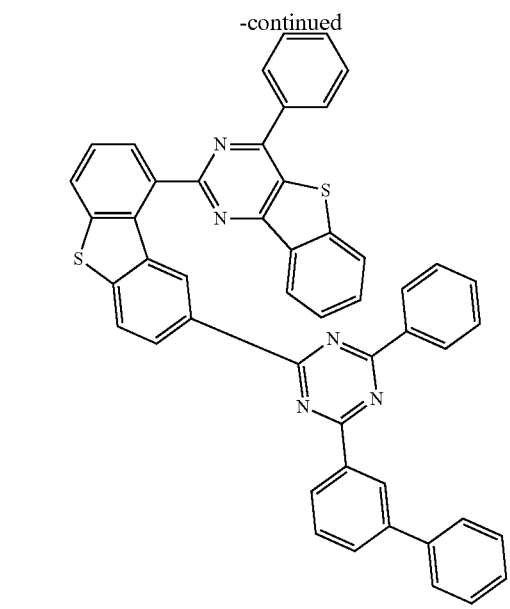
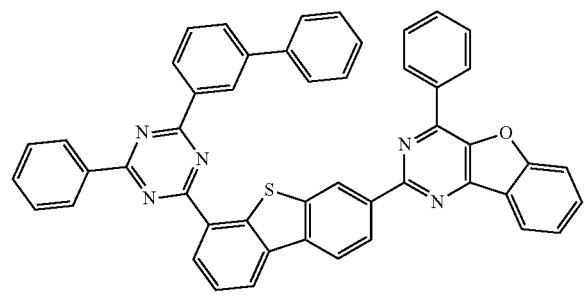
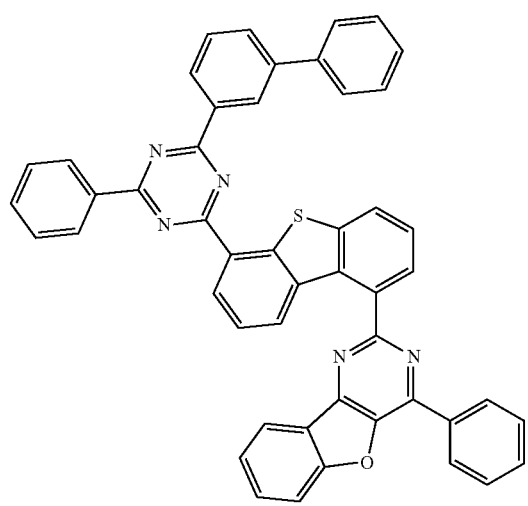
420
-continued
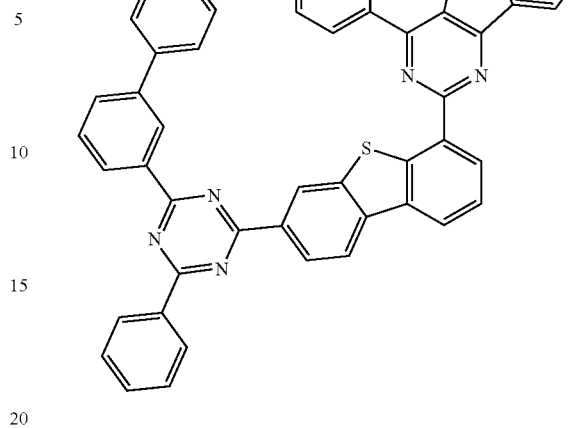
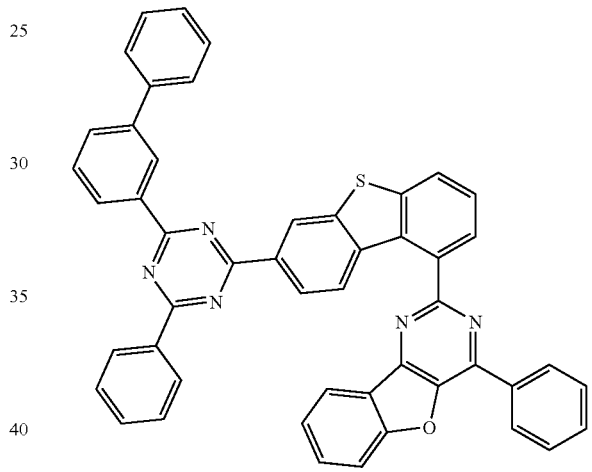
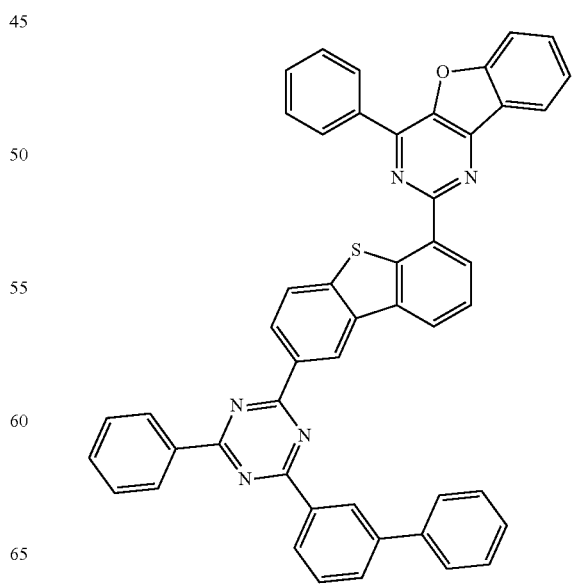

421
-continued
422
-continued
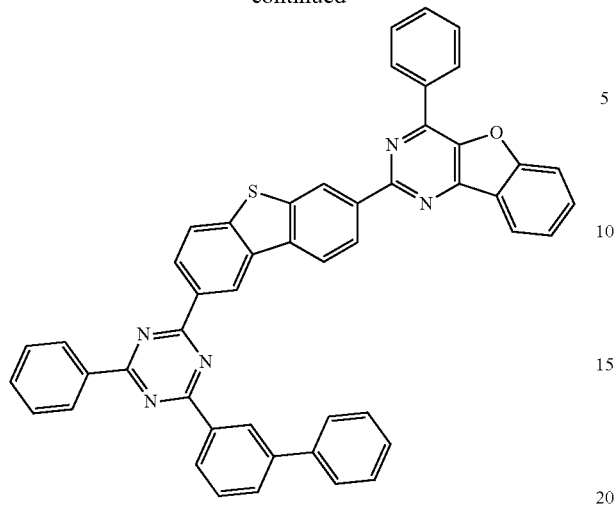
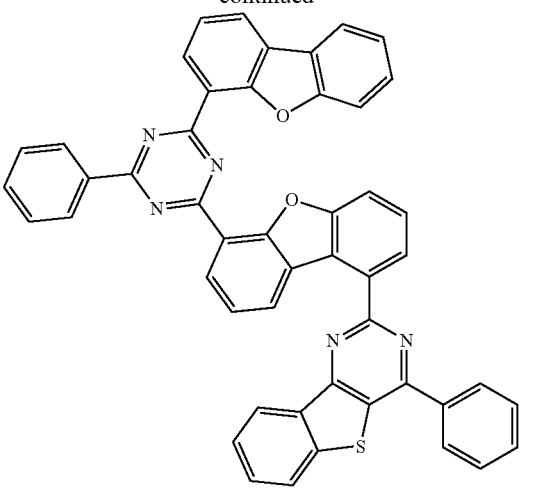
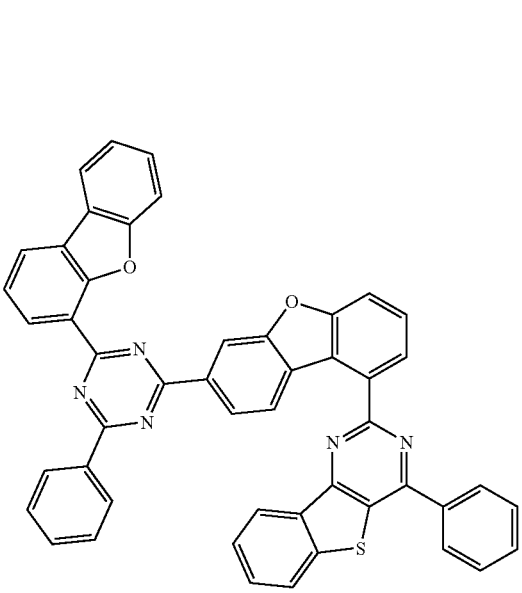

423
-continued
424
-continued
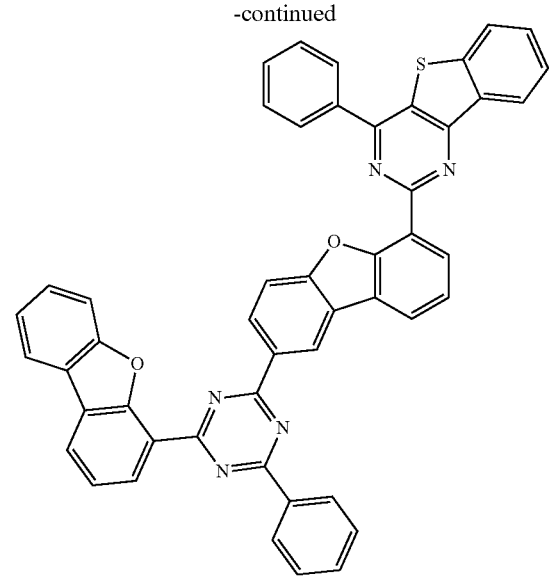
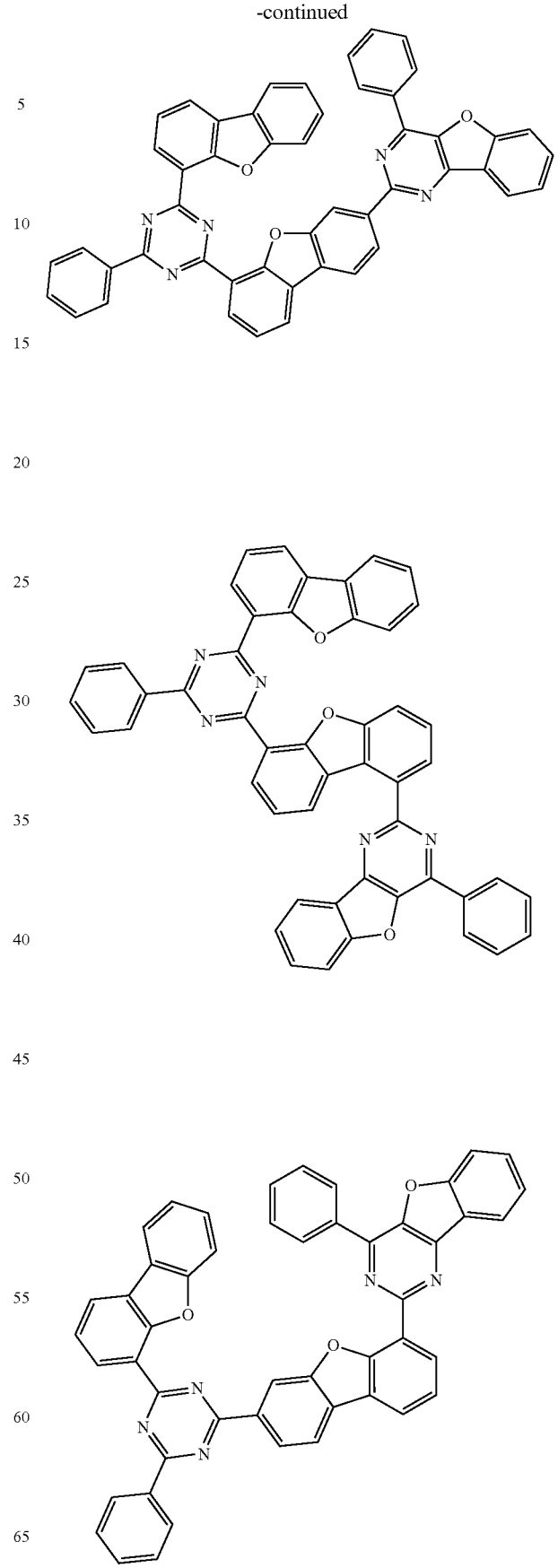

425
-continued
426
-continued
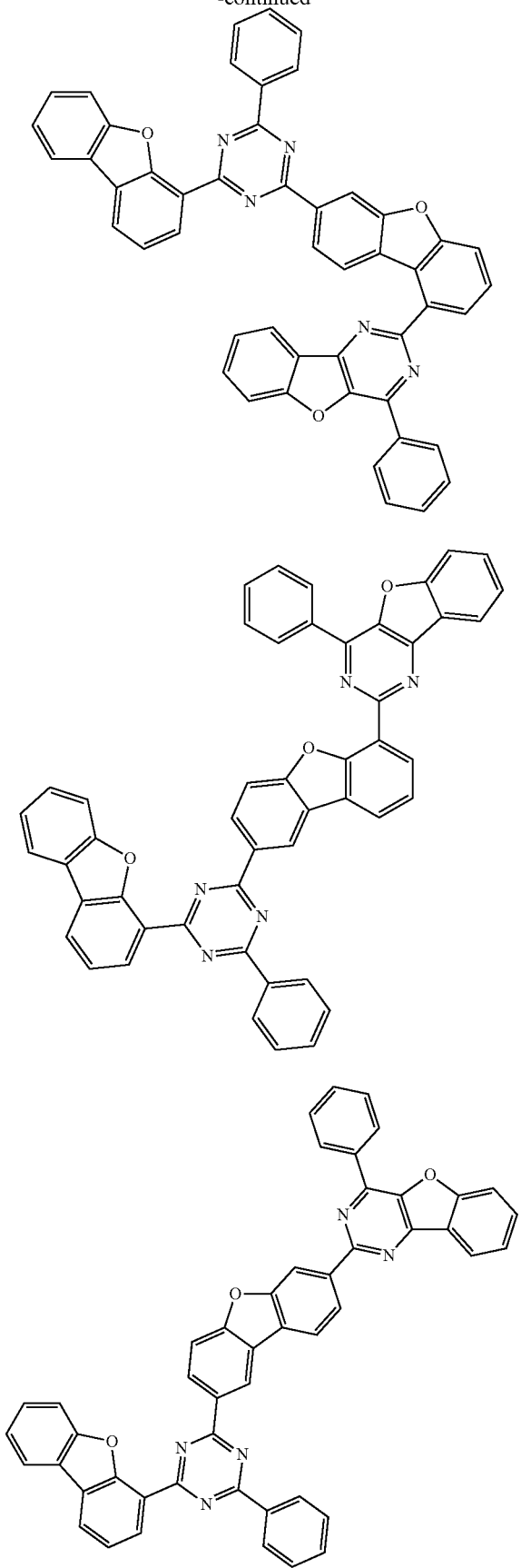
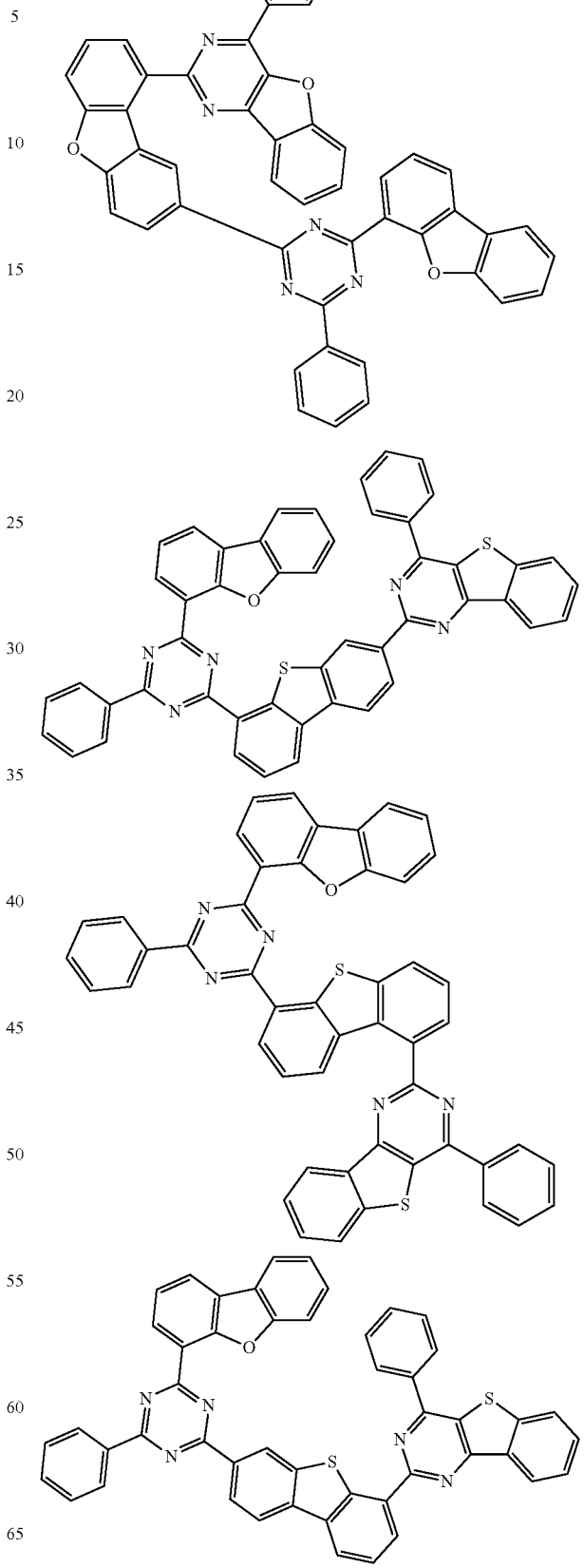

427
-continued
428
-continued
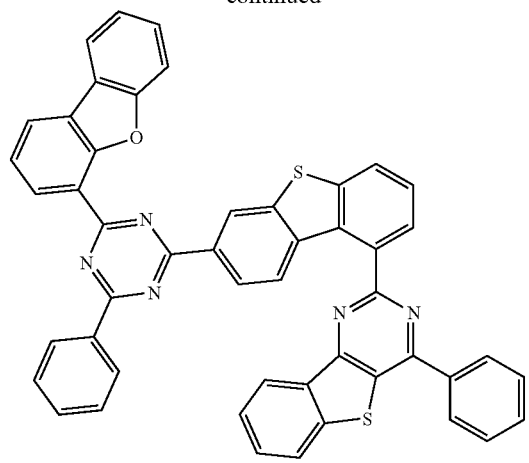
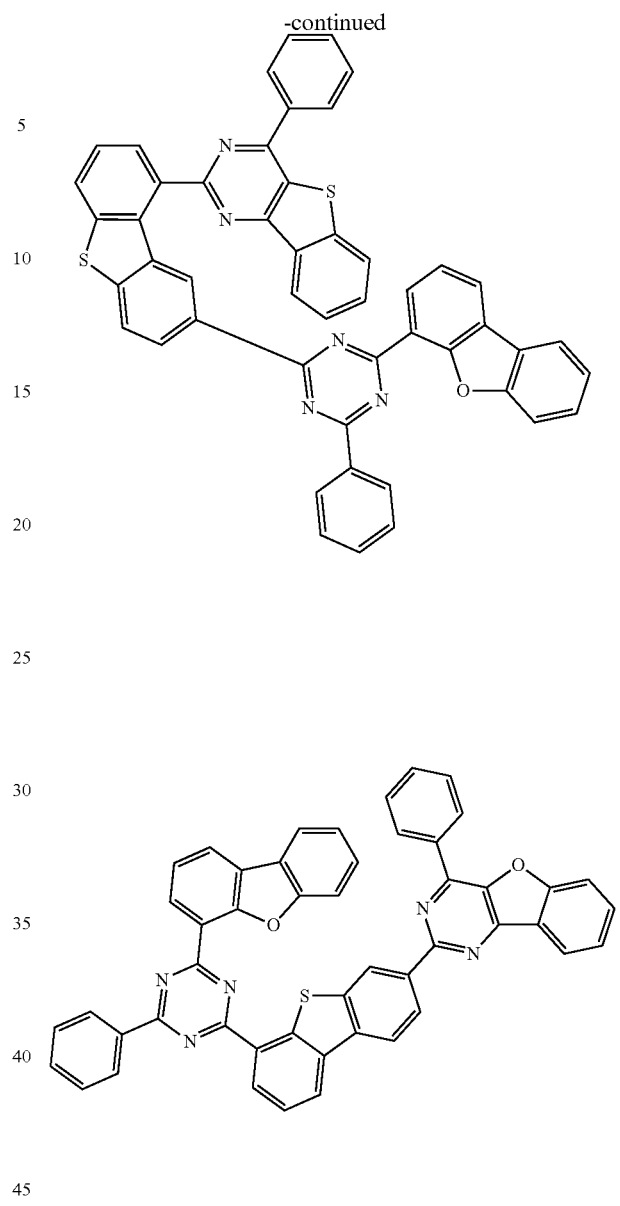
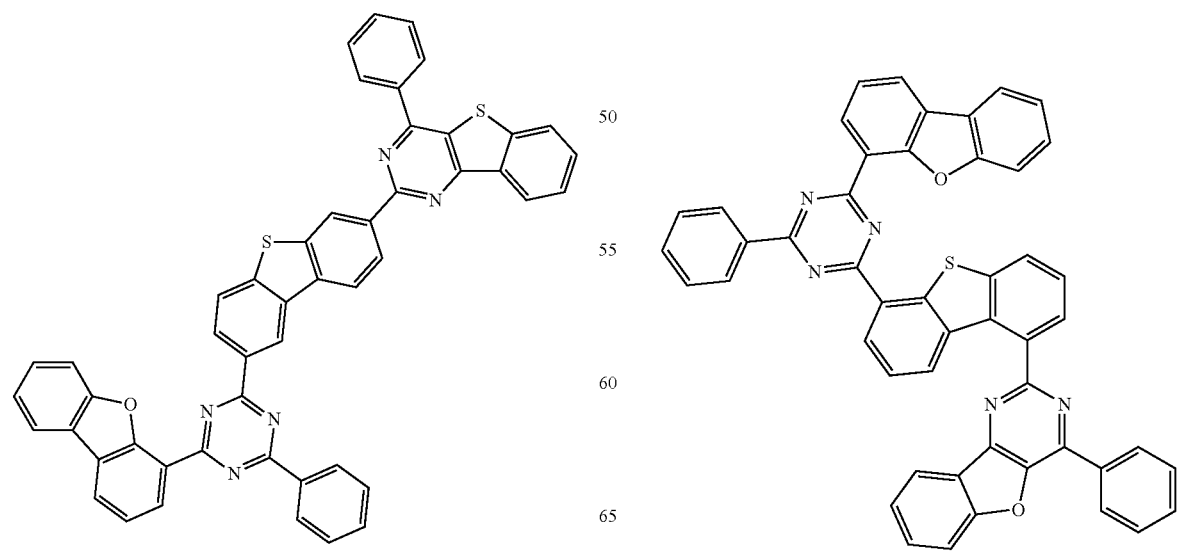

429
-continued
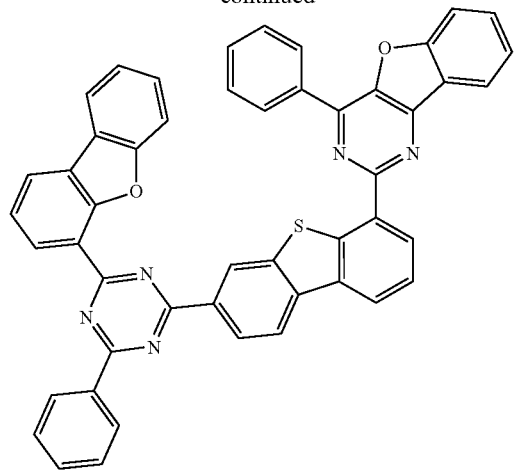
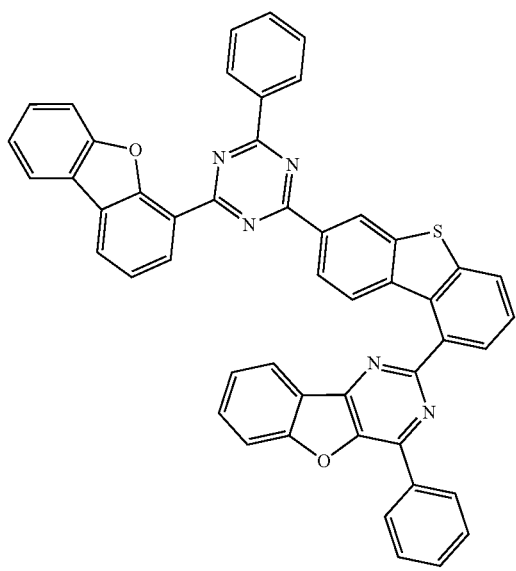
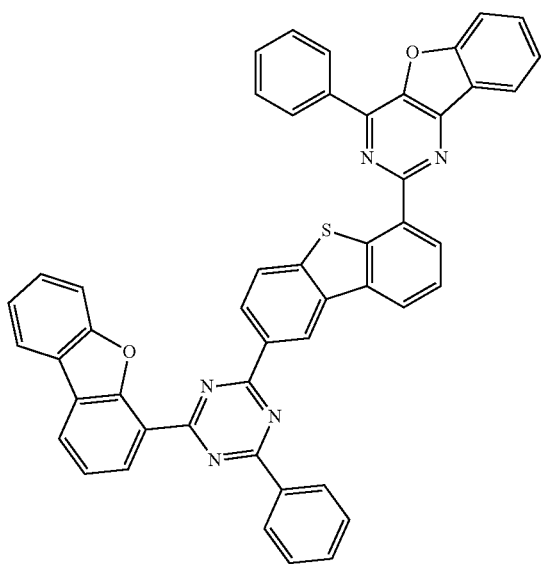
430
-continued
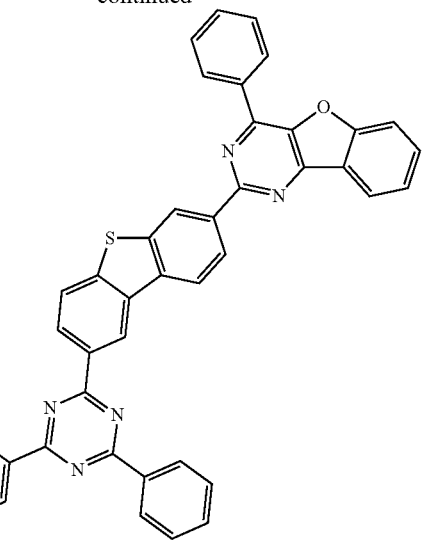
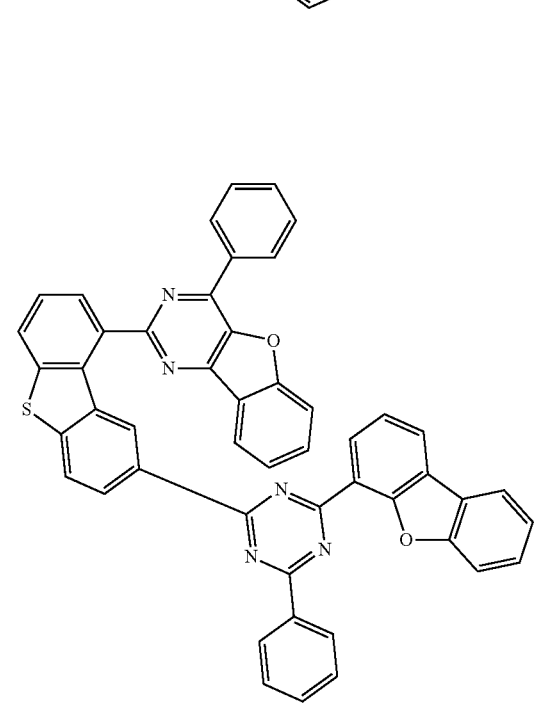
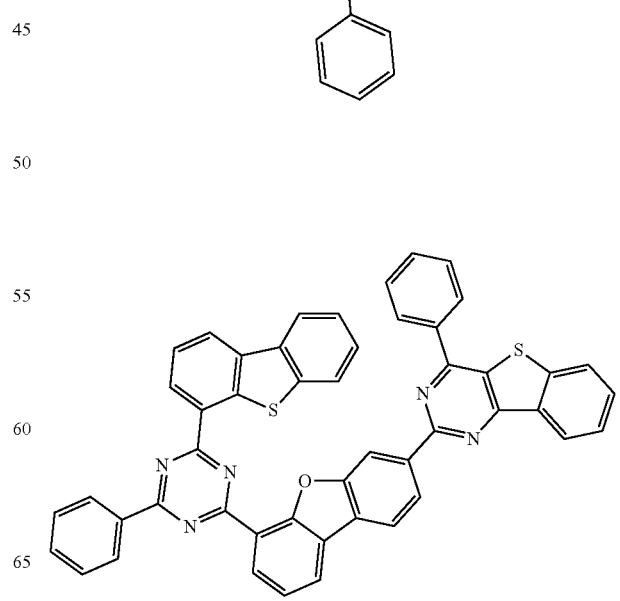

431
-continued
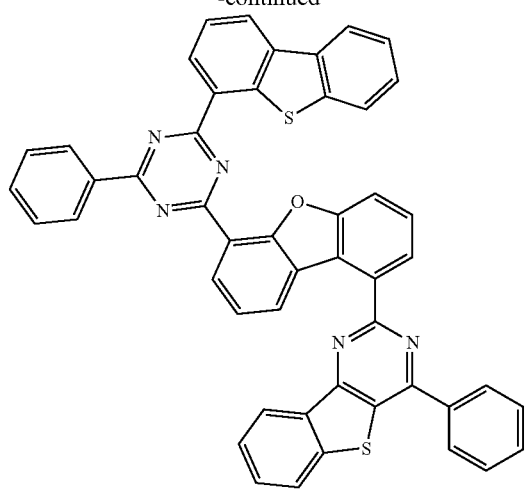
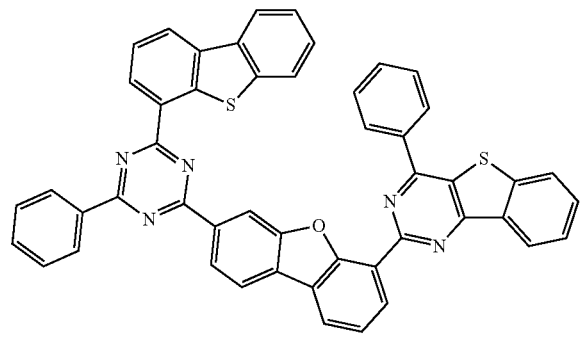
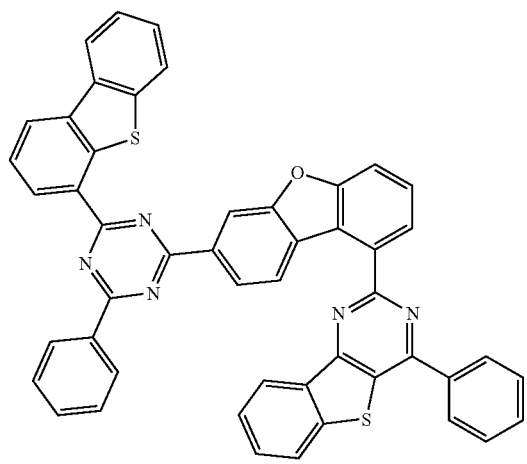
432
-continued
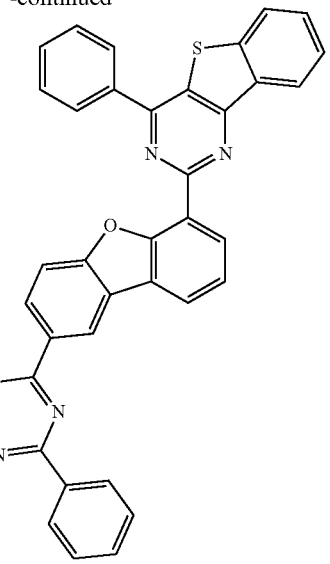
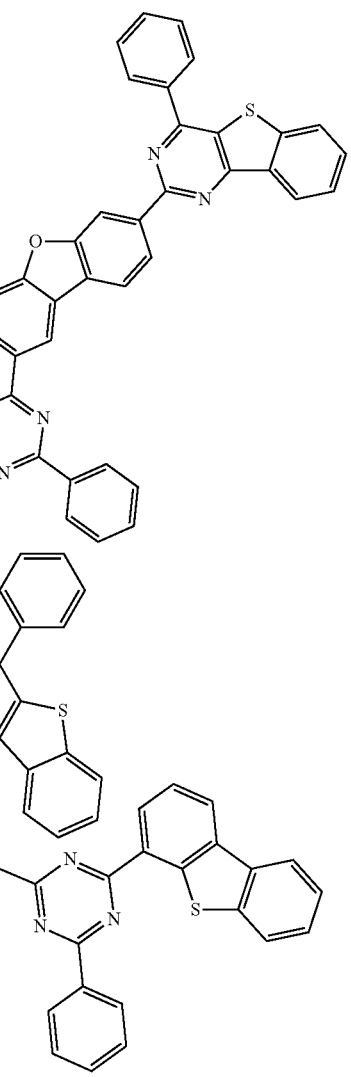

433
-continued
434
-continued
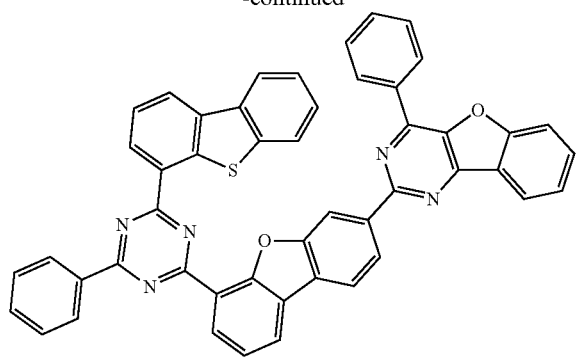
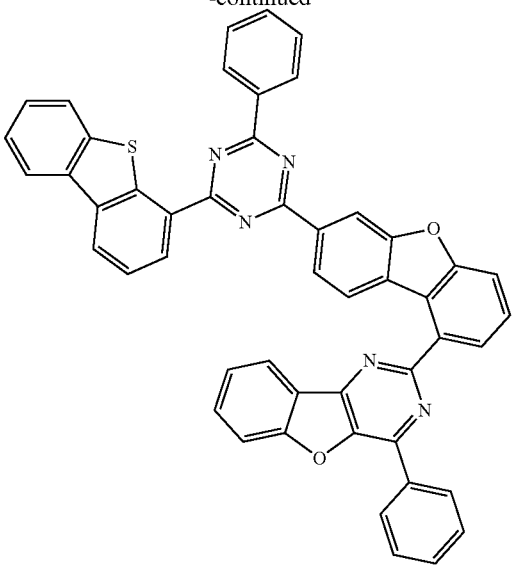
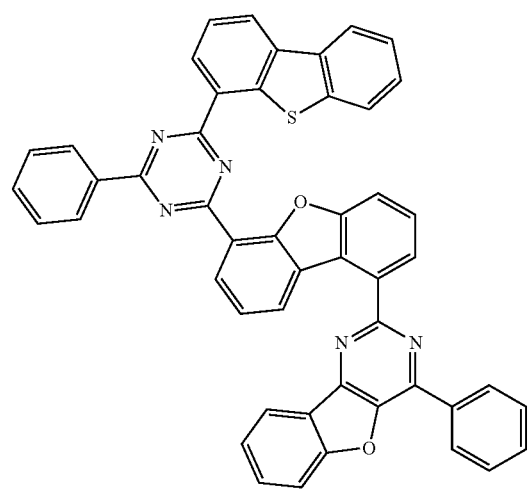
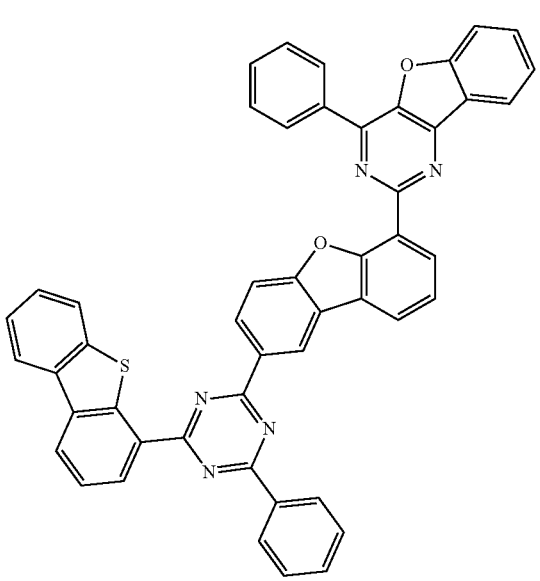
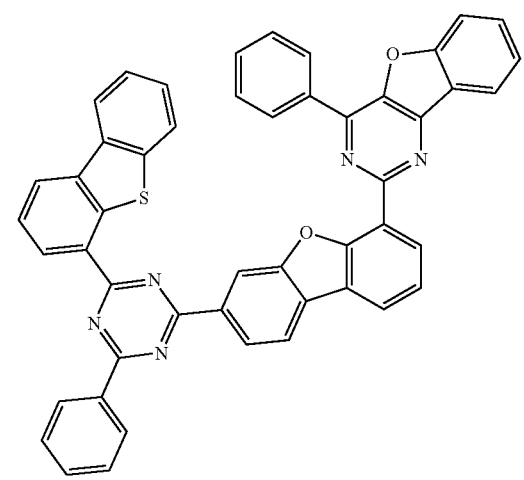
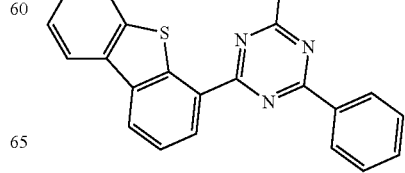

435
-continued
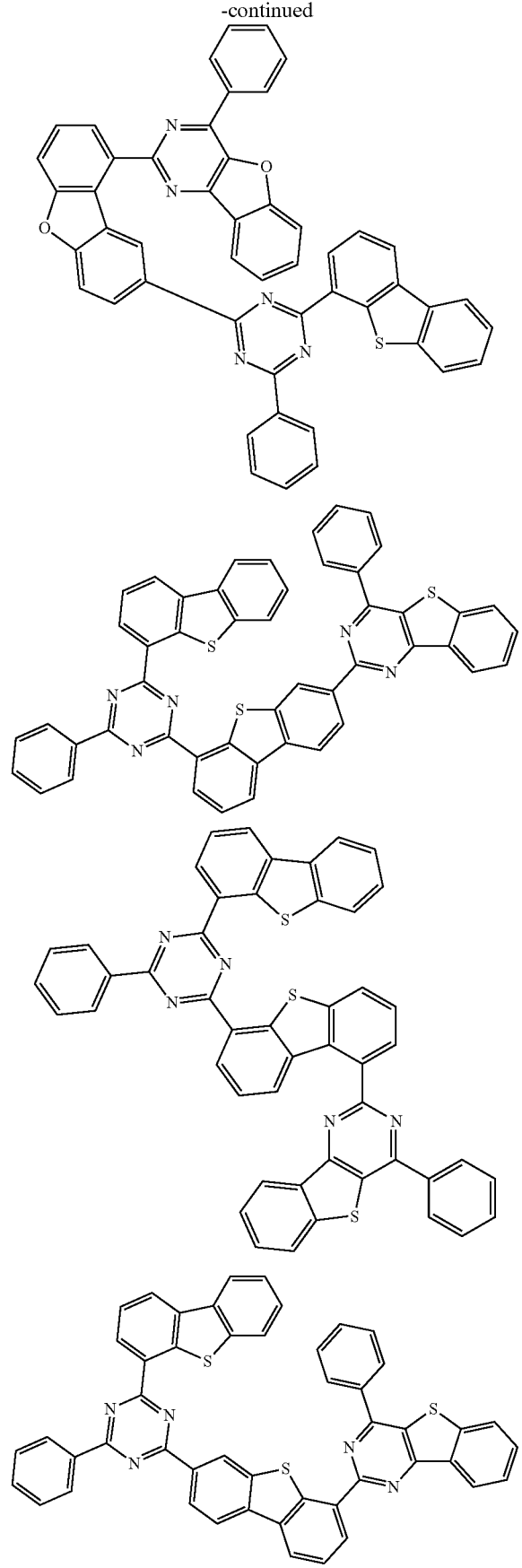
436
-continued
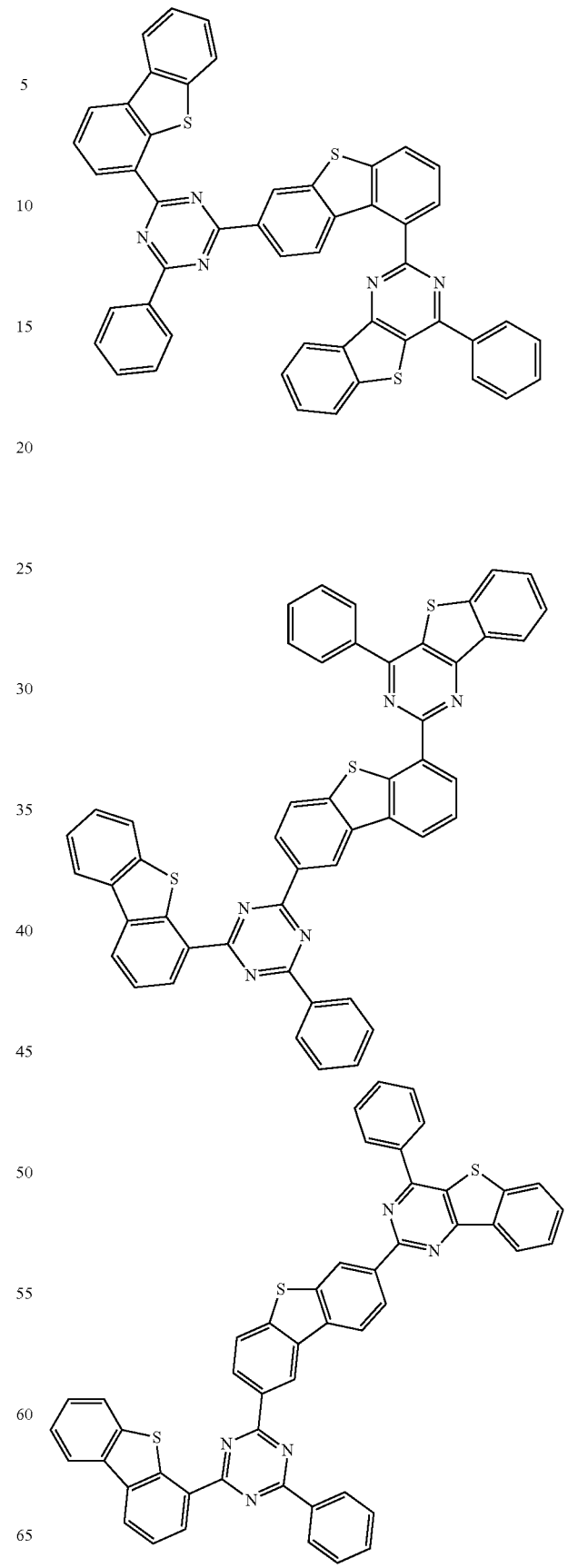

437
-continued
438
-continued
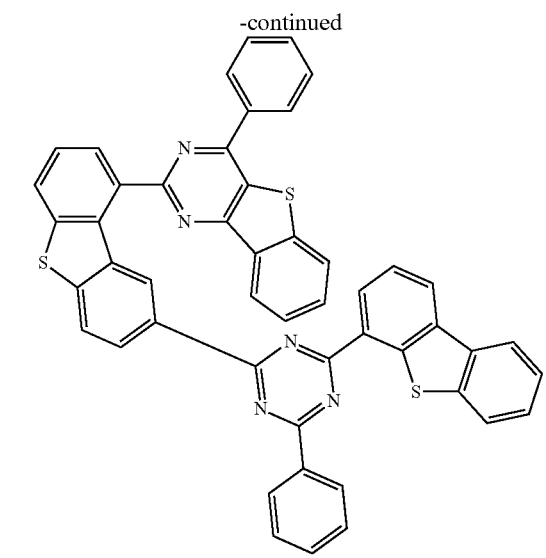
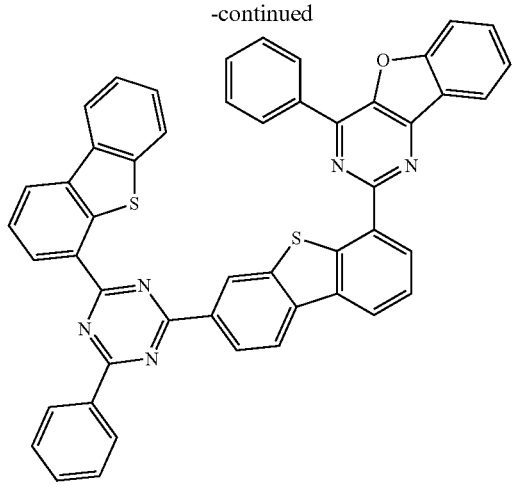
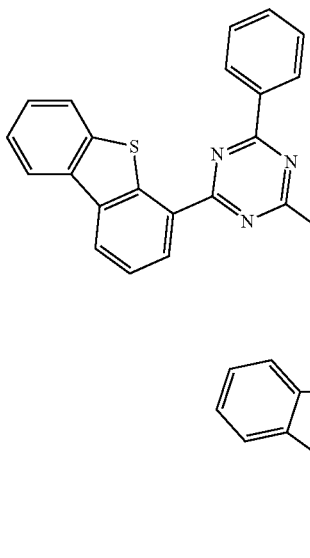
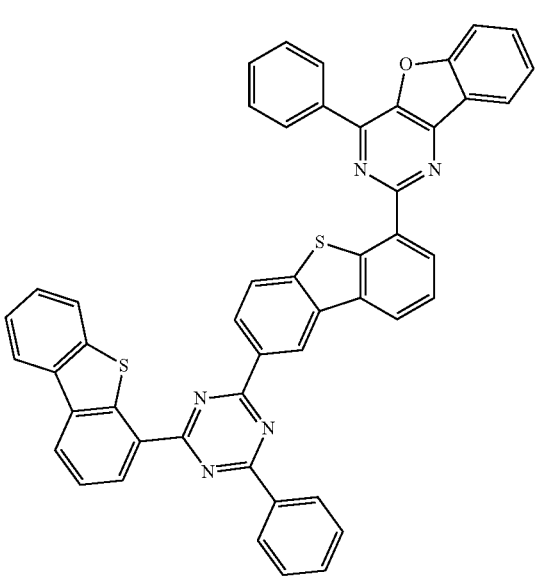

439
-continued
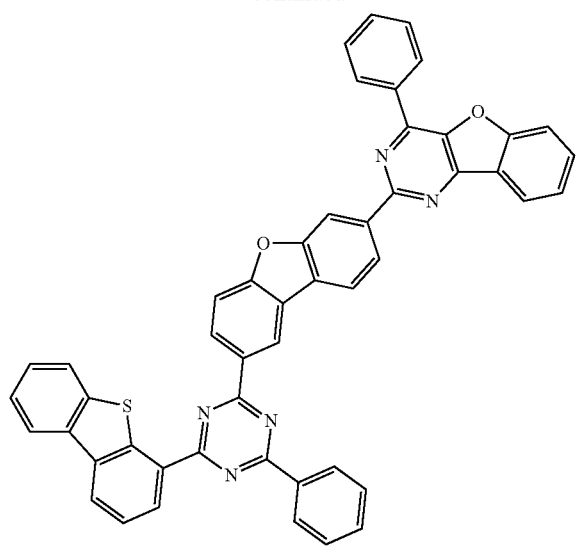
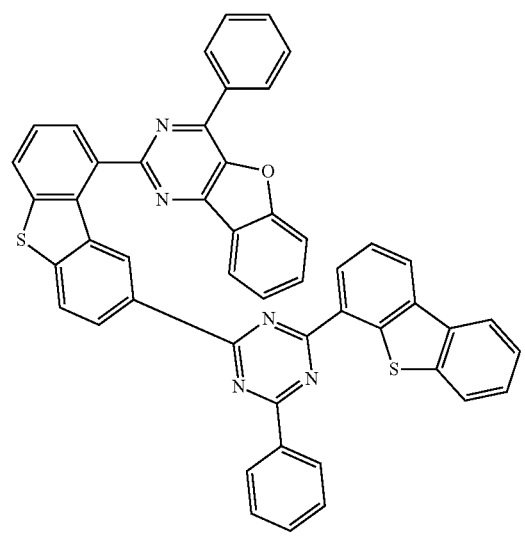
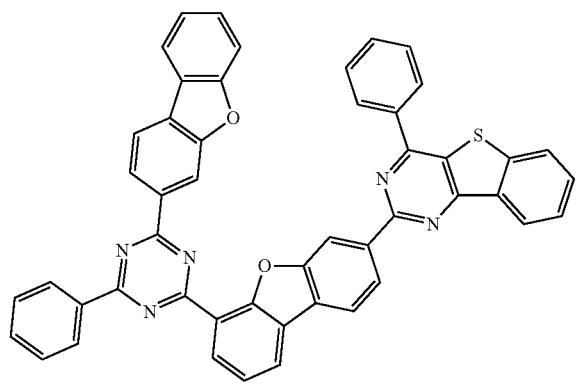
440
-continued
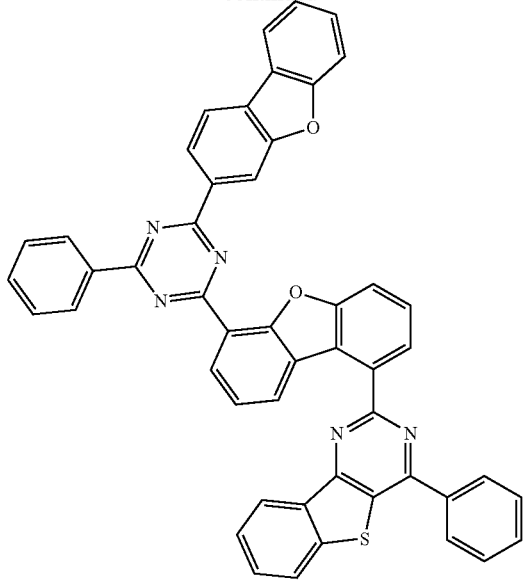
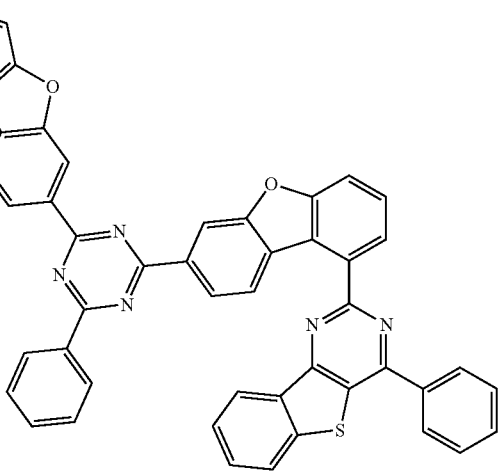

441
-continued
442
-continued
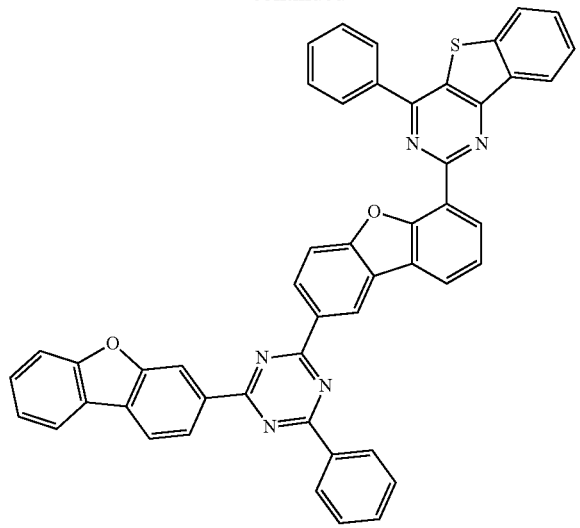
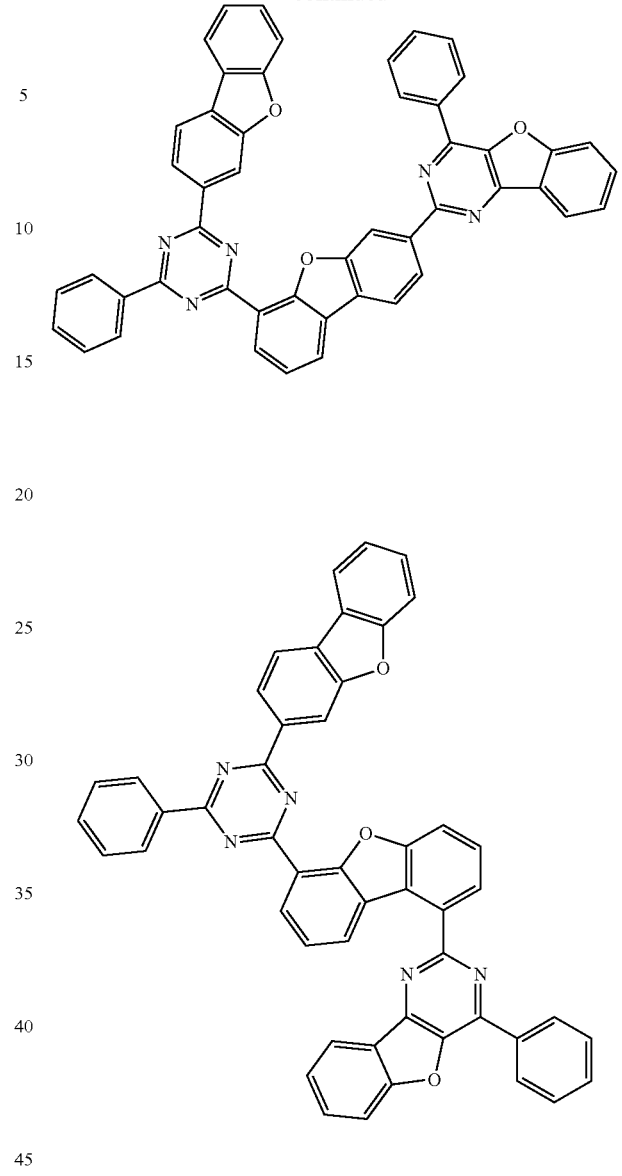
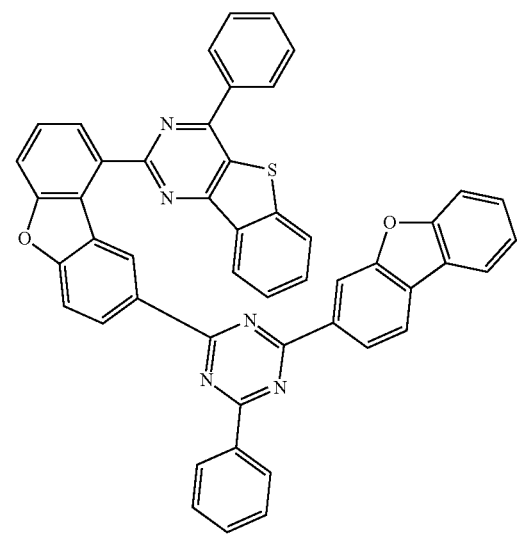
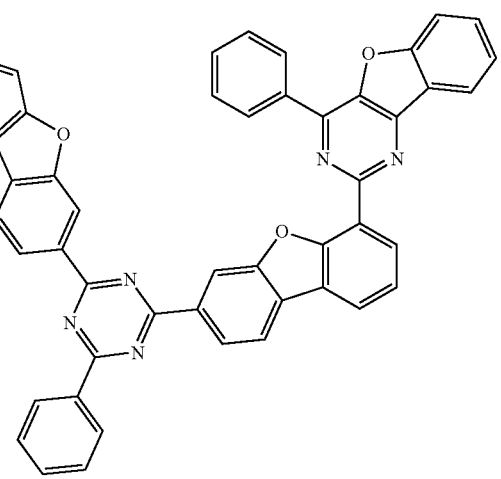

-continued
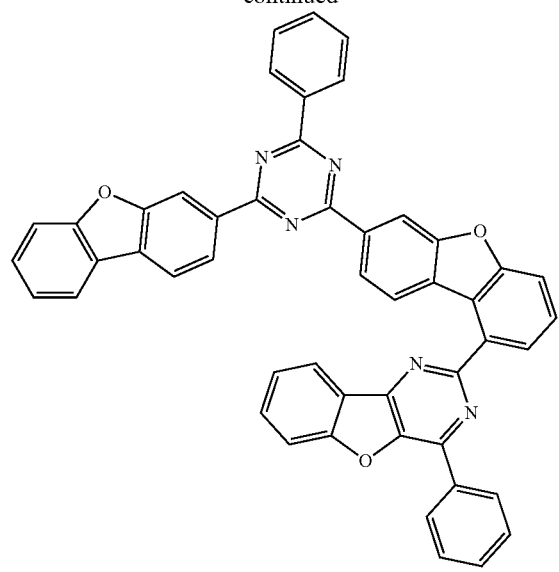
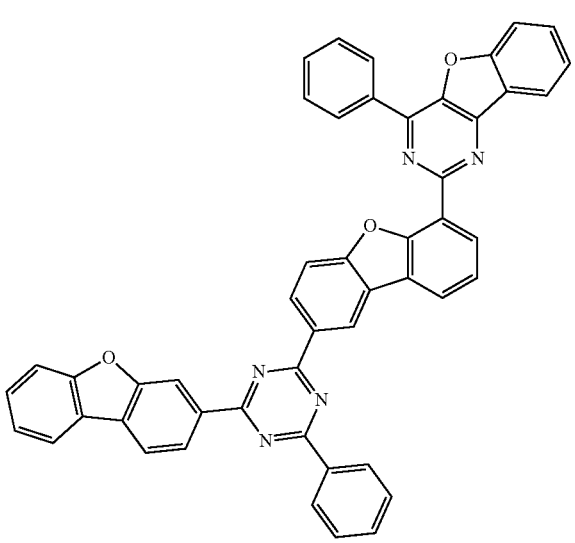
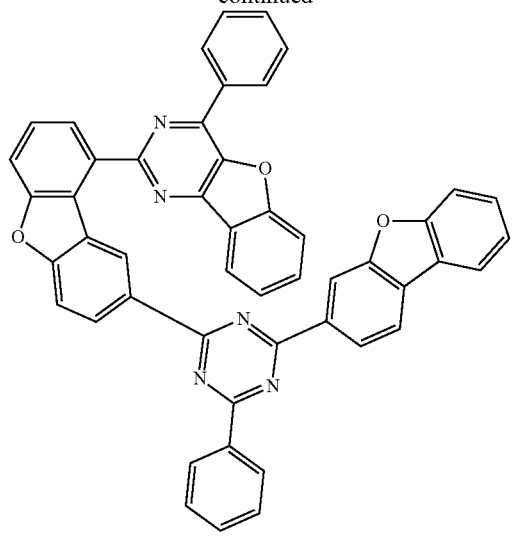
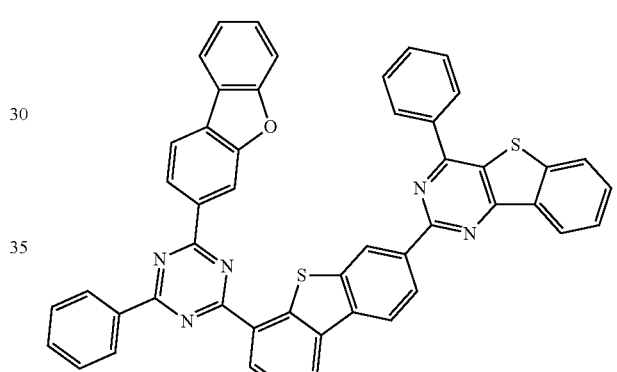
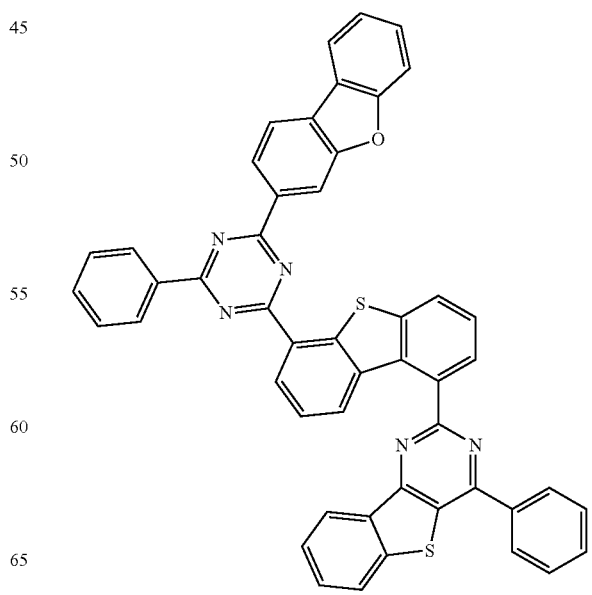

445
-continued
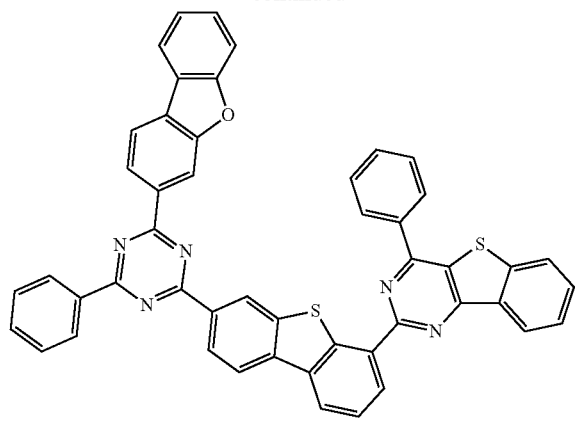
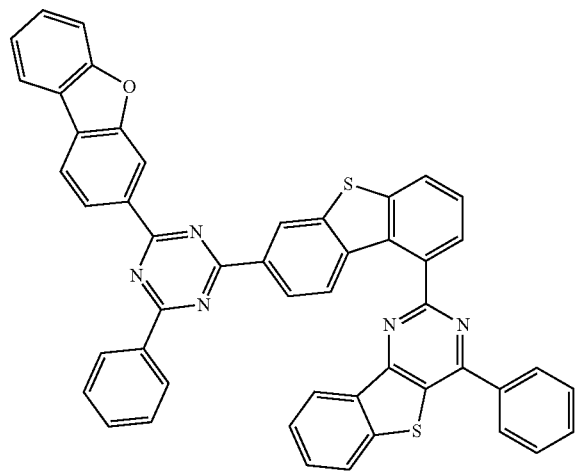
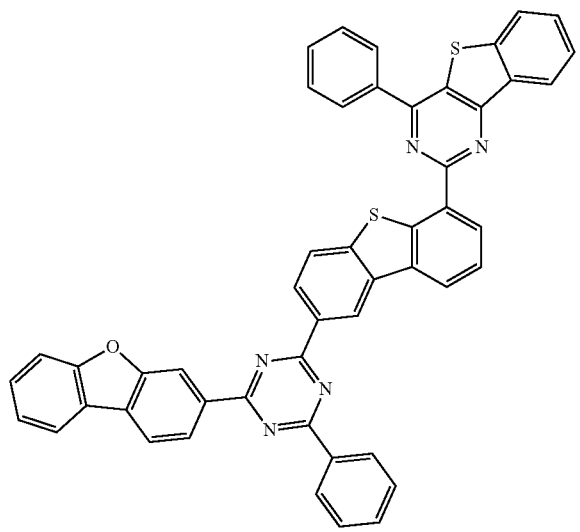
446
-continued
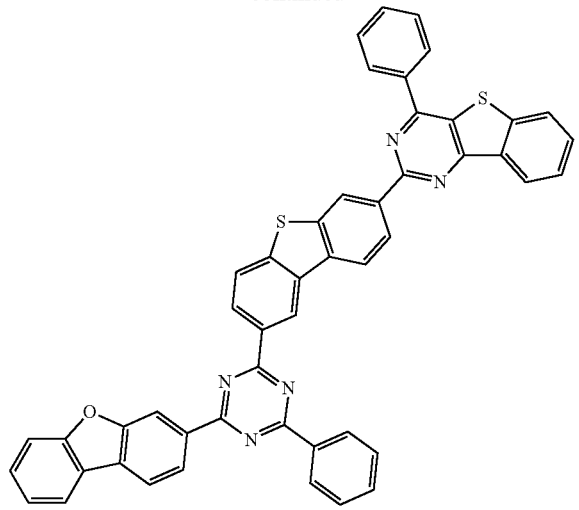
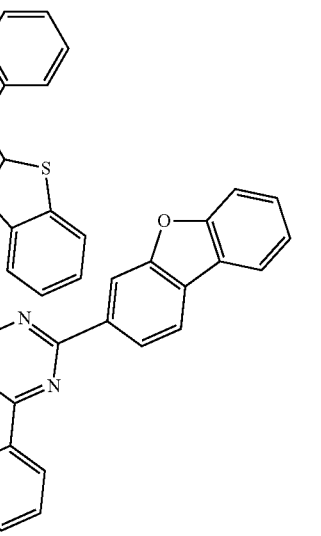
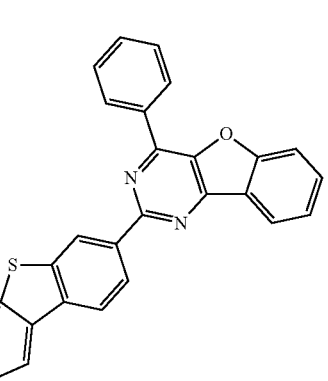

447
-continued
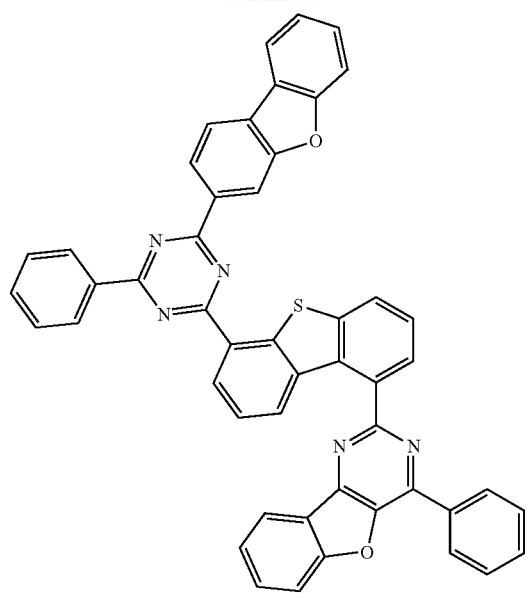
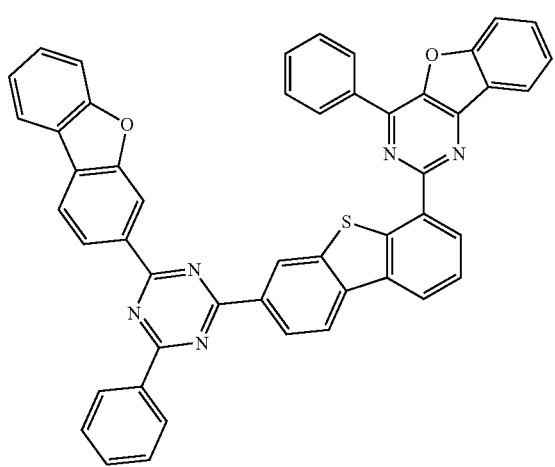
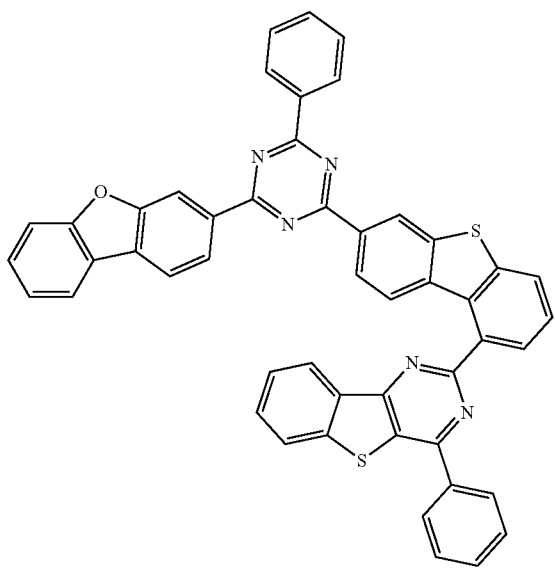
448
-continued
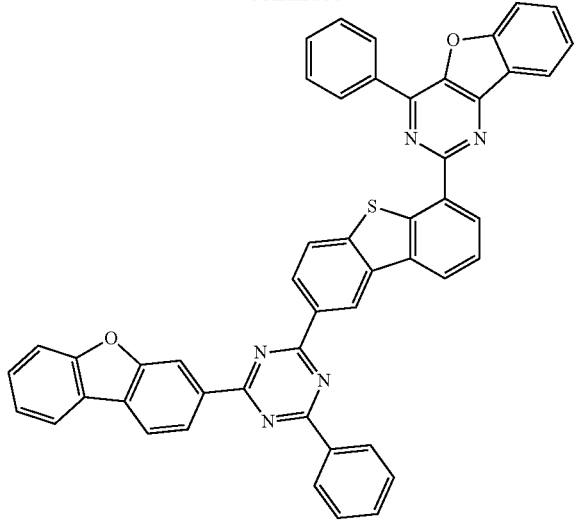
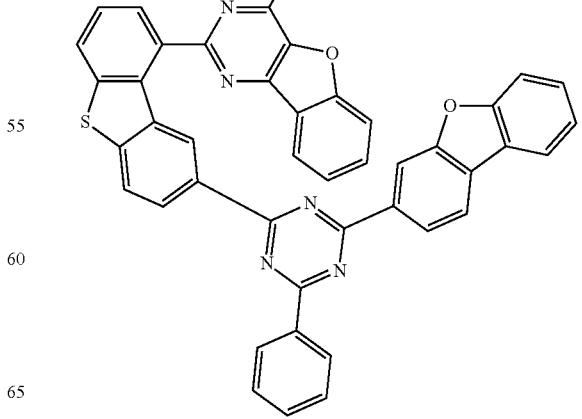

449
-continued
450
-continued
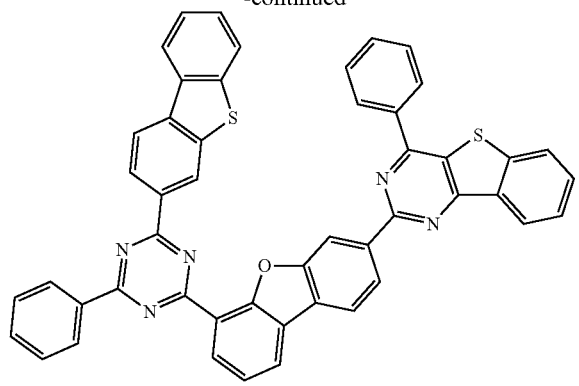
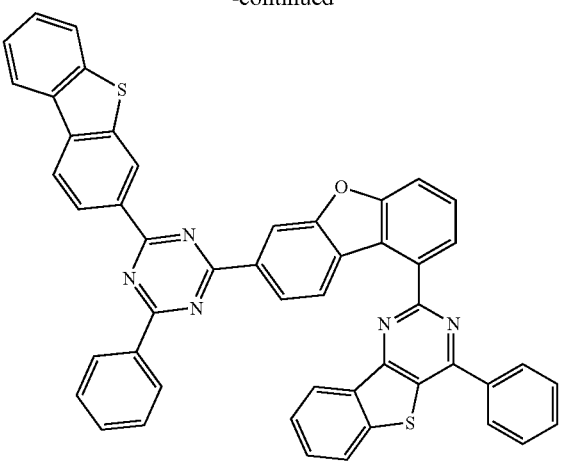
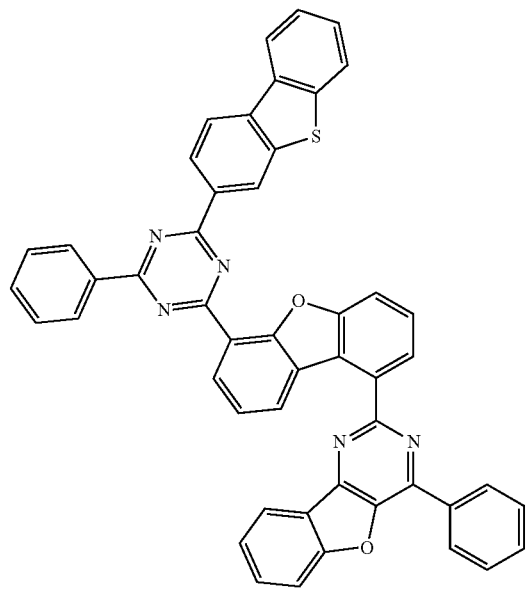
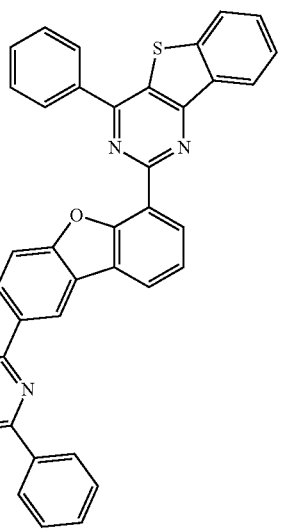
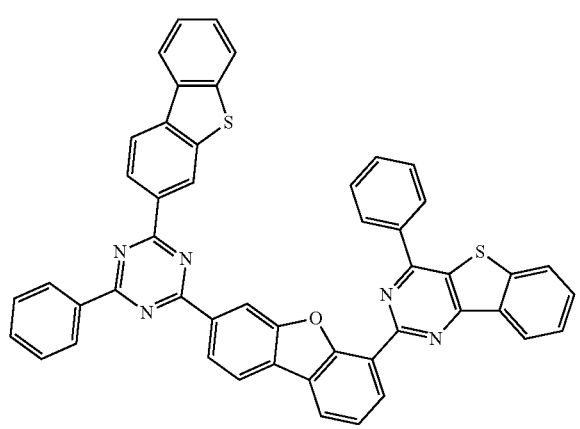
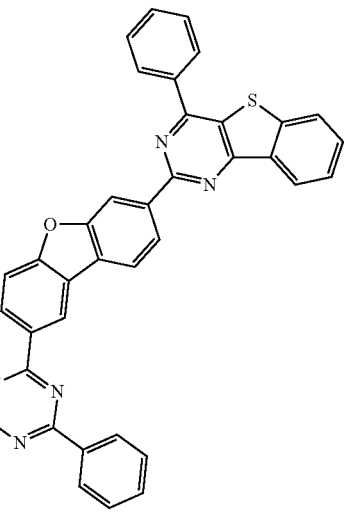

451
-continued
452
-continued
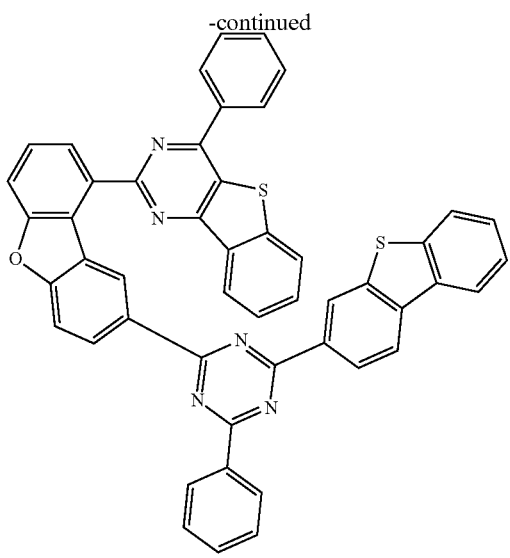
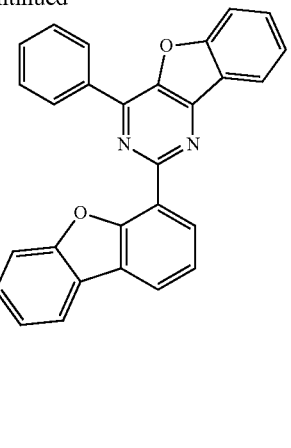
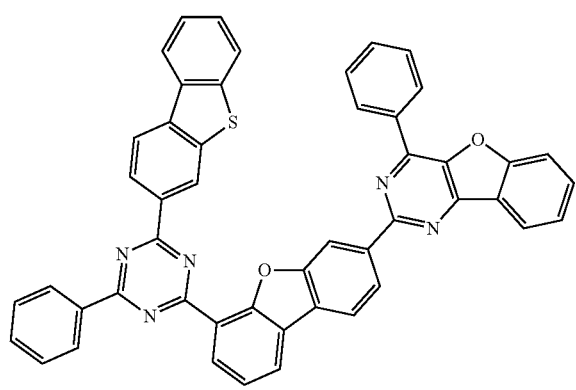
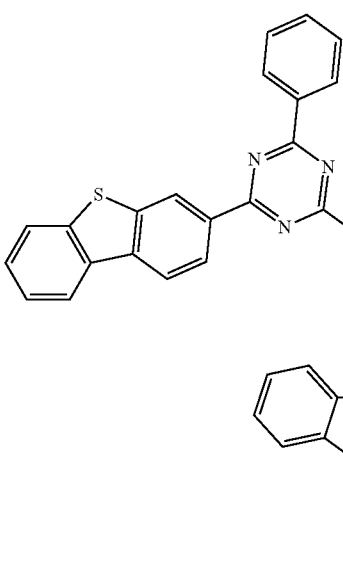
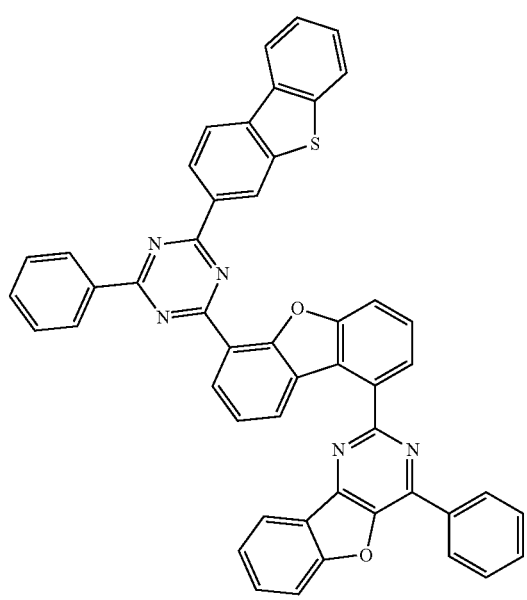
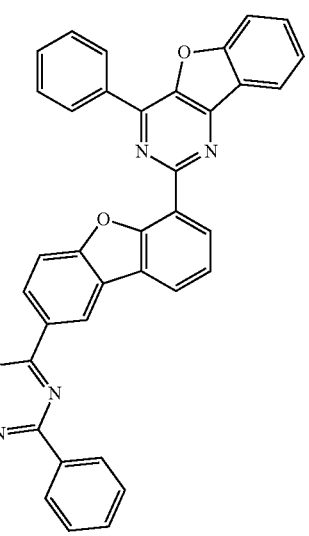

453
-continued
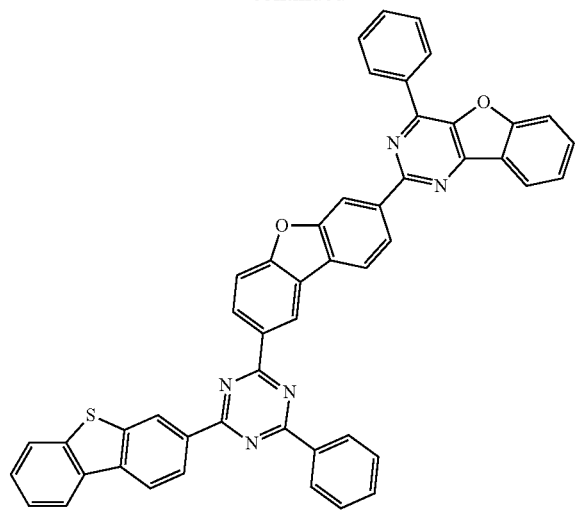
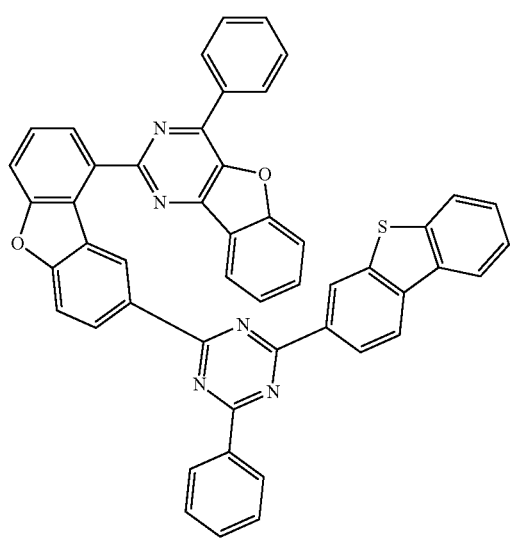
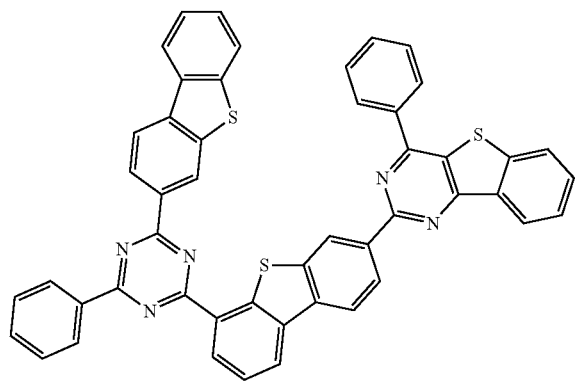
454
-continued
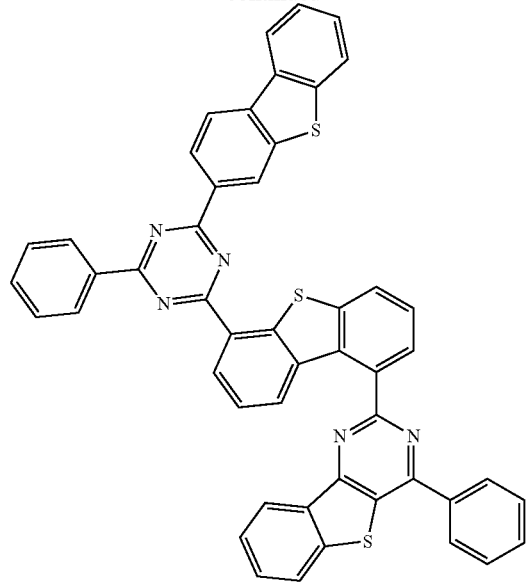
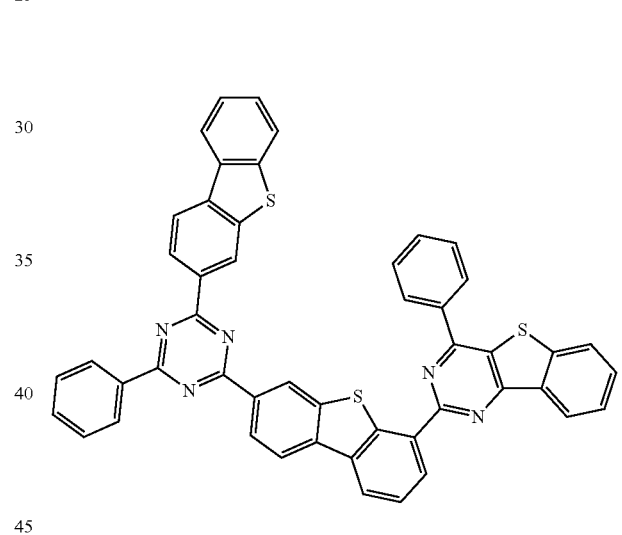
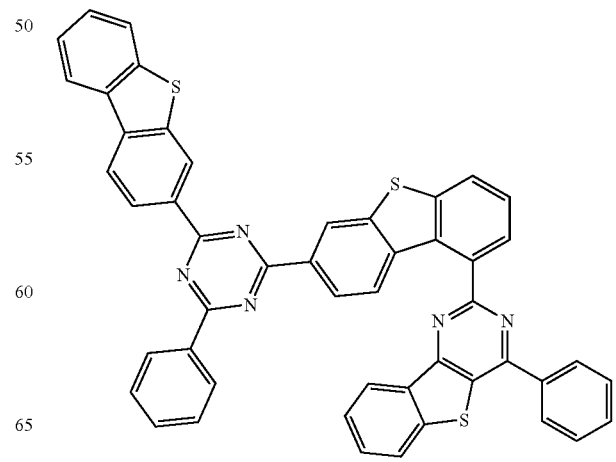

455
-continued
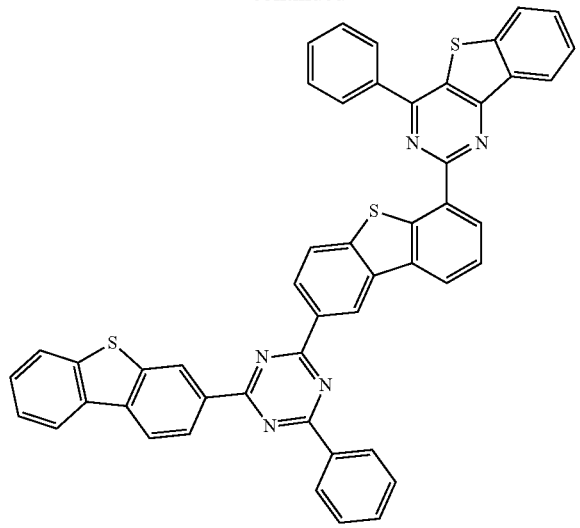
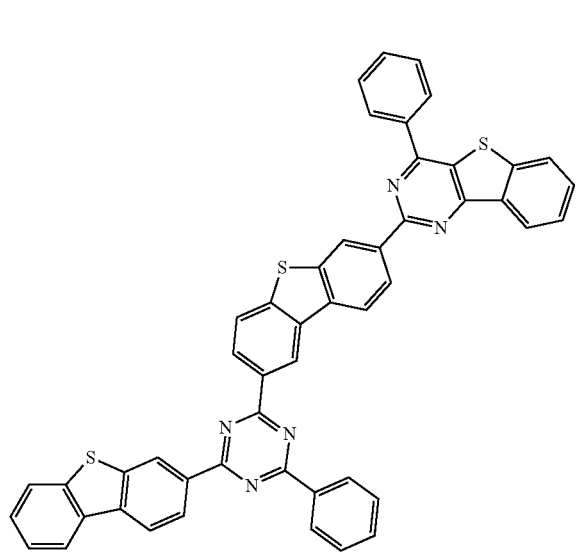
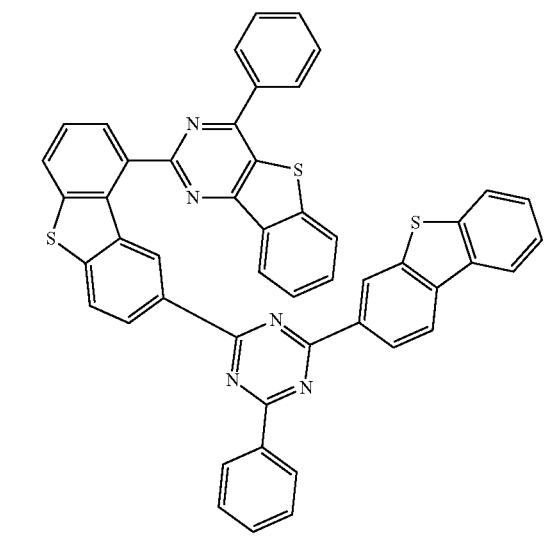
456
-continued
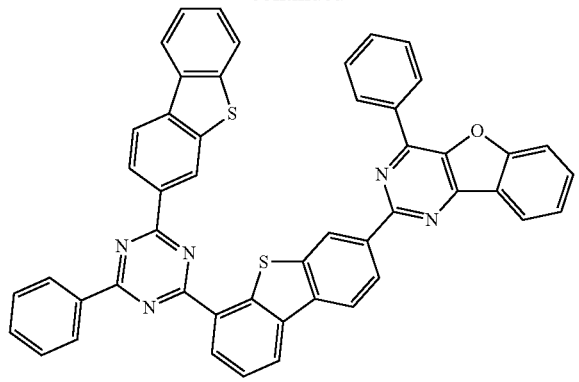
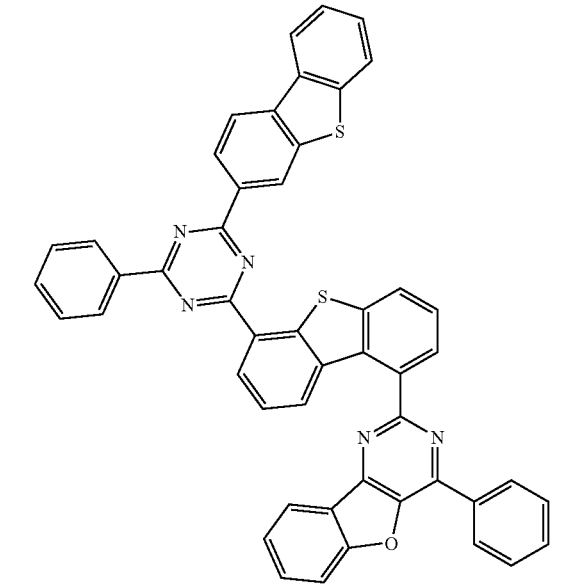
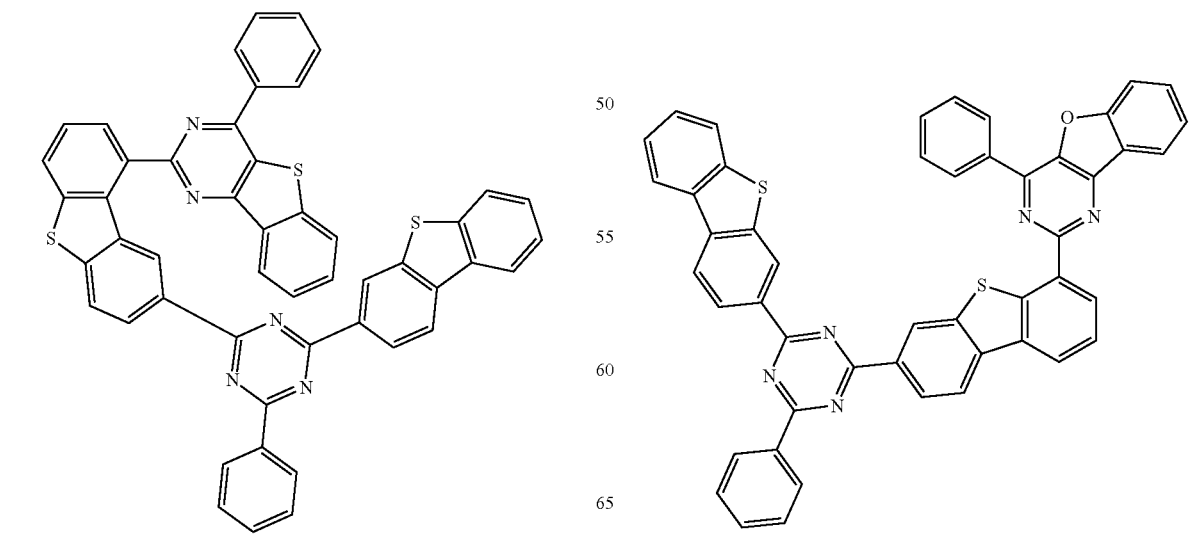

457
-continued
458
-continued
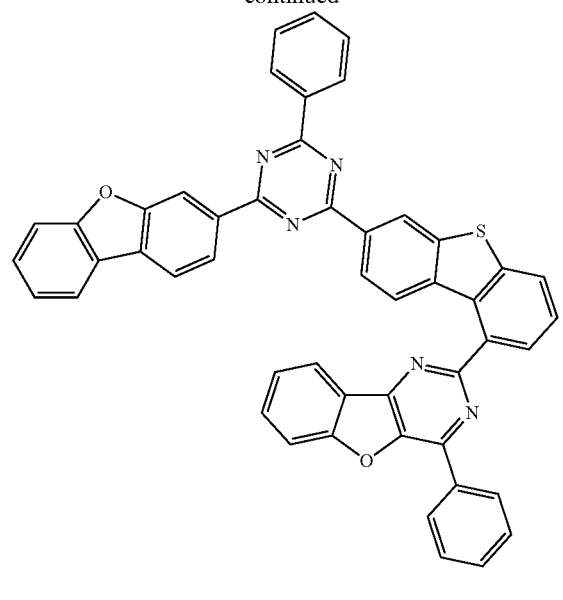
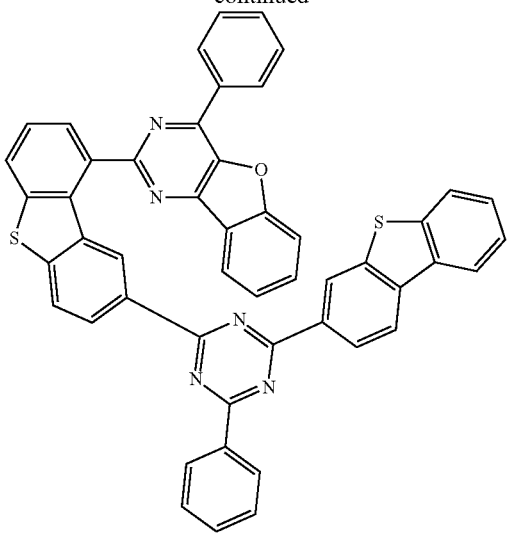
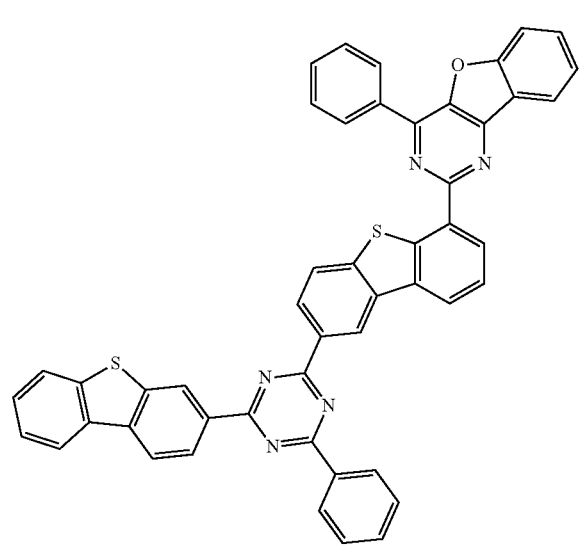
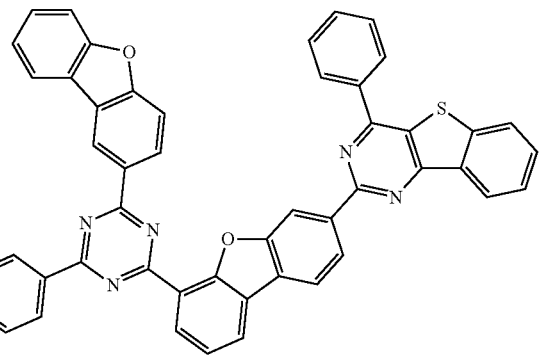
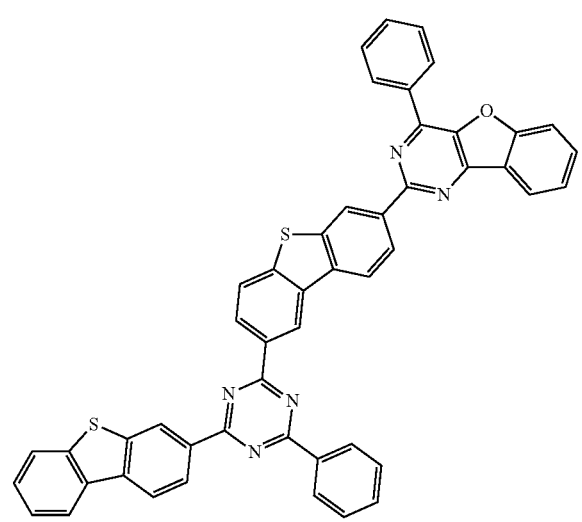
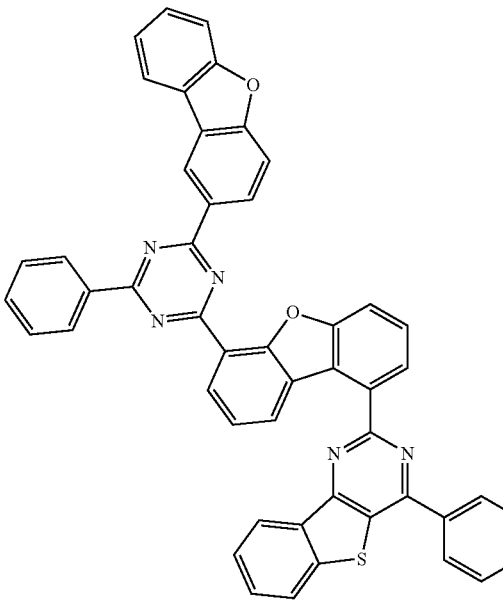

459
-continued
460
-continued
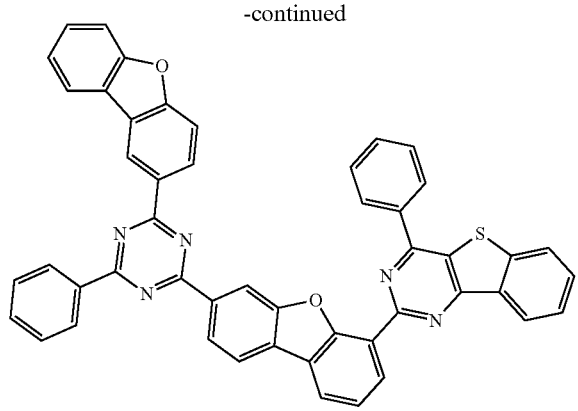
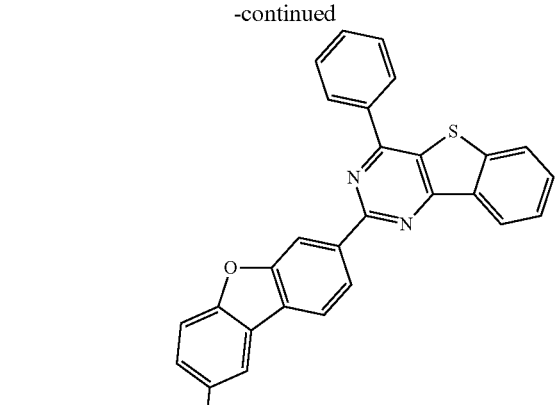
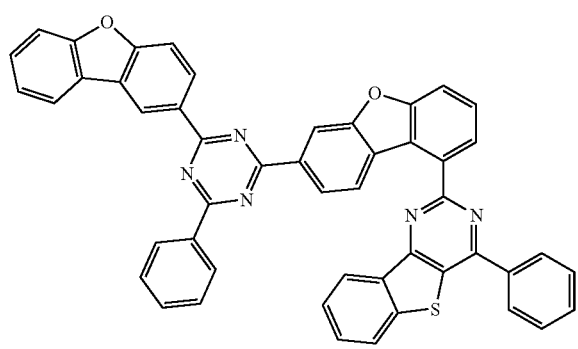
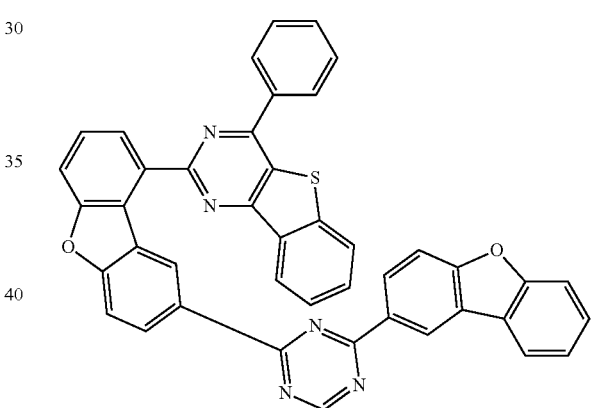
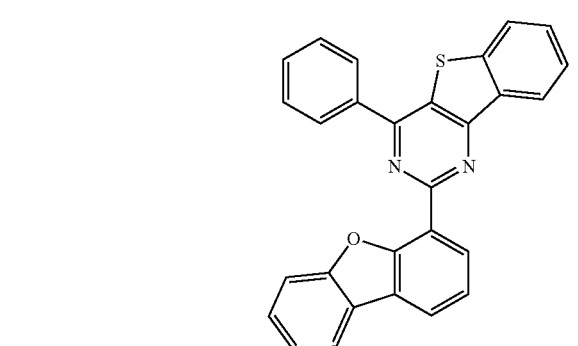
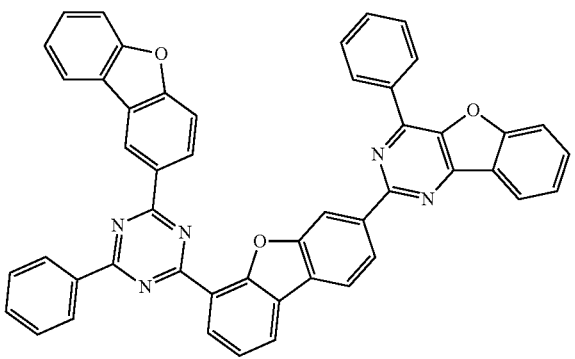
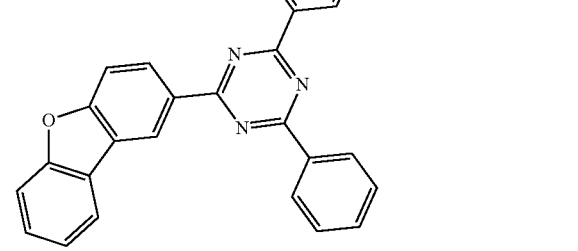

461
-continued
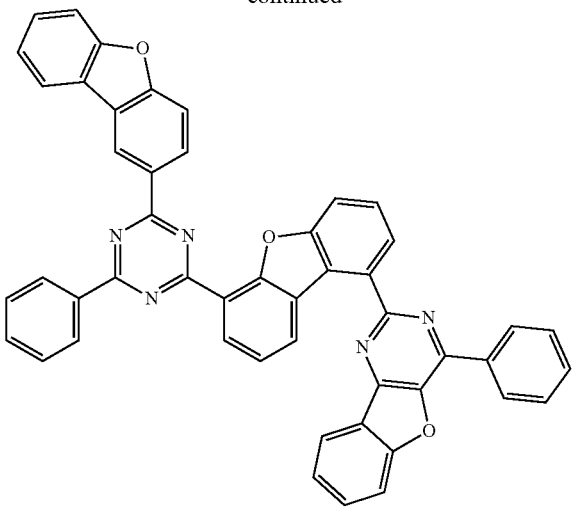
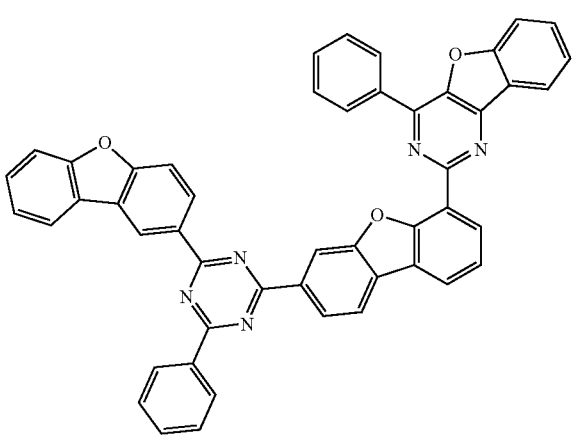
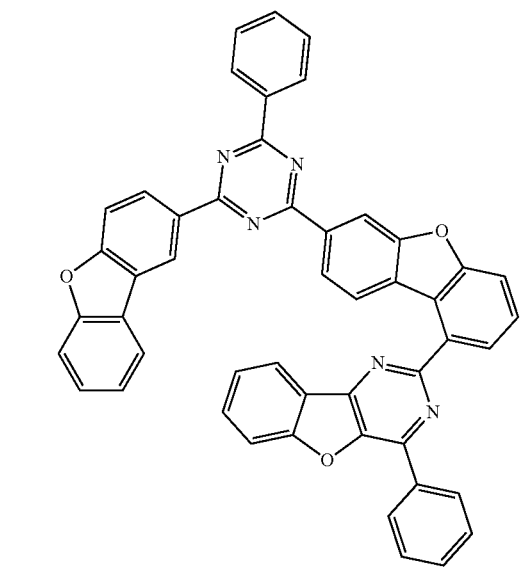
462
-continued
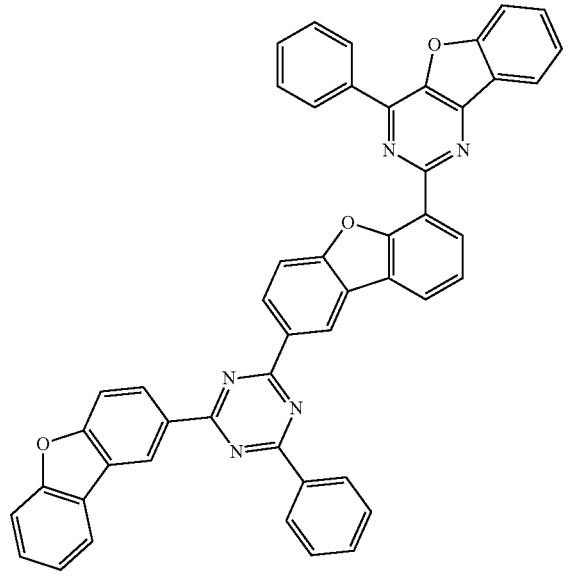
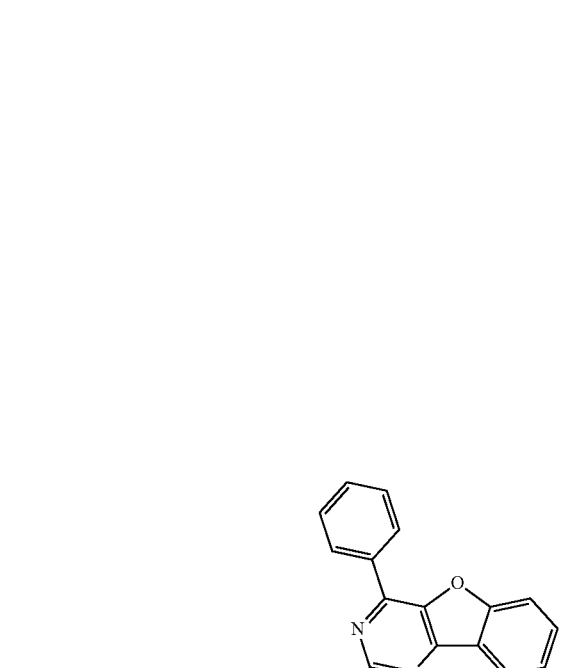

463
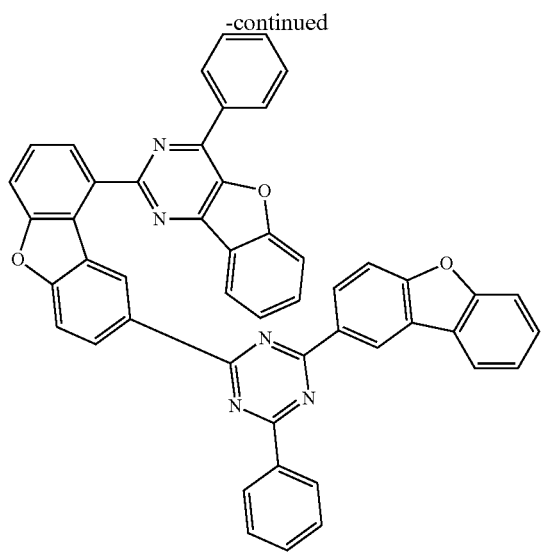
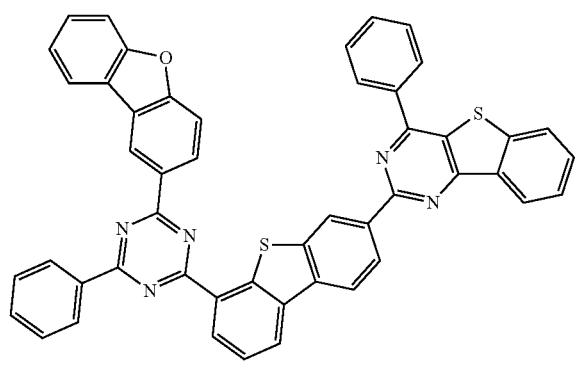
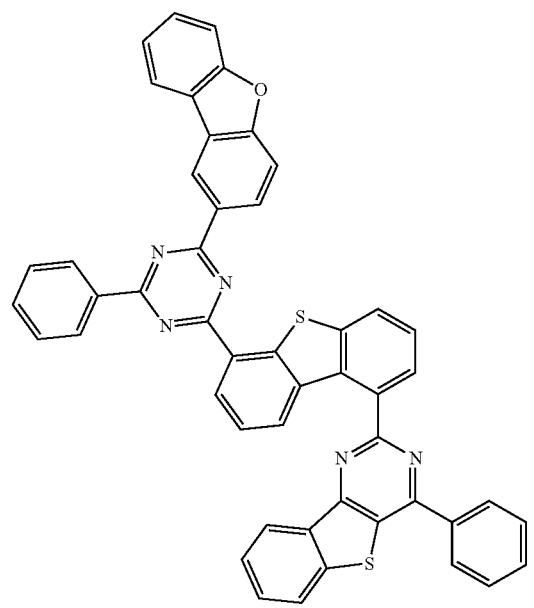
464
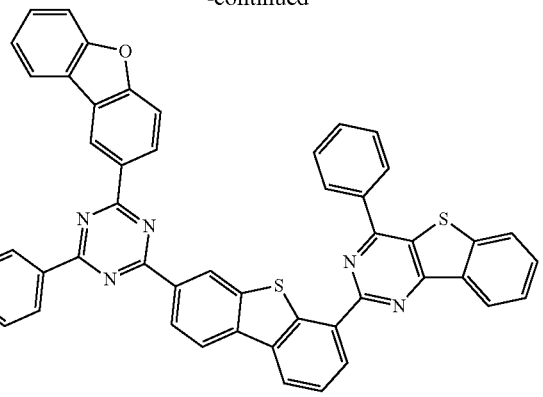
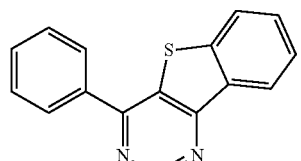
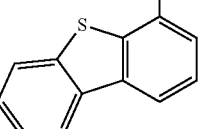
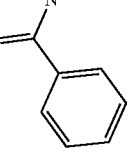

-continued
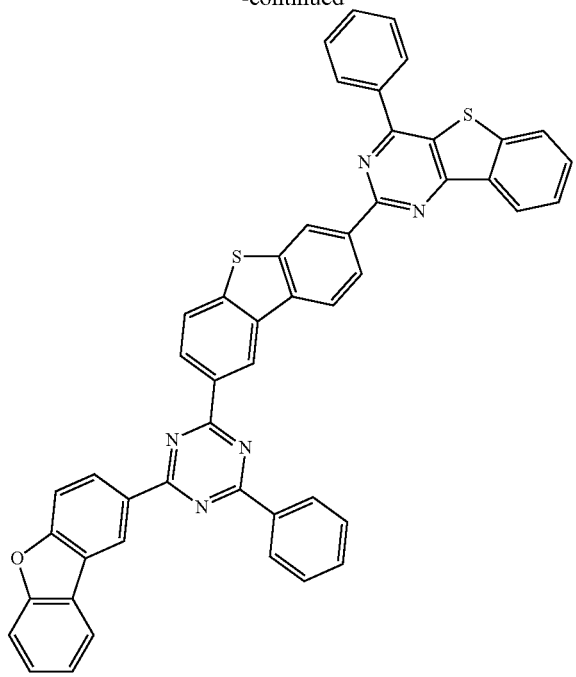
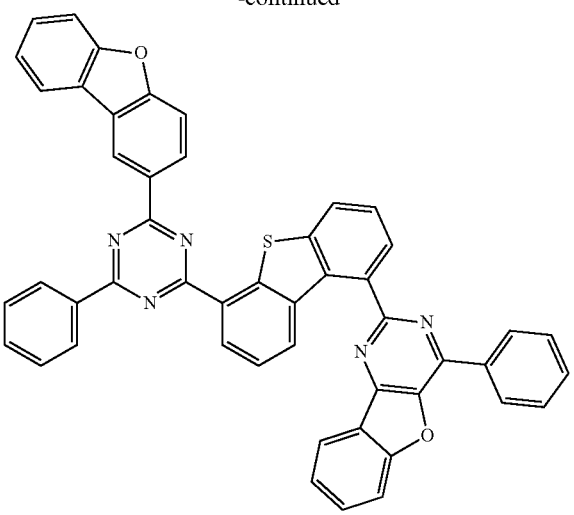
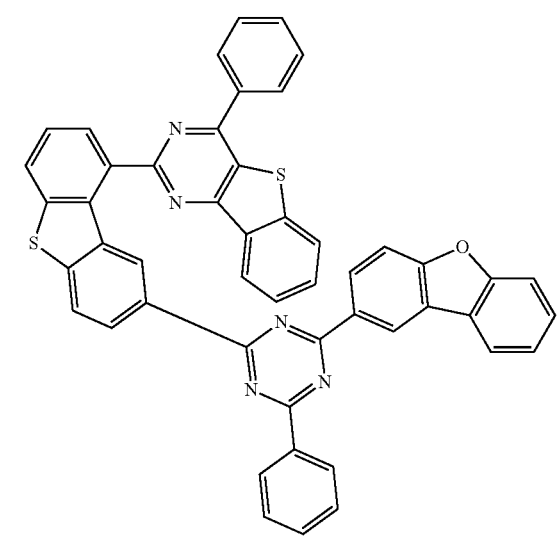
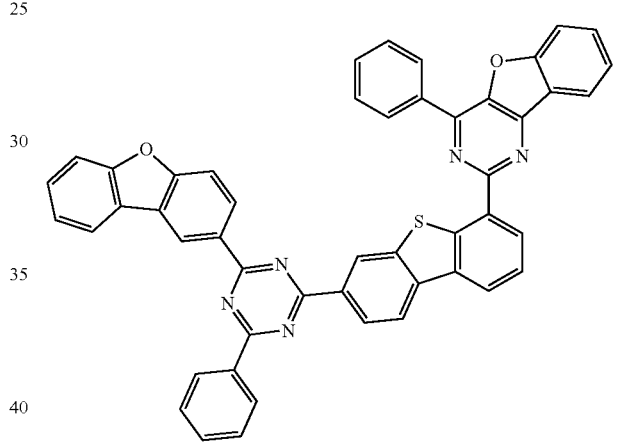
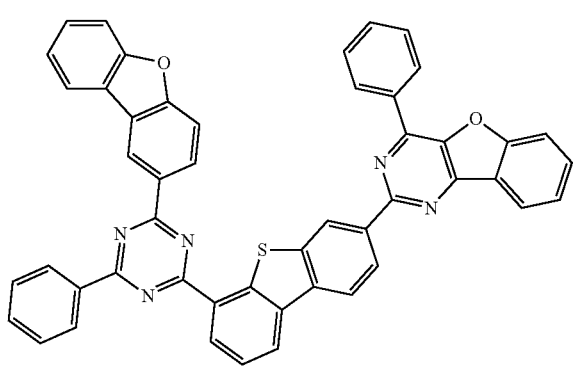
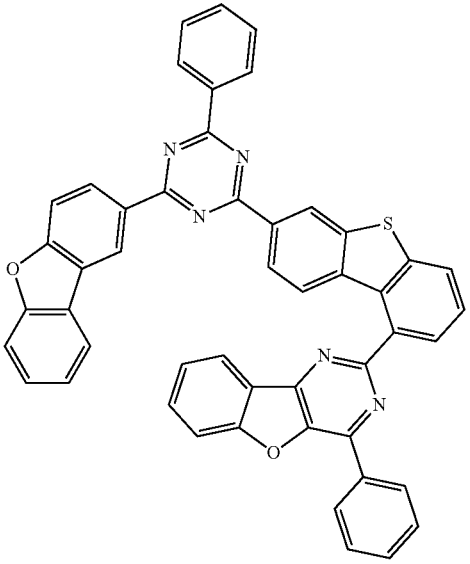

467
-continued
468
-continued
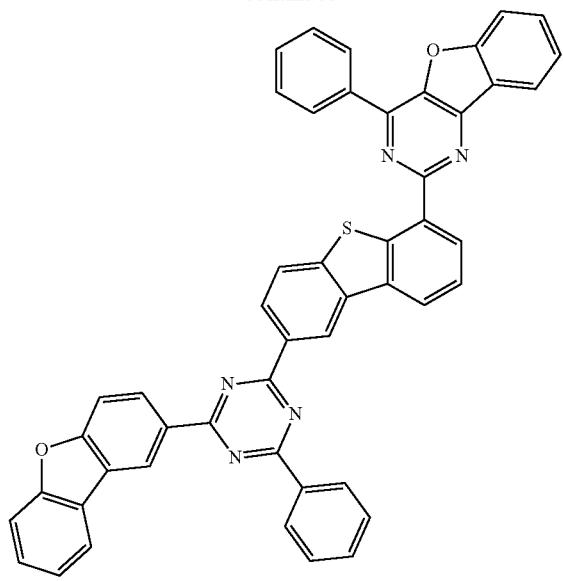
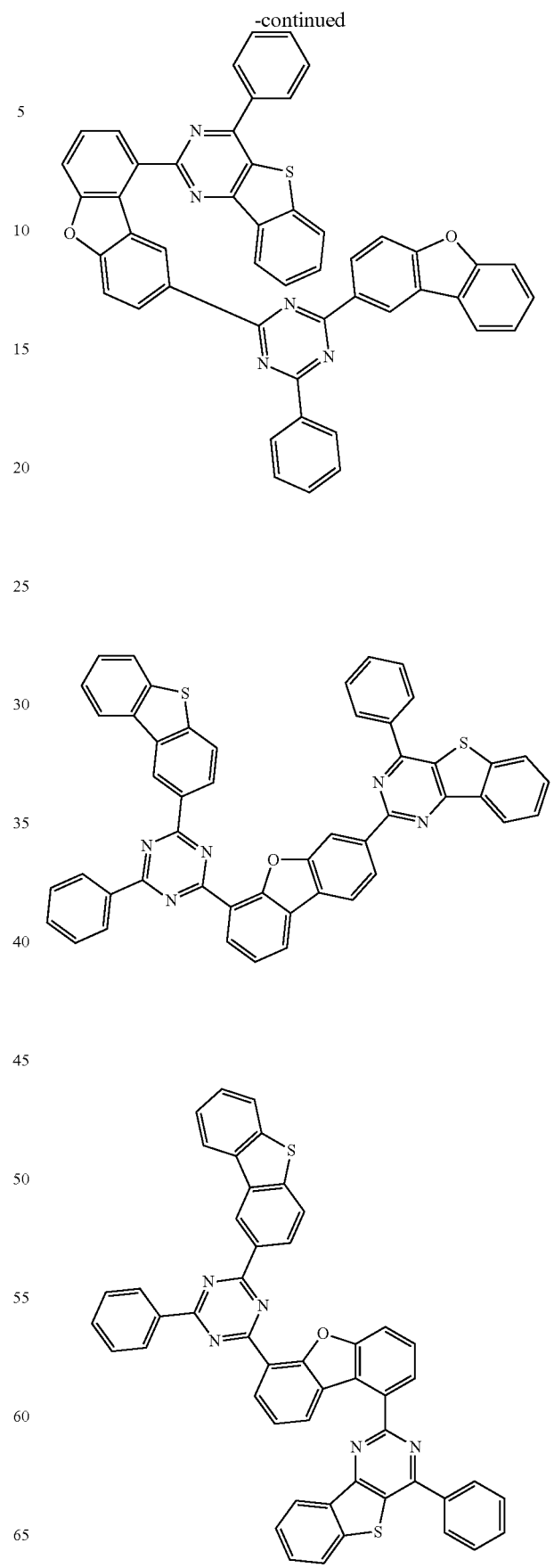

469
-continued
470
-continued
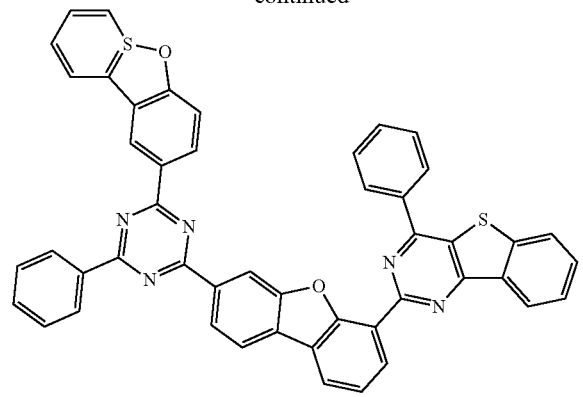
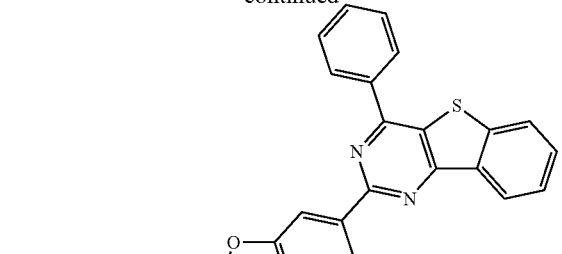
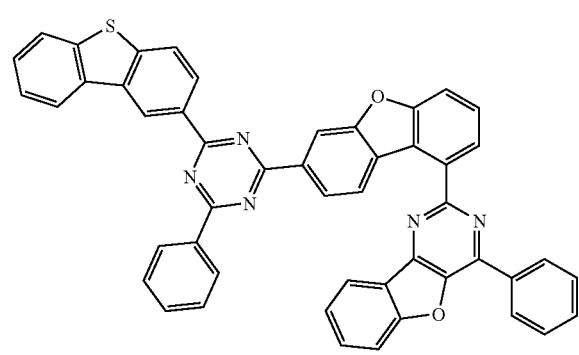
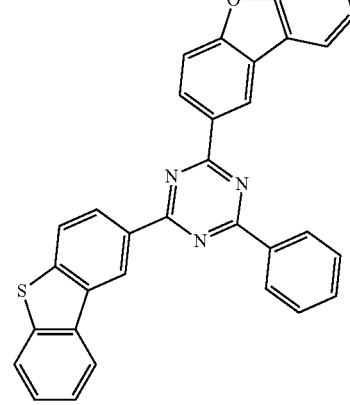
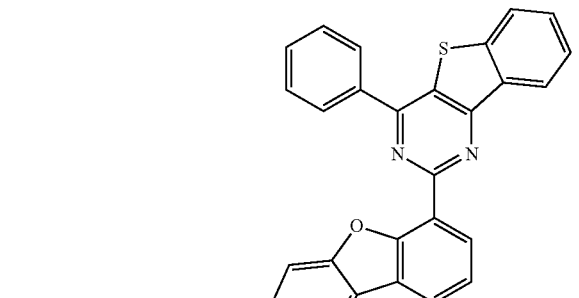
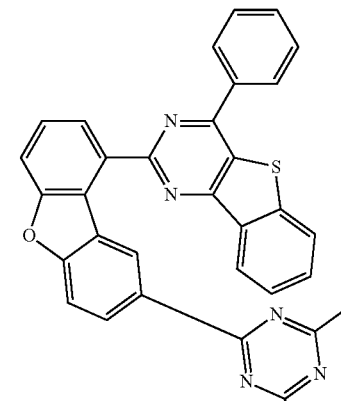
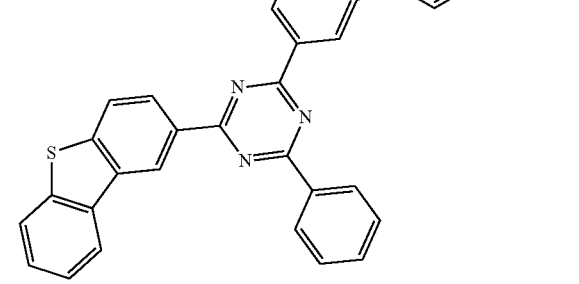
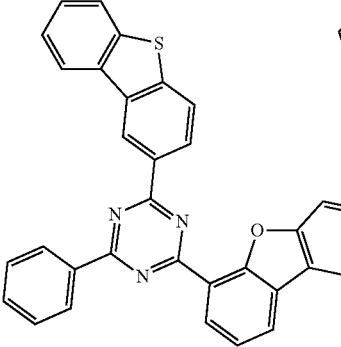

471
-continued
472
-continued
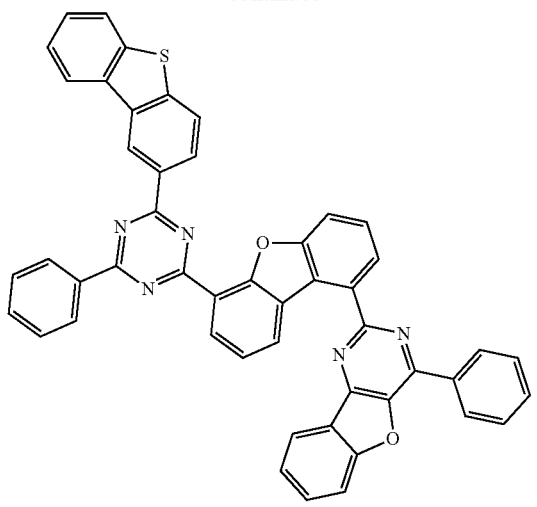
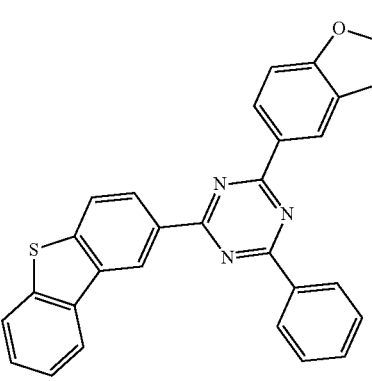

473
-continued
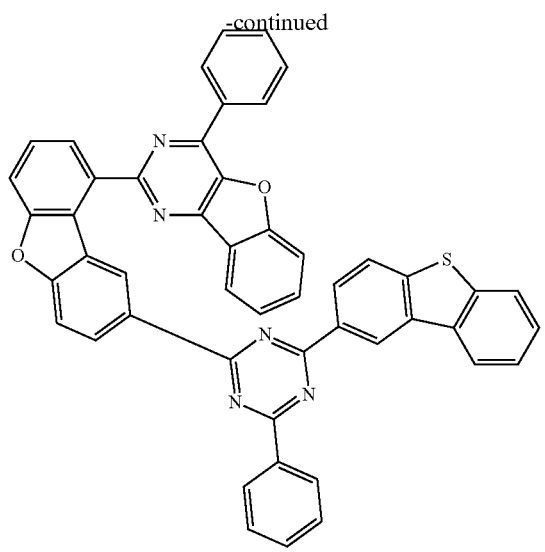
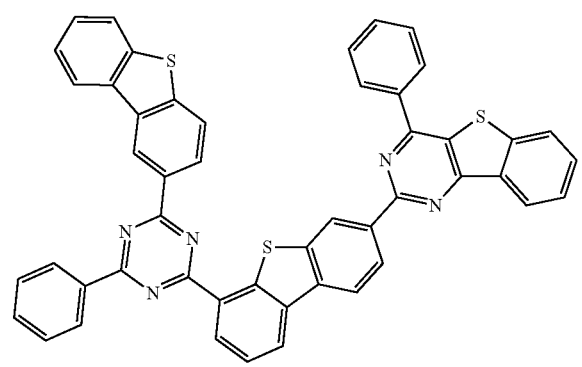
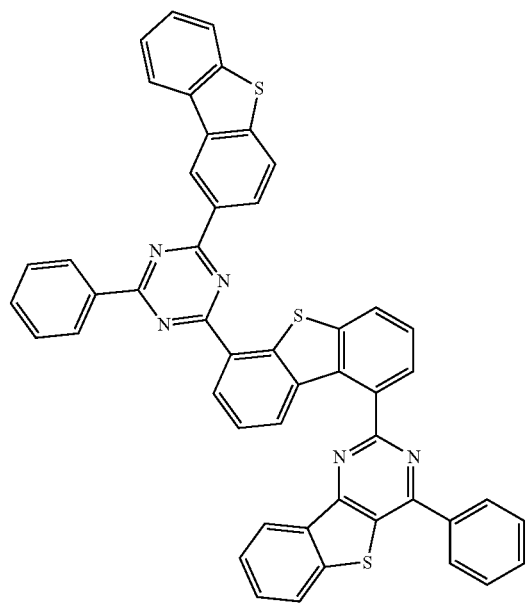
474
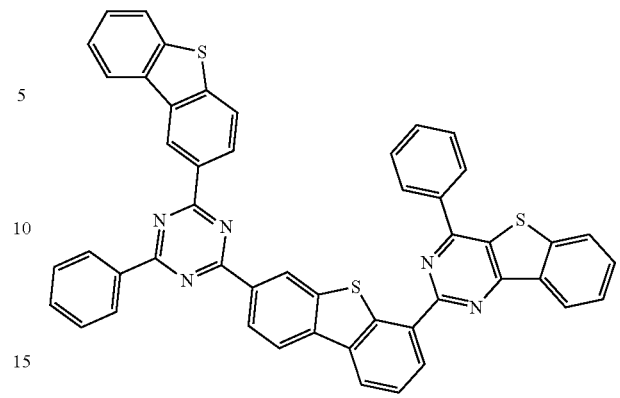
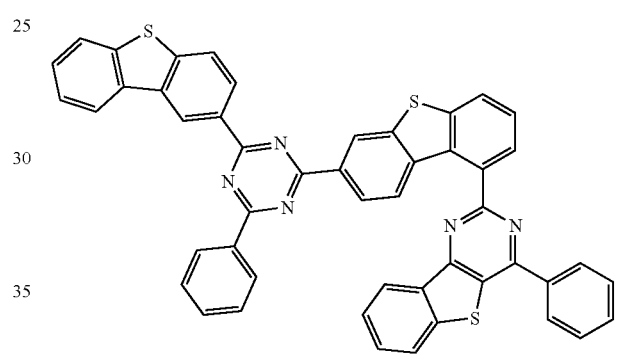
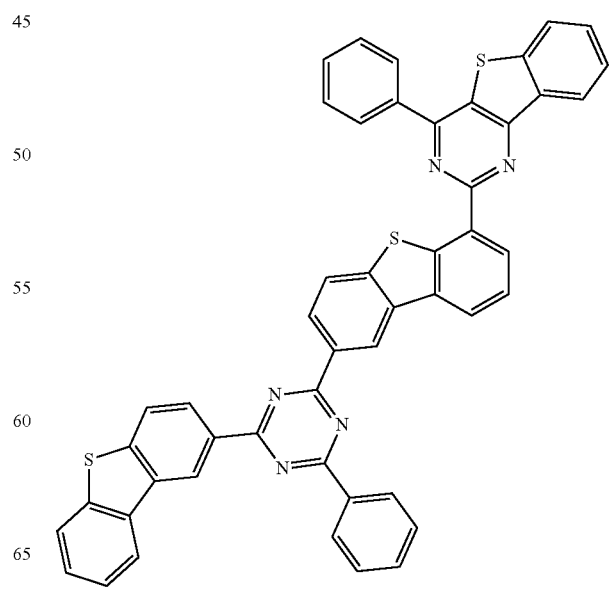

475
-continued
476
-continued
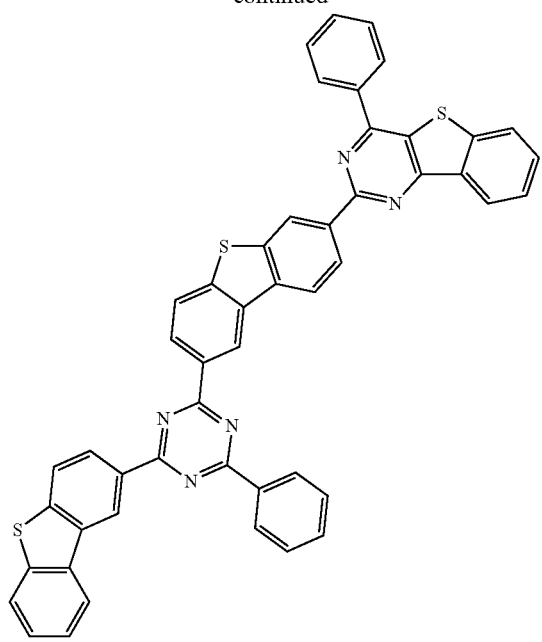
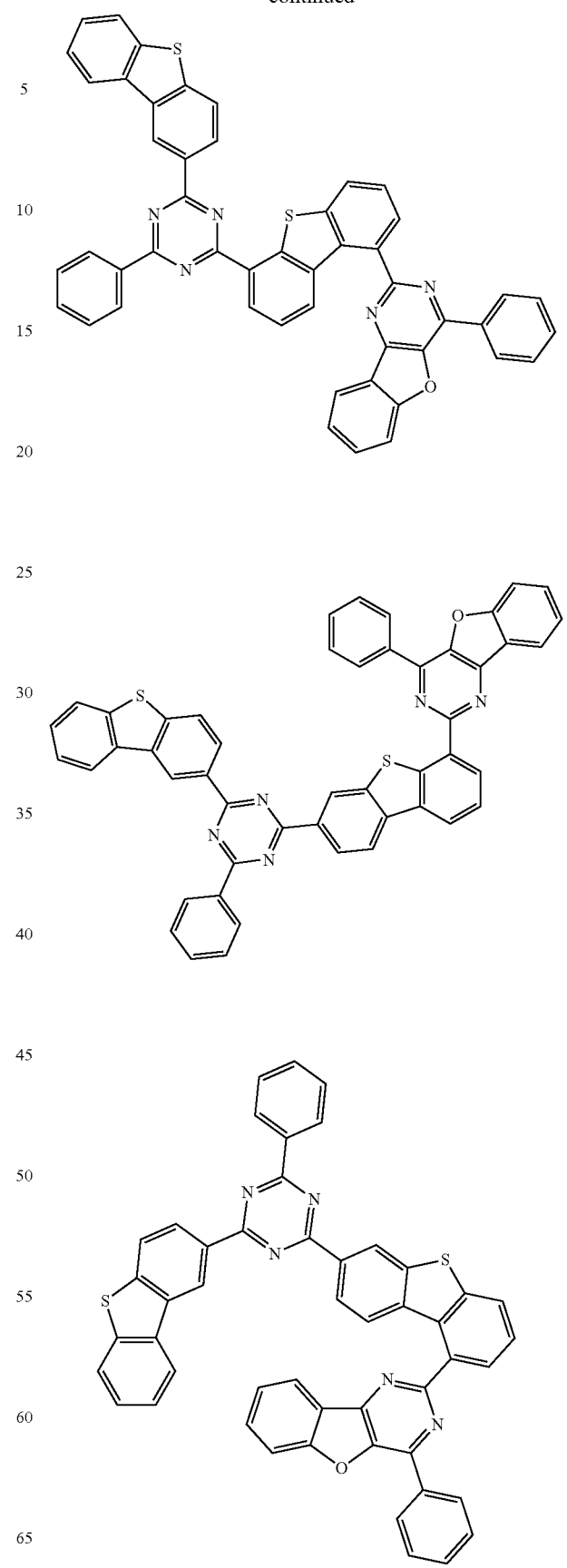

477
-continued
478
-continued
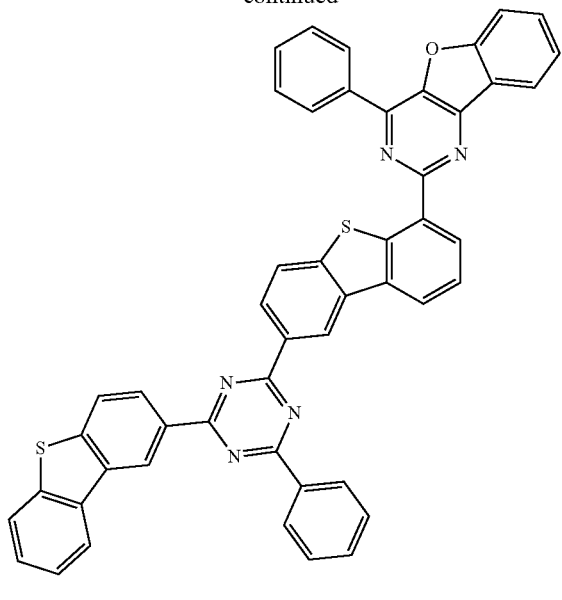
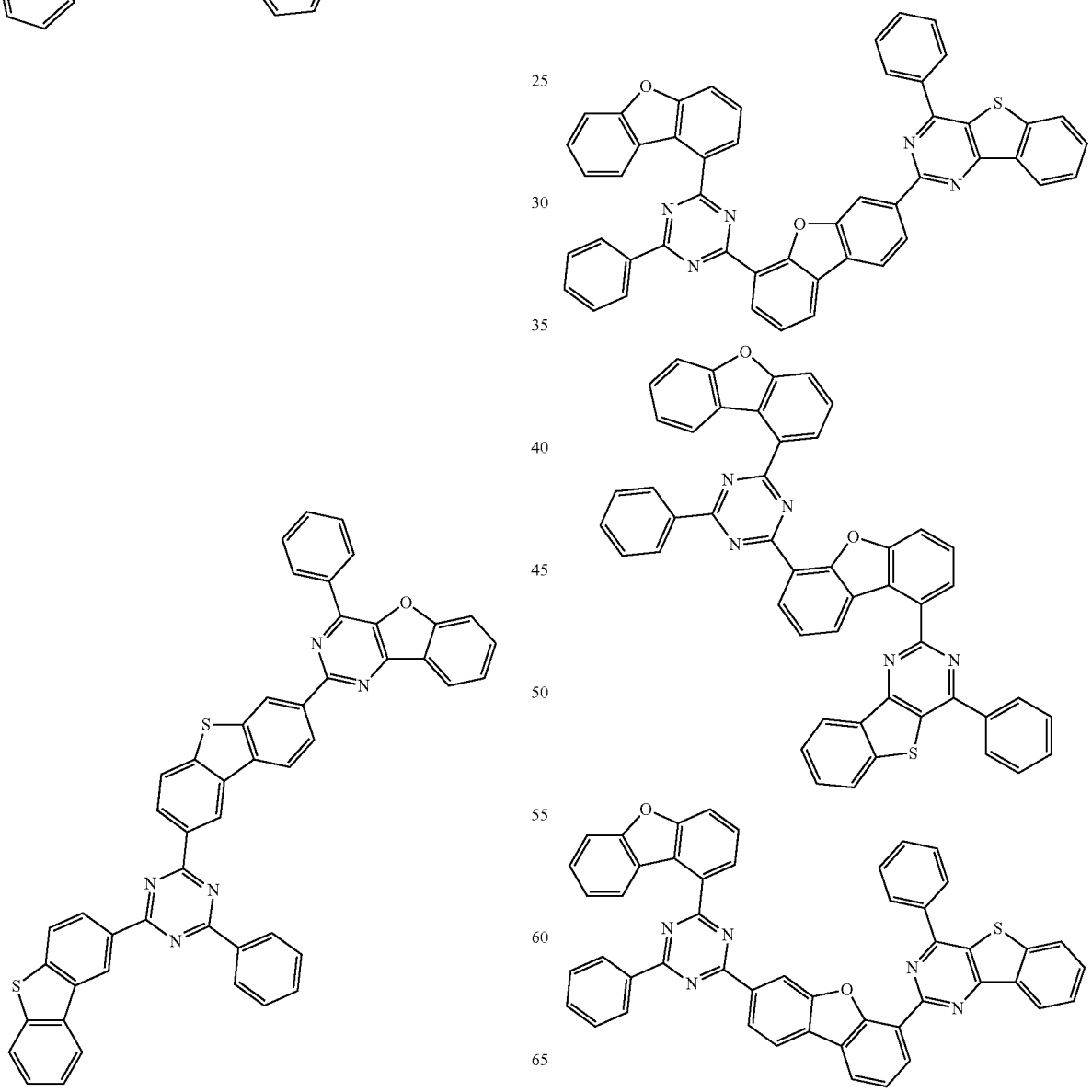

479
-continued
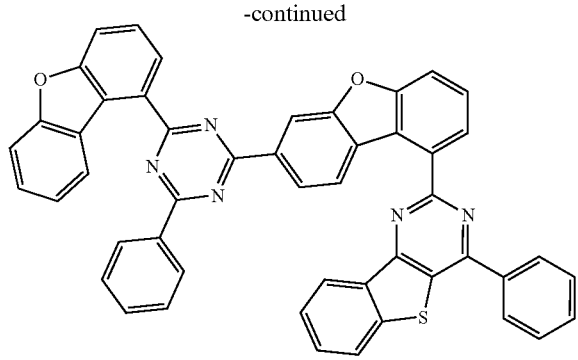
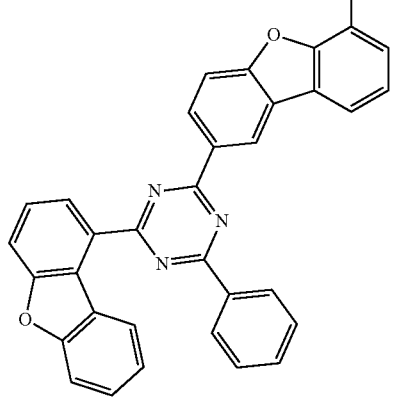
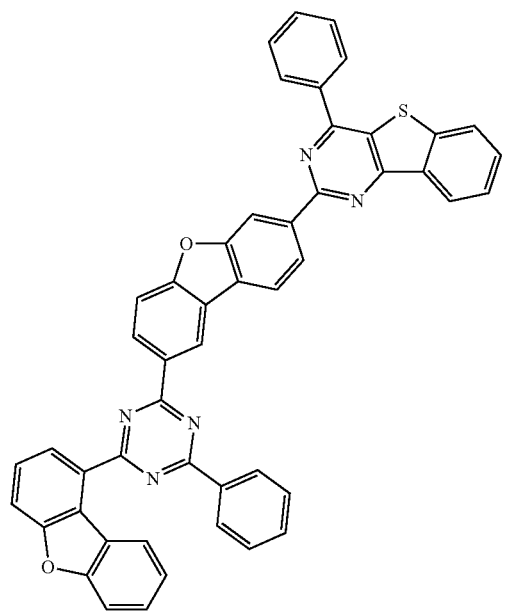
480
-continued
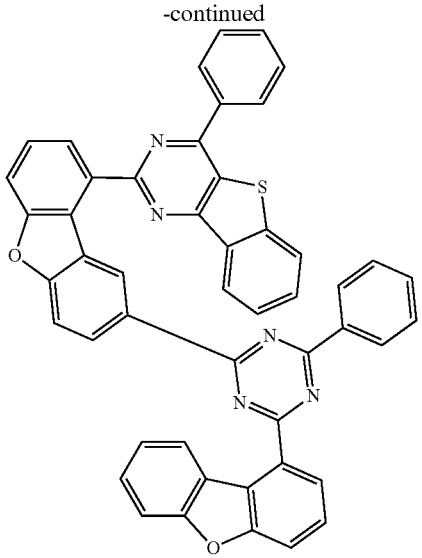
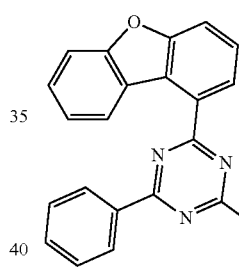
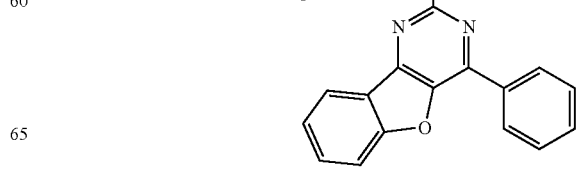

481
-continued
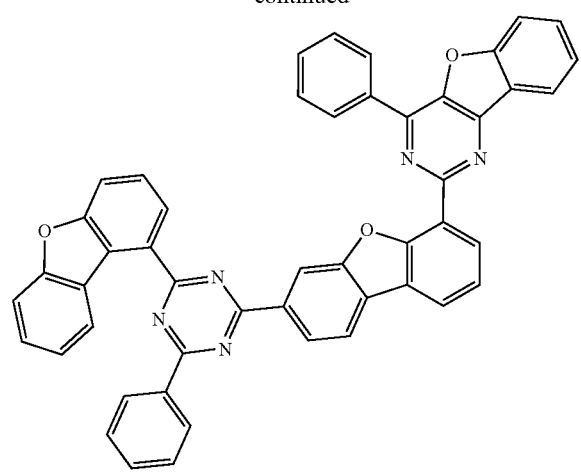
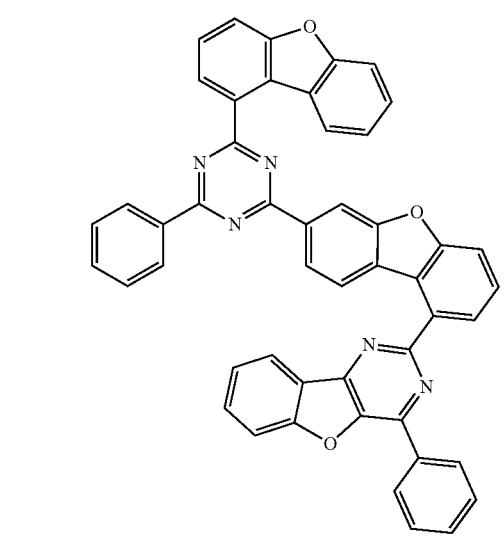
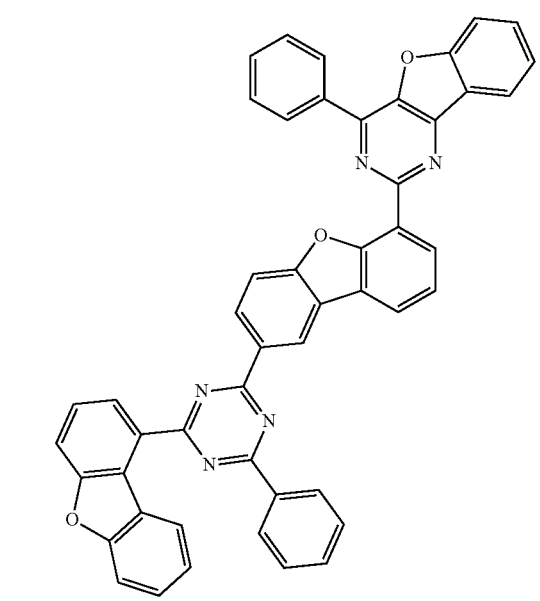
482
-continued
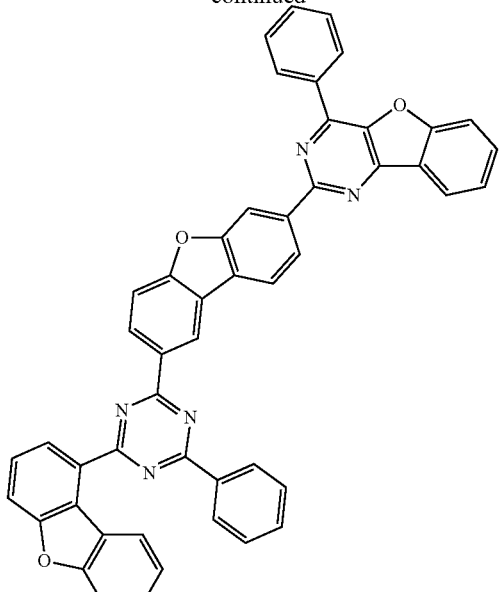
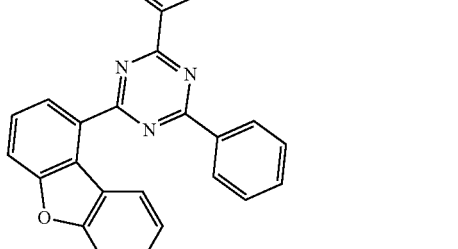
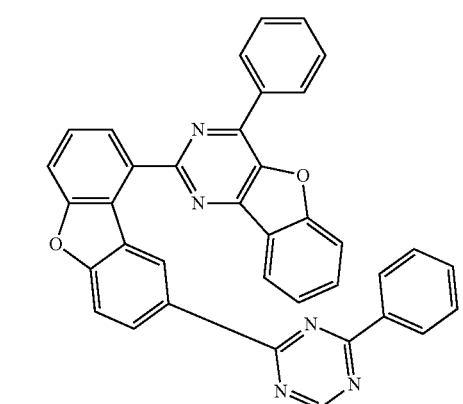
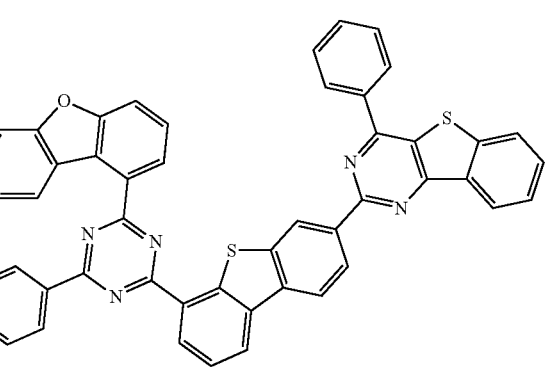

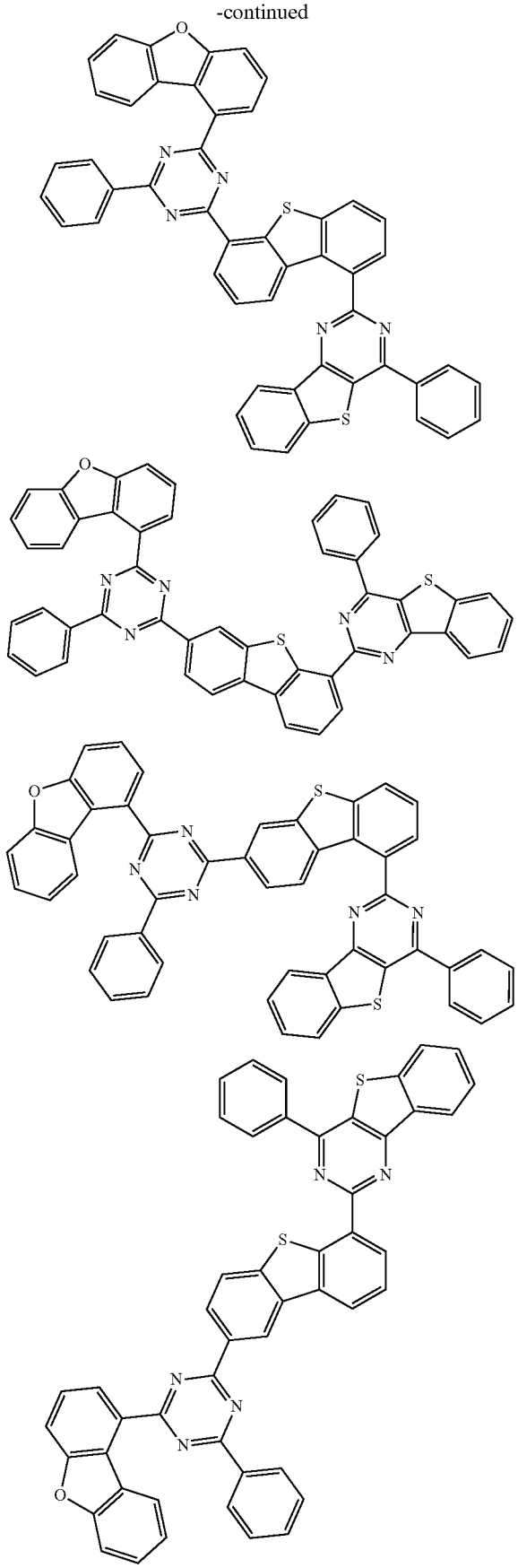
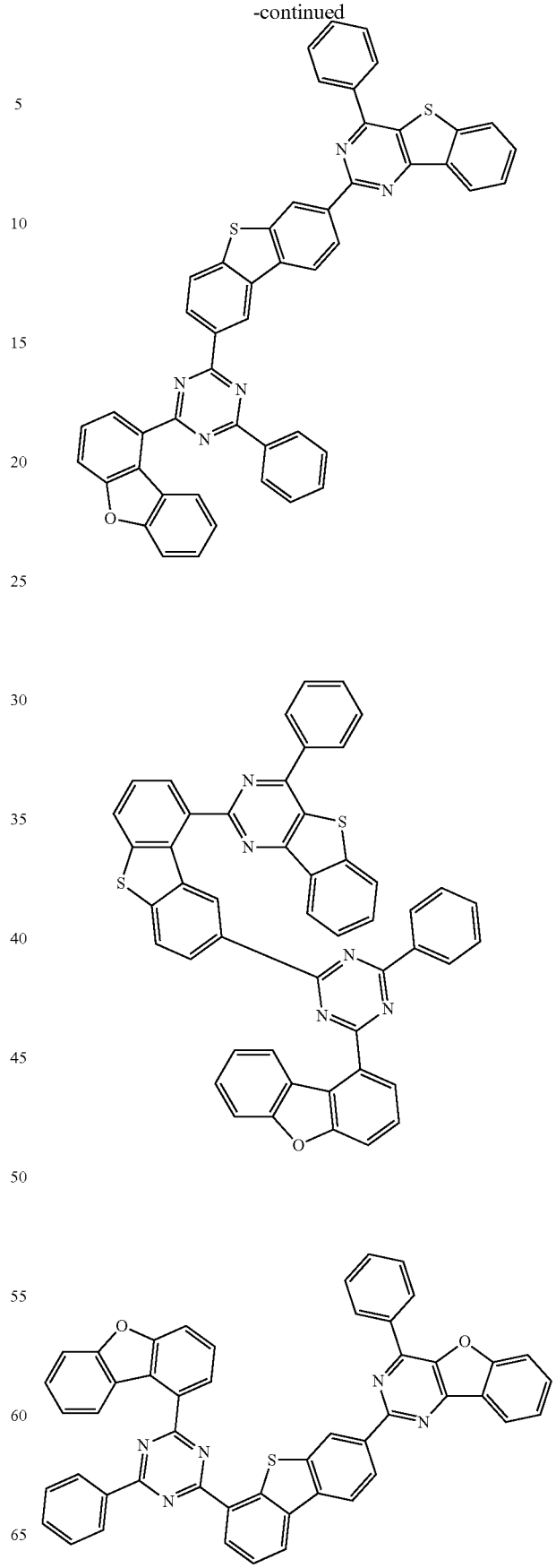

485
-continued
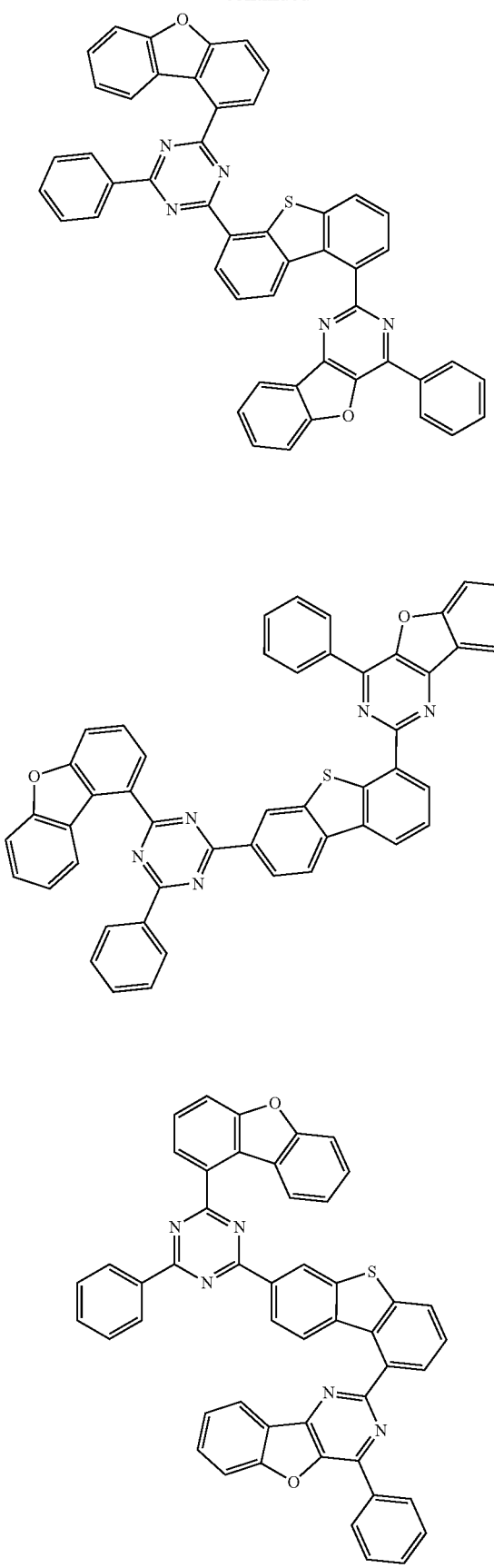
486
-continued
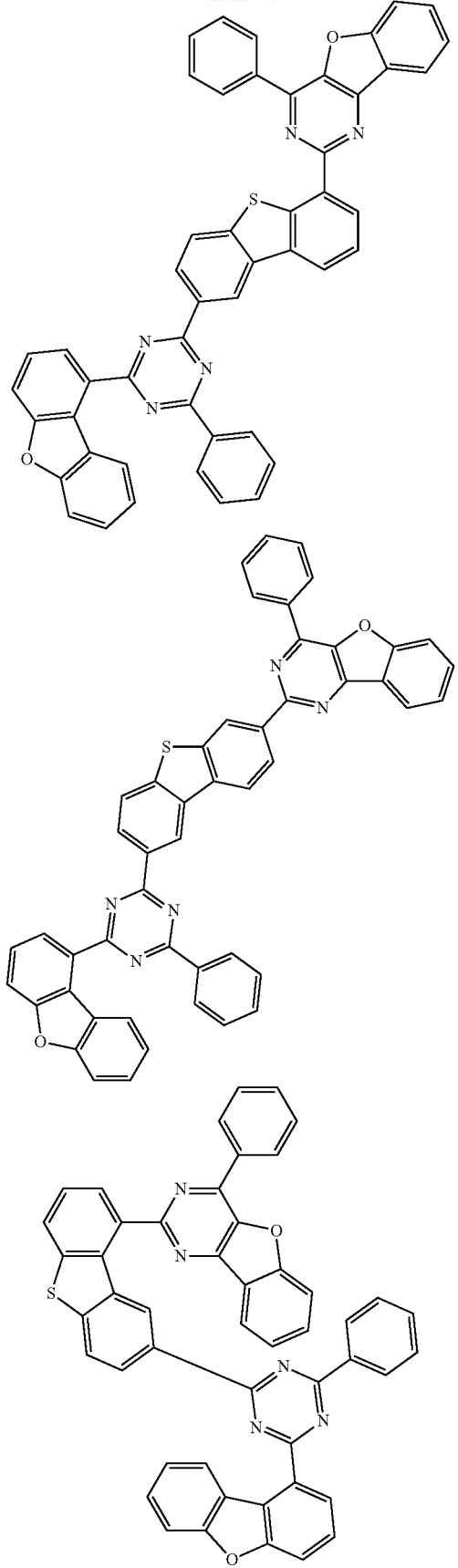

487
-continued
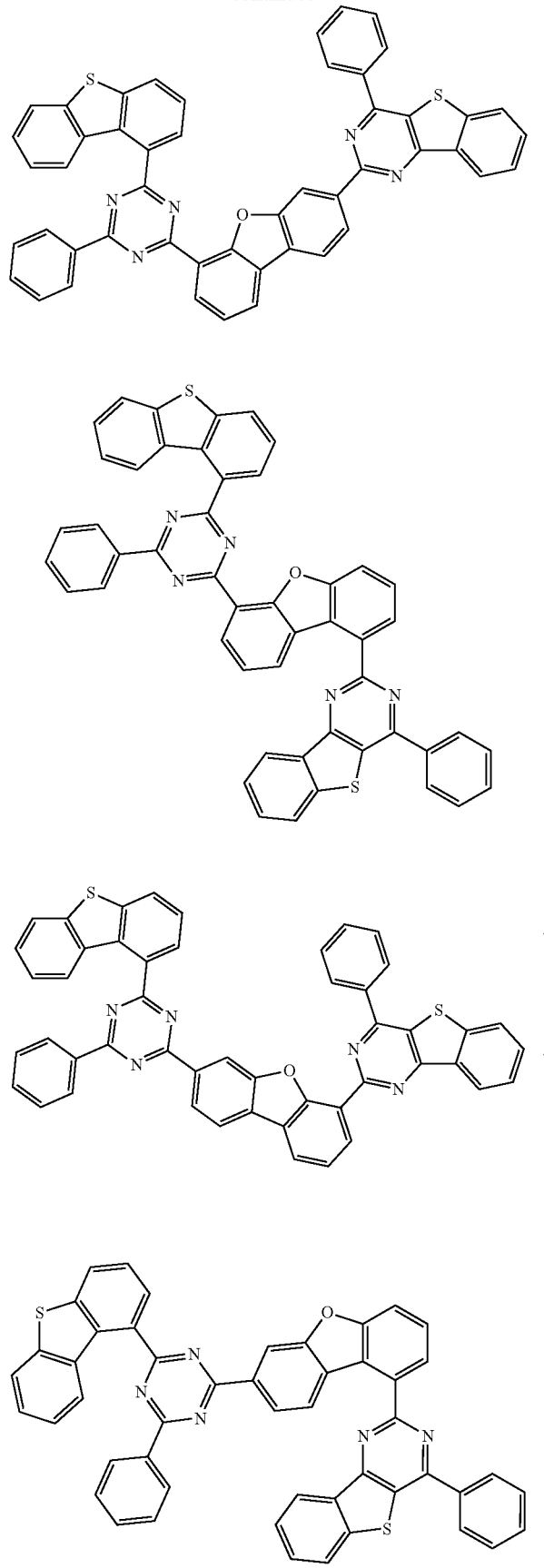
488
-continued
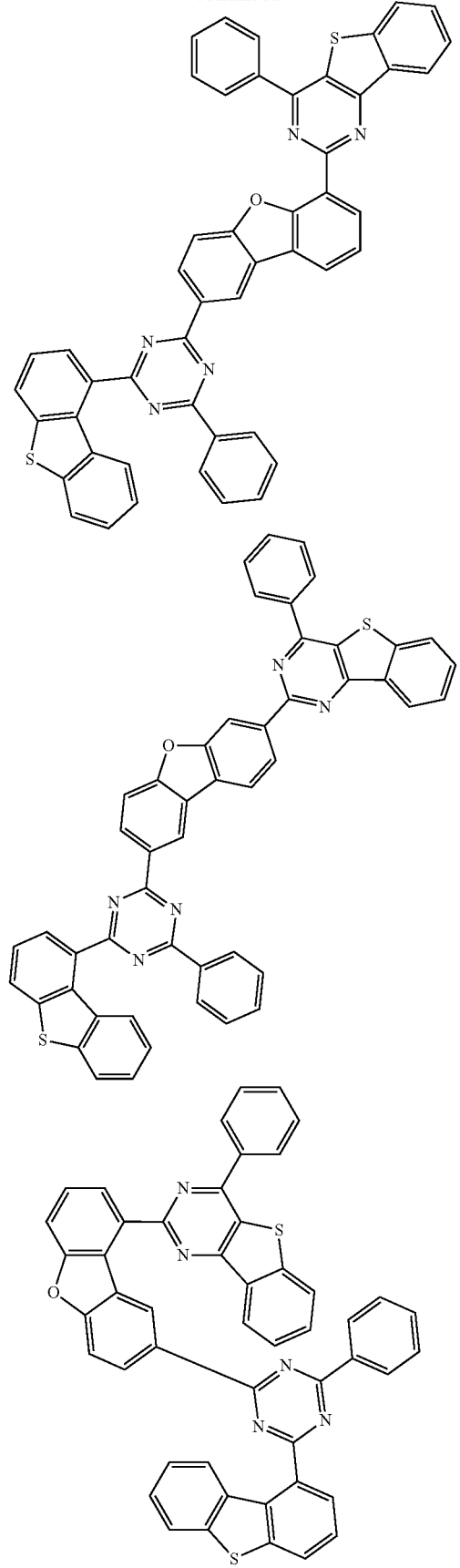

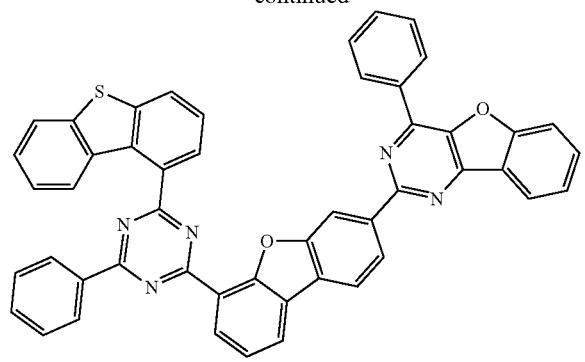
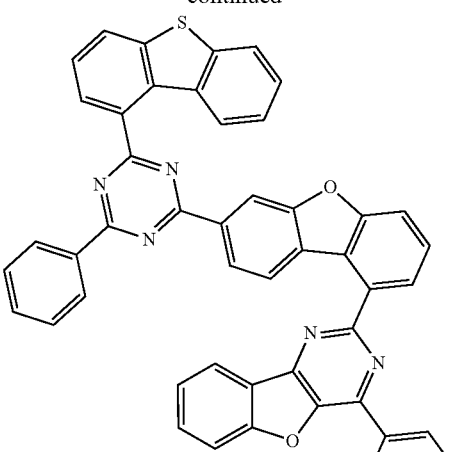
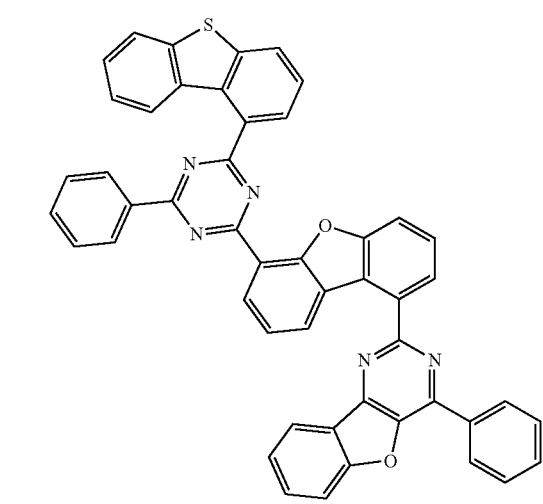
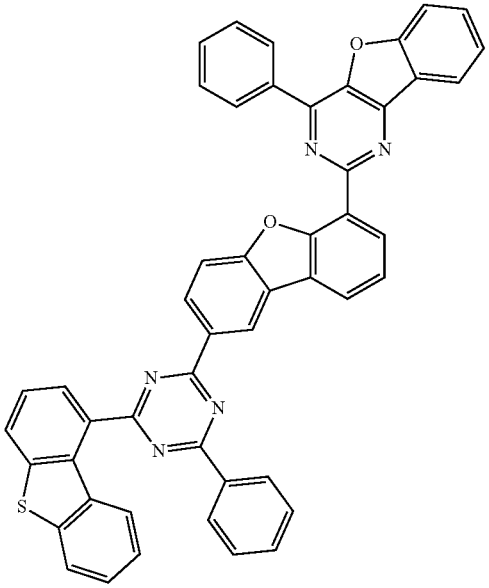
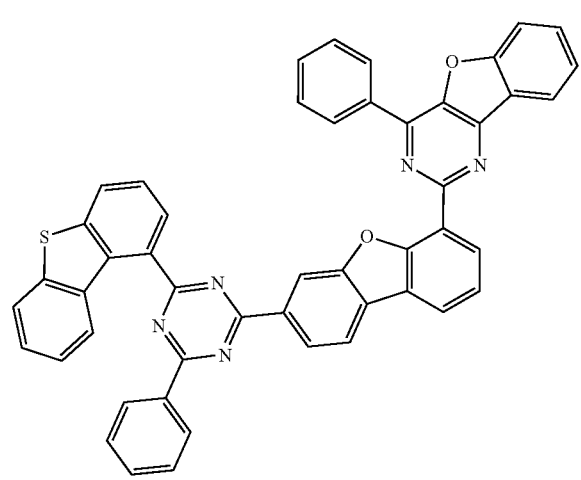
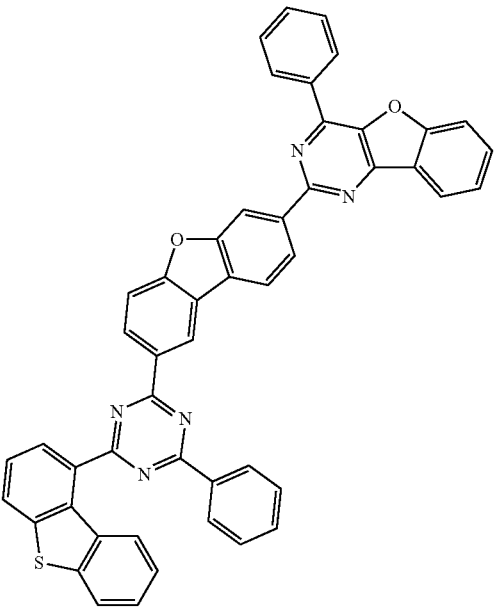

491
-continued
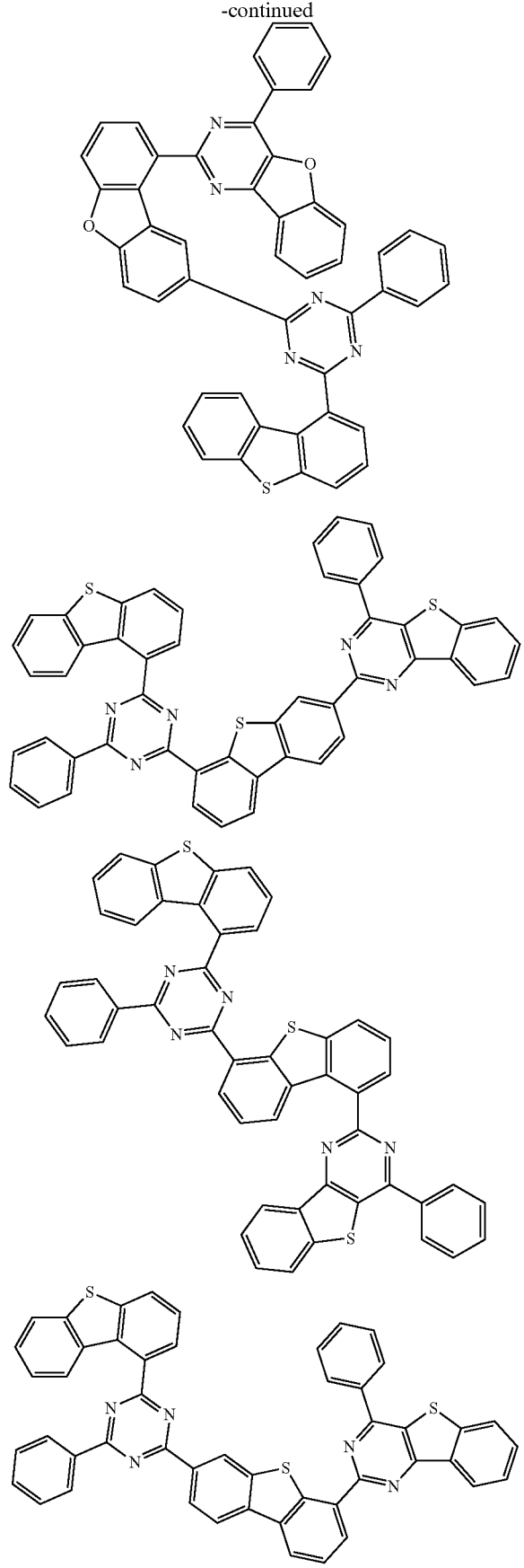
492
-continued
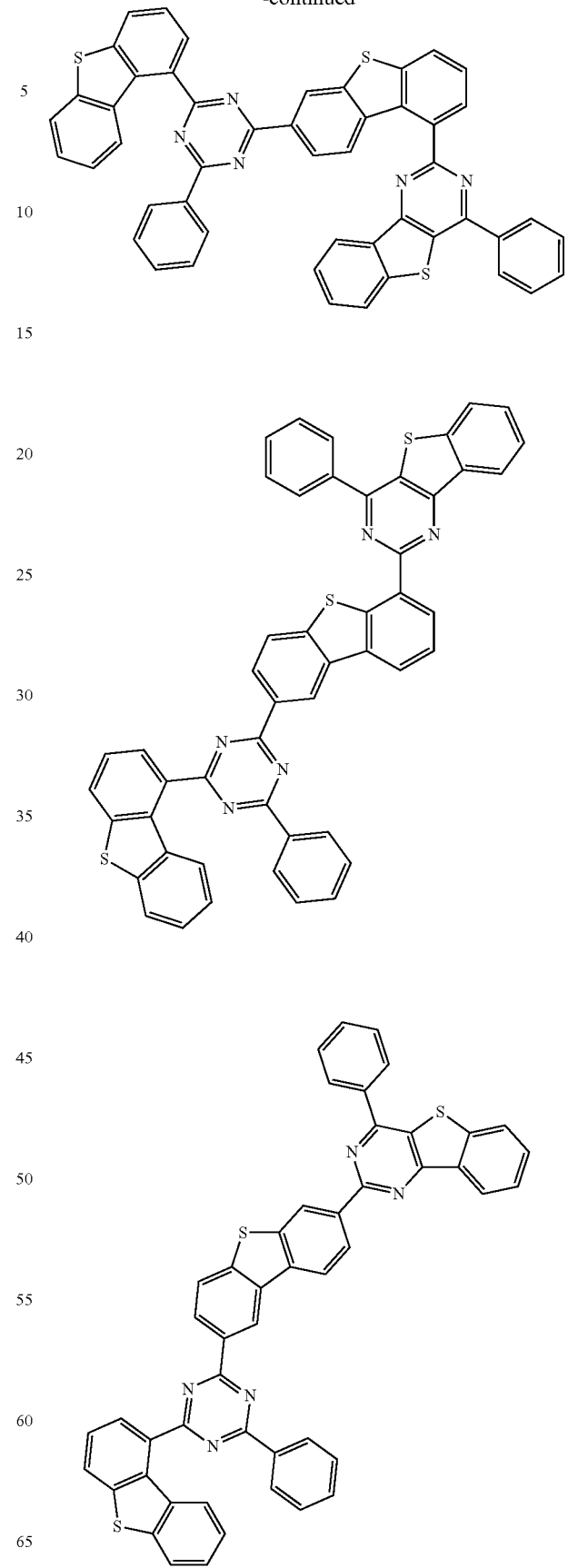

493
-continued
494
-continued
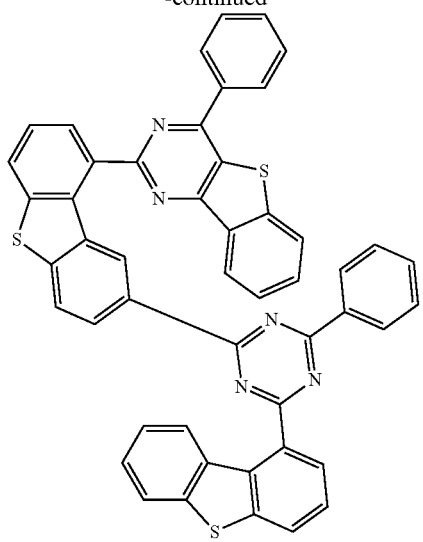
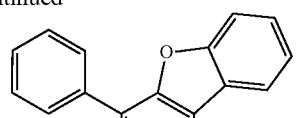
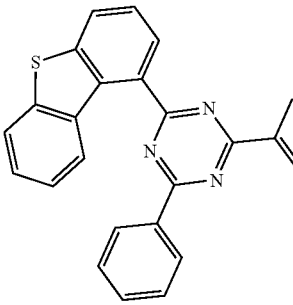
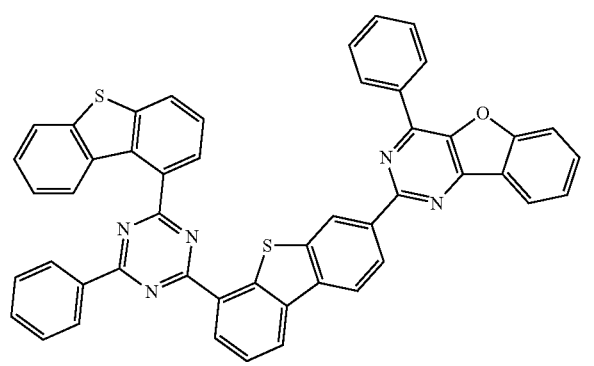
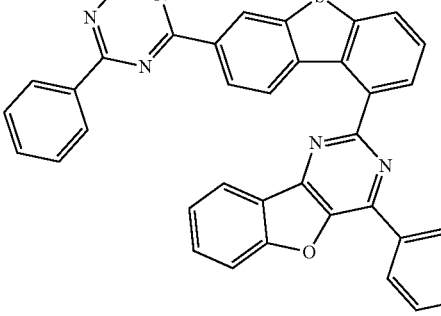
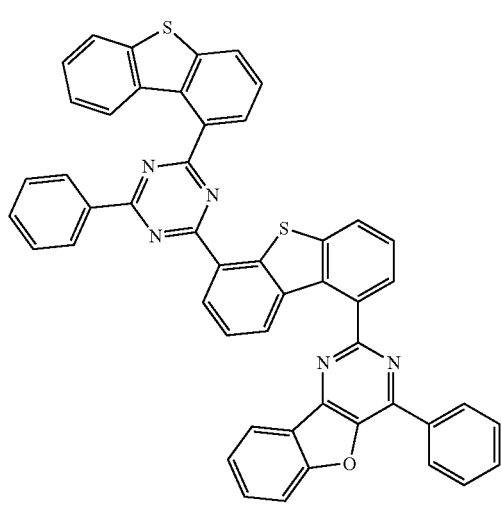
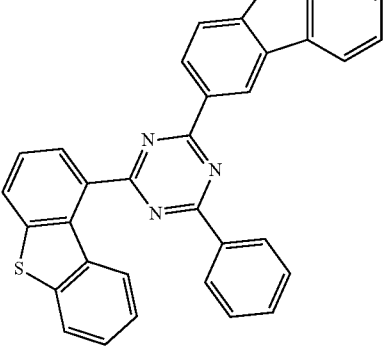

495
-continued
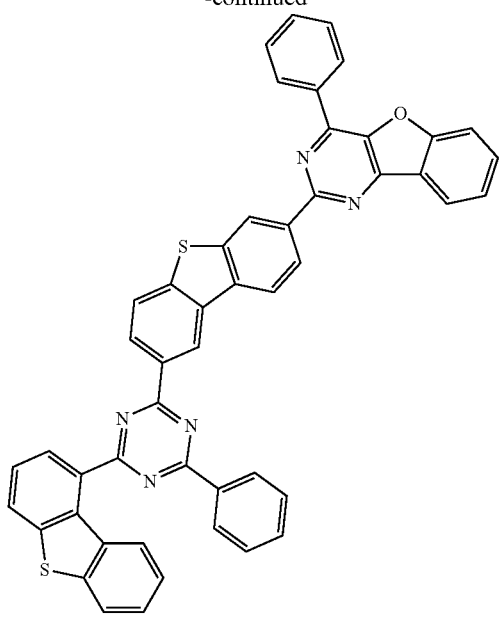
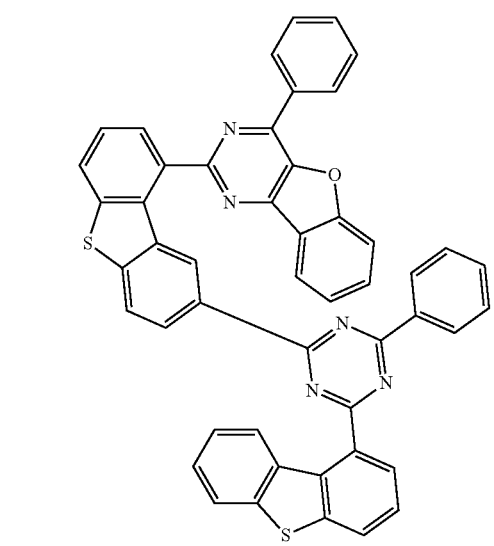
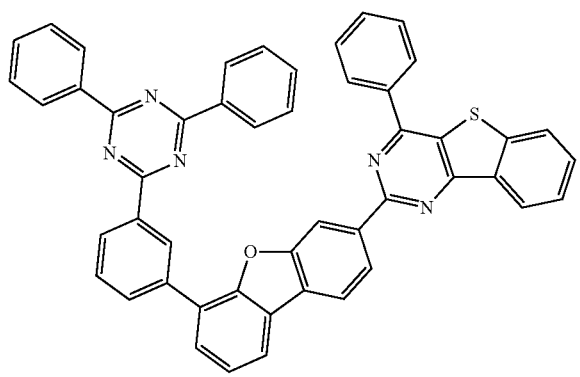
496
-continued
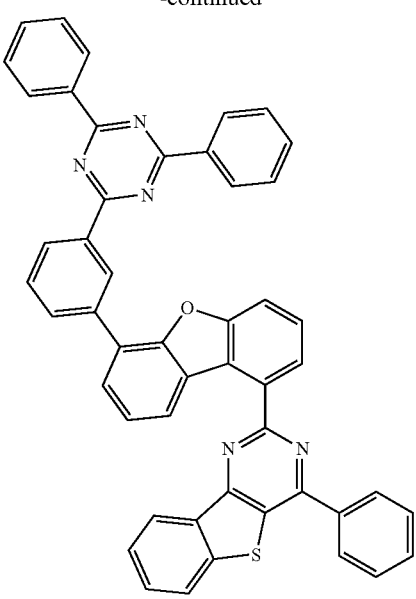
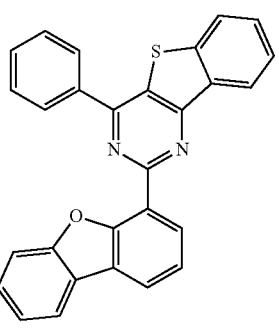
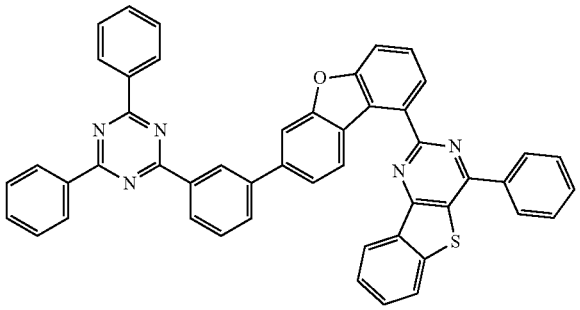

497
-continued
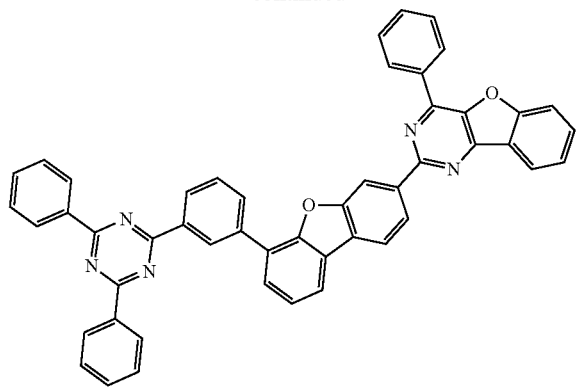
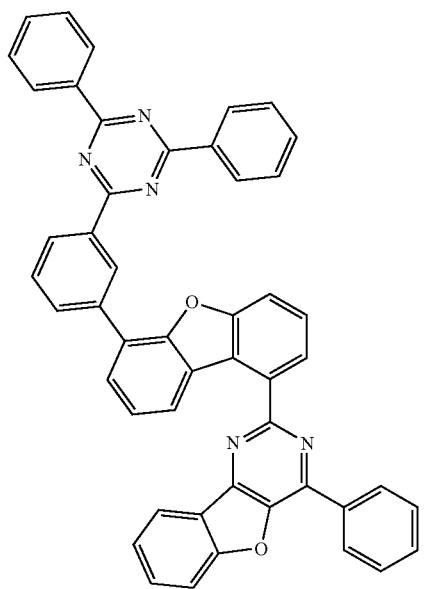
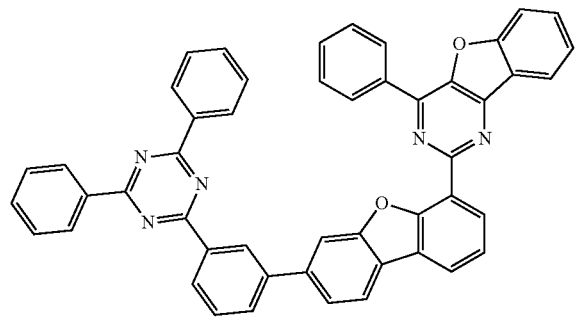
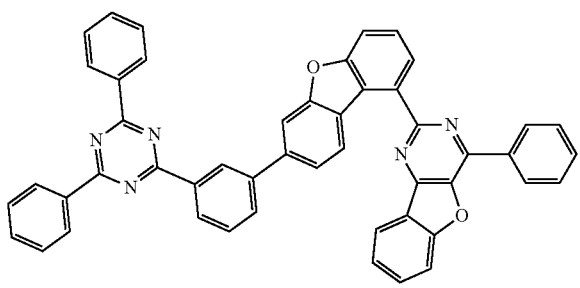
498
-continued
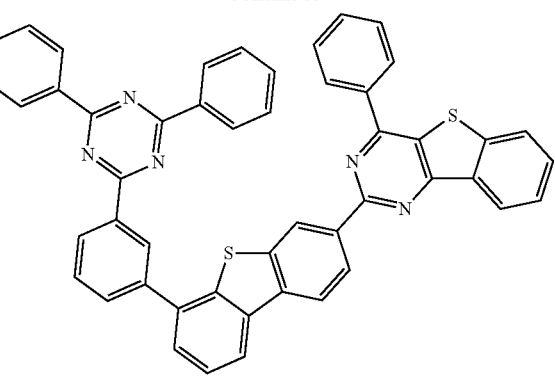
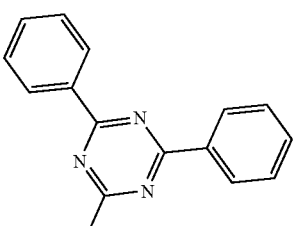
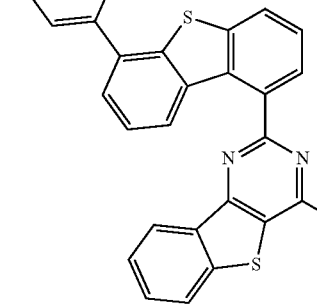
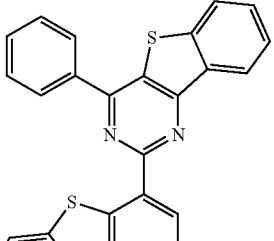

499
-continued
500
-continued
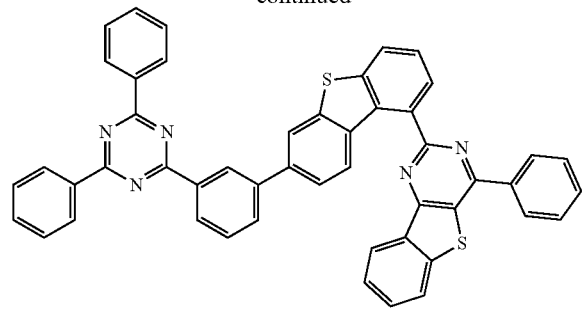
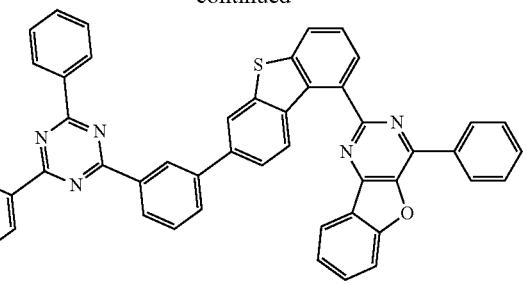
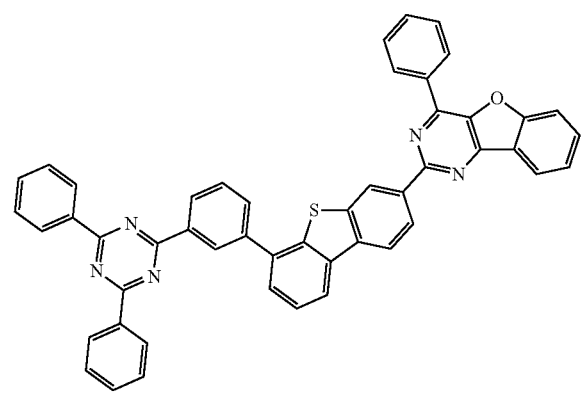
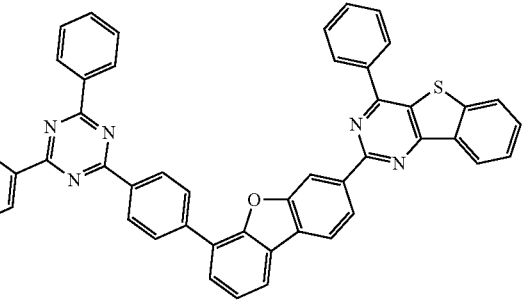
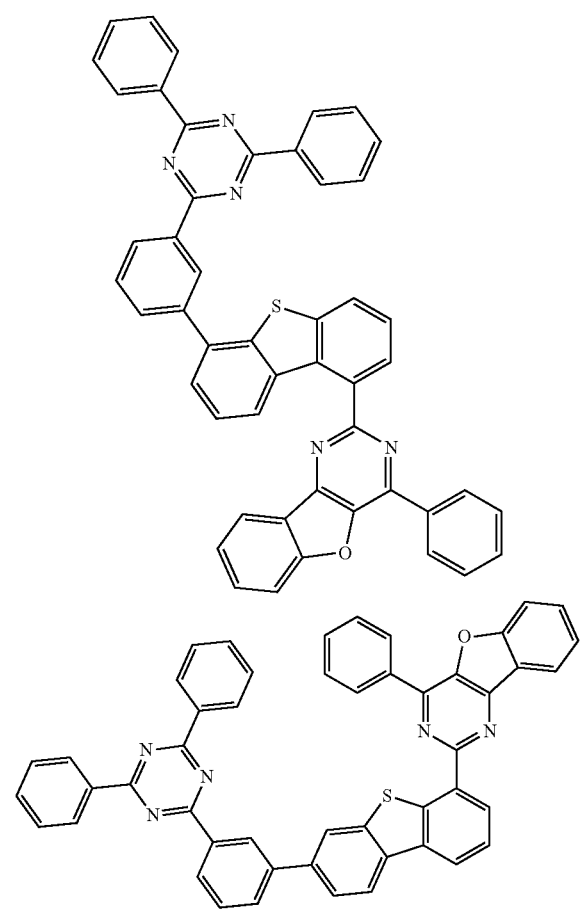
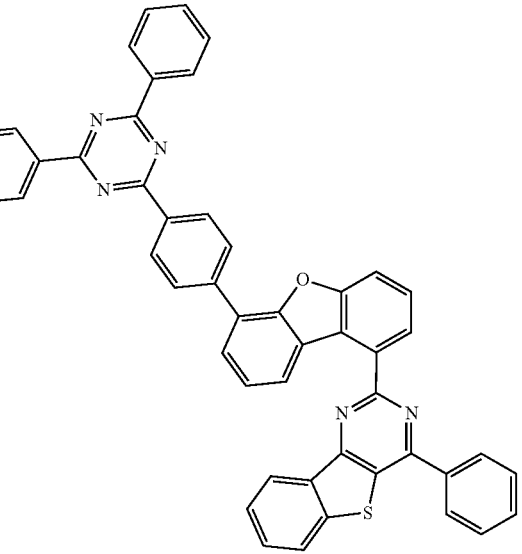
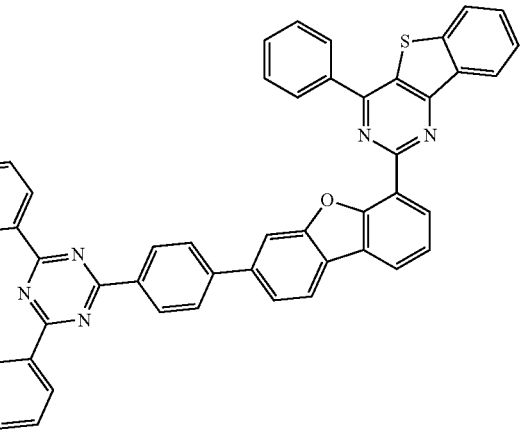

501
-continued
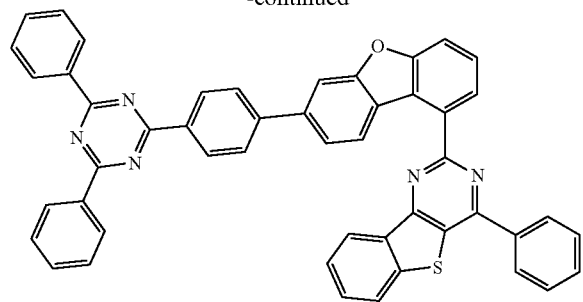
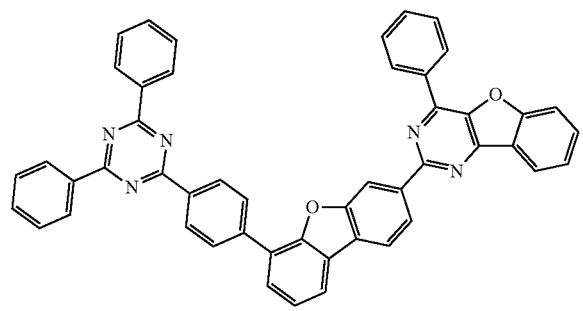
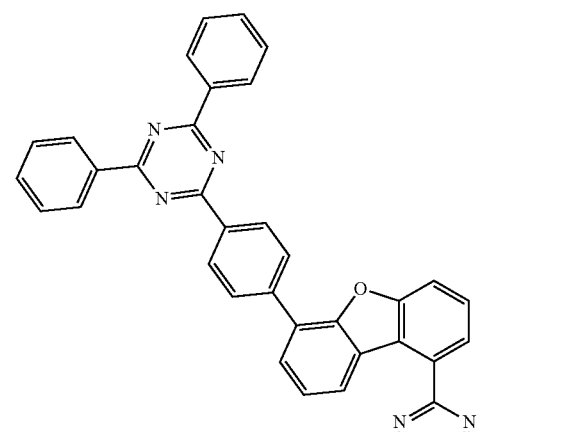
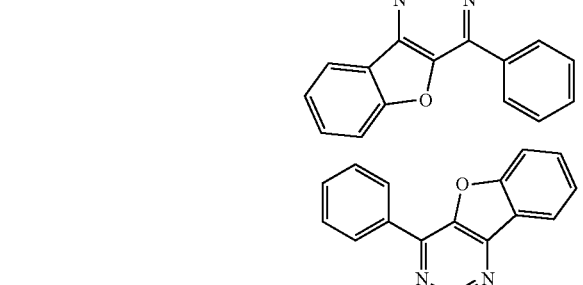
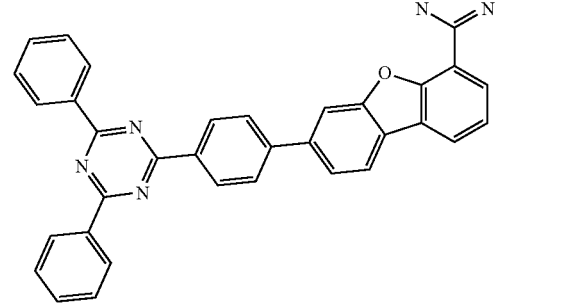
502
-continued
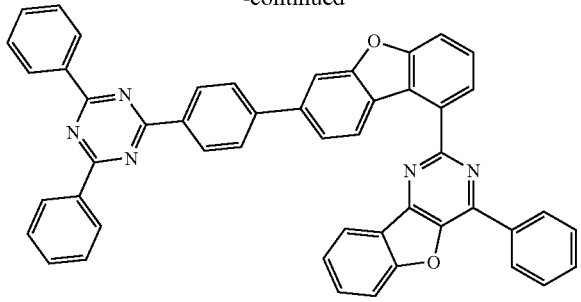
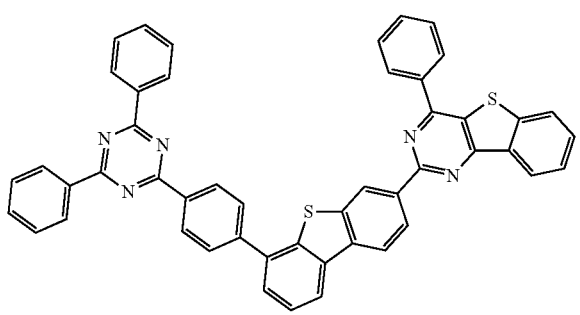
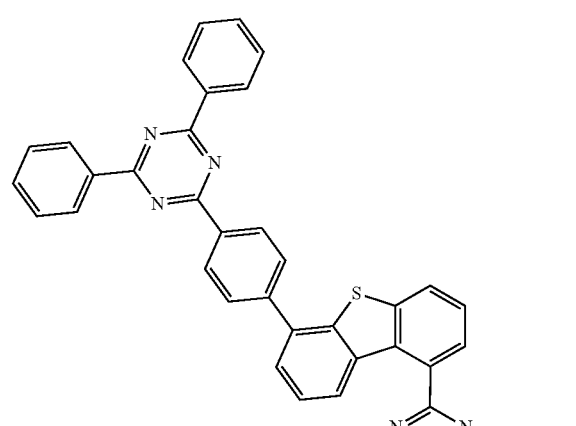
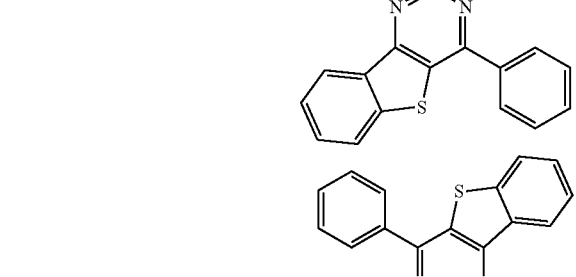
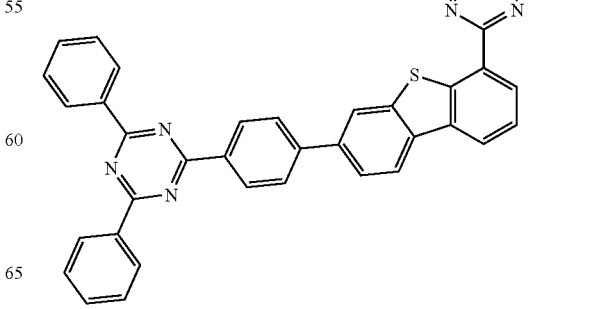

503
-continued
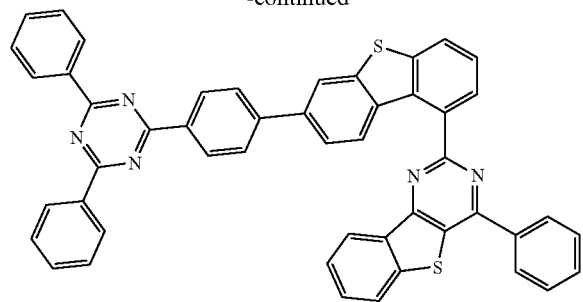
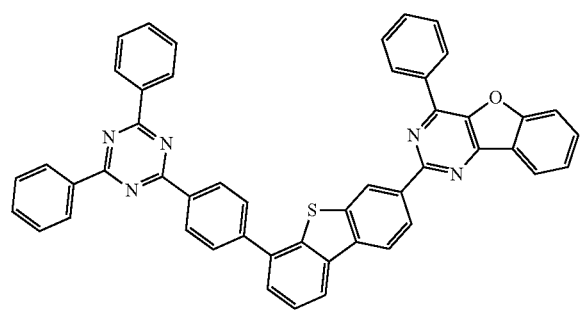
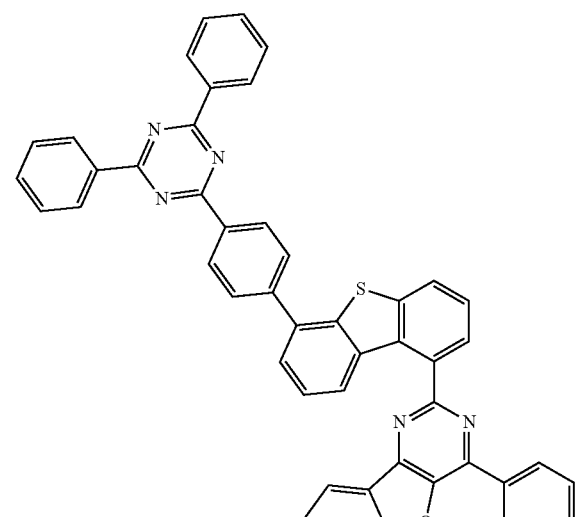
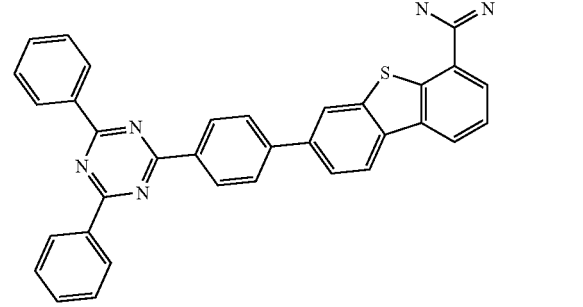
504
-continued
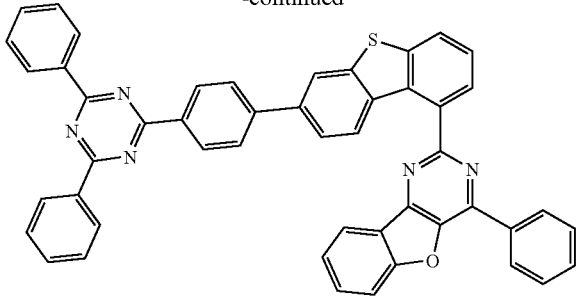
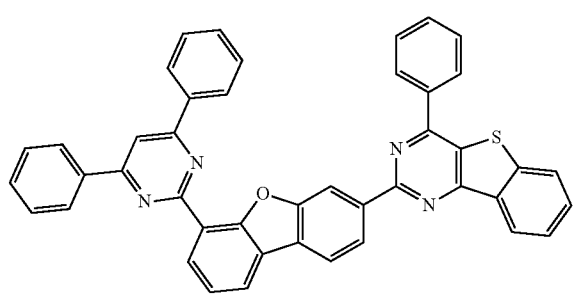
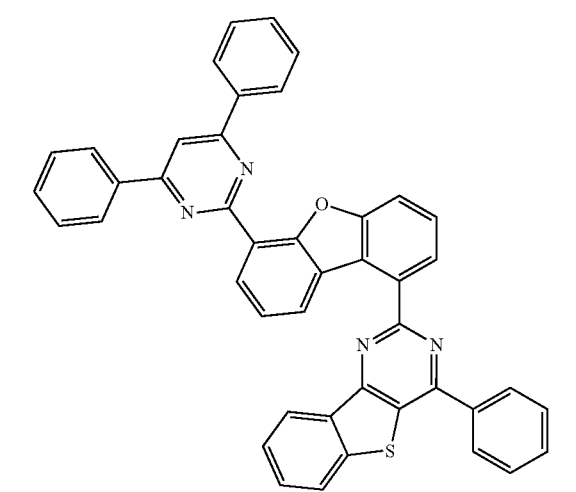

505
-continued
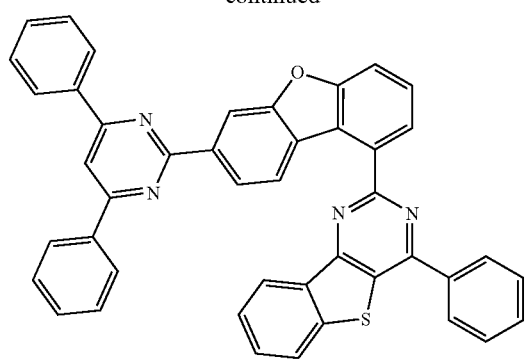
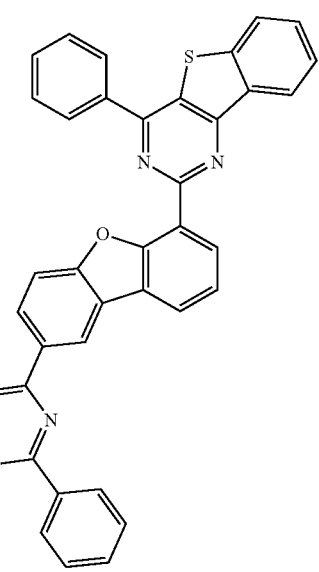
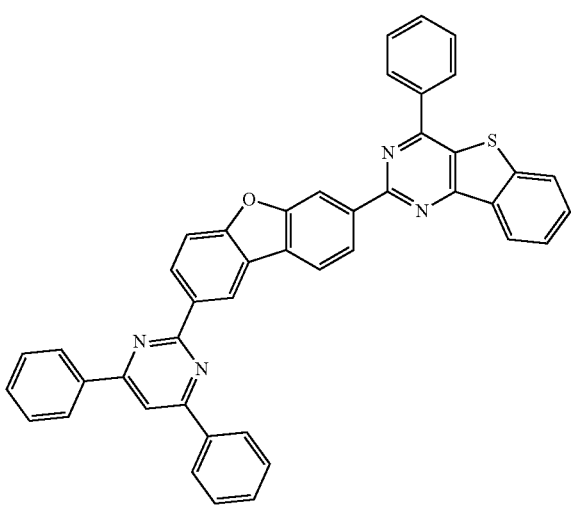
506
-continued
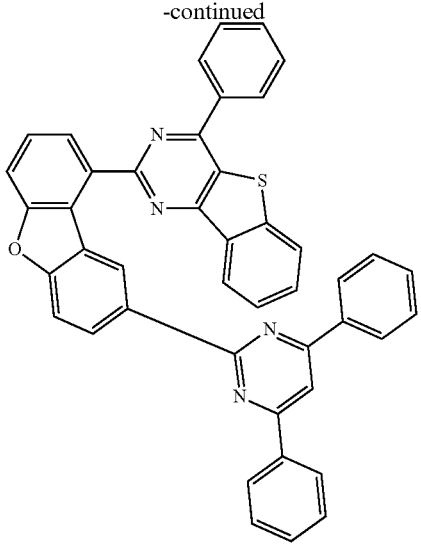
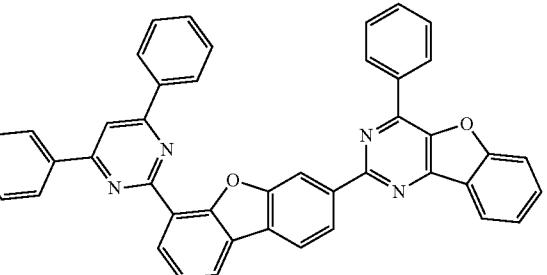
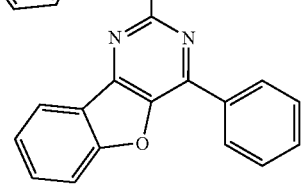

507
-continued
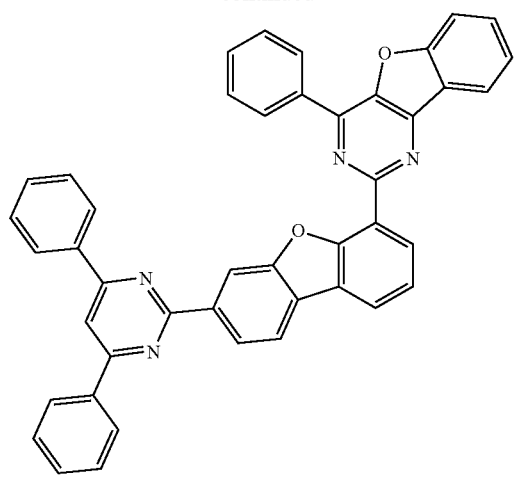
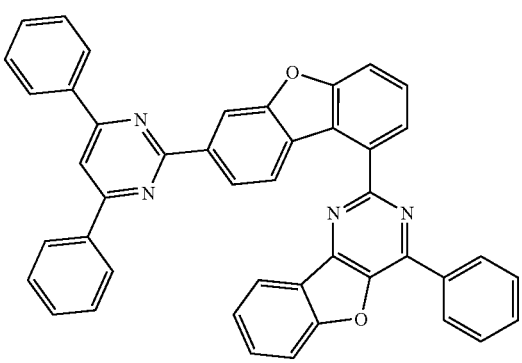
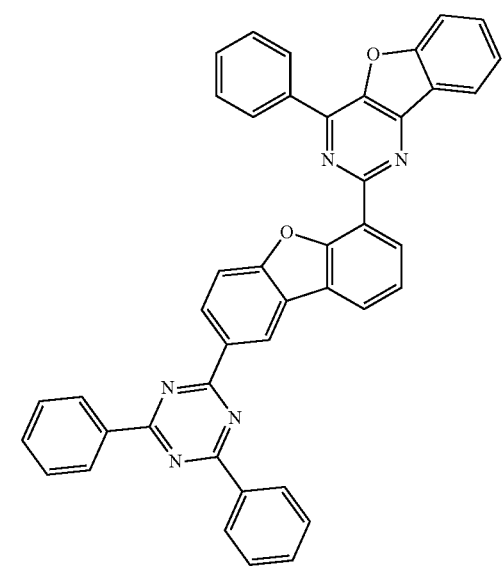
508
-continued
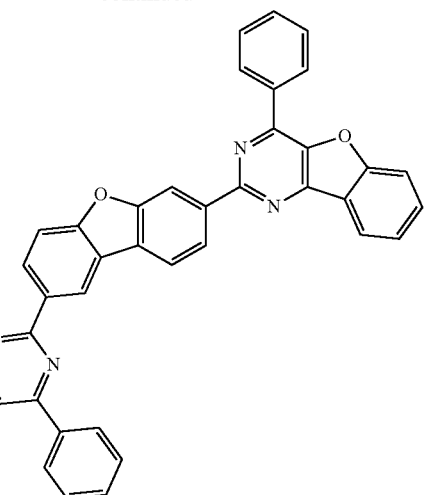
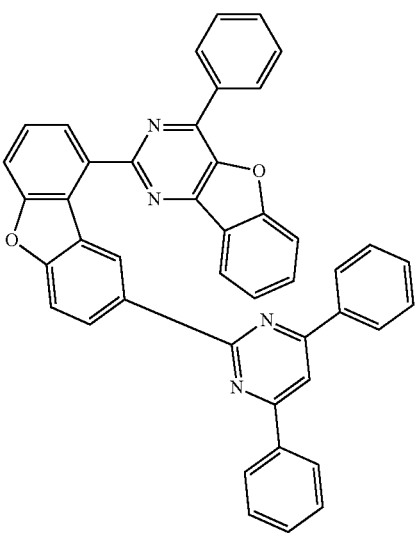
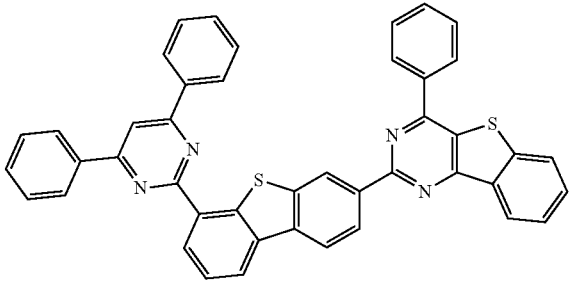

509
-continued
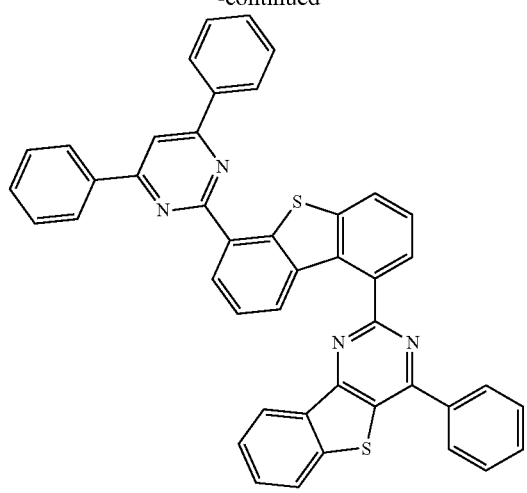
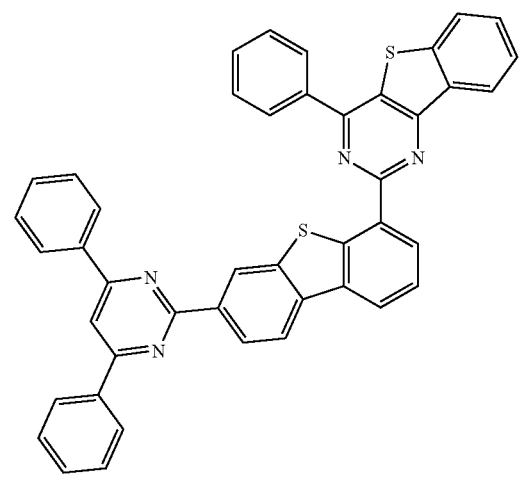
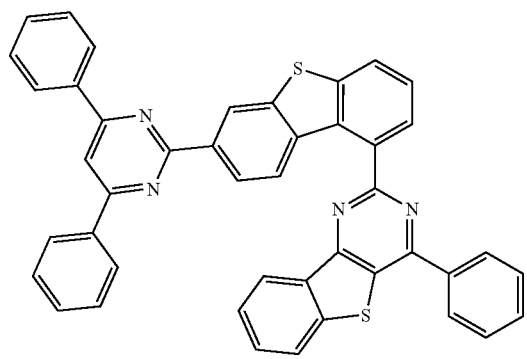
510
-continued
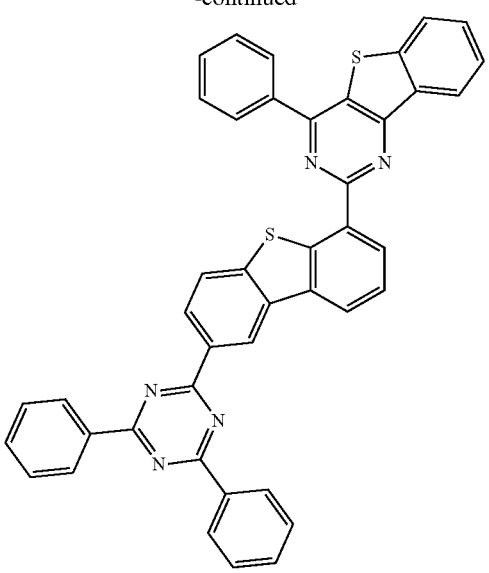
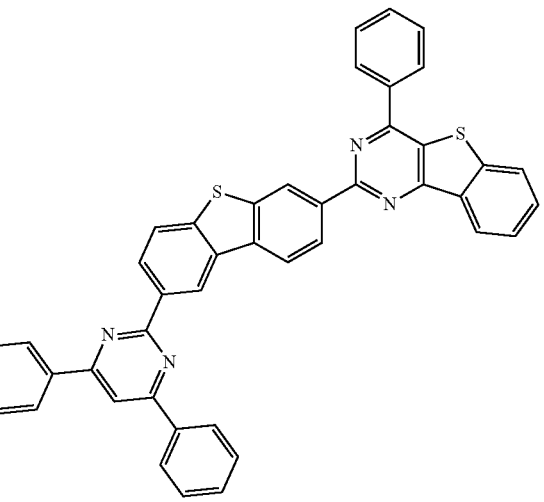
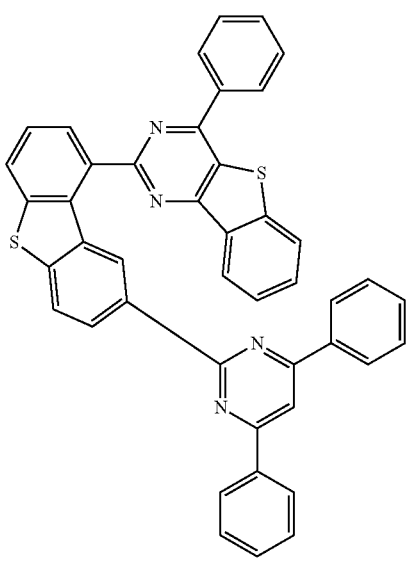

511
-continued
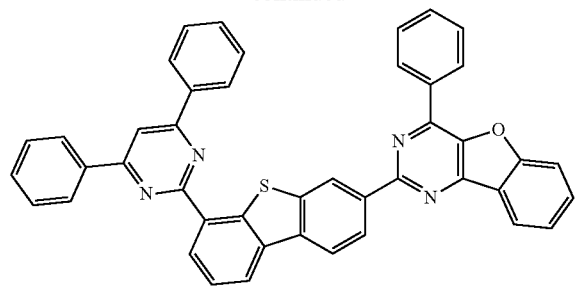
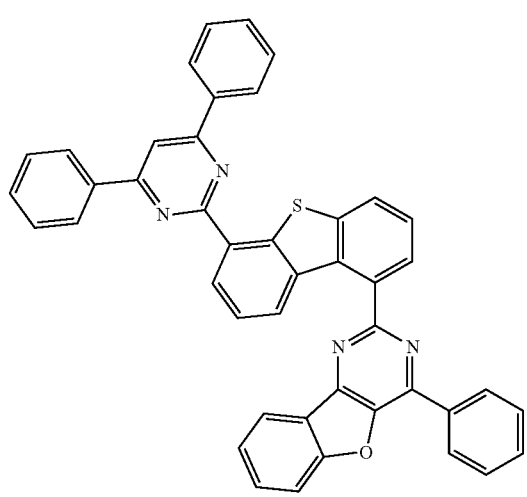
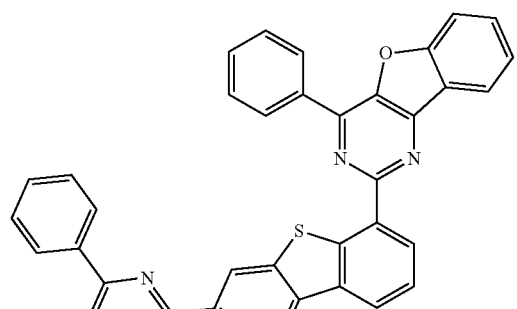
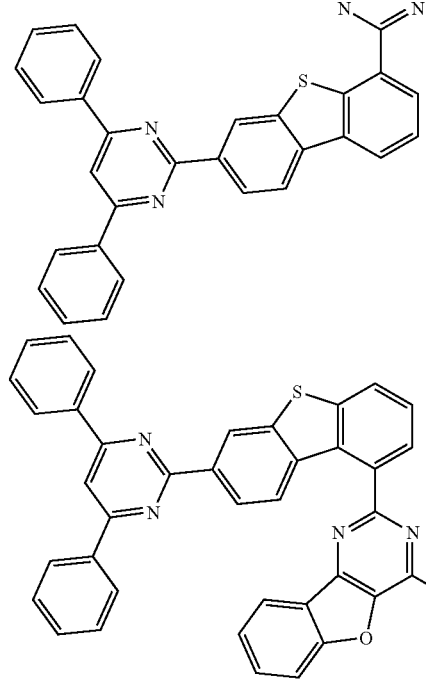
512
-continued
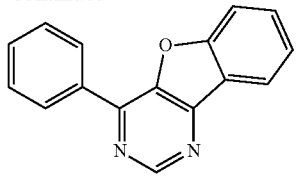
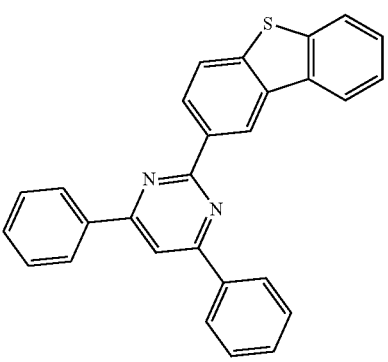
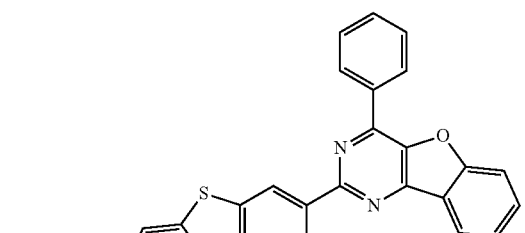
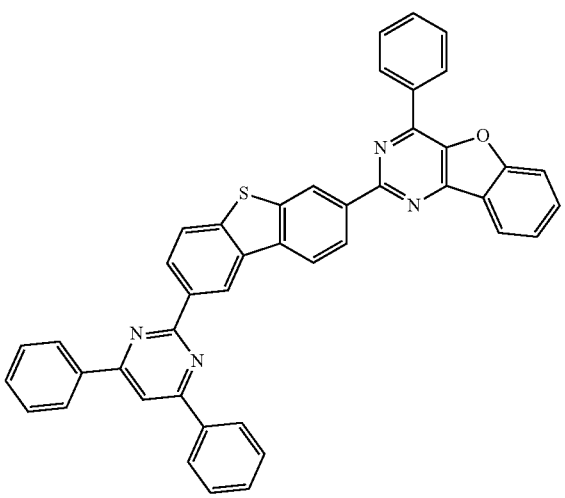
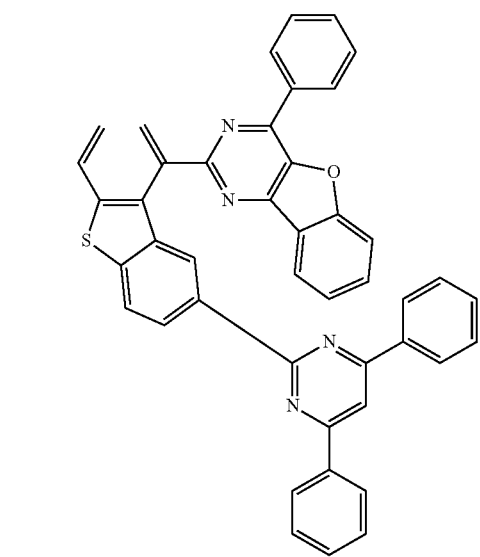

513
-continued
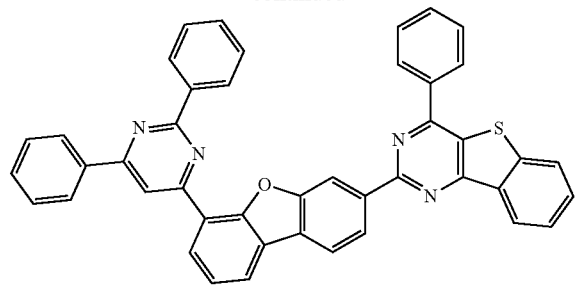
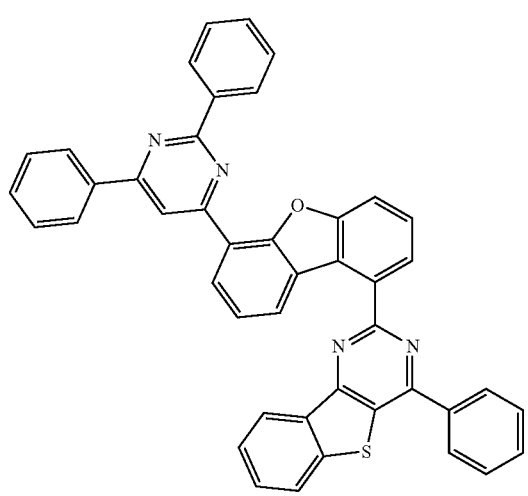
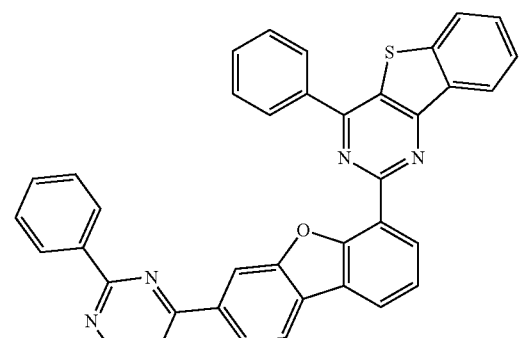
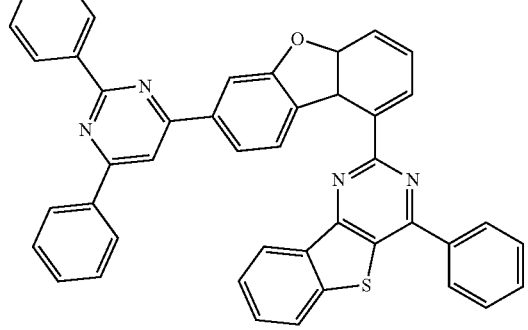
514
-continued
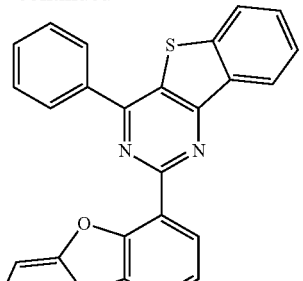
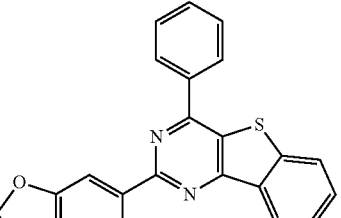
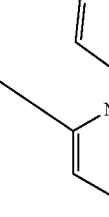

515
-continued
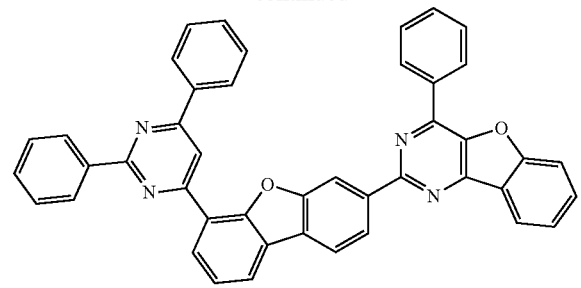
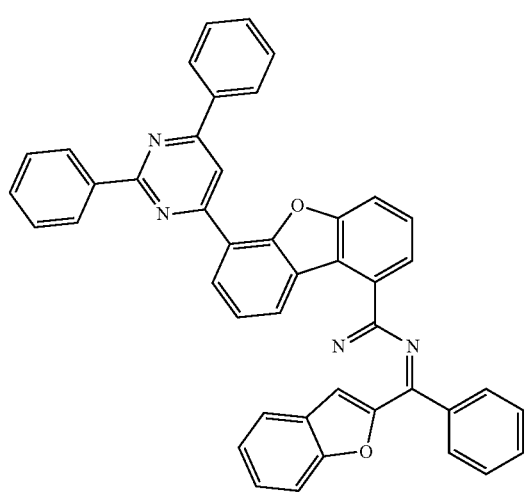
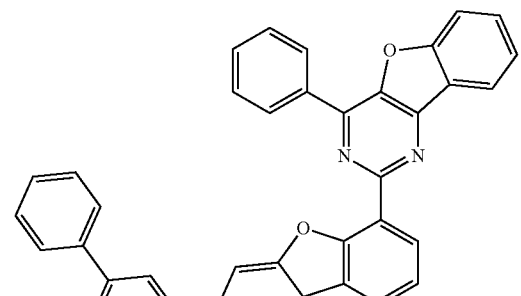
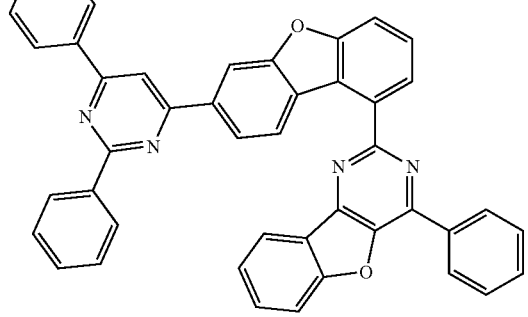
516
-continued
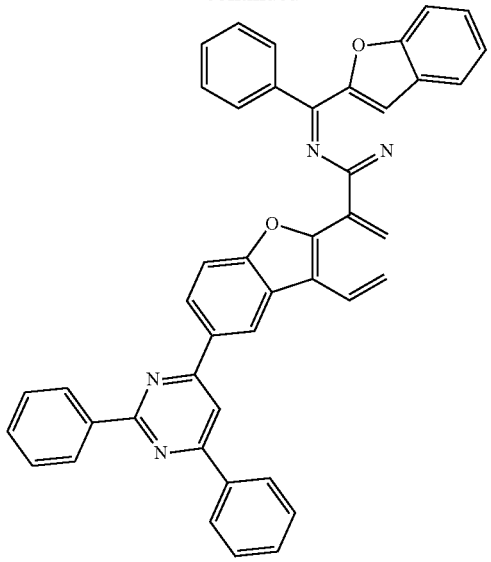
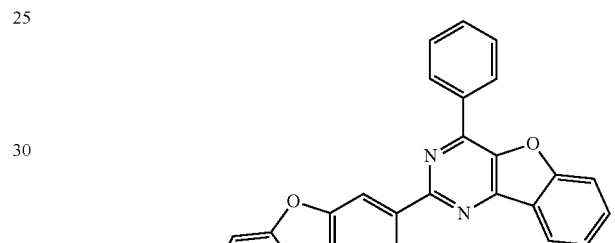
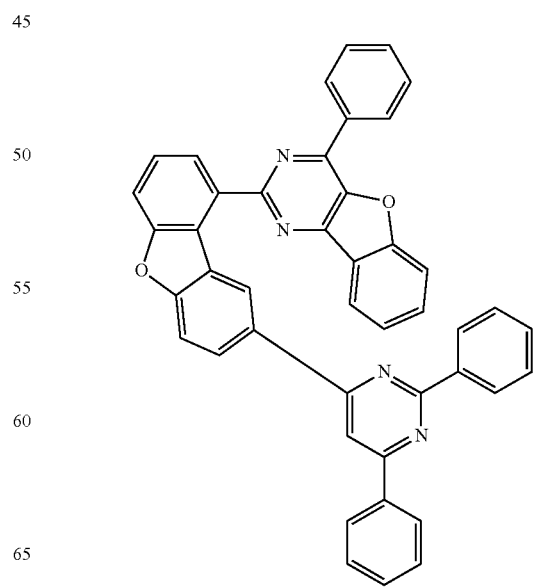

517
-continued
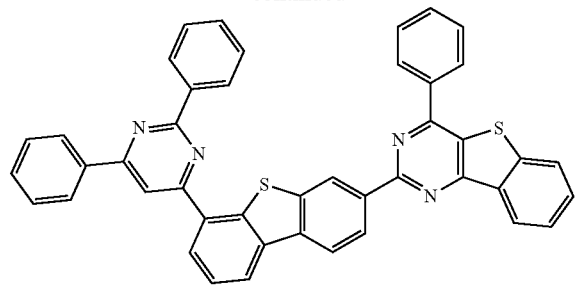
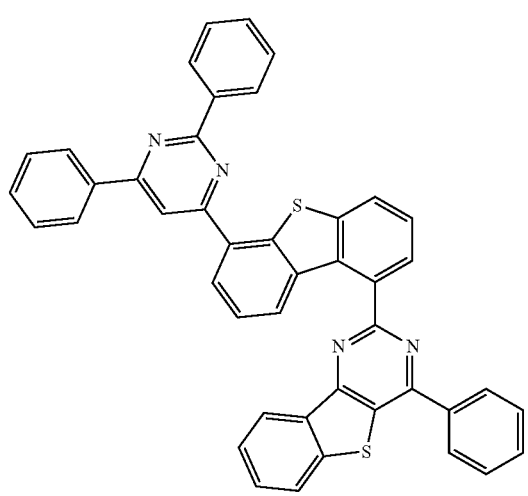
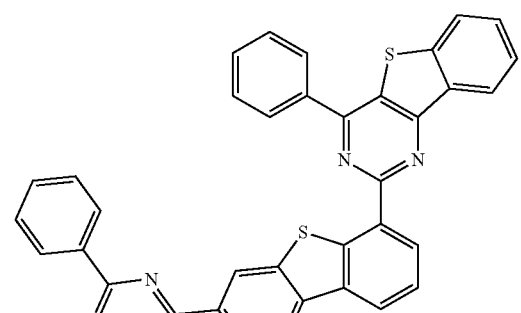
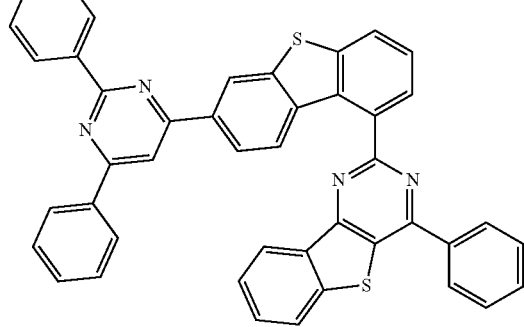
518
-continued
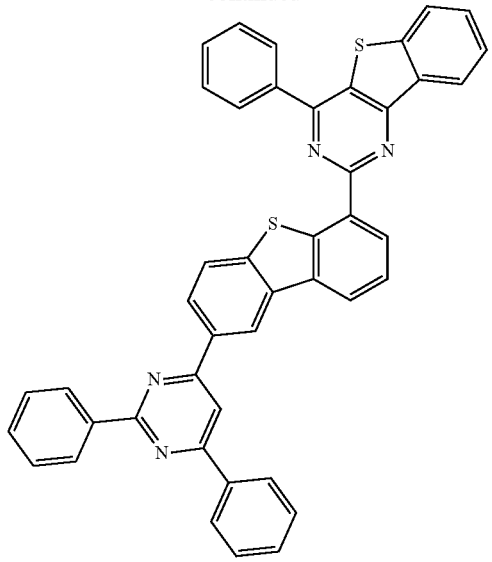
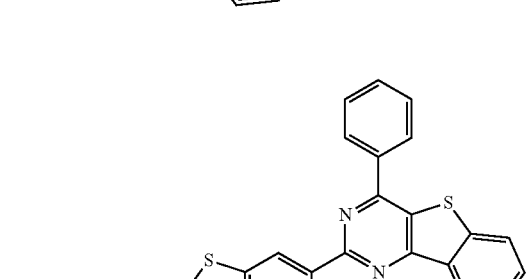
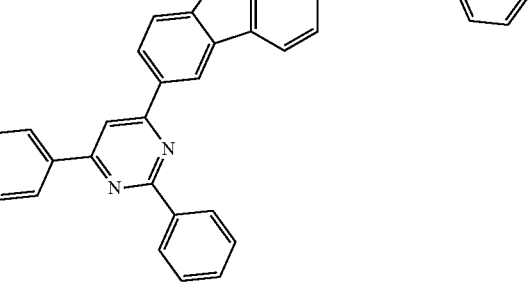
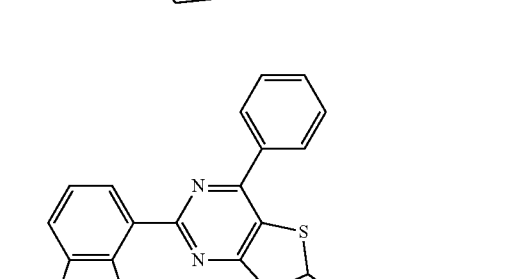
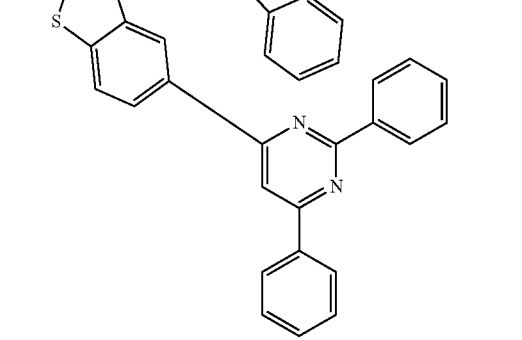

519
-continued
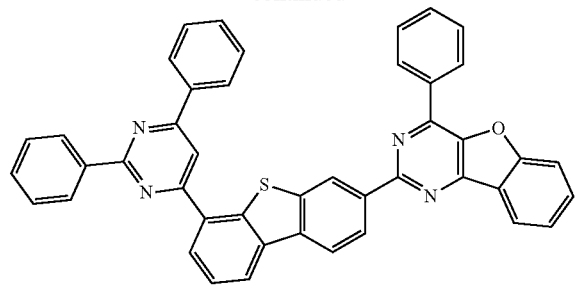
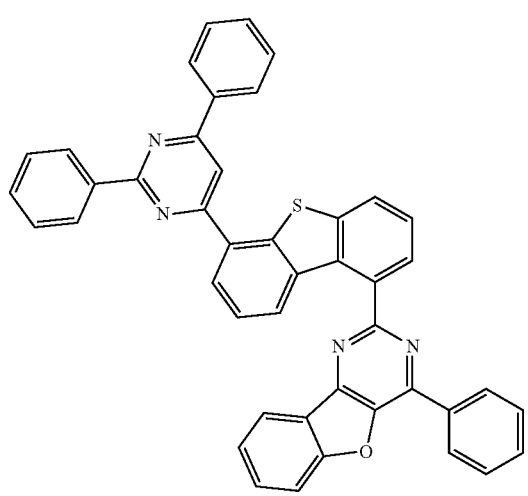
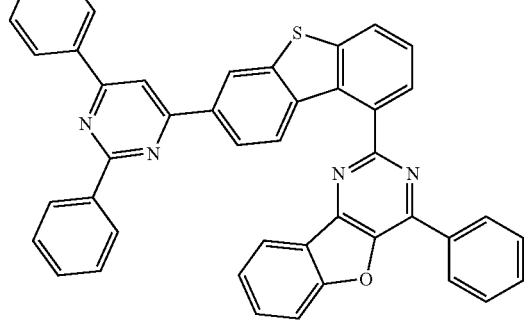
520
-continued
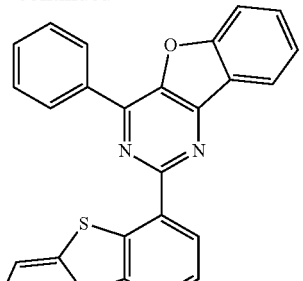
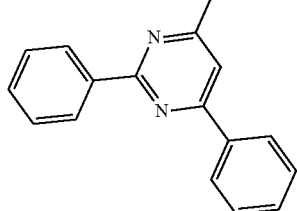
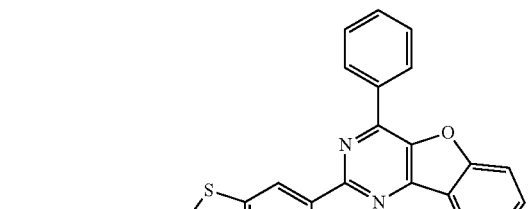
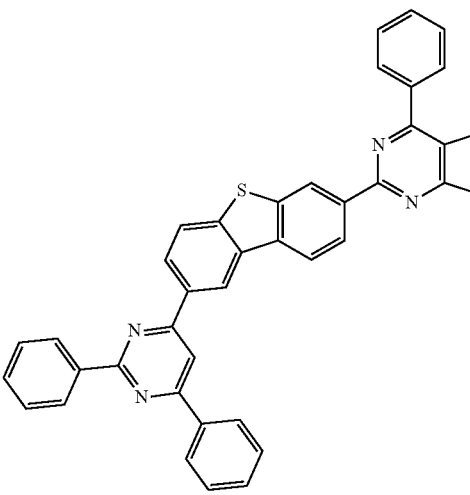
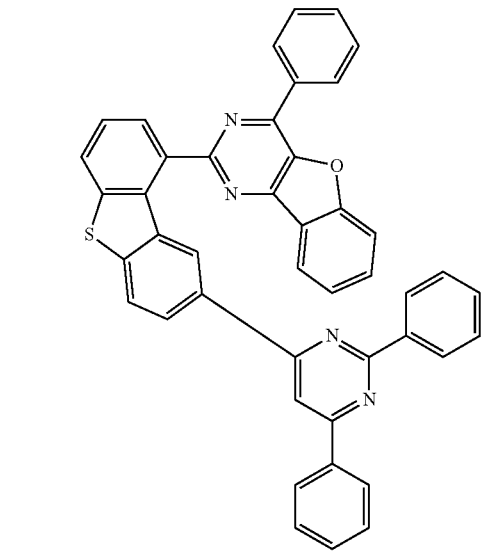

521
-continued
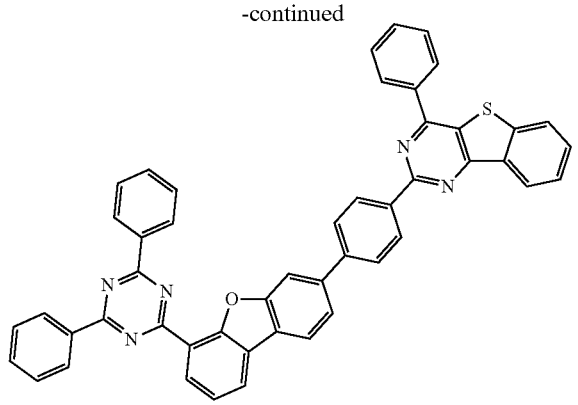
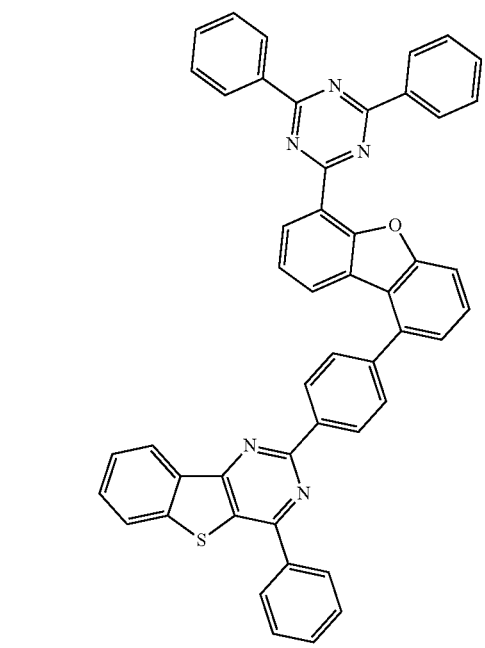
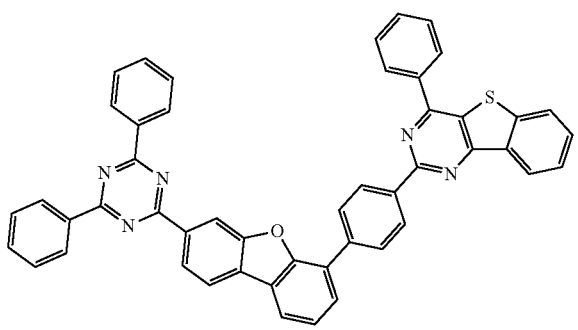
522
-continued
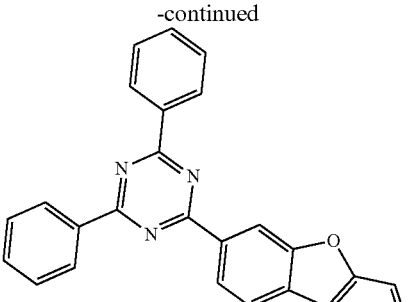
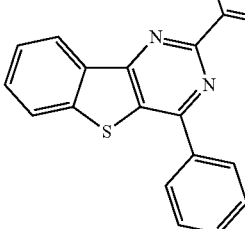
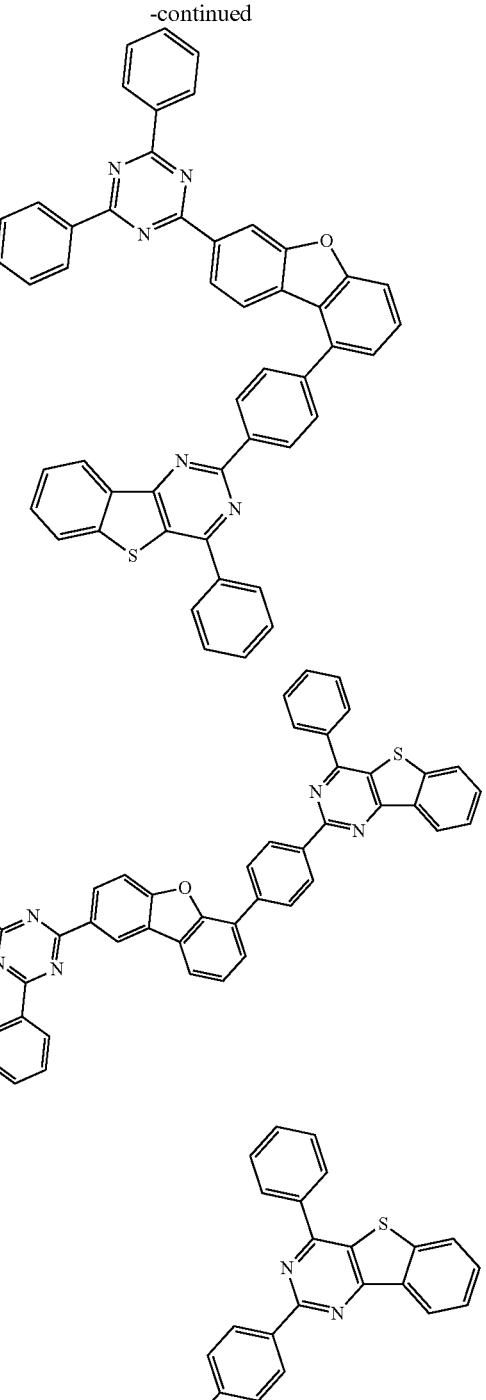
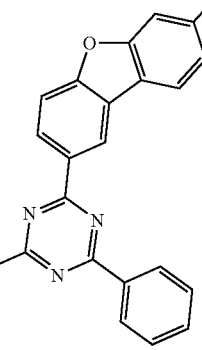

523
-continued
524
-continued
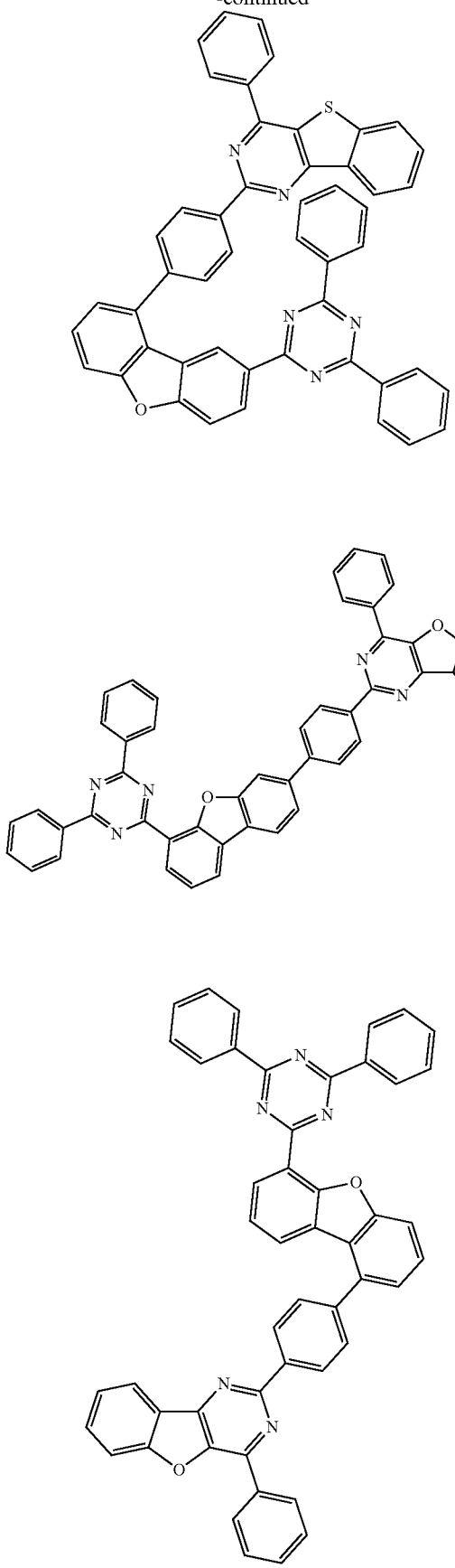
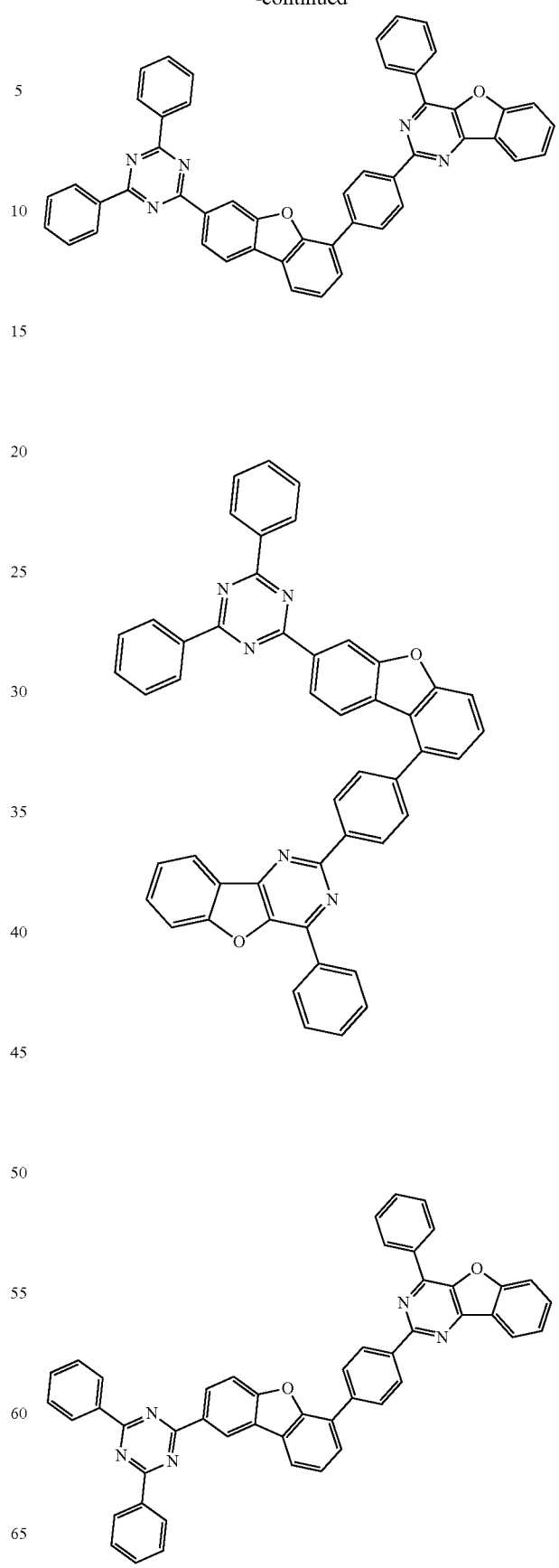

525
-continued
526
-continued
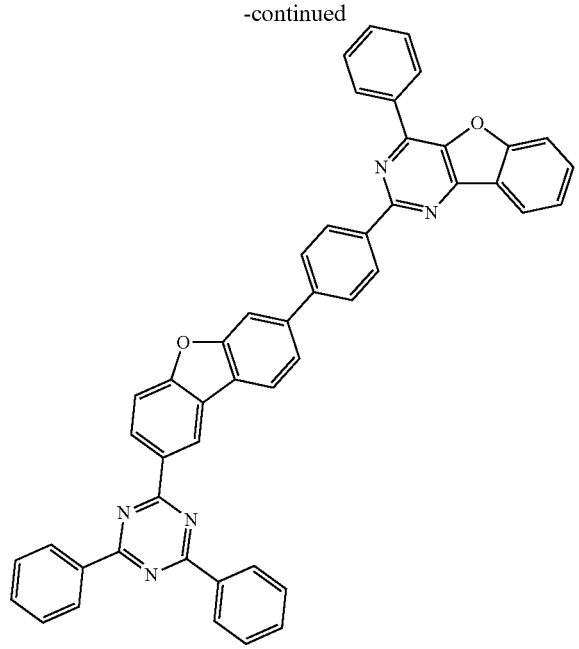
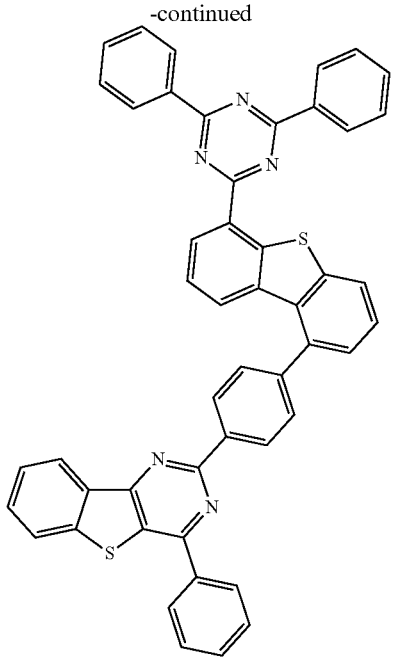
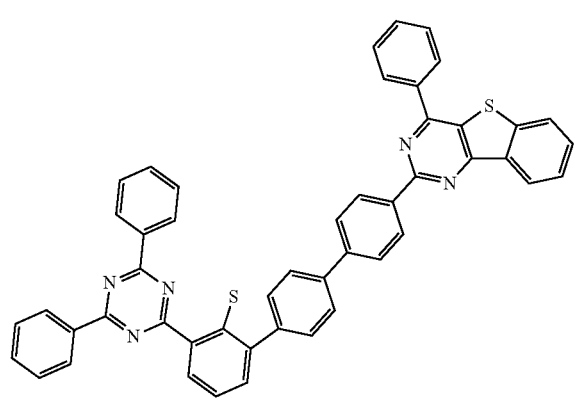
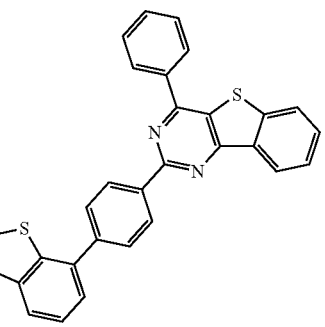

527
-continued
528
-continued
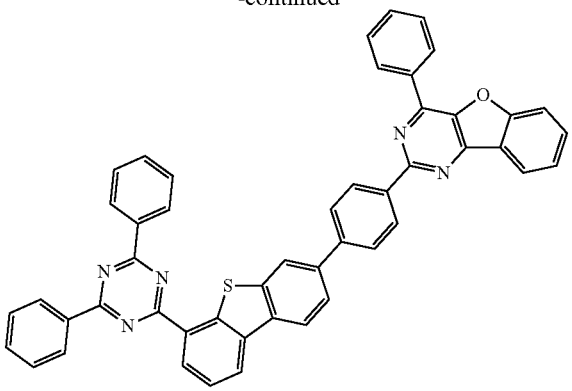
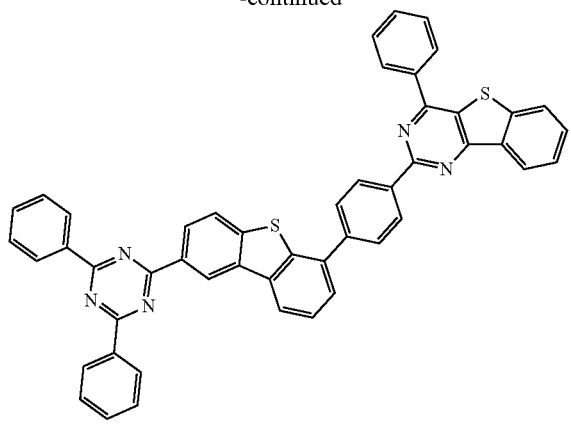
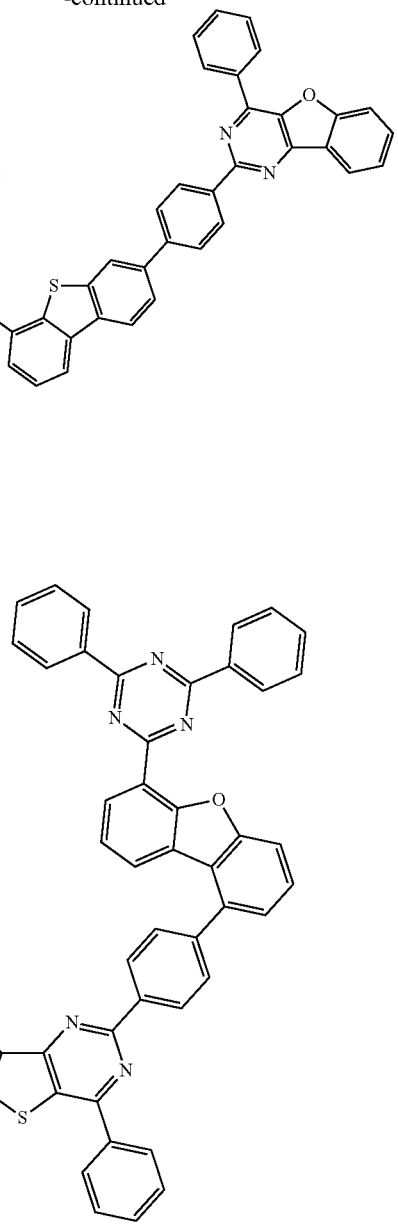
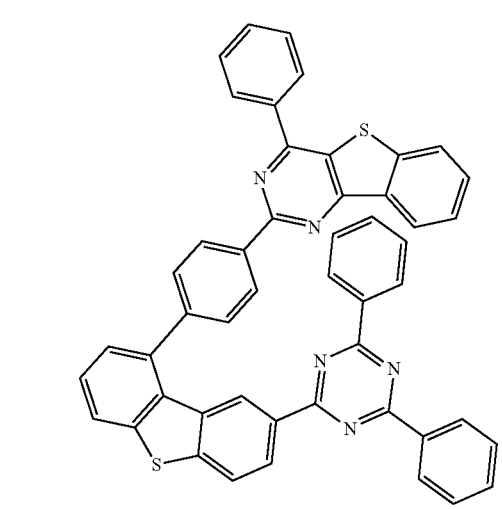
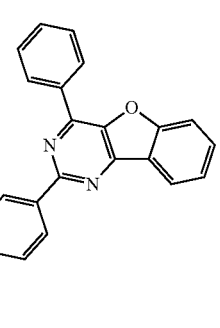

529
-continued
530
-continued
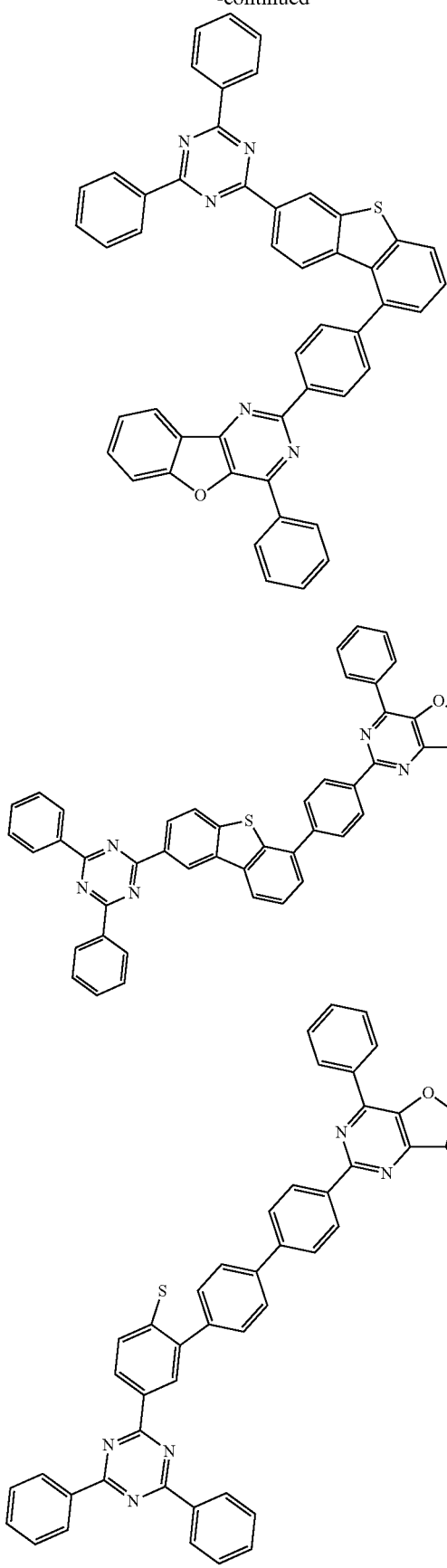
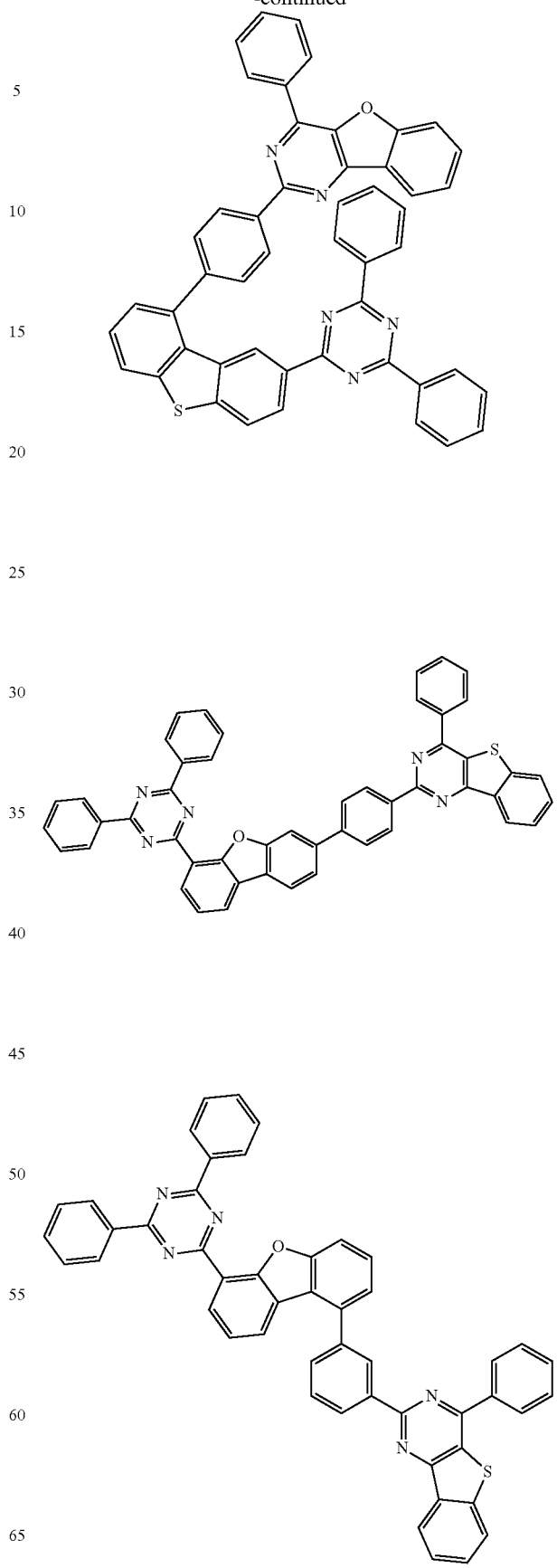

| 531 -continued | 532 -continued |
|---|---|
| 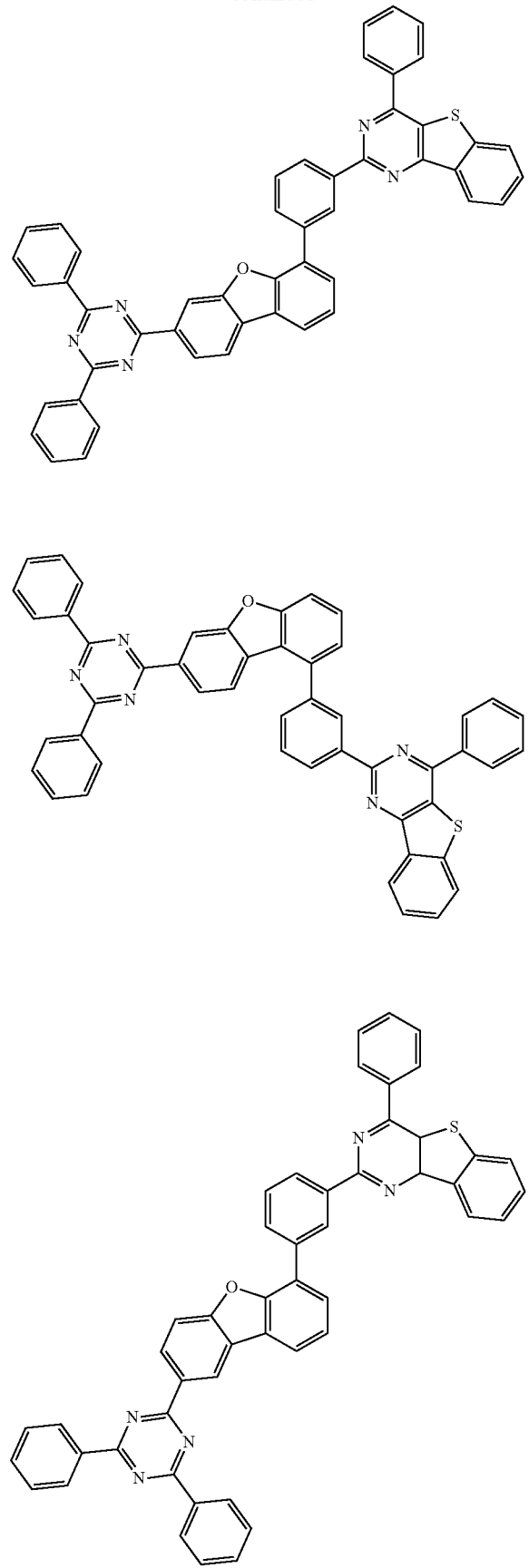 | 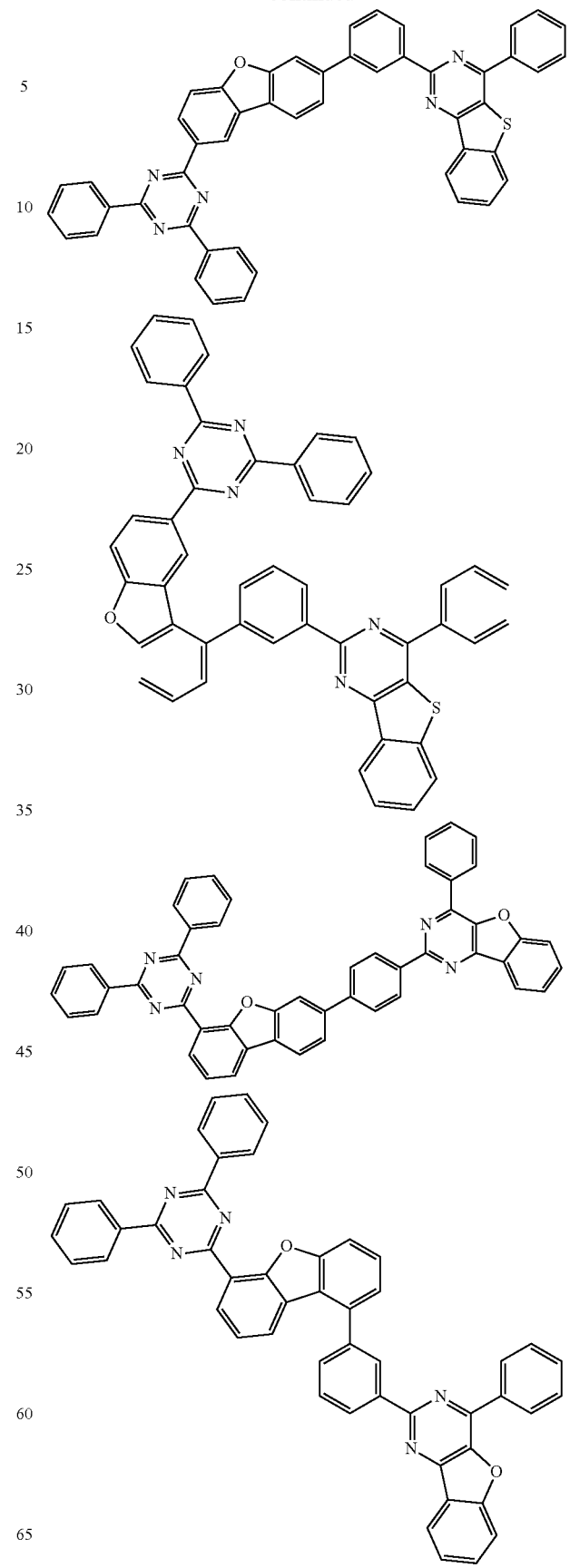 |

533
-continued
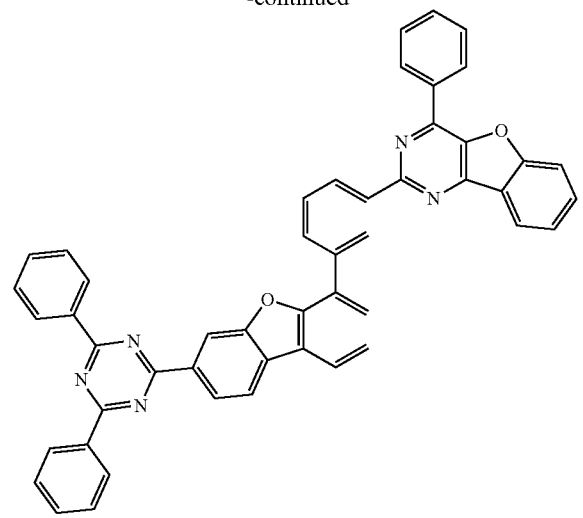
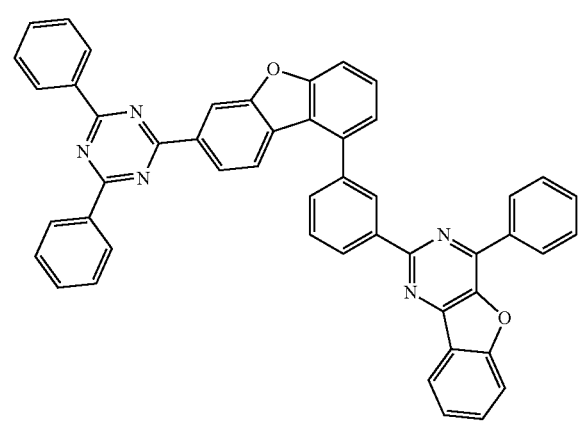
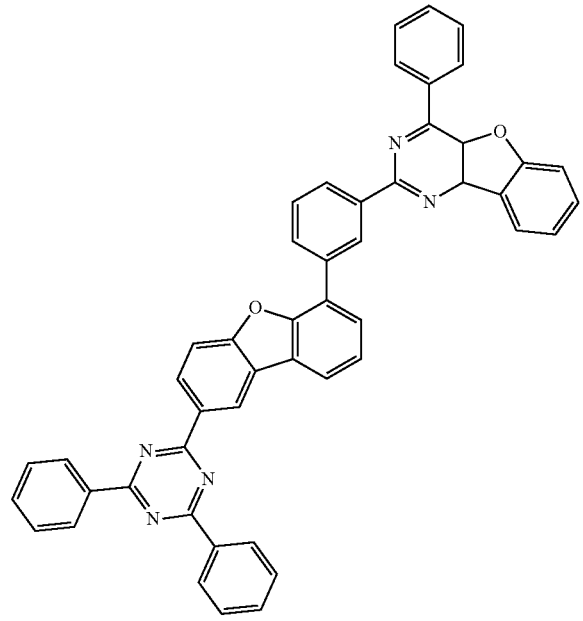
534
-continued
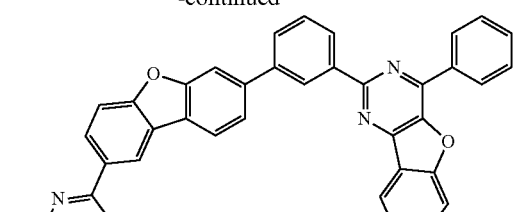
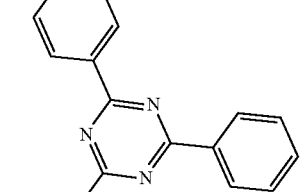
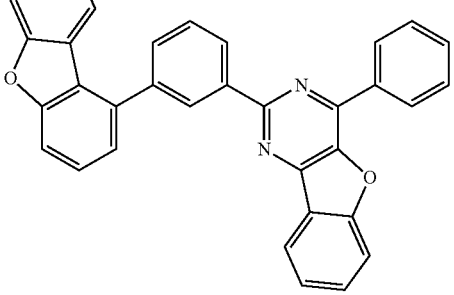
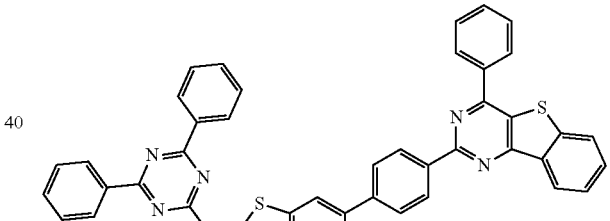
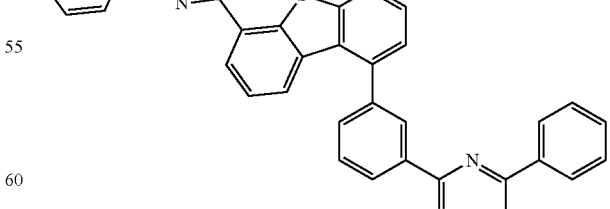

535
-continued
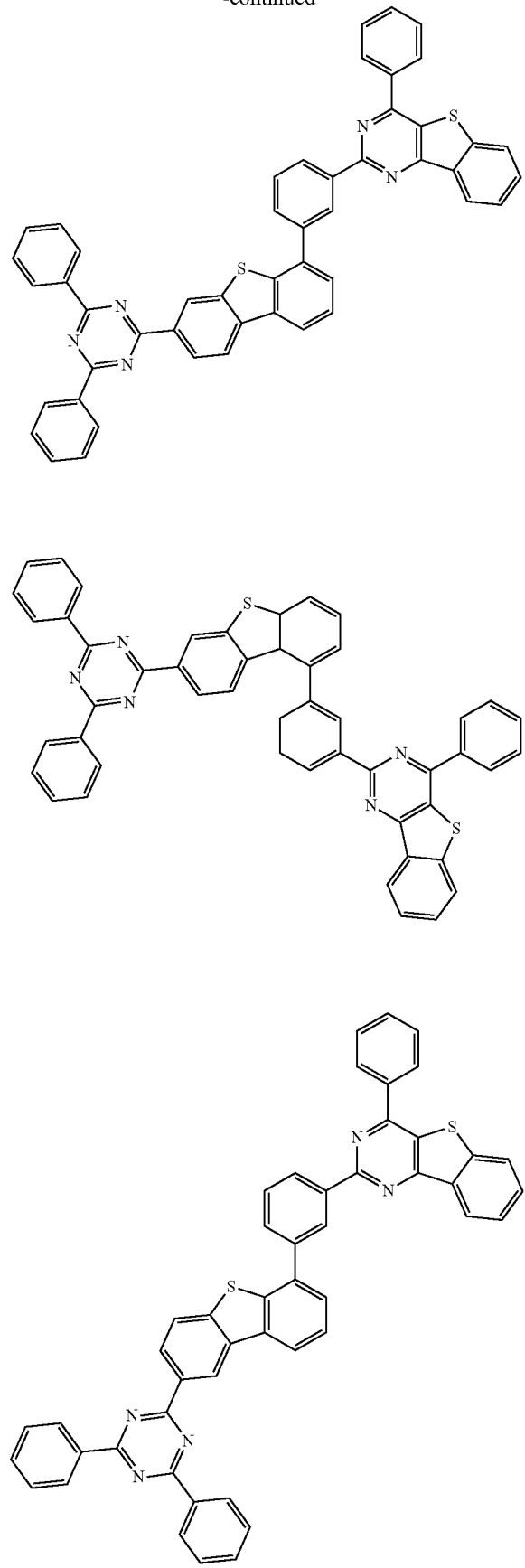 [SMILES: c1ccc(-c2nc(-c3ccccc3)nc(-c3ccc4c(c3)sc3c(-c5cccc(-c6nc(-c7ccccc7)c7oc8ccccc8c7n6)c5)cccc34)n2)cc1 ; c1ccc(-c2nc(-c3ccccc3)nc(-c3ccc4c(c3)sc3cccc(-c5cccc(-c6nc(-c7ccccc7)c7oc8ccccc8c7n6)c5)c34)n2)cc1 ; c1ccc(-c2nc(-c3ccccc3)nc(-c3ccc4sc5c(-c6cccc(-c7nc(-c8ccccc8)c8oc9ccccc9c8n7)c6)cccc5c4c3)n2)cc1]
536
-continued
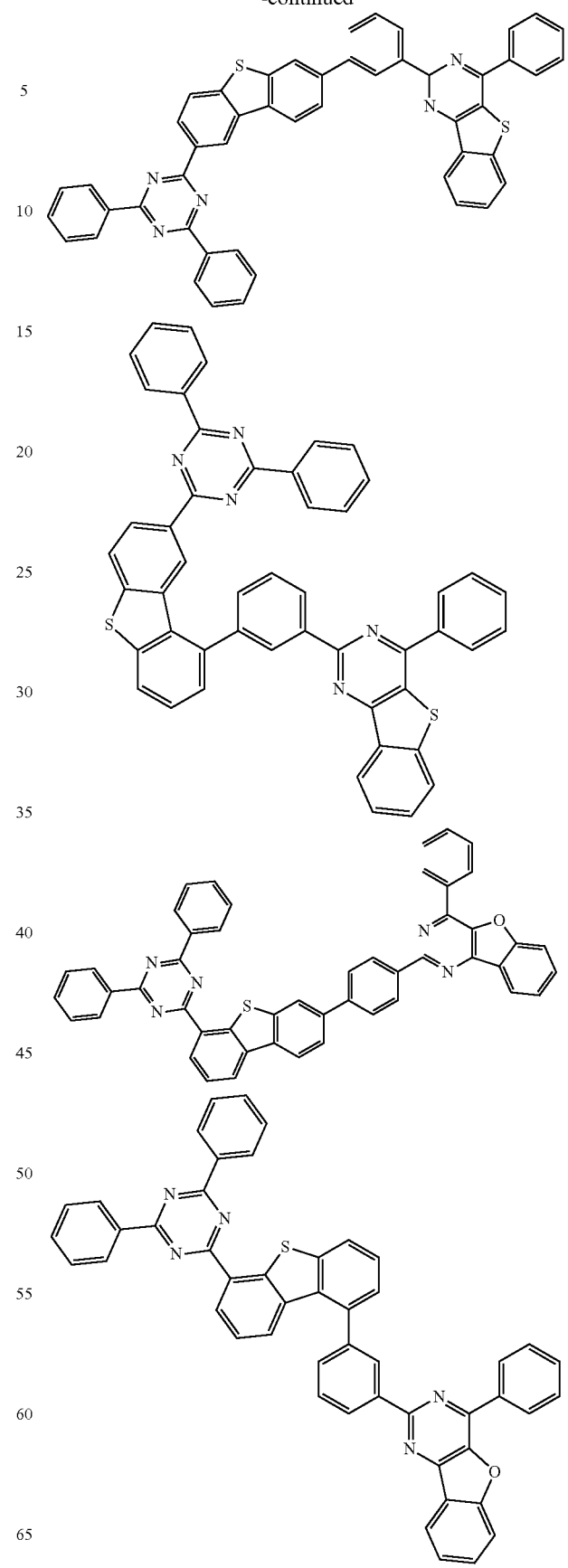

537
-continued
538
-continued
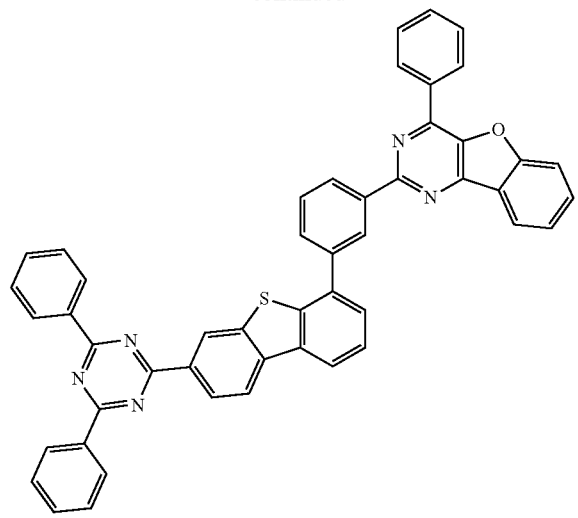
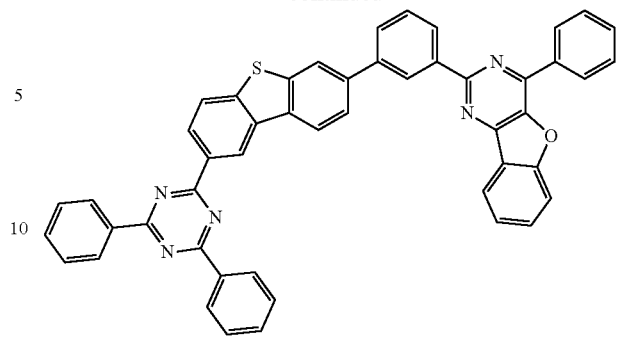
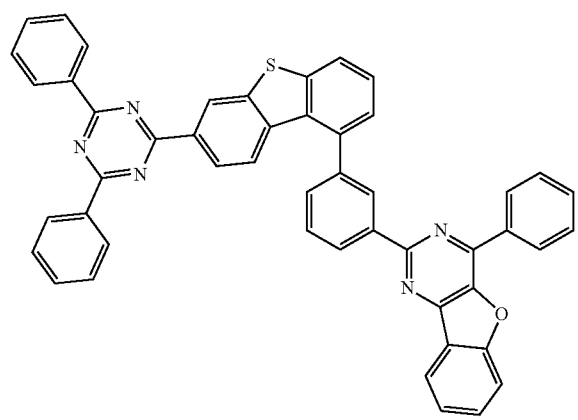
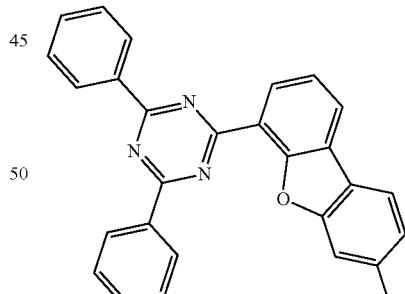
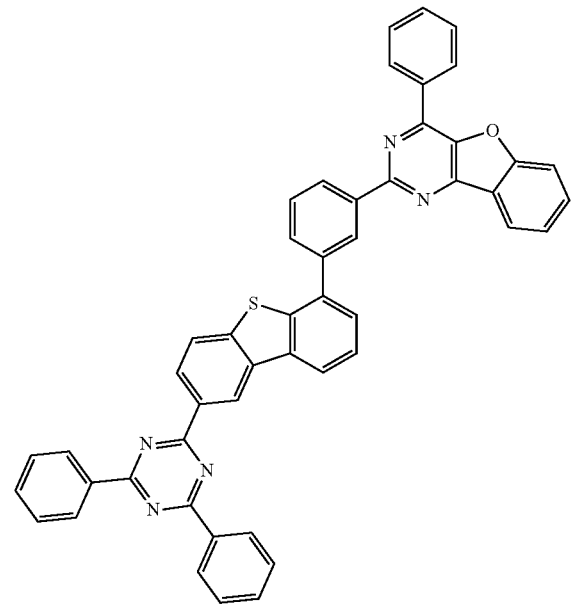
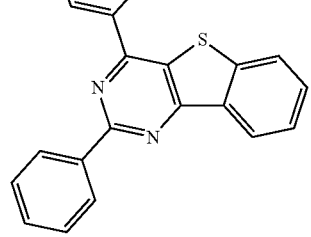

539
-continued
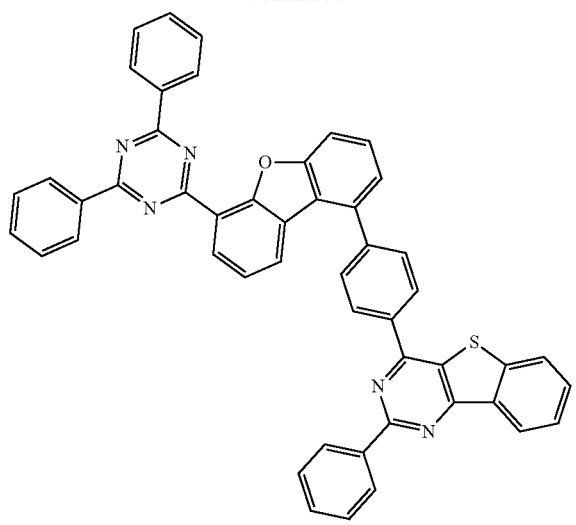
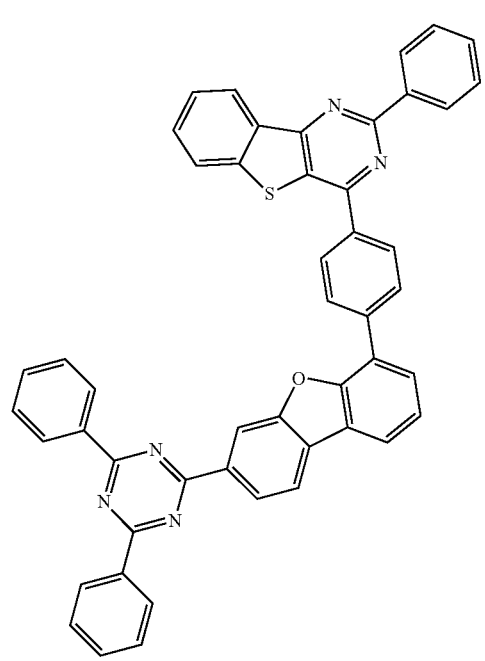
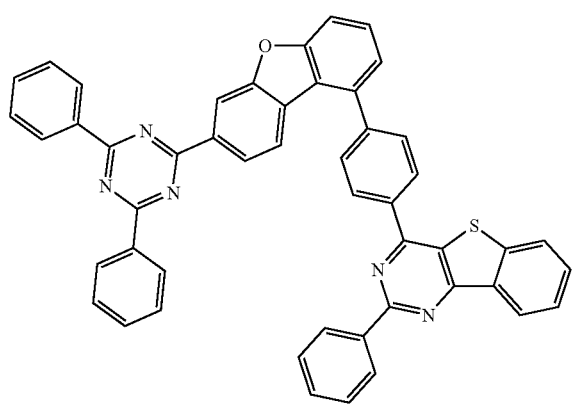
540
-continued
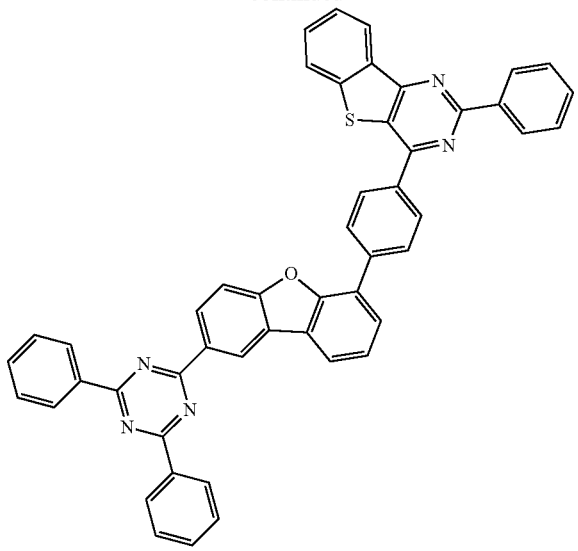
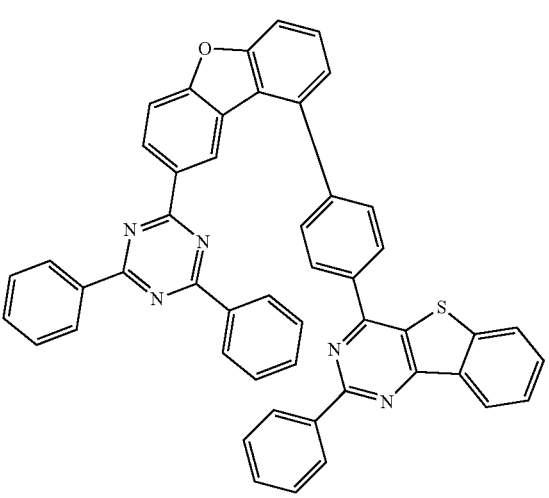

541
-continued
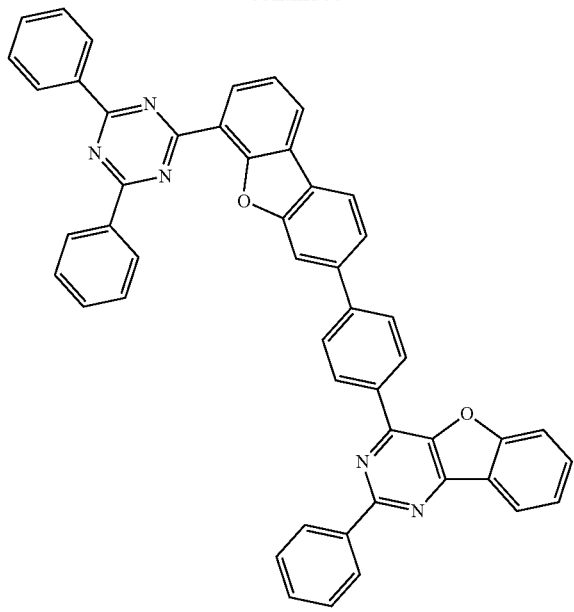
542
-continued
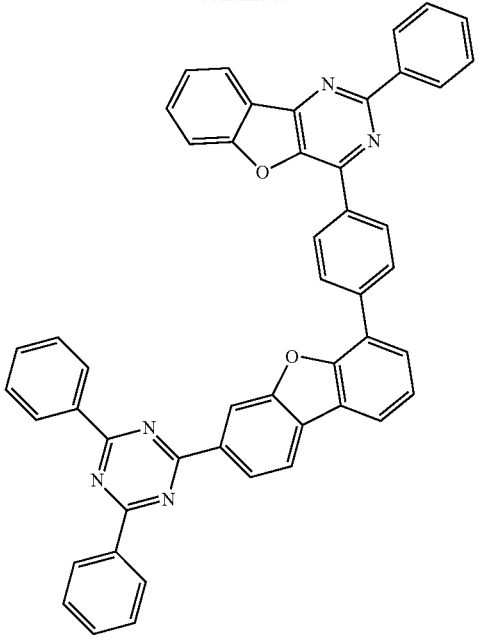
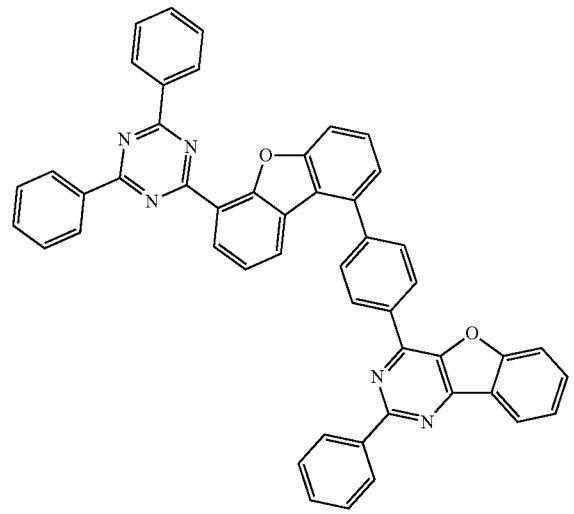
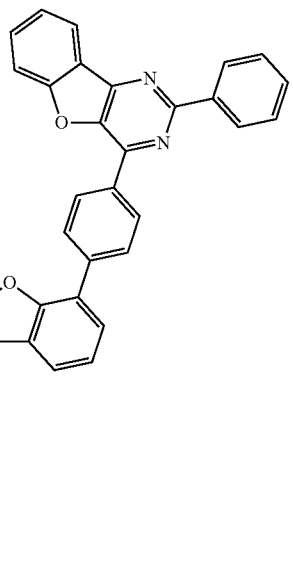

543
-continued
544
-continued
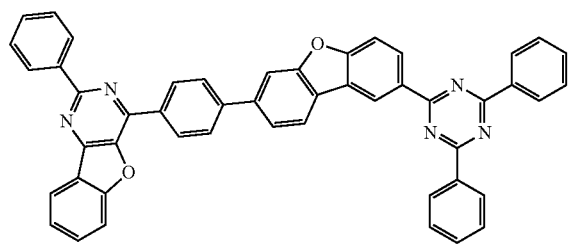
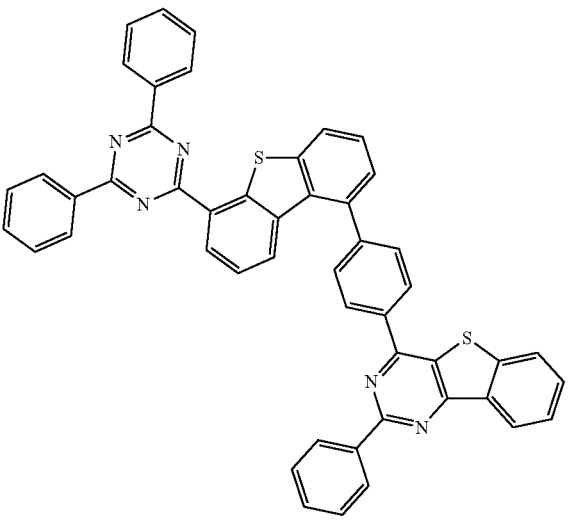
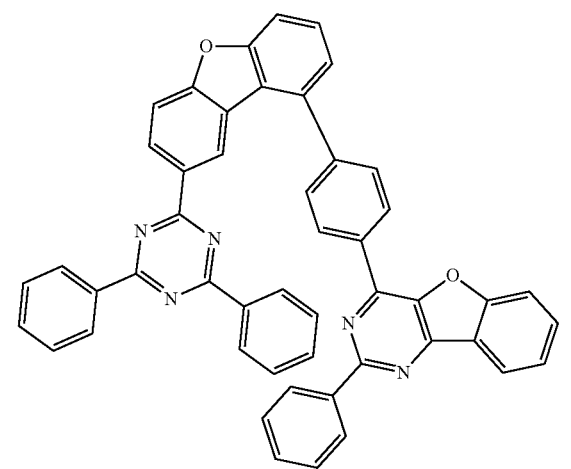
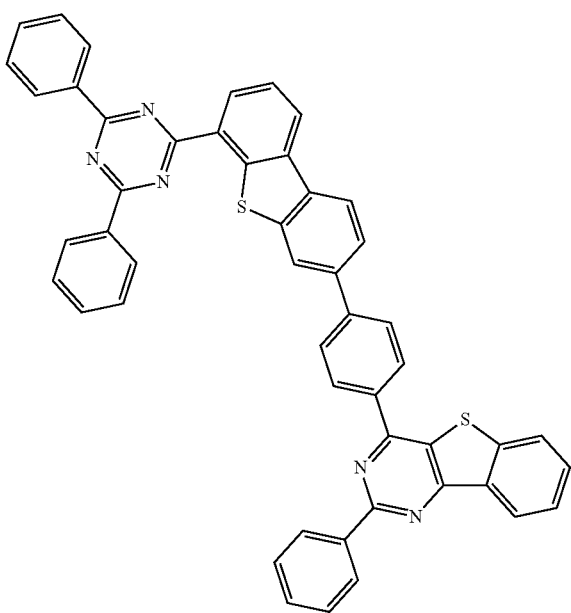

545
-continued
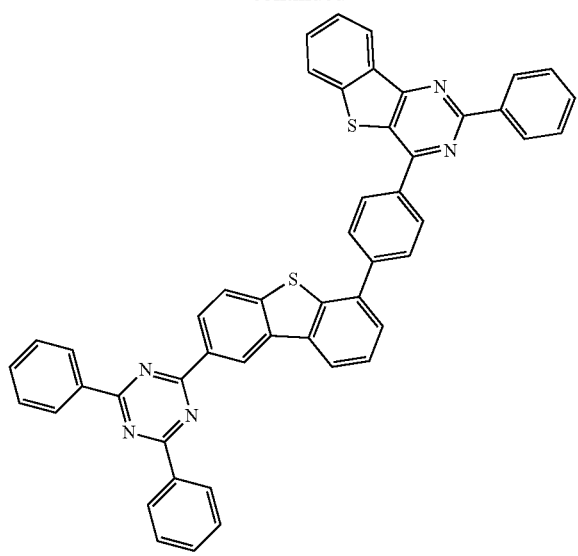
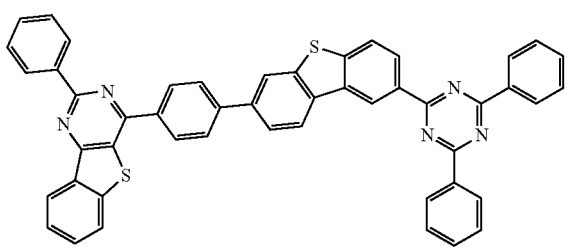
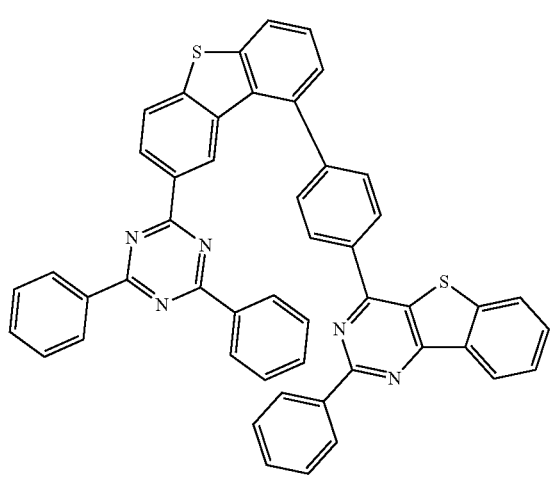
546
-continued
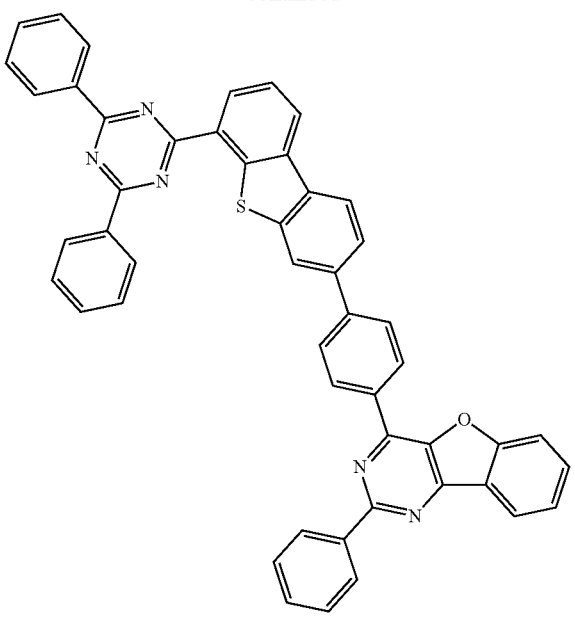
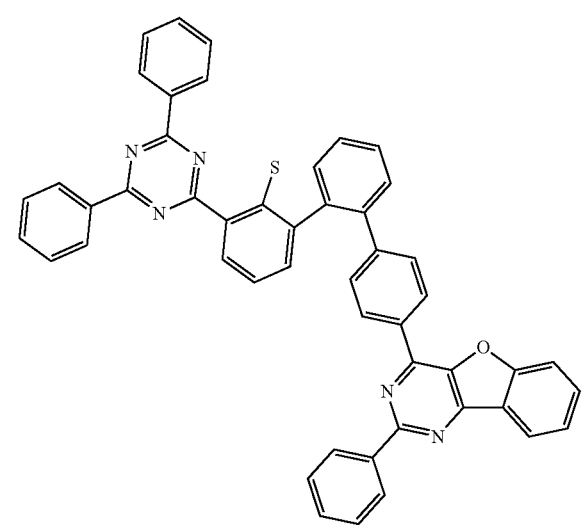

547
-continued
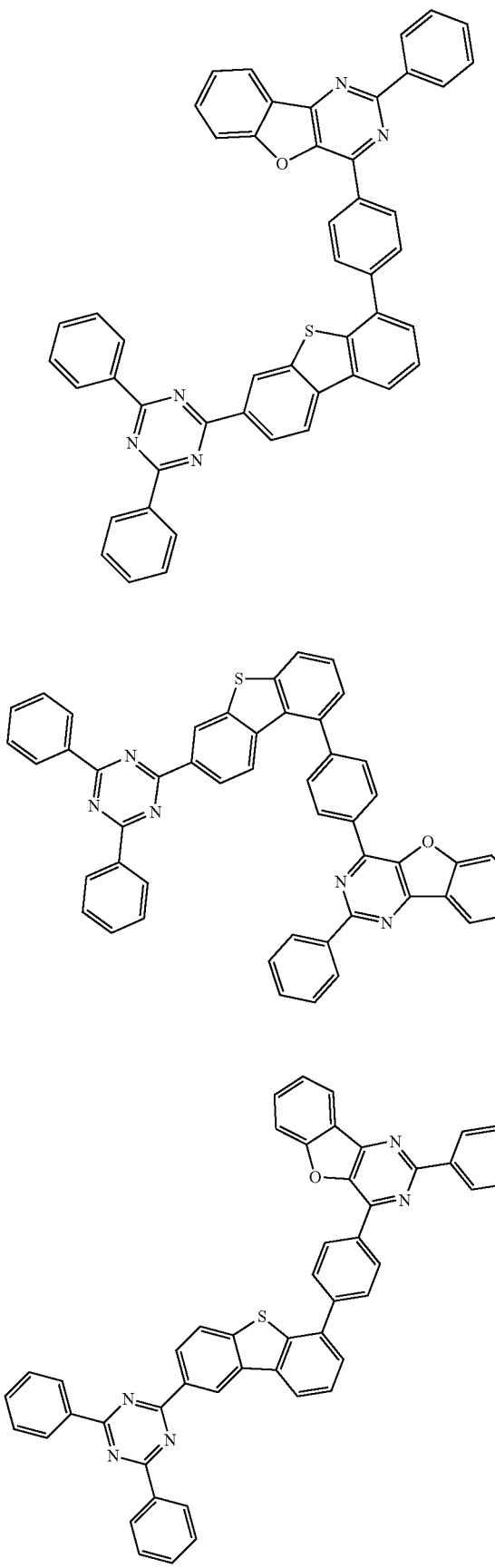
548
-continued
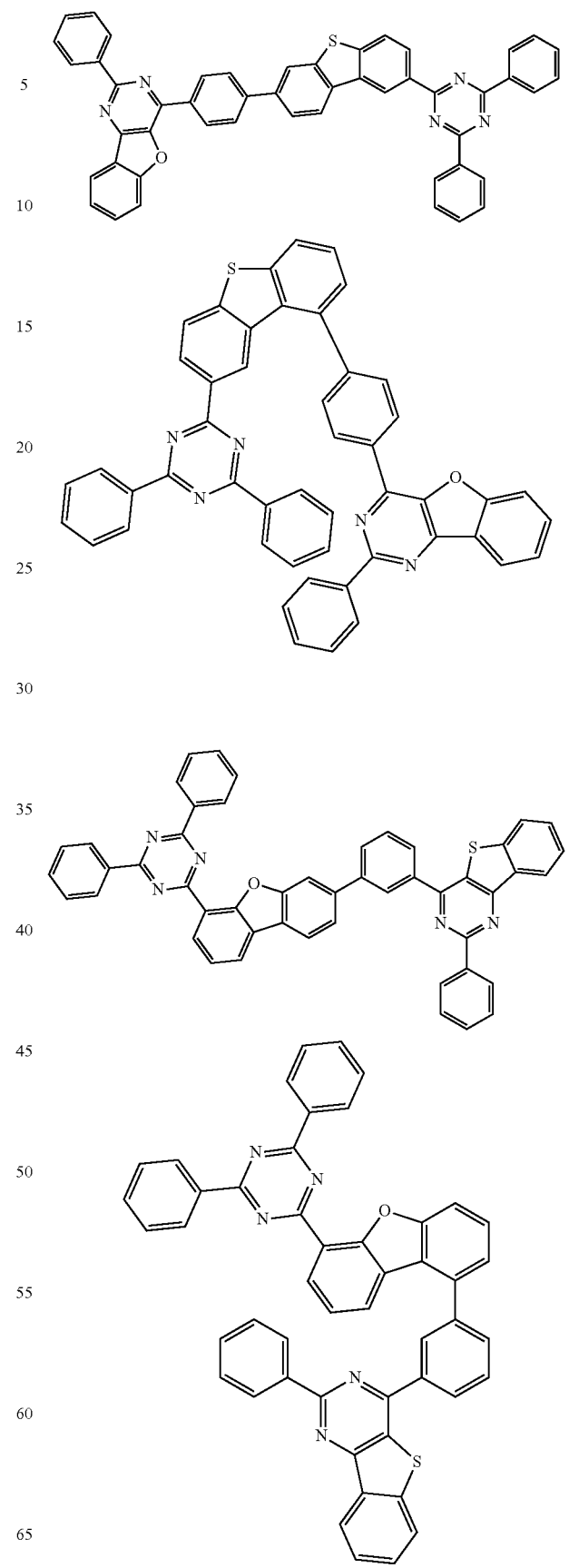

549
-continued
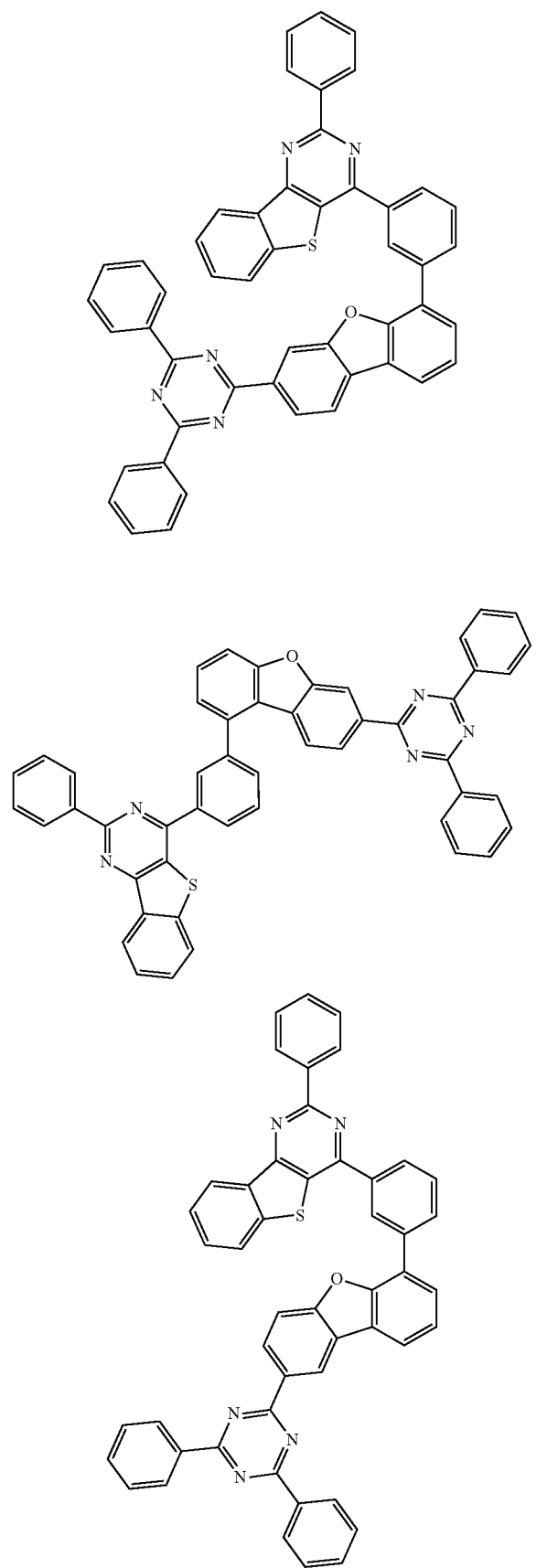
550
-continued
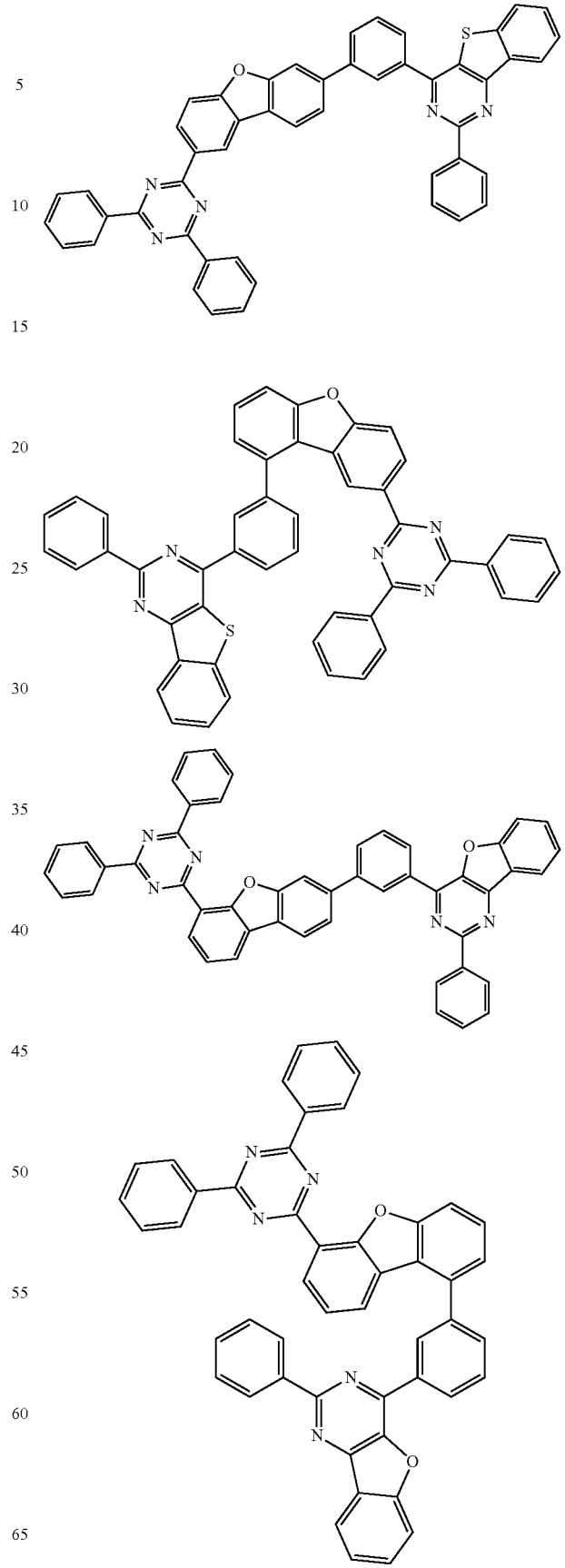

551
-continued
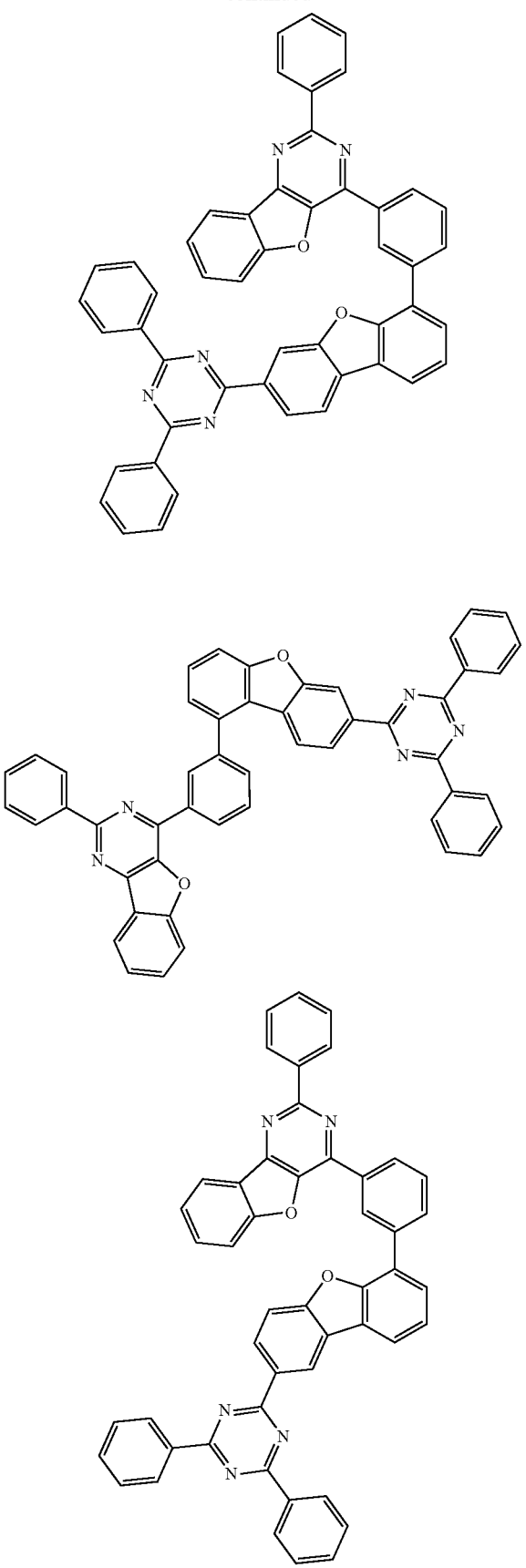
552
-continued
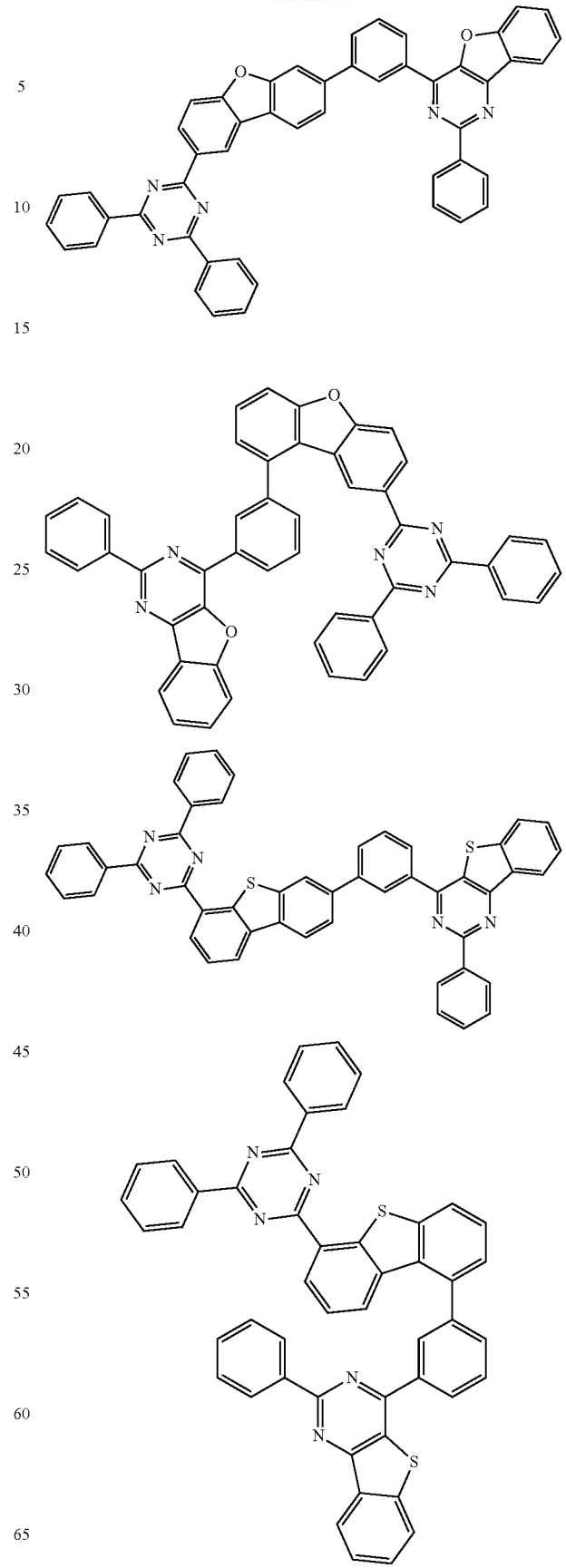

553
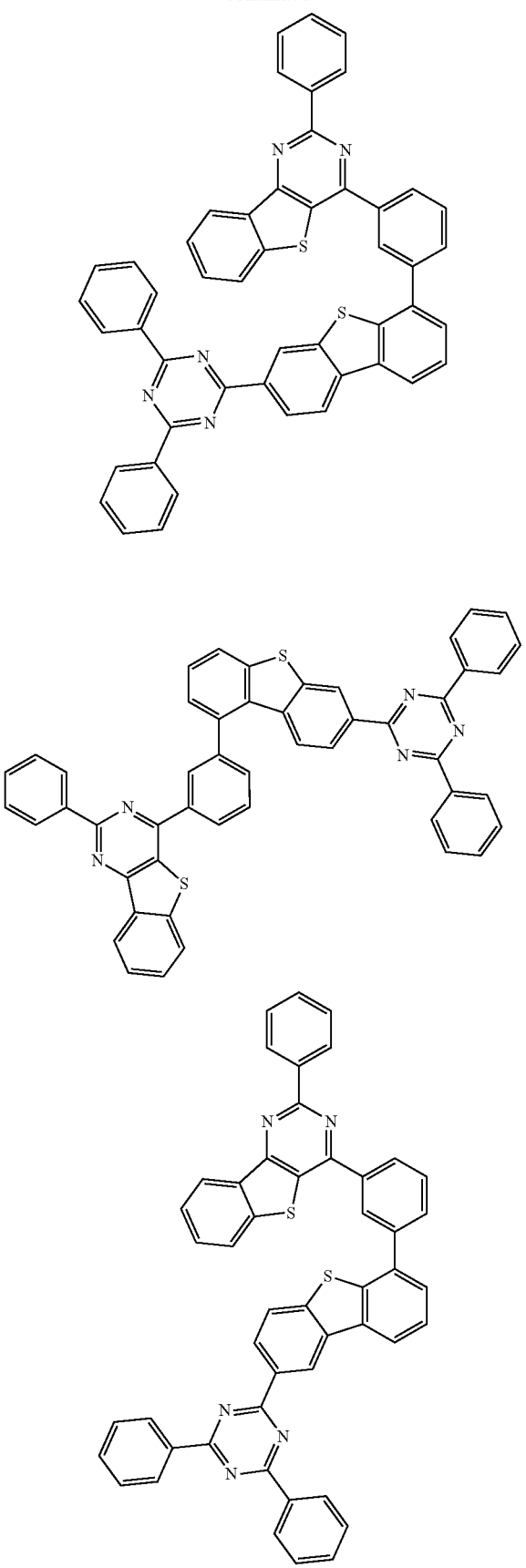
554
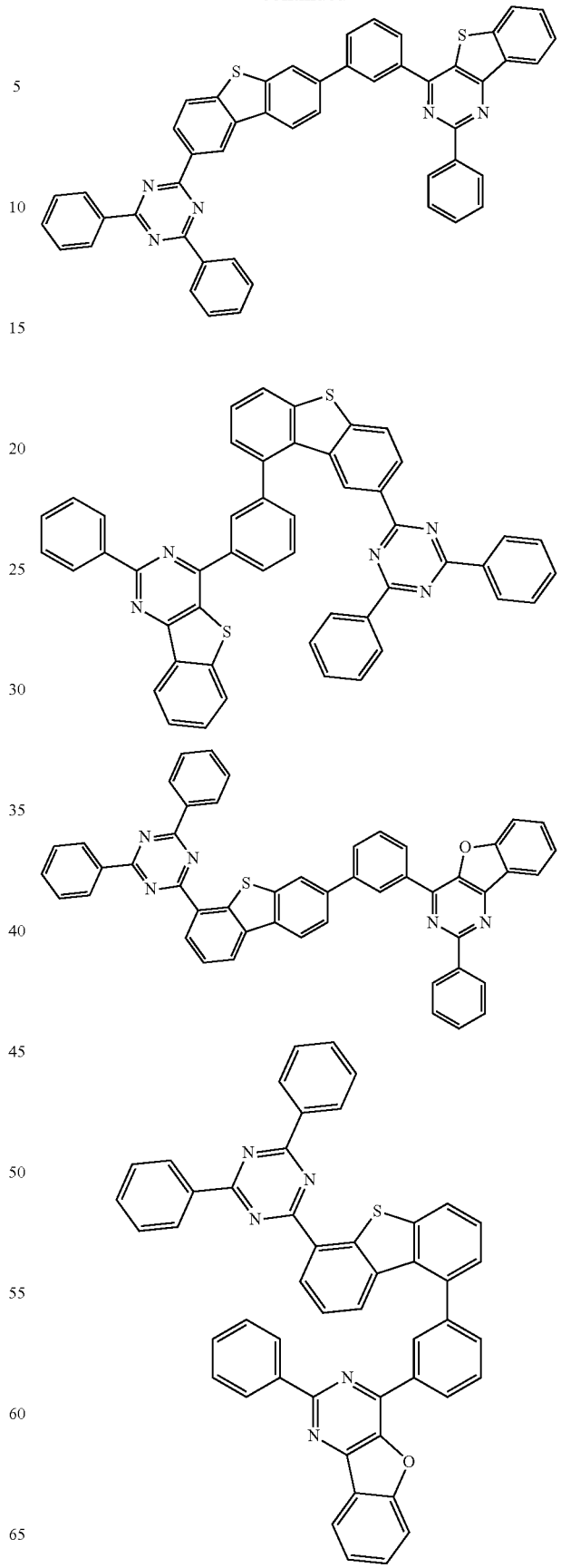

555
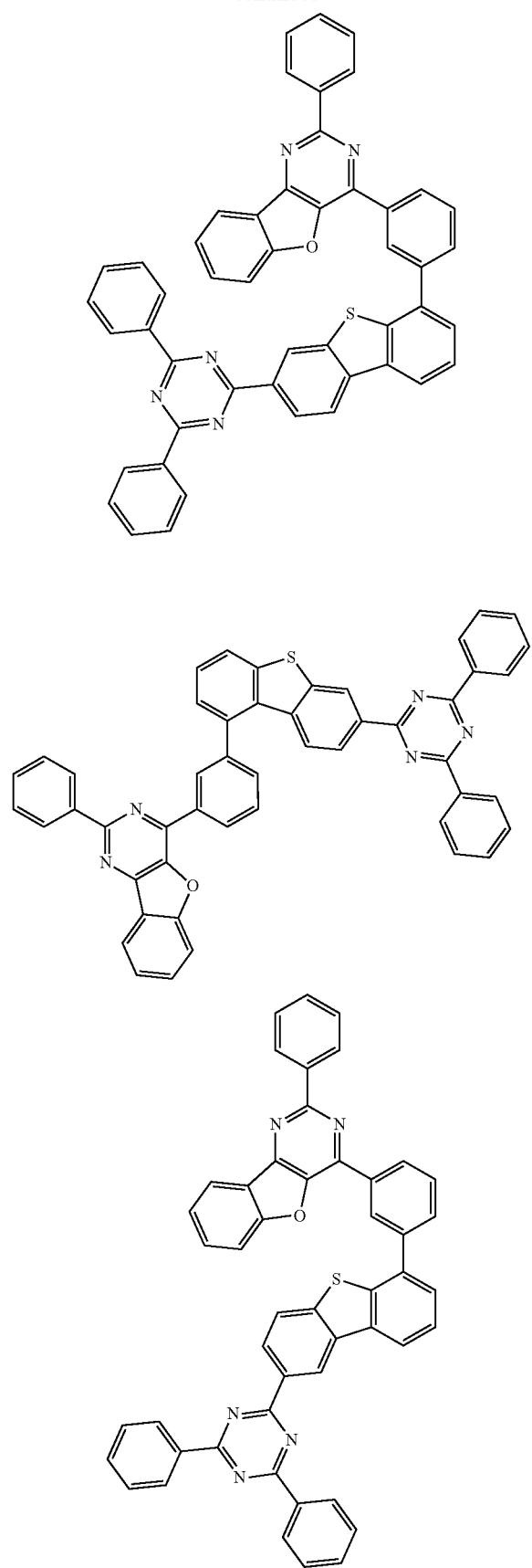
556
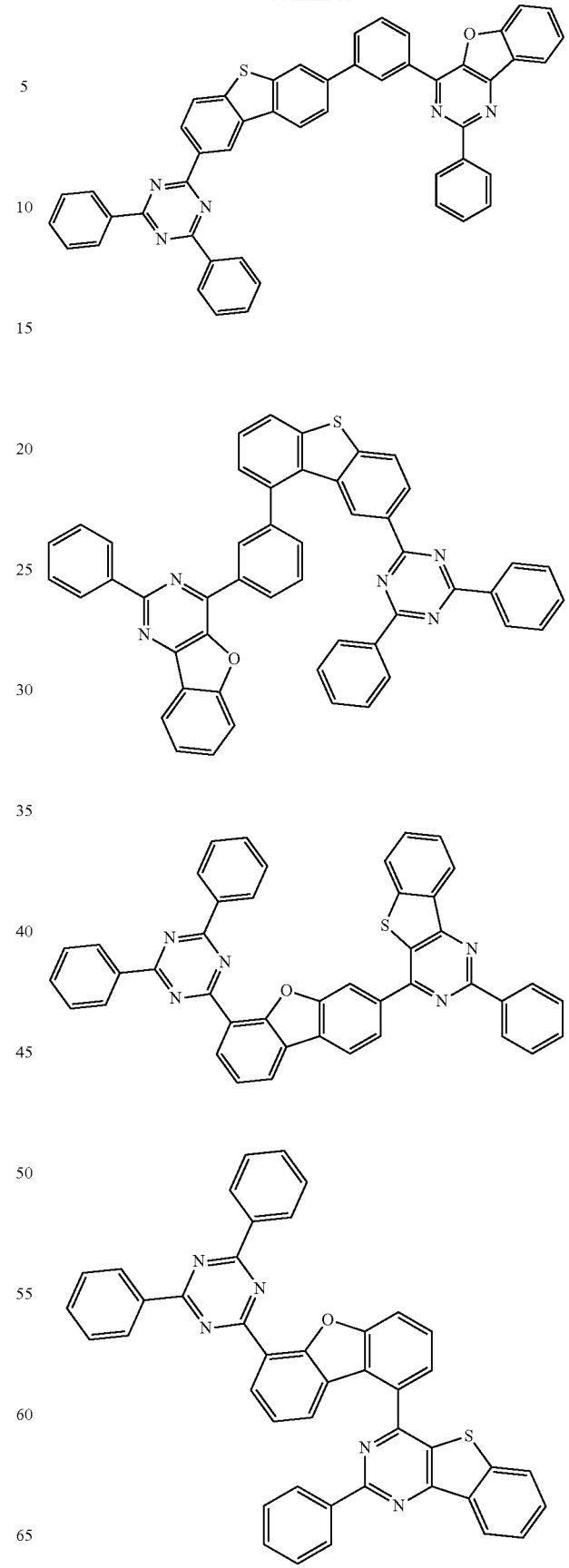

557
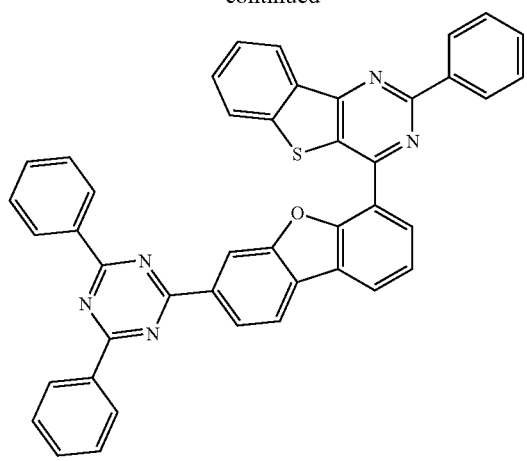
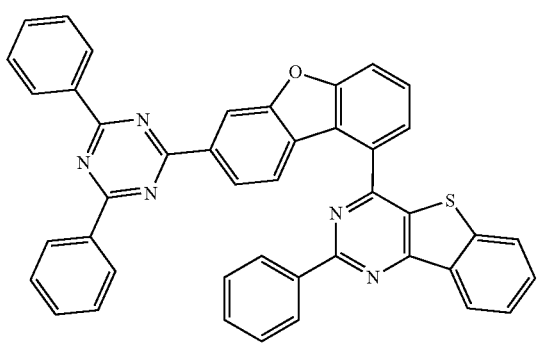
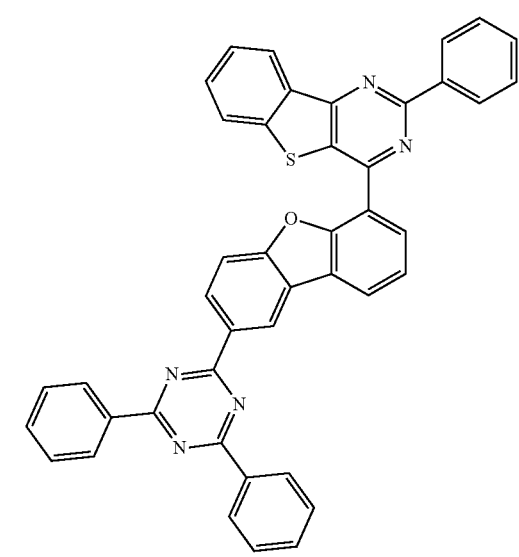
558
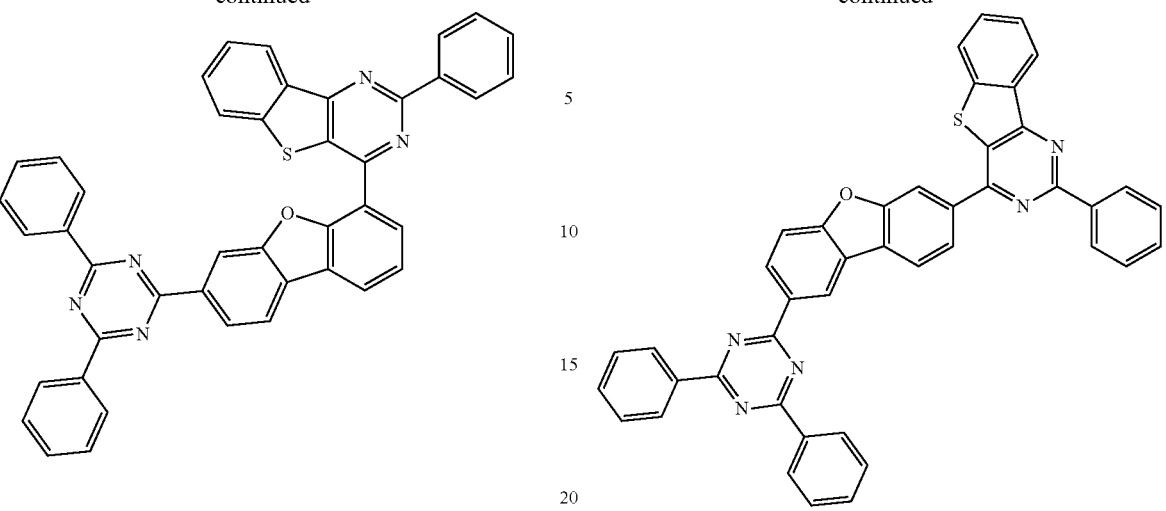
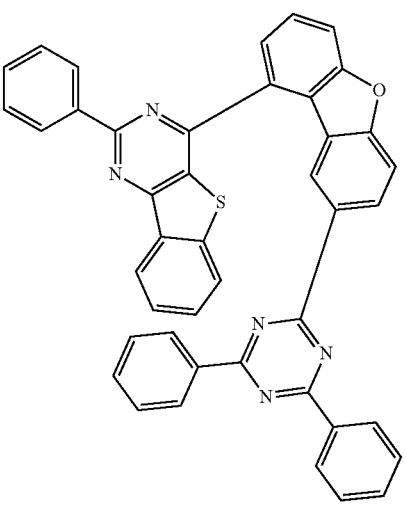
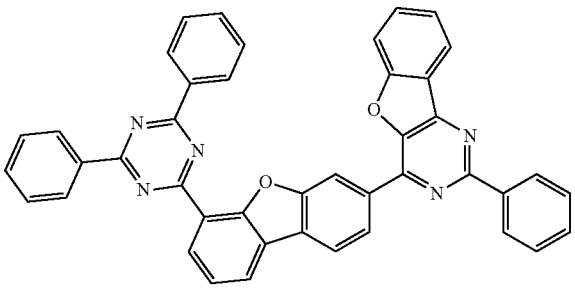

559
-continued
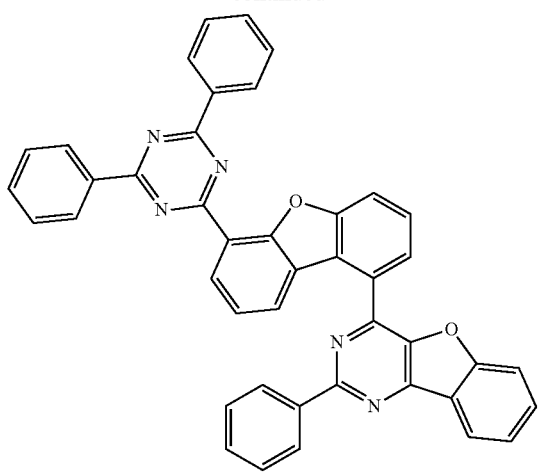
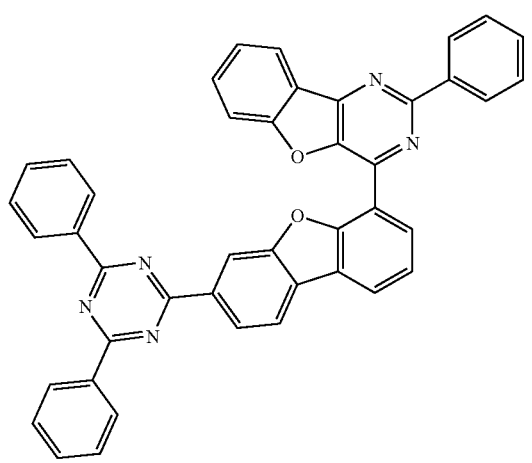
560
-continued
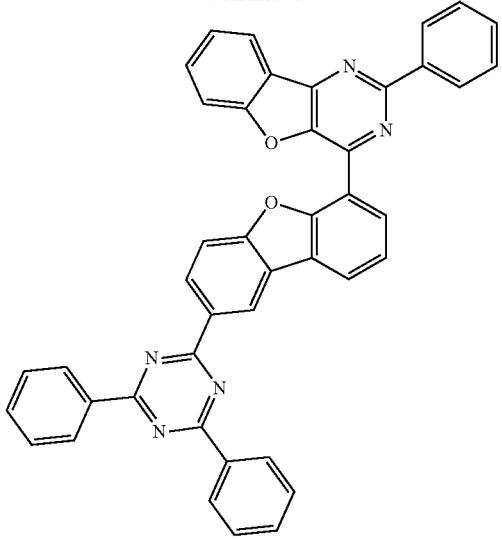
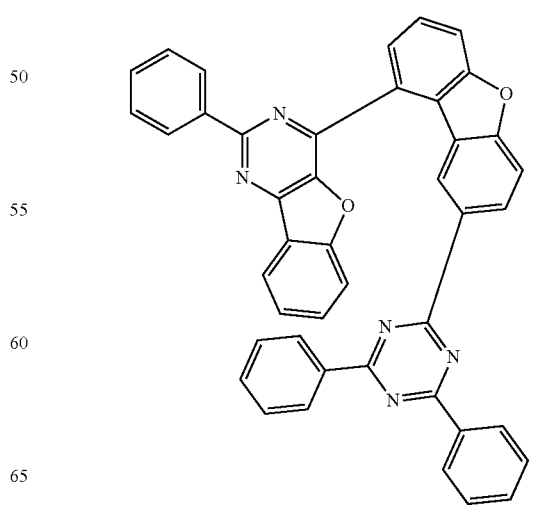

561
-continued
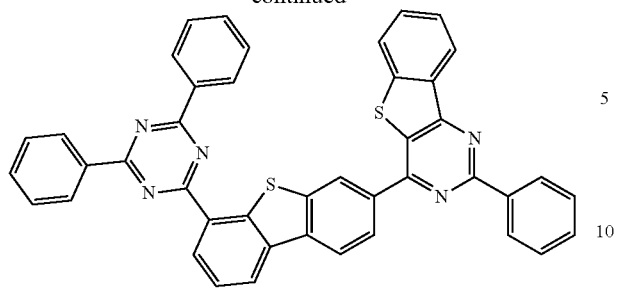
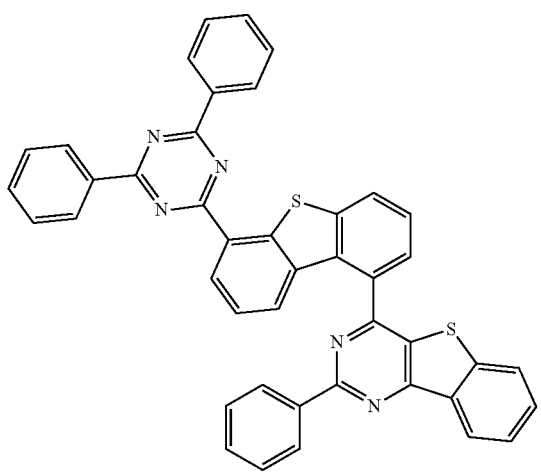
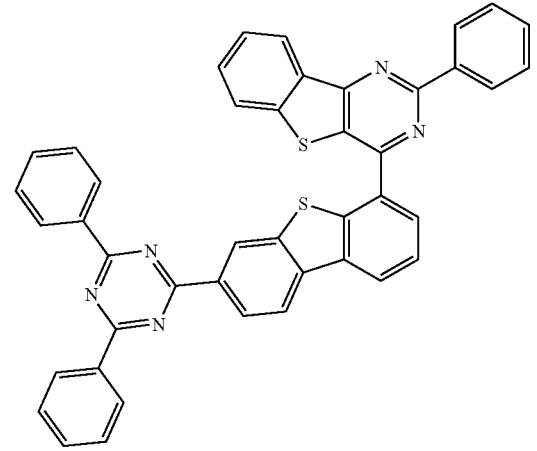
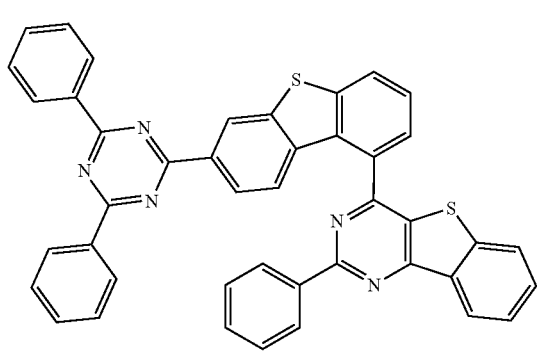
562
-continued
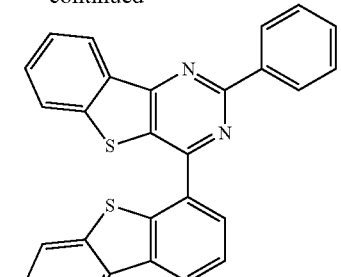
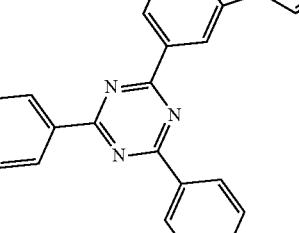

563
-continued
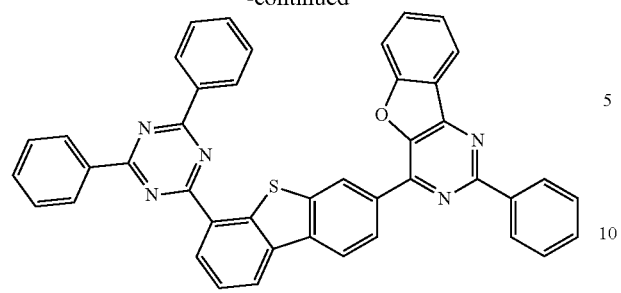
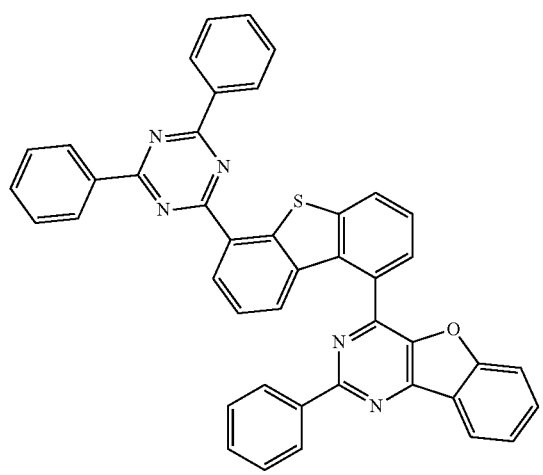
564
-continued
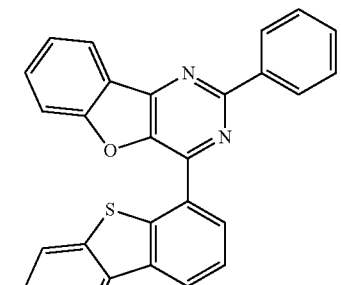
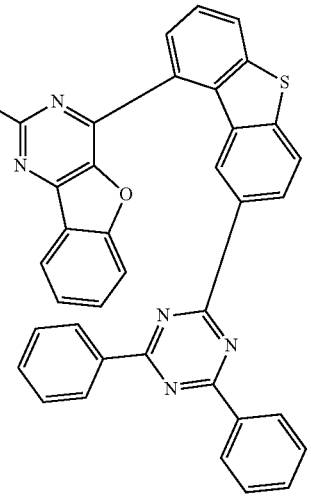

565
-continued
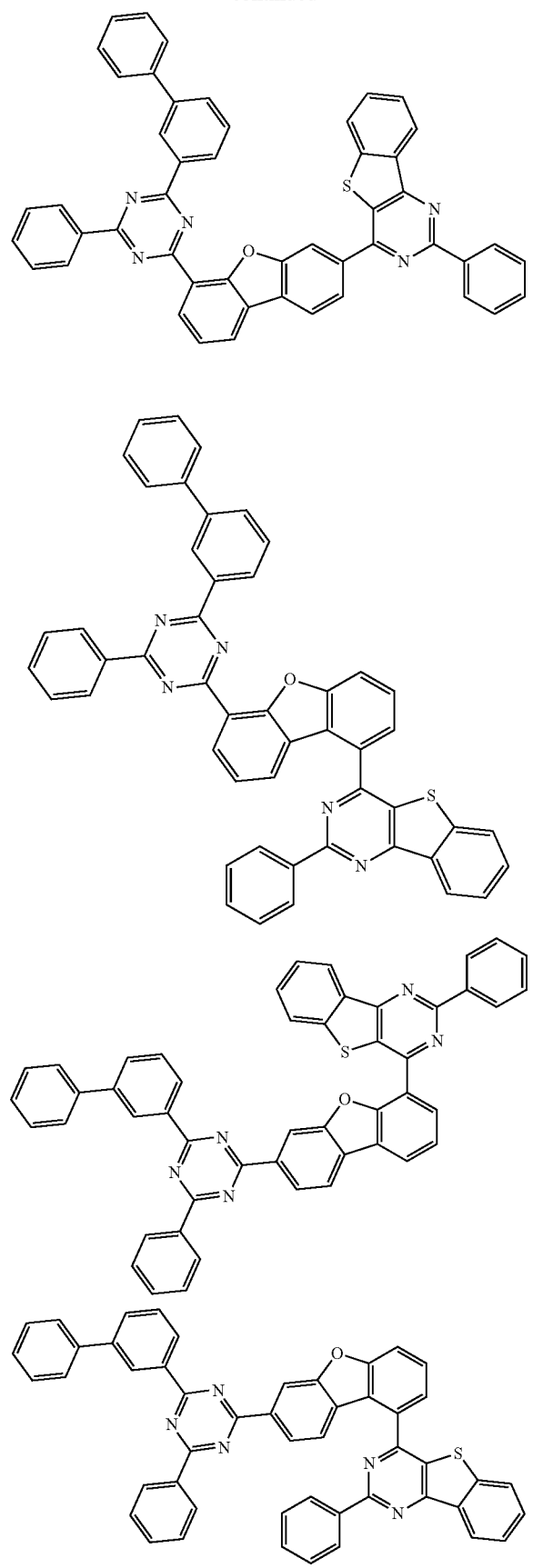
566
-continued
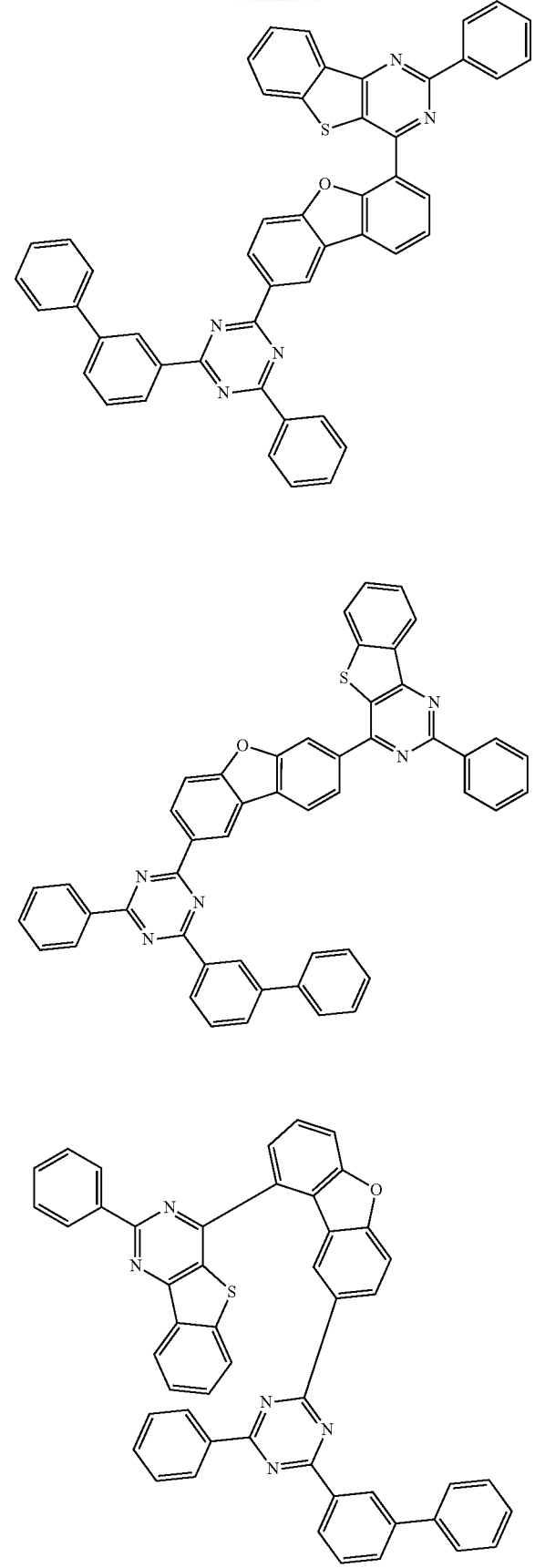

567
-continued
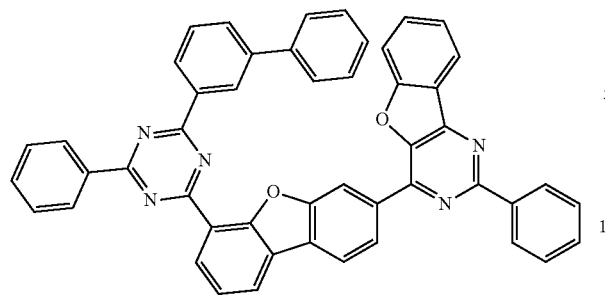
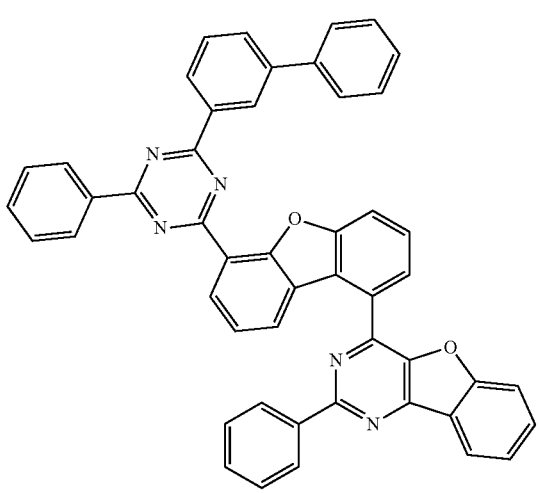
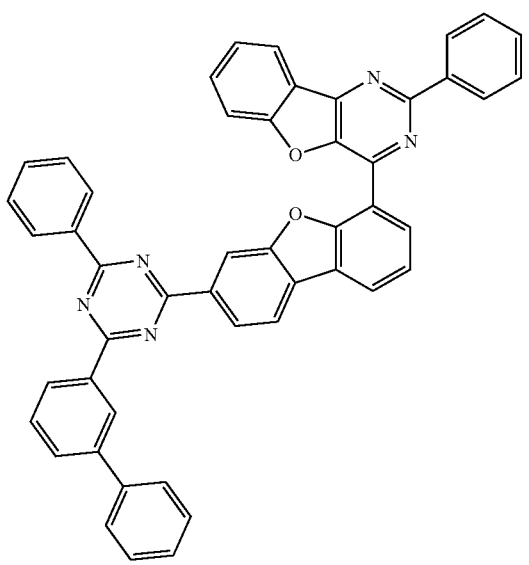
568
-continued
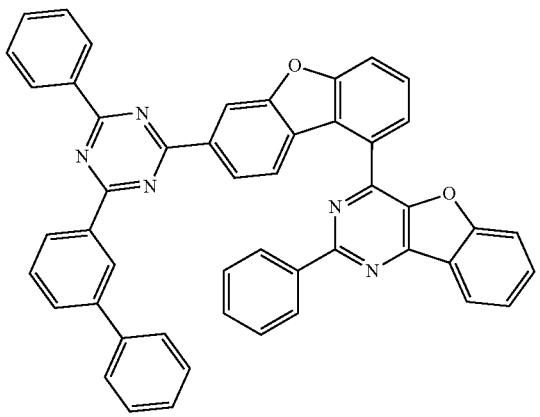
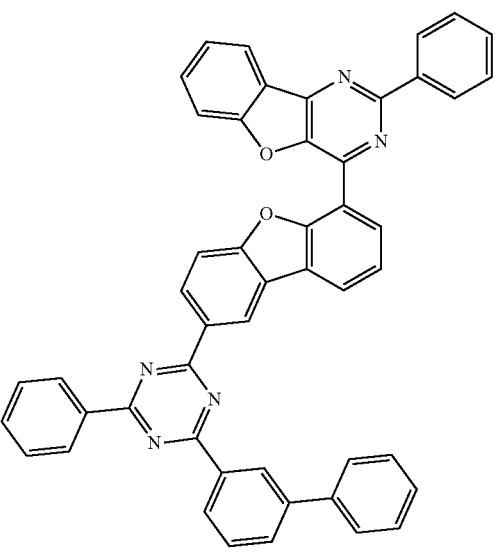
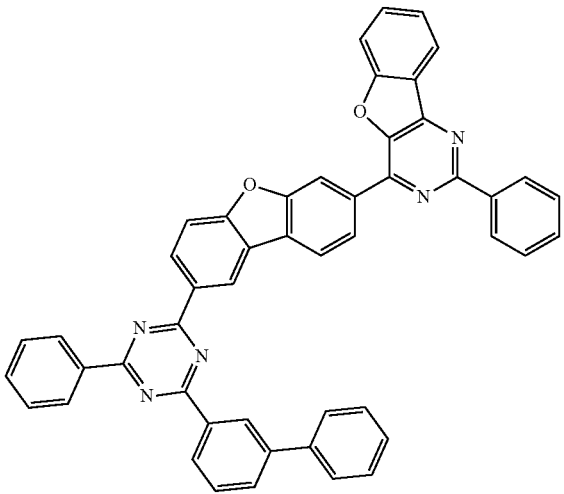

569
-continued
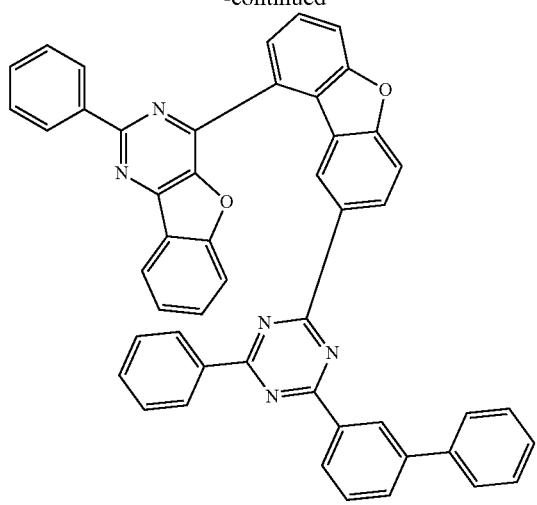
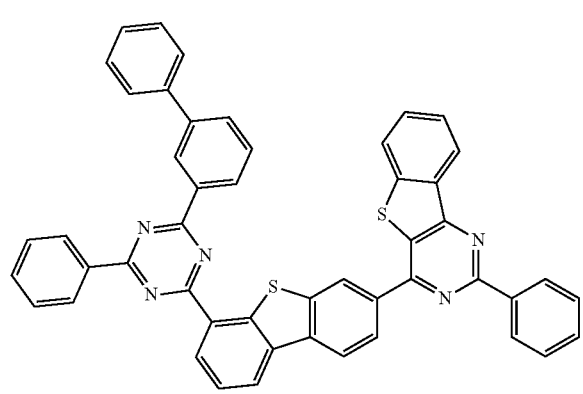
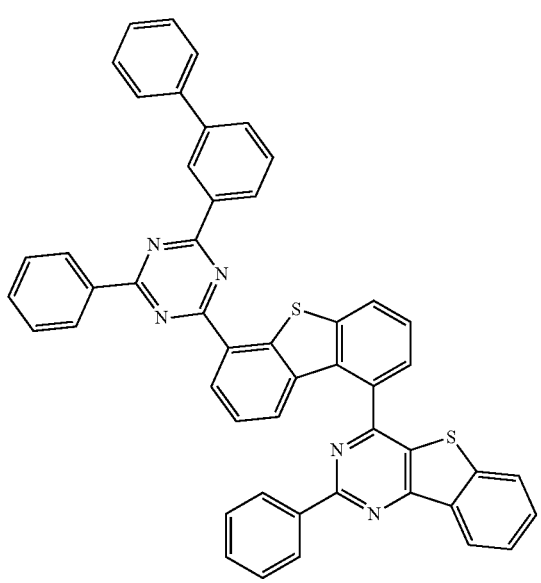
570
-continued
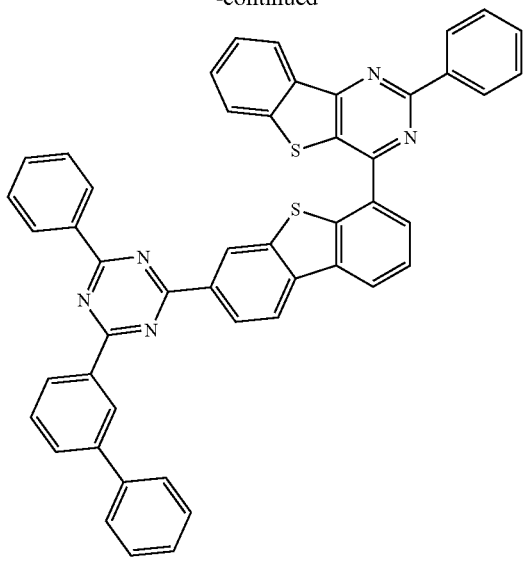
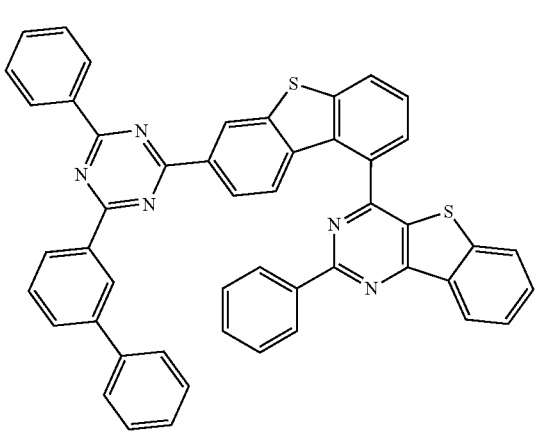
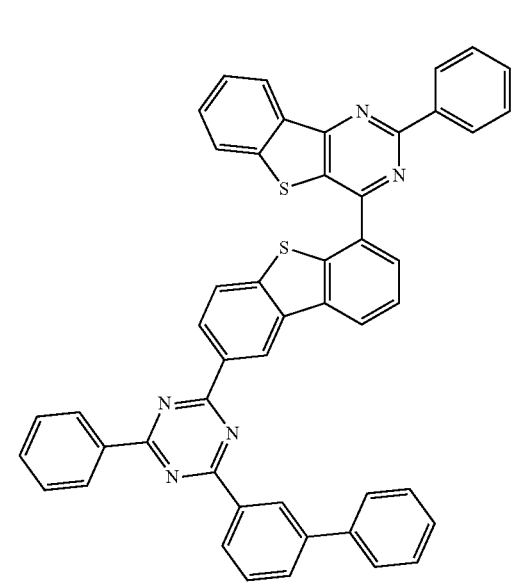

571
-continued
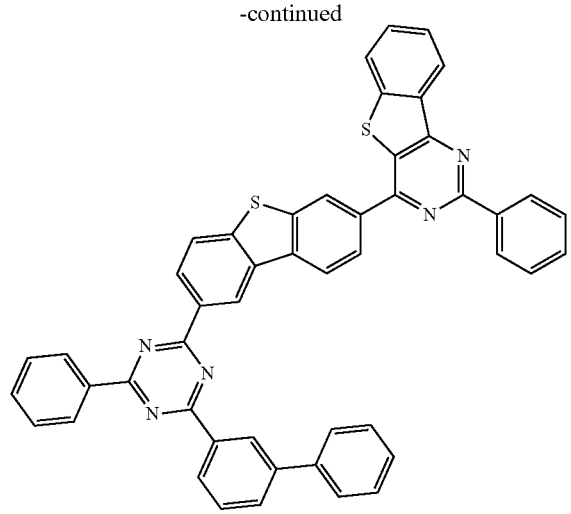
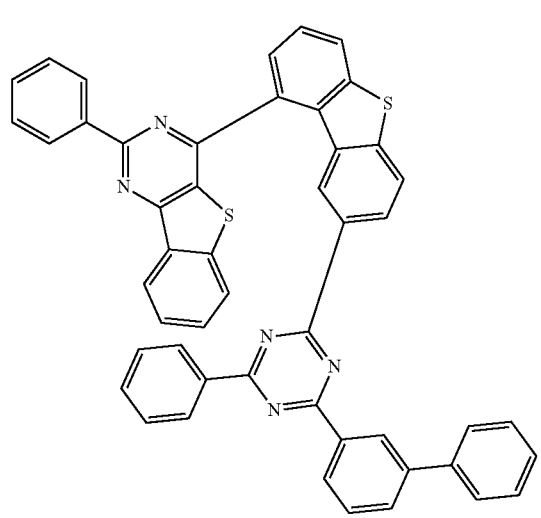
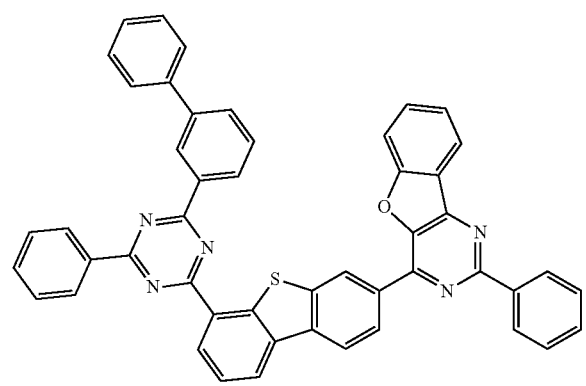
572
-continued
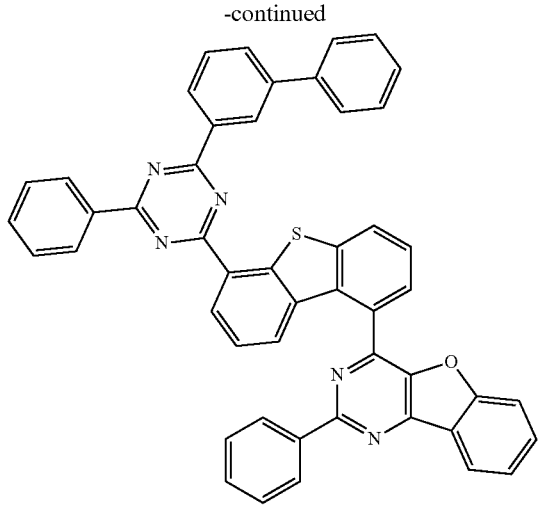
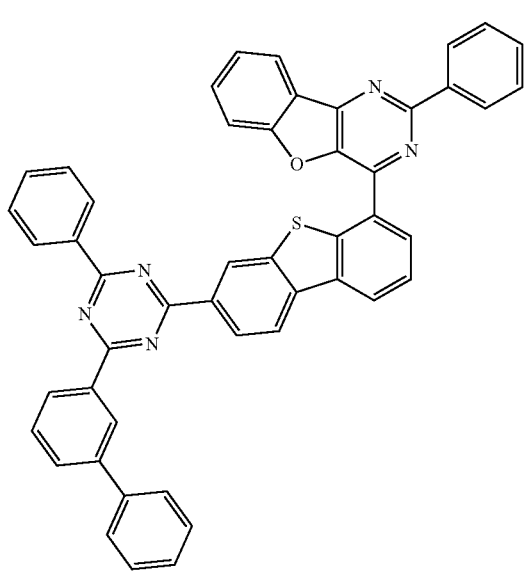
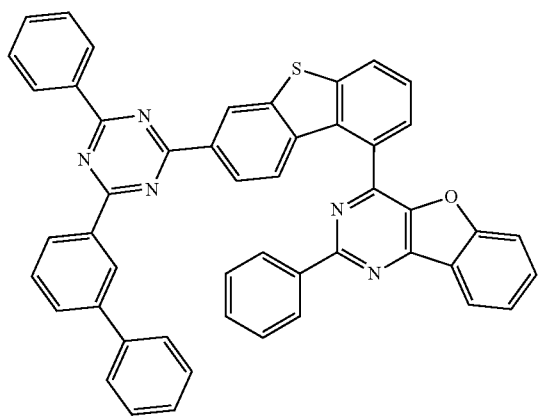

573
-continued
574
-continued
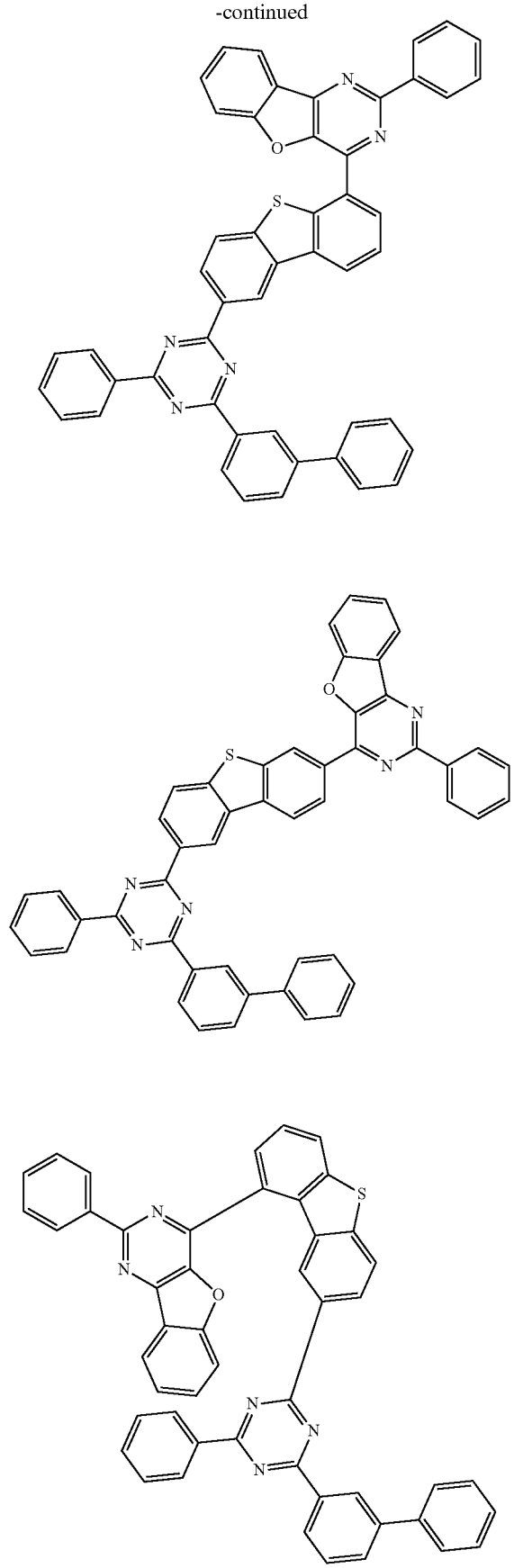
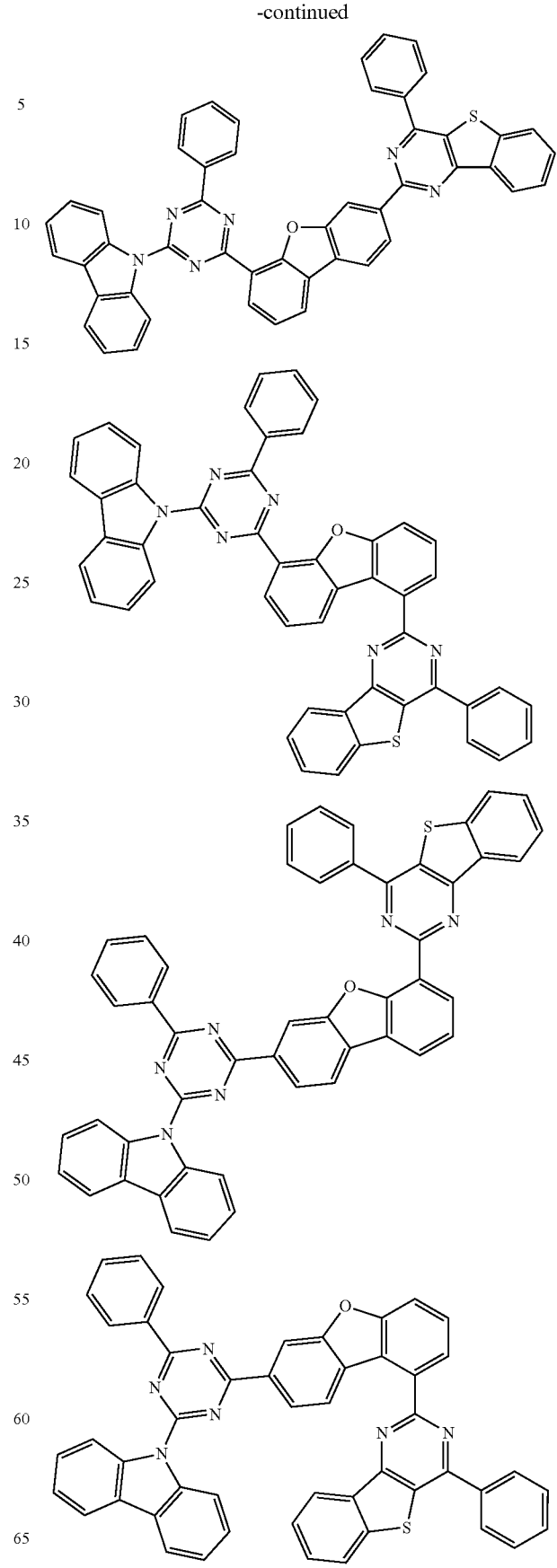

575
-continued
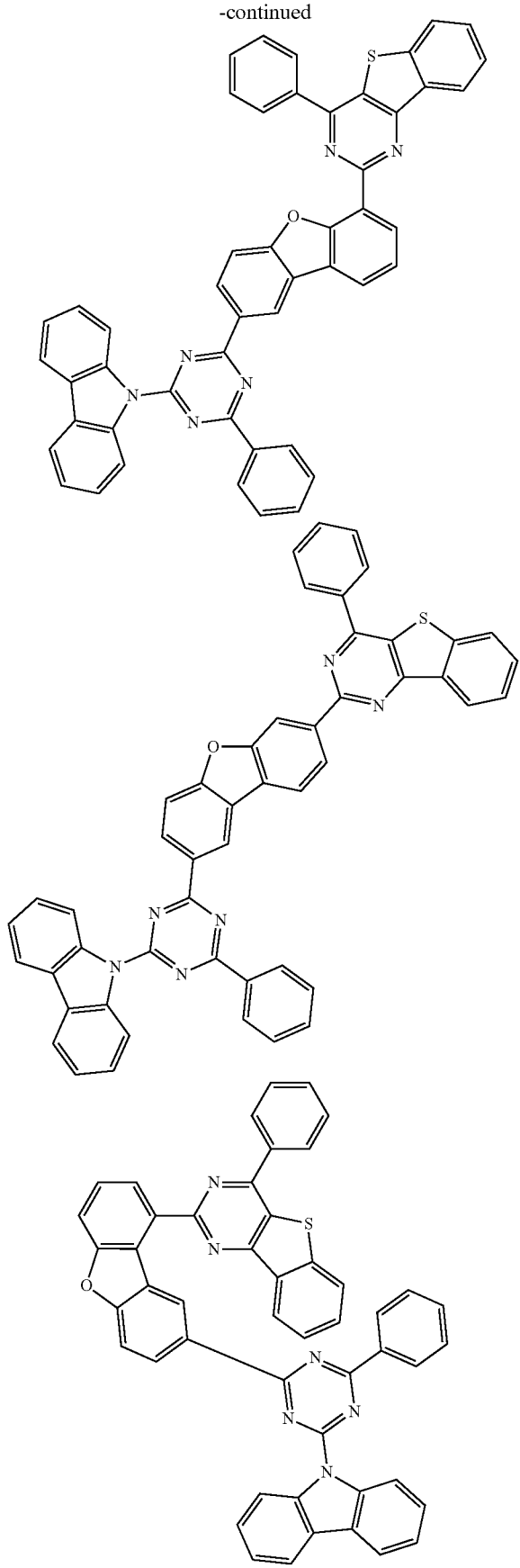
576
-continued
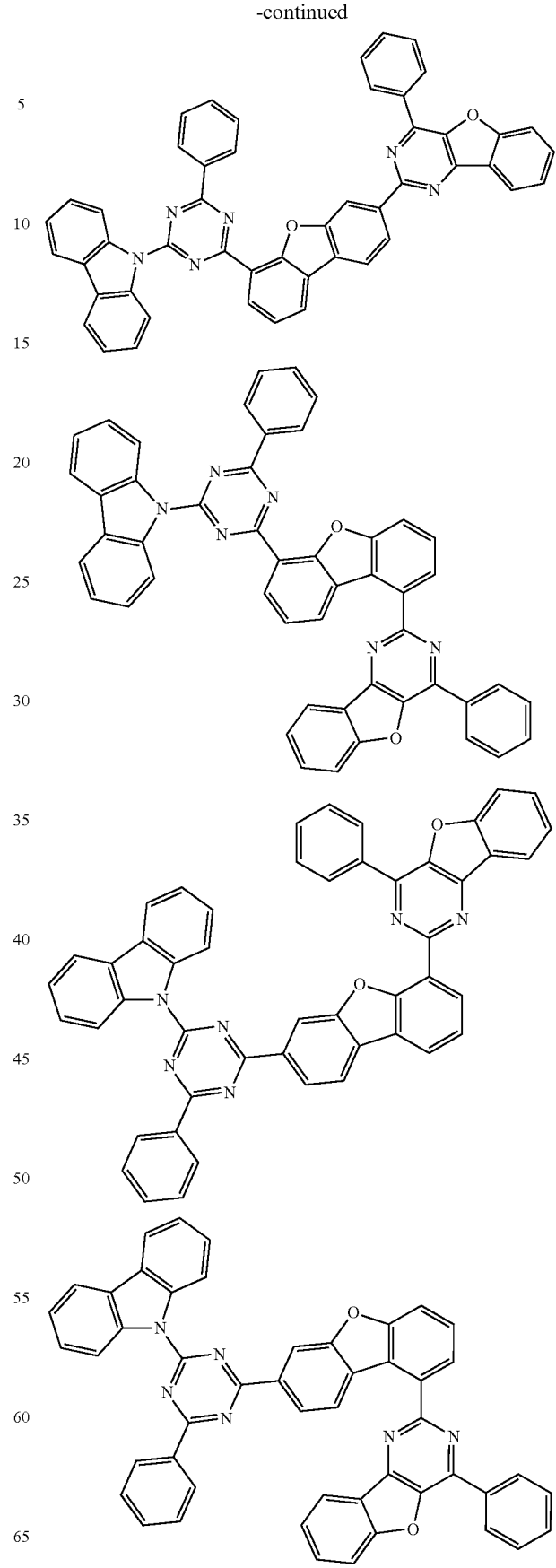

577
-continued
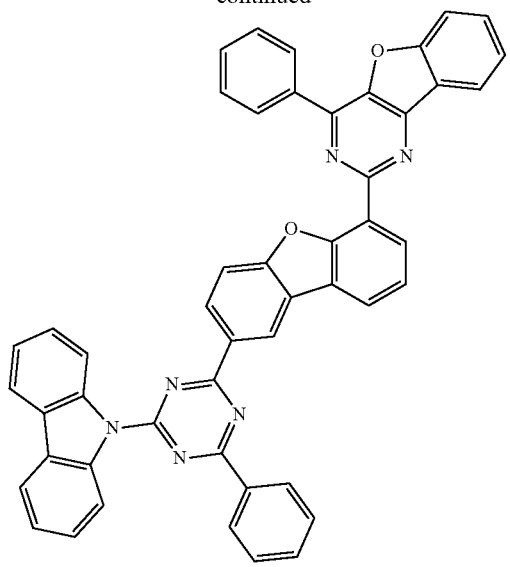
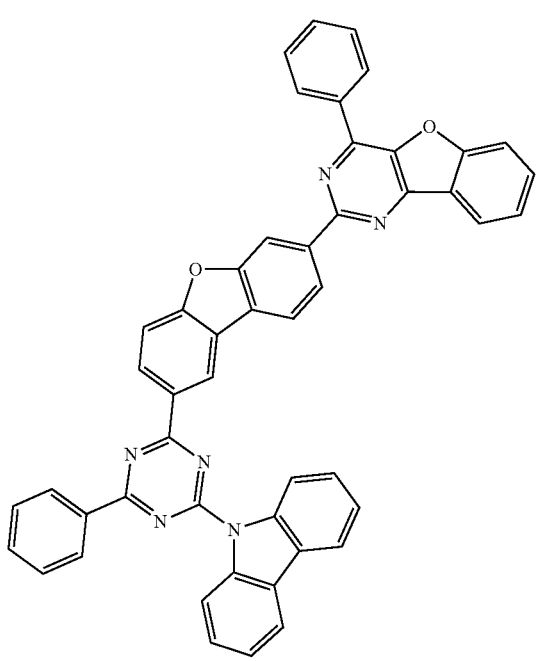
578
-continued
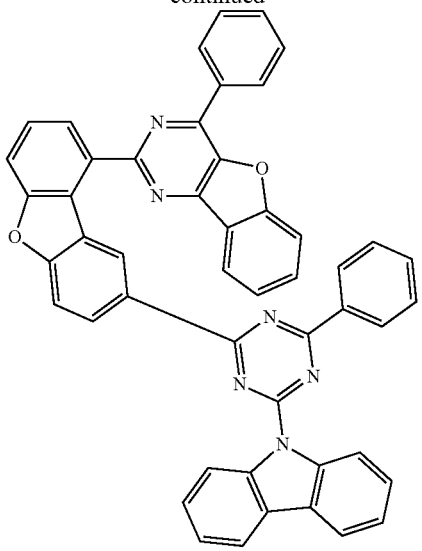
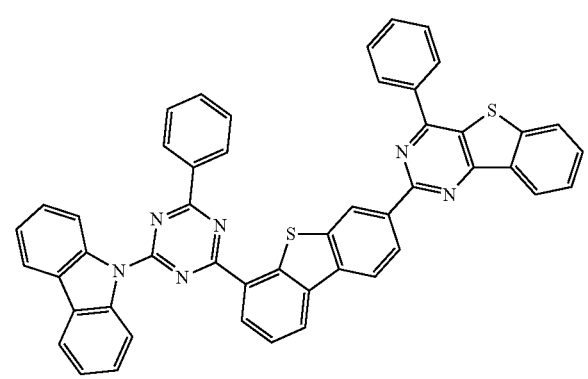

579
-continued
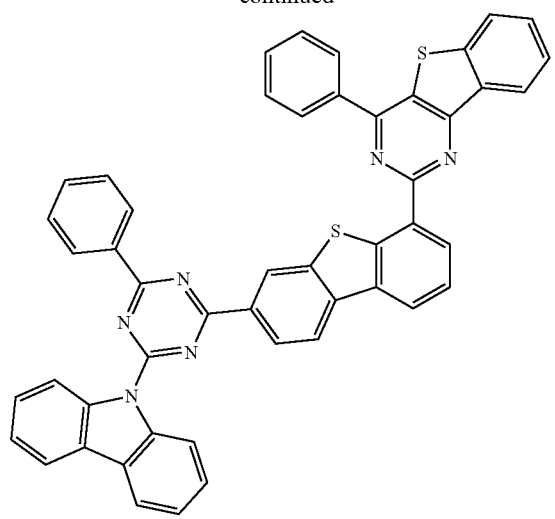
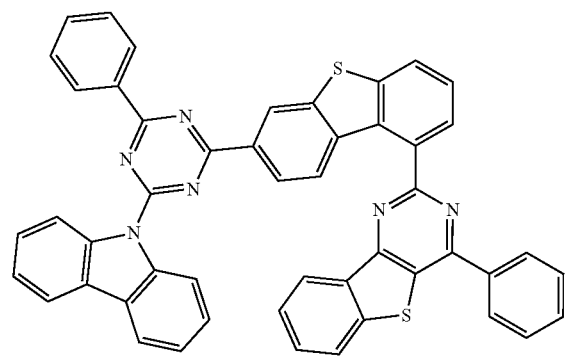
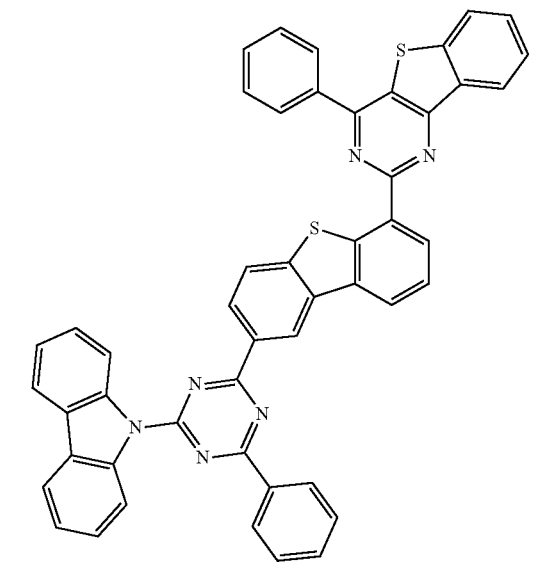
580
-continued
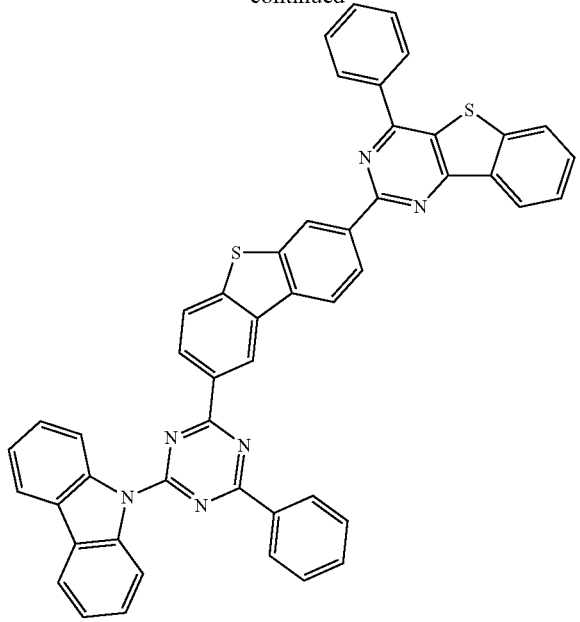
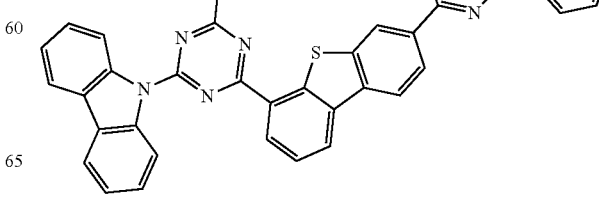

-continued
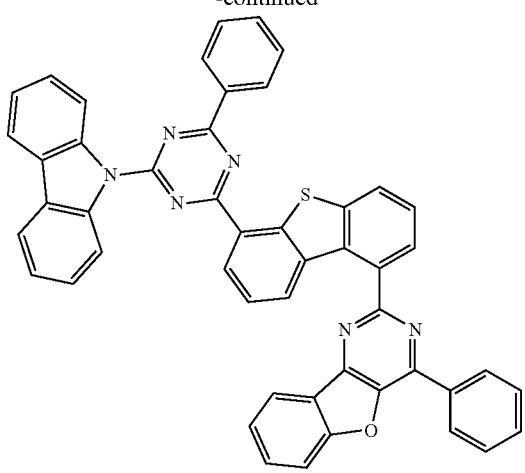
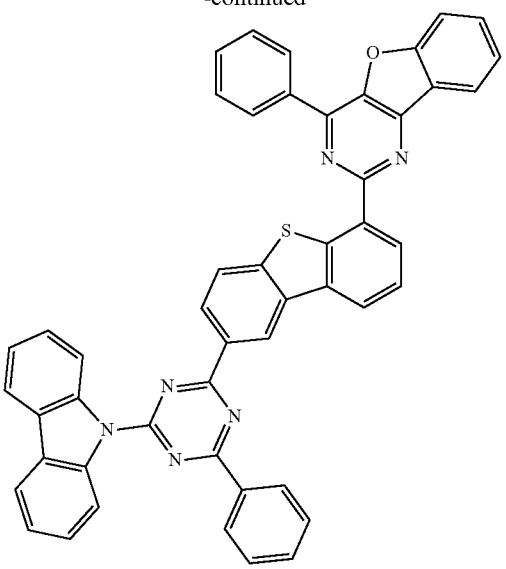
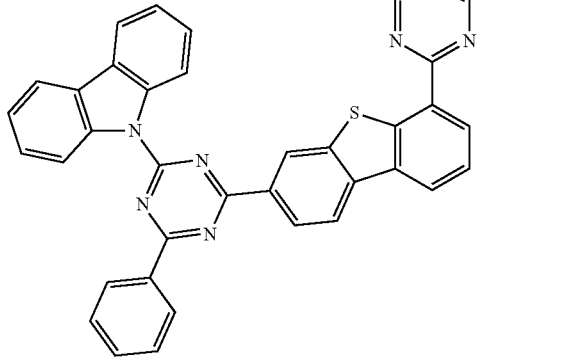
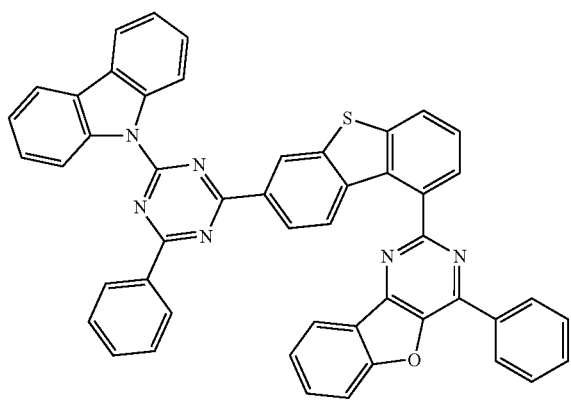
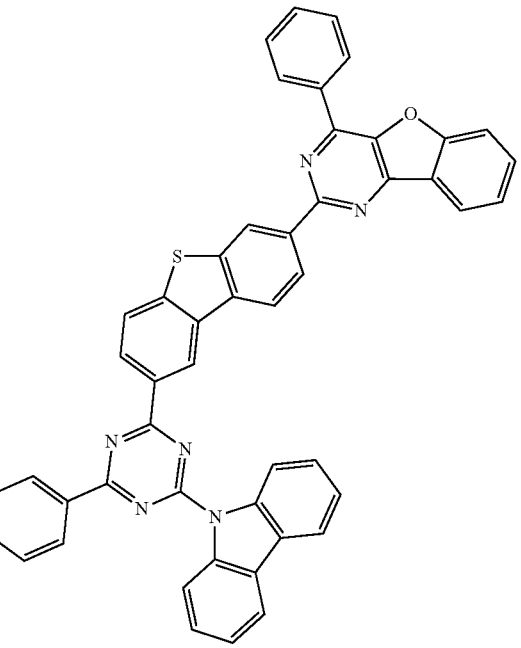

583
-continued
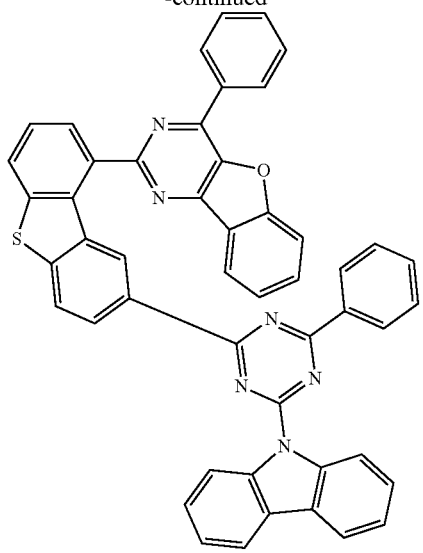
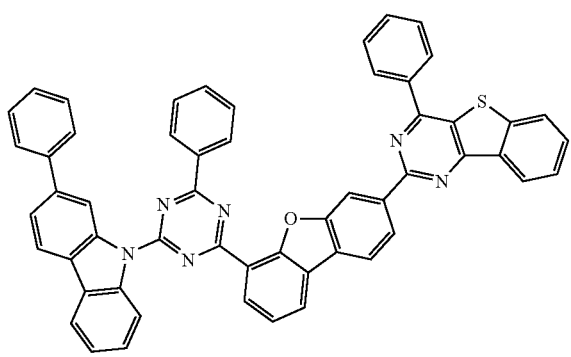
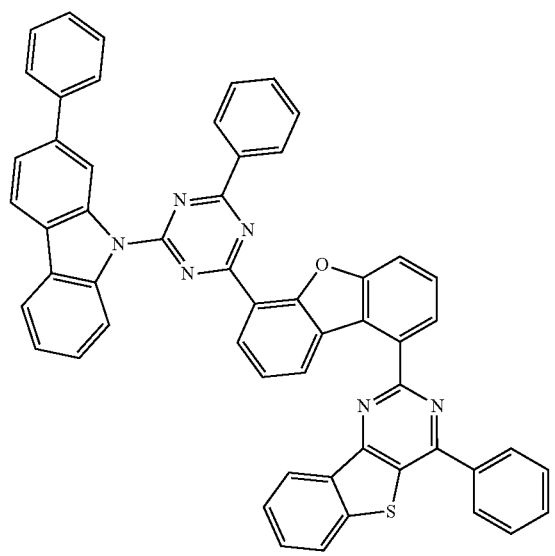
584
-continued
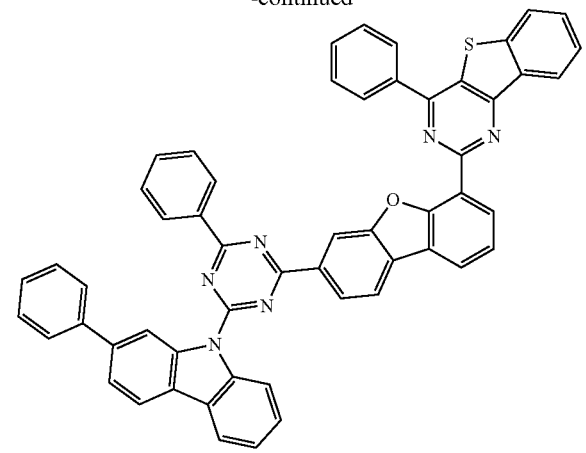
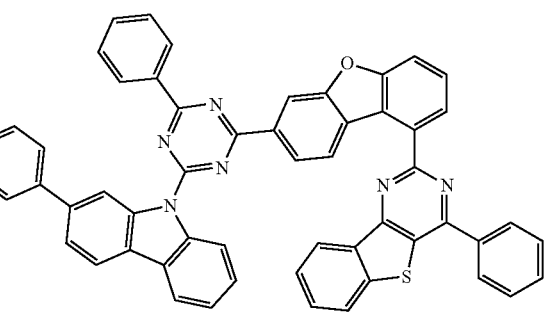
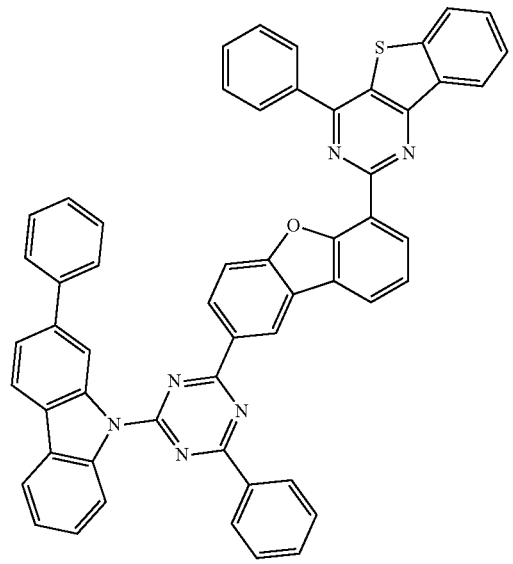

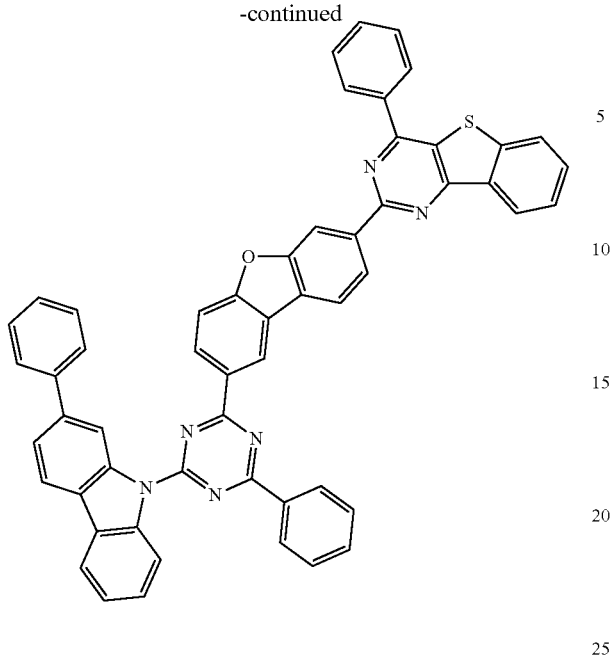
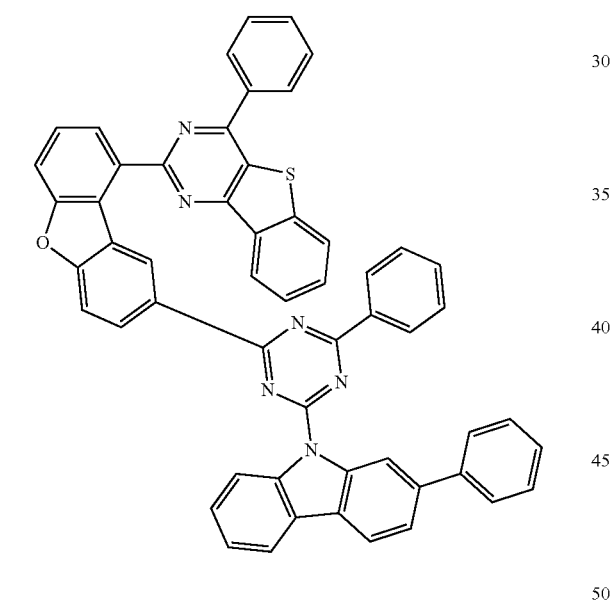
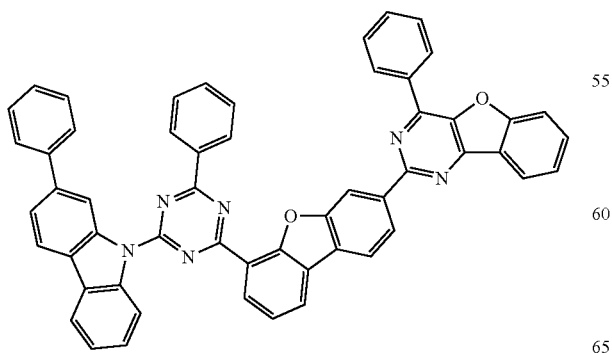

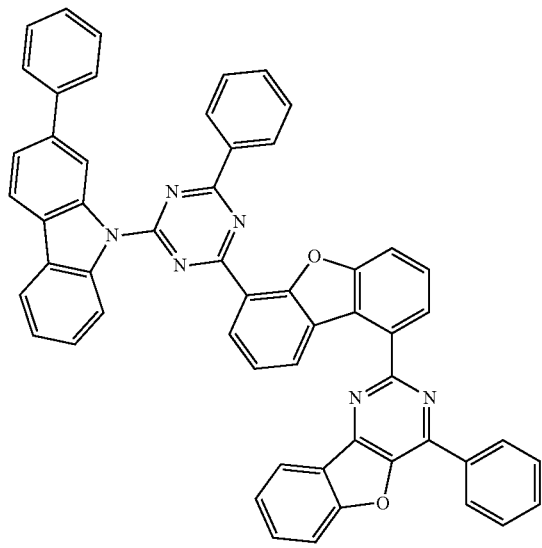
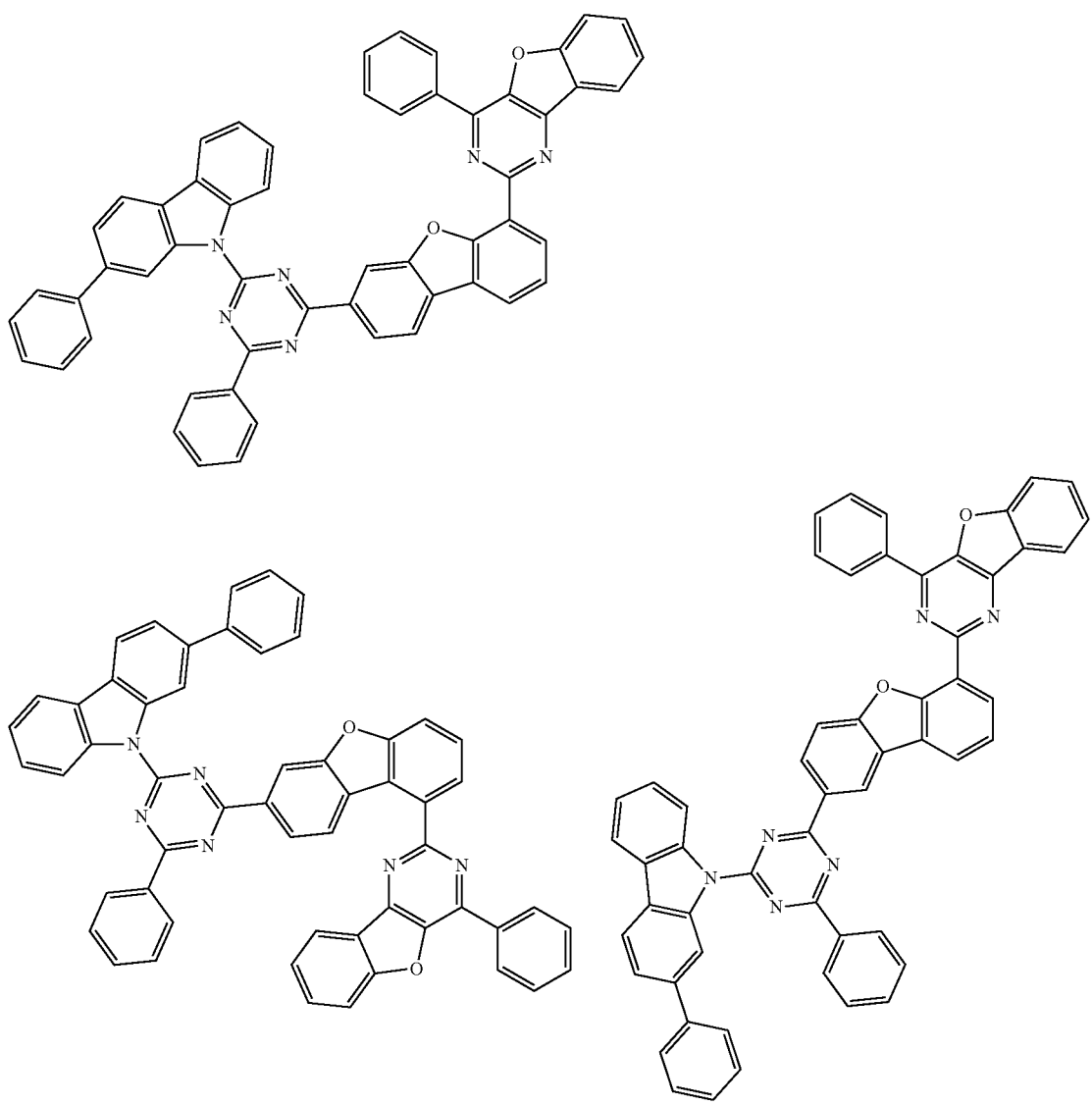

-continued
589 590
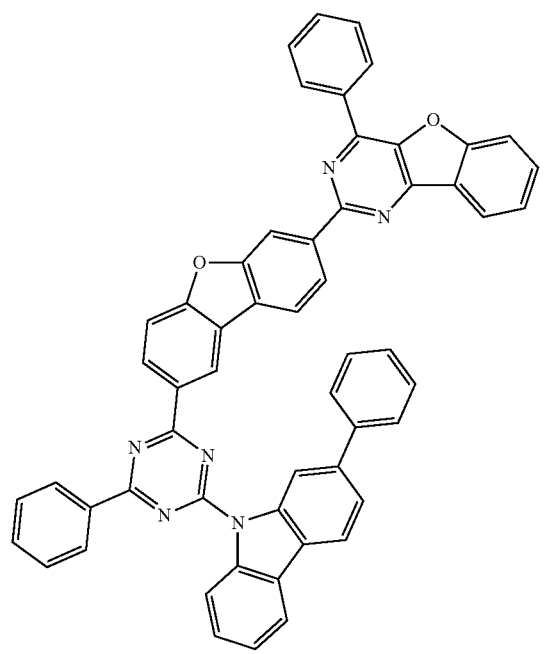
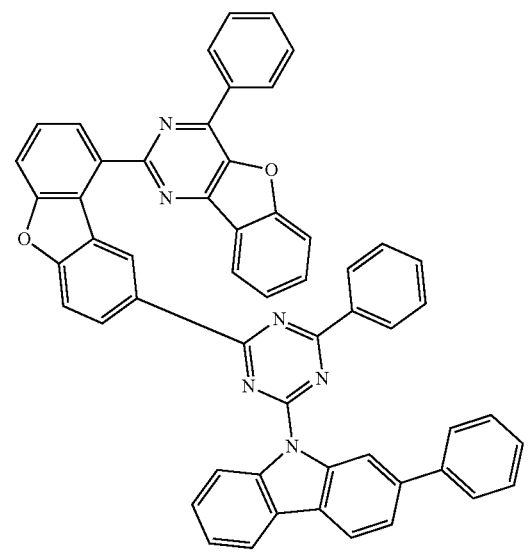
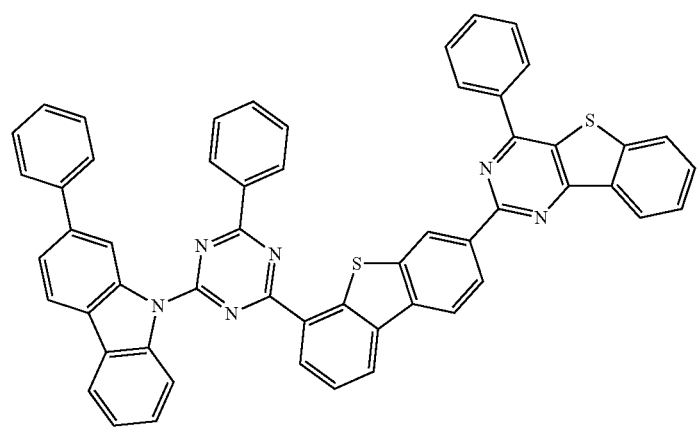
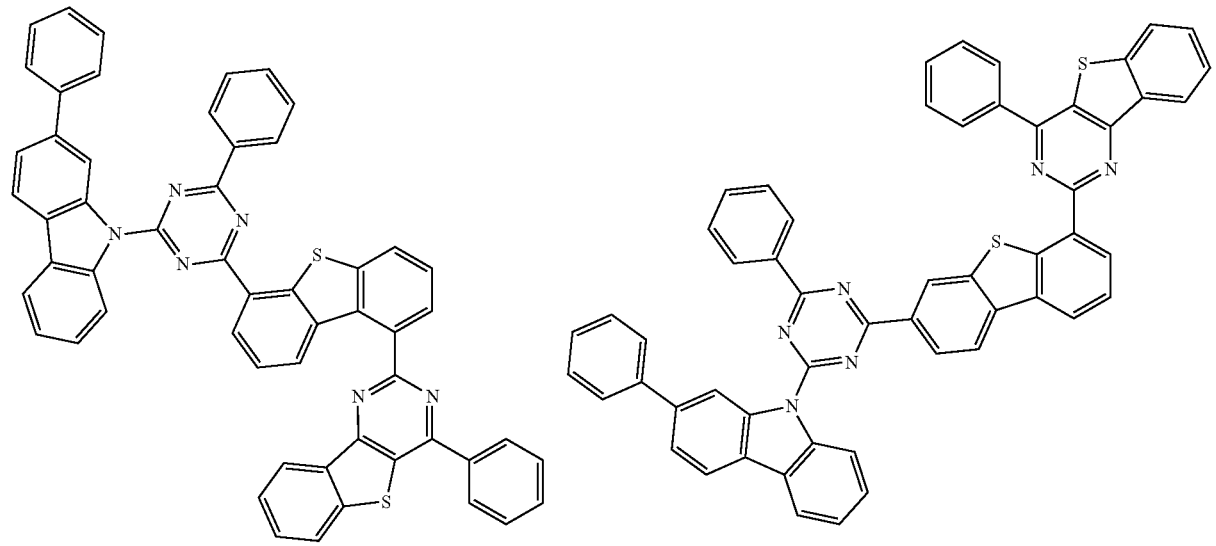

591 592
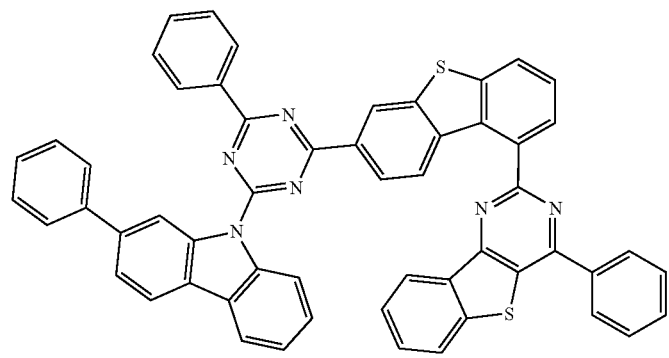
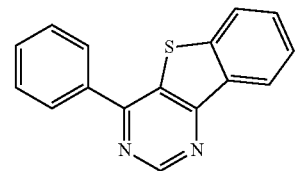
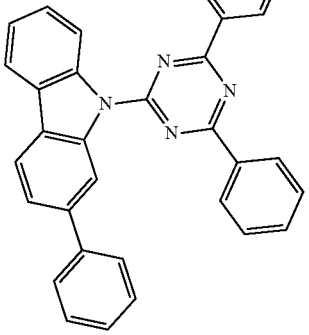
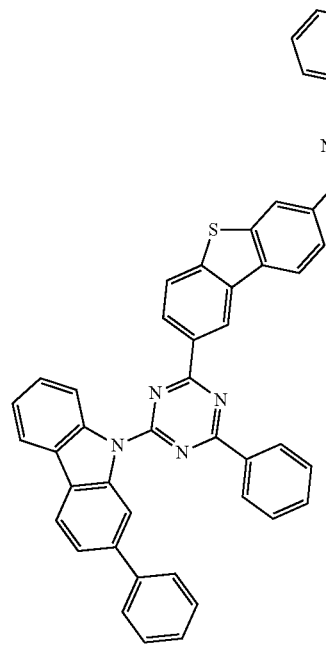
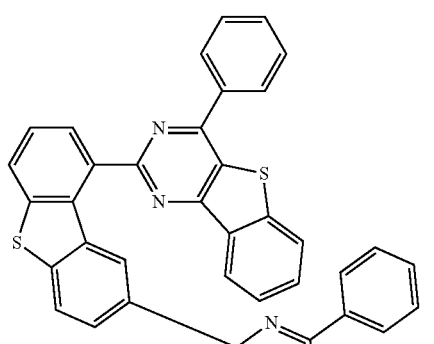
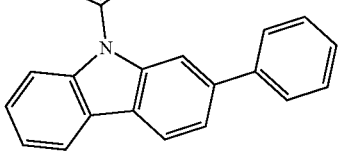
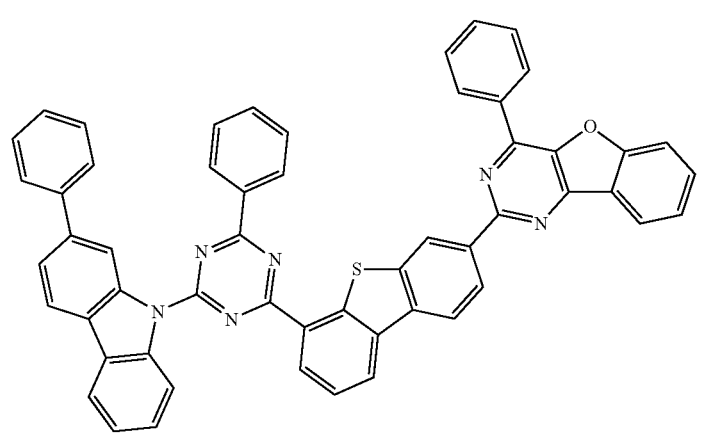

-continued
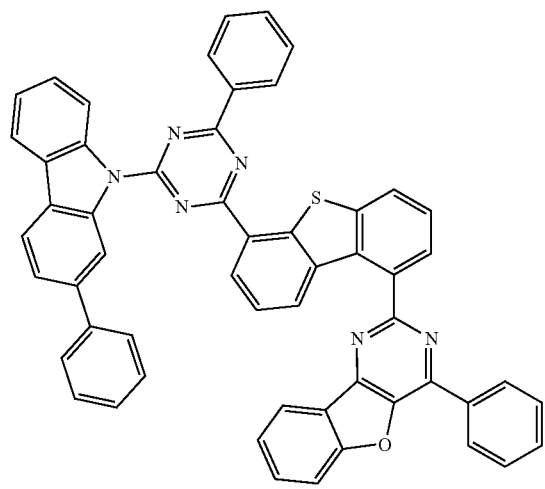
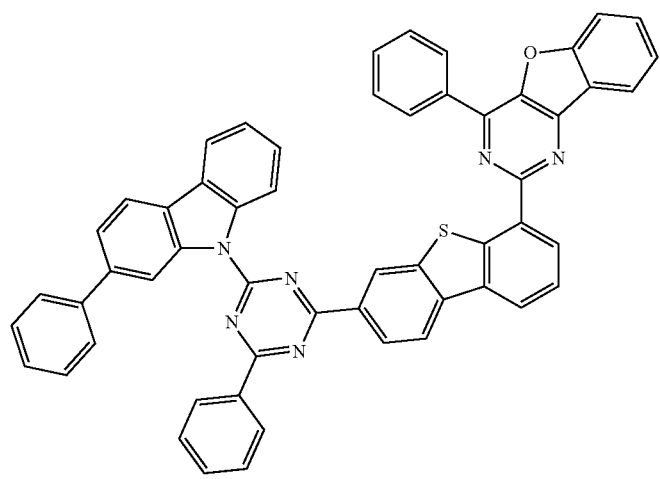
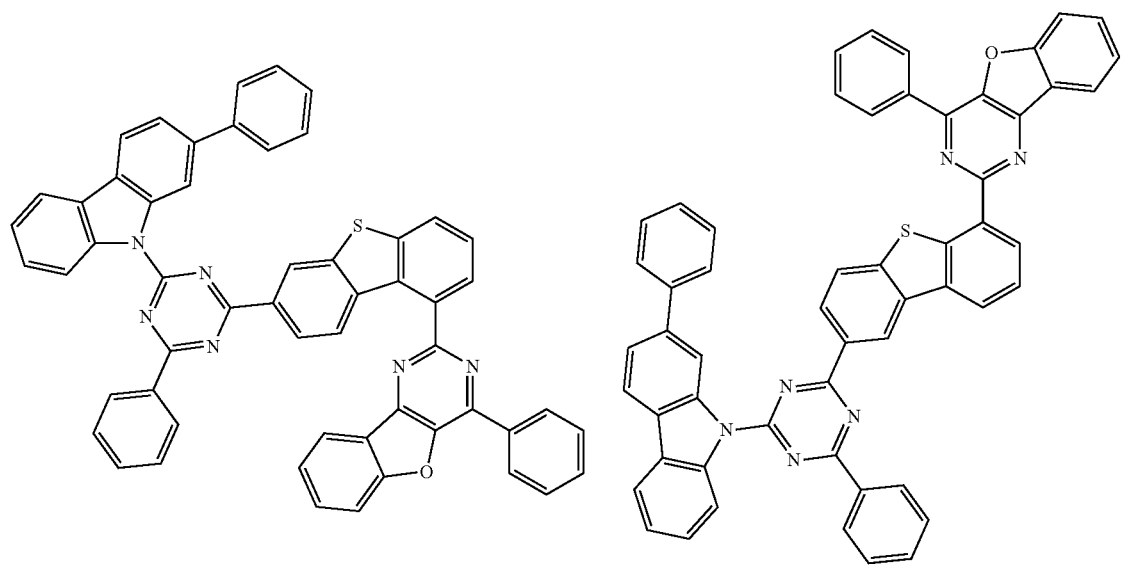

-continued
595
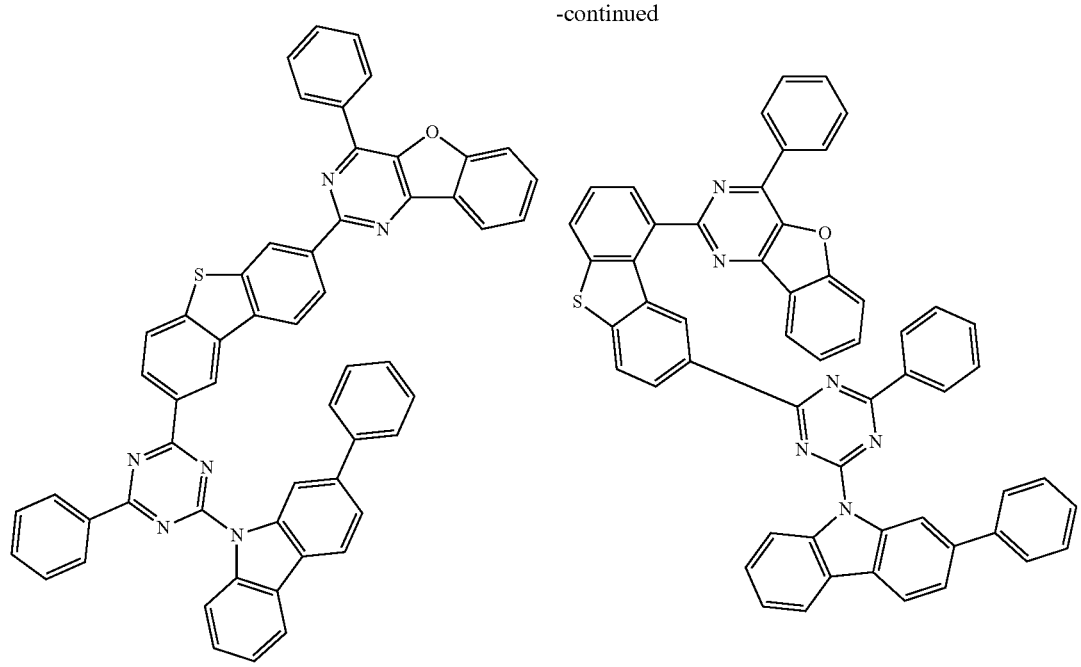
596
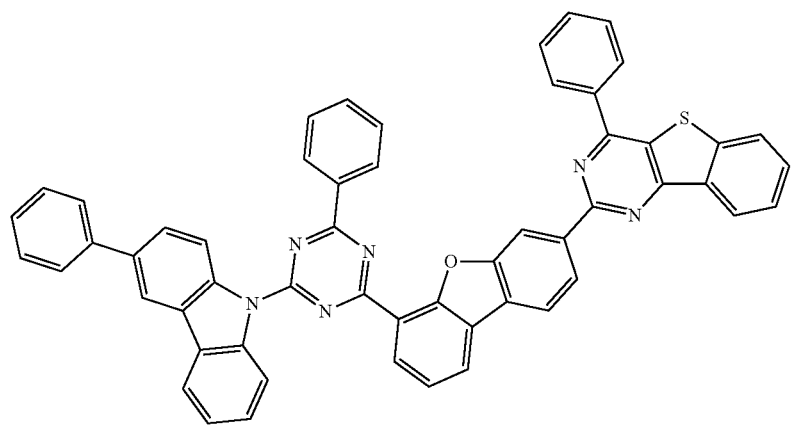
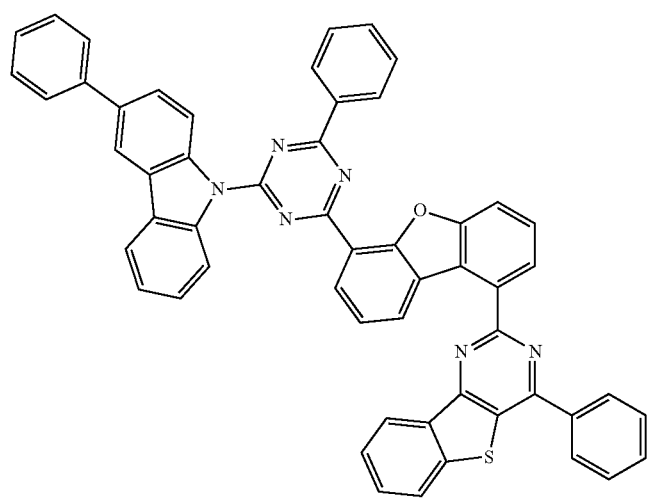

-continued
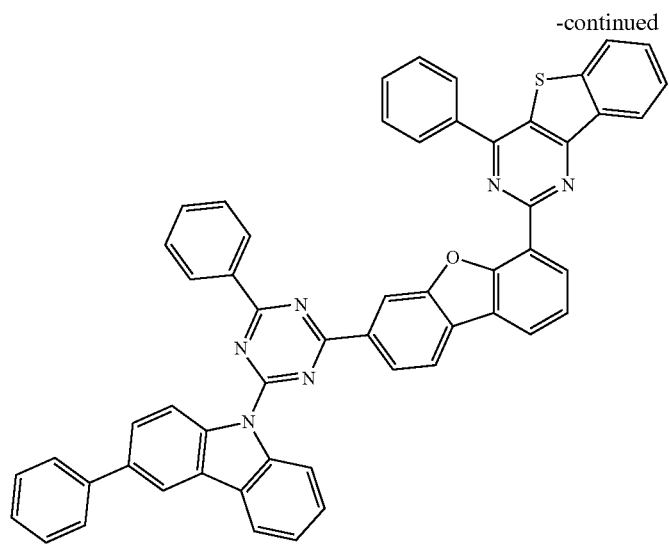
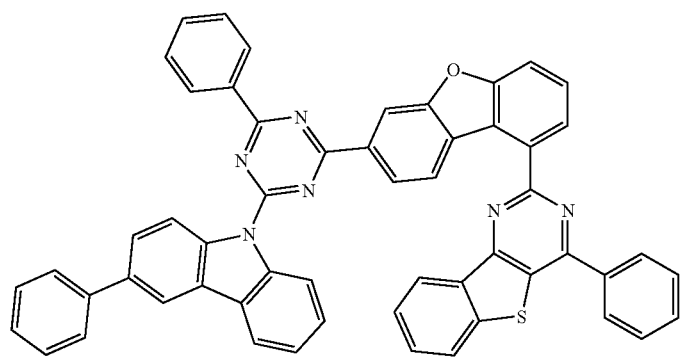
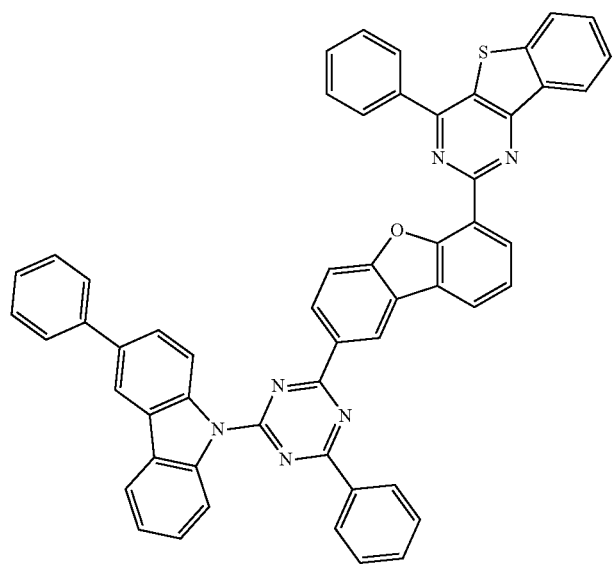

599
600
-continued
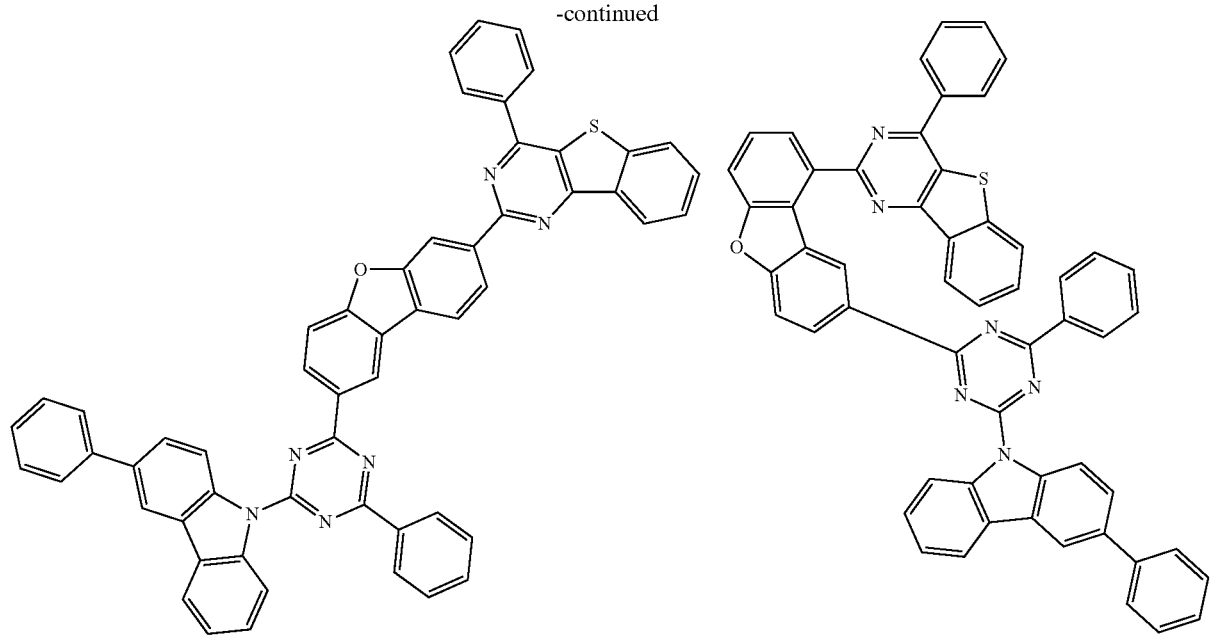
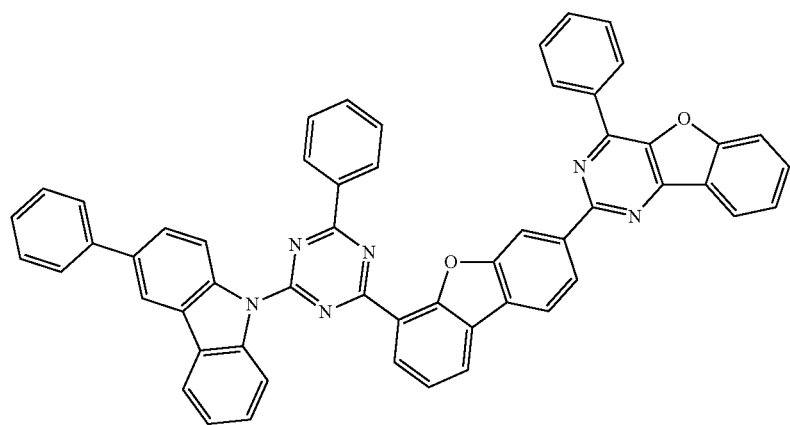
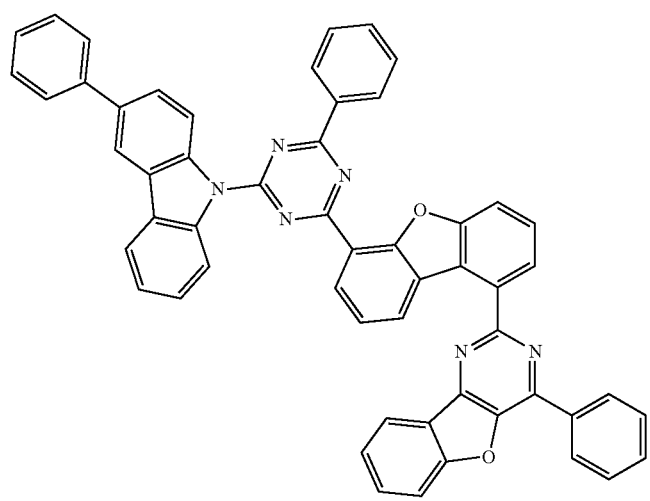

-continued
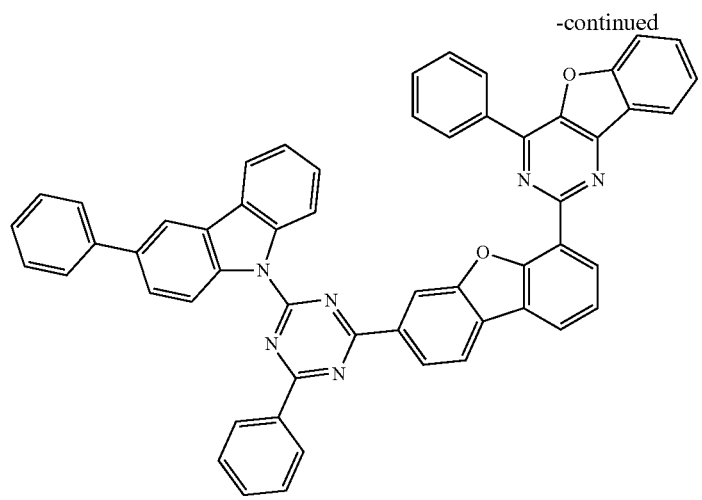
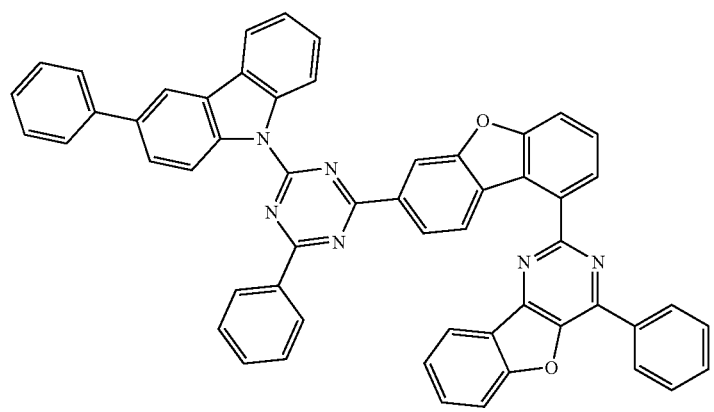
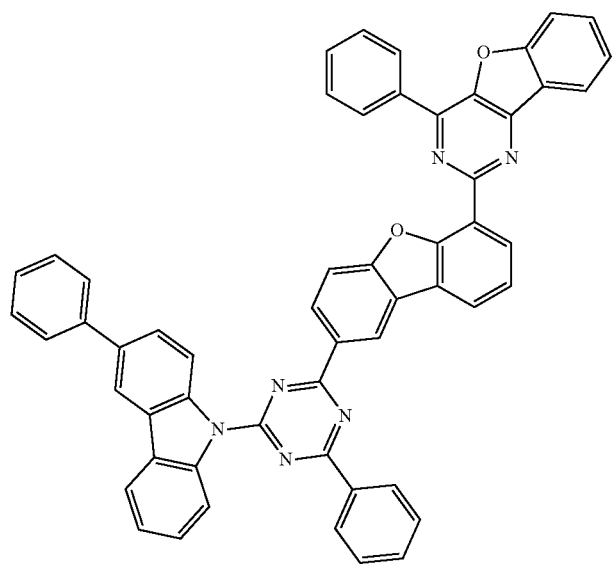

603 604
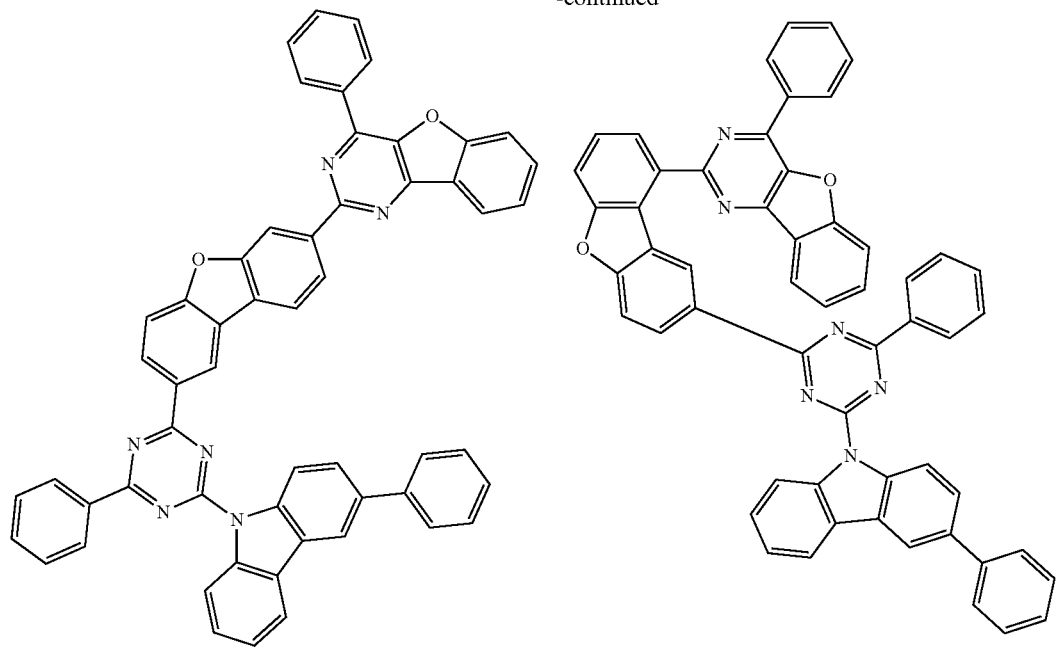
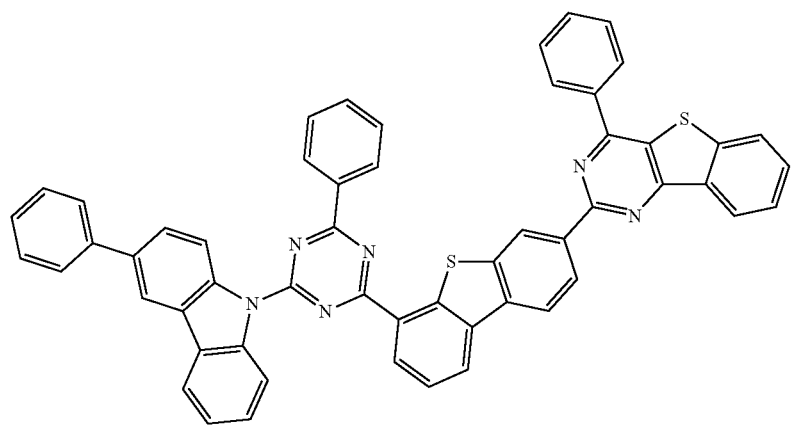
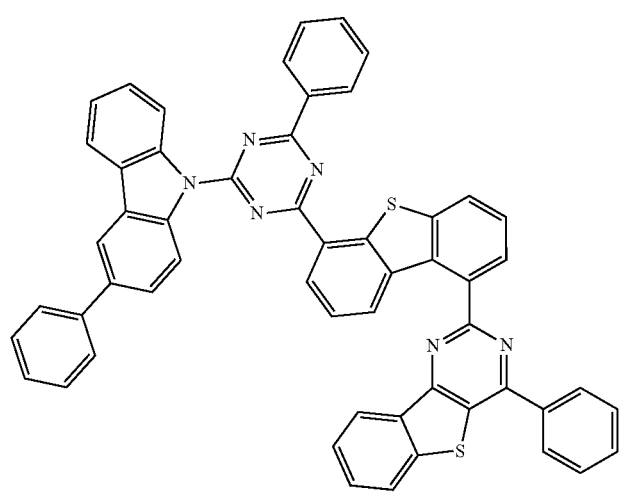

-continued
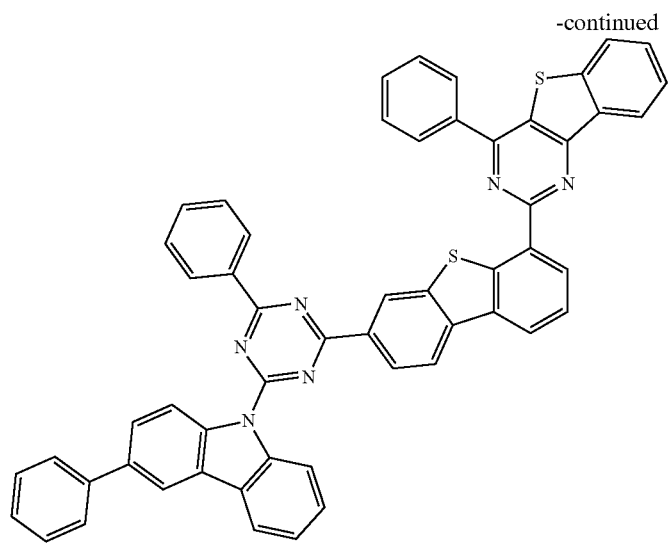
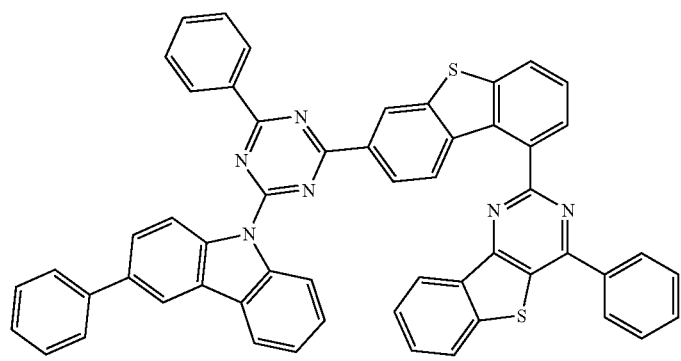
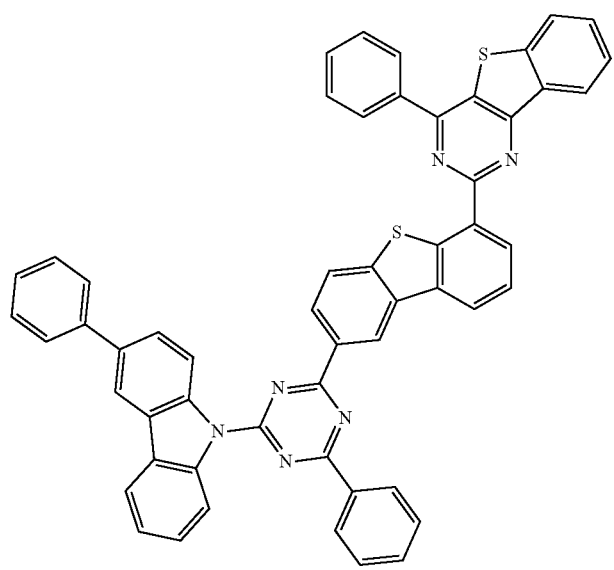

-continued
607 608
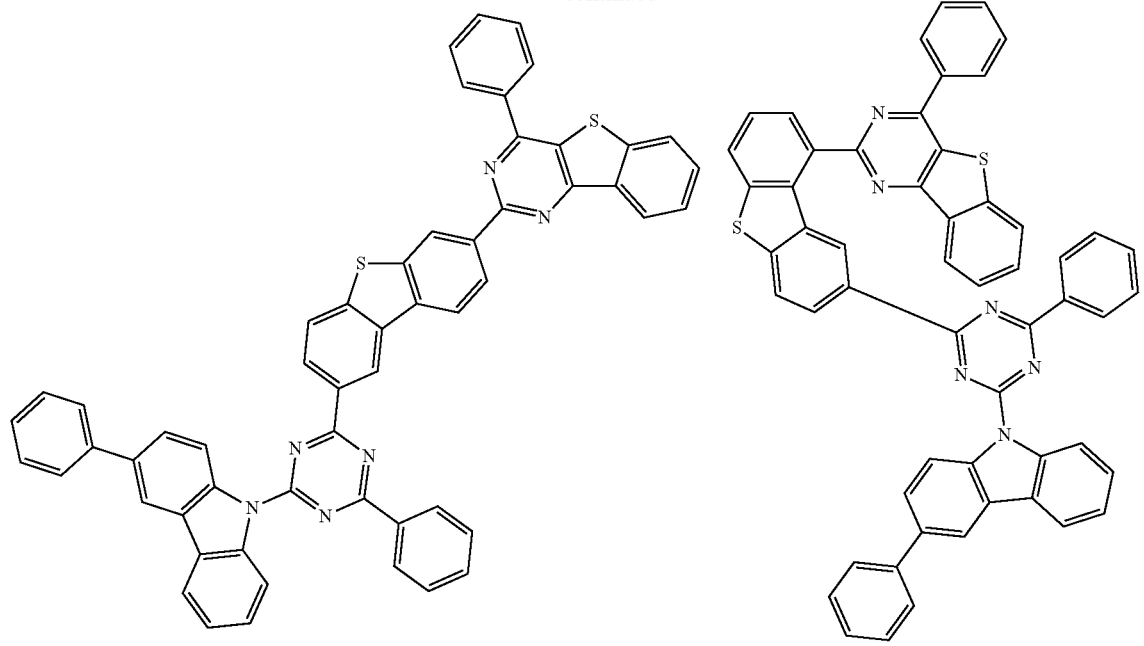
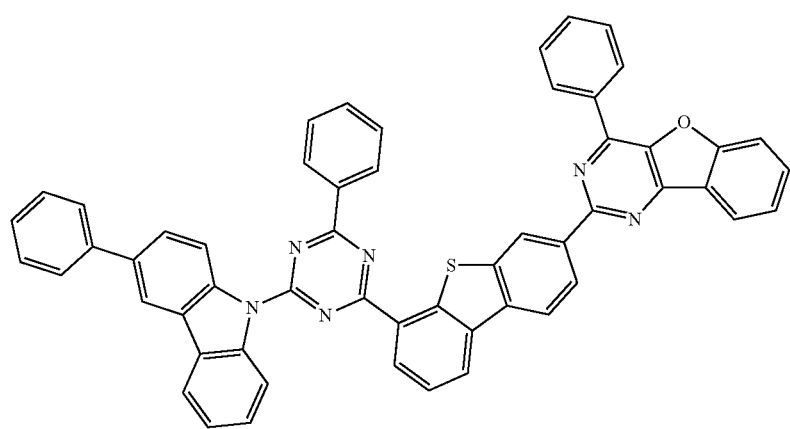
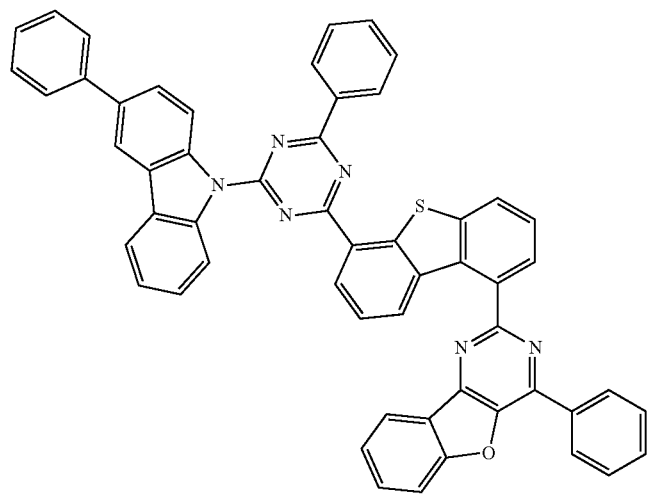

-continued
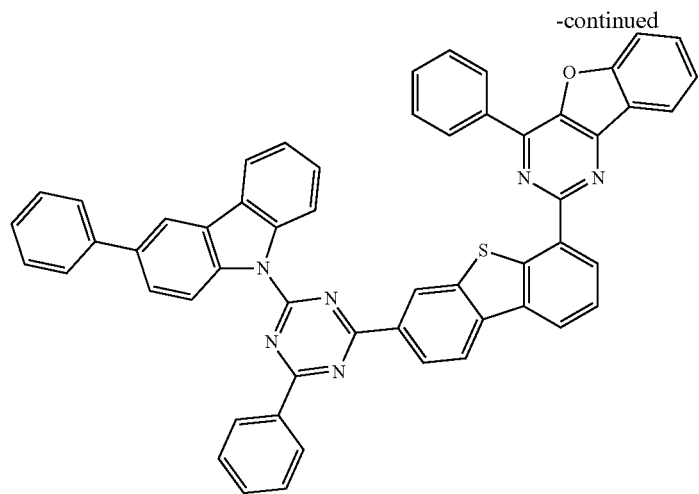
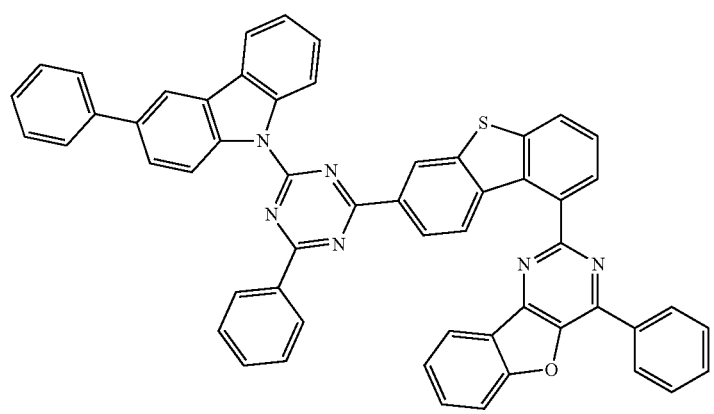
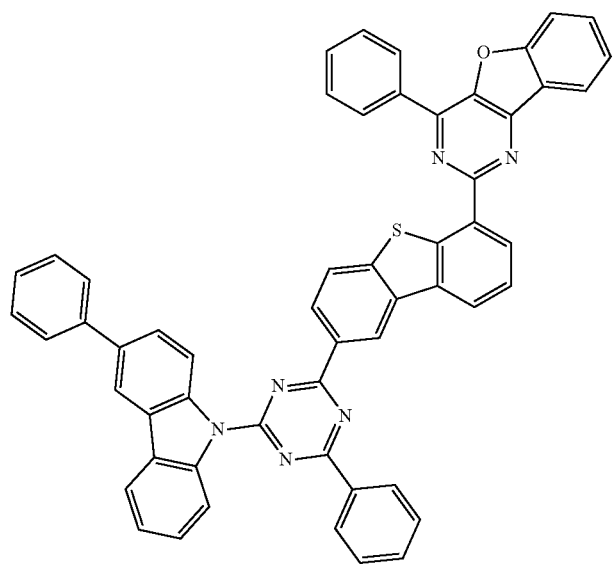

-continued
611 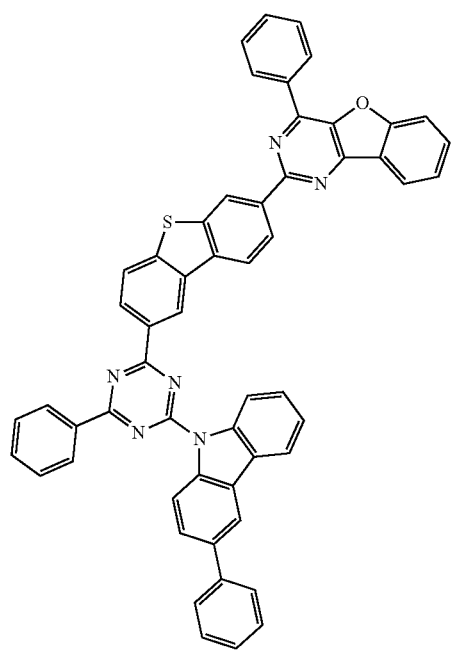
612 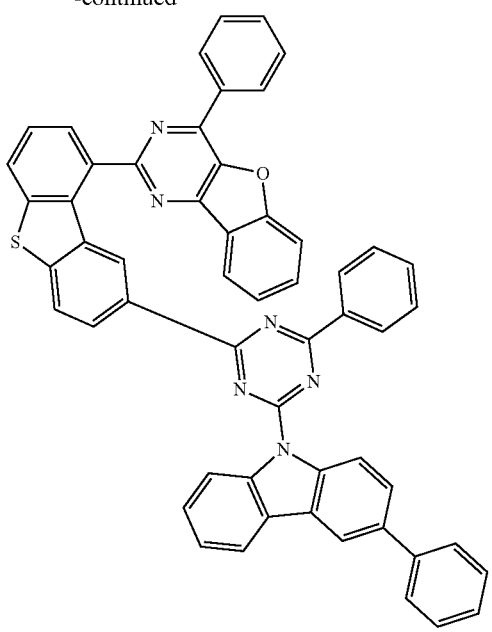
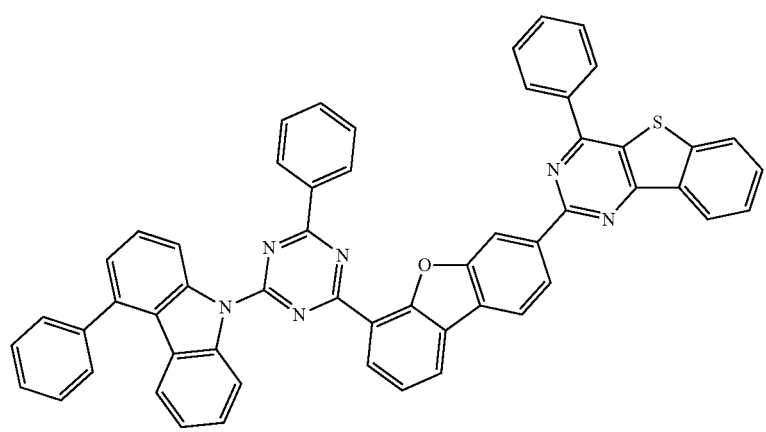
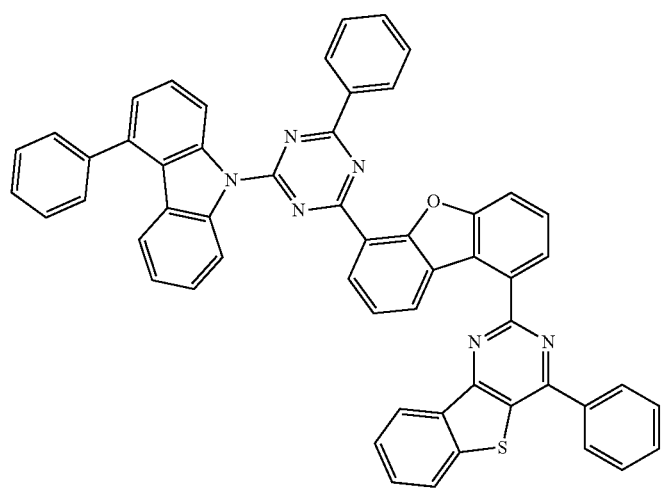

-continued
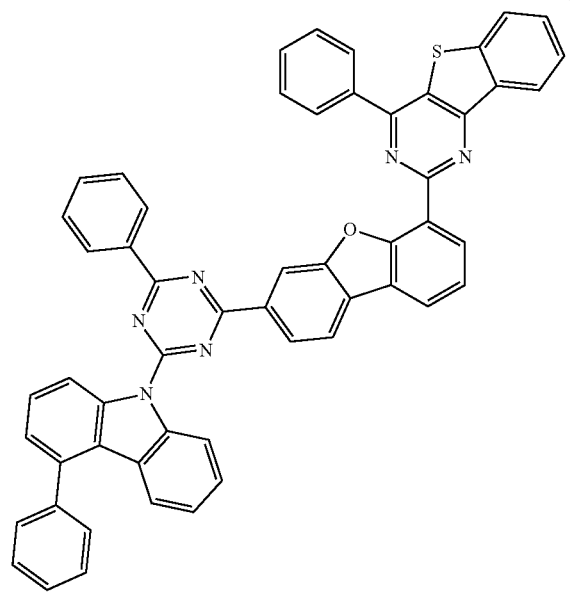
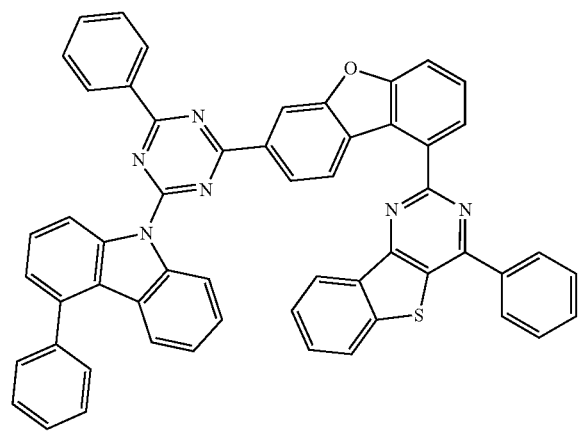
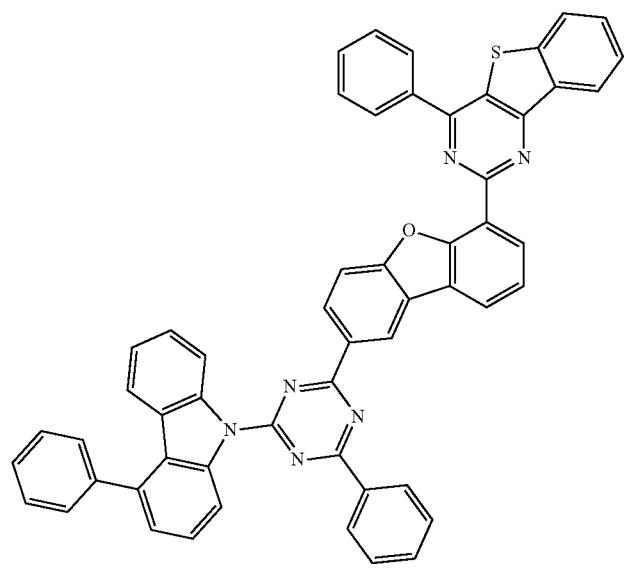

615 616
-continued
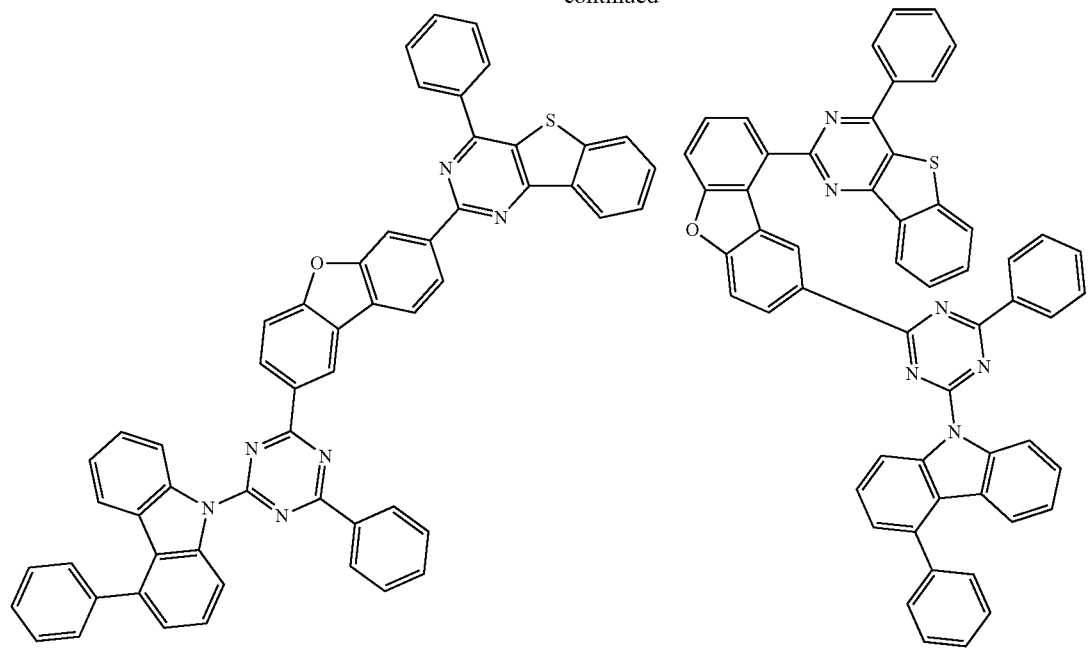
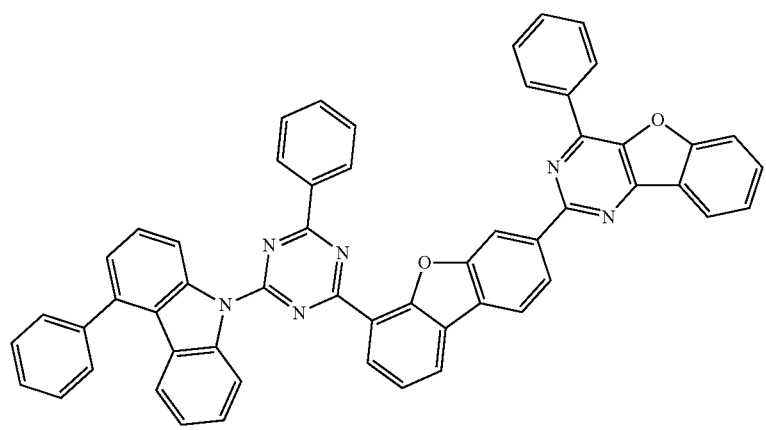
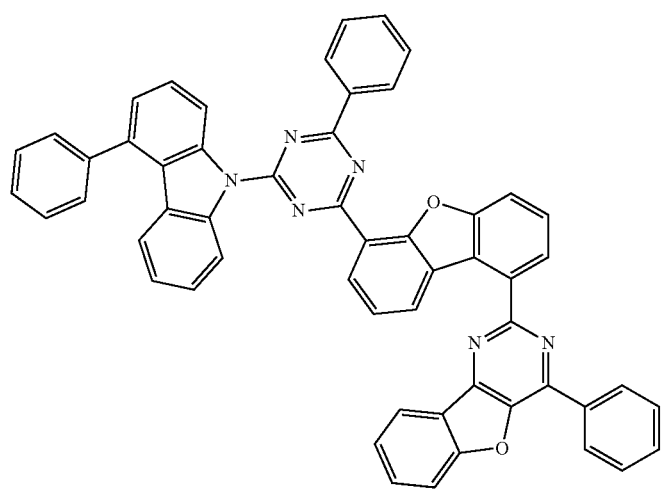

-continued
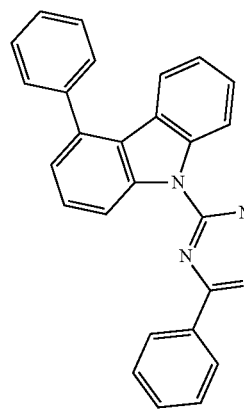
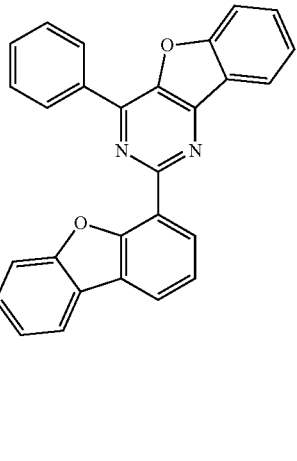
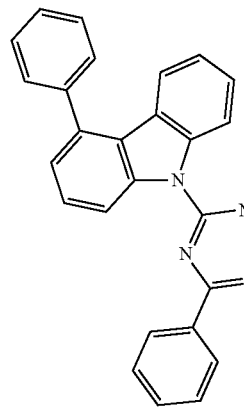
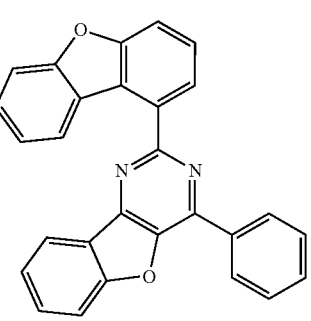
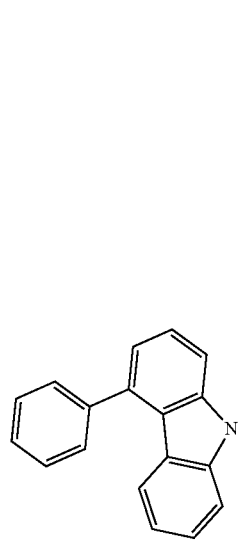
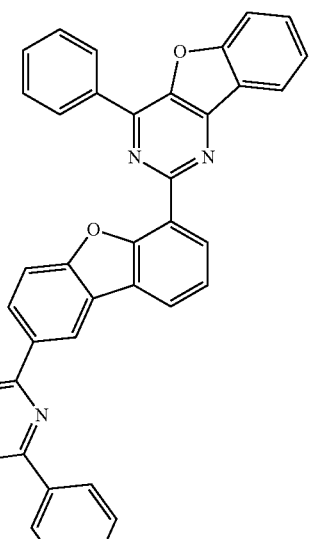

619 620
-continued
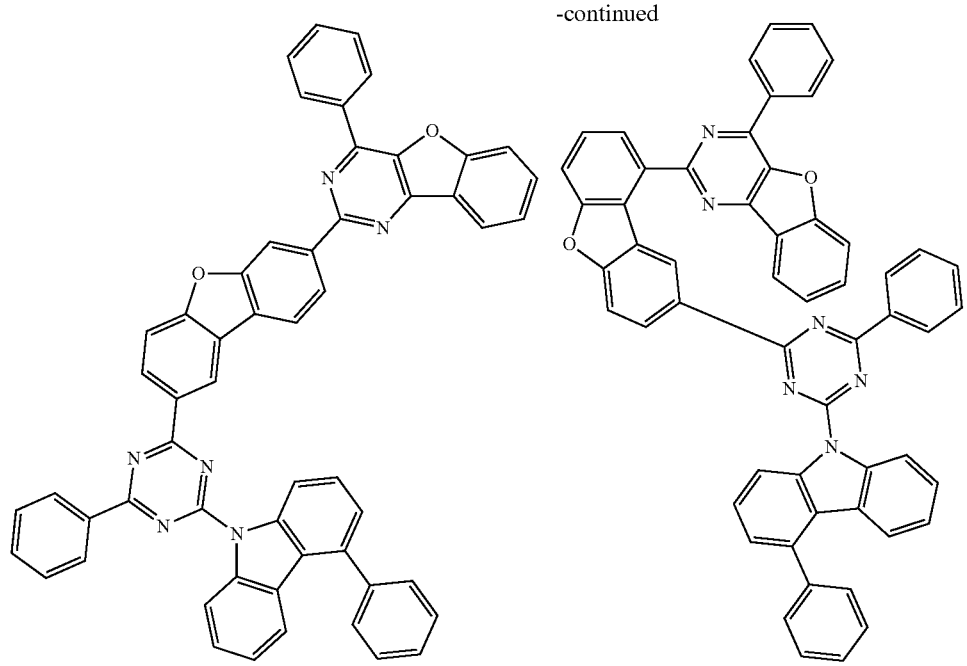
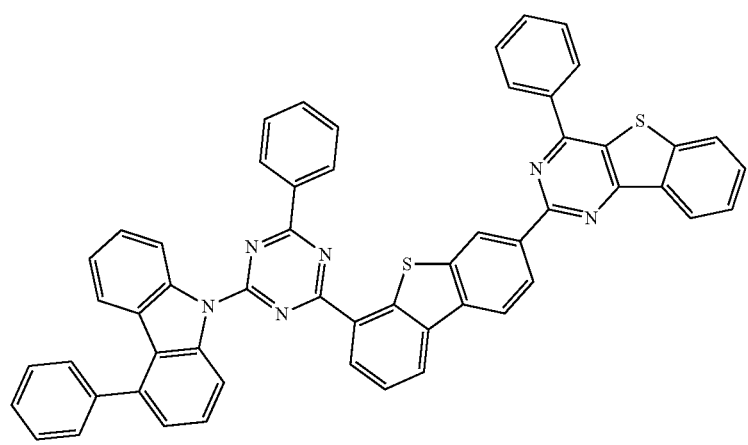
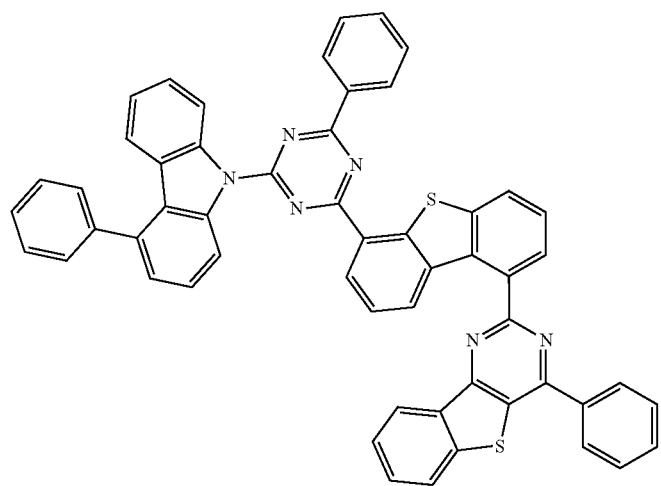

-continued
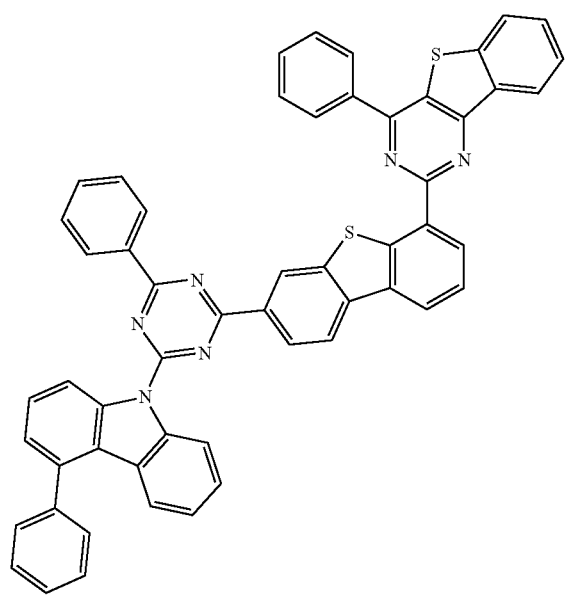
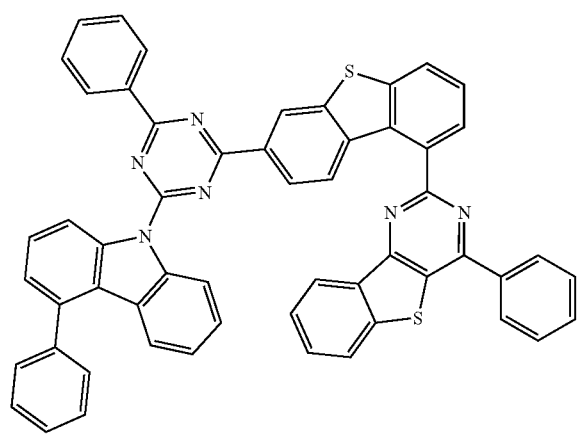
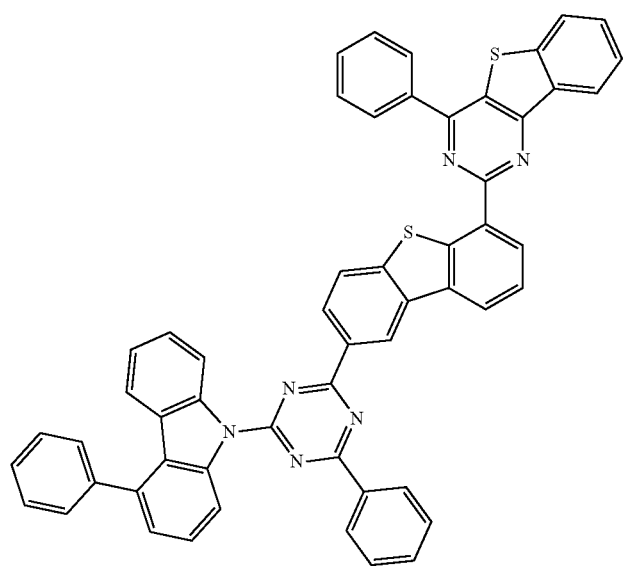

623 624
-continued
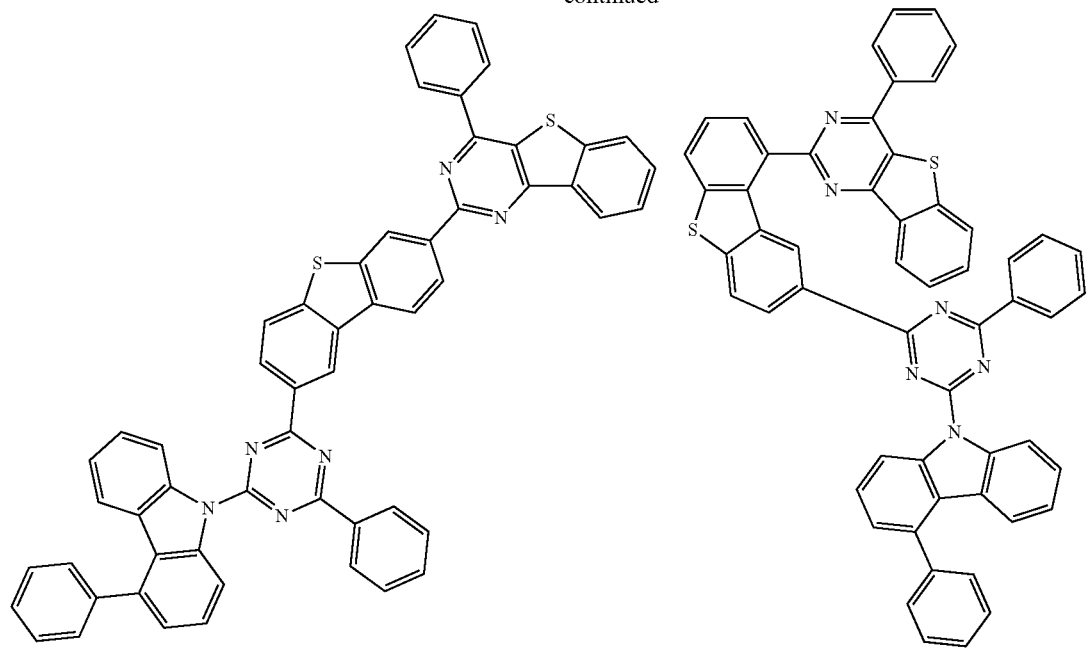
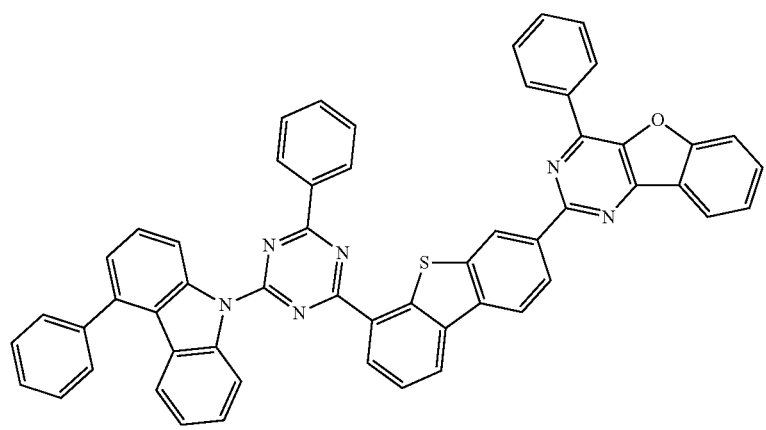
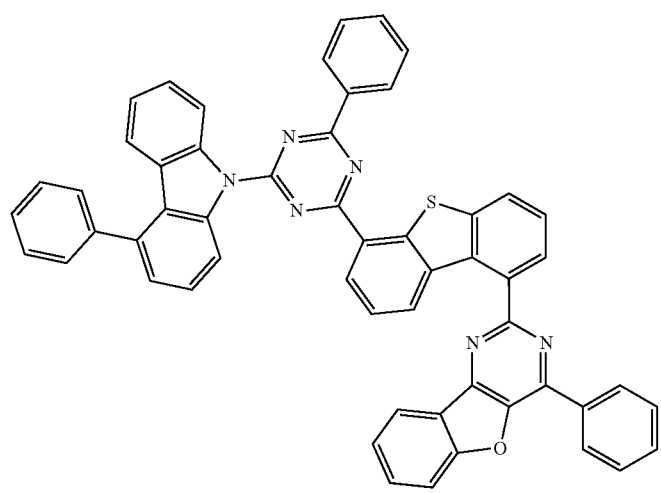

-continued
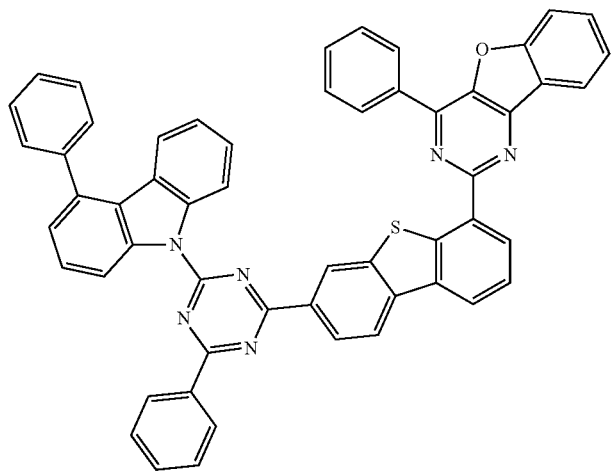
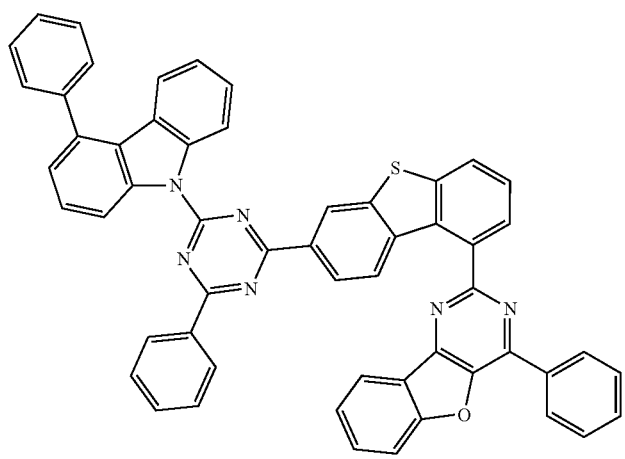
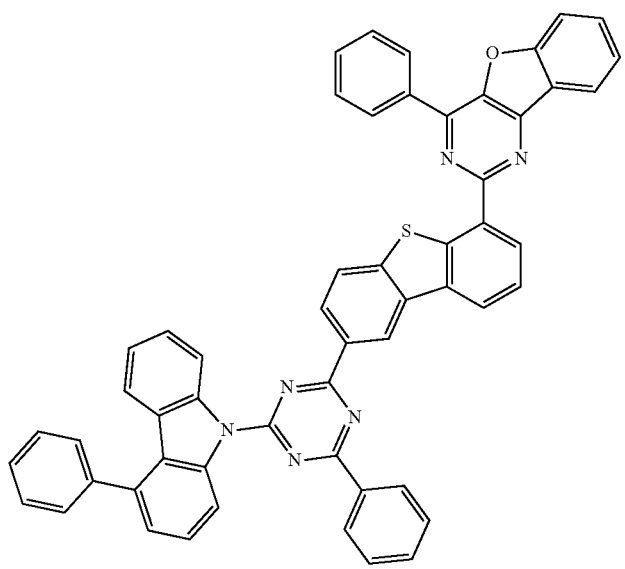

-continued
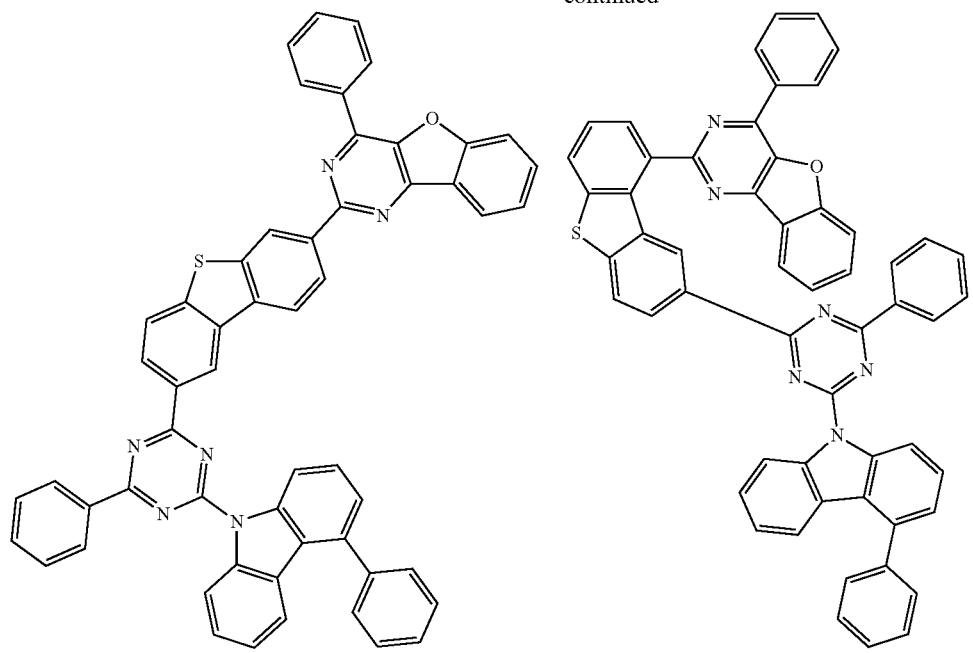
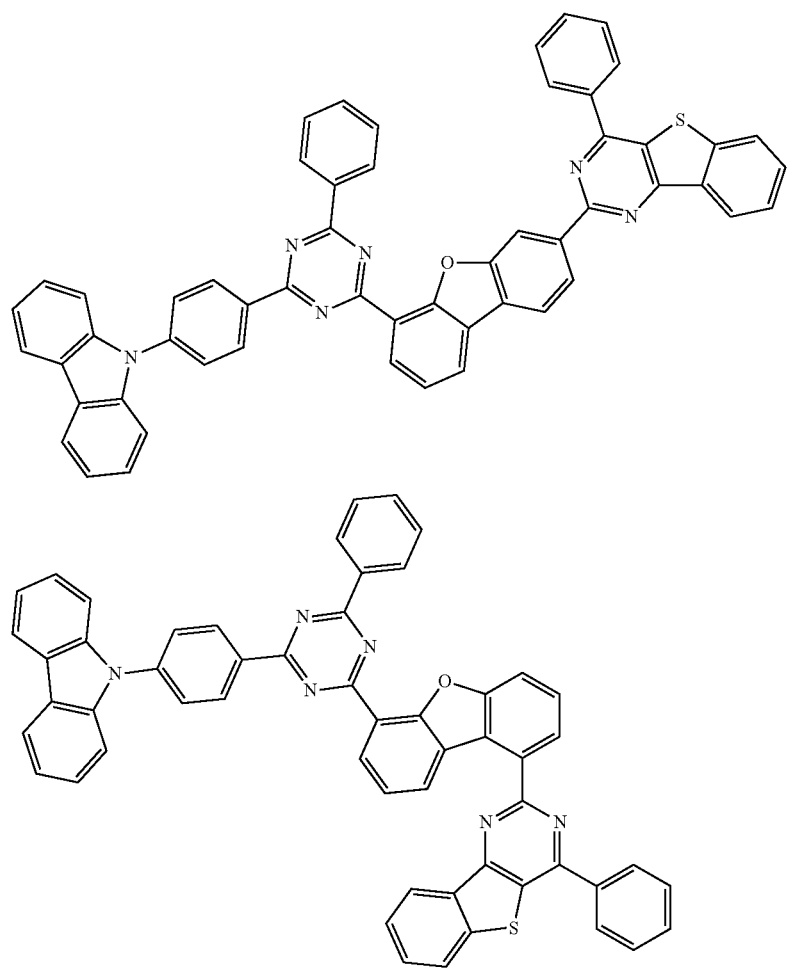

-continued
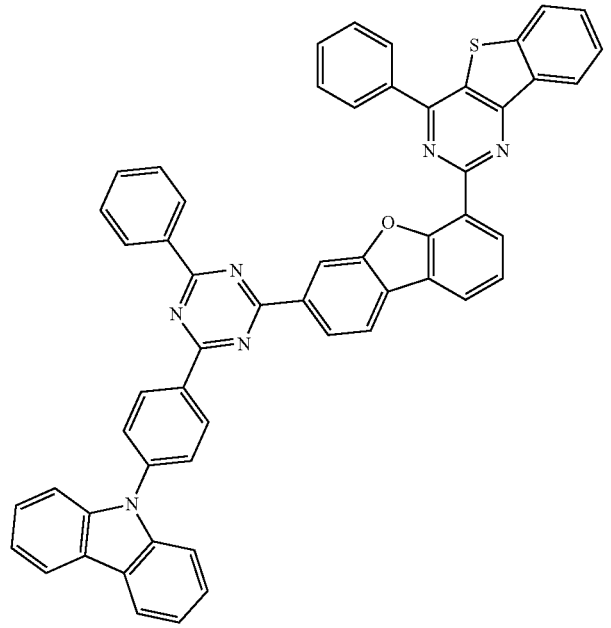
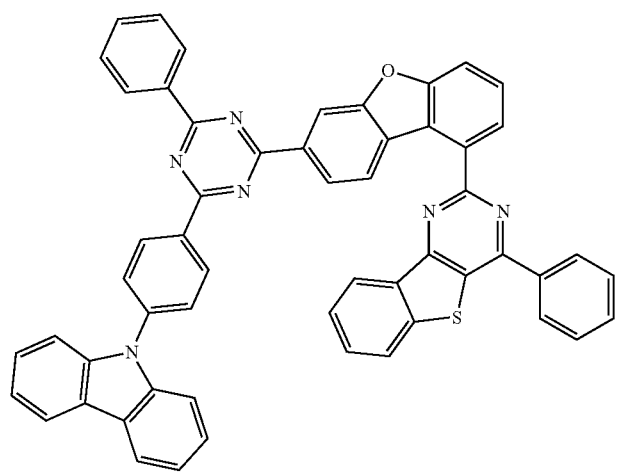
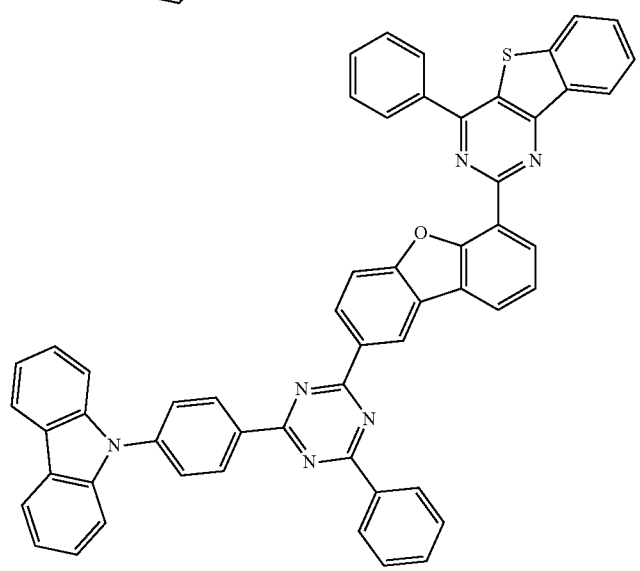

-continued
631
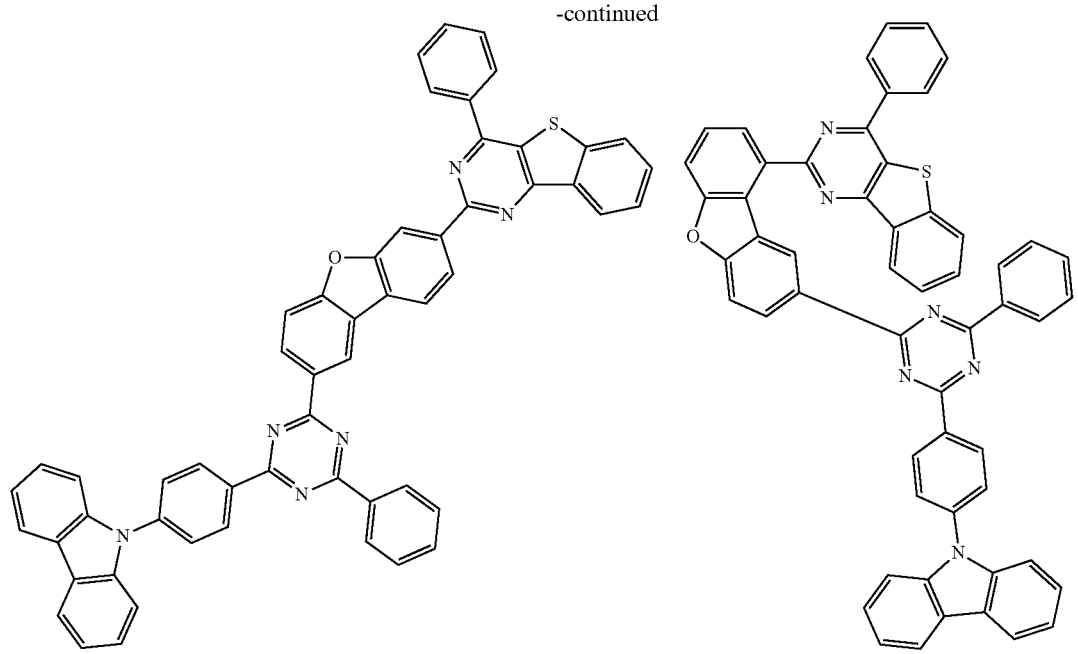
632
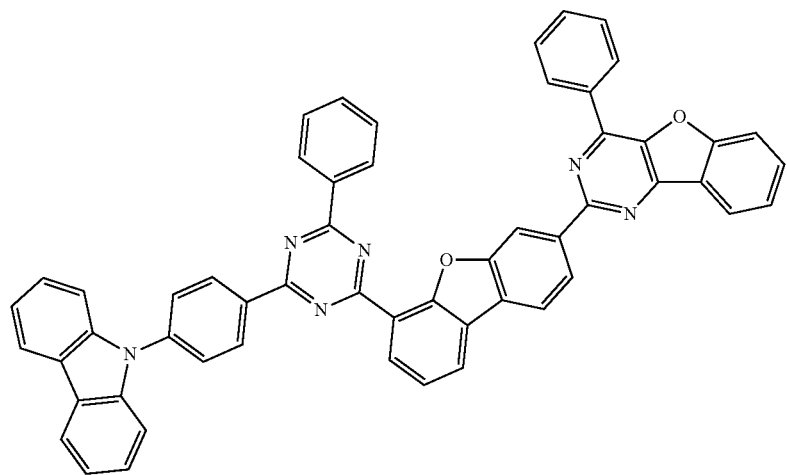
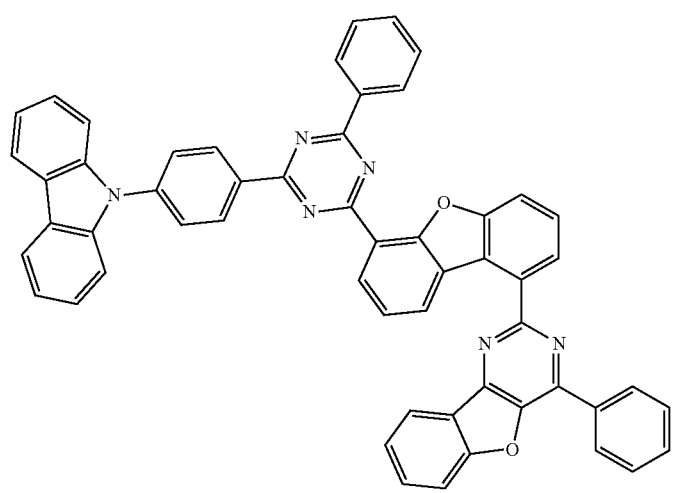

633
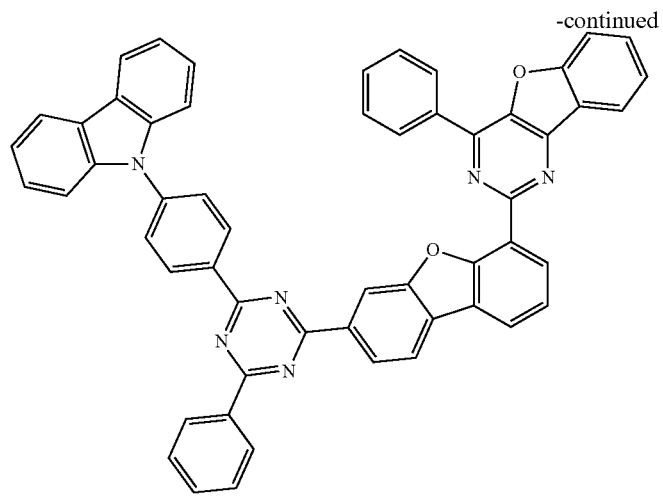
634
-continued
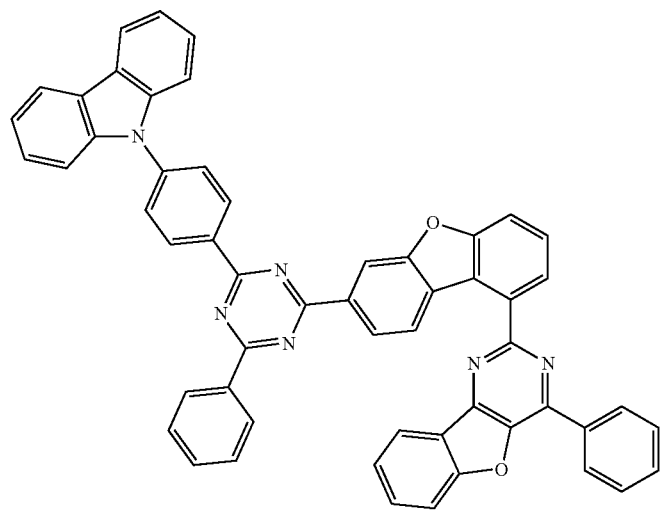
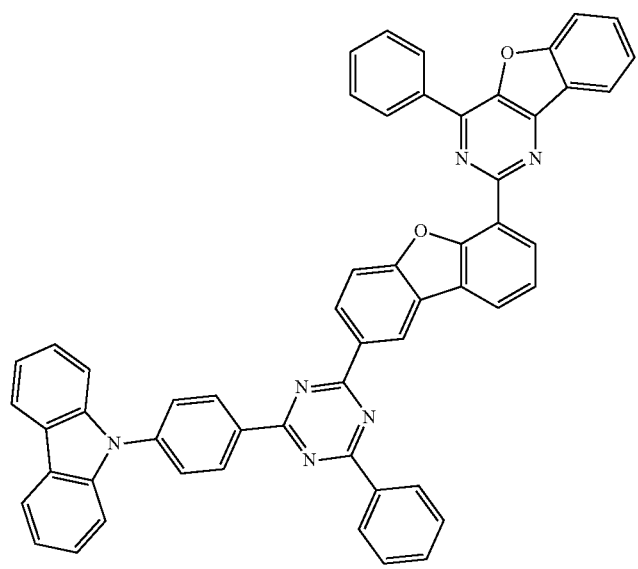

635
636
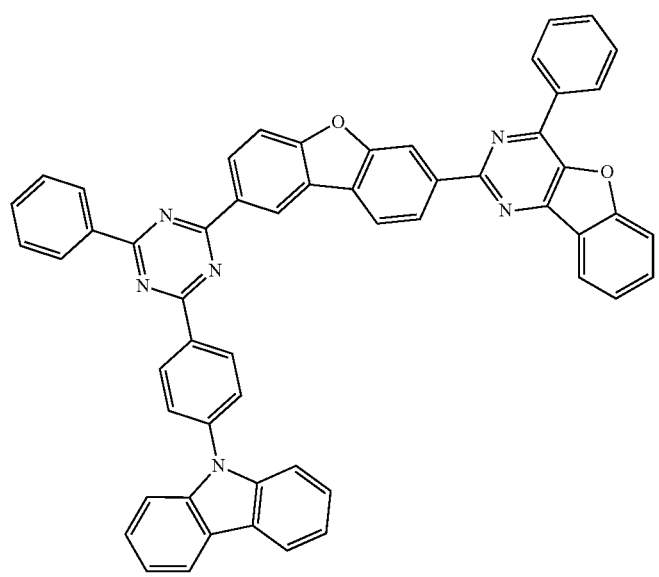
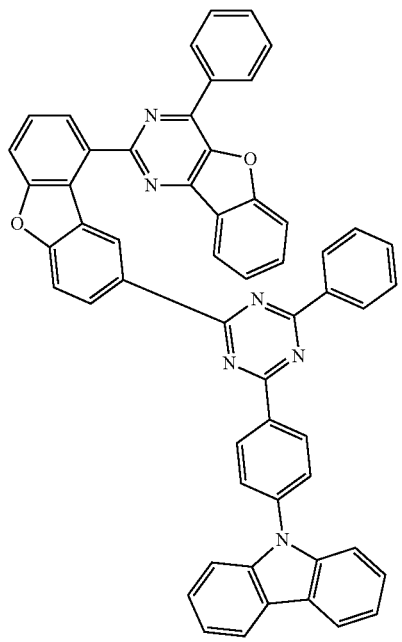
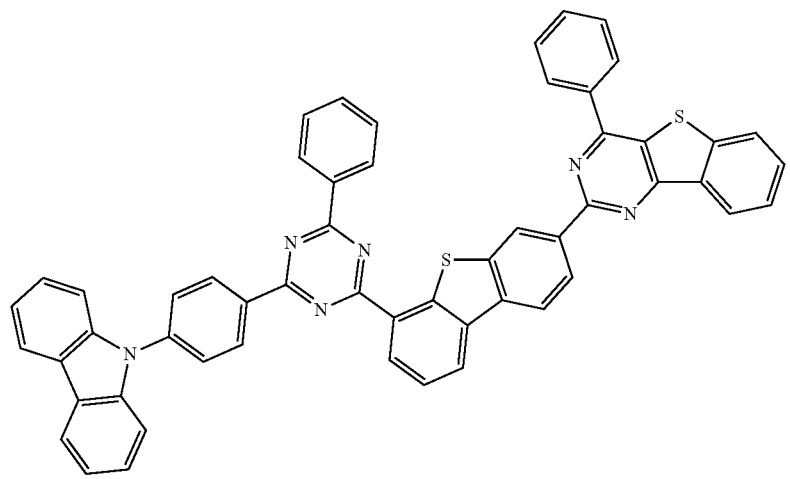
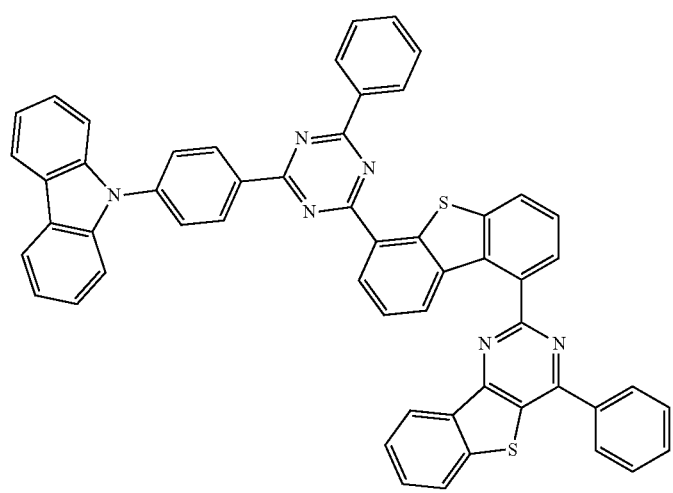

-continued
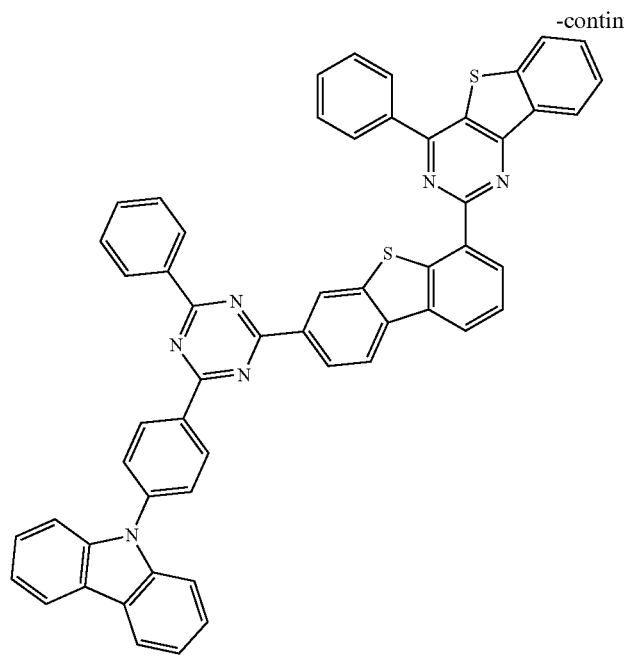
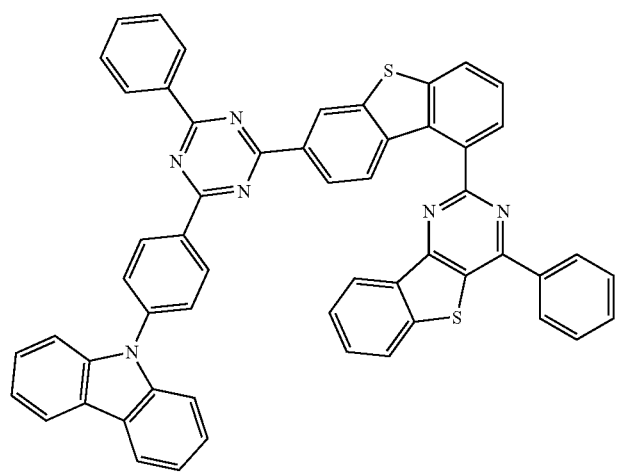
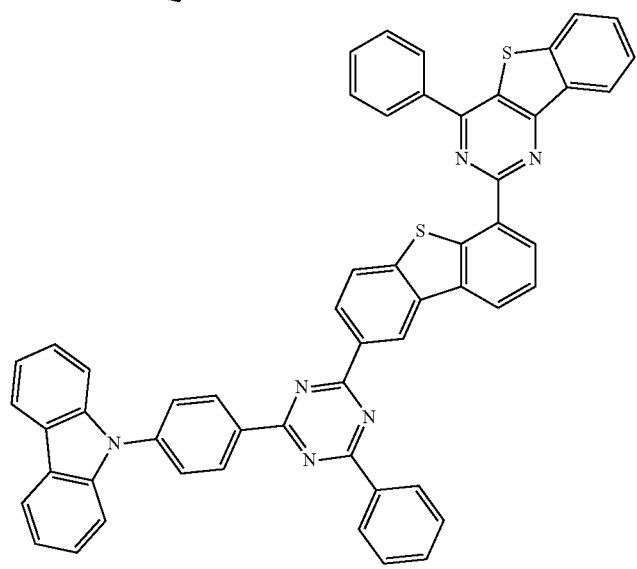

639   640
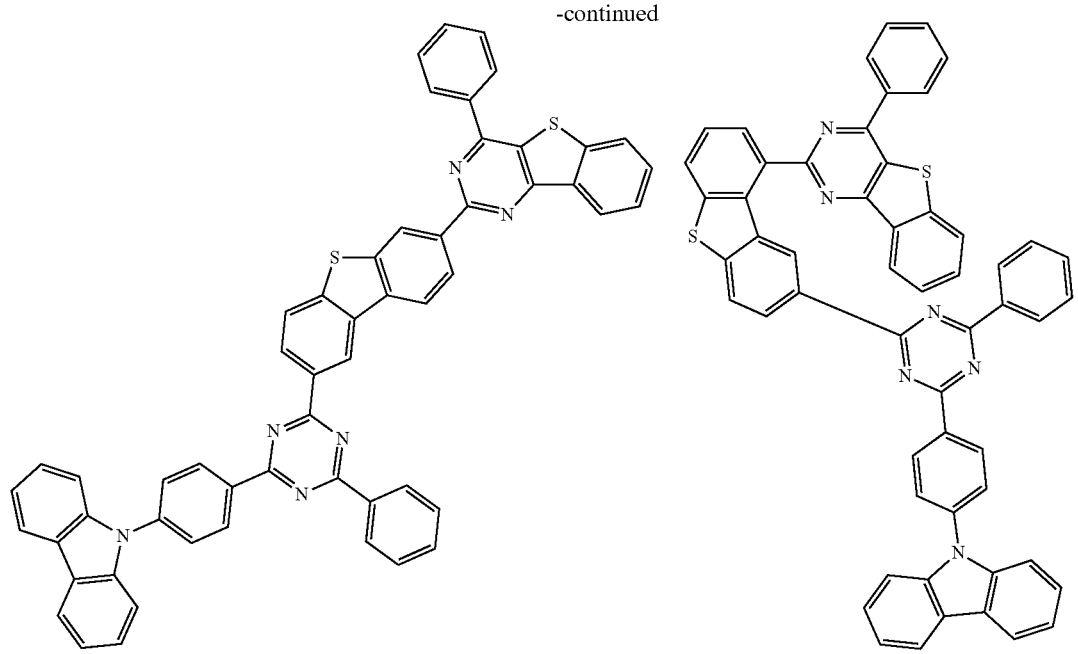
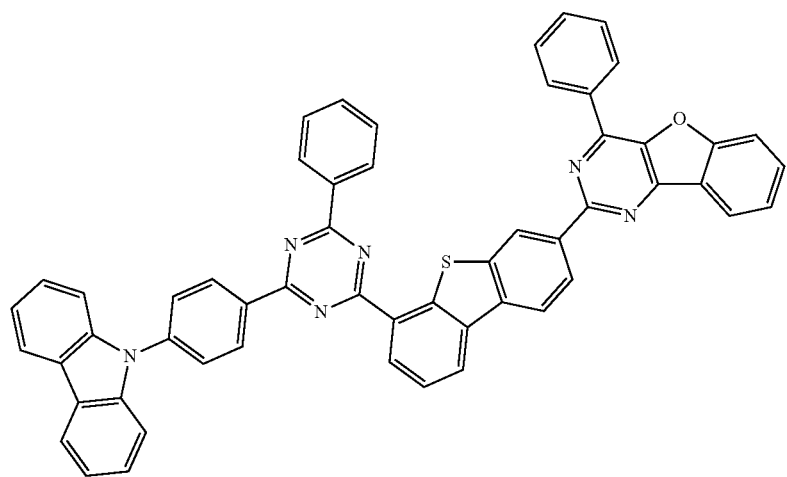
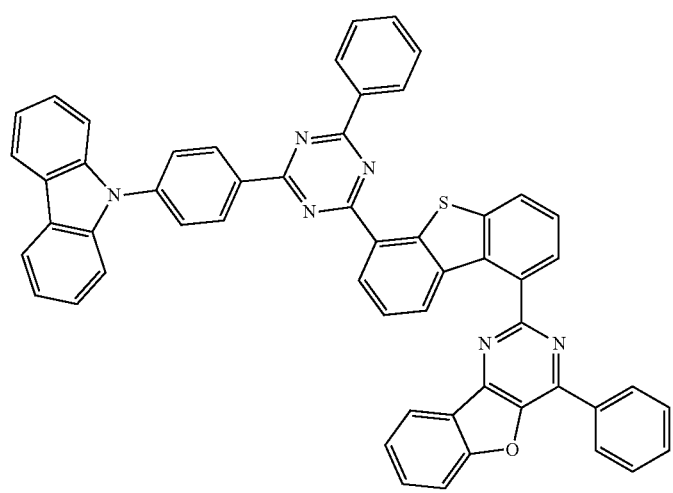

-continued
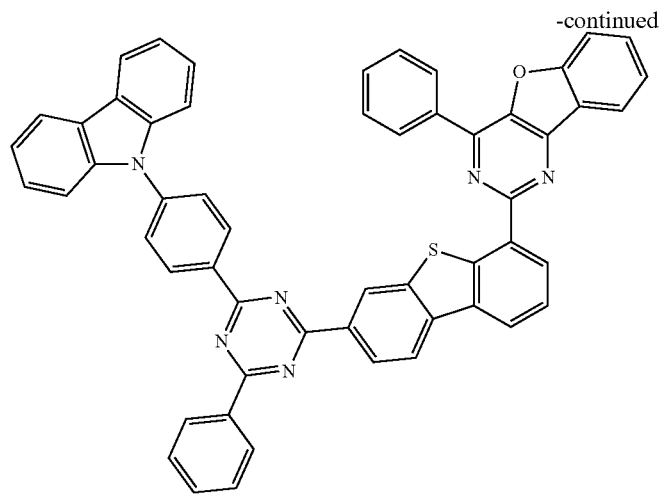
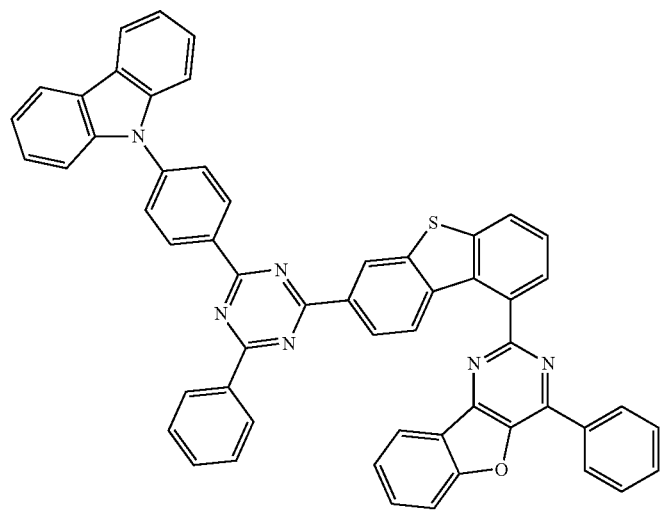
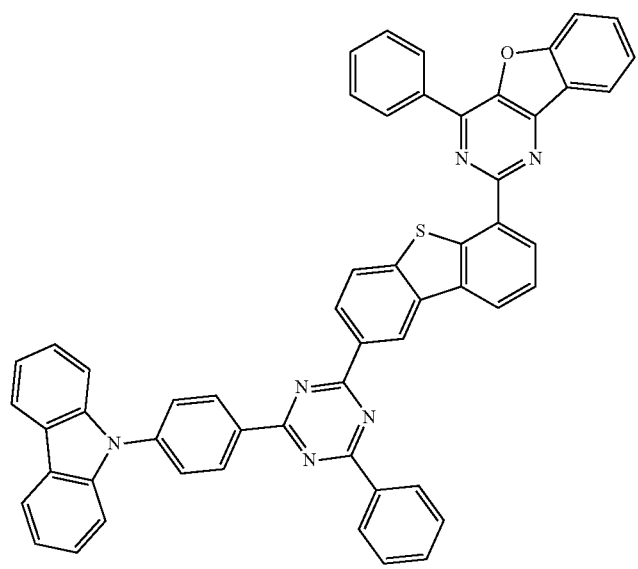

643 644
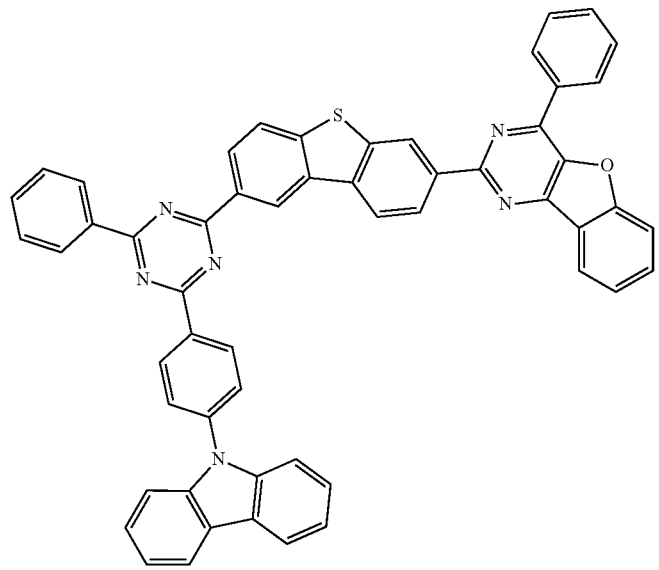
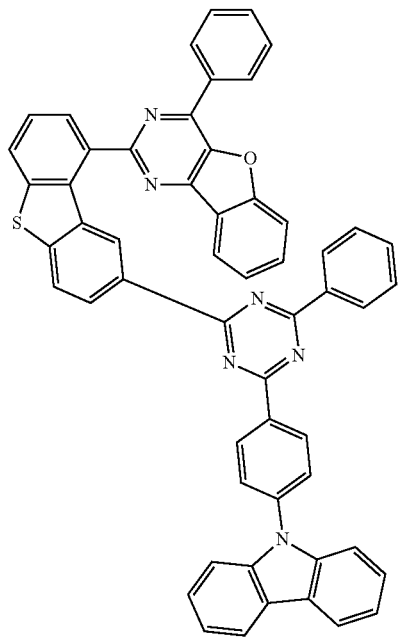
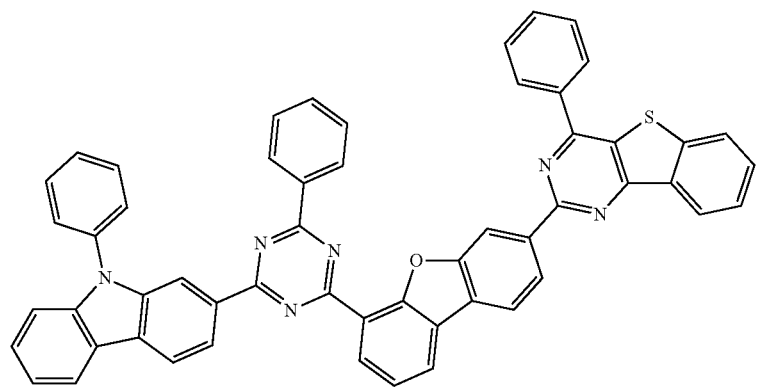
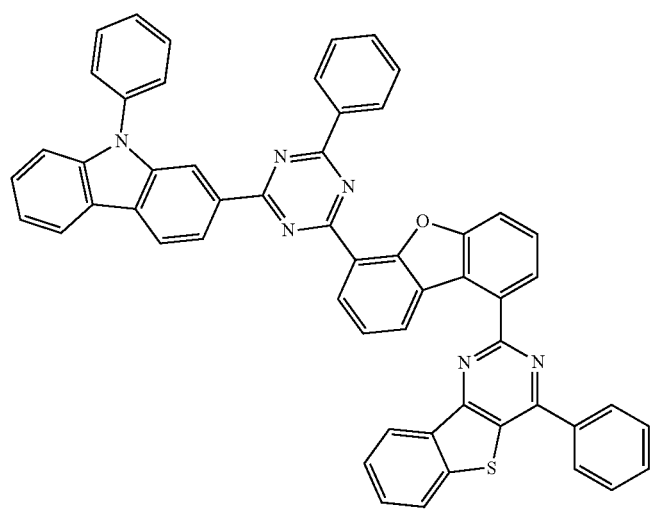

-continued
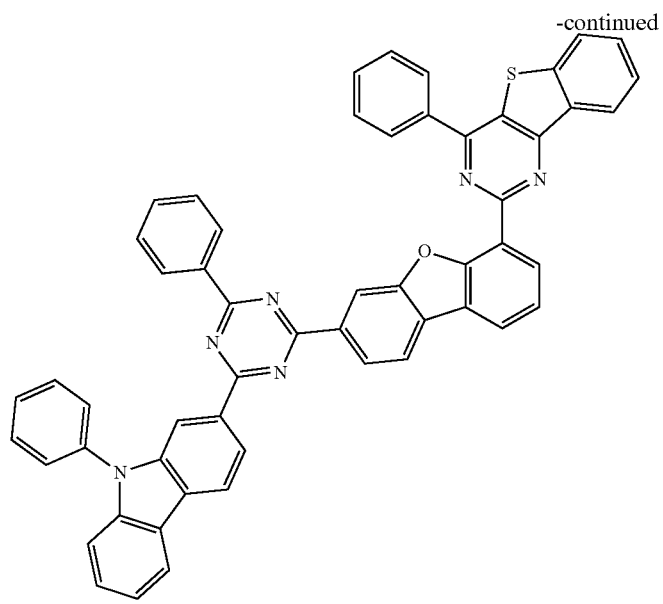
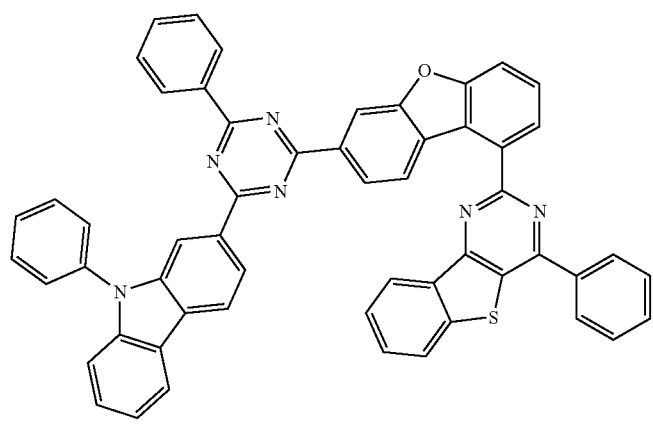
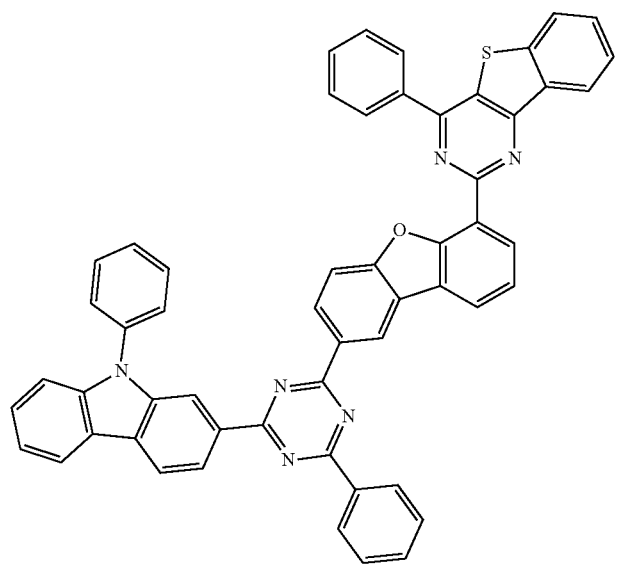

647 648
-continued
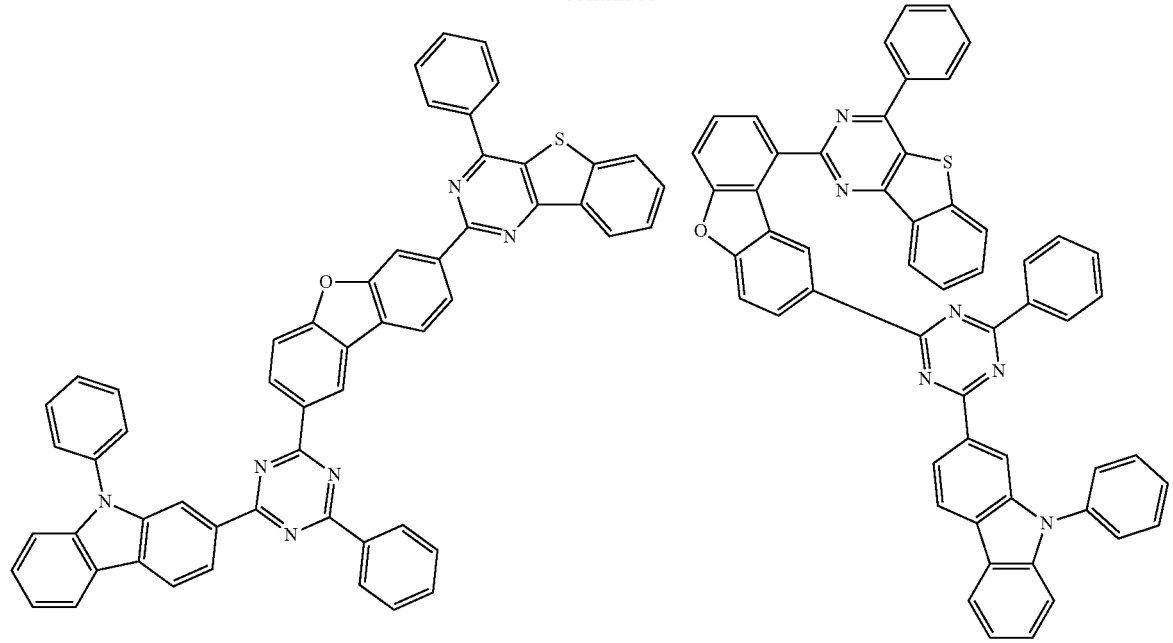
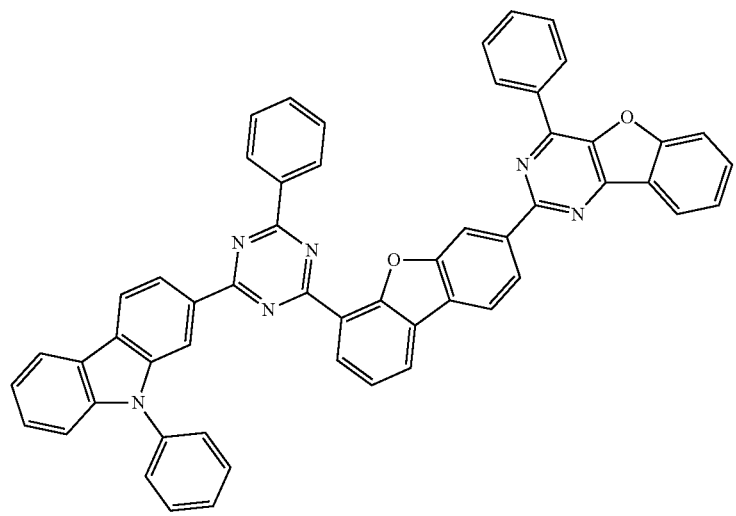
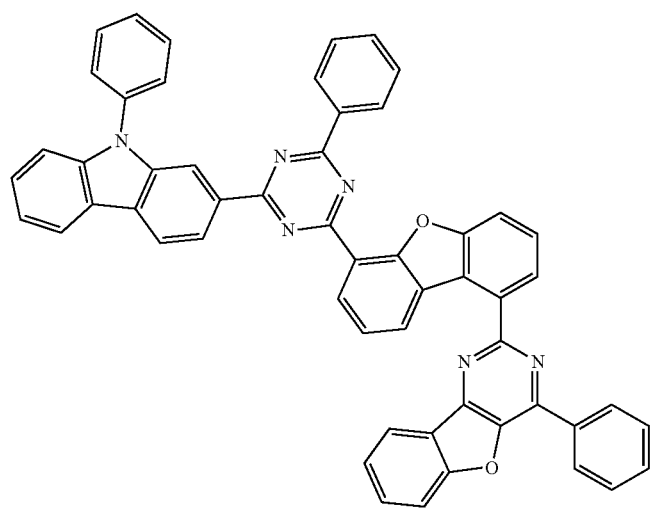

649
-continued
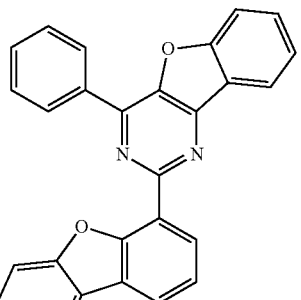
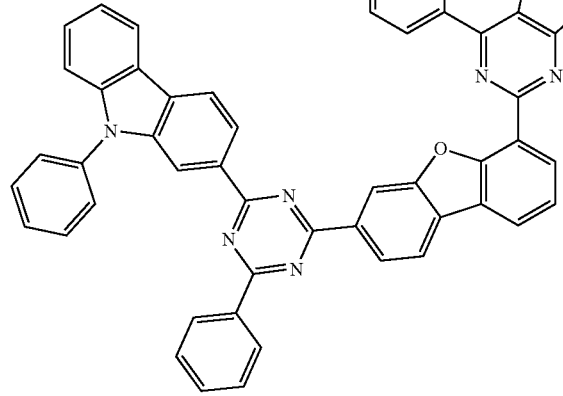
650
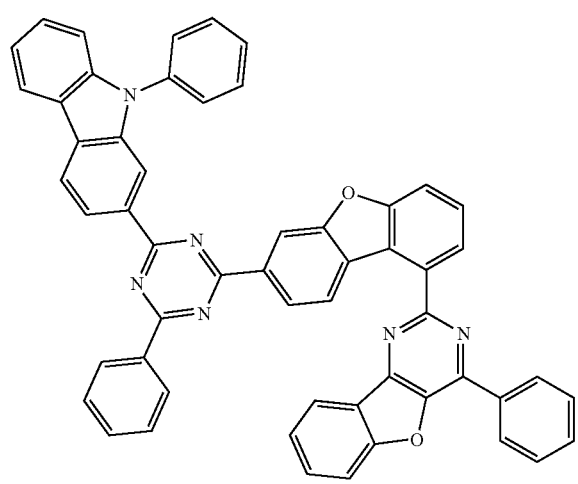
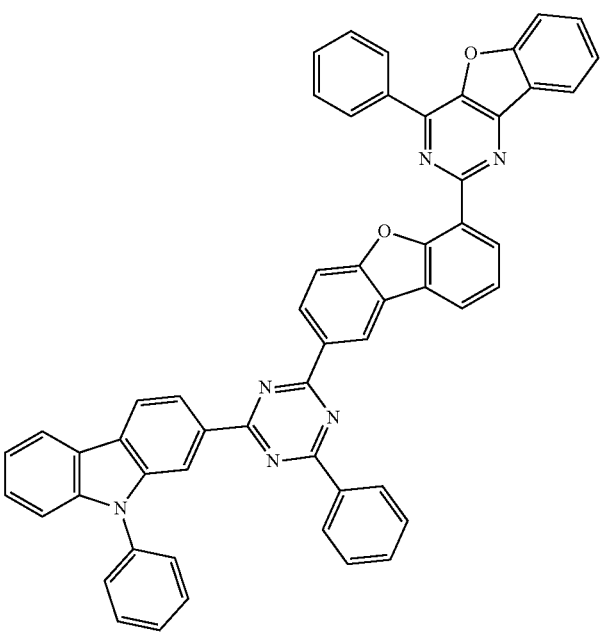

651
652
-continued
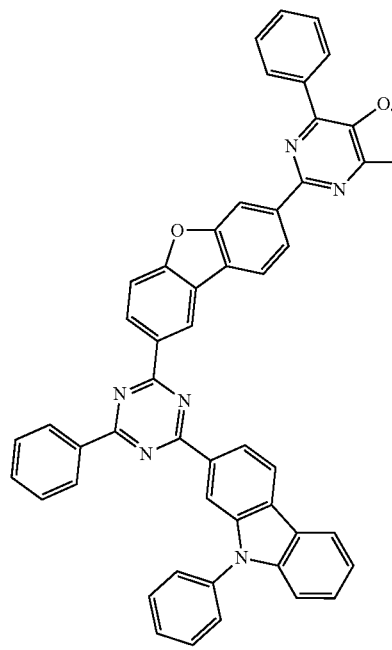 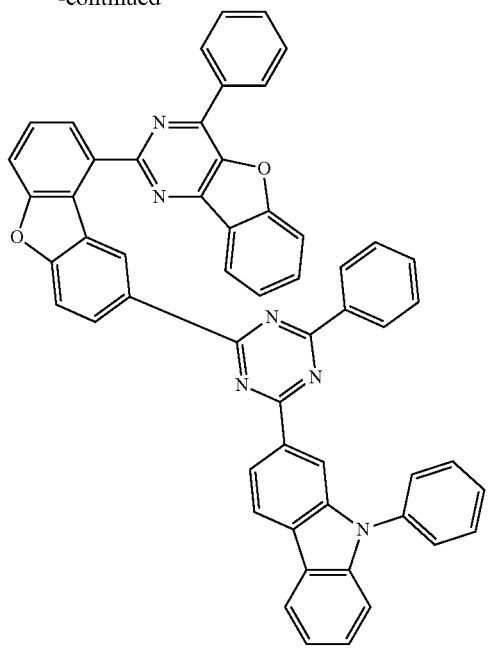
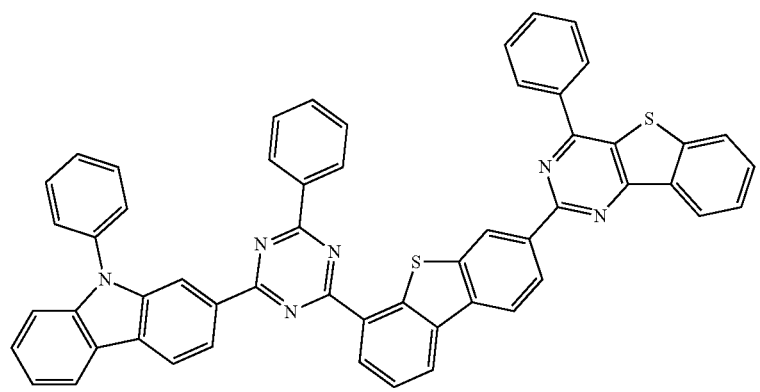
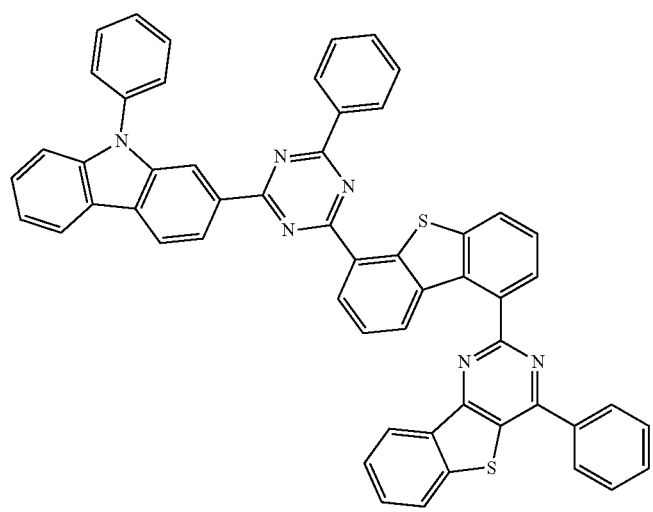

653
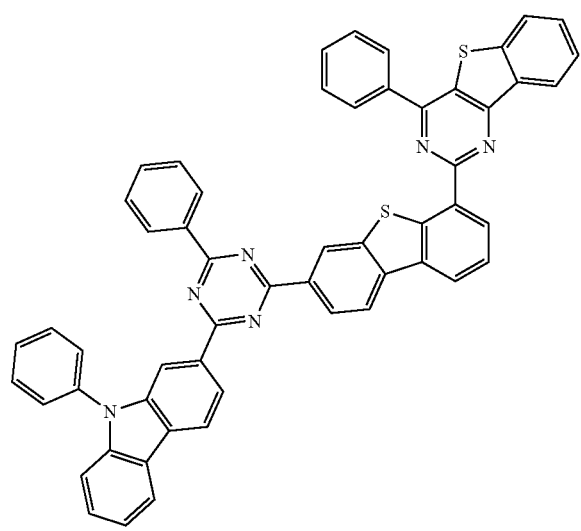
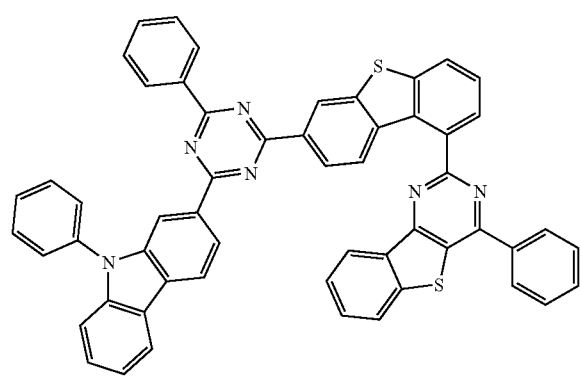
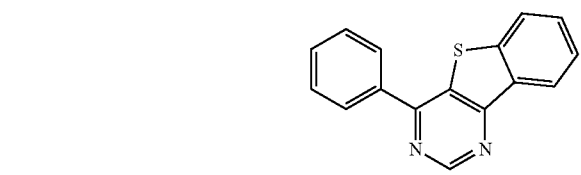
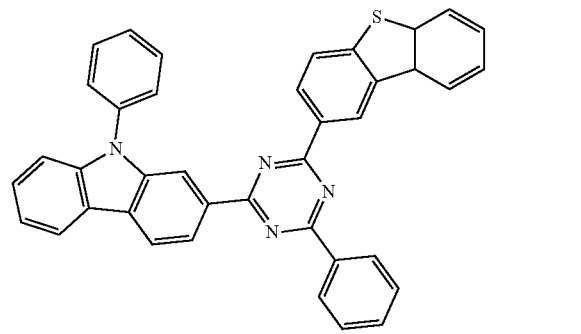
654
-continued
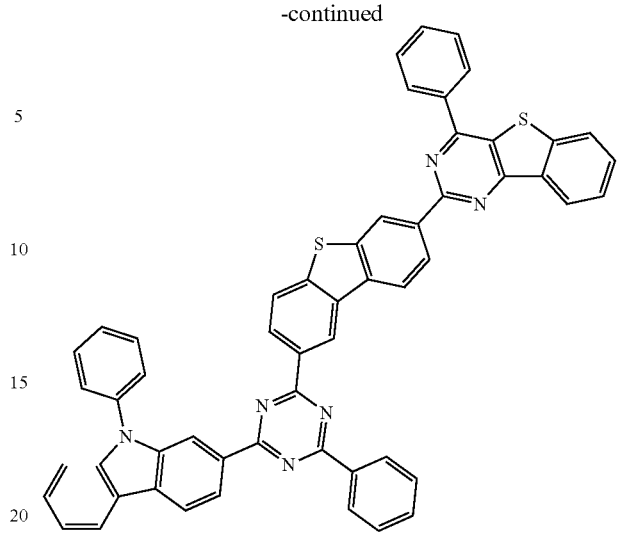
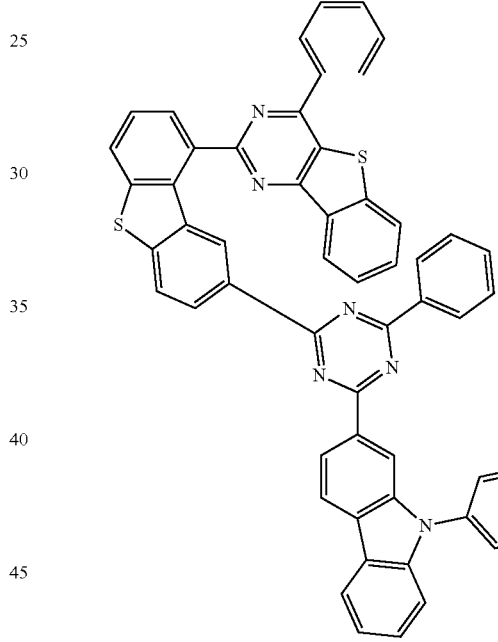
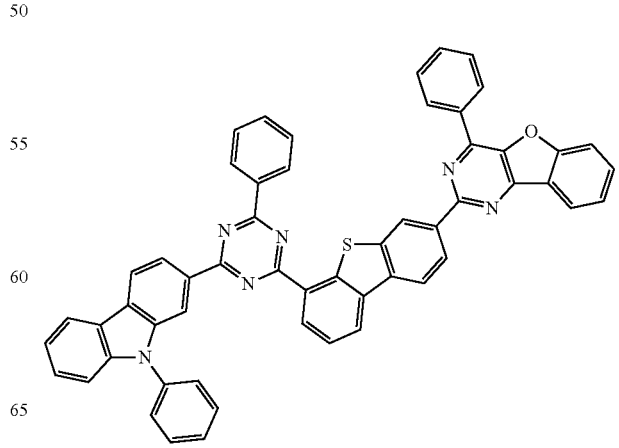

655
-continued
656
-continued
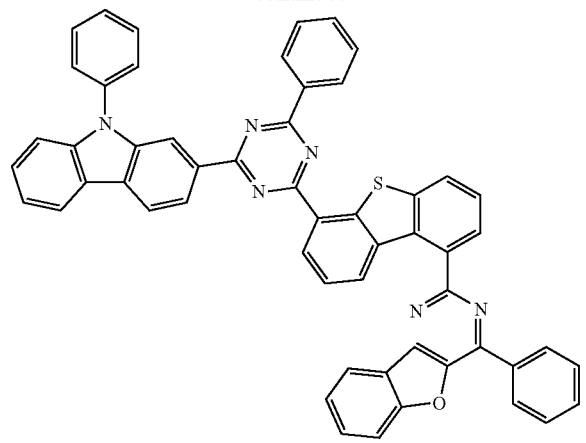
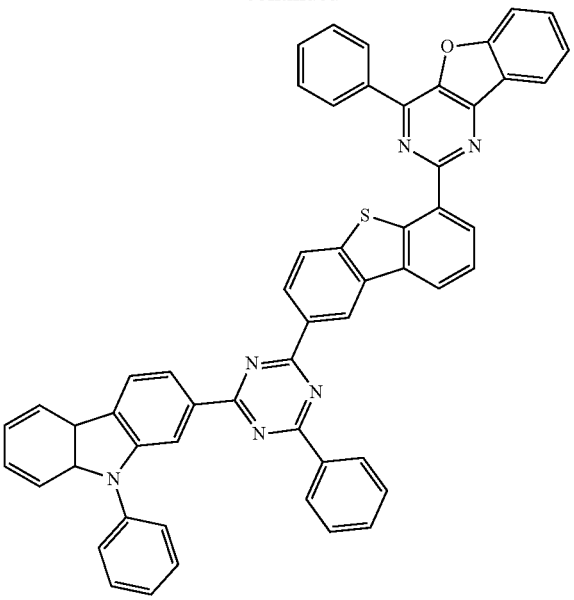
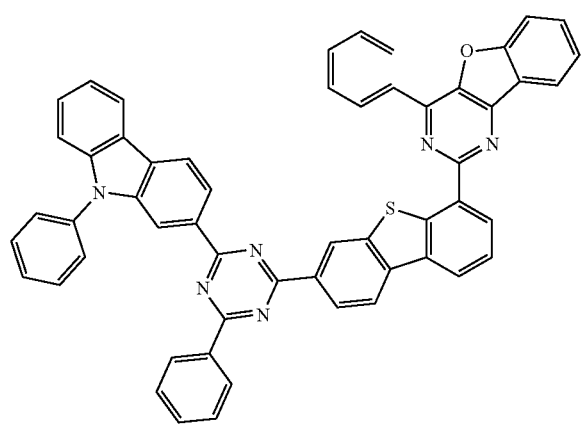
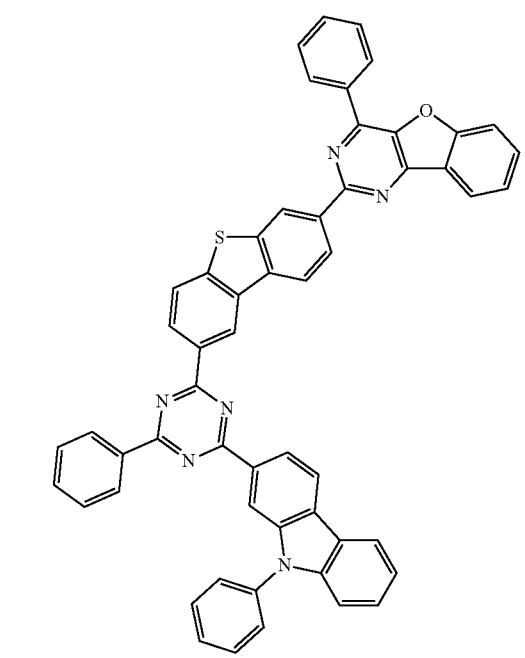

657
-continued
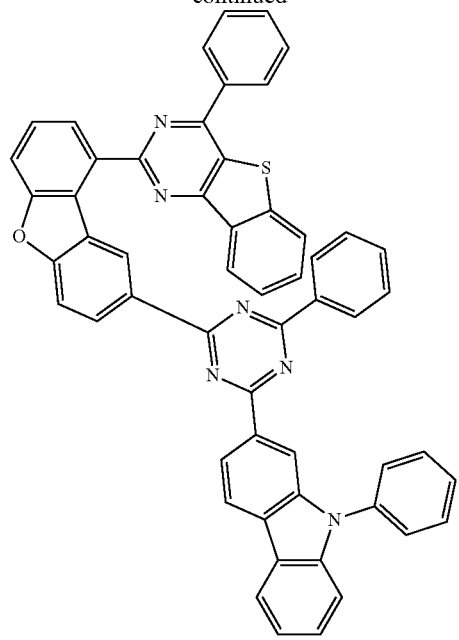
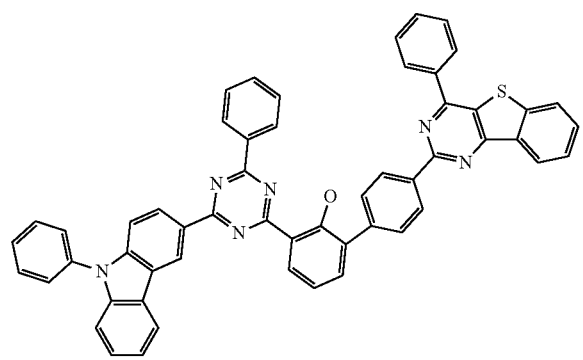
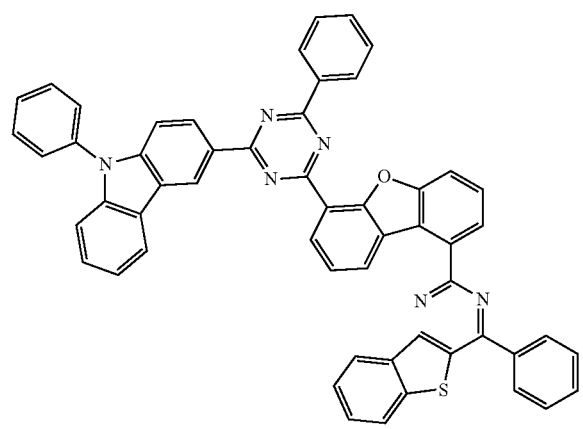
658
-continued
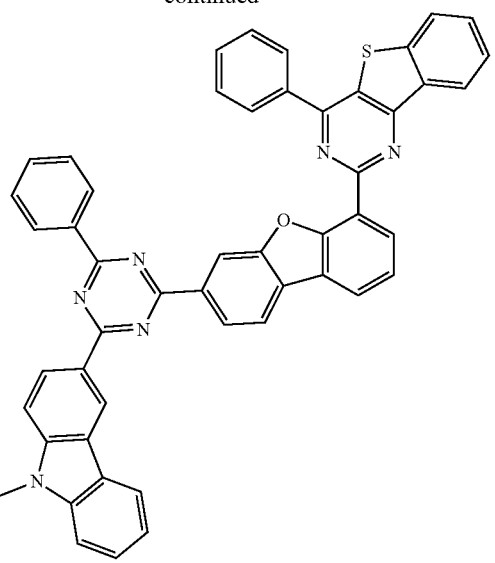
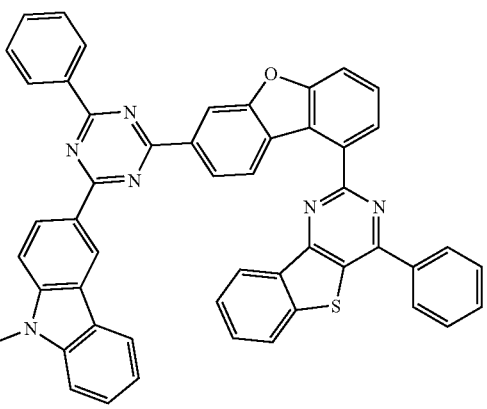
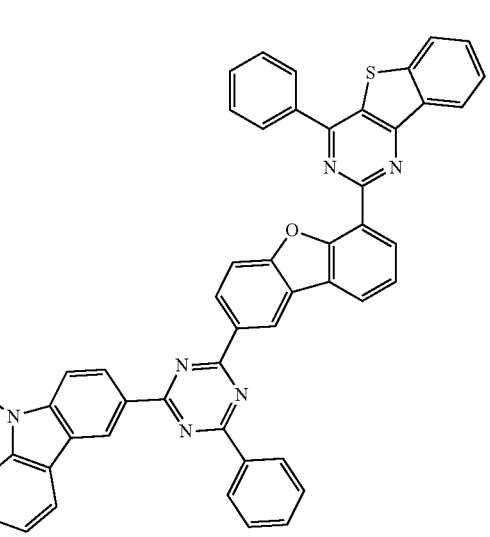

659
-continued
660
-continued
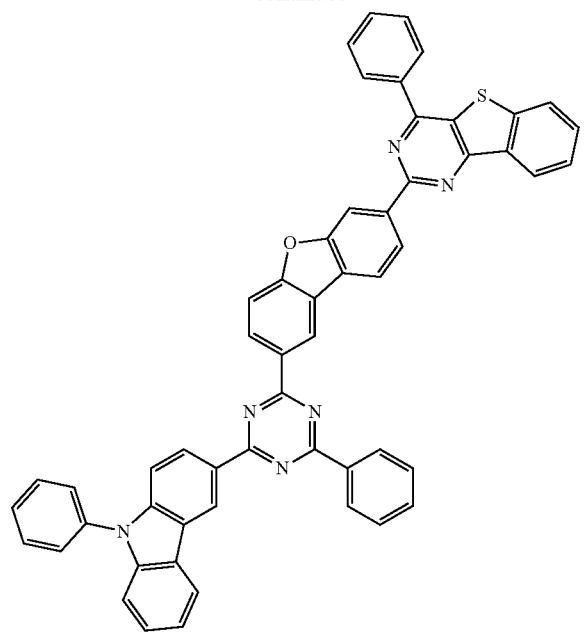
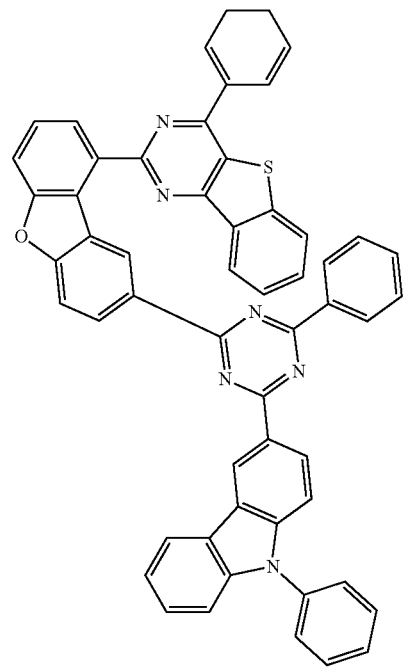
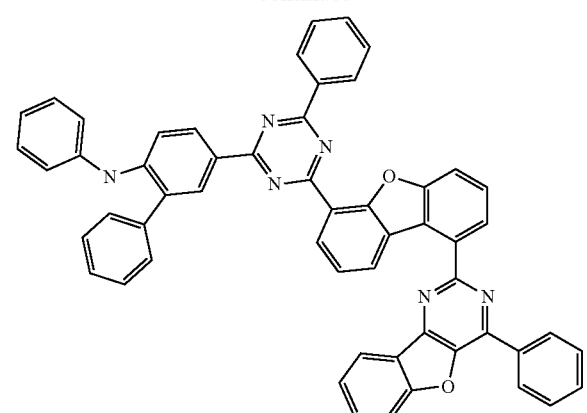
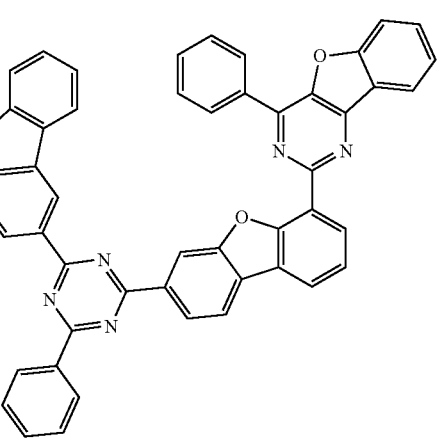
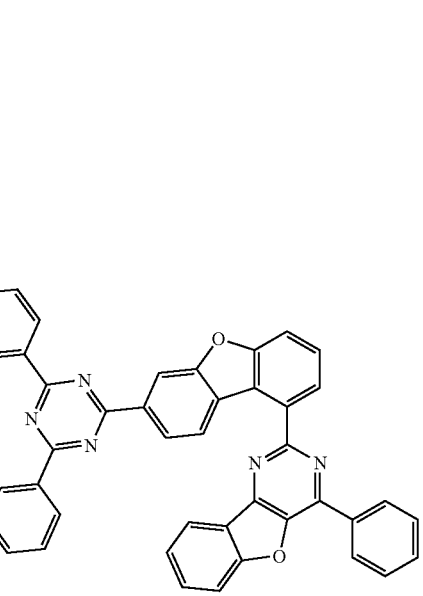

661
-continued
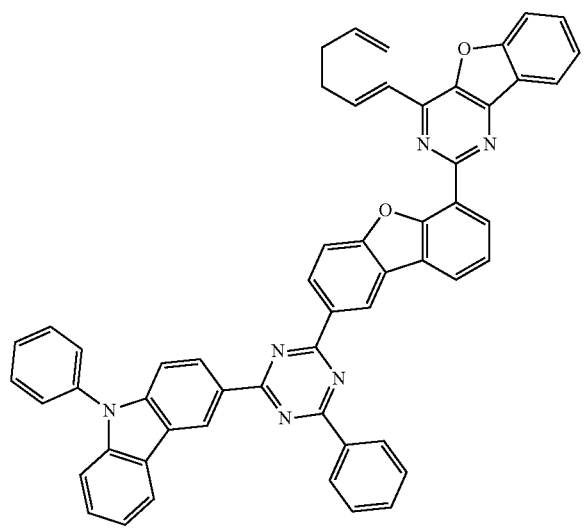
662
-continued
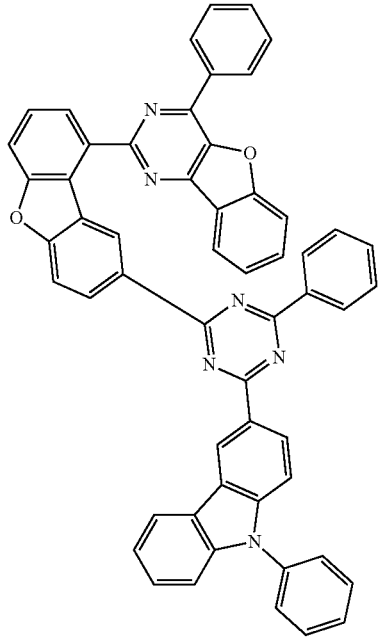
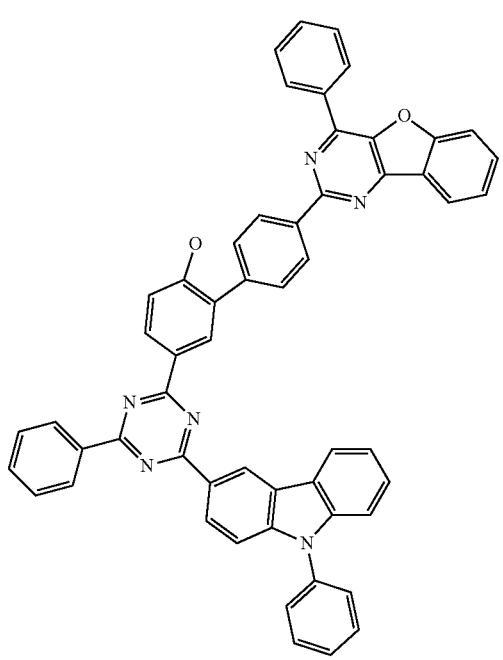
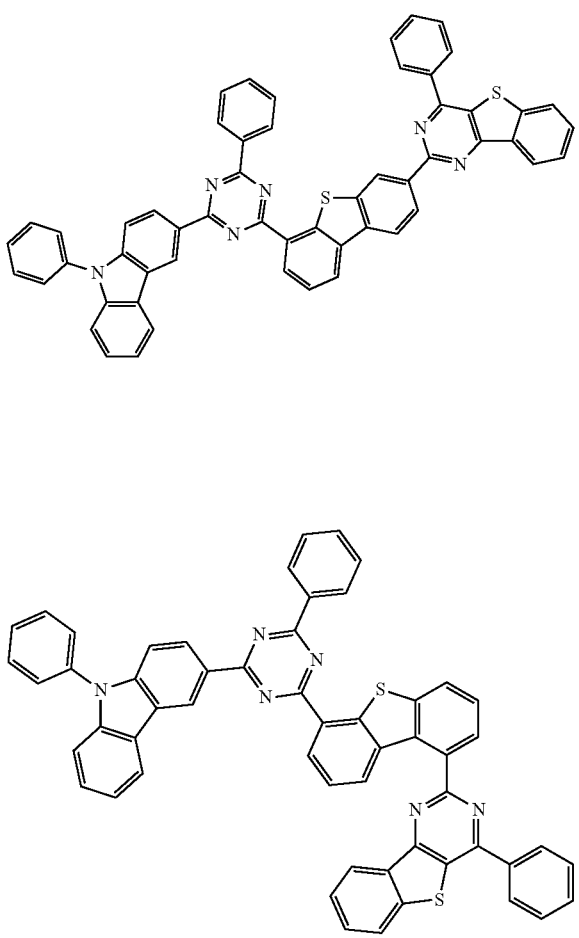

663
-continued
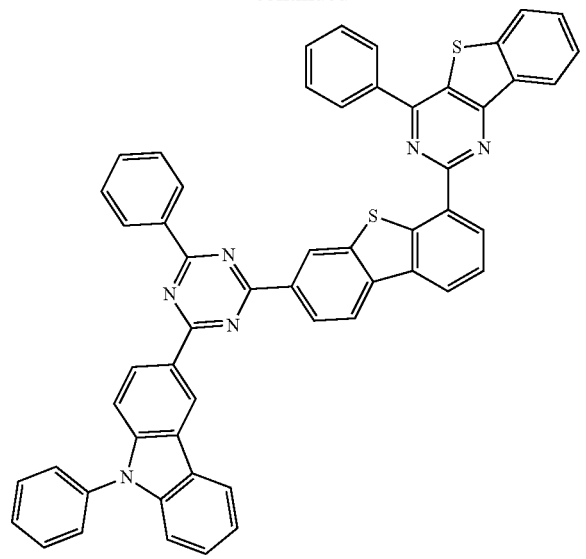
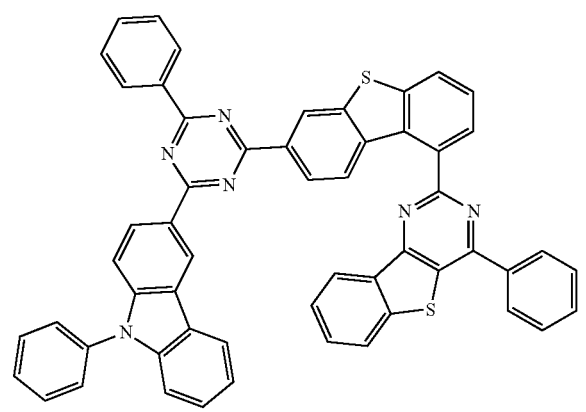
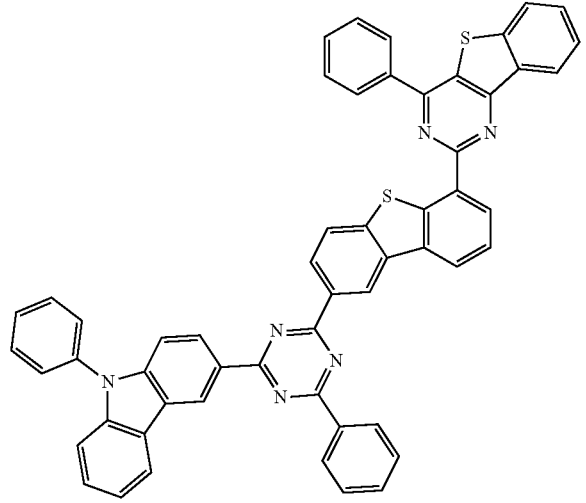
664
-continued
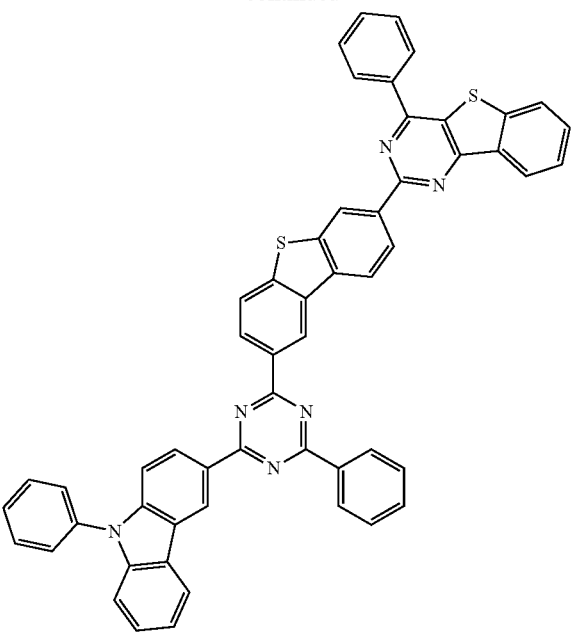
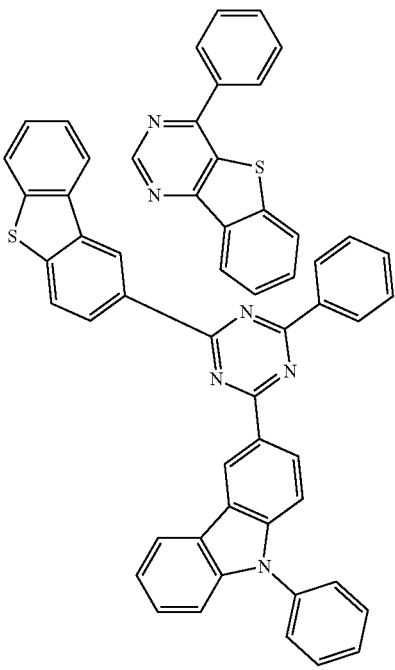

665
-continued
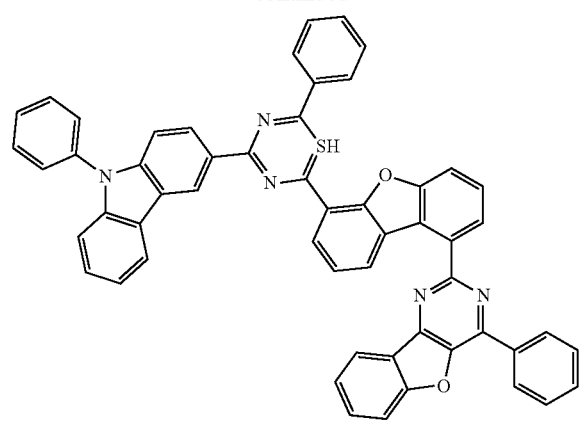
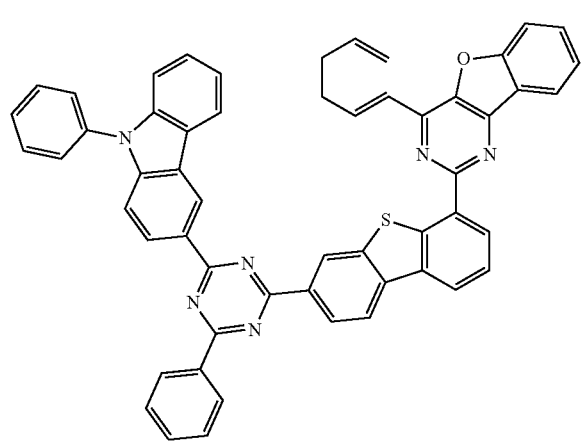
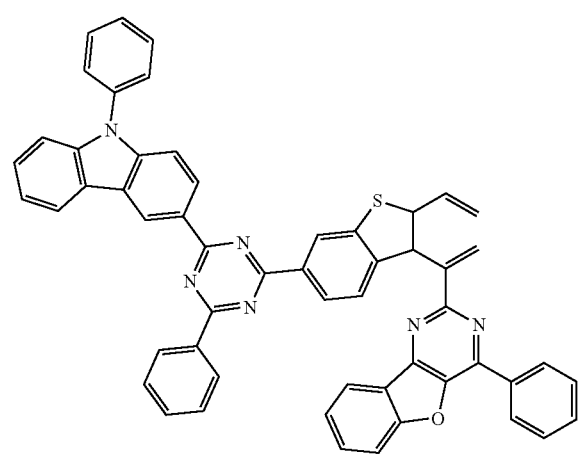
666
-continued
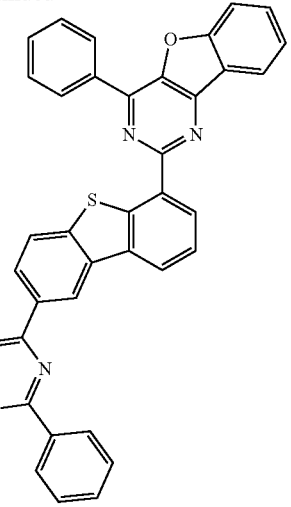
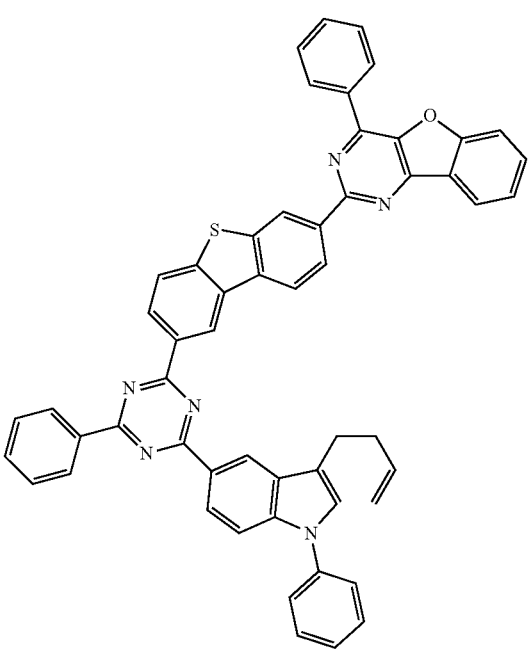

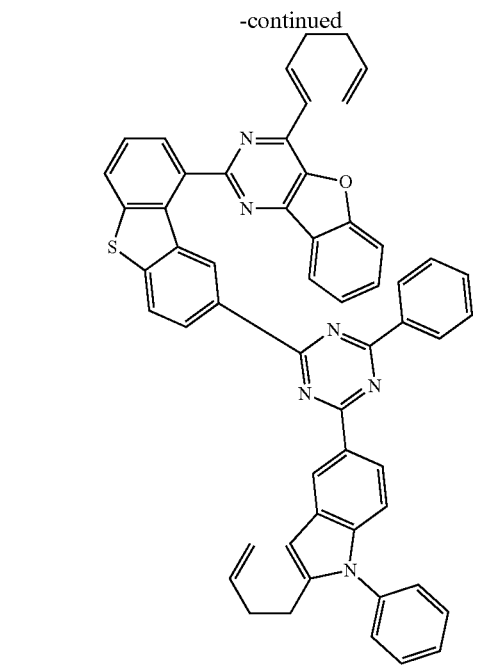
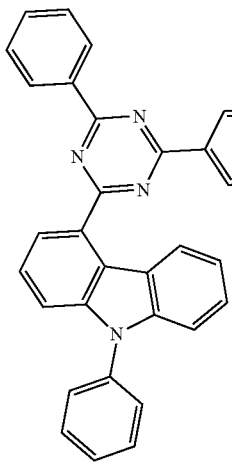
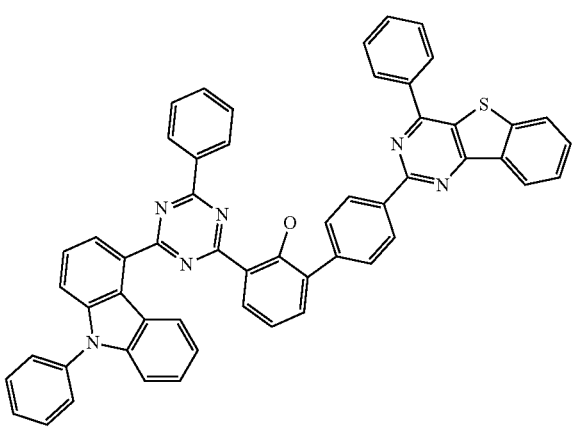
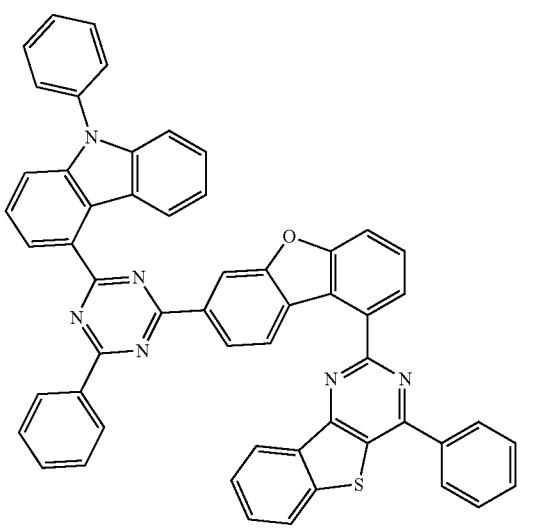
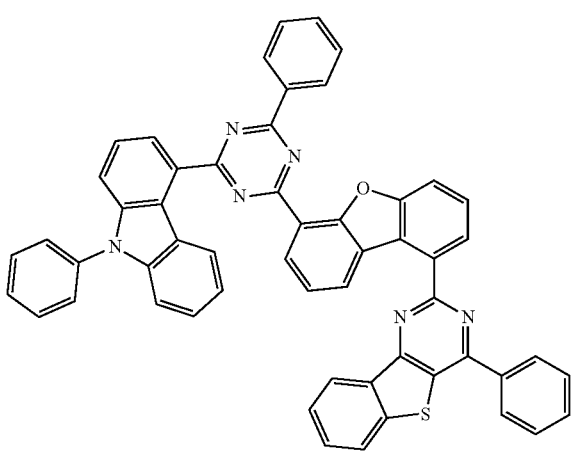
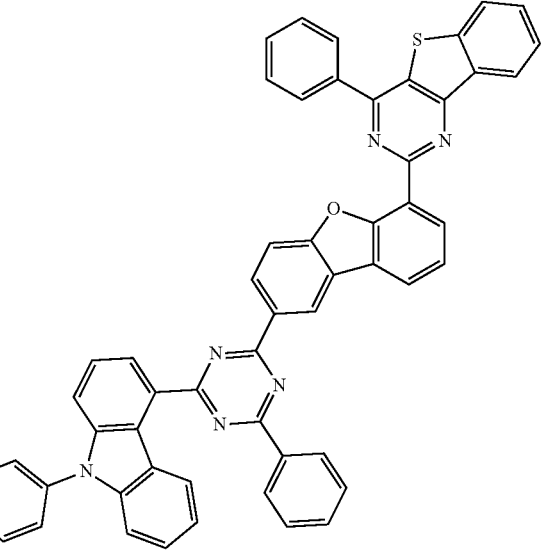

669
-continued
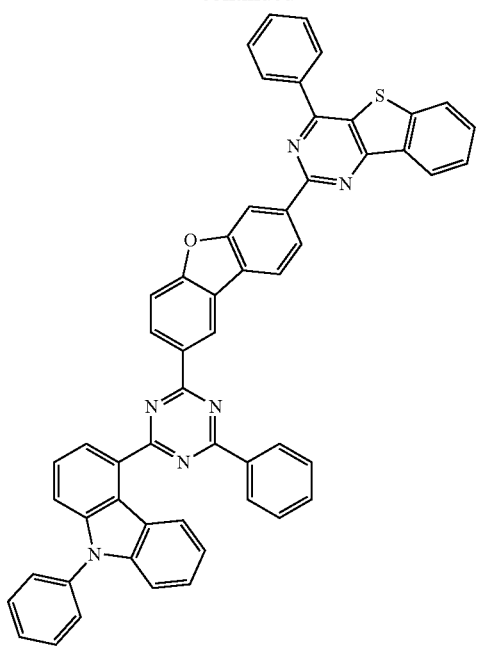
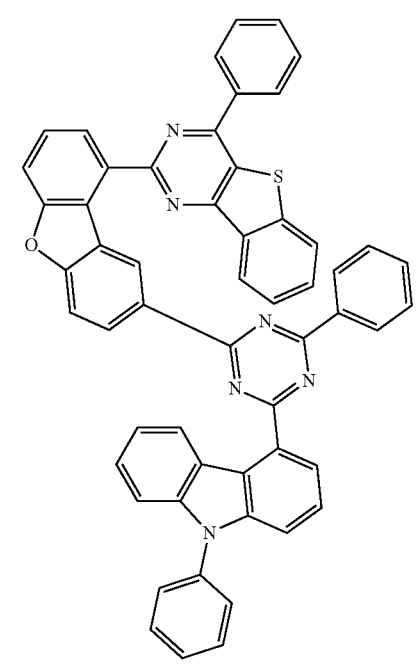
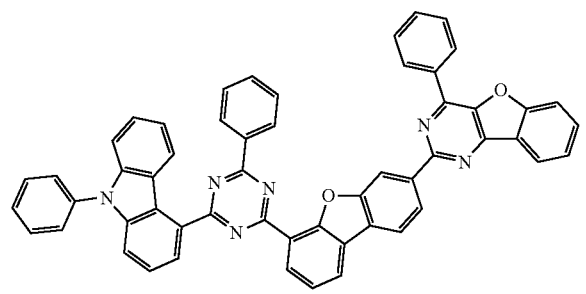
670
-continued
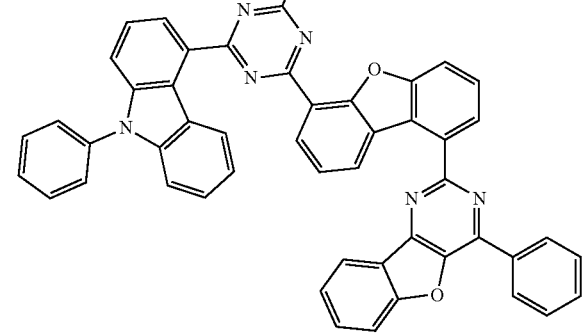
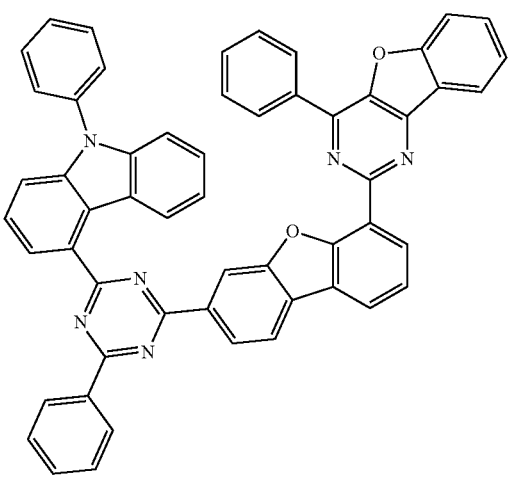
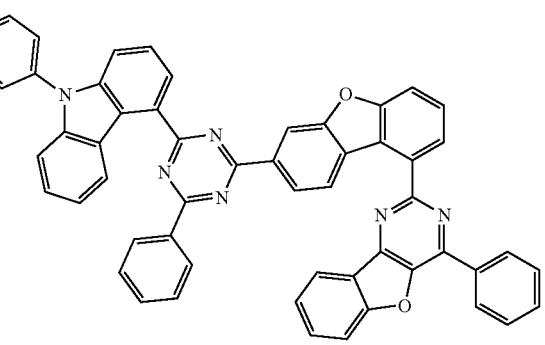

671
-continued
672
-continued
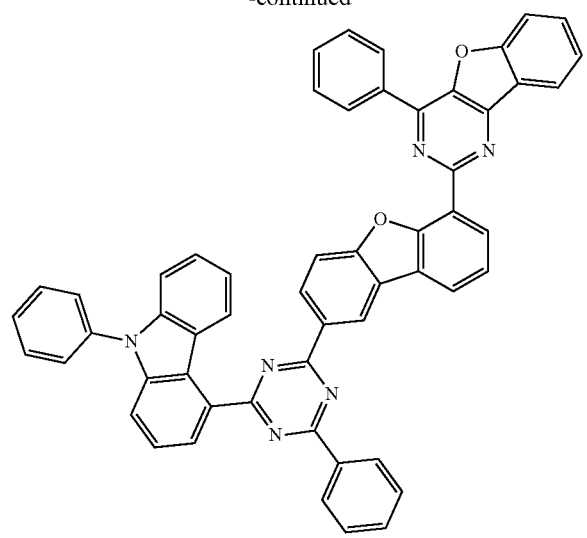
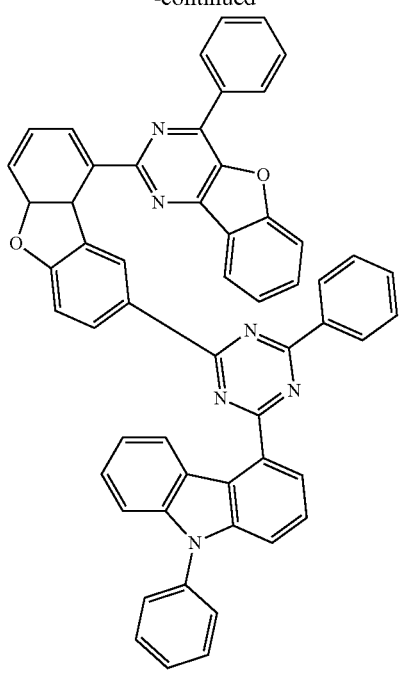

673
-continued
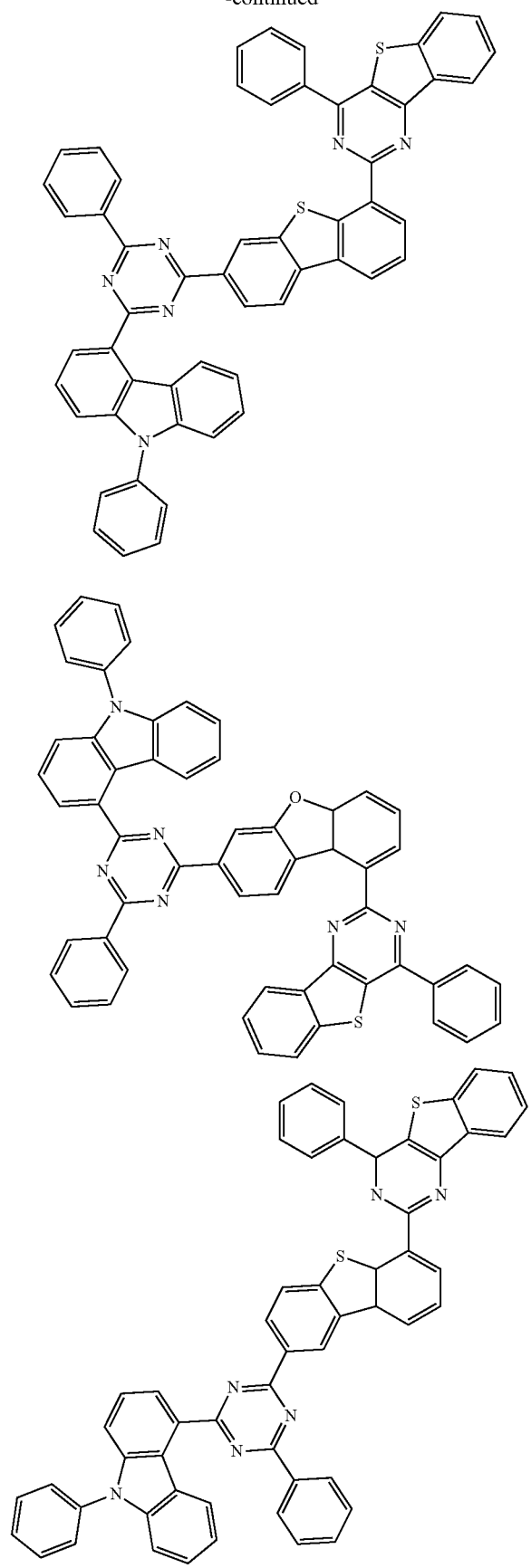
674
-continued
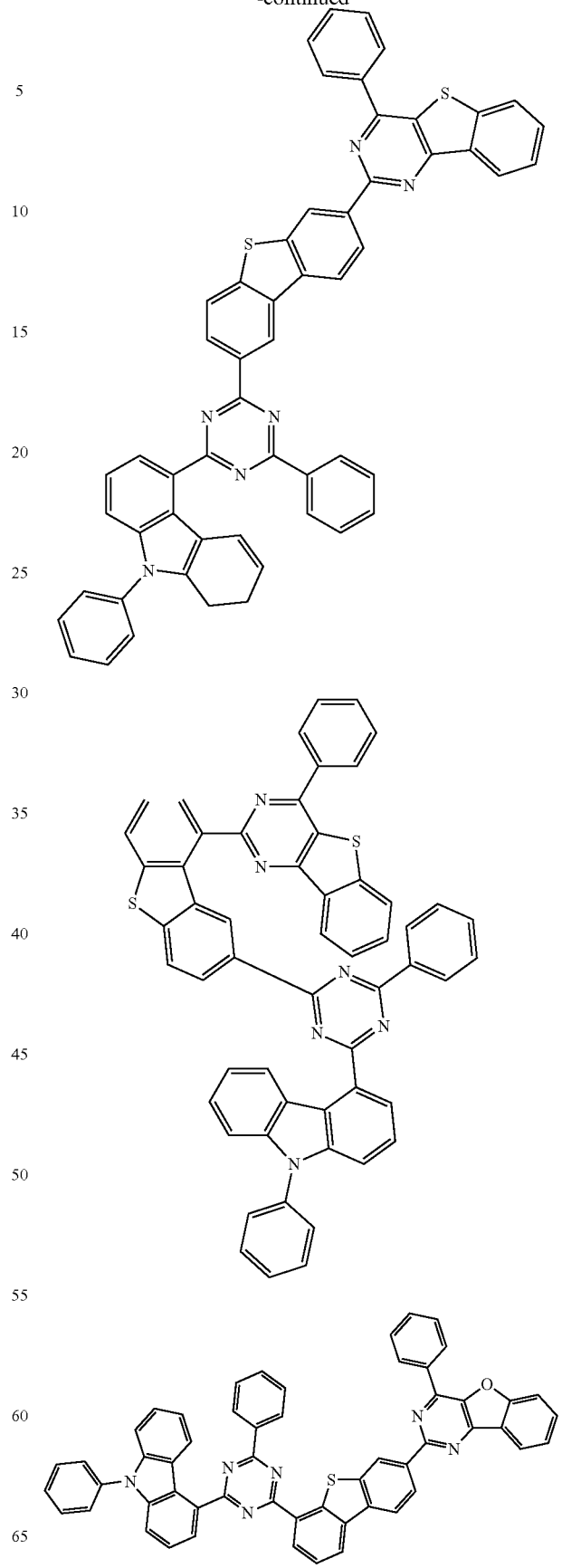

675
-continued
676
-continued
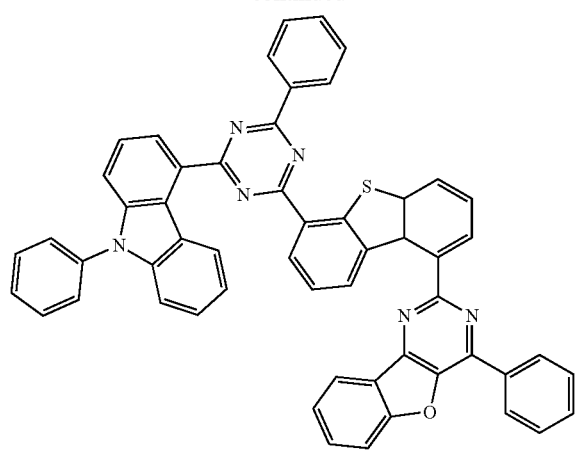
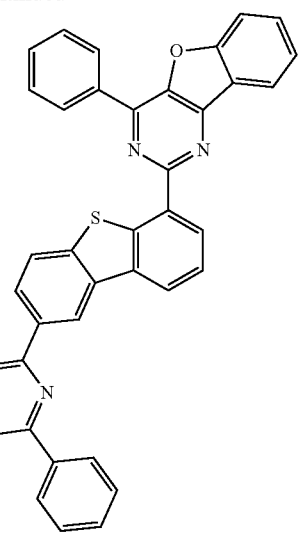
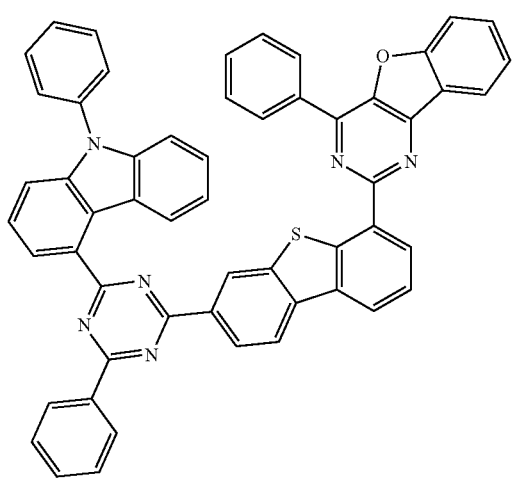
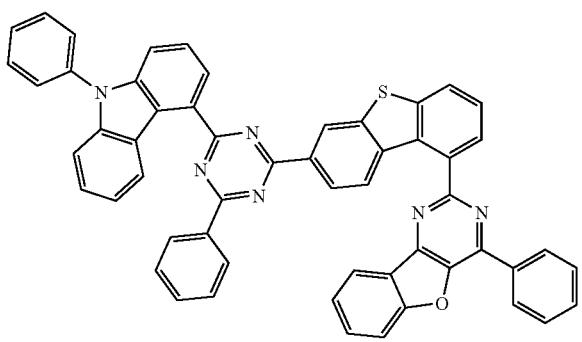
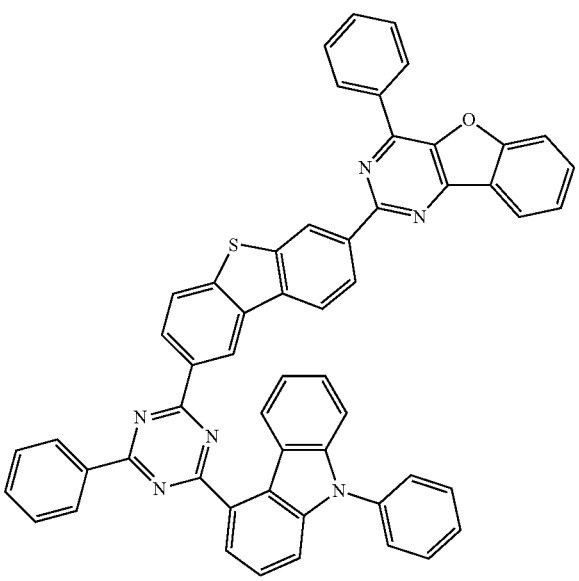

677
-continued

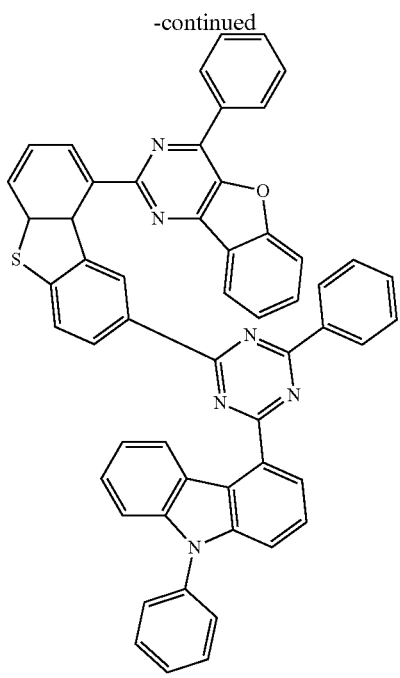

678
-continued

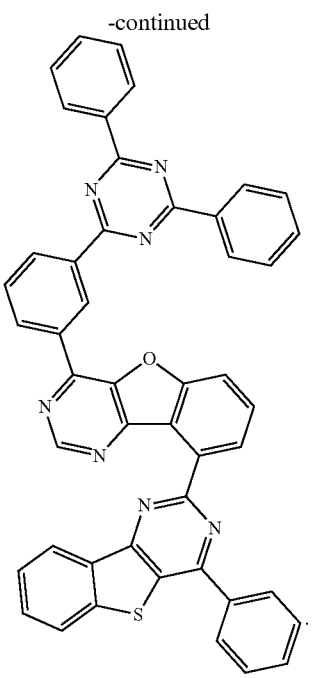

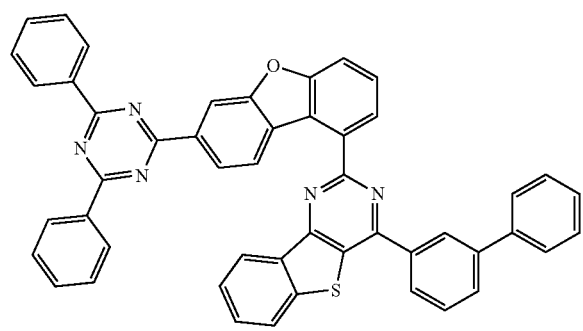

5. An organic light emitting device comprising: a first electrode; a second electrode that is provided to face the first electrode; and one or more organic material layers that are provided between the first electrode and the second electrode, wherein one or more layers of the organic material layers include the compound according to claim 1.

6. The organic light emitting device of claim 5, wherein the organic material layers include a light emitting layer, and the light emitting layer includes two or more types of host materials.

7. The organic light emitting device of claim 6, wherein the two or more types of host materials include the compound.

* * * * *